US012637468B2

(12) United States Patent
Jin et al.

(10) Patent No.: US 12,637,468 B2
(45) Date of Patent: May 26, 2026

(54) SUBSTITUTED [1,2,4]TRIAZOLO[4,3-b]PYRIDAZINES AS $GABA_A$ RECEPTOR MODULATORS

(71) Applicants: SHANGHAI SIMR BIOTECHNOLOGY CO., LTD., Shanghai (CN); SHANGHAI SIMRD BIOTECHNOLOGY CO., LTD., Shanghai (CN)

(72) Inventors: Yun Jin, Shanghai (CN); Fei Wang, Shanghai (CN); Jinhua Wu, Shanghai (CN); Nanyang Chen, Shanghai (CN); Yong Sun, Shanghai (CN); Shuai Li, Shanghai (CN)

(73) Assignees: SHANGHAI SIMR BIOTECHNOLOGY CO., LTD., Shanghai (CN); SHANGHAI SIMRD BIOTECHNOLOGY CO., LTD., Shanghai (CN)

( * ) Notice: Subject to any disclaimer, the term of this patent is extended or adjusted under 35 U.S.C. 154(b) by 855 days.

(21) Appl. No.: 17/786,528

(22) PCT Filed: Dec. 16, 2020

(86) PCT No.: PCT/CN2020/136998
§ 371 (c)(1),
(2) Date: Jun. 16, 2022

(87) PCT Pub. No.: WO2021/121294
PCT Pub. Date: Jun. 24, 2021

(65) Prior Publication Data

US 2023/0136194 A1 May 4, 2023

(30) Foreign Application Priority Data

Dec. 16, 2019 (CN) ........................ 201911296884.9

(51) Int. Cl.
*A61K 31/5025* (2006.01)
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .......................... A61K 31/5025; C07D 487/04
USPC .......................................... 514/248; 544/236
See application file for complete search history.

(56) References Cited

U.S. PATENT DOCUMENTS

| | | |
|---|---|---|
| 6,110,915 A | 8/2000 | Castro Pineiro et al. |
| 6,174,886 B1 | 1/2001 | Pineiro et al. |
| 6,444,666 B1 | 9/2002 | Ladduwahetty et al. |
| 7,943,619 B2 | 5/2011 | Buettelmann et al. |
| 2007/0213338 A1 | 9/2007 | Lebsack et al. |
| 2011/0224278 A1 | 9/2011 | Carmichael et al. |
| 2012/0208805 A1 | 8/2012 | Heinelt et al. |
| 2013/0338139 A1 | 12/2013 | Allan et al. |
| 2015/0111876 A1 | 4/2015 | Shiraishi et al. |
| 2020/0165253 A1 | 5/2020 | Li et al. |
| 2023/0044787 A1 | 2/2023 | Jin et al. |

FOREIGN PATENT DOCUMENTS

| | | | | |
|---|---|---|---|---|
| CN | 1871008 A | 11/2006 | | |
| CN | 101868458 A | 10/2010 | | |
| CN | 103239720 A | 8/2013 | | |
| CN | 107344936 A | 11/2017 | | |
| CN | 107344938 A | 11/2017 | | |
| CN | 110256440 A | 9/2019 | | |
| CO | 2022008171 A2 | 8/2022 | | |
| EP | 2231651 A | 9/2010 | | |
| GB | 2345443 A | 7/2000 | | |
| MX | 2010006182 A | 7/2010 | | |
| WO | 92/22652 A1 | 12/1992 | | |
| WO | 94/13799 A1 | 6/1994 | | |
| WO | 2005041971 A1 | 5/2005 | | |
| WO | 2017190707 A1 | 11/2017 | | |
| WO | WO-2021121294 A1 * | 6/2021 | ............. | A61P 29/00 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Mar. 21, 2024 the Second Office Action issued in European Patent Application No. 20904065.8.
May 22, 2024 the Second Office Action issued in Eurasian Patent Application No. 202291909.
Aug. 2, 2023 The First Office Action issued in Canadian Patent Application No. 3,161,739.
Jun. 13, 2023 The First Office Action issued in Japanese Patent Application No. 2022-537266.
Sep. 1, 2023 The Second Office Action issued in Chinese Patent Application No. 202080061283.4.

(Continued)

*Primary Examiner* — Douglas M Willis

(57) ABSTRACT

Provided is a triazolopyridazine derivative, a preparation method therefor, a pharmaceutical composition thereof, and an application thereof. The triazolopyridazine derivative is represented by formula I. The triazolopyridazine derivative has excellent inverse agonistic activity, thermodynamic solubility, bioavailability, and pharmacokinetic properties; thus having promising application prospects.

I

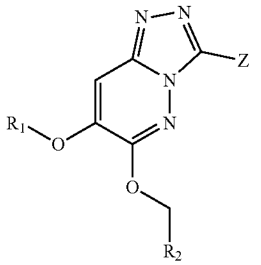

17 Claims, No Drawings

(56) References Cited

OTHER PUBLICATIONS

Jul. 31, 2024 the Second Office Action issued in Canadian Patent Application No. 3161739.
Sep. 13, 2024 the Second Office Action issued in Korean Patent Application No. 10-2022-7024733.
Sep. 19, 2024 the First Office Action issued in Vietnamese Patent Application No. 1-2022-04487.
Jan. 4, 2023 European Search Report issued in European Patent Application No. 20904065.8.
Mar. 4, 2023 Chinese Office Action issued in Chinese Patent Application No. 202080061283.4.
Feb. 1, 2023 European Office Action issued in European Patent Application No. 20904065.8.
Mar. 24, 2023 Australian Office Action issued in Australian Patent Application No. 2020410470.
Mar. 3, 2023 Chinese Search Report issued in Chinese Patent Application No. 202080061283.4.
Feb. 26, 2021 International Search Report issued in International Patent Application No. PCT/CN2020/136998.
Feb. 26, 2021 Written Opinion of the International Searching Authority issued in International Patent Application No. PCT/CN2020/136998.
Feb. 26, 2021 International Preliminary Report on Patentability issued in International Patent Application No. PCT/CN2020/136998.
Zlokovic et al., Neurovascular pathways to neurodegeneration in Alzheimer's disease and other disorders, Nat Rev Neurosci. 12(12): 723-738.
Xiao HS et al., Identification of gene expression profile of dorsal root ganglion in the rat peripheral axotomy model of neuropathic pain, Proc Natl Acad Sci USA, Jun. 11, 2002; 99(12): 8360-8365.
Goeders N E and Kuhar M J (1985) Benzodiazepine receptor binding in vivo with [3H]-RO 15-1788, Life Sci 37: 345-355.
Wafford K A, Whiting P J and Kemp J A (1993) Differences in affinity and efficacy of benzodiazepine receptor ligands at recombinant GABA.sub.A receptor subtypes, Mol. Pharmacol 43: 240-244.
Jones et al., Pharmacokinetics and metabolism studies on (3-tert-butyl-7-(5-methylisoxazol-3-yl)-2-(1-methyl-1H-1,2,4-triazol-5-ylmethoxy) pyrazolo[1,5-d][1,2,4]triazine, a functionally selective GABAA α5 inverse agonist for cognitive dysfunction, Bioorg Med Chem Lett. Feb. 15, 2006; 16(4): 872-875.
Brickley, S.G. and Mody, I. Extrasynaptic GABAA receptors: their function in the CNS and implications for disease, Neuron 73, 23-34 (2012).
Harris, D. et al., Selective influence on contextual memory: physiochemical properties associated with selectivity of benzodiazepine ligands at GABAA receptors containing the α5 subunit, J. Med. Chem. 51, 3788-3803 (2008).
Savić, M.M. et al., PWZ-029, a compound with moderate inverse agonist functional selectivity at GABAA receptors containing α5 subunits, improves passive, but not active, avoidance learning in rats, Brain Res. 1208, 150-159 (2008).
Clément, Y. et al., Gabra5-gene haplotype block associated with behavioral properties of the full agonist benzodiazepine chlordiazepoxide, Behav. Brain Res. 233, 474-482 (2012).
Heldt, S.A. and Ressler, K.J., Training-induced changes in the expression of GABAA-associated genes in the amygdala after the acquisition and extinction of Pavlovian fear, Eur. J. Neurosci. 26, 3631-3644 (2007).
Tasan, R.O. et al., Altered GABA transmission in a mouse model of increased trait anxiety, Neuroscience 183, 71-80 (2011).
Hubert Maehr, A Proposed New Convention for Graphic Presentation of Molecular Geometry and Topography, J. Che. Ed. 1985, 62: 114-120.
Bonica et al., The Management of Pain, vol. 1(2), Philadelphia, Lea and Feboger, 1990.
I. Lecker, Y. Yin, D. S. Wang and B. A. Orser, (2013) Potentiation of GABAA receptor activity by volatile anaesthetics is reduced by α5GABAA receptor-preferring inverse agonists, British Journal of Anaesthesia 110 (S1): i73-i81.
Pharmaceutical Bulletin, 1958, vol. 6, p. 641.
Farrant M. et al., (2005) Variations on an inhibitory theme: phasic and tonic activation of GABA(A) receptors, Nat Rev Neurosci 6: 215-229.
Yeung et al., (2003) Tonically activated GABAA receptors in hippocampal neurons are high-affinity, low-conductance sensors for extracellular GABA, Mol Pharmacol; 63: 2-8.
K. Y. Lee et al., Upregulation of high-affinity GABA(A) receptors in cultured rat dorsal root ganglion neurons, Neuroscience 208 (2012) 133-142.
Aug. 13, 2025 First Office Action issued in Indian Patent Application No. 202217039825.
Aug. 26, 2025 First Office Action issued in Mexican Patent Application No. MX/a/2022/007426.
Sep. 15, 2025 First Office Action issued in Colombian Patent Application No. NC2022/0009489.
Oct. 7, 2025 First Office Action issued in Philippine Patent Application No. 1-2022-551483.
Oct. 14, 2025 Third Office Action issued in Canadian Patent Application No. 3,161,739.
Mar. 9, 2026 Hearing Notice issued in Indian Patent Application No. 202217039825.
Feb. 20, 2026 Search Report issued in Brazilian Patent Application No. BR112022011946-1.

* cited by examiner

SUBSTITUTED [1,2,4]TRIAZOLO[4,3-b]PYRIDAZINES AS $GABA_A$ RECEPTOR MODULATORS

The present application claims the priority of Chinese patent application 201911296884.9 filed on Dec. 16, 2019. This application refers to the full text of the above Chinese patent application.

TECHNICAL FIELD

The present disclosure relates to triazolopyridazine derivatives with a regulatory function on an α5-$GABA_A$ receptor, a preparation method therefor, a pharmaceutical composition containing the triazolopyridazine derivatives, and a use thereof as a medicament.

BACKGROUND

γ-aminobutyric acid (GABA) is an important inhibitory neurotransmitter in mammal central nervous system. There are two classes of GABA receptors in nature. One is $GABA_A$ receptor, which is a member of ligand-gated ion channel superfamily, and the other is $GABA_B$ receptor, which is a member of G protein-coupled receptor superfamily. It is found that there are several subunits in mammal $GABA_A$ receptor, including α1-6, β1-4, γ1-3, δ, ε, θ and ρ1-2, among which α subunit, β subunit and γ subunit are essential for forming a complete and functional $GABA_A$ receptor, and α subunit is crucial for the combination between benzodiazepine and $GABA_A$ receptor.

The percentage of $GABA_A$ receptor that contains α5 subunit (α5-$GABA_A$ receptor) in mammal brain $GABA_A$ receptors is less than 5%. The expression level of α5-$GABA_A$ receptor in cerebral cortex is very low, while the percentage of $GABA_A$ receptor in hippocampal tissue is more than 20%. There is almost no expression in other brain regions. Considering the specific distribution and functional research of α5-$GABA_A$ receptor in hippocampal tissue, a large number of pharmaceutical companies including Roche are working on α5-$GABA_A$ receptor. Many compounds have been synthesized gradually, particularly inverse agonists for α5-$GABA_A$ receptor in hippocampal tissue, and among them α5IA and MRK-016 showed good therapeutic effects on the treatment of cognition related diseases in animal models. It is widely thought that α5-$GABA_A$ receptor inverse agonists can be used for the treatment of cognition related diseases, especially for Alzheimer's disease. The patent application US20110224278 A1 discloses α5-$GABA_A$ receptor inverse agonists can be used for the treatment of multi-infarct dementia and stoke related diseases.

In the last decade, studies have shown that the blood-brain barrier is damaged under some disease conditions, especially those neurodegenerative diseases like Alzheimer's and stroke (Zlokovic et al. *Nat Rev Neurosci.;* 12(12): 723-738). As a result, even those substances that cannot enter the brain can also play a corresponding pharmacological effect. Therefore, the inverse agonists of α5-$GABA_A$ receptors that cannot cross the blood-brain barrier can also be used to treat Alzheimer's disease and stroke.

In 2002, Xu Zhang's lab reported that the α5-$GABA_A$ receptor was mainly expressed in the small neurons and its expression level increased in the nerve cutting model (Xiao H S et al., "Identification of gene expression profile of dorsal root ganglion in the rat peripheral axotomy model of neuropathic pain." *Proc Natl Acad Sci USA. Jun.* 11, 2002; 99(12)). The patent application CN103239720A discloses that the α5-$GABA_A$ receptor also expresses in the peripheral nerves system and its expression increases dramatically in the partial nerve injury model. The α5-$GABA_A$ receptor inverse agonists act to inhibit various pains by selectively binding to the α5-$GABA_A$ receptor of the peripheral nerves system. The animal model data show that the stronger the inverse agonism of the inverse agonist, the better the pain-inhibiting effect is.

There are many researches on the detection whether a compound is an inverse agonist or an antagonist of α5-$GABA_A$ receptors. For example, in the international patent applications WO 92/22652 and WO 94/13799, combination of α5, β3 and γ2 of $GABA_A$ receptor was used to detect the binding of the compounds and the receptor. In the process of drug screening, the method developed by Goeders et al., is widely used (Goeders N E and Kuhar M J (1985) Benzodiazepine binding in vivo with [$^3$H]RO15-1788. *Life Sci* 37:345-355). There are also many researches on the detection whether a ligand which can bind with α5-$GABA_A$ receptor is an agonist, an antagonist or an inverse antagonist of α5-$GABA_A$ receptors, which can be referred to the method described by Wafford et al (Wafford K A, Whiting P J and Kemp J A (1993) Differences in affinity and efficacy of benzodiazepine receptor ligands on recombinant GABA-.sub.A receptor subtypes. *Mol. Pharmacol* 43:240-244).

The method for screening whether drugs enter the blood brain barrier is relatively wide. It has been reported that compound inhibition of ($^3$H) RO-15-1788 (a specific inverse agonist labeled with α5-GABAA receptor) binding in the brain can be detected. MRK016 can effectively inhibit ($^3$H)RO-15-1788 binding in the central nervous system, while MRK016-M3 can hardly inhibit ($^3$H)RO-15-1788 binding in the central nervous system. It can also be detected by detecting drugs in different tissues, for example, to determine whether drugs can effectively enter the blood-brain barrier by detecting the distribution ratio of drugs in the brain and plasma.

Previous studies have shown that inhibiting or decreasing the α5-$GABA_A$ receptor mediated extrasynaptic inhibition by drugs or genetic method could improve cognitive and learning ability but also cause mild anxiety like behavior. (Brickley, S. G. & Mody, I. Extrasynaptic $GABA_A$ receptors: their function in the CNS and implications for disease. Neuron 73, 23-34 (2012); Harris, D. et al. Selective influence on contextual memory: physiochemical properties associated with selectivity of benzodiazepine ligands at GABAA receptors containing the alpha5 subunit. J. Med. Chem. 51, 3788-3803 (2008).; Savic', M. M. et al. PWZ-029, a compound with moderate inverse agonist functional selectivity at GABAA receptors containing α5 subunits, improves passive, but not active, avoidance learning in rats. Brain Res. 1208, 150-159 (2008); Clement, Y. et al. Gabra5-gene haplotype block associated with behavioral properties of the full agonist benzodiazepine chlordiazepoxide. Behav. Brain Res. 233, 474-482 (2012)). There are also studies showing that fear and anxiety traits are correlated with the decrease of Gabra5 mRNA. (Heldt, S. A. & Ressler, K. J. Training-induced changes in the expression of GABAAassociated genes in the amygdala after the acquisition and extinction of Pavlovian fear. Eur. J. Neurosci. 26, 3631-3644 (2007); Tasan, R. O. et al. Altered GABA transmission in a mouse model of increased trait anxiety. Neuroscience 183, 71-80 (2011).) Paolo Botta et al., have disclosed that the α5-$GABA_A$ receptor are involved in the mechanism of fear and anxiety. Selectively knocking out the expression of α5-$GABA_A$ receptor in some brain regions could induce fear and anxiety behaviors in animals. Therefore, the previously disclosed α5-GABAA inverse agonist can cause side effects of fear and anxiety when it enters the brain, which is not suitable for application in the pharmaceutical field, and requires to be modified.

Content of the Present Invention

The present disclosure provides a triazolopyridazine derivative, a preparation method therefor, a pharmaceutical composition thereof, and a use thereof. This class of compounds have good inverse agonistic activity, thermodynamic solubility, bioavailability, and pharmacokinetic properties for α5-$GABA_A$.

The present disclosure provides a compound represented by formula I, a cis-trans isomer thereof, an enantiomer thereof, a diastereomer thereof, a racemate thereof, a solvate thereof, a hydrate thereof, a pharmaceutically acceptable salt thereof or a prodrug thereof,

I

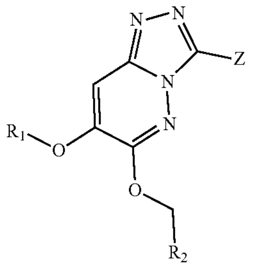

wherein, Z is a 5- or 6-membered heteroaromatic ring containing 1, 2 or 3 heteroatoms independently selected from oxygen, nitrogen and sulfur, and the heteroaromatic ring is optionally substituted by one or more $R_3$;

$R_3$ is independently halogen, cyano, $C_{1-6}$ alkyl, $C_{1-6}$ alkoxy ($C_{1-6}$ alkyl), $C_{3-6}$ cycloalkyl ($C_{1-6}$) alkoxy, $C_{3-6}$ cycloalkyl ($C_{1-6}$) alkoxy ($C_{1-6}$) alkyl, $C_{3-7}$ heterocycloalkyl, or $C_{3-7}$ heterocycloalkyl ($C_{1-6}$) alkyl, and each of which is optionally substituted by 1-4 substituents independently selected from the group consisting of halogen, cyano, hydroxyl, $C_{1-6}$ alkyl and $C_{1-6}$ alkylamino;

$R_1$ is H, $C_{1-6}$ alkyl, $C_{3-6}$ cycloalkyl, $C_{3-7}$ heterocycloalkyl, $C_{3-6}$ cycloalkyl ($C_{1-6}$) alkyl, or $C_{1-6}$ alkoxy ($C_{1-6}$) alkyl, and each of which is optionally substituted by 1-4 substituents independently selected from the group consisting of halogen, cyano, hydroxyl, $C_{1-6}$ alkyl, $C_{1-6}$ alkoxy and $C_{1-6}$ alkylamino;

$R_2$ is heterocyclyl, phenyl or heteroaryl, and each of which is optionally substituted by 1-4 substituents independently selected from the group consisting of halogen, cyano, oxo, —R, —OR, —C(O)R, —NHR, $C_{3-6}$ cycloalkenyl, —$NR_4R_5$, —C(O)$NR_4R_5$, —COOH, —$SO_2$—$C_{1-6}$ alkyl and —$SO_2NR_6R_7$;

R is independently H, $C_{1-6}$ alkyl, $C_{1-6}$ alkenyl, $C_{3-6}$ cycloalkyl, $C_{3-6}$ cycloalkenyl, heterocyclyl, aryl or heteroaryl, and each of which is optionally substituted by 1-3 R';

R' is independently halogen, cyano, hydroxyl, $C_{3-6}$ cycloalkyl, $C_{1-6}$ alkylamino, $C_{1-6}$ alkyl, ($C_{1-6}$) alkoxy, $C_{1-3}$ alkyl substituted by cyano or halogen, $C_{1-6}$ alkylsulfuryl, heterocyclyl, heteroaryl, 5- to 10-membered heteroaryl substituted by 1-3 $R'^{-1}$, —(C═O) $NR_8R_9$, $C_{3-6}$ cycloalkyl substituted by 1-3 cyano, —(C═O) $R'^{-2}$, $C_{6-18}$ aryl or 3- to 9-membered heterocyclyl substituted by 1-3 $R'^{-3}$, —$SO_2R_{10}$;

$R'^{-1}$ is independently $C_{1-6}$ alkyl;

$R_8$ and $R_9$ are independently H or $C_{1-6}$ alkyl, or $R_8$ and $R_9$ together with the nitrogen atom to which they are attached form a 5- or 6-membered heterocyclyl, and the heteroatom is selected from one or more of N, S and O, and the number of the heteroatom is 1, 2 or 3;

$R'^{-2}$ is $C_{3-6}$ cycloalkyl or $C_{1-6}$ alkyl;

$R'^{-3}$ is independently $C_{1-6}$ alkyl;

$R_{10}$ is $C_{1-6}$ alkyl;

$R_4$ and $R_5$ are independently H, $C_{1-6}$ alkyl or $C_{3-6}$ cycloalkyl, or $R_4$ and $R_5$ together with the nitrogen atom to which they are attached form a 5- or 6-membered heterocycloalkyl, and the heteroatom is selected from one or more of N, S and O, and the number of the heteroatom is 1, 2 or 3; each of $R_4$ and $R_5$ is optionally substituted by 1-5 substituents independently selected from: amino, halogen, hydroxyl, $C_{1-6}$ alkyl and $C_{1-6}$ alkoxy;

$R_6$ and $R_7$ are independently $C_{1-6}$ alkyl.

In an embodiment, in the compound I, the cis-trans isomer thereof, the enantiomer thereof, the diastereomer thereof, the racemate thereof, the solvate thereof, the hydrate thereof, the pharmaceutically acceptable salt thereof or the prodrug thereof, some groups may be defined as follows (unannotated definitions are as described in any one of the above embodiments, hereinafter referred to as in an embodiment): the formula I may be further represented by formula II,

II

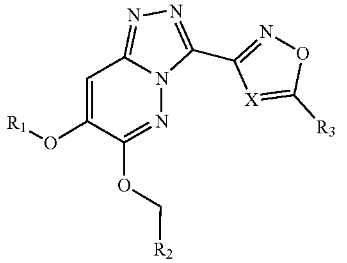

wherein, X is N or CH;

preferably, the formula II is represented by formula III, IV or V:

III

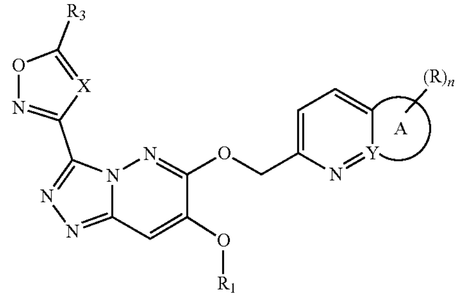

wherein, Y is C or N; A is a 5- to 6-membered heterocyclic ring, a 5- to 6-membered heteroaromatic ring or absent, and the heteroatoms in the 5- to 6-membered heterocyclic ring and the 5- to 6-membered heteroaromatic ring are independently N, and the number of the heteroatoms is 1 or 2; n is any integer from 0 to 4.

In an embodiment, when the Z is a 5-membered heteroaromatic ring containing 1, 2 or 3 heteroatoms independently selected from oxygen, nitrogen and sulfur, the 5-membered heteroaromatic ring containing 1, 2 or 3 heteroatoms independently selected from oxygen, nitrogen and sulfur is, for example, a 5-membered heteroaromatic ring containing 2 heteroatoms independently selected from oxygen, nitrogen and sulfur, for example, isoxazole, for another example,

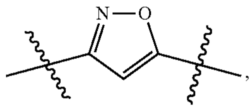 [SMILES: *c1cc(*)on1]

, for still another example,

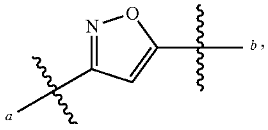 [SMILES: *c1cc(*)on1]

, the b end thereof is connected to the $R_3$.

In an embodiment, when the $R_3$ is multiple, the $R_3$ is the same or different.

In an embodiment, the number of the $R_3$ is, for example, 1 or 2.

In an embodiment, when the $R_3$ is $C_{1-6}$ alkyl, the $C_{1-6}$ alkyl is, for example, $C_{1-3}$ alkyl, for another example, methyl, ethyl, n-propyl or isopropyl, and for still another example, methyl.

In an embodiment, when the $R_3$ is $C_{1-6}$ alkoxy $C_{1-6}$ alkyl, an alkyl end thereof may be connected to the Z.

In an embodiment, when the $R_3$ is $C_{1-6}$ alkoxy $C_{1-6}$ alkyl, the $C_{1-6}$ alkoxy is, for example, $C_{1-4}$ alkoxy (such as methoxy, ethoxy, n-propoxy, isopropoxy, n-butoxy, isobutoxy, sec-butoxy or tert-butoxy), for another example, $C_{1-3}$ alkoxy (such as methoxy, ethoxy, n-propoxy, isopropoxy), and for still another example, methoxy.

In an embodiment, when the $R_3$ is $C_{1-6}$ alkoxy $C_{1-6}$ alkyl, the $C_{1-6}$ alkyl is, for example, $C_{1-4}$ alkyl (methyl, ethyl, n-propyl, isopropyl, n-butyl, isobutyl, sec-butyl or tert-butyl), for another example, $C_{1-3}$ alkyl (methyl, ethyl, n-propyl, isopropyl), and for still another example, methyl.

In an embodiment, when the $R_3$ is $C_{1-6}$ alkoxy $C_{1-6}$ alkyl, the $C_{1-6}$ alkoxy $C_{1-6}$ alkyl is, for example, $C_{1-3}$ alkoxy $C_{1-3}$ alkyl, and for another example,

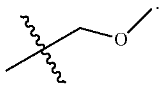 [SMILES: *COC]

.

In an embodiment, when the $R_3$ is substituted by 1-4 substituents, the number of the substituents is, for example, 1, 2, 3 or 4, and for another example, 1 or 2.

In an embodiment, when the $R_3$ is $C_{1-6}$ alkyl, the $C_{1-6}$ alkyl is, for example, $C_{1-4}$ alkyl (such as methyl, ethyl, n-propyl, isopropyl, n-butyl, isobutyl, sec-butyl or tert-butyl), for another example, $C_{1-3}$ alkyl (such as methyl, ethyl, n-propyl, isopropyl), and for still another example, methyl.

In an embodiment, when the $R_3$ is $C_{1-6}$ alkyl substituted by hydroxyl, the $R_3$ is, for example,

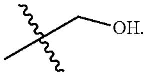 [SMILES: *CO]

.

In an embodiment, when the $R_1$ is $C_{1-6}$ alkyl, the $C_{1-6}$ alkyl is, for example, $C_{1-4}$ alkyl, for another example, methyl, ethyl, n-propyl, isopropyl, n-butyl, isobutyl, sec-butyl or tert-butyl.

In an embodiment, when the $R_1$ is substituted by halogen, the halogen is, for example, fluorine, chlorine, bromine or iodine, and for another example, fluorine.

In an embodiment, when the $R_1$ is substituted by 1-4 substituents, the number of the substituents is, for example, 1, 2, 3 or 4, and for another example, 1 or 2.

In an embodiment, when the R; is $C_{1-6}$ alkyl and the $C_{1-6}$ alkyl is substituted by 1-4 substituents, the $R_1$ is, for example, methyl substituted by two halogens, and for another example, difluoromethyl.

In an embodiment, when the $R_1$ is $C_{3-6}$ cycloalkyl ($C_{1-6}$) alkyl, the $C_{1-6}$ alkyl is, for example, $C_{1-4}$ alkyl, for another example, methyl, ethyl, n-propyl, isopropyl, n-butyl, isobutyl, sec-butyl or tert-butyl, and for still another example, methyl.

In an embodiment, when the $R_1$ is $C_{3-6}$ cycloalkyl ($C_{1-6}$) alkyl, the $C_{3-6}$ cycloalkyl is, for example, cyclopropyl, cyclobutyl, cyclopentyl or cyclohexyl, and for another example, cyclopropyl or cyclobutyl.

In an embodiment, when the $R_1$ is $C_{3-6}$ cycloalkyl ($C_{1-6}$) alkyl, the $C_{3-6}$ cycloalkyl ($C_{1-6}$) alkyl is, for example, $C_3$ cycloalkyl ($C_{1-3}$) alkyl, and for another example,

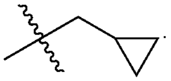 [SMILES: *CC1CC1]

.

In an embodiment, when the $R_2$ is substituted by 1-4 substituents, and a carbon atom connecting the substituent and $R_2$ is a chiral carbon atom, and the chiral carbon atom is, for example, a R configuration carbon atom or a S configuration carbon atom.

In an embodiment, when the $R_2$ is heteroaryl, the heteroaryl is, for example, a 5- to 10-membered heteroaryl, wherein the heteroatoms are nitrogen and/or oxygen, and the number of the heteroatoms is 1-4; for another example, a 5- to 6-membered monocyclic heteroaryl or a 9- to 10-membered bicyclic heteroaryl (the 9- to 10-membered bicyclic heteroaryl is, for example, a bicyclic heteroaryl of a 5- to 6-membered heteroaryl-fused a 5- to 6-membered heteroaryl, or, a bicyclic heteroaryl of a 5- to 6-membered heteroaryl-fused a 5- to 6-membered heterocyclyl), for still another example, triazolyl, pyridyl, pyridazinyl, pyrimidinyl, pyrazinyl, pyrazolopyridyl, pyrrolopyridyl, pyridopyrrolonyl, naphthyridinyl, quinolyl, imidazopyridyl, dioxinopyridyl, pyridooxazinyl, pyrazolopyrimidinyl, pyridopyrazolyl, pyridopyrrolyl, pyridopyrazolyl, pyridonyl, pyridoimidazolyl, pyridotriazolyl, pyridinyl, pyridotriazolyl, pyridazinonyl, heteronaphthyl, naphthyridinonyl, imidazopyridazinyl, indolyl, diazanaphthyl, tetrahydronaphthyridinyl or naphthyridinyl, for still another example,
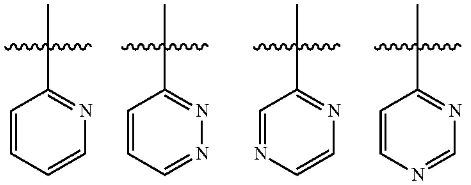
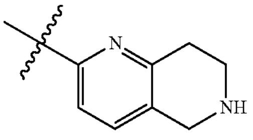
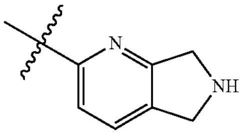
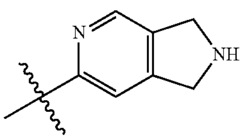
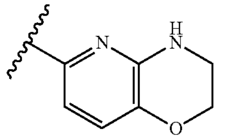
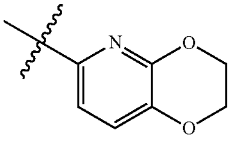
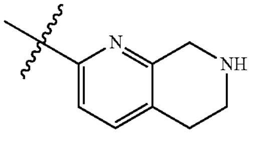
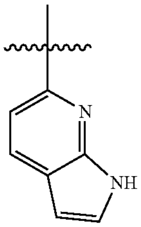
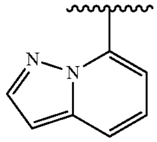
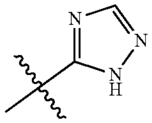
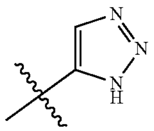
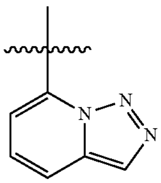
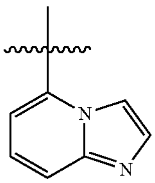
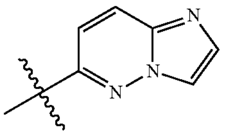
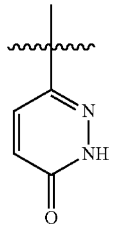
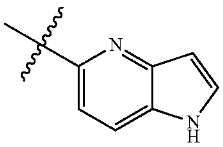
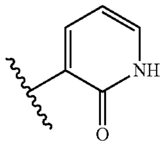
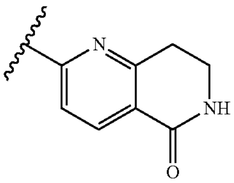
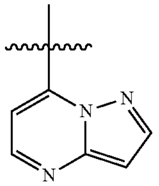
-continued
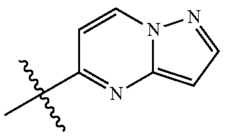
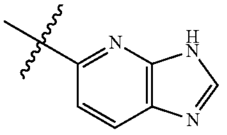
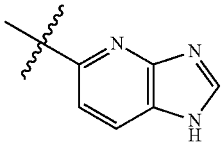
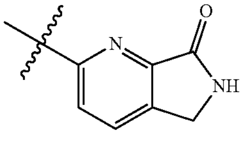
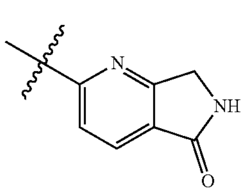
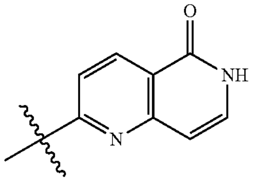
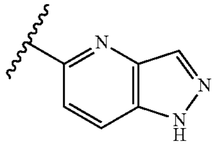
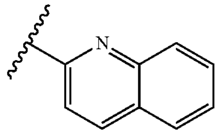
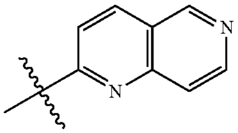
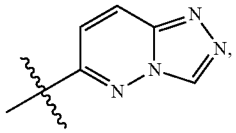
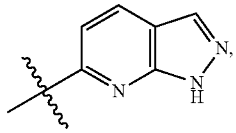
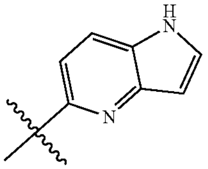
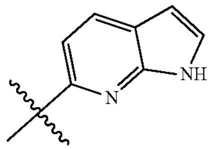
or
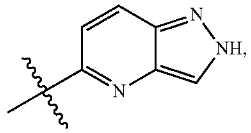
and for a further example,
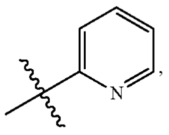
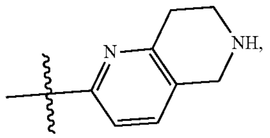
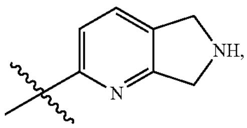
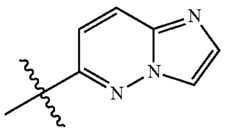
or
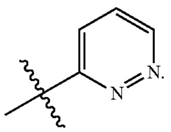
In an embodiment, when the $R_2$ is a 9- to 10-membered bicyclic heteroaryl formed by a 5- to 6-membered heteroaryl-fused a 5- to 6-membered heterocyclyl, the substitution position of the substituent is on the heteroatom in the 5- to 6-membered heterocyclyl.

In an embodiment, when the $R_2$ is substituted by 1-4 substituents, the number of the substituents is, for example, 1, 2, 3 or 4, and for another example, 1 or 2.

In an embodiment, when the $R_2$ is substituted by 2, 3 or 4 substituents, the substituents are, for example, the same or different.

In an embodiment, when the $R_2$ is substituted by halogen, the halogen is, for example, fluorine, chlorine, bromine or iodine, and for another example, fluorine or chlorine.

In an embodiment, when the Rz is substituted by $C_{3-6}$ cycloalkenyl, the $C_{3-6}$ cycloalkenyl is, for example, cyclopropenyl, cyclobutenyl, cyclopentenyl or cyclohexenyl, and for another example,

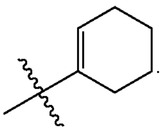

In an embodiment, when the $R_2$ is substituted by —$SO_2$—$C_{1-6}$ alkyl, the $C_{1-6}$ alkyl is, for example, $C_{1-4}$ alkyl (such as methyl, ethyl, n-propyl, isopropyl, n-butyl, isobutyl, sec-butyl or tert-butyl), for another example, $C_{1-3}$ alkyl (such as methyl, ethyl, n-propyl, isopropyl), and for still another example, methyl and ethyl.

In an embodiment, when the R is independently $C_{1-6}$ alkyl, the $C_{1-6}$ alkyl is, for example, $C_{1-4}$ alkyl, for another example, methyl, ethyl, n-propyl, isopropyl, n-butyl, isobutyl, sec-butyl or tert-butyl, for still another example, methyl, ethyl, n-propyl, isopropyl or tert-butyl.

In an embodiment, when the R is independently $C_{1-6}$ alkenyl, the $C_{1-6}$ alkenyl is, for example, $C_{2-3}$ alkenyl, and for another example, ethenyl,

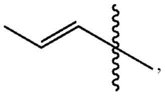,
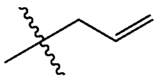
or
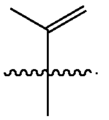

In an embodiment, when the R is independently $C_{3-6}$ cycloalkyl, the $C_{3-6}$ cycloalkyl is cyclopropyl, cyclobutyl, cyclopentyl or cyclohexyl, for example, cyclobutyl or cyclopropyl.

In an embodiment, when the R is independently heterocyclyl, the heterocyclyl is, for example, a 3- to 10-membered heterocyclyl, wherein the heteroatoms are nitrogen and/or oxygen, and the number of the heteroatoms is 1, 2 or 3, for another example, a 5- to 6-membered monoheterocyclyl or a 7- to 8-membered heterospirocyclyl, wherein the heteroatoms are nitrogen and/or oxygen, and the number of the heteroatom is 1 or 2, and for still another example, morpholinyl, pyrrolidinyl, azetidinyl, oxetanyl, piperidinyl, tetrahydropyranyl, tetrahydrofuranyl or 2-oxo-[3,3]heptyl, for yet another example,

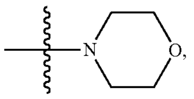
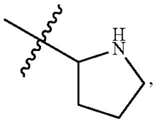
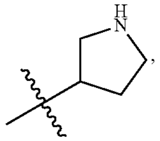
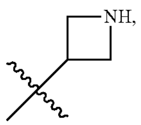
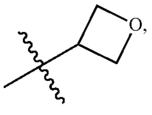
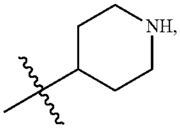
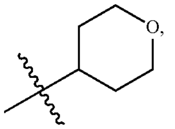
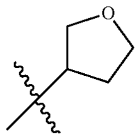
or
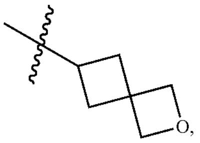

for a further example,

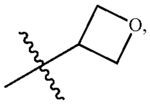
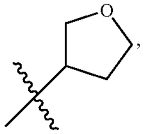
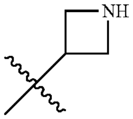
or
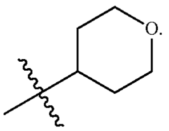

In an embodiment, when the R is $C_{3-6}$ cycloalkenyl, the $C_{3-6}$ cycloalkenyl is, for example, cyclohexenyl, cyclopropenyl or cyclobutenyl, for another example,

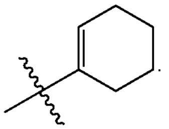 [SMILES: *C1=CCCCC1]

In an embodiment, when the R is aryl, the aryl is, for example, $C_{6-14}$ aryl, for another example, phenyl, naphthyl, phenanthryl or anthranyl, and for still another example, phenyl.

In an embodiment, when the R is heteroaryl, the heteroaryl is, for example, a 5- to 10-membered heteroaryl, wherein the heteroatom is nitrogen and/or oxygen, and the number of the heteroatom is 1, 2 or 3, for another example, a 5-membered monocyclic heteroaryl, wherein the heteroatom is nitrogen and/or oxygen, and the number of the heteroatom is 2 or 3, for still another example, pyrimidinyl, oxadiazolyl or isoxazolyl, for another example,

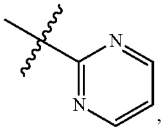, 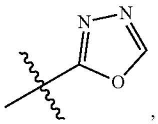, or 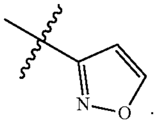.

In an embodiment, when the R' is independently halogen, the halogen is, for example, fluorine, chlorine, bromine or iodine, and for another example, fluorine.

In an embodiment, when the R' is $C_{3-6}$ cycloalkyl, the $C_{3-6}$ cycloalkyl is, for example, cyclopropyl, cyclobutyl, cyclopentyl or cyclohexyl, for example, cyclopropyl.

In an embodiment, when the R' is independently $C_{1-6}$ alkylamino, the $C_{1-6}$ alkylamino is, for example, $C_{1-3}$ alkylamino, for another example, ethylamino, for still another example, —NHEt.

In an embodiment, when the R' is independently $C_{1-6}$ alkyl, the $C_{1-6}$ alkyl is, for example, $C_{1-4}$ alkyl (such as methyl, ethyl, n-propyl, isopropyl, n-butyl, isobutyl, sec-butyl or tert-butyl), for another example, $C_{1-3}$ alkyl (methyl, ethyl, n-propyl, isopropyl), and for still another example, methyl.

In an embodiment, when the R' is independently $C_{1-6}$ alkoxy, the $C_{1-6}$ alkoxy is, for example, $C_{1-4}$ alkoxy (methoxy, ethoxy, n-propoxy, isopropoxy, n-butoxy, isobutoxy, sec-butoxy or tert-butoxy), for another example, $C_{1-3}$ alkoxy (methoxy, ethoxy, n-propoxy, isopropoxy), and for still another example, methoxy.

In an embodiment, when the R' is independently $C_{1-3}$ alkyl substituted by cyano or halogen, the $C_{1-3}$ alkyl is, for example, methyl, ethyl, n-propyl or isopropyl, for another example, methyl.

In an embodiment, when the R' is independently $C_{1-3}$ alkyl substituted by cyano or halogen, the R' is, for example,

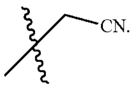 [SMILES: *CC#N]

In an embodiment, when the R' is independently $C_{1-6}$ alkylsulfuryl, the $C_{1-6}$ alkyl is, for example, $C_{1-4}$ alkyl (methyl, ethyl, n-propyl, isopropyl, n-butyl, isobutyl, sec-butyl or tert-butyl), for another example, $C_{1-3}$ alkyl (methyl, ethyl, n-propyl, isopropyl), and for still another example, methyl.

In an embodiment, when the R' is independently $C_{1-6}$ alkylsulfuryl, the $C_{1-6}$ alkylsulfuryl is, for example, $—SO_2Me$, $—CH_2CH_2SO_2Me$, and for another example, $—SO_2Me$.

In an embodiment, when the R' is independently heterocyclyl, the heterocyclyl is, for example, a 3- to 6-membered monocyclic heterocyclyl, wherein the heteroatom is nitrogen and/or oxygen, and the number of the heteroatom is 1 or 2, for another example, tetrahydrofuranyl, oxetanyl, azetidinyl, morpholinyl or piperazinyl, for still another example,

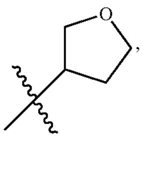, 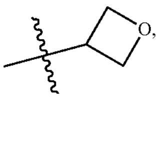 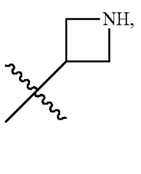

-continued

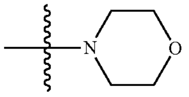 or 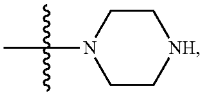

for still another example,

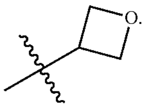 [SMILES: *C1COC1]

In an embodiment, when the R' is heteroaryl, the heteroaryl is, for example, a 5- to 10-membered heteroaryl, wherein the heteroatom is nitrogen and/or oxygen, and the number of the heteroatom is 1, 2 or 3, for another example, a 5-membered monocyclic heteroaryl, wherein the heteroatom is nitrogen and/or oxygen, and the number of the heteroatom is 2 or 3, for still another example, pyrimidinyl, oxadiazolyl or isoxazolyl, for another example,

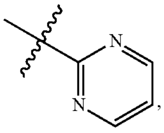, 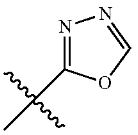 or

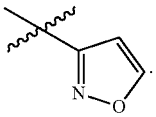

In an embodiment, when the R' is independently a 5- to 10-membered heteroaryl substituted by 1-3 $R''^{-1}$, the heteroaryl is, for example, a 5- to 6-membered heteroaryl, wherein the heteroatoms are nitrogen and/or oxygen, and the number of the heteroatoms is 1, 2 or 3, for example, oxadiazolyl, for another example,

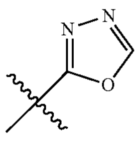 or 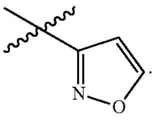

In an embodiment, when the $R''^{-1}$ is independently $C_{1-6}$ alkyl, the $C_{1-6}$ alkyl is, for example, $C_{1-4}$ alkyl (such as methyl, ethyl, n-propyl, isopropyl, n-butyl, isobutyl, sec-butyl or tert-butyl), for another example, $C_{1-3}$ alkyl (such as methyl, ethyl, n-propyl, isopropyl), and for still another example, methyl.

In an embodiment, when the R' is independently a 5- to 10-membered heteroaryl substituted by R'', the 5- to 10-membered heteroaryl substituted by $R'^{-1}$ is, for example,

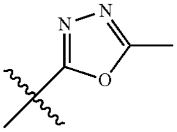 or 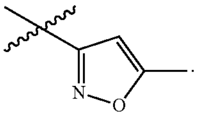.

In an embodiment, when the R' is independently $C_{3-6}$ cycloalkyl substituted by 1-3 cyano, the $C_{3-6}$ cycloalkyl is, for example, a 5-membered bicyclic bridged cycloalkyl, for another example,

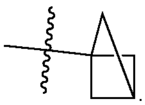 [SMILES: *C12CC(C1)C2].

In an embodiment, when the R' is independently $C_{6-14}$ aryl, the $C_{6-14}$ aryl is, for example, phenyl, naphthyl, phenanthryl or anthranyl, for another example, phenyl.

In an embodiment, when the R' is independently a 3- to 6-membered heterocyclyl substituted by 1-3 $R'^{-3}$, the 3- to 6-membered heterocyclyl is, for example, a 4- to 6-membered monobeterocyclyl, wherein the heteroatoms are nitrogen and/or oxygen, and the number of the heteroatoms is 1 or 2, for another example, piperazinyl or oxetanyl, for still another example,

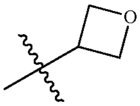 or 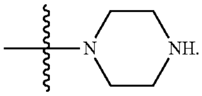.

In an embodiment, when the $R'^{-3}$ is independently $C_{1-6}$ alkyl, the $C_{1-6}$ alkyl is, for example, $C_{1-4}$ alkyl (such as methyl, ethyl, n-propyl, isopropyl, n-butyl, isobutyl, sec-butyl or tert-butyl), for another example, $C_{1-3}$ alkyl (such as methyl, ethyl, n-propyl, isopropyl), and for still another example, methyl.

In an embodiment, when the R' is independently a 3- to 6-membered heterocyclyl substituted by 1-3 $R'^{-3}$, the 3- to 6-membered heterocyclyl substituted by 1-3 $R'^{-3}$ is, for example,

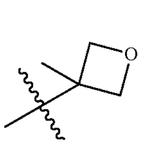 or 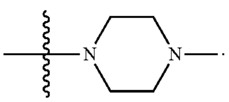.

In an embodiment, when the $R_8$ and $R_9$ are independently $C_{1-6}$ alkyl, the $C_{1-6}$ alkyl is, for example, $C_{1-4}$ alkyl (such as methyl, ethyl, n-propyl, isopropyl, n-butyl, isobutyl, sec-butyl or tert-butyl), for another example, $C_{1-3}$ alkyl (such as methyl, ethyl, n-propyl or isopropyl), and for still another example, methyl.

In an embodiment, when the $R_8$ and $R_9$ together with the nitrogen atom to which they are attached form a 5- or 6-membered heterocyclyl, the 5- or 6-membered heterocyclyl is, for example,

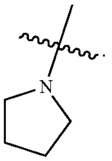.

In an embodiment, when the $R_{10}$ is $C_{1-6}$ alkyl, the $C_{1-6}$ alkyl is, for example, $C_{1-4}$ alkyl (such as methyl, ethyl, n-propyl, isopropyl, n-butyl, isobutyl, sec-butyl or tert-butyl), for another example, $C_{1-3}$ alkyl (such as methyl, ethyl, n-propyl, isopropyl), and for still another example, methyl.

In an embodiment, when the $R_4$ and $R_5$ are independently $C_{1-6}$ alkyl, the $C_{1-6}$ alkyl is, for example, $C_{1-4}$ alkyl, for another example, methyl, ethyl, n-propyl, isopropyl, n-butyl, isobutyl, sec-butyl or tert-butyl, for still another example, methyl, ethyl and n-propyl.

In an embodiment, when the $R_4$ and $R_5$ are independently $C_{3-6}$ cycloalkyl, the $C_{3-6}$ cycloalkyl is, for example, cyclopropyl, cyclobutyl, cyclopentyl or cyclohexyl, and for another example, cyclohexyl.

In an embodiment, when the $R_4$ and $R_5$ together with the nitrogen atom to which they are attached form a 5- or 6-membered heterocycloalkyl, the 5- or 6-membered heterocycloalkyl is, for example,

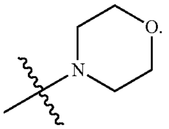 [SMILES: *N1CCOCC1].

In an embodiment, when the $R_4$ and $R_5$ are substituted by 1-5 substituents, and the substituents are independently halogen, the halogen is, for example, fluorine, chlorine, bromine or iodine, and for another example, fluorine.

In an embodiment, when the $R_4$ and $R_5$ are substituted by 1-5 substituents, the number of the substituents is, for example, 1, 2, 3, 4 or 5, and for another example, 1 or 2 or 3.

In an embodiment, when the $R_4$ and $R_5$ are independently substituted by 1-5 substituents, the $R_4$ and $R_5$ are independently, for example,

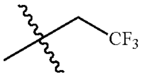 or 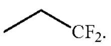.

In an embodiment, when the $R_6$ and $R_7$ are independently $C_{1-6}$ alkyl, the $C_{1-6}$ alkyl is, for example, $C_{1-4}$ alkyl (such as methyl, ethyl, n-propyl, isopropyl, n-butyl, isobutyl, sec-butyl or tert-butyl), for another example, $C_{1-3}$ alkyl (such as methyl, ethyl, n-propyl, isopropyl), and for still another example, methyl.

In an embodiment, when the $R_2$ is substituted by 1-4 substituents and the substituents are —R, the —R is —$C_{1-6}$ alkyl, —$C_{1-6}$ alkenyl, —$C_{3-6}$ cycloalkyl, -heterocyclyl, -aryl or -heteroaryl.

In an embodiment, when the $R_2$ is substituted by 1-4 substituents and the substituents are —OR, the —OR is —O—$C_{1-6}$ alkyl or —O-heterocyclyl.

In an embodiment, when the $R_2$ is substituted by 1-4 substituents and the substituents are —C(O)R, the —C(O)R is —C(O)—$C_{1-6}$ alkyl, —C(O)—$C_{1-6}$ alkenyl, —C(O)—$C_{3-6}$ cycloalkyl or —C(O)-aryl.

In an embodiment, $R_3$ is independently $C_{1-6}$ alkyl or $C_{1-6}$ alkoxy ($C_{1-6}$) alkyl; $R_3$ is optionally substituted by 1-4 hydroxyl.

In an embodiment, $R_3$ is methyl,

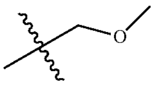 or 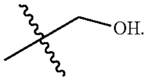

In an embodiment, —Z is a 5-membered heteroaromatic ring containing 2 heteroatoms independently selected from oxygen and nitrogen.

In an embodiment, —Z is

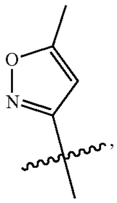, 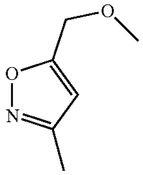 or 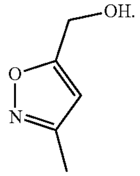

In an embodiment, $R_1$ is $C_{1-6}$ alkyl or $C_{3-6}$ cycloalkyl ($C_{1-6}$) alkyl, and $R_1$ is optionally substituted by 1-4 halogens.

In an embodiment, $R_1$ is methyl, ethyl,

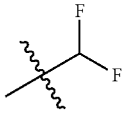 or 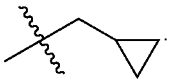

In an embodiment, $R_2$ is phenyl or heteroaryl; the heteroaryl is a 5- to 10-membered heteroaryl, wherein the heteroatoms are nitrogen and/or oxygen, and the number of heteroatoms is 1-4; preferably a 5- to 6-membered monocyclic heteroaryl or a 9- to 10-membered bicyclic heteroaryl.

In an embodiment, $R_2$ is pheny, triazolyl, pyridyl, pyridazinyl, pyrimidinyl, pyrazinyl, pyrazolopyridyl, pyrrolopyridyl, pyridopyrrolonyl, naphthyridinyl, quinolyl, imidazopyridyl, dioxinopyridyl, pyridooxazinyl, pyrazolopyrimidinyl, pyridopyrazolyl, pyridopyrrolyl, pyridopyrazolyl, pyridonyl, pyridoimidazolyl, pyridotriazolyl, pyridinyl, pyridotriazolyl, pyridazinonyl, heteronaphthyl, naphthyridinonyl, imidazopyridazinyl, indolyl, or diazanaphthyl, preferably pyridyl, pyridazinyl,

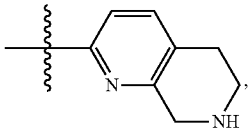, 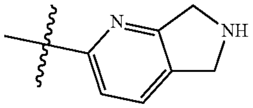 or

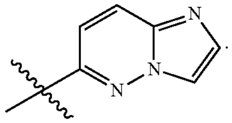

In an embodiment, the $R_2$ is optionally substituted by 1-4 substituents independently selected from the group consisting of halogen, cyano, oxo, —R, —OR, —NHR, $C_{3-6}$ cycloalkenyl, —$NR_4R_5$, —$SO_2$—$C_{1-6}$ alkyl and —$SO_2NR_6R_7$, preferably cyano, —R and —OR.

In an embodiment, the $R_2$ is substituted by 1-4 substituents independently selected from the group consisting of Me, -Et, -iPr, —$CF_3$, —$OCF_3$, —$OCHF_2$, —Cl, —F, —CN, —OMe, —OEt, —$NMe_2$, —$CH_2CF_3$, —$(CH_2)_2CN$, —$(CH_2)_3CN$, —$CH_2NHEt$, —$OCHF_2$, —$OCH(CH_3)_2$, —$CH_2OCH_3$, —$(CH_2)_2OCH_3$, —$(CH_2)_3OCH_3$, —$SO_2Me$, —$CH_2CH_2SO_2Me$, —COOH,

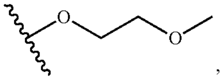, 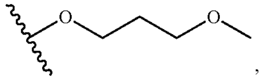,

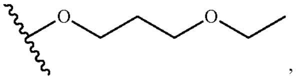,

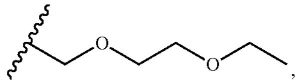,

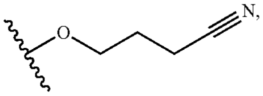 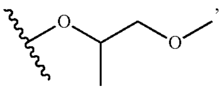,

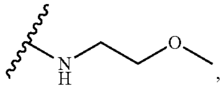, 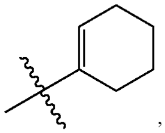, 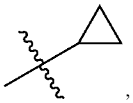,

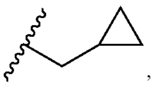, 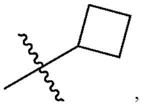, 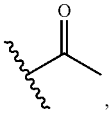,

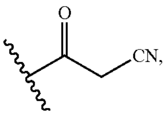 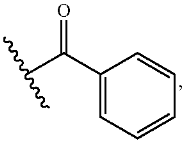, 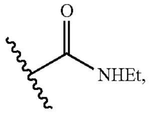

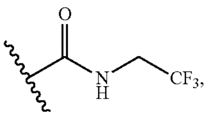 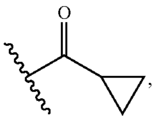, 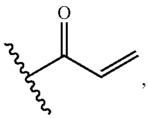,

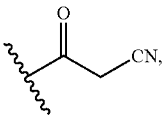 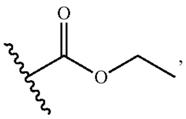,

-continued
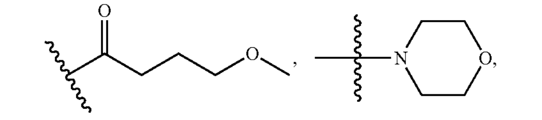
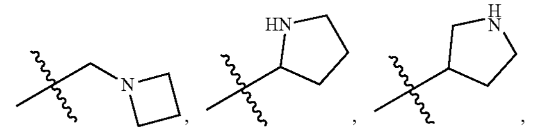
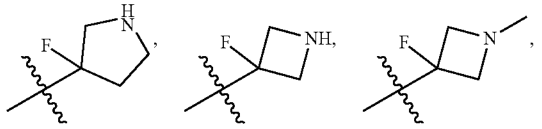
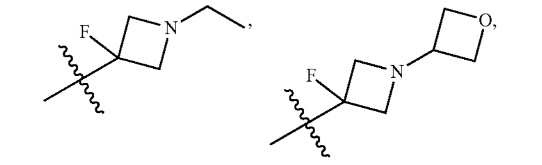
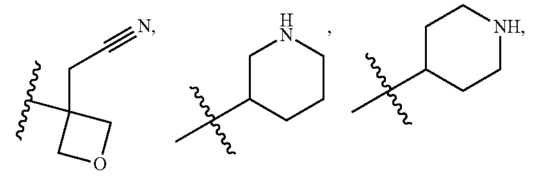
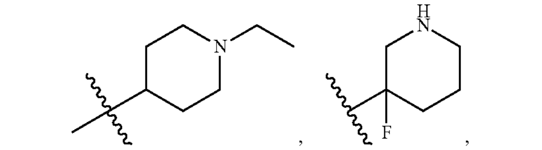
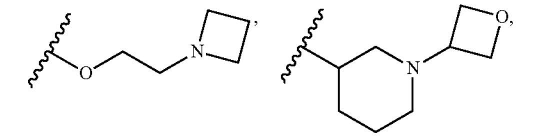
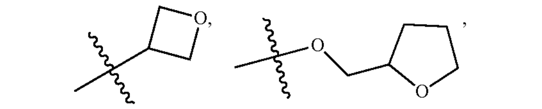
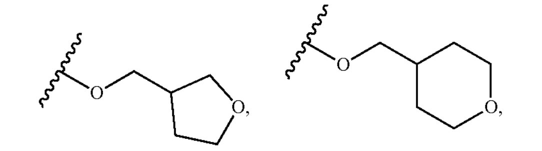
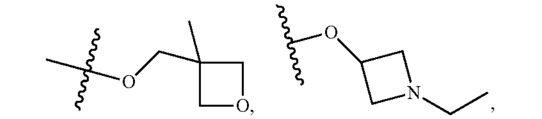
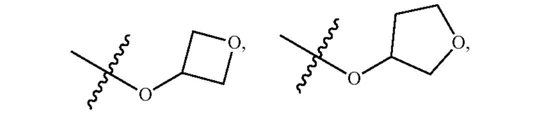
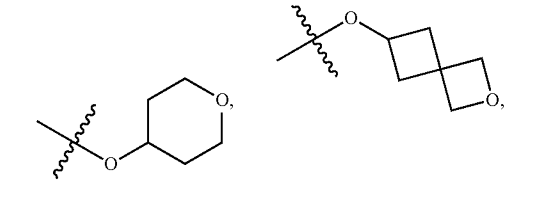
-continued
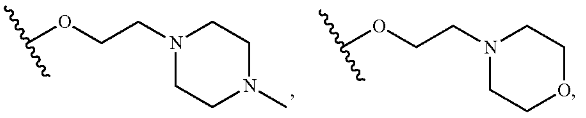
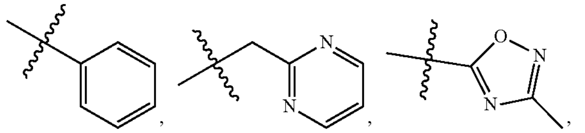
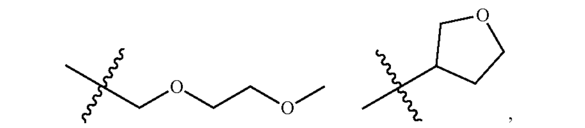
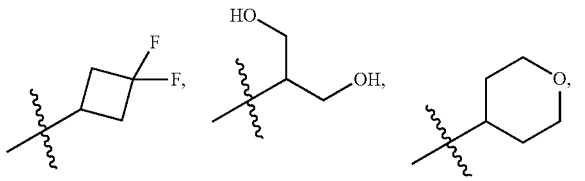
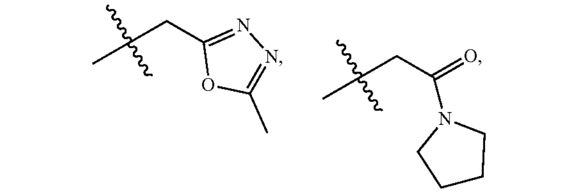
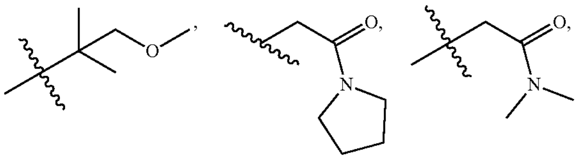
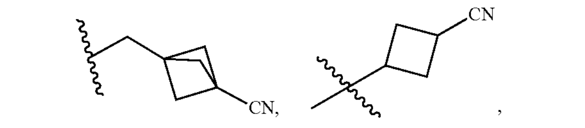
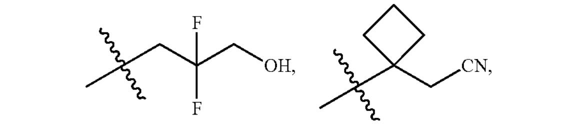
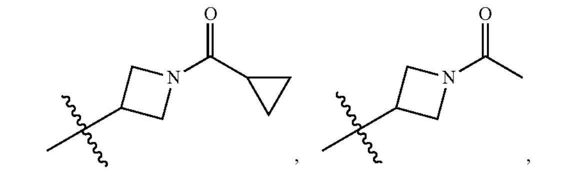
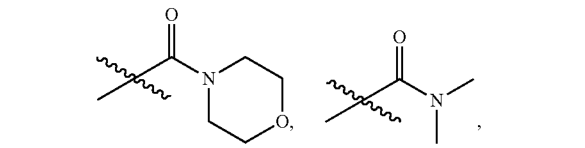
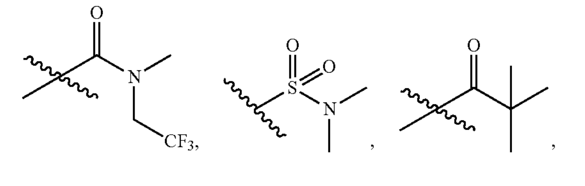

-continued
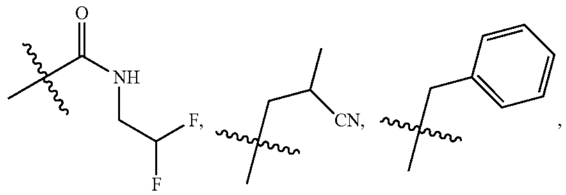
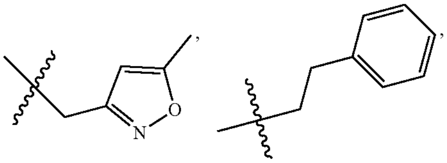
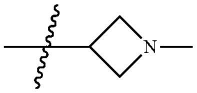
and
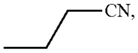
preferably, Me, -Et, -iPr, —$CF_3$, —$OCF_3$, —$OCHF_2$, —Cl, —F, —CN, —OMe, —OEt, —$NMe_2$, —$CH_2CF_3$, —$(CH_2)_3CN$, —$(CH_2)_3CN$, —$CH_2NHEt$, —$OCHF_2$, —$OCH(CH_3)_2$, —$CH_2OCH_3$, —$(CH_2)_2OCH_3$, —$(CH))_3OCH_3$, —$SO_2Me$, —$CH_2CH_2SO_2Me$, —COOH,
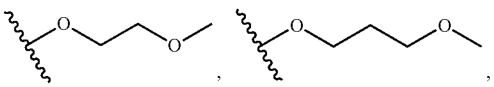
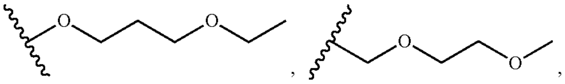
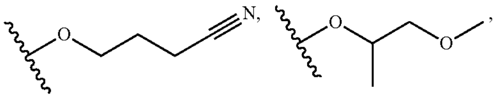
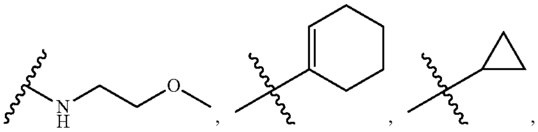
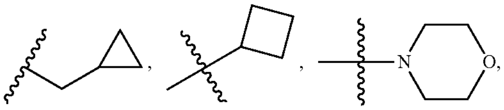
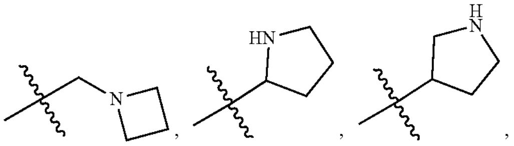
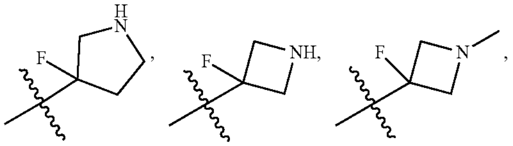
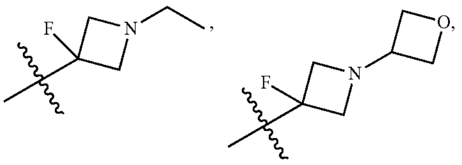
-continued
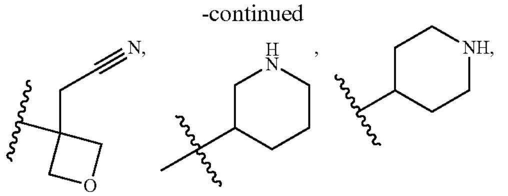
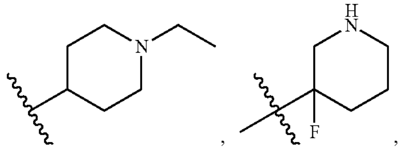
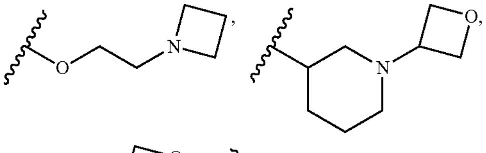
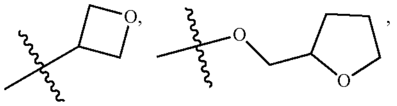
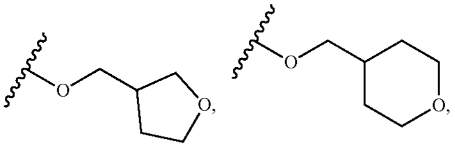
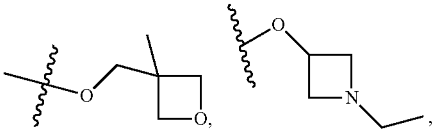
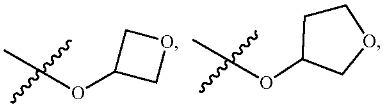
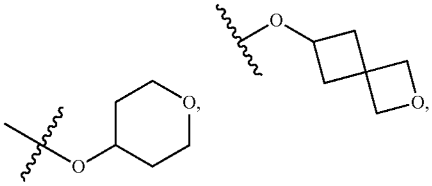
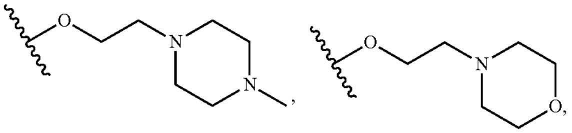
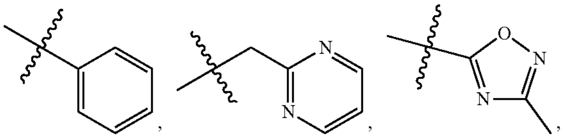
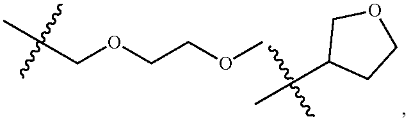
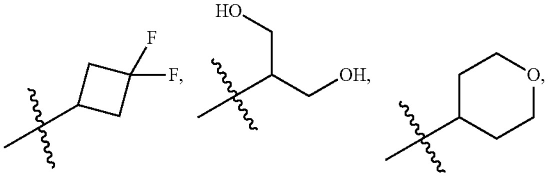

-continued

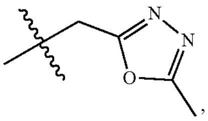, 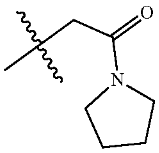,

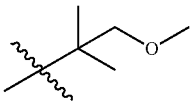, 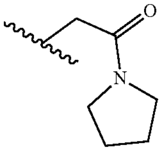, 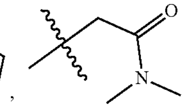,

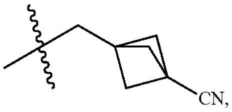

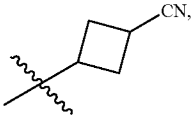 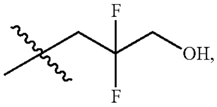

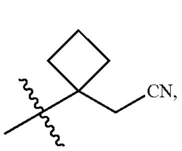 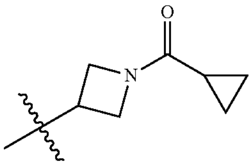,

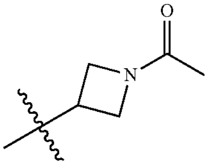, 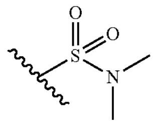,

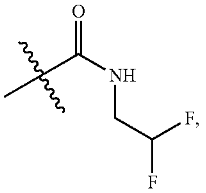 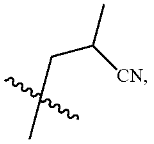 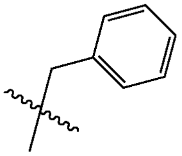,

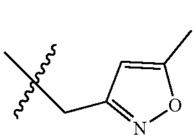, 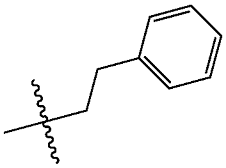,

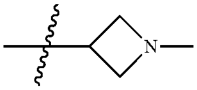, and 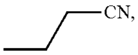

more preferably, Me, —CN,

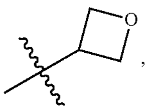, 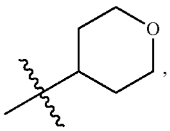, 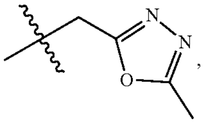,

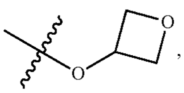, 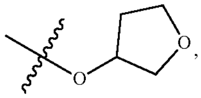,

-continued

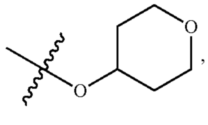, 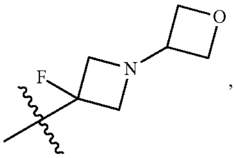,

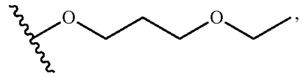, 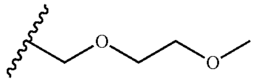

and —$CH_2OCH_3$.

In an embodiment, $R_3$ is $C_{1-6}$ alkyl or $C_{1-6}$ alkoxy $(C_{1-6})$ alkyl, and $R_3$ is optionally substituted by 1-4 hydroxyl;

$R_1$ is $C_{1-4}$ alkyl or $C_{3-6}$ cycloalkyl $(C_{1-6})$alkyl, and $R_1$ is optionally substituted by 1-4 halogens;

$R_2$ is phenyl or heteroaryl; $R_2$ is optionally substituted by 1-4 substituents independently selected from the group consisting of halogen, cyano, oxo, —R, —OR, —C(O)R, $C_{3-6}$ cycloalkenyl, —$NR_4R_5$, —C(O)$NR_4R_5$, —COOH, —$SO_2$—$C_{1-6}$ alkyl and —$SO_2NR_6R_7$; the —R is —$C_{1-6}$ alkyl, —$C_{1-6}$ alkenyl, —$C_{3-6}$ cycloalkyl, -heterocyclyl, -aryl or -heteroaryl; the —OR is —O—$C_{1-6}$ alkyl or —O-heterocyclyl; the —C(O)R is —C(O)—$C_{1-6}$ alkyl, —C(O)—$C_{1-6}$ alkenyl, —C(O)—$C_{3-6}$ cycloalkyl or —C(O)-aryl.

In an embodiment, $R_1$ is methyl, ethyl,

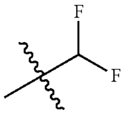 or 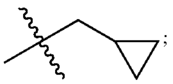;

$R_3$ is methyl,

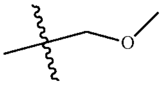 or 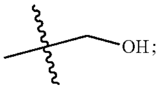;

$R_2$ is pheny, triazolyl, pyridyl, pyridazinyl, pyrimidinyl, pyrazinyl, pyrazolopyridyl, pyrrolopyridyl, pyridopyrrolonyl, naphthyridinyl, quinolyl, imidazopyridyl, dioxinopyridyl, pyridooxazinyl, pyrazolopyrimidinyl, pyridopyrazolyl, pyridopyrrolyl, pyridopyrazolyl, pyridonyl, pyridoimidazolyl, pyridotriazolyl, pyridazinonyl, heteronaphthyl, naphthyridinonyl, imidazopyridazinyl, indolyl, or diazanaphthyl, and $R_2$ is optionally substituted by 1-4 substituents independently selected from the group consisting of Me, -Et, -iPr, —$CF_3$, —$OCF_3$, —$OCHF_2$, —Cl, —F, —CN, —OMe, —OEt, —$NMe_2$, —$CH_2CF_3$, —$(CH_2)_2CN$, —$(CH_2)_3CN$, —$CH_2NHEt$, —$OCHF_2$, —$OCH(CH_3)_2$, —$CH_2OCH_3$, —$(CH_2)_2OCH_3$, —$(CH_2)_3OCH_3$, —$SO_2Me$, —$CH_2CH_2SO_2Me$, —COOH,

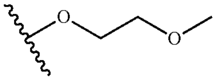, 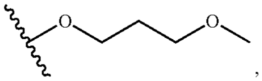,

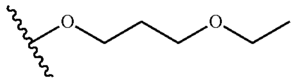, 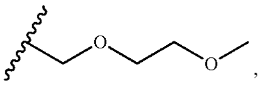,

-continued
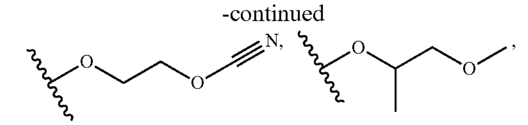
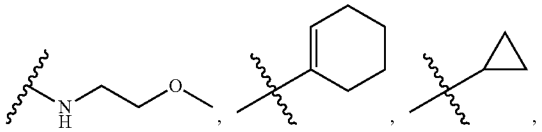
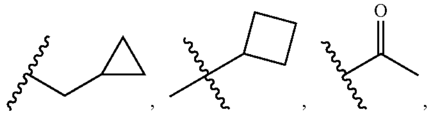
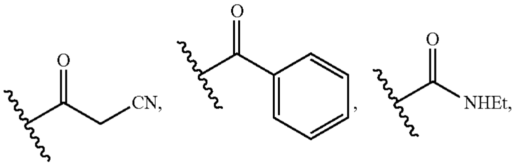
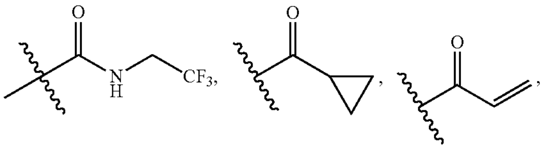
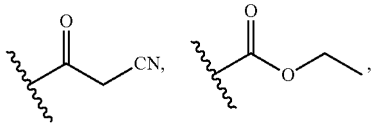
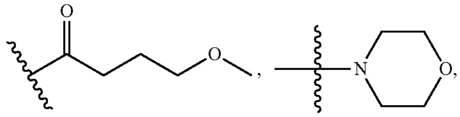
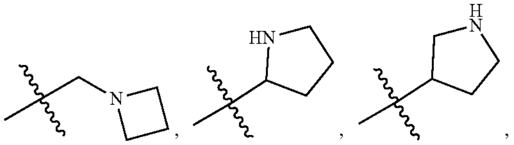
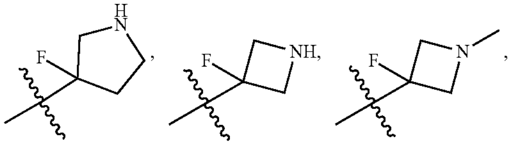
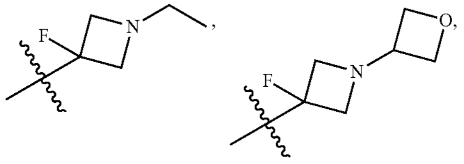
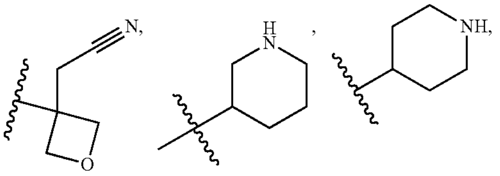
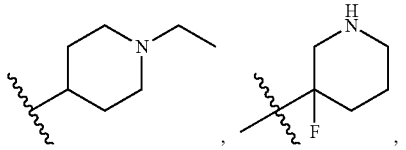
-continued
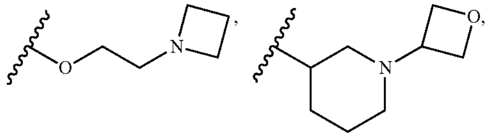
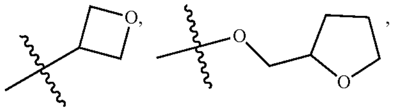
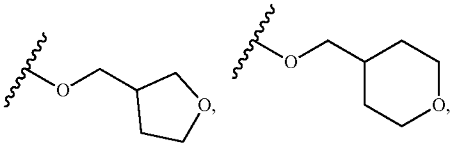
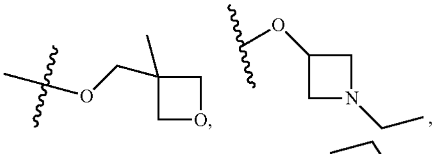
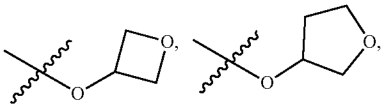
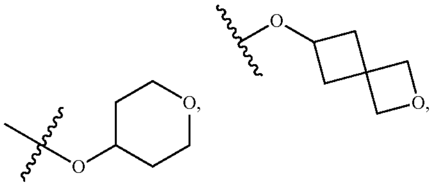
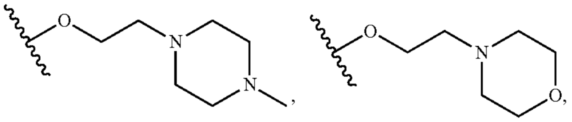
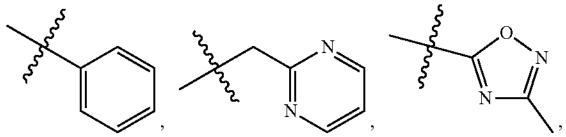
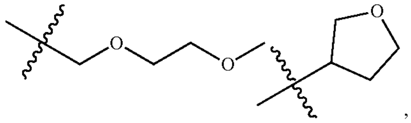
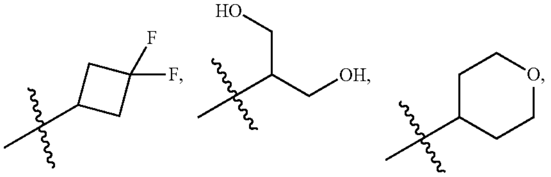
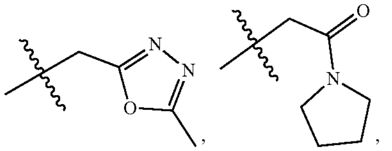
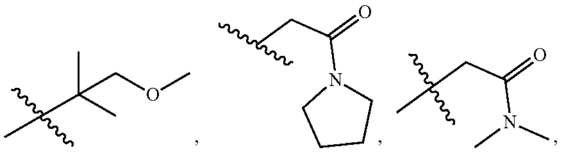

-continued

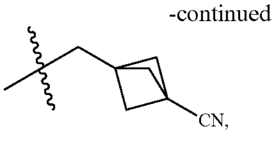

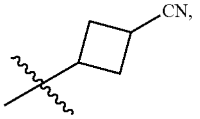

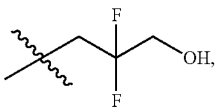

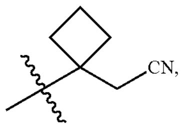

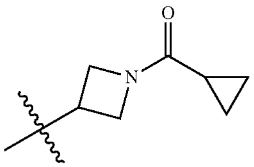
,
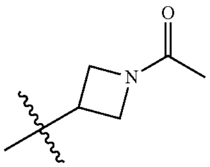
,
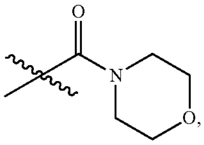

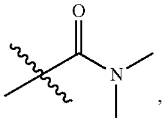
,
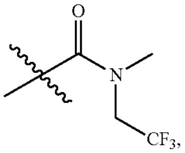

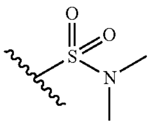
,
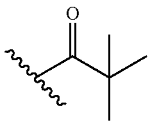
,
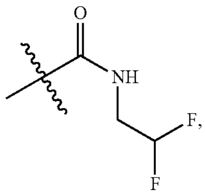

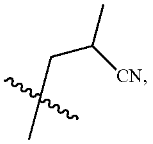

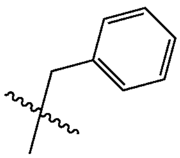
,
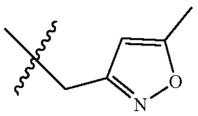
,
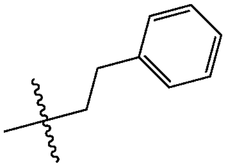
,
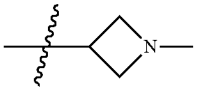
, or
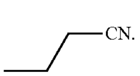

In an embodiment, $R_3$ is $C_{1-4}$ alkyl or $C_{1-6}$ alkoxy $(C_{1-6})$ alkyl, and $R_3$ is optionally substituted by 1-4 hydroxyl;

$R_1$ is $C_{1-4}$ alkyl or $C_{3-6}$ cycloalkyl $(C_{1-6})$alkyl, and $R_1$ is optionally substituted by 1-4 halogens;

$R_2$ is phenyl or heteroaryl; $R_2$ is optionally substituted by 1-4 substituents independently selected from the group consisting of halogen, cyano, oxo, —R, —OR, $C_{3-6}$ cycloalkenyl, —$NR_4R_5$, —$SO_2$—$C_{1-6}$ alkyl and —$SO_2NR_6R_7$; the —$R_1$ is —$C_{1-6}$ alkyl, —$C_{1-6}$ alkenyl, —$C_{3-6}$ cycloalkyl, -heterocyclyl, -aryl or -heteroaryl; the —OR is —O—$C_{1-6}$ alkyl or —O-heterocyclyl; the —C(O)R is —C(O)—$C_{1-6}$ alkyl, —C(O)—$C_{1-6}$ alkenyl, —C(O)—$C_{3-6}$ cycloalkyl or —C(O)-aryl.

In an embodiment, $R_3$ is $C_{1-6}$ alkyl or $C_{1-6}$ alkoxy $(C_{1-6})$ alkyl, and $R_3$ is optionally substituted by 1-4 hydroxyl;

$R_1$ is $C_{1-6}$ alkyl or $C_{3-6}$ cycloalkyl $(C_{1-6})$alkyl, and $R_1$ is optionally substituted by 1-4 halogens;

$R_2$ is phenyl or heteroaryl, and the heteroaryl is a 5- to 6-membered monocyclic heteroaryl or a 9- to 10-membered bicyclic heteroaryl, and the 9- to 10-membered bicyclic heteroaryl is a heteroaryl of a 5- to 6-membered heteroaryl-fused a 5- to 6-membered heteroaryl;

$R_2$ is optionally substituted by 1-4 substituents independently selected from the group consisting of halogen, cyano, oxo, —R, —OR, $C_{3-6}$ cycloalkenyl, —$NR_4R_5$, —$SO_2$—$C_{1-6}$ alkyl and —$SO_2NR_6R_7$; the —R is —$C_{1-6}$ alkyl, —$C_{1-6}$ alkenyl, —$C_{3-6}$ cycloalkyl, -heterocyclyl, -aryl or -heteroaryl; the —OR is —O—$C_{1-6}$ alkyl or —O-heterocyclyl; the —C(O)R is —C(O)—$C_{1-6}$ alkyl, —C(O)—$C_{1-6}$ alkenyl, —C(O)—$C_{3-6}$ cycloalkyl or —C(O)-aryl.

In an embodiment, $R^3$ is $C_{1-6}$ alkyl;

$R_1$ is $C_{1-6}$ alkyl;

$R_2$ is heteroaryl, and the heteroaryl is a bicyclic 9- to 10-membered heteroaryl of a 5- to 6-membered heteroaryl-fused a 5- to 6-membered heterocyclyl;

$R_2$ is optionally substituted by 1-4 substituents independently selected from the group consisting of halogen, cyano, oxo, —R, —OR, $C_{3-6}$ cycloalkenyl, —$NR_4R_5$, —$SO_2$—$C_{1-6}$ alkyl and —$SO_2NR_6R_7$; the —R is —$C_{1-6}$ alkyl, —$C_{1-6}$ alkenyl, —$C_{3-6}$ cycloalkyl, -heterocyclyl, -aryl or -heteroaryl; the —OR is —O—$C_{1-6}$ alkyl or —O-heterocyclyl; the —C(O)R is —C(O)—$C_{1-6}$ alkyl, —C(O)—$C_{1-6}$ alkenyl, —C(O)—$C_{3-6}$ cycloalkyl or —C(O)-aryl.

In an embodiment, $R_1$ is $C_{1-6}$ alkyl (such as methyl, ethyl, n-propyl, isopropyl, n-butyl, isobutyl, sec-butyl or tert-butyl);

$R_3$ is $C_{1-6}$ alkyl (such as methyl, ethyl, n-propyl or isopropyl, for another example, methyl);

$R_2$ is a heteroaryl; the heteroaryl is a 5- to 10-membered heteroaryl, the heteroatom is N, and the number of the heteroatom is 1, 2 or 3 (for example, a 5- to 6-membered monocyclic heteroaryl or a 9- to 10-membered bicyclic heteroaryl; for another example, pyridyl, pyrazolopyridyl, tetrahydronaphthyridinyl, pyrrolopyridyl, pyridazinyl or imidazopyridazinyl; and for still another example,

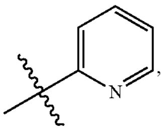
,
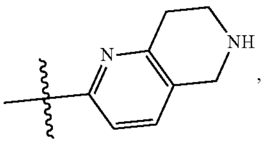
,
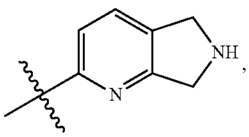
,
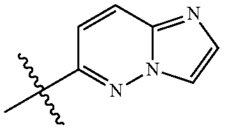
or
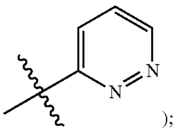
);

$R_2$ is optionally substituted by 1-4 substituents independently selected from the group consisting of cyano, —R or —OR;

R is independently $C_{1-6}$ alkyl (for example, methyl, ethyl, n-propyl, isopropyl, n-butyl, isobutyl, sec-butyl or tert-butyl, for another example, methyl, ethyl, n-propyl, isopropyl or tert-butyl) or heterocyclyl R (for another example, a 3- to 10-membered heterocyclyl, wherein the heteroatom is nitrogen and/or oxygen, and the number of the heteroatom is 1, 2 or 3, for another example, a 5- to 6-membered monoheterocyclyl or a 7- to 8-membered heterospirocyclyl, wherein the heteroatoms are nitrogen and/or oxygen, and the number of the heteroatoms is I or 2, and for still another example, morpholinyl, pyrrolidinyl, azetidinyl, oxetanyl, piperidinyl, tetrahydropyranyl, tetrahydrofuranyl or 2-oxo-[3,3]heptyl, for yet another example,

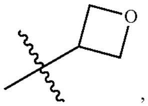 , 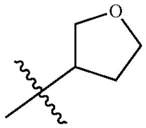 or 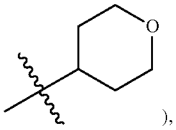 ),

R is optionally substituted by 1-3 R';

R' is independently halogen, hydroxyl, 3- to 9-membered heterocyclyl substituted by 1-3 $R'^{-3}$ (for example, 4- to 6-membered monoheterocyclyl, wherein the heteroatoms are nitrogen and/or oxygen, and the number of the heteroatoms is 1 or 2, for another example, piperazinyl or oxetanyl, for still another example,

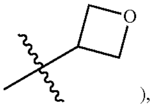 [SMILES: *C1COC1] ), 5- to 10-membered heteroaryl substituted by $R'^{-1}$ (for example,

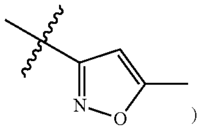 [SMILES: *c1cc(C)on1] )

or ($C_{1-6}$) alkoxy (for example, methoxy, ethoxy, n-propoxy, isopropoxy, n-butoxy, isobutoxy, sec-butoxy or tert-butoxy, for another example, methoxy, ethoxy, n-propoxy or isopropoxy, and for still another example, methoxy).

In an embodiment, $R_1$ is $C_{1-6}$ alkyl (such as methyl, ethyl, n-propyl, isopropyl, n-butyl, isobutyl, sec-butyl or tert-butyl);

$R_3$ is $C_{1-6}$ alkyl (such as methyl, ethyl, n-propyl or isopropyl, for another example, methyl);

$R_2$ is

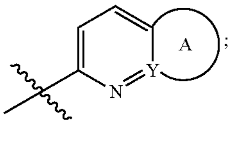 ;

Y is C or N; A is a 5- to 6-membered heterocyclic ring, and the heteroatom in the 5- to 6-membered heterocyclic ring is N, and the number of the heteroatom is 1 or 2 (for example,

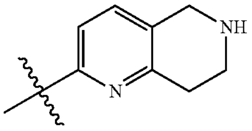 or 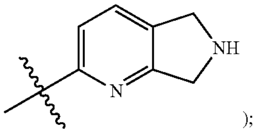 );

$R_2$ is optionally substituted by 1-4 substituents selected from $C_{1-6}$ alkyl or heterocyclyl (the heterocyclyl is, for example, a 3- to 10-membered heterocyclyl, wherein the heteroatom is nitrogen and/or oxygen, and the number of the heteroatom is 1, 2 or 3, for another example, a 5- to 6-membered monoheterocyclyl or a 7- to 8-membered heterospirocyclyl, wherein the heteroatoms are nitrogen and/or oxygen, and the number of the heteroatom is 1 or 2, and for still another example, morpholinyl, pyrrolidinyl, azetidinyl, oxetanyl, piperidinyl, tetrahydropyranyl, tetrahydrofuranyl or 2-oxo-[3,3]heptyl, for yet another example,

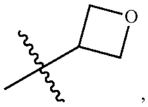 , 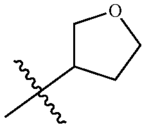 or 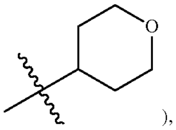 ),

R' is independently hydroxyl or a 5- to 10-membered heteroaryl substituted by 1-3 $R'^{-1}$ (for example,

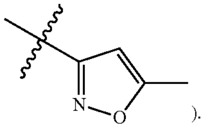 [SMILES: *c1cc(C)on1] ).

In an embodiment, $R_1$ is $C_{1-6}$ alkyl (such as methyl, ethyl, n-propyl, isopropyl, n-butyl, isobutyl, sec-butyl or tert-butyl);

$R_3$ is $C_{1-6}$ alkyl (such as methyl, ethyl, n-propyl or isopropyl, for another example, methyl);

$R_2$ is

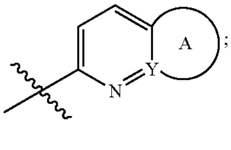 ;

Y is C or N; A is a 5- to 6-membered heterocyclic ring, and the heteroatom in the 5- to 6-membered heterocyclic ring is N, and the number of the heteroatom is 1 or 2 (for example,

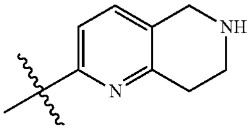 or 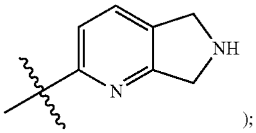 );

$R_2$ is optionally substituted by 1-4 substituents selected from $C_{1-6}$ alkyl or heterocyclyl (the heterocyclyl is, for example, a 3- to 10-membered heterocyclyl, wherein the heteroatom is nitrogen and/or oxygen, and the number of the heteroatom is 1, 2 or 3, for another example, a 5- to 6-membered monoheterocyclyl or a 7- to 8-membered heterospirocyclyl, wherein the heteroatoms are nitrogen and/or oxygen, and the number of the heteroatom is 1 or 2, and for still another example, morpholinyl, pyrrolidinyl, azetidinyl, oxetanyl, piperidinyl, tetrahydropyranyl, tetrahydrofuranyl or 2-oxo-[3,3]heptyl, for yet another example,

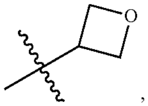
,
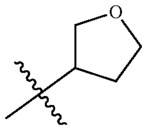
or
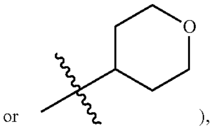
),

R' is independently hydroxyl or a 5- to 10-membered heteroaryl substituted by 1-3 $R'^{-1}$ (for example,

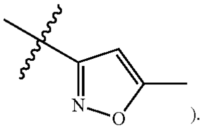
).

When $R_2$ is optionally substituted by 1-4 $C_{1-6}$ alkyl or heterocyclyl, the position of the substitution is on a heteroatom of an A ring.

In an embodiment, in the compound I, the cis-trans isomer thereof, the enantiomer thereof, the diastereomer thereof, the racemate thereof, the solvate thereof, the hydrate thereof, the pharmaceutically acceptable salt thereof or the prodrug thereof, some groups may be defined as follows (unannotated definitions are described in any one of the above embodiments):

(I)

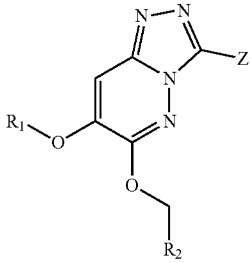

wherein, Z is a 5- or 6-membered heteroaromatic ring containing 1, 2 or 3 heteroatoms independently selected from oxygen, nitrogen and sulfur, and the heteroaromatic ring is optionally substituted by one or more $R_3$;

$R_3$ is selected from halogen, cyano, $C_{1-6}$ alkyl, $C_{1-6}$ alkoxy ($C_{1-6}$ alkyl), $C_{3-6}$ cycloalkyl ($C_{1-6}$) alkoxy, $C_{3-6}$ cycloalkyl ($C_{1-6}$) alkoxy ($C_{1-6}$) alkyl, $C_{3-7}$ heterocycloalkyl, $C_{3-7}$ heterocycloalkyl ($C_{1-6}$) alkyl, and each of which is optionally substituted by 1-4 substituents independently selected from the group consisting of halogen, cyano, hydroxyl, $C_{1-6}$ alkyl and $C_{1-6}$ alkylamino;

$R_1$ is selected from H, $C_{1-6}$ alkyl, $C_{3-6}$ cycloalkyl, $C_{3-7}$ heterocycloalkyl, $C_{3-6}$ cycloalkyl ($C_{1-6}$) alkyl, $C_1$-6 alkoxy ($C_{1-6}$) alkyl, and each of which is optionally substituted by 1-4 substituents independently selected from the group consisting of halogen, cyano, hydroxyl, $C_{1-6}$ alkyl, $C_{1-6}$ alkoxy and $C_{1-6}$ alkylamino;

$R_2$ is heterocyclyl, phenyl or heteroaryl;

$R_2$ is optionally substituted by 1-4 substituents independently selected from the group consisting of halogen, cyano, oxo, —R, —OR, —C(O)R, —NHR, $C_{3-6}$ cycloalkenyl, $—NR_4R_5$, $—C(O)NR_4R_5$, —COOH, $—SO_2—C_{1-6}$ alkyl;

R is selected from H, $C_{1-6}$ alkyl, $C_{1-4}$ alkenyl, $C_{3-6}$ cycloalkyl, heterocyclyl, aryl, and heteroaryl, and each of which is optionally substituted by 1-3 R';

R' is selected from halogen, cyano, hydroxyl, $C_{3-6}$ cycloalkyl, $C_{1-6}$ alkylamino, $C_{1-6}$ alkyl, ($C_{1-6}$) alkoxy, cyano or $C_{1-3}$ alkyl substituted by halogen, $C_{1-6}$ alkylsulfuryl, heterocyclyl, heteroaryl;

$R_4$ or $R_5$ is independently H or $C_{1-6}$ alkyl, and each of which is optionally substituted by 1-5 substituents, the substituents are independently selected from amino, halogen, hydroxyl, $C_{1-6}$ alkyl, and $C_{1-6}$ alkoxy.

In an embodiment, in the compound I, the cis-trans isomer thereof, the enantiomer thereof, the diastereomer thereof, the racemate thereof, the solvate thereof, hydrate thereof, the pharmaceutically acceptable salt thereof or the prodrug thereof, some groups may be defined as follows (unannotated definitions are described in any one of the above embodiments):

the formula I may be further represented by formula II, (II)

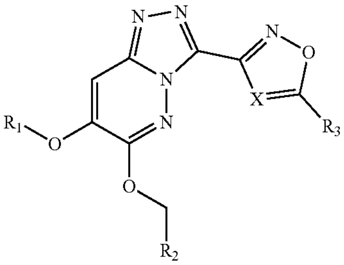

In an embodiment, when the Z is a 5-membered heteroaromatic ring containing 1, 2 or 3 heteroatoms independently selected from oxygen, nitrogen and sulfur, the 5-membered heteroaromatic ring containing 1, 2 or 3 heteroatoms independently selected from oxygen, nitrogen and sulfur is, for example, a 5-membered heteroaromatic ring containing 2 heteroatoms independently selected from oxygen, nitrogen and sulfur, for example, isoxazole, for another example,

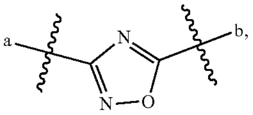

for still another example,

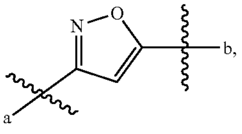

the b end thereof is connected to the $R_3$.

In an embodiment, when the $R_3$ is $C_{1-6}$ alkyl, the $C_{1-6}$ alkyl is, for example, $C_{1-3}$ alkyl, for another example, methyl, ethyl, n-propyl or isopropyl, and for still another example, methyl.

In an embodiment, when the $R_3$ is $C_{1-6}$ alkoxy $C_{1-6}$ alkyl, an alkyl end thereof may be connected to the Z.

In an embodiment, when the $R_3$ is $C_{1-6}$ alkoxy $C_{1-6}$ alkyl, the $C_{1-6}$ alkoxy is, for example, $C_{1-3}$ alkoxy, for another example, methoxy, ethoxy, n-propoxy, isopropoxy, and for still another example, methoxy.

In an embodiment, when the $R_3$ is $C_{1-6}$ alkoxy $C_{1-6}$ alkyl, the $C_{1-6}$ alkyl is, for example, $C_{1-3}$ alkyl, for another example, methyl, ethyl, n-propyl or isopropyl, and for still another example, methyl.

In an embodiment, when the $R_3$ is $C_{1-6}$ alkyl substituted by hydroxyl, the $C_{1-6}$ alkyl is $C_{1-3}$ alkyl, for another example, methyl, ethyl, n-propyl or isopropyl, and for still another example, methyl.

In an embodiment, when the $R_3$ is substituted by one or more substituents, the number of the substituents is, for example, 1, 2, 3, 4 or 5, and for another example, 1 or 2.

In an embodiment, when the Z is substituted by one or more $R_3$, the number of the substituents is, for example, 1, 2, 3, 4 or 5, and for another example, 1 or 2.

In an embodiment, when the $R_1$ is $C_{1-6}$ alkyl, the $C_{1-6}$ alkyl is, for example, $C_{1-3}$ alkyl, for another example, methyl, ethyl, n-propyl or isopropyl, and for still another example, methyl or ethyl.

In an embodiment, when the $R_1$ is $C_{3-6}$ cycloalkyl ($C_{1-6}$) alkyl, the $C_{1-6}$ alkyl is, for example, $C_{1-3}$ alkyl, for another example, methyl, ethyl, n-propyl or isopropyl, and for still another example, methyl.

In an embodiment, when the $R_1$ is $C_{3-6}$ cycloalkyl ($C_{1-6}$) alkyl, the $C_{3-6}$ cycloalkyl is, for example, cyclopropyl, cyclobutyl, cyclopentyl or cyclohexyl, and for another example, cyclopropyl or cyclobutyl.

In an embodiment, when the $R_1$ is substituted by halogen, the halogen is, for example, fluorine, chlorine, bromine or iodine, and for another example, fluorine.

In an embodiment, when the $R_1$ is substituted by 1-4 groups, the number of the substituents is, for example, 1, 2, 3, 4 or 5, and for another example, 1 or 2.

In an embodiment, when the $R_2$ is heteroaryl, the heteroaryl is, for example, triazolyl, pyridyl, pyridopyrrolonyl, pyridopyrrolyl, pyridopyrazolyl, pyridonyl, pyridoimidazolyl, pyridotriazolyl, pyridooxazinyl, dioxinopyridyl, pyridazinyl, pyrazinyl, pyrimidinyl, pyridazinonyl, pyrazolopyrimidinyl, heteronaphthyl, naphthyridinonyl, imidazopyridazinyl, naphthyridinyl, quinolyl, such as 1,2,4-triazolyl, diazanaphthyl, for example,

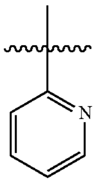
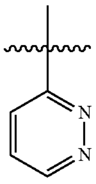
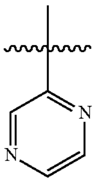
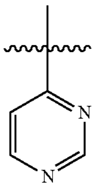
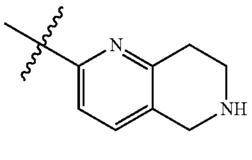
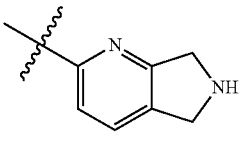

-continued

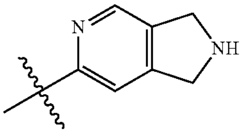
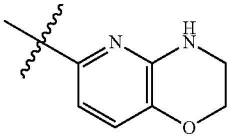
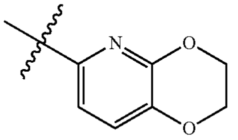
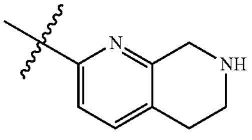
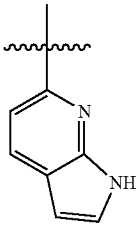
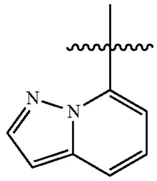
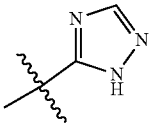
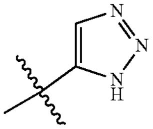
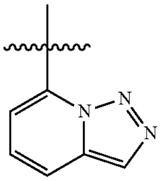
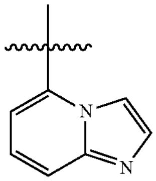
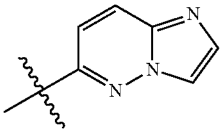
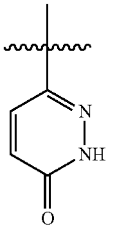
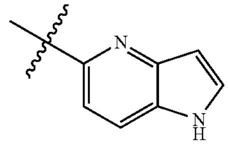
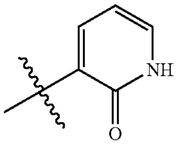
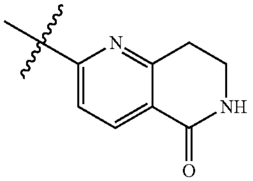
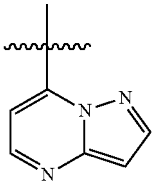
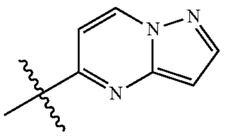
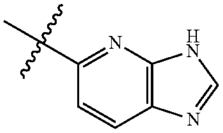
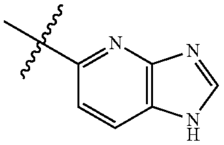
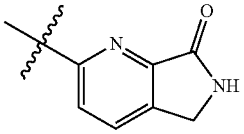
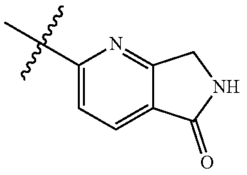
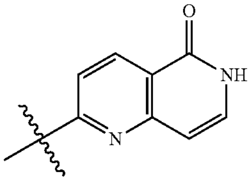

-continued

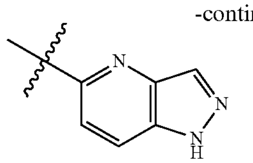
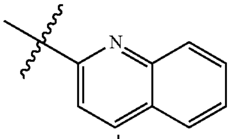
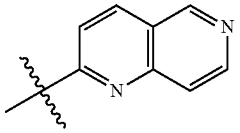
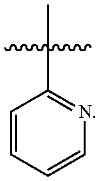

In an embodiment, when the $R_2$ is substituted by 1-4 substituents, the number of the substituents is, for example, 1, 2, 3, 4 or 5, and for another example, 1 or 2.

In an embodiment, when the $R_2$ is substituted by halogen, the halogen is, for example, fluorine, chlorine, bromine or iodine, and for another example, fluorine or chlorine.

In an embodiment, when the $R_2$ is substituted by —$SO_2$—$C_{1-6}$ alkyl, the $C_{1-6}$ alkyl is, for example, $C_{1-3}$ alkyl, for another example, methyl and ethyl.

In an embodiment, when the R is $C_{1-6}$ alkyl, the $C_{1-6}$ alkyl is, for example, $C_{1-3}$ alkyl, for another example, methyl, ethyl, n-propyl or isopropyl.

In an embodiment, when the R is $C_{1-6}$ alkoxy, the $C_{1-6}$ alkoxy is, for example, $C_{1-3}$ alkoxy, for another example, methoxy, ethoxy, n-propoxy, isopropoxy, and for still another example, methoxy.

In an embodiment, when the R is $C_{1-4}$ alkenyl, the $C_{1-6}$ alkenyl is, for example, $C_{1-3}$ alkenyl, and for another example, ethenyl or propenyl.

In an embodiment, when the R is heterocyclyl, the heterocyclyl is, for example, morpholinyl, pyrrolidinyl, azetidinyl, oxetanyl, piperidinyl, tetrahydropyranyl, tetrahydrofuranyl, spiro ring, for another example,

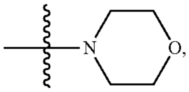
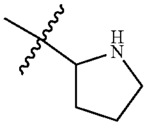 ,
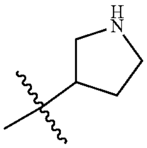 ,
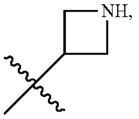
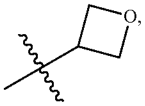
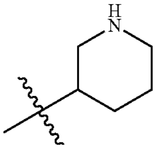 ,
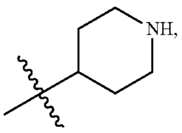
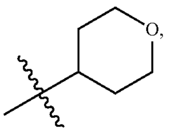
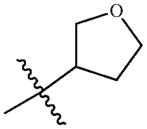 ,
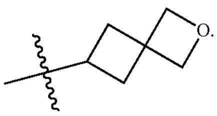

In an embodiment, when the R is $C_{3-6}$ cycloalkyl, the $C_{3-6}$ cycloalkyl is, for example, cyclohexenyl, cyclopropyl, cyclobutenyl, for another example,

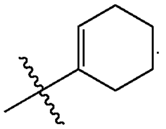

In an embodiment, when the R is heteroaryl, the heteroaryl is, for example, pyrimidinyl, oxadiazolyl, and for another example,

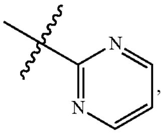 ,
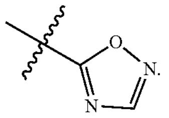

In an embodiment, when the R is substituted by 1-3 R', the number of the substituents is, for example, 1, 2, 3, 4 or 5, and for another example, 1, 2 or 3.

In an embodiment, when the R' is $C_{1-6}$ alkoxy, the $C_{1-6}$ alkoxy is, for example, $C_{1-3}$ alkoxy, for another example, methoxy, ethoxy, n-propoxy, isopropoxy, and for still another example, methoxy.

In an embodiment, when the R' is $C_{1-6}$ alkylamino, the $C_{1-6}$ alkylamino is, for example, $C_{1-3}$ alkylamino, for another example, ethylamino, for still another example, NHEt.

In an embodiment, when the R' is halogen, the halogen is, for example, fluorine, chlorine, bromine or iodine, and for another example, fluorine.

In an embodiment, when the R' is $C_{3-6}$ cycloalkyl, the $C_{3-6}$ cycloalkyl is, for example, cyclopropyl.

In an embodiment, when the R' is heteroaryl, the heteroaryl is, for example, pyrimidinyl, and for another example,

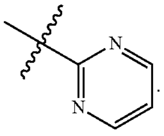 [SMILES: *c1ncccn1]

In an embodiment, when the R' is heterocyclyl, the heterocyclyl is, for example, tetrahydrofuranyl, oxetanyl, azetidinyl, morpholinyl, piperazinyl, and for another example,

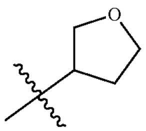 ,
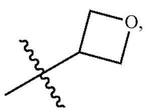
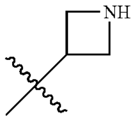 ,
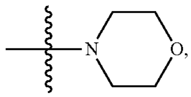
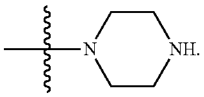

In an embodiment, when the R' is $C_{1-6}$ alkylsulfuryl, the $C_{1-6}$ alkylsulfuryl is, for example, —$SO_2Me$, —$CH_2CH_2SO_2Me$, and for another example, —$SO_2Me$.

In an embodiment, when the $R_4$ or $R_5$ is $C_{1-6}$ alkyl, the $C_{1-6}$ alkyl is, for example, $C_{1-3}$ alkyl, for another example, methyl, ethyl, n-propyl or isopropyl, and for still another example, methyl, ethyl or n-propyl.

In an embodiment, when the $R_4$ or $R_5$ is halogen, the halogen is, for example, fluorine, chlorine, bromine or iodine, and for another example, fluorine.

In an embodiment, when the $R_4$ and $R_5$ are substituted by 1-5 substituents, the substituents are, for example, halogen, for another example, fluorine, chlorine, bromine or iodine, and for still another example, fluorine.

In an embodiment, when the $R_4$ or $R_5$ are optionally substituted by 1-5 substituents, the number of the substituents is, for example, 1, 2, 3, 4 or 5, and for another example, 1 or 2 or 3.

In an embodiment, X is N or CH;

$R_1$ is selected from $C_{1-6}$ alkyl, $C_{1-6}$ alkyl substituted by halogen, $C_{1-6}$ alkyl substituted by $C_{3-6}$ cycloalkyl;

$R_3$ is selected from $C_{1-6}$ alkyl, $C_{1-6}$ alkyl substituted by hydroxyl, and $C_{1-6}$ alkyl substituted by $C_{1-6}$ alkoxy.

$R_2$ is phenyl or heteroaryl;

$R_2$ is optionally substituted by 1-4 substituents independently selected from the group consisting of halogen, cyano, oxo, —R, —OR, —C(O)R, —NHR, $C_{3-6}$ cycloalkenyl, —$NR_4R_5$, —C(O)$NR_4R_5$, —COOH, —$SO_2$—$C_{1-6}$ alkyl;

R is selected from H, $C_{1-6}$ alkyl, $C_{1-6}$ alkenyl, $C_{3-6}$ cycloalkyl, heterocyclyl, aryl, and heteroaryl, and each of which is optionally substituted by 1-3 R'.

R' is selected from halogen, cyano, hydroxyl, $C_{3-6}$ cycloalkyl, $C_{1-6}$ alkylamino, $C_{1-6}$ alkyl, ($C_{1-6}$) alkoxy, $C_{1-3}$ alkyl substituted by cyano or halogen, $C_{1-6}$ alkylsulfuryl, heterocyclyl, heteroaryl;

$R_4$ or $R_5$ is independently H or $C_{1-6}$ alkyl, and the $C_{1-6}$ alkyl may be substituted by 1-5 substituents, the substituents are independently selected from amino, halogen, $C_{1-6}$ alkoxy substituted by halogen, hydroxyl and $C_{1-6}$ alkoxy.

In an embodiment, X is N or CH;

$R_1$ is selected from $C_{1-3}$ alkyl, Cis alkyl substituted by fluorine, or $C_{1-3}$ alkyl substituted by $C_{3-6}$ cycloalkyl;

$R_3$ is selected from $C_{1-3}$ alkyl, $C_{1-3}$ alkyl substituted by hydroxyl, or $C_{1-3}$ alkyl substituted by $C_{1-3}$ alkoxy.

$R_2$ is phenyl or heteroaryl;

$R_2$ is optionally substituted by 1-4 substituents independently selected from the group consisting of halogen, cyano, oxo, —R, —OR, —C(O)R, —NHR, $C_{3-6}$ cycloalkenyl, —$NR_4R_5$, —C(O)$NR_4R_5$, —COOH, —$SO_2$—$C_{1-6}$ alkyl;

R is selected from H, $C_{1-6}$ alkyl, $C_{1-6}$ alkenyl, $C_{3-6}$ cycloalkyl, heterocyclyl, aryl, and heteroaryl, and each of which is optionally substituted by 1-3 R'.

R' is selected from halogen, cyano, hydroxyl, $C_{3-6}$ cycloalkyl, $C_{1-6}$ alkylamino, $C_{1-6}$ alkyl, ($C_{1-6}$) alkoxy, cyano or $C_{1-3}$ alkyl substituted by halogen, $C_{1-6}$ alkylsulfuryl, heterocyclyl, heteroaryl;

$R_4$ or $R_5$ is independently H or $C_{1-6}$ alkyl, and the $C_{1-6}$ alkyl may be substituted by 1-5 substituents, and the substituents are independently selected from amino, halogen, $C_{1-6}$ alkoxy substituted by halogen, hydroxyl and $C_{1-6}$ alkoxy.

In an embodiment, X is N or CH;

$R_1$ is selected from methyl, ethyl, cyclopropylmethyl, difluoromethyl;

$R_3$ is selected from methyl, hydroxymethyl, methoxymethyl;

$R_2$ is phenyl or heteroaryl;

$R_2$ is optionally substituted by 1-4 substituents independently selected from the group consisting of halogen, cyano, oxo, —R, —OR, —C(O)R, —NHR, $C_{3-6}$ cycloalkenyl, —$NR_4R_5$, —C(O)$NR_4R_5$, —COOH, —$SO_2$—$C_{1-6}$ alkyl;

R is selected from H, $C_{1-6}$ alkyl, $C_{1-6}$ alkenyl, $C_{3-6}$ cycloalkyl, heterocyclyl, aryl, and heteroaryl, and each of which is optionally substituted by 1-3 R'.

R' is selected from halogen, cyano, hydroxyl, $C_{3-6}$ cycloalkyl, $C_{1-6}$ alkylamino, $C_{1-6}$ alkyl, ($C_{1-6}$) alkoxy, cyano or $C_{1-3}$ alkyl substituted by halogen, $C_{1-6}$ alkylsulfuryl, heterocyclyl, heteroaryl;

$R_4$ or $R_5$ is independently H or $C_{1-6}$ alkyl, and the $C_{1-6}$ alkyl may be substituted by 1-5 substituents, the substituents are independently selected from amino, halogen, $C_{1-6}$ alkoxy substituted by halogen, hydroxyl and $C_{1-6}$ alkoxy.

In an embodiment, X is N or CH;

$R_1$ is selected from $C_{1-6}$ alkyl, $C_{1-6}$ alkyl substituted by halogen, $C_{1-6}$ alkyl substituted by $C_{3-6}$ cycloalkyl;

$R_3$ is selected from $C_{1-6}$ alkyl, $C_{1-6}$ alkyl substituted by hydroxyl, and $C_{1-6}$ alkyl substituted by $C_{1-6}$ alkoxy;

$R_2$ is selected from phenyl, triazolyl, pyridyl, triazolopyridyl, pyridinonyl, pyridazinyl, pyridazinonyl, pyrazinyl, pyrimidinyl, pyrazolopyrimidinyl, pyrrolopyridyl, dihydropyrrolopyridyl, dihydropyrrolidinopyridyl, pyrazolopyridyl, imidazopyridyl, imidazopyridazinyl, pyridooxazinyl, 1,4-dioxinopyridyl, imidazopyridazinyl, heteronaphthyl, naphthyridinyl, naphthyridinonyl, dihydronaphthyridinonyl, quinolyl;

$R_2$ is optionally substituted by 1-4 substituents independently selected from the group consisting of halogen, cyano, oxo, —R, —OR, —C(O)R, —NHR, $C_{3-6}$ cycloalkenyl, —$NR_4R_5$, —C(O)$NR_4R_5$, —COOH, —$SO_2$—$C_{1-6}$ alkyl;

R is selected from $C_{1-6}$ alkyl, $C_{1-6}$ alkenyl, $C_{3-6}$ cycloalkyl, heterocyclyl, aryl, and heteroaryl, and each of which is optionally substituted by 1-3 R';

R' is selected from halogen, cyano, $C_{3-6}$ cycloalkyl, $C_{1-6}$ alkylamino, $C_{1-6}$ alkyl, ($C_{1-6}$) alkoxy, cyano or $C_{1-3}$ alkyl substituted by halogen, $C_{1-6}$ alkylsulfuryl, heterocyclyl, heteroaryl;

$R_4$ or $R_5$ is independently selected from H, $C_{1-6}$ alkyl substituted by 1-5 halogens.

In an embodiment, X is N or CH;

$R_1$ is selected from $C_{1-3}$ alkyl, $C_{1-3}$ alkyl substituted by fluorine, or $C_{1-3}$ alkyl substituted by $C_{3-6}$ cycloalkyl;

$R_3$ is selected from $C_{1-3}$ alkyl, $C_{1-3}$ alkyl substituted by hydroxyl, and $C_{1-3}$ alkyl substituted by $C_{1-3}$ alkoxy.

$R_2$ is selected from phenyl, triazolyl, pyridyl, triazolopyridyl, pyridonyl, pyridazinyl, pyridazinonyl, pyrazinyl, pyrimidinyl, pyrazolopyrimidinyl, pyrrolopyridyl, dihydropyrrolopyridyl, dihydropyrrolidinopyridyl, pyrazolopyridyl, imidazopyridyl, imidazopyridazinyl, pyridooxazinyl, 1,4-dioxinopyridyl, imidazopyridazinyl, heteronaphthyl, naphthyridinyl, naphthyridinonyl, dihydronaphthyridinonyl, quinolyl;

$R_2$ is optionally substituted by 1-4 substituents independently selected from the group consisting of halogen, cyano, oxo, —R, —OR, —C(O)R, —NHR, $C_{3-6}$ cycloalkenyl, —$NR_4R_5$, —C(O)$NR_4R_5$, —COOH, —$SO_2$—$C_{1-6}$ alkyl;

R is selected from $C_{1-6}$ alkyl, $C_{1-6}$ alkenyl, $C_{3-6}$ cycloalkyl, heterocyclyl, aryl, and heteroaryl, and each of which is optionally substituted by 1-3 R';

R' is selected from halogen, cyano, $C_{3-6}$ cycloalkyl, $C_{1-6}$ alkylamino, $C_{1-6}$ alkyl, ($C_{1-6}$) alkoxy, $C_{1-3}$ alkyl substituted by cyano or halogen, $C_{1-6}$ alkylsulfuryl, heterocyclyl, heteroaryl;

$R_4$ or $R_5$ is independently selected from H, $C_{1-6}$ alkyl substituted by 1-5 halogens.

In an embodiment, X is N or CH;

$R_1$ is selected from methyl, ethyl, cyclopropylmethyl, difluoromethyl;

$R_3$ is selected from methyl, hydroxymethyl, methoxymethyl.

$R_2$ is selected from phenyl, triazolyl, pyridyl, triazolopyridyl, pyridonyl, pyridazinyl, pyridazinonyl, pyrazinyl, pyrimidinyl, pyrazolopyrimidinyl, pyrrolopyridyl, dihydropyrrolopyridyl, dihydropyrrolidinopyridyl, pyrazolopyridyl, imidazopyridyl, imidazopyridazinyl, pyridooxazinyl, 1,4-dioxinopyridyl, imidazopyridazinyl, heteronaphthyl, naphthyridinyl, naphthyridinonyl dihydronaphthyridinonyl, quinolyl;

$R_2$ is optionally substituted by 1-4 substituents independently selected from the group consisting of halogen, cyano, oxo, —R, —OR, —C(O)R, —NHR, $C_{3-6}$ cycloalkenyl, —$NR_4R_5$, —C(O)$NR_4R_5$, —COOH, —$SO_2$—$C_{1-6}$ alkyl;

R is selected from $C_{1-6}$ alkyl, $C_{1-6}$ alkenyl, $C_{3-6}$ cycloalkyl, heterocyclyl, aryl, and heteroaryl, and each of which is optionally substituted by 1-3 R';

R' is selected from halogen, cyano, $C_{3-6}$ cycloalkyl, $C_{1-6}$ alkylamino, $C_{1-6}$ alkyl, ($C_{1-6}$) alkoxy, $C_{1-3}$ alkyl substituted by cyano or halogen, $C_{1-6}$ alkylsulfuryl, heterocyclyl, heteroaryl;

$R_4$ or $R_5$ is independently selected from H, $C_{1-6}$ alkyl substituted by 1-5 halogens.

In an embodiment, X is N or CH;

$R_1$ is selected from $C_{1-3}$ alkyl, $C_{1-3}$ alkyl substituted by fluorine, or $C_{1-3}$ alkyl substituted by $C_{3-6}$ cycloalkyl;

$R_3$ is selected from $C_{1-3}$ alkyl, $C_{1-3}$ alkyl substituted by hydroxyl, or $C_{1-3}$ alkyl substituted by $C_{1-3}$ alkoxy;

$R_2$ is selected from phenyl, triazolyl, pyridyl, triazolopyridyl, pyridonyl, pyridazinyl, pyridazinonyl, pyrrolopyridyl, pyrazinyl, pyrimidinyl, pyrazolopyrimidinyl, dihydropyrrolopyridyl, dihydropyrrolidinopyridyl, pyrazolopyridyl, imidazopyridyl, imidazopyridazinyl, pyridooxazinyl, 1,4-dioxinopyridyl, imidazopyridazinyl, heteronaphthyl, naphthyridinyl, naphthyridinonyl, dihydronaphthyridinonyl, quinolyl;

$R_2$ is optionally substituted by 1-2 substituents independently selected from the group consisting of halogen, cyano, oxo, —R, —OR, —C(O)R, —NHR, cyclohexenyl, —$NR_4R_5$, —C(O)$NR_4R_5$, —COOH, —$SO_2$—$C_{1-3}$ alkyl;

R is selected from $C_{1-3}$ alkyl, $C_{1-3}$ alkenyl, cyclopropyl, cyclobutyl, morpholinyl, pyrrolidinyl, azetidinyl, oxetanyl, piperidinyl, tetrahydropyranyl, tetrahydrofuranyl, spiro ring, aryl, pyrimidinyl, oxadiazolyl, and each of which is optionally substituted by 1-3 R';

R' is selected from halogen, cyano, cyclopropyl, $C_{1-3}$ alkylamino, $C_{1-3}$ alkyl, $C_{1-3}$ alkoxy, $C_{1-3}$ alkyl substituted by cyano or halogen, $C_{1-3}$ alkylsulfuryl, tetrahydrofuranyl, oxetanyl, azetidinyl, morpholinyl, piperazinyl, methylpiperazinyl, pyrimidinyl;

$R_4$ or $R_5$ is selected from H, $C_{1-3}$ alkyl substituted by 1-3 fluorine.

In an embodiment, X is N or CH;

$R_1$ is selected from methyl, ethyl, cyclopropylmethyl, difluoromethyl;

$R_3$ is selected from methyl, hydroxymethyl, methoxymethyl.

$R_2$ is selected from phenyl, triazolyl, pyridyl, triazolopyridyl, pyridonyl, pyridazinyl, pyridazinonyl, pyrazinyl, pyrimidinyl, pyrazolopyrimidinyl, pyrrolopyridyl, dihydropyrrolopyridyl, dihydropyrrolidinopyridyl, pyrazolopyridyl, imidazopyridyl, imidazopyridazinyl, pyridooxazinyl, 1,4-dioxanopyridyl, imidazopyridazinyl, heteronaphthyl, naphthyridinyl, naphthyridinonyl, dihydronaphthyridinonyl, quinolinyl;

$R_2$ is optionally substituted by 1-2 substituents independently selected from the group consisting of halogen, cyano, oxo, —R, —OR, —C(O)R, —NHR, cyclohexenyl, —$NR_4R_5$, —C(O)$NR_4R_5$, —COOH, —$SO_2$—$C_{1-3}$ alkyl;

R is selected from $C_{1-3}$ alkyl, $C_{1-3}$ alkenyl, cyclopropyl, cyclobutyl, morpholinyl, pyrrolidinyl, azetidinyl, oxetanyl, piperidinyl, tetrahydropyranyl, tetrahydrofuranyl, spiro ring, aryl, pyrimidinyl, oxadiazolyl, and each of which is optionally substituted by 1-3 R';

R' is selected from halogen, cyano, cyclopropyl, $C_{1-3}$ alkylamino, $C_{1-3}$ alkyl, $C_{1-3}$ alkoxy, $C_{1-3}$ alkyl substituted by cyano or halogen, $C_{1-3}$ alkylsulfuryl, tetrahydrofuranyl, oxetanyl, azetidinyl, morpholinyl, piperazinyl, methylpiperazinyl, pyrimidinyl;

$R_4$ or $R_5$ is selected from H, $C_{1-3}$ alkyl substituted by 1-3 fluorine.

In an embodiment, X is N or CH;

$R_1$ is selected from methyl, ethyl, cyclopropylmethyl, difluoromethyl;

$R_3$ is selected from methyl, hydroxymethyl, methoxymethyl.

$R_2$ is selected from phenyl and the following substituents:

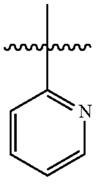
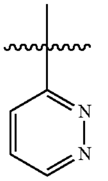
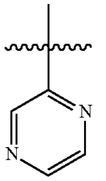
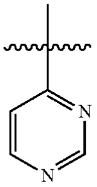
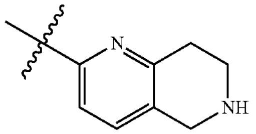
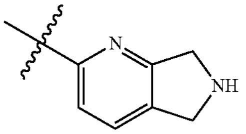
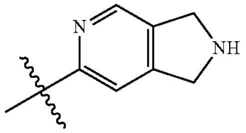
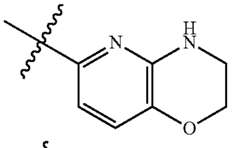
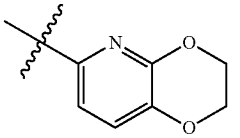
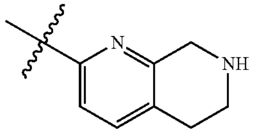
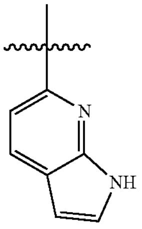
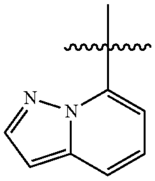
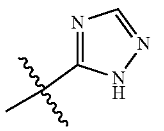
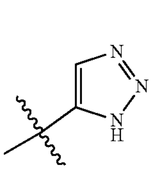
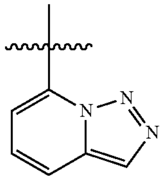
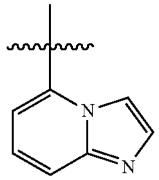

-continued

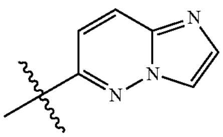
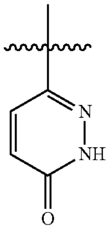
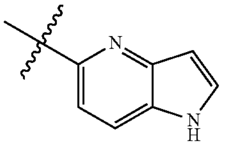
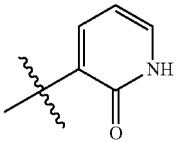
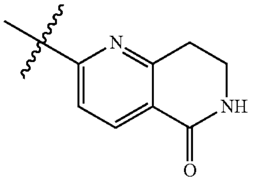
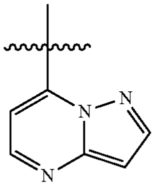
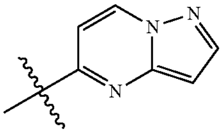
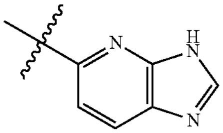
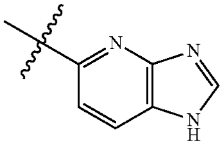
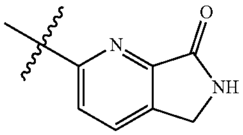
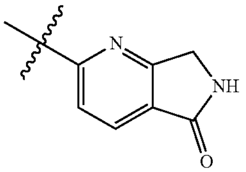
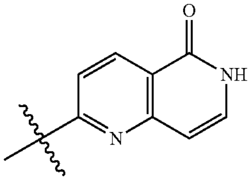
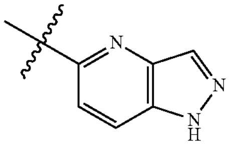
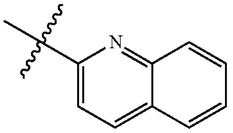
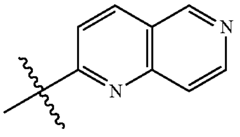

$R_2$ is optionally substituted by 1-2 substituents independently selected from the group consisting of halogen, cyano, oxo, —R, —OR, —C(O)R, —NHR, cyclohexenyl, —$NR_4R_5$, —C(O)$NR_4R_5$, —COOH, —$SO_2$—$C_{1-3}$ alkyl;

R is selected from $C_{1-3}$ alkyl, $C_{1-3}$ alkenyl, cyclopropyl, cyclobutyl, morpholinyl, pyrrolidinyl, azetidinyl, oxetanyl, piperidinyl, tetrahydropyranyl, tetrahydrofuranyl, spiro ring, aryl, pyrimidinyl, oxadiazolyl, and each of which is optionally substituted by 1-3 R';

R' is selected from halogen, cyano, cyclopropyl, $C_{1-3}$ alkylamino, $C_{1-3}$ alkyl, $C_{1-3}$ alkoxy, $C_{1-3}$ alkyl substituted by cyano or halogen, $C_{1-3}$ alkylsulfuryl, tetrahydrofuranyl, oxetanyl, azetidinyl, morpholinyl, piperazinyl, methylpiperazinyl, pyrimidinyl;

$R_4$ or $R_5$ is selected from H, $C_{1-3}$ alkyl substituted by 1-3 fluorine.

In an embodiment, X is N or CH;

$R_1$ is selected from methyl, ethyl, cyclopropylmethyl, difluoromethyl;

$R_3$ is selected from methyl, hydroxymethyl, methoxymethyl.

$R_2$ is selected from phenyl, triazolyl, pyridyl, triazolopyridyl, pyridonyl, pyridazinyl, pyridazinonyl, pyrazinyl, pyrimidinyl, pyrazolopyrimidinyl, pyrrolopyridyl, dihydropyrrolopyridyl, dihydropyrrolidinopyridyl, pyrazolopyridyl, imidazopyridyl, imidazopyridazinyl, pyridooxazinyl, 1,4-dioxinopyridyl, imidazopyridazinyl, heteronaphthyl, naphthyridinyl, naphthyridinonyl, dihydronaphthyridinonyl, quinolyl;

$R_2$ is optionally substituted by 1-4 substituents independently selected from the group consisting of -Me, -Et, -iPr, —$CF_3$, —$OCF_3$, —$OCHF_2$, —Cl, —F, —CN, —OMe, —OEt, —$NMe_2$, —$CH_2CF_3$, —$(CH_2)_2CN$, —$(CH_2)_3CN$, —$CH_2NHEt$, —$OCHF_2$, —$OCH(CH_3)_2$, —$CH_2OCH_3$, —$(CH_2)_2OCH_3$, —$(CH_2)_3OCH_3$, —$SO_2Me$, —$CH_2CH_2SO_2Me$, —COOH,

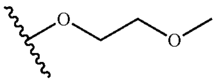,
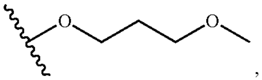,
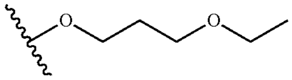,
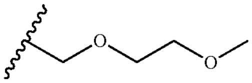,
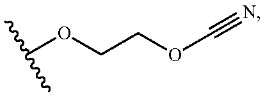
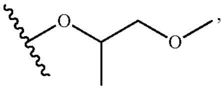,
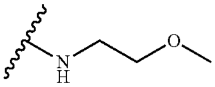,
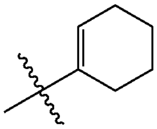,
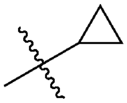,
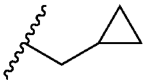,
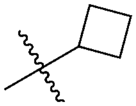,
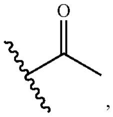,
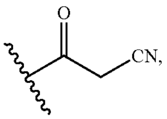
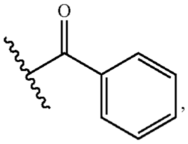,
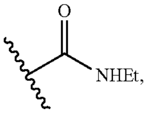
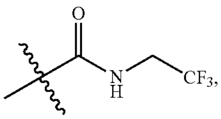
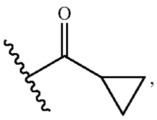,
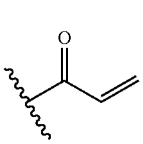,
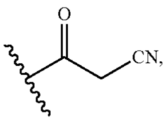
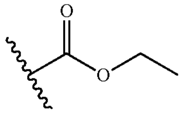,
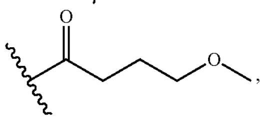,
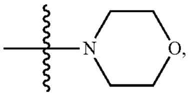

-continued
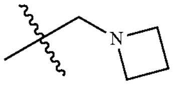,
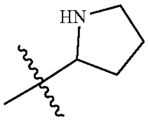,
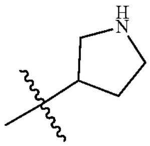,
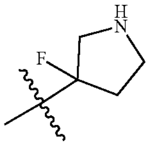,
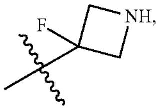
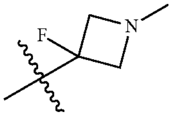,
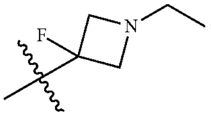,
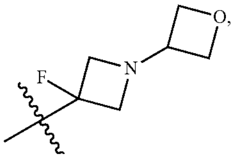
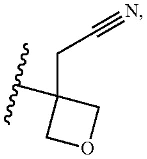
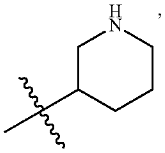,
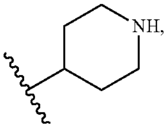
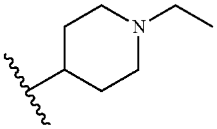,
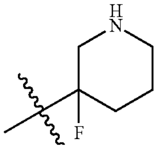,
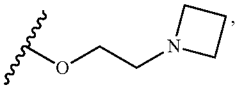
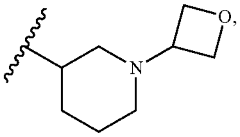
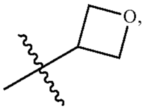,
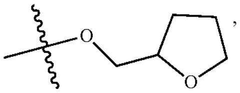
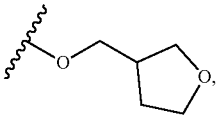
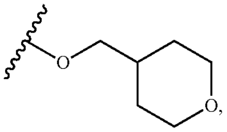
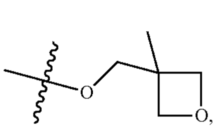
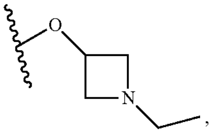
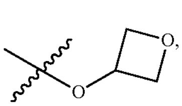,
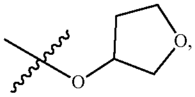
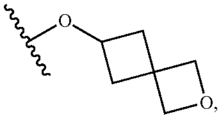
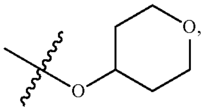
-continued
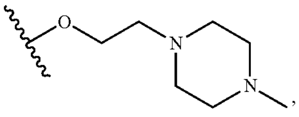,
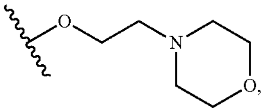
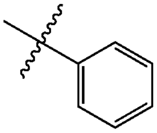,
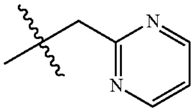, or
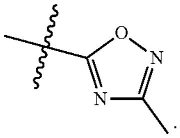.
In an embodiment, X is N or CH;
$R_1$ is selected from methyl, ethyl, cyclopropylmethyl, difluoromethyl;
$R_3$ is selected from methyl, hydroxymethyl, methoxymethyl;
$R_2$ is selected from phenyl and the following substituents:
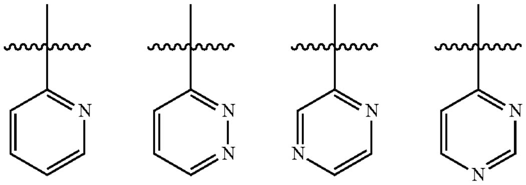
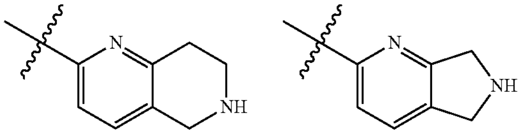
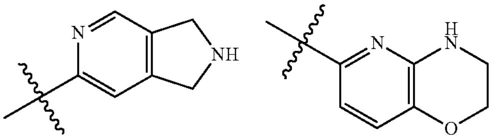
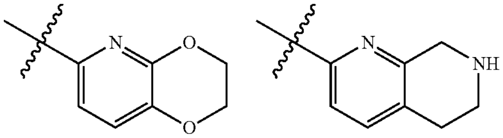
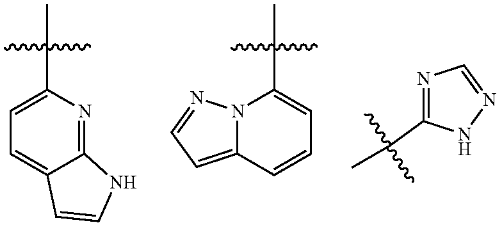
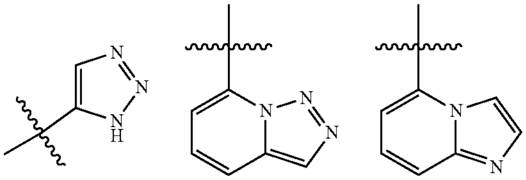

-continued
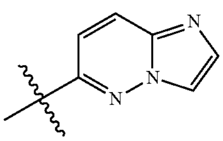
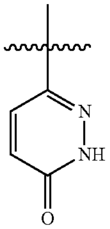
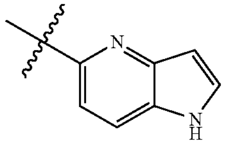
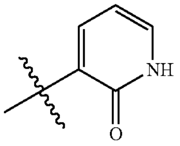
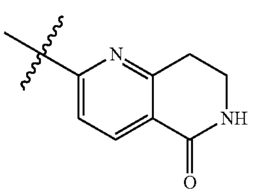
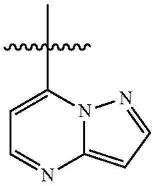
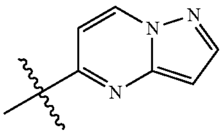
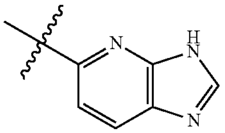
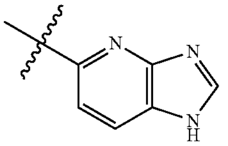
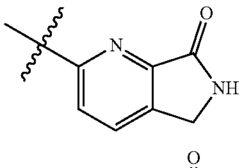
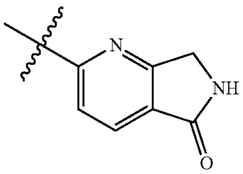
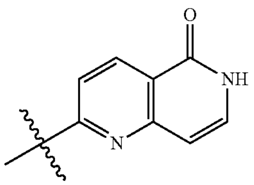
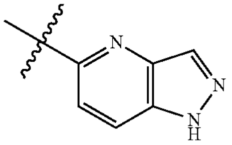
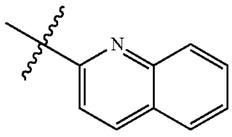
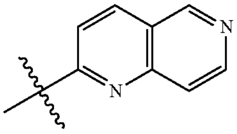
$R_2$ is optionally substituted by 1-4 substituents independently selected from the group consisting of -Me, -Et, -$^i$Pr, —$CF_3$, —$OCF_3$, —$OCHF_2$, —Cl, —F, —CN, —OMe, —OEt, —NMez, —$CH_2CF_3$, —$(CH_2)_2CN$, —$(CH_2)_3CN$, —$CH_2NHEt$, —$OCHF_2$, —$OCH(CH_3)_2$, —$CH_2OCH_3$, —$(CH_2)_2OCH_3$, —$(CH_2)_3OCH_3$, —$SO_2Me$, —$CH_2CH_2SO_2Me$, —COOH,
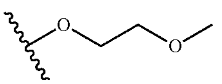
,
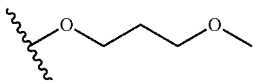
,
-continued
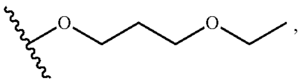
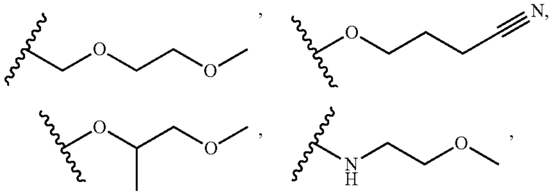
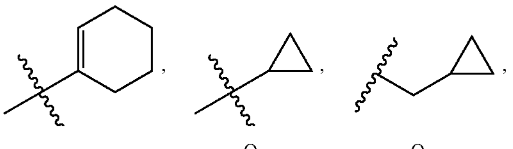
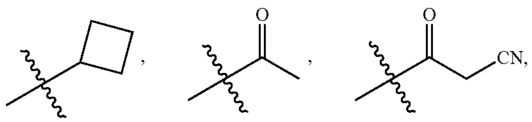
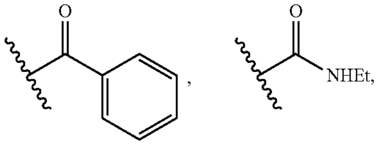
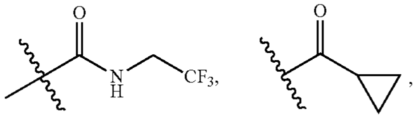
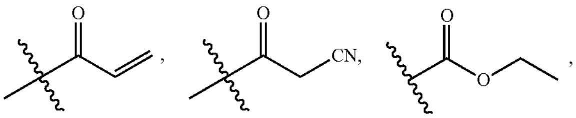
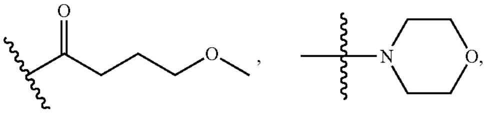
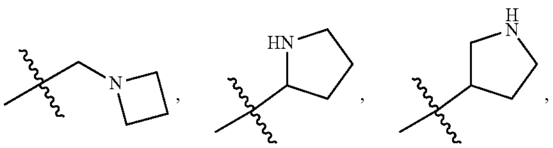
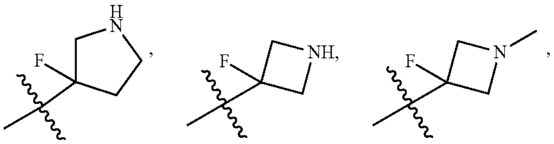
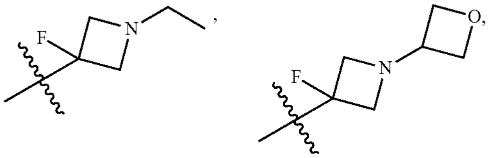
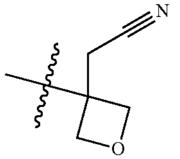
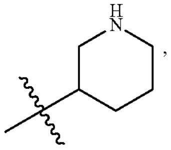
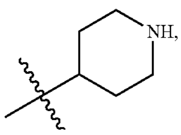

-continued
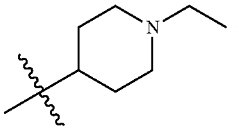,
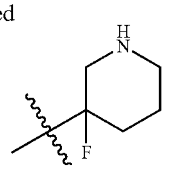,
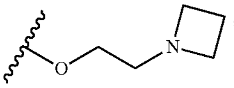,
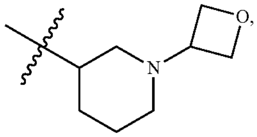,
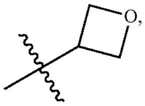,
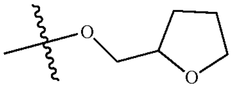,
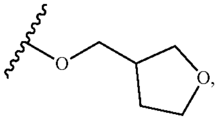,
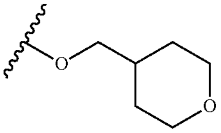,
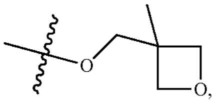,
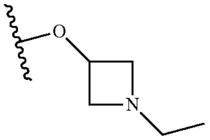,
-continued
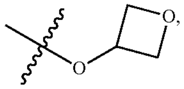,
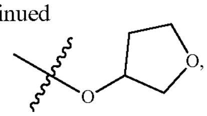,
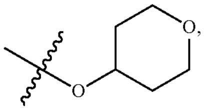,
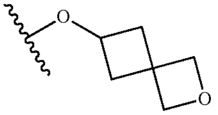,
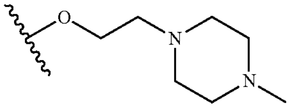,
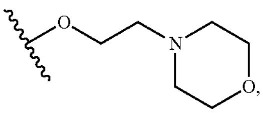,
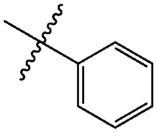,
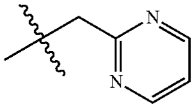,
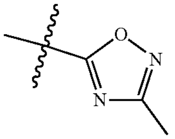.
In an embodiment, the compound I is any of the following compounds:
| Embodiment | Structure |
|---|---|
| 1 | 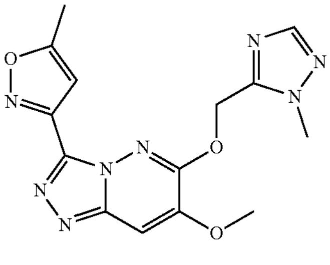 [SMILES: COc1cc2nnc(-c3cc(C)on3)n2nc1OCc1ncnn1C] |
| 2 | 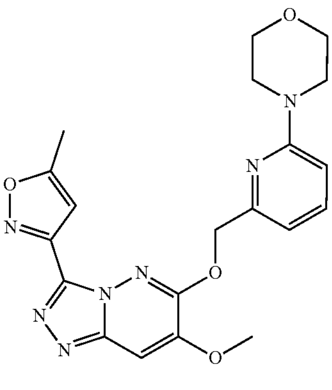 [SMILES: COc1cc2nnc(-c3cc(C)on3)n2nc1OCc1cccc(N2CCOCC2)n1] |

-continued
| Embodiment | Structure |
| --- | --- |
| 3 | 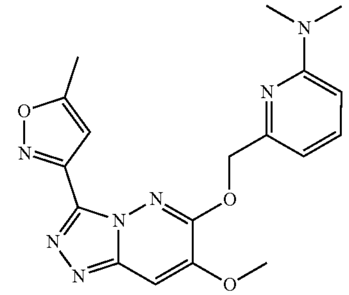 [SMILES: COc1cc2nnc(-c3cc(C)on3)n2nc1OCc1cccc(N(C)C)n1] |
| 4 | 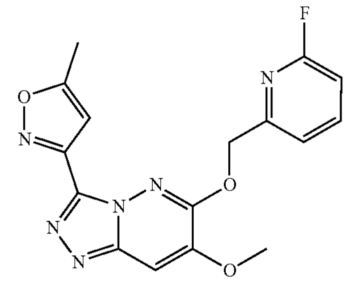 [SMILES: COc1cc2nnc(-c3cc(C)on3)n2nc1OCc1cccc(F)n1] |
| 5 | 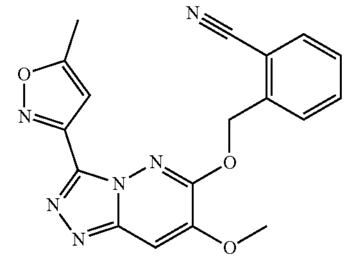 [SMILES: COc1cc2nnc(-c3cc(C)on3)n2nc1OCc1ccccc1C#N] |
| 6 | 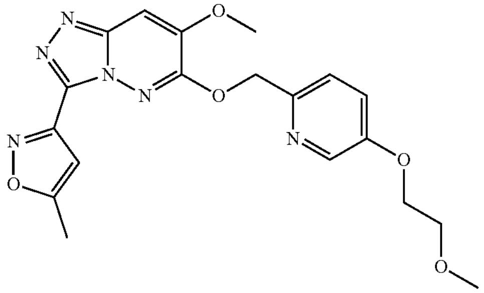 [SMILES: COCCOc1ccc(COc2nn3c(-c4cc(C)on4)nnc3cc2OC)nc1] |
| 7 | 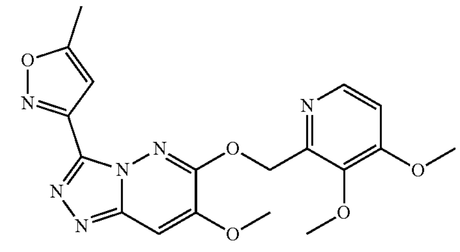 [SMILES: COc1cc2nnc(-c3cc(C)on3)n2nc1OCc1nccc(OC)c1OC] |

-continued
| Embodiment | Structure |
| --- | --- |
| 8 | 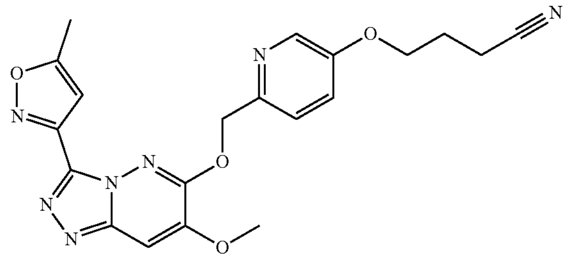 [SMILES: COc1cc2nnc(-c3cc(C)on3)n2nc1OCc1ccc(OCCCC#N)cn1] |
| 9 | 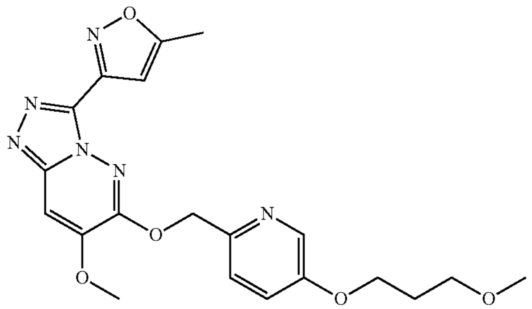 [SMILES: COCCCOc1ccc(COc2nn3c(-c4cc(C)on4)nnc3cc2OC)nc1] |
| 10 | 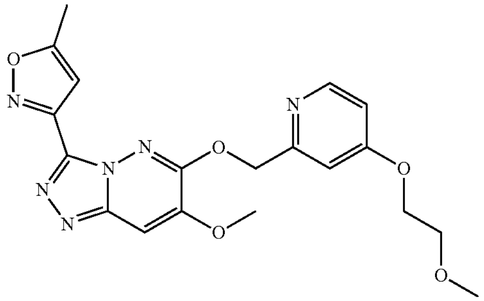 [SMILES: COCCOc1ccnc(COc2nn3c(-c4cc(C)on4)nnc3cc2OC)c1] |
| 11 | 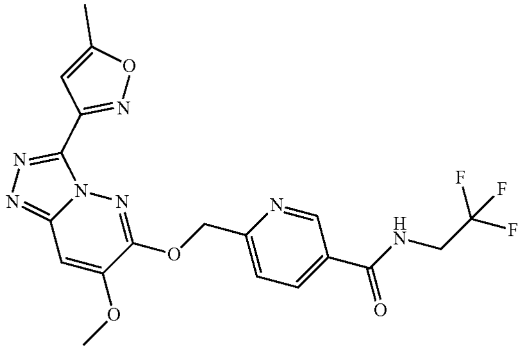 [SMILES: COc1cc2nnc(-c3cc(C)on3)n2nc1OCc1ccc(C(=O)NCC(F)(F)F)cn1] |

-continued
| Embodiment | Structure |
| --- | --- |
| 12 | 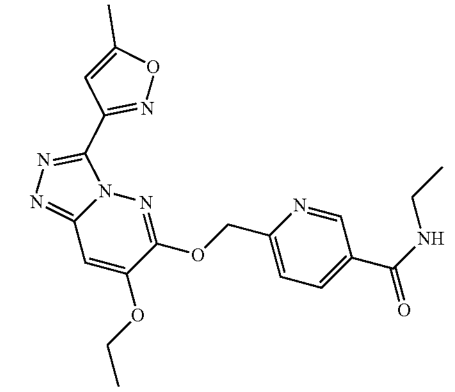 [SMILES: CCNC(=O)c1ccc(COc2nn3c(-c4cc(C)on4)nnc3cc2OCC)nc1] |
| 13 | 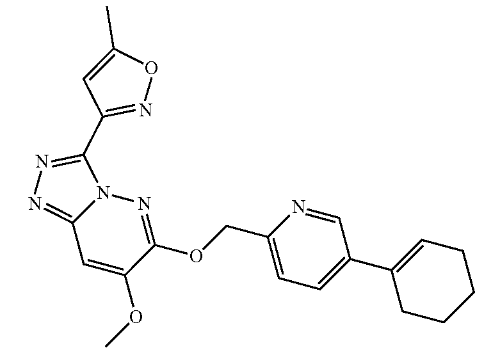 [SMILES: COc1cc2nnc(-c3cc(C)on3)n2nc1OCc1ccc(C2=CCCCC2)cn1] |
| 14 | 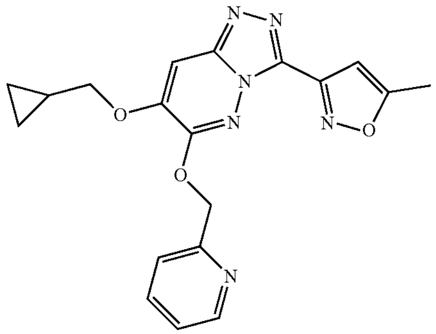 [SMILES: Cc1cc(-c2nnc3cc(OCC4CC4)c(OCc4ccccn4)nn23)no1] |
| 15 | 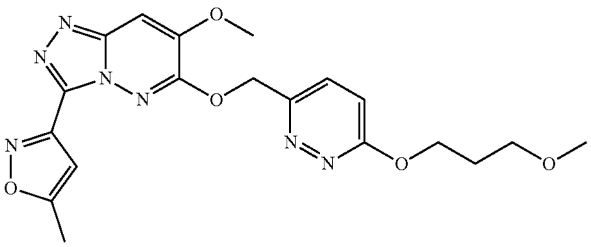 [SMILES: COCCCOc1ccc(COc2nn3c(-c4cc(C)on4)nnc3cc2OC)nn1] |

-continued
| Embodiment | Structure |
| --- | --- |
| 16 | 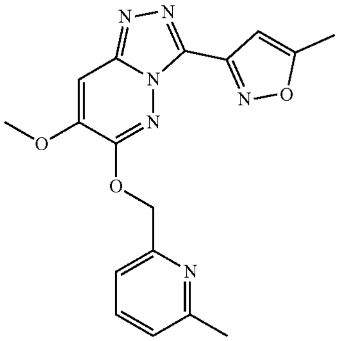 |
| 17 | 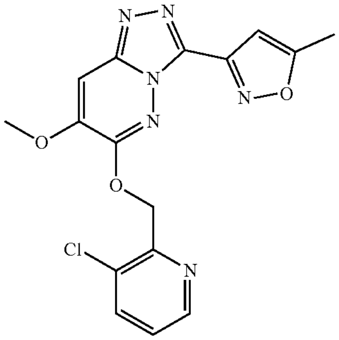 |
| 18 | 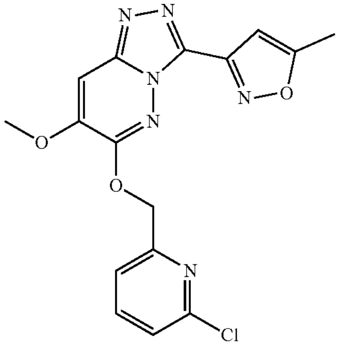 |
| 19 | 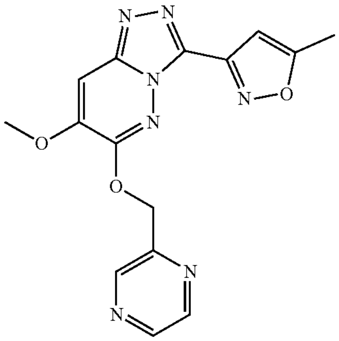 |

-continued
| Embodiment | Structure |
|---|---|
| 20 | 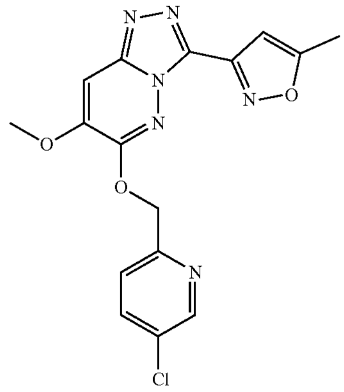 |
| 21 | 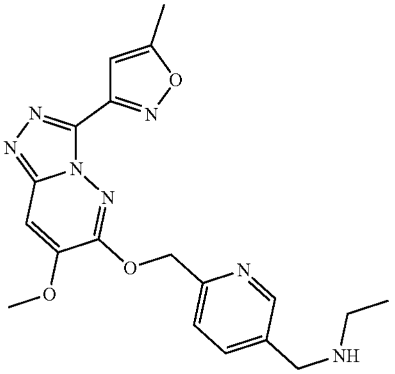 [SMILES: CCNCc1ccc(COc2nn3c(-c4cc(C)on4)nnc3cc2OC)nc1] |
| 22 | 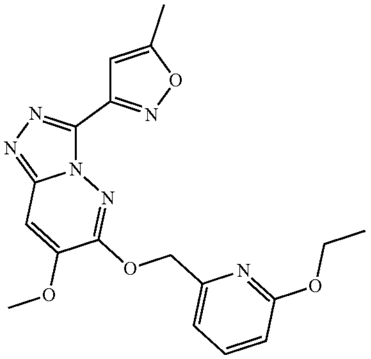 [SMILES: CCOc1cccc(COc2nn3c(-c4cc(C)on4)nnc3cc2OC)n1] |
| 23 | 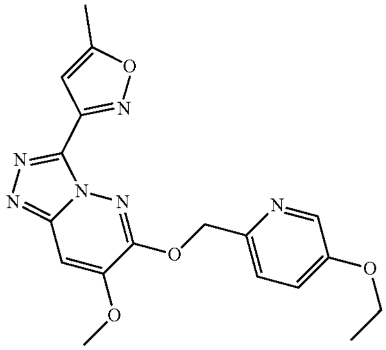 [SMILES: CCOc1ccc(COc2nn3c(-c4cc(C)on4)nnc3cc2OC)nc1] |

-continued
| Embodiment | Structure |
| --- | --- |
| 24 | 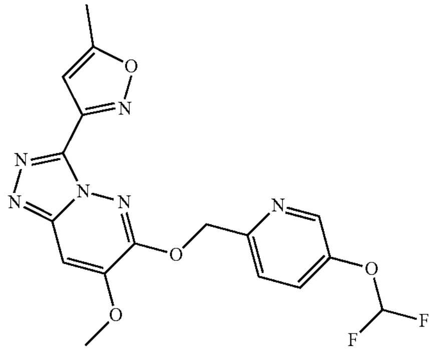 [SMILES: COc1cc2nnc(-c3cc(C)on3)n2nc1OCc1ccc(OC(F)F)cn1] |
| 25 | 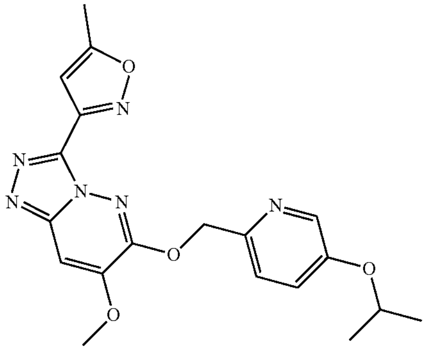 [SMILES: COc1cc2nnc(-c3cc(C)on3)n2nc1OCc1ccc(OC(C)C)cn1] |
| 26 | 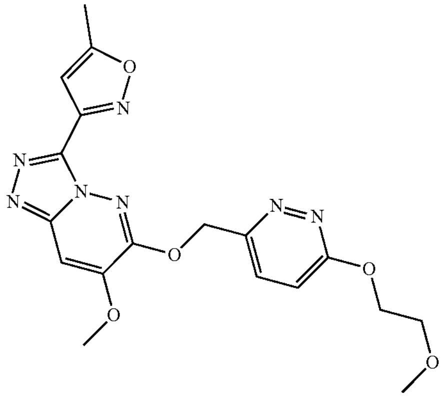 [SMILES: COCCOc1ccc(COc2nn3c(-c4cc(C)on4)nnc3cc2OC)nn1] |
| 27 | 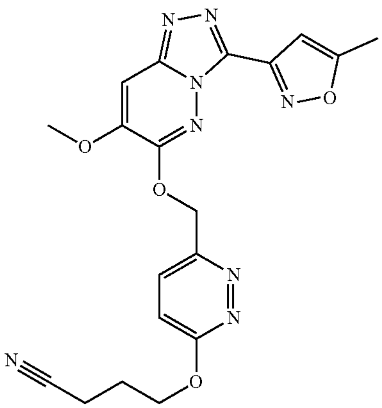 [SMILES: COc1cc2nnc(-c3cc(C)on3)n2nc1OCc1ccc(OCCCC#N)nn1] |

-continued
| Embodiment | Structure |
| --- | --- |
| 28 | 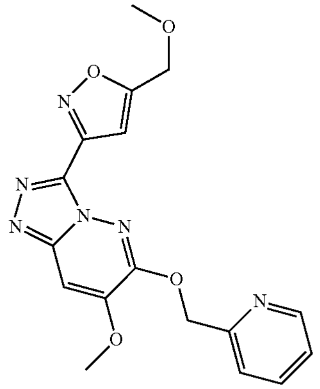 [SMILES: COCc1cc(-c2nnc3cc(OC)c(OCc4ccccn4)nn23)no1] |
| 29 | 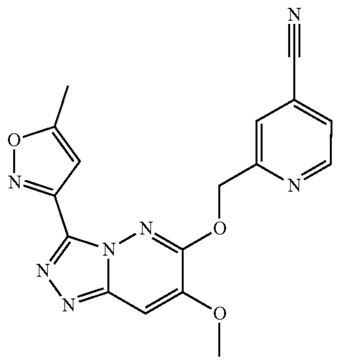 [SMILES: COc1cc2nnc(-c3cc(C)on3)n2nc1OCc1cc(C#N)ccn1] |
| 30 | 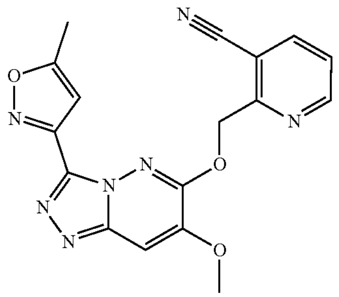 [SMILES: COc1cc2nnc(-c3cc(C)on3)n2nc1OCc1ncccc1C#N] |
| 31 | 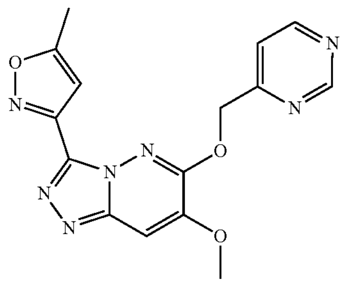 [SMILES: COc1cc2nnc(-c3cc(C)on3)n2nc1OCc1ccncn1] |

-continued
| Embodiment | Structure |
|---|---|
| 32 | 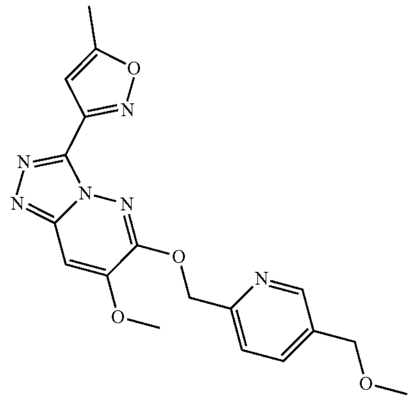 [SMILES: COCc1ccc(COc2nn3c(-c4cc(C)on4)nnc3cc2OC)nc1] |
| 33 | 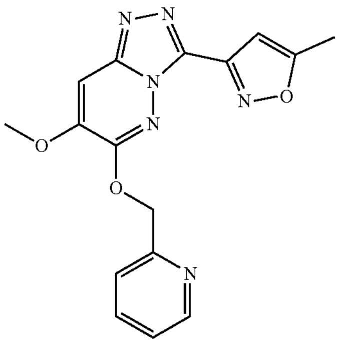 |
| 34 | 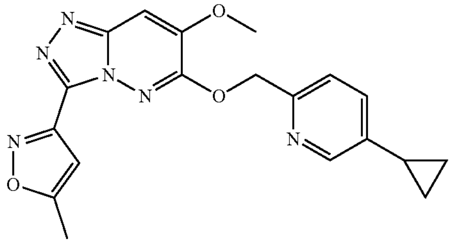 [SMILES: COc1cc2nnc(-c3cc(C)on3)n2nc1OCc1ccc(C2CC2)cn1] |
| 35 | 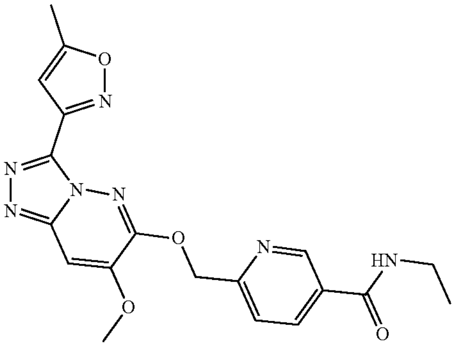 [SMILES: CCNC(=O)c1ccc(COc2nn3c(-c4cc(C)on4)nnc3cc2OC)nc1] |

-continued
| Embodiment | Structure |
|---|---|
| 36 | 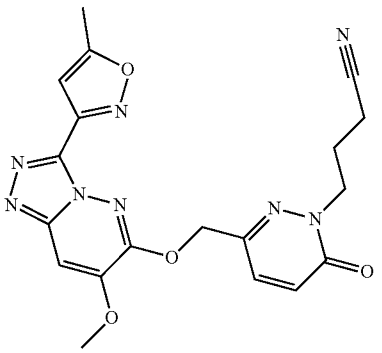 [SMILES: COc1cc2nnc(-c3cc(C)on3)n2nc1OCc1ccc(=O)n(CCCC#N)n1] |
| 37 | 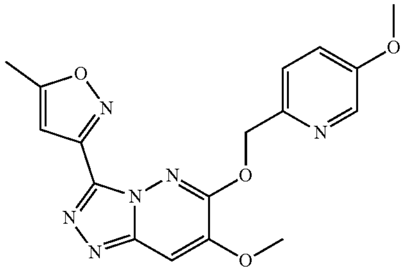 |
| 38 | 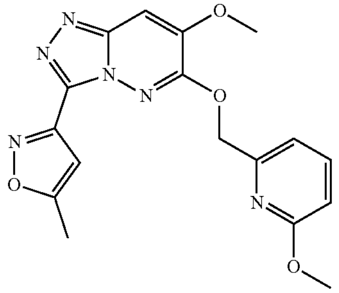 [SMILES: COc1cccc(COc2nn3c(-c4cc(C)on4)nnc3cc2OC)n1] |
| 39 | 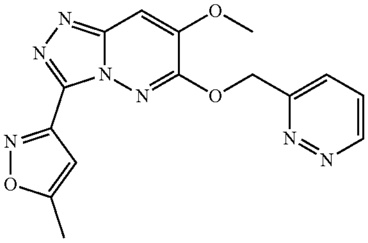 [SMILES: COc1cc2nnc(-c3cc(C)on3)n2nc1OCc1cccnn1] |
| 40 | 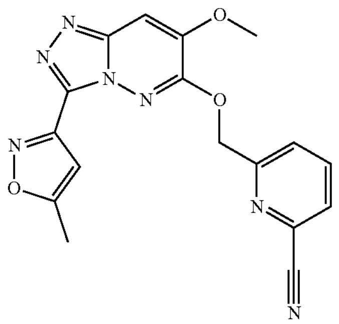 [SMILES: COc1cc2nnc(-c3cc(C)on3)n2nc1OCc1cccc(C#N)n1] |

-continued
| Embodiment | Structure |
|---|---|
| 41 | 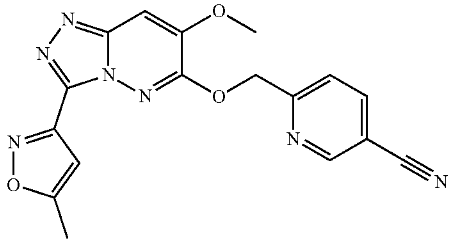 [SMILES: COc1cc2nnc(-c3cc(C)on3)n2nc1OCc1ccc(C#N)cn1] |
| 42 | 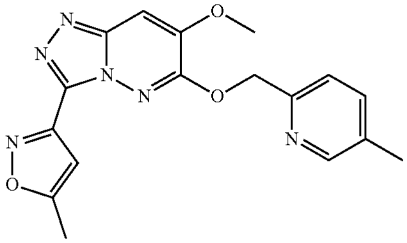 [SMILES: COc1cc2nnc(-c3cc(C)on3)n2nc1OCc1ccc(C)cn1] |
| 43 | 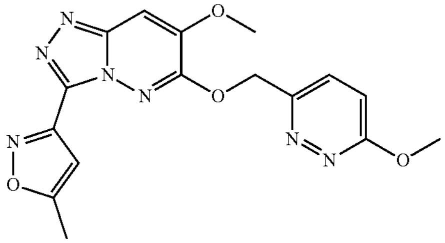 [SMILES: COc1ccc(COc2nn3c(-c4cc(C)on4)nnc3cc2OC)nn1] |
| 44 | 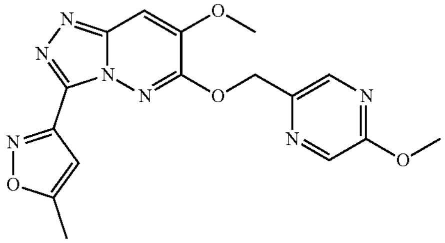 [SMILES: COc1cnc(COc2nn3c(-c4cc(C)on4)nnc3cc2OC)cn1] |
| 45 | 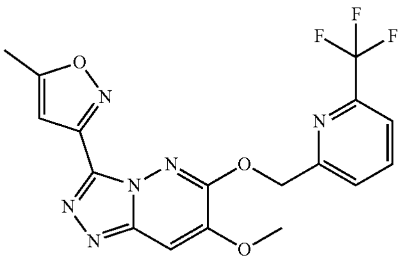 [SMILES: COc1cc2nnc(-c3cc(C)on3)n2nc1OCc1cccc(C(F)(F)F)n1] |

-continued
| Embodiment | Structure |
|---|---|
| 46 | 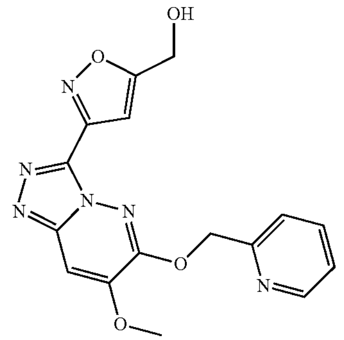 [SMILES: COc1cc2nnc(-c3cc(CO)on3)n2nc1OCc1ccccn1] |
| 47 | 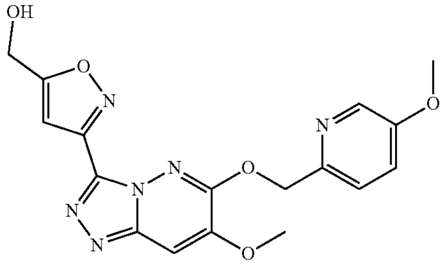 [SMILES: COc1ccc(COc2nn3c(-c4cc(CO)on4)nnc3cc2OC)nc1] |
| 48 | 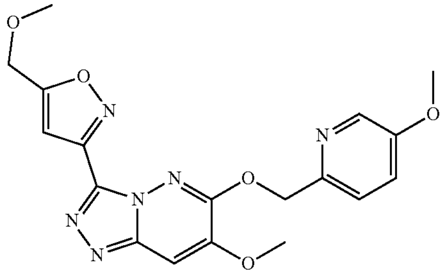 [SMILES: COCc1cc(-c2nnc3cc(OC)c(OCc4ccc(OC)cn4)nn23)no1] |
| 49 | 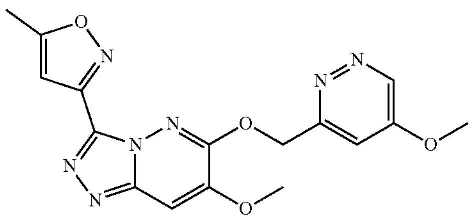 |
| 50 | 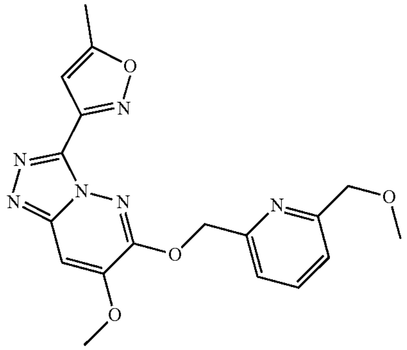 [SMILES: COCc1cccc(COc2nn3c(-c4cc(C)on4)nnc3cc2OC)n1] |

-continued
| Embodiment | Structure |
|---|---|
| 51 | 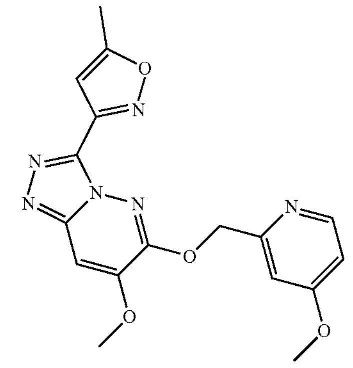 [SMILES: COc1ccnc(COc2nn3c(-c4cc(C)on4)nnc3cc2OC)c1] |
| 52 | 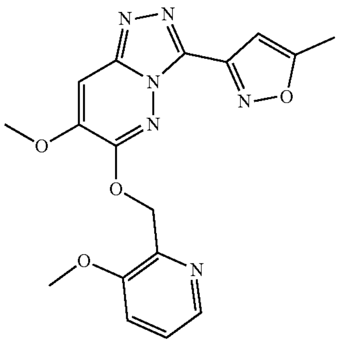 |
| 53 | 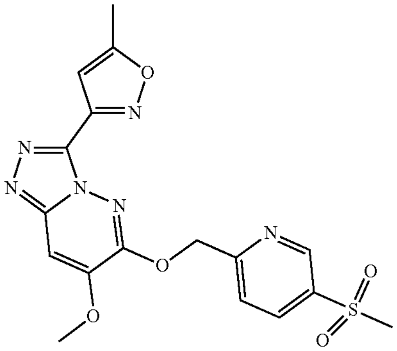 [SMILES: COc1cc2nnc(-c3cc(C)on3)n2nc1OCc1ccc(S(C)(=O)=O)cn1] |
| 54 | 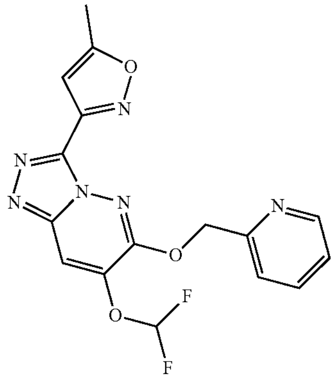 [SMILES: Cc1cc(-c2nnc3cc(OC(F)F)c(OCc4ccccn4)nn23)no1] |

-continued
| Embodiment | Structure |
| --- | --- |
| 55 | 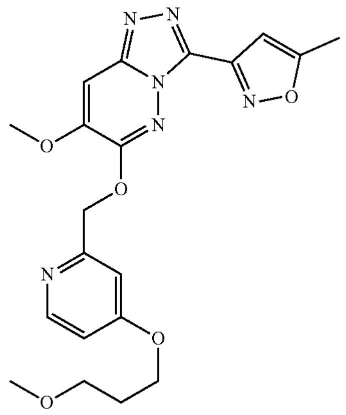 |
| 56 | 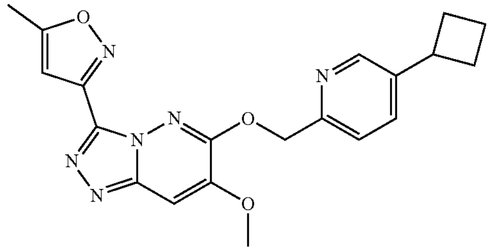 [SMILES: COc1cc2nnc(-c3cc(C)on3)n2nc1OCc1ccc(C2CCC2)cn1] |
| 57 | 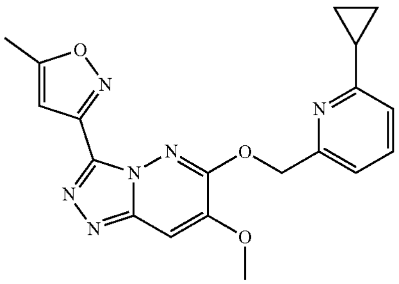 [SMILES: COc1cc2nnc(-c3cc(C)on3)n2nc1OCc1cccc(C2CC2)n1] |
| 58 | 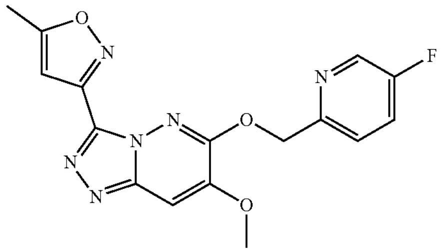 [SMILES: COc1cc2nnc(-c3cc(C)on3)n2nc1OCc1ccc(F)cn1] |
| 59 | 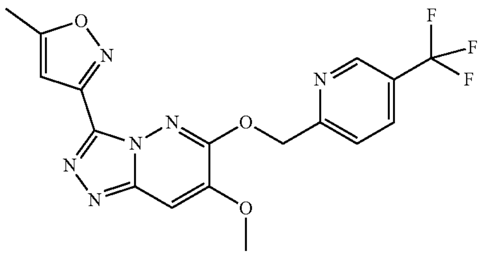 [SMILES: COc1cc2nnc(-c3cc(C)on3)n2nc1OCc1ccc(C(F)(F)F)cn1] |

-continued
| Embodiment | Structure |
|---|---|
| 60 | 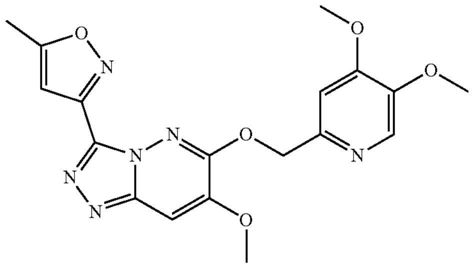 |
| 61 | 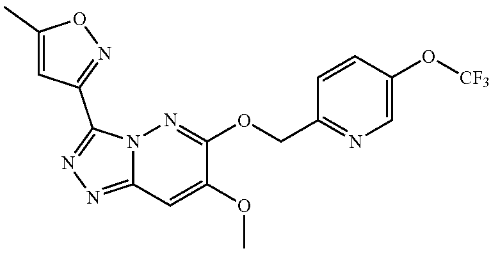 [SMILES: COc1cc2nnc(-c3cc(C)on3)n2nc1OCc1ccc(OC(F)(F)F)cn1] |
| 62 | 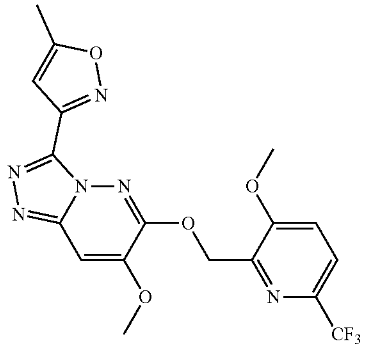 [SMILES: COc1ccc(C(F)(F)F)nc1COc1nn2c(-c3cc(C)on3)nnc2cc1OC] |
| 63 | 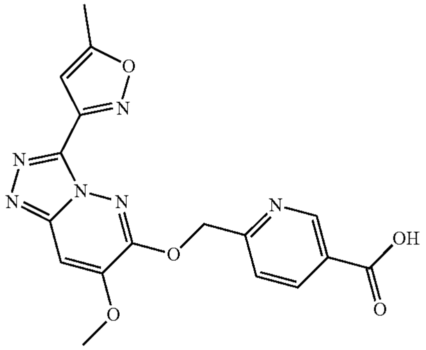 [SMILES: COc1cc2nnc(-c3cc(C)on3)n2nc1OCc1ccc(C(=O)O)cn1] |
| 64 | 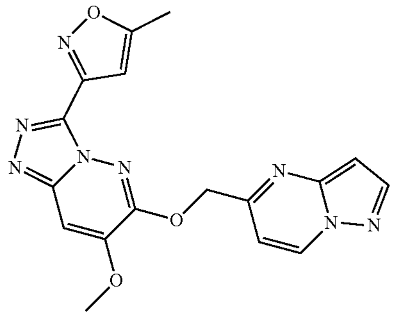 [SMILES: COc1cc2nnc(-c3cc(C)on3)n2nc1OCc1ccn2nccc2n1] |

-continued
| Embodiment | Structure |
|---|---|
| 65 | 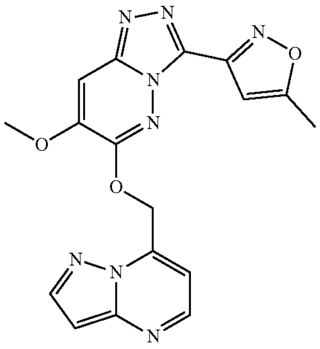 |
| 66 | 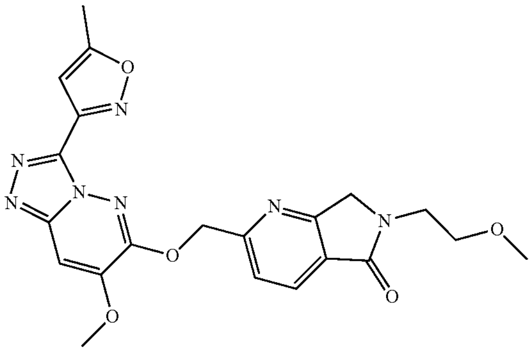 [SMILES: COCCN1Cc2nc(COc3nn4c(-c5cc(C)on5)nnc4cc3OC)ccc2C1=O] |
| 67 | 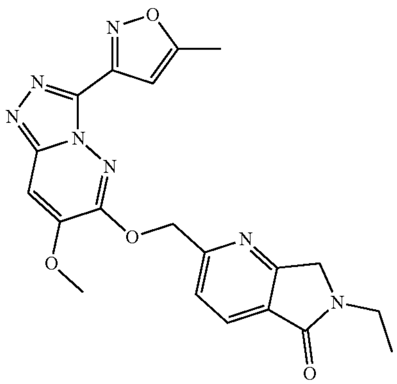 [SMILES: CCN1Cc2nc(COc3nn4c(-c5cc(C)on5)nnc4cc3OC)ccc2C1=O] |
| 68 | 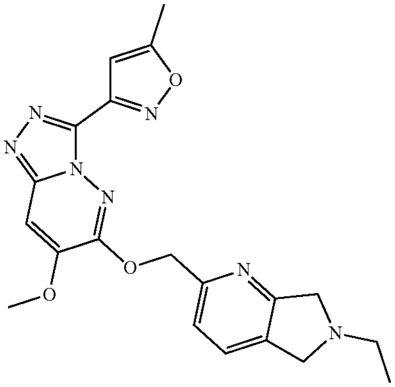 [SMILES: CCN1Cc2ccc(COc3nn4c(-c5cc(C)on5)nnc4cc3OC)nc2C1] |

-continued
| Embodiment | Structure |
|---|---|
| 69 | 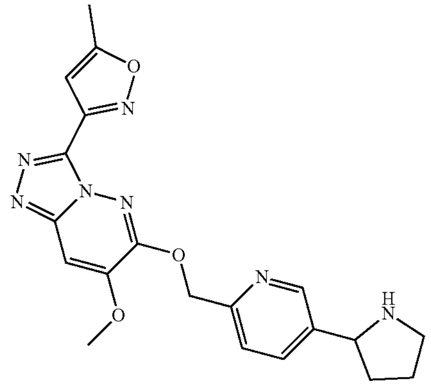 [SMILES: COc1cc2nnc(-c3cc(C)on3)n2nc1OCc1ccc(C2CCCN2)cn1] |
| 70 | 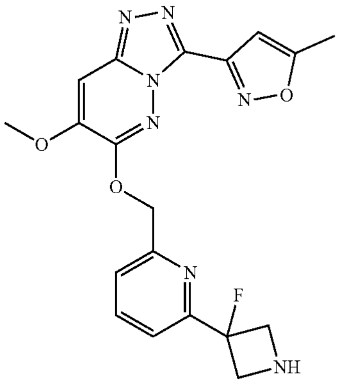 |
| 71 | 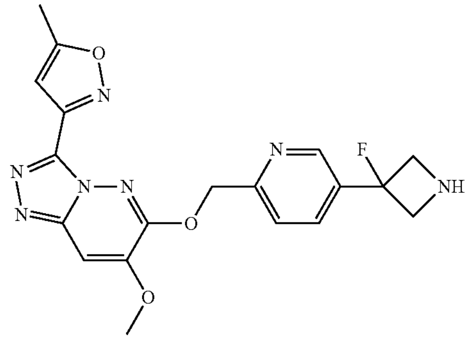 [SMILES: COc1cc2nnc(-c3cc(C)on3)n2nc1OCc1ccc(C2(F)CNC2)cn1] |
| 72 | 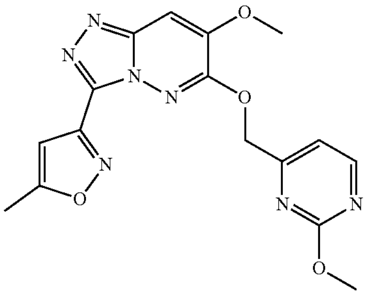 |

-continued
| Embodiment | Structure |
|---|---|
| 73 | 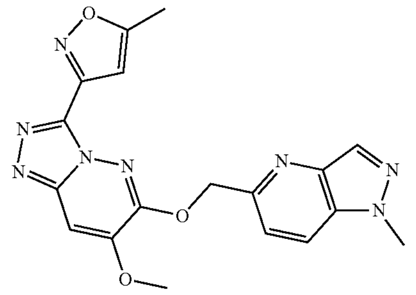 [SMILES: COc1cc2nnc(-c3cc(C)on3)n2nc1OCc1ccc2c(cnn2C)n1] |
| 74 | 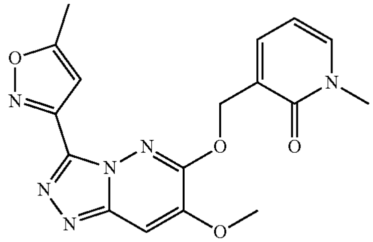 [SMILES: COc1cc2nnc(-c3cc(C)on3)n2nc1OCc1cccn(C)c1=O] |
| 75 | 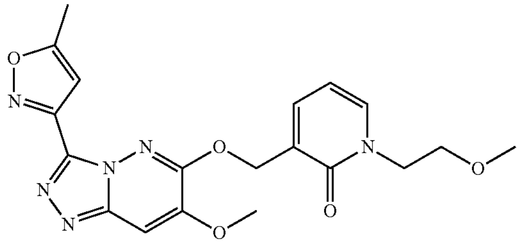 [SMILES: COCCn1cccc(COc2nn3c(-c4cc(C)on4)nnc3cc2OC)c1=O] |
| 76 | 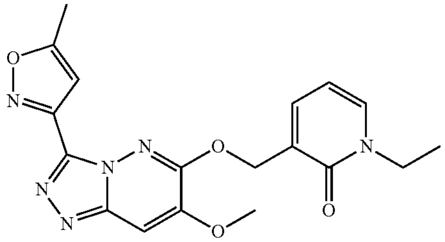 [SMILES: CCn1cccc(COc2nn3c(-c4cc(C)on4)nnc3cc2OC)c1=O] |
| 77 | 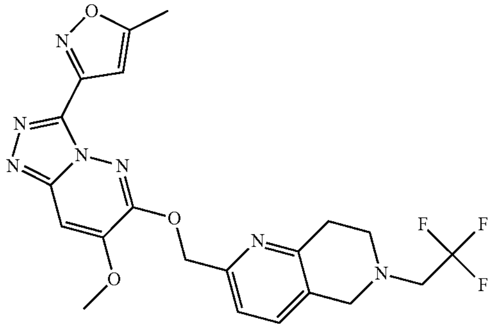 [SMILES: COc1cc2nnc(-c3cc(C)on3)n2nc1OCc1ccc2c(n1)CCN(CC(F)(F)F)C2] |

-continued
| Embodiment | Structure |
| --- | --- |
| 78 | 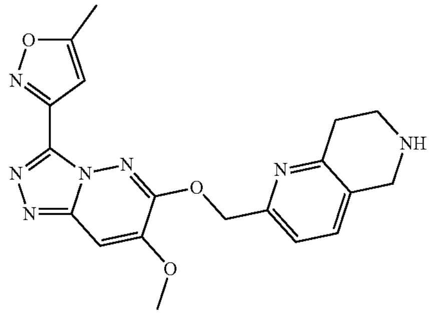 [SMILES: COc1cc2nnc(-c3cc(C)on3)n2nc1OCc1ccc2c(n1)CCNC2] |
| 79 | 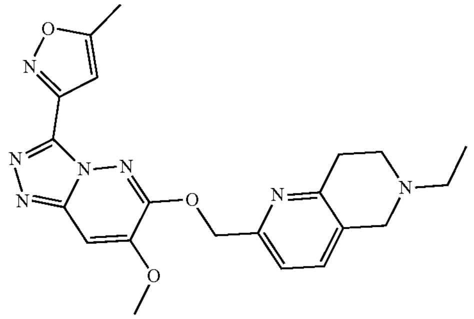 [SMILES: CCN1CCc2nc(COc3nn4c(-c5cc(C)on5)nnc4cc3OC)ccc2C1] |
| 80 | 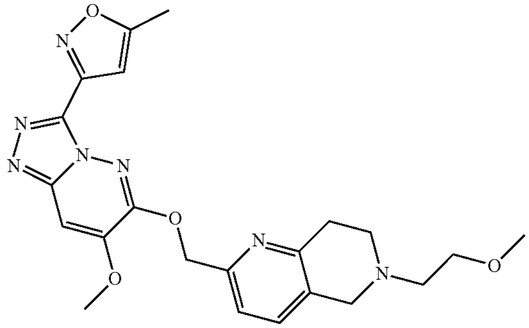 [SMILES: COCCN1CCc2nc(COc3nn4c(-c5cc(C)on5)nnc4cc3OC)ccc2C1] |
| 81 | 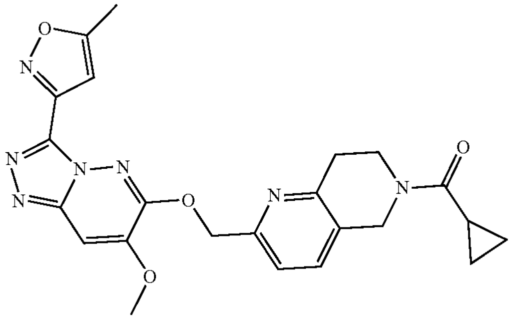 [SMILES: COc1cc2nnc(-c3cc(C)on3)n2nc1OCc1ccc2c(n1)CCN(C(=O)C1CC1)C2] |

-continued
| Embodiment | Structure |
| --- | --- |
| 82 | 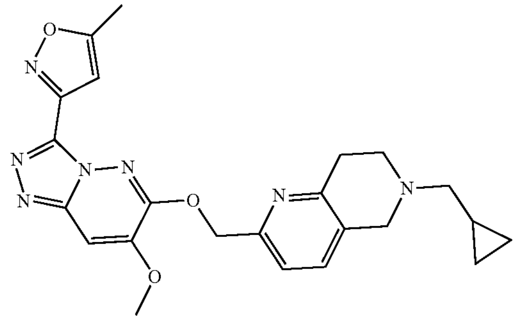 [SMILES: COc1cc2nnc(-c3cc(C)on3)n2nc1OCc1ccc2c(n1)CCN(CC1CC1)C2] |
| 83 | 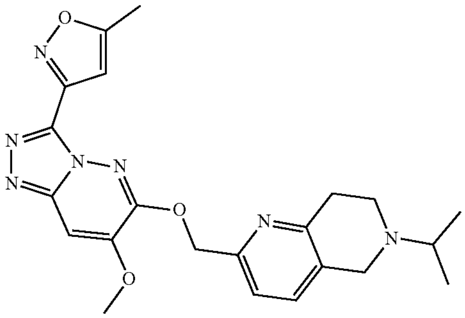 [SMILES: COc1cc2nnc(-c3cc(C)on3)n2nc1OCc1ccc2c(n1)CCN(C(C)C)C2] |
| 84 | 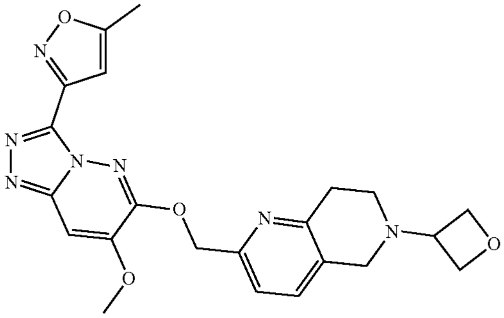 [SMILES: COc1cc2nnc(-c3cc(C)on3)n2nc1OCc1ccc2c(n1)CCN(C1COC1)C2] |
| 85 | 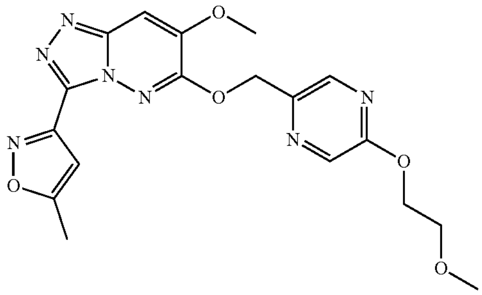 [SMILES: COCCOc1cnc(COc2nn3c(-c4cc(C)on4)nnc3cc2OC)cn1] |
| 86 | 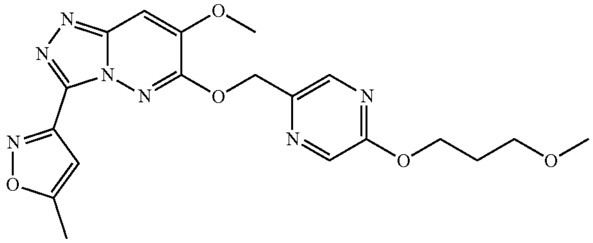 [SMILES: COCCCOc1cnc(COc2nn3c(-c4cc(C)on4)nnc3cc2OC)cn1] |

-continued
| Embodiment | Structure |
| --- | --- |
| 87 | 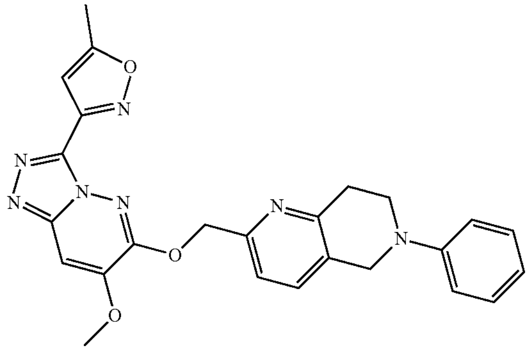 [SMILES: COc1cc2nnc(-c3cc(C)on3)n2nc1OCc1ccc2c(n1)CCN(c1ccccc1)C2] |
| 88 | 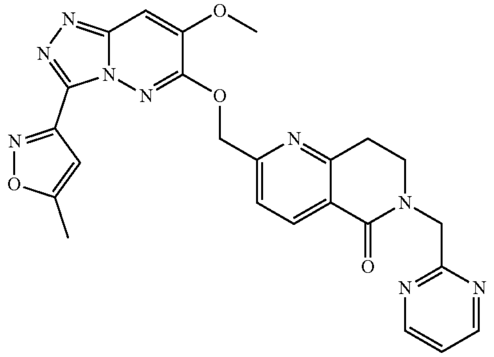 [SMILES: COc1cc2nnc(-c3cc(C)on3)n2nc1OCc1ccc2c(n1)CCN(Cc1ncccn1)C2=O] |
| 89 | 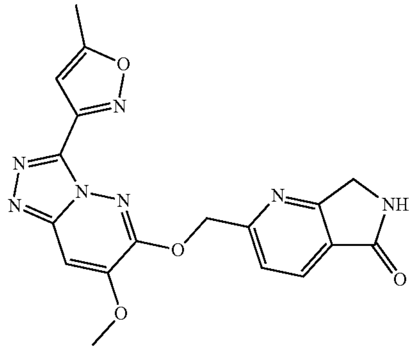 [SMILES: COc1cc2nnc(-c3cc(C)on3)n2nc1OCc1ccc2c(n1)CNC2=O] |
| 90 | 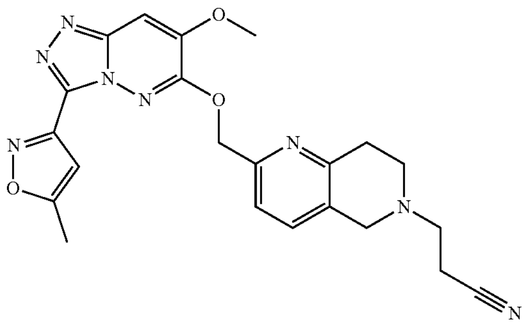 [SMILES: COc1cc2nnc(-c3cc(C)on3)n2nc1OCc1ccc2c(n1)CCN(CCC#N)C2] |

-continued
| Embodiment | Structure |
| --- | --- |
| 91 | 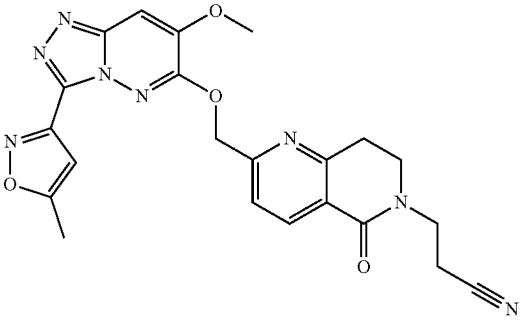 [SMILES: COc1cc2nnc(-c3cc(C)on3)n2nc1OCc1ccc2c(n1)CCN(CCC#N)C2=O] |
| 92 | 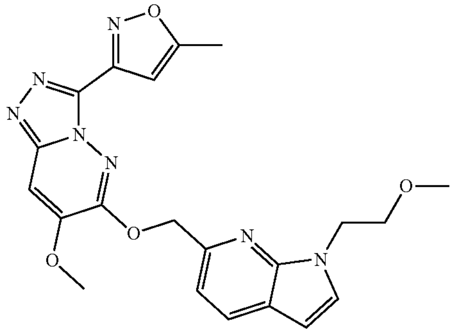 [SMILES: COCCn1ccc2ccc(COc3nn4c(-c5cc(C)on5)nnc4cc3OC)nc21] |
| 93 | 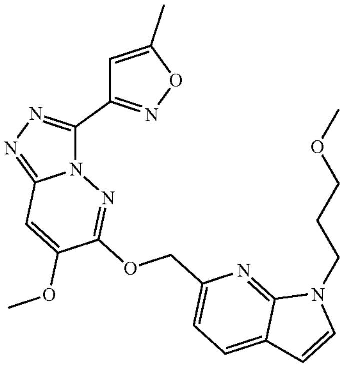 |
| 94 | 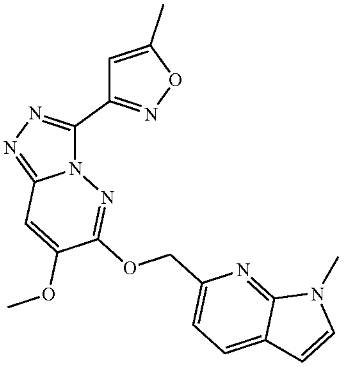 |

-continued
| Embodiment | Structure |
| --- | --- |
| 95 | 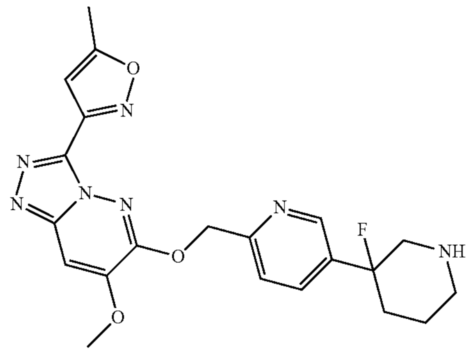 [SMILES: COc1cc2nnc(-c3cc(C)on3)n2nc1OCc1ccc(C2(F)CCCNC2)cn1] |
| 96 | 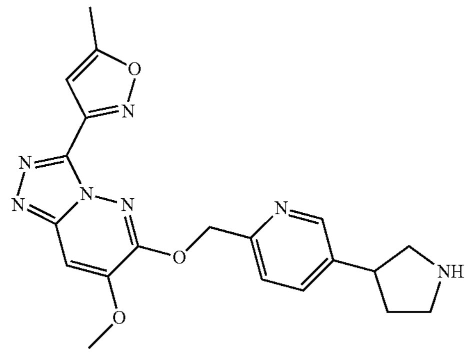 [SMILES: COc1cc2nnc(-c3cc(C)on3)n2nc1OCc1ccc(C2CCNC2)cn1] |
| 97 | 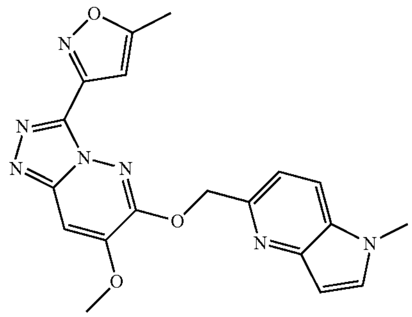 [SMILES: COc1cc2nnc(-c3cc(C)on3)n2nc1OCc1ccc2c(ccn2C)n1] |
| 98 | 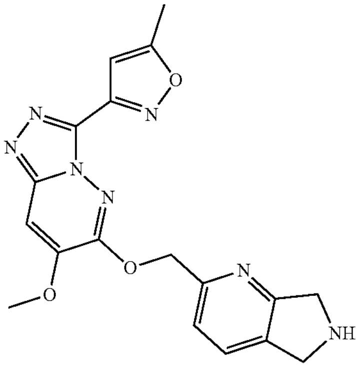 [SMILES: COc1cc2nnc(-c3cc(C)on3)n2nc1OCc1ccc2c(n1)CNC2] |

-continued
| Embodiment | Structure |
|---|---|
| 99 | 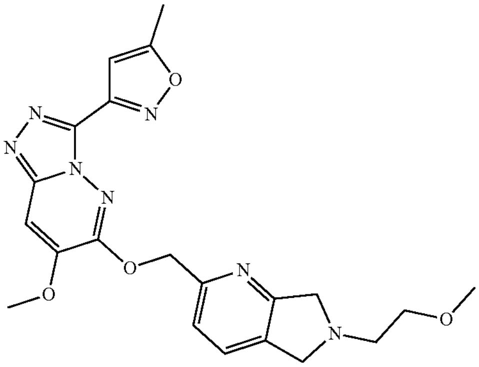 |
| 100 | 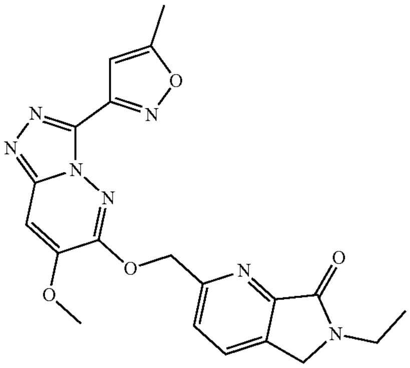 [SMILES: CCN1Cc2ccc(COc3nn4c(-c5cc(C)on5)nnc4cc3OC)nc2C1=O] |
| 101 | 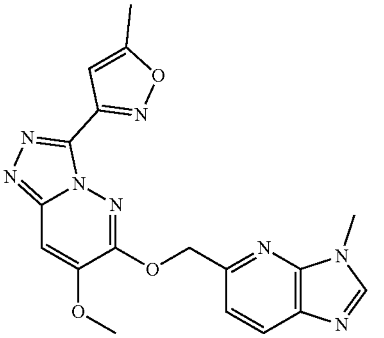 [SMILES: COc1cc2nnc(-c3cc(C)on3)n2nc1OCc1ccc2ncn(C)c2n1] |
| 102 | 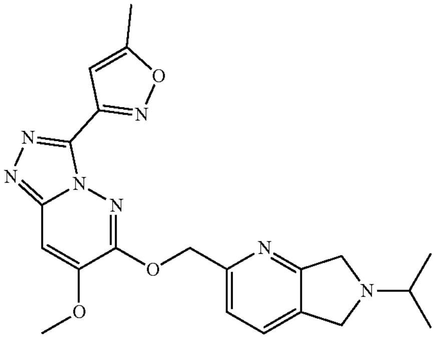 [SMILES: COc1cc2nnc(-c3cc(C)on3)n2nc1OCc1ccc2c(n1)CN(C(C)C)C2] |

-continued
| Embodiment | Structure |
|---|---|
| 103 | 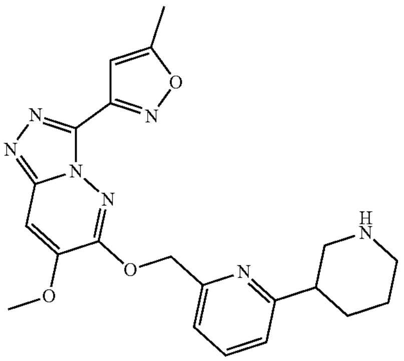 [SMILES: COc1cc2nnc(-c3cc(C)on3)n2nc1OCc1cccc(C2CCCNC2)n1] |
| 104 | 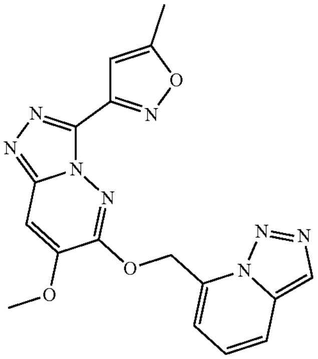 [SMILES: COc1cc2nnc(-c3cc(C)on3)n2nc1OCc1cccc2cnnn12] |
| 105 | 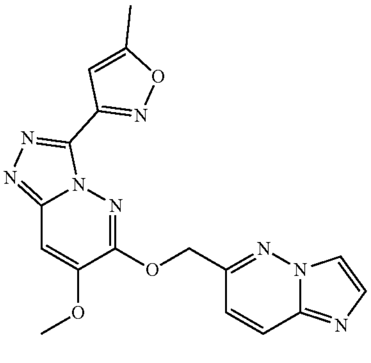 [SMILES: COc1cc2nnc(-c3cc(C)on3)n2nc1OCc1ccc2nccn2n1] |
| 106 | 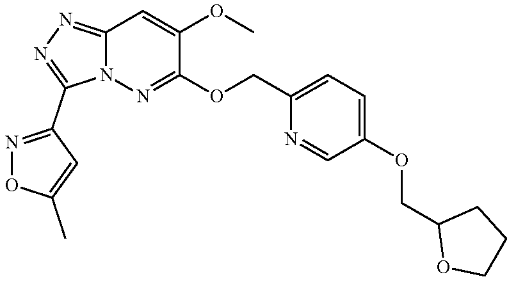 [SMILES: COc1cc2nnc(-c3cc(C)on3)n2nc1OCc1ccc(OCC2CCCO2)cn1] |

-continued
| Embodiment | Structure |
|---|---|
| 107 | 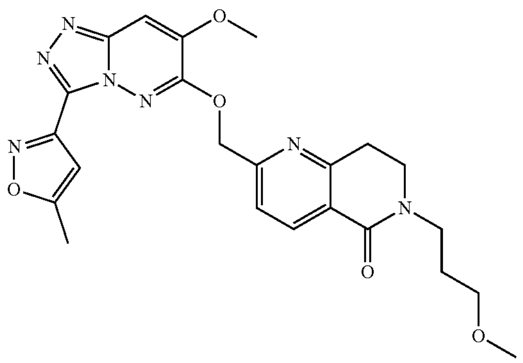 [SMILES: COCCCN1CCc2nc(COc3nn4c(-c5cc(C)on5)nnc4cc3OC)ccc2C1=O] |
| 108 | 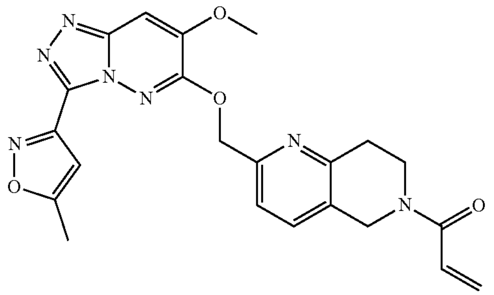 [SMILES: C=CC(=O)N1CCc2nc(COc3nn4c(-c5cc(C)on5)nnc4cc3OC)ccc2C1] |
| 109 | 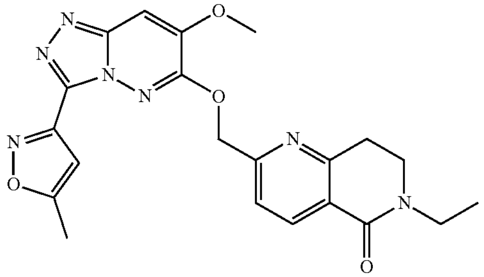 [SMILES: CCN1CCc2nc(COc3nn4c(-c5cc(C)on5)nnc4cc3OC)ccc2C1=O] |
| 110 | 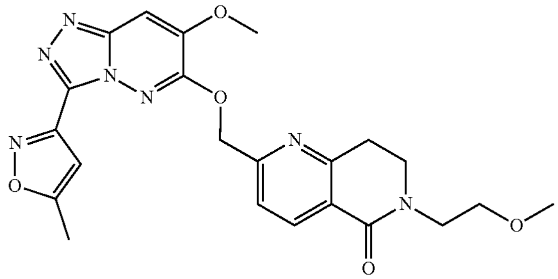 [SMILES: COCCN1CCc2nc(COc3nn4c(-c5cc(C)on5)nnc4cc3OC)ccc2C1=O] |
| 111 | 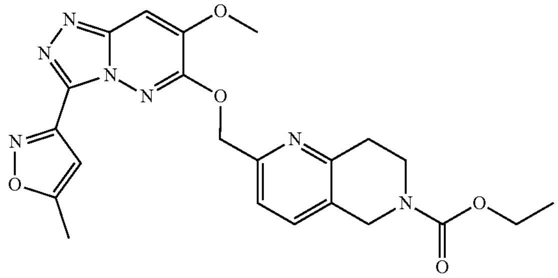 [SMILES: CCOC(=O)N1CCc2nc(COc3nn4c(-c5cc(C)on5)nnc4cc3OC)ccc2C1] |

-continued
| Embodiment | Structure |
|---|---|
| 112 | 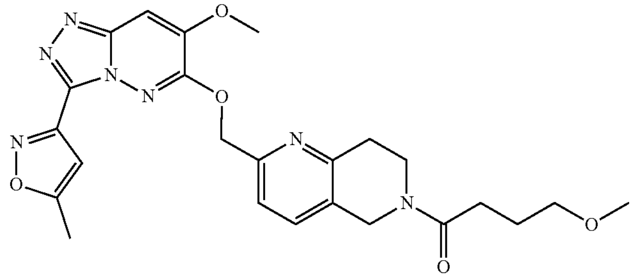 [SMILES: COCCCC(=O)N1CCc2nc(COc3nn4c(-c5cc(C)on5)nnc4cc3OC)ccc2C1] |
| 113 | 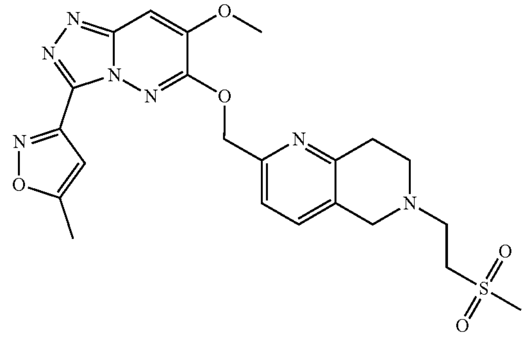 [SMILES: COc1cc2nnc(-c3cc(C)on3)n2nc1OCc1ccc2c(n1)CCN(CCS(C)(=O)=O)C2] |
| 114 | 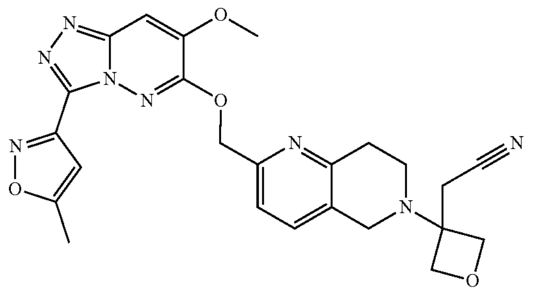 [SMILES: COc1cc2nnc(-c3cc(C)on3)n2nc1OCc1ccc2c(n1)CCN(C1(CC#N)COC1)C2] |
| 115 | 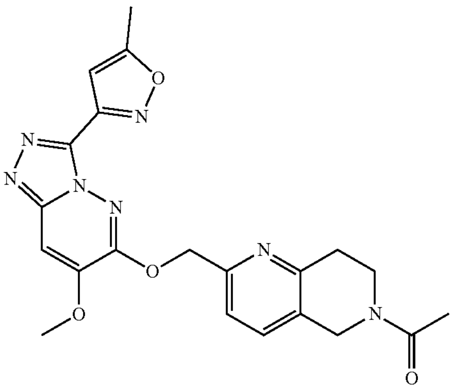 [SMILES: COc1cc2nnc(-c3cc(C)on3)n2nc1OCc1ccc2c(n1)CCN(C(C)=O)C2] |
| 116 | 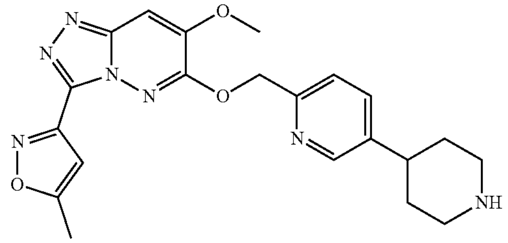 [SMILES: COc1cc2nnc(-c3cc(C)on3)n2nc1OCc1ccc(C2CCNCC2)cn1] |

-continued
| Embodiment | Structure |
|---|---|
| 117 | 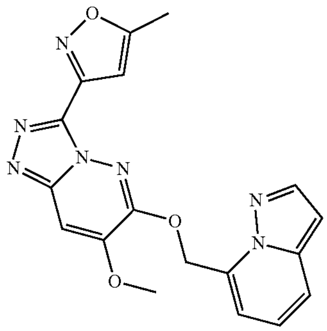 [SMILES: COc1cc2nnc(-c3cc(C)on3)n2nc1OCc1cccc2ccnn12] |
| 118 | 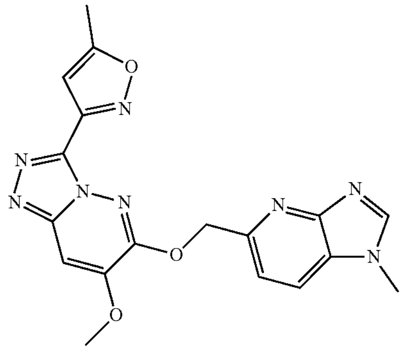 [SMILES: COc1cc2nnc(-c3cc(C)on3)n2nc1OCc1ccc2c(ncn2C)n1] |
| 119 | 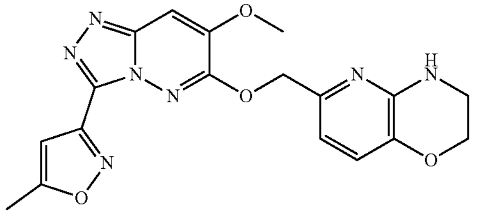 [SMILES: COc1cc2nnc(-c3cc(C)on3)n2nc1OCc1ccc2c(n1)NCCO2] |
| 120 | 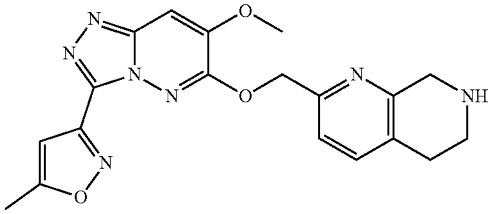 [SMILES: COc1cc2nnc(-c3cc(C)on3)n2nc1OCc1ccc2c(n1)CNCC2] |
| 121 | 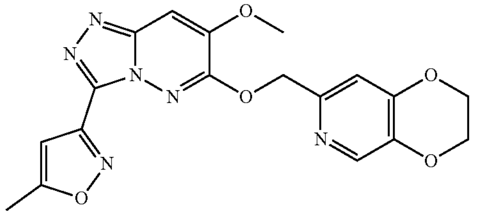 [SMILES: COc1cc2nnc(-c3cc(C)on3)n2nc1OCc1cc2c(cn1)OCCO2] |
| 122 | 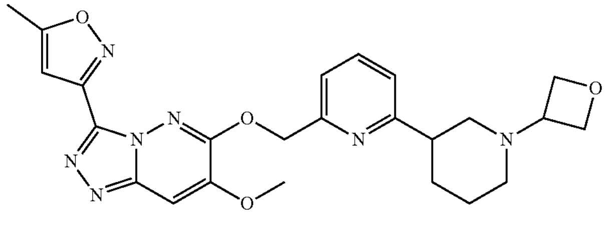 [SMILES: COc1cc2nnc(-c3cc(C)on3)n2nc1OCc1cccc(C2CCCN(C3COC3)C2)n1] |

-continued
| Embodiment | Structure |
|---|---|
| 123 | 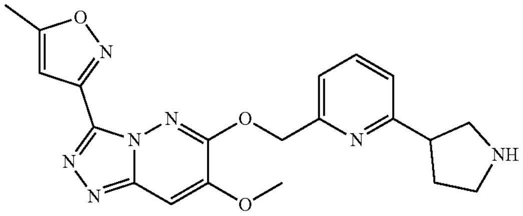 [SMILES: COc1cc2nnc(-c3cc(C)on3)n2nc1OCc1cccc(C2CCNC2)n1] |
| 124 | 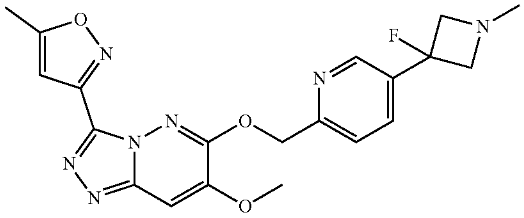 |
| 125 | 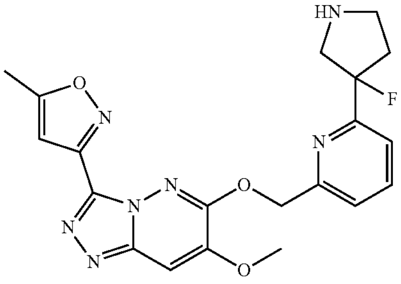 [SMILES: COc1cc2nnc(-c3cc(C)on3)n2nc1OCc1cccc(C2(F)CCNC2)n1] |
| 126 | 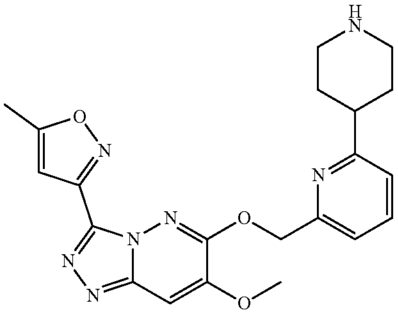 [SMILES: COc1cc2nnc(-c3cc(C)on3)n2nc1OCc1cccc(C2CCNCC2)n1] |
| 127 | 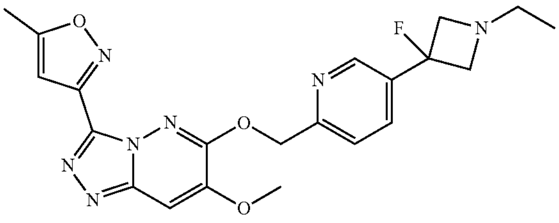 [SMILES: CCN1CC(F)(c2ccc(COc3nn4c(-c5cc(C)on5)nnc4cc3OC)nc2)C1] |
| 128 | 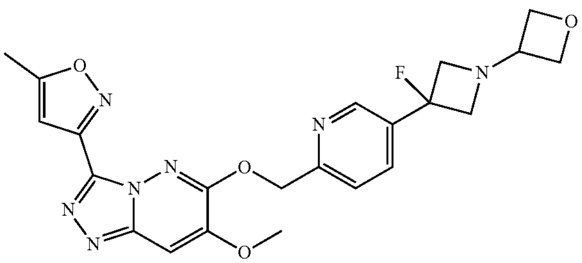 [SMILES: COc1cc2nnc(-c3cc(C)on3)n2nc1OCc1ccc(C2(F)CN(C3COC3)C2)cn1] |

-continued
| Embodiment | Structure |
| --- | --- |
| 129 | 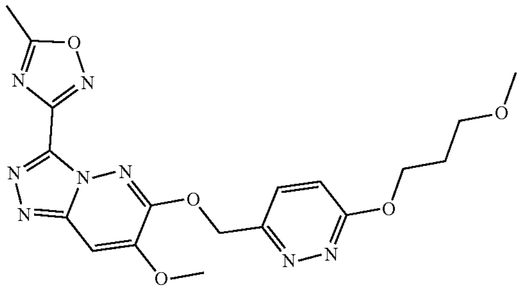 |
| 130 | 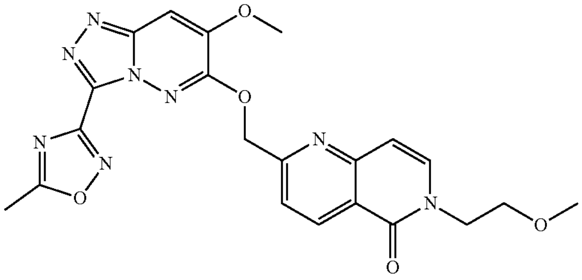 |
| 131 | 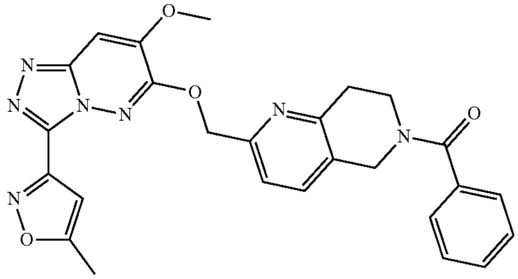 [SMILES: COc1cc2nnc(-c3cc(C)on3)n2nc1OCc1ccc2c(n1)CCN(C(=O)c1ccccc1)C2] |
| 132 | 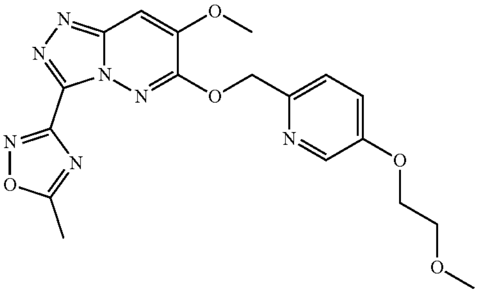 [SMILES: COCCOc1ccc(COc2nn3c(-c4noc(C)n4)nnc3cc2OC)nc1] |
| 133 | 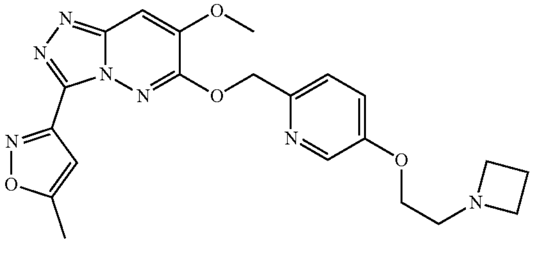 [SMILES: COc1cc2nnc(-c3cc(C)on3)n2nc1OCc1ccc(OCCN2CCC2)cn1] |

-continued
| Embodiment | Structure |
| --- | --- |
| 134 | 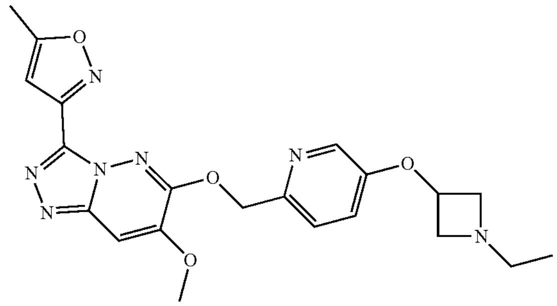 [SMILES: CCN1CC(Oc2ccc(COc3nn4c(-c5cc(C)on5)nnc4cc3OC)nc2)C1] |
| 135 | 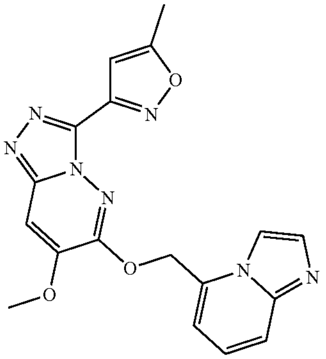 [SMILES: COc1cc2nnc(-c3cc(C)on3)n2nc1OCc1cccc2nccn12] |
| 136 | 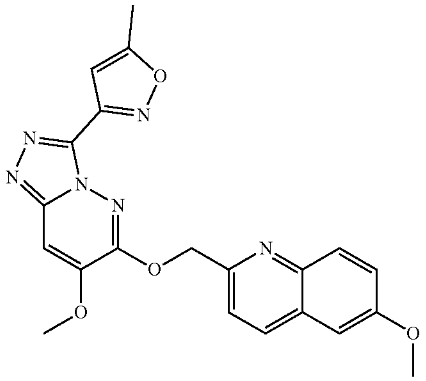 [SMILES: COc1ccc2nc(COc3nn4c(-c5cc(C)on5)nnc4cc3OC)ccc2c1] |
| 137 | 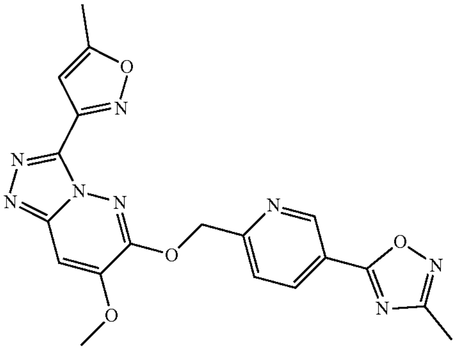 [SMILES: COc1cc2nnc(-c3cc(C)on3)n2nc1OCc1ccc(-c2nc(C)no2)cn1] |

-continued
| Embodiment | Structure |
|---|---|
| 138 | 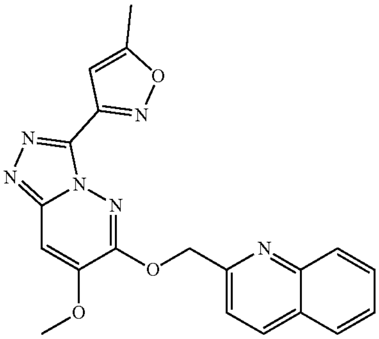 [SMILES: COc1cc2nnc(-c3cc(C)on3)n2nc1OCc1ccc2ccccc2n1] |
| 139 | 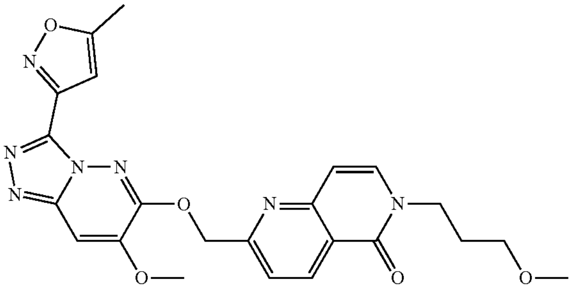 [SMILES: COCCCn1ccc2nc(COc3nn4c(-c5cc(C)on5)nnc4cc3OC)ccc2c1=O] |
| 140 | 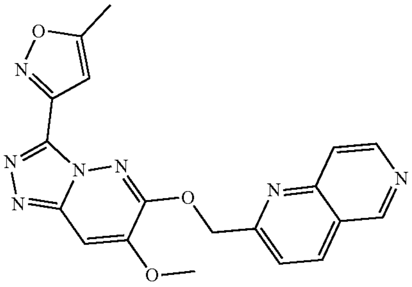 [SMILES: COc1cc2nnc(-c3cc(C)on3)n2nc1OCc1ccc2cnccc2n1] |
| 141 | 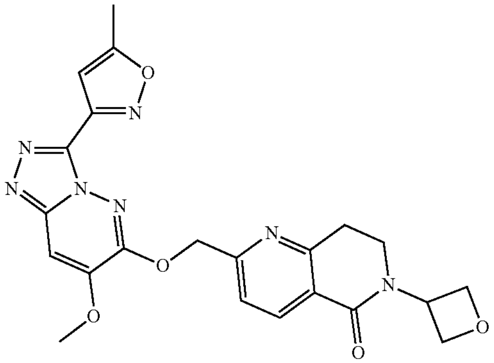 [SMILES: COc1cc2nnc(-c3cc(C)on3)n2nc1OCc1ccc2c(n1)CCN(C1COC1)C2=O] |

-continued
| Embodiment | Structure |
| --- | --- |
| 142 | 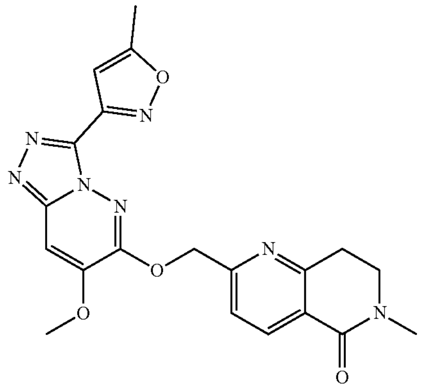 [SMILES: COc1cc2nnc(-c3cc(C)on3)n2nc1OCc1ccc2c(n1)CCN(C)C2=O] |
| 143 | 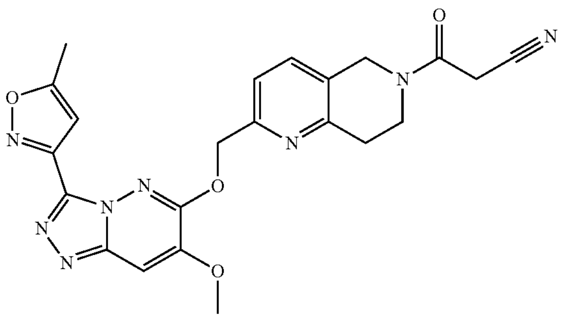 [SMILES: COc1cc2nnc(-c3cc(C)on3)n2nc1OCc1ccc2c(n1)CCN(C(=O)CC#N)C2] |
| 144 | 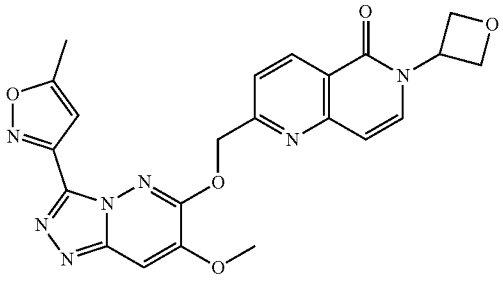 [SMILES: COc1cc2nnc(-c3cc(C)on3)n2nc1OCc1ccc2c(=O)n(C3COC3)ccc2n1] |
| 145 | 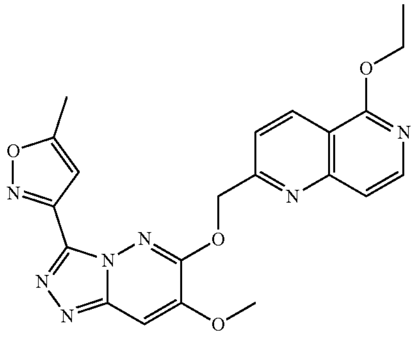 [SMILES: CCOc1nccc2nc(COc3nn4c(-c5cc(C)on5)nnc4cc3OC)ccc12] |

-continued
| Embodiment | Structure |
|---|---|
| 146 | 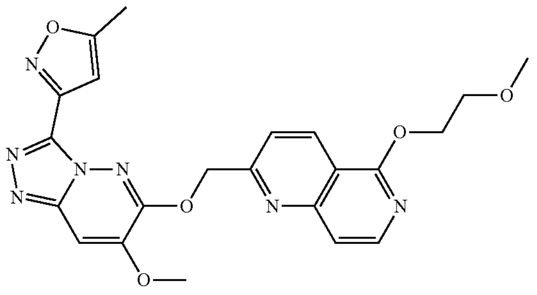 [SMILES: COCCOc1nccc2nc(COc3nn4c(-c5cc(C)on5)nnc4cc3OC)ccc12] |
| 147 | 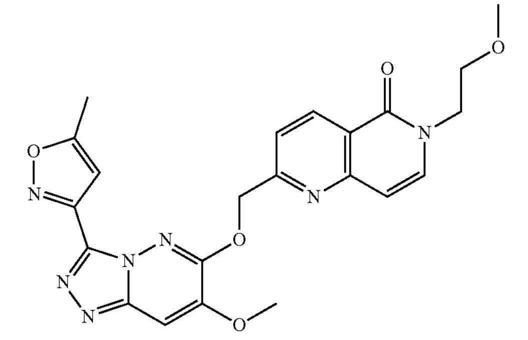 [SMILES: COCCn1ccc2nc(COc3nn4c(-c5cc(C)on5)nnc4cc3OC)ccc2c1=O] |
| 148 | 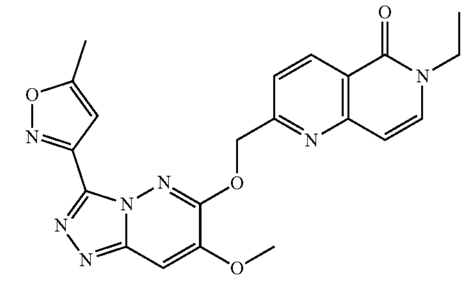 [SMILES: CCn1ccc2nc(COc3nn4c(-c5cc(C)on5)nnc4cc3OC)ccc2c1=O] |
| 149 | 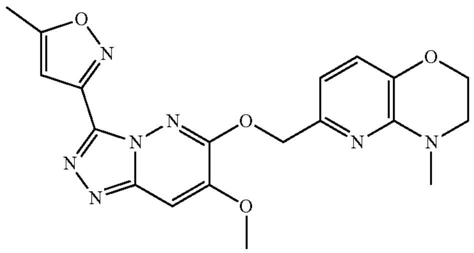 [SMILES: COc1cc2nnc(-c3cc(C)on3)n2nc1OCc1ccc2c(n1)N(C)CCO2] |
| 150 | 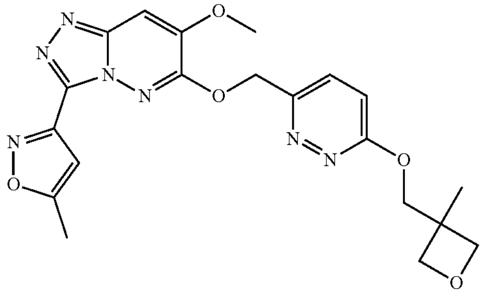 [SMILES: COc1cc2nnc(-c3cc(C)on3)n2nc1OCc1ccc(OCC2(C)COC2)nn1] |

-continued
| Embodiment | Structure |
|---|---|
| 151 | 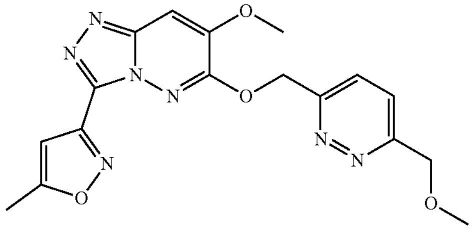 |
| 152 | 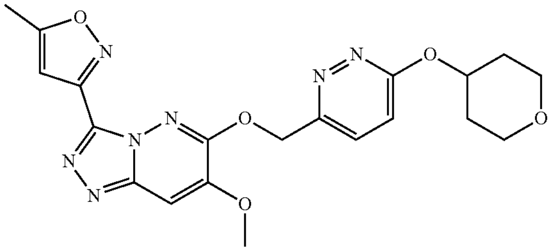 [SMILES: COc1cc2nnc(-c3cc(C)on3)n2nc1OCc1ccc(OC2CCOCC2)nn1] |
| 153 | 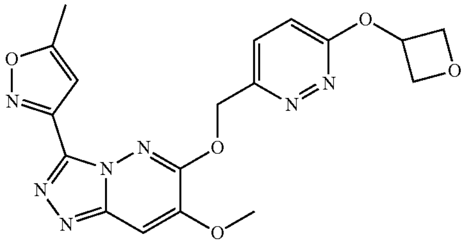 [SMILES: COc1cc2nnc(-c3cc(C)on3)n2nc1OCc1ccc(OC2COC2)nn1] |
| 154 | 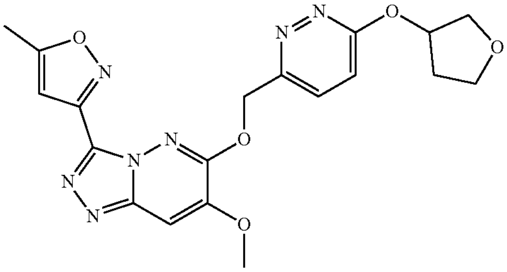 [SMILES: COc1cc2nnc(-c3cc(C)on3)n2nc1OCc1ccc(OC2CCOC2)nn1] |
| 155 | 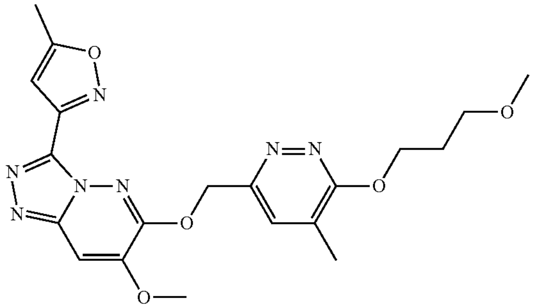 [SMILES: COCCCOc1nnc(COc2nn3c(-c4cc(C)on4)nnc3cc2OC)cc1C] |
| 156 | 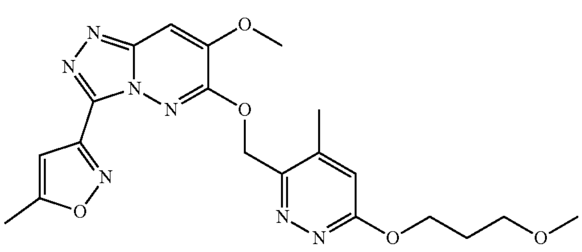 |

-continued
| Embodiment | Structure |
| --- | --- |
| 157 | 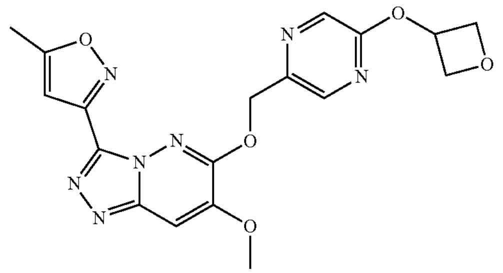 [SMILES: COc1cc2nnc(-c3cc(C)on3)n2nc1OCc1cnc(OC2COC2)cn1] |
| 158 | 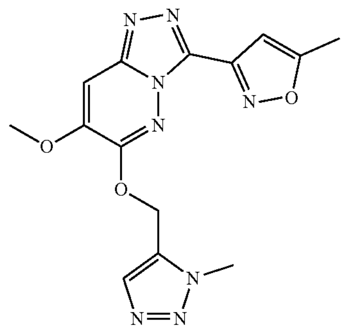 |
| 159 | 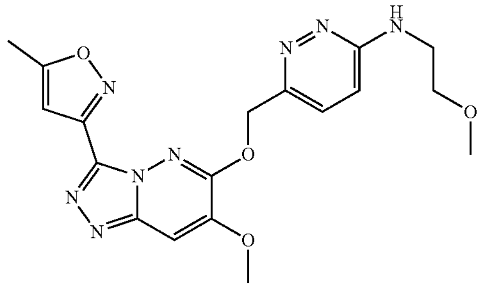 |
| 160 | 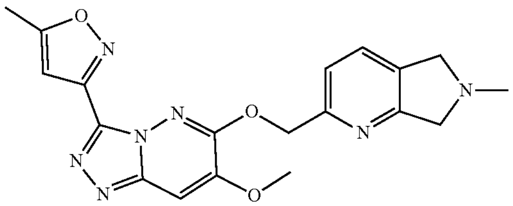 |
| 161 | 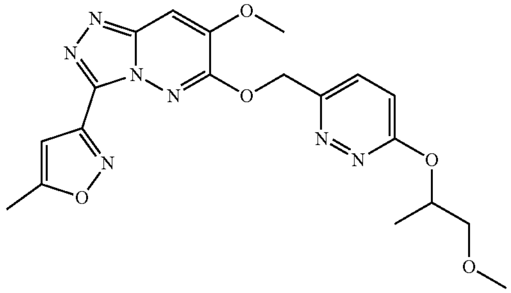 |

-continued
| Embodiment | Structure |
|---|---|
| 162 | 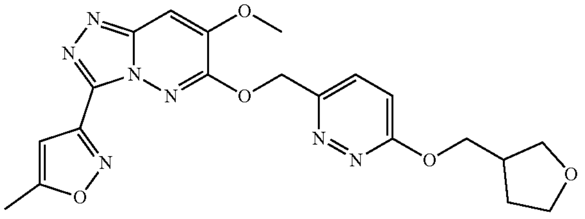 [SMILES: COc1cc2nnc(-c3cc(C)on3)n2nc1OCc1ccc(OCC2CCOC2)nn1] |
| 163 | 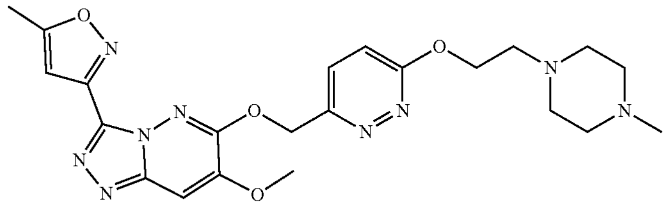 |
| 164 | 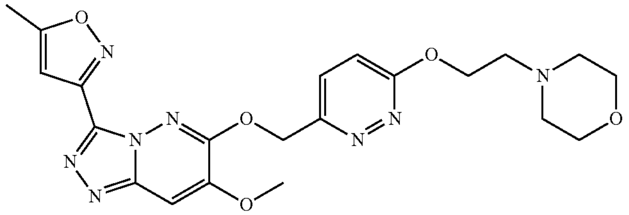 [SMILES: COc1cc2nnc(-c3cc(C)on3)n2nc1OCc1ccc(OCCN2CCOCC2)nn1] |
| 165 | 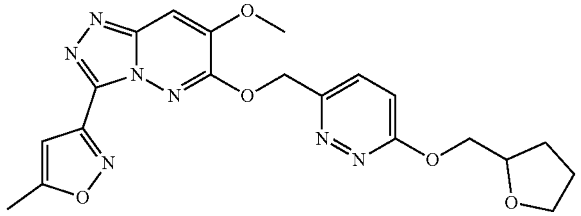 [SMILES: COc1cc2nnc(-c3cc(C)on3)n2nc1OCc1ccc(OCC2CCCO2)nn1] |
| 166 | 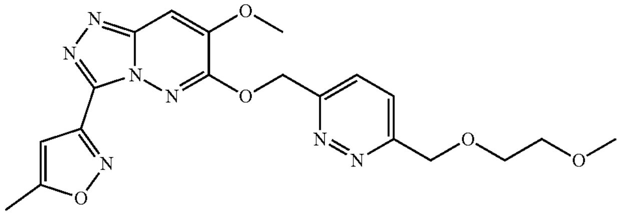 |
| 167 | 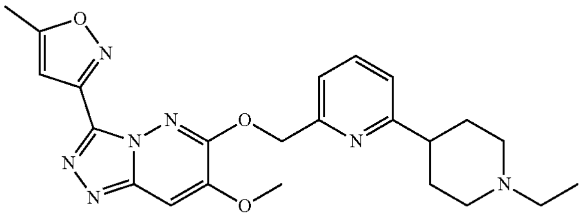 [SMILES: CCN1CCC(c2cccc(COc3nn4c(-c5cc(C)on5)nnc4cc3OC)n2)CC1] |
| 168 | 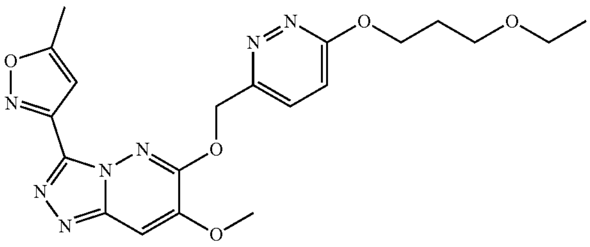 [SMILES: CCOCCCOc1ccc(COc2nn3c(-c4cc(C)on4)nnc3cc2OC)nn1] |

-continued
| Embodiment | Structure |
| --- | --- |
| 169 | 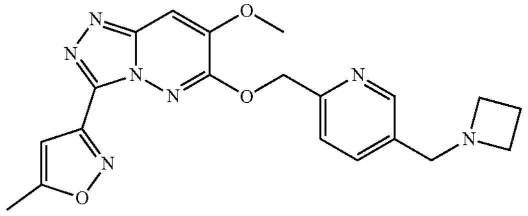 [SMILES: COc1cc2nnc(-c3cc(C)on3)n2nc1OCc1ccc(CN2CCC2)cn1] |
| 170 | 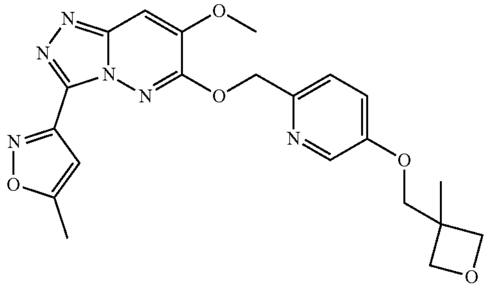 [SMILES: COc1cc2nnc(-c3cc(C)on3)n2nc1OCc1ccc(OCC2(C)COC2)cn1] |
| 171 | 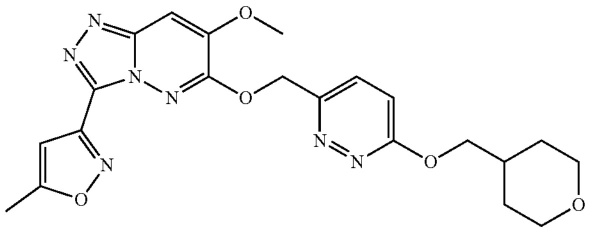 [SMILES: COc1cc2nnc(-c3cc(C)on3)n2nc1OCc1ccc(OCC2CCOCC2)nn1] |
| 172 | 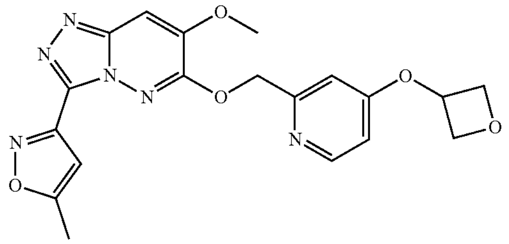 [SMILES: COc1cc2nnc(-c3cc(C)on3)n2nc1OCc1cc(OC2COC2)ccn1] |
| 173 | 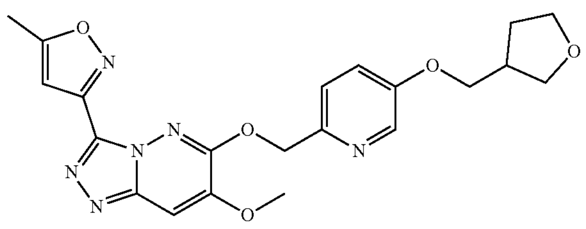 [SMILES: COc1cc2nnc(-c3cc(C)on3)n2nc1OCc1ccc(OCC2CCOC2)cn1] |
| 174 | 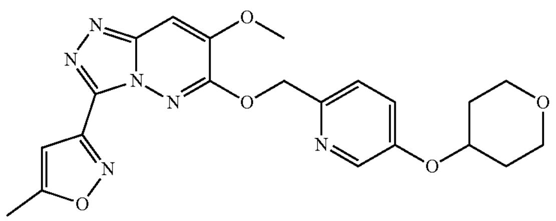 [SMILES: COc1cc2nnc(-c3cc(C)on3)n2nc1OCc1ccc(OC2CCOCC2)cn1] |

-continued
| Embodiment | Structure |
| --- | --- |
| 175 | 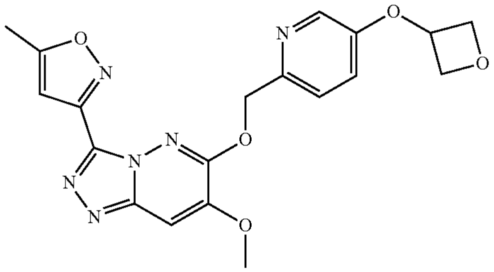 [SMILES: COc1cc2nnc(-c3cc(C)on3)n2nc1OCc1ccc(OC2COC2)cn1] |
| 176 | 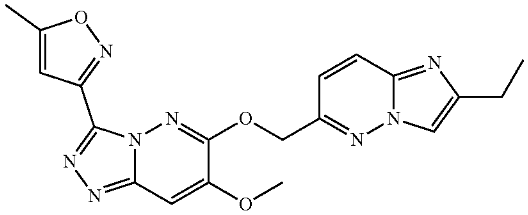 [SMILES: CCc1cn2nc(COc3nn4c(-c5cc(C)on5)nnc4cc3OC)ccc2n1] |
| 177 | 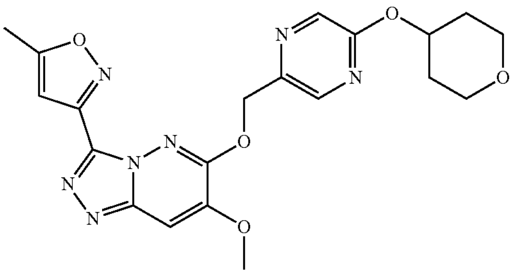 [SMILES: COc1cc2nnc(-c3cc(C)on3)n2nc1OCc1cnc(OC2CCOCC2)cn1] |
| 178 | 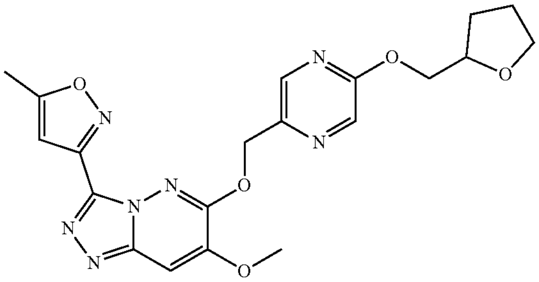 [SMILES: COc1cc2nnc(-c3cc(C)on3)n2nc1OCc1cnc(OCC2CCCO2)cn1] |
| 179 | 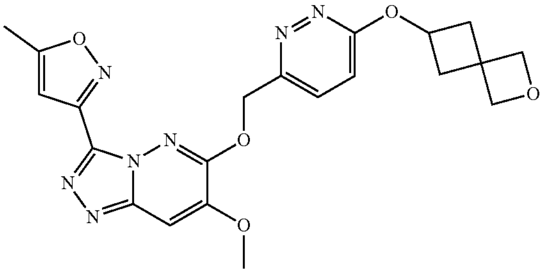 [SMILES: COc1cc2nnc(-c3cc(C)on3)n2nc1OCc1ccc(OC2CC3(COC3)C2)nn1] |
| 180 | 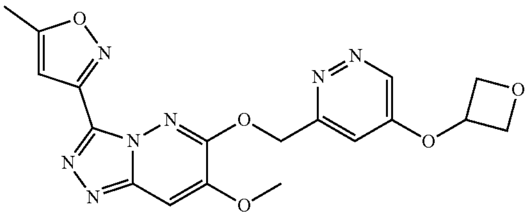 [SMILES: COc1cc2nnc(-c3cc(C)on3)n2nc1OCc1cc(OC2COC2)cnn1] |

-continued
| Embodiment | Structure |
|---|---|
| 181 | 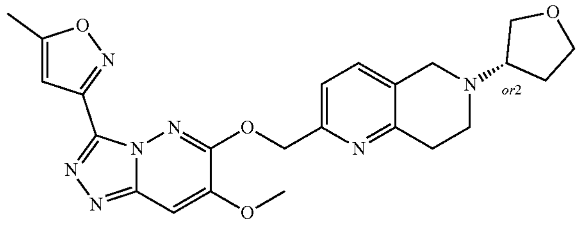 [SMILES: COc1cc2nnc(-c3cc(C)on3)n2nc1OCc1ccc2c(n1)CCN([C@H]1CCOC1)C2] |
| 182 | 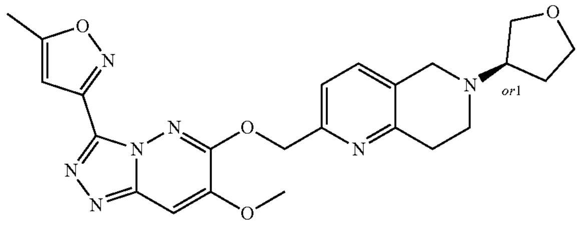 [SMILES: COc1cc2nnc(-c3cc(C)on3)n2nc1OCc1ccc2c(n1)CCN([C@@H]1CCOC1)C2] |
| 183 | 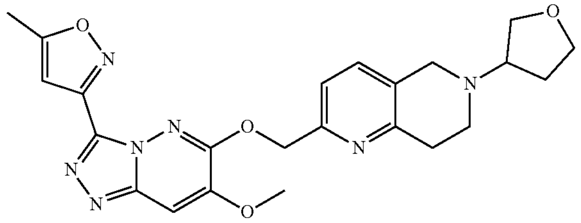 [SMILES: COc1cc2nnc(-c3cc(C)on3)n2nc1OCc1ccc2c(n1)CCN(C1CCOC1)C2] |
| 184 | 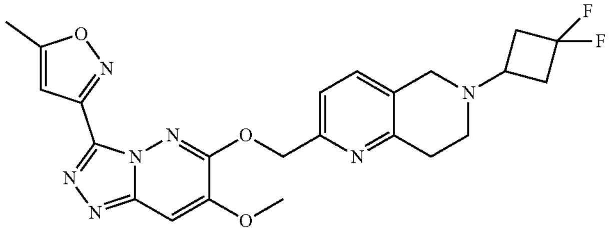 [SMILES: COc1cc2nnc(-c3cc(C)on3)n2nc1OCc1ccc2c(n1)CCN(C1CC(F)(F)C1)C2] |
| 185 | 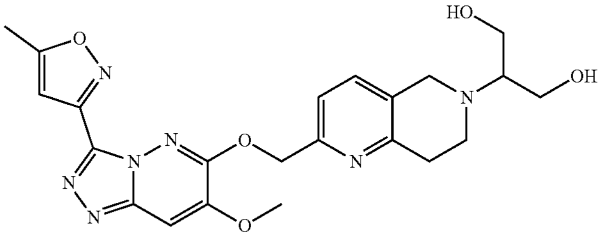 [SMILES: COc1cc2nnc(-c3cc(C)on3)n2nc1OCc1ccc2c(n1)CCN(C(CO)CO)C2] |
| 186 | 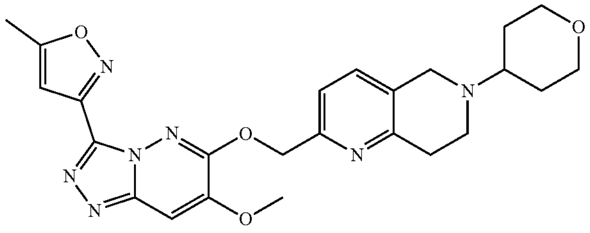 [SMILES: COc1cc2nnc(-c3cc(C)on3)n2nc1OCc1ccc2c(n1)CCN(C1CCOCC1)C2] |

-continued
| Embodiment | Structure |
|---|---|
| 187 | 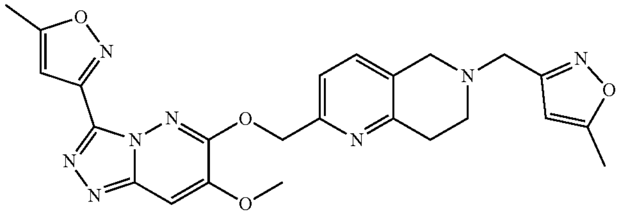 [SMILES: COc1cc2nnc(-c3cc(C)on3)n2nc1OCc1ccc2c(n1)CCN(Cc1cc(C)on1)C2] |
| 188 | 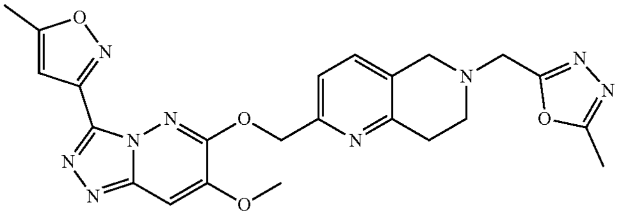 [SMILES: COc1cc2nnc(-c3cc(C)on3)n2nc1OCc1ccc2c(n1)CCN(Cc1nnc(C)o1)C2] |
| 189 | 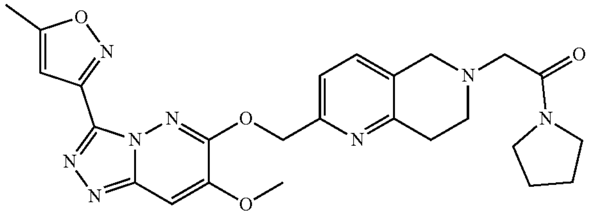 [SMILES: COc1cc2nnc(-c3cc(C)on3)n2nc1OCc1ccc2c(n1)CCN(CC(=O)N1CCCC1)C2] |
| 190 | 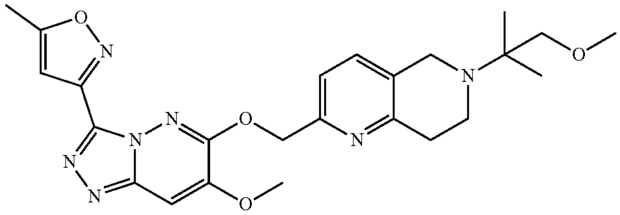 |
| 191 | 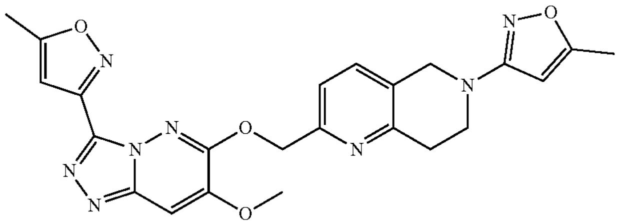 |
| 192 | 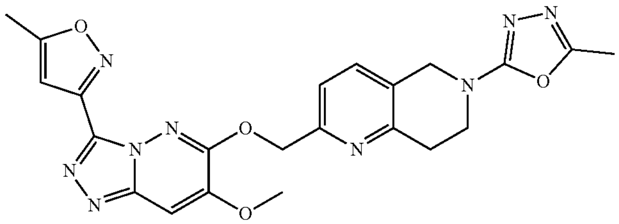 |
| 193 | 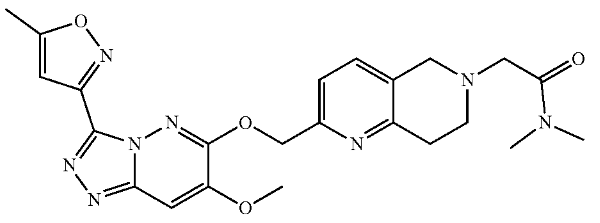 |

-continued
| Embodiment | Structure |
|---|---|
| 194 | 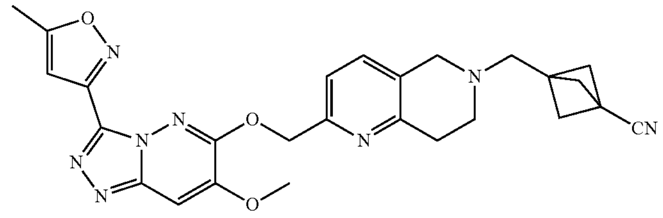 [SMILES: COc1cc2nnc(-c3cc(C)on3)n2nc1OCc1ccc2c(n1)CCN(CC13CC(C#N)(C1)C3)C2] |
| 195 | 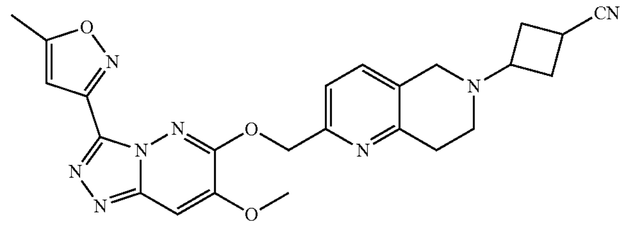 [SMILES: COc1cc2nnc(-c3cc(C)on3)n2nc1OCc1ccc2c(n1)CCN(C1CC(C#N)C1)C2] |
| 196 | 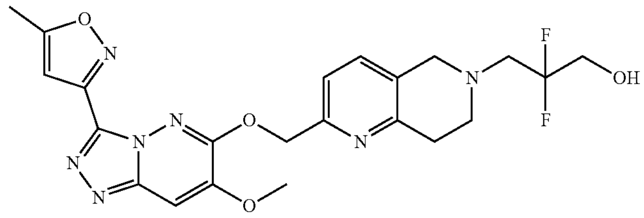 [SMILES: COc1cc2nnc(-c3cc(C)on3)n2nc1OCc1ccc2c(n1)CCN(CC(F)(F)CO)C2] |
| 197 | 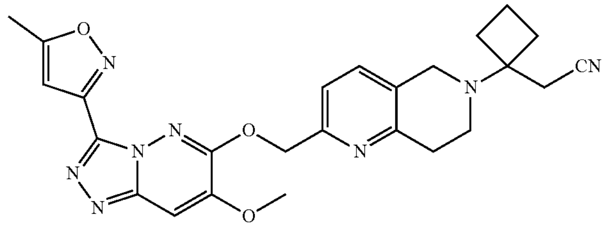 [SMILES: COc1cc2nnc(-c3cc(C)on3)n2nc1OCc1ccc2c(n1)CCN(C1(CC#N)CCC1)C2] |
| 198 | 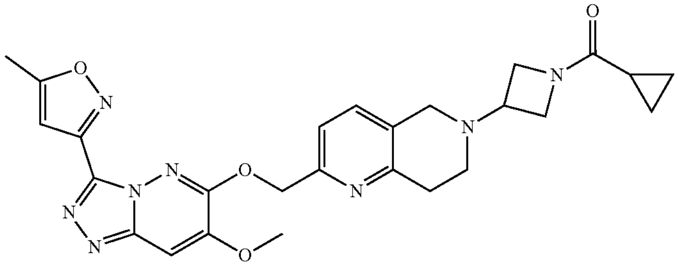 [SMILES: COc1cc2nnc(-c3cc(C)on3)n2nc1OCc1ccc2c(n1)CCN(C1CN(C(=O)C3CC3)C1)C2] |
| 199 | 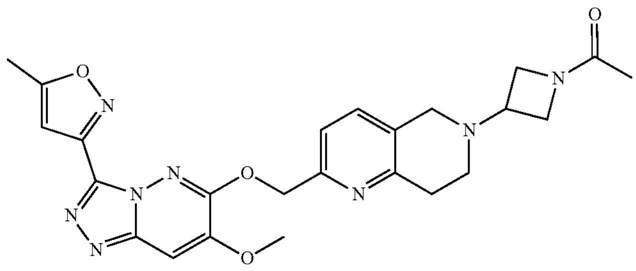 [SMILES: COc1cc2nnc(-c3cc(C)on3)n2nc1OCc1ccc2c(n1)CCN(C1CN(C(C)=O)C1)C2] |

-continued
| Embodiment | Structure |
| --- | --- |
| 200 | 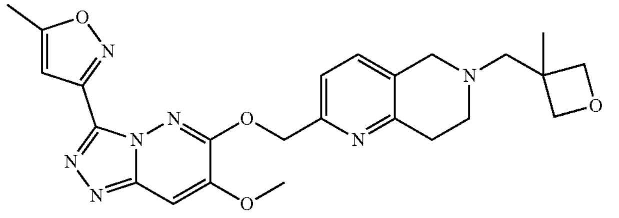 [SMILES: COc1cc2nnc(-c3cc(C)on3)n2nc1OCc1ccc2c(n1)CCN(CC1(C)COC1)C2] |
| 201 | 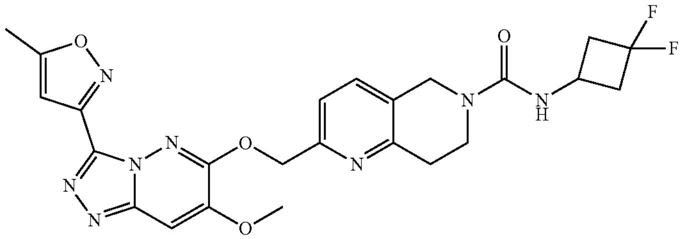 [SMILES: COc1cc2nnc(-c3cc(C)on3)n2nc1OCc1ccc2c(n1)CCN(C(=O)NC1CC(F)(F)C1)C2] |
| 202 | 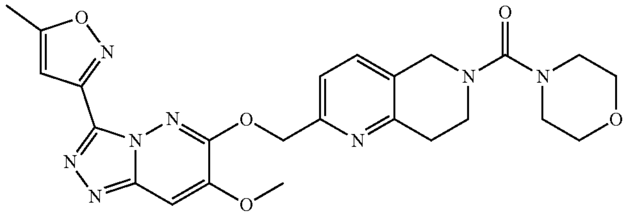 [SMILES: COc1cc2nnc(-c3cc(C)on3)n2nc1OCc1ccc2c(n1)CCN(C(=O)N1CCOCC1)C2] |
| 203 | 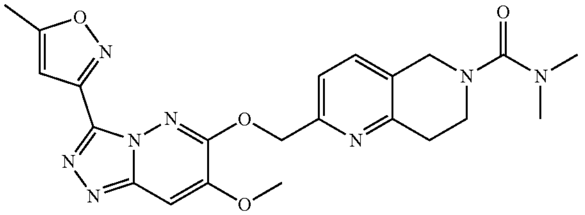 |
| 204 | 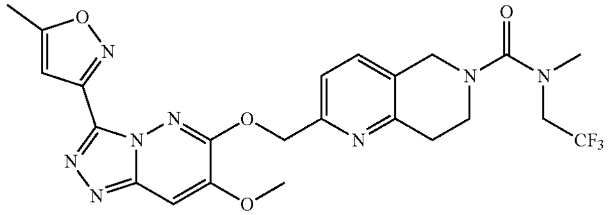 [SMILES: COc1cc2nnc(-c3cc(C)on3)n2nc1OCc1ccc2c(n1)CCN(C(=O)N(C)CC(F)(F)F)C2] |
| 205 | 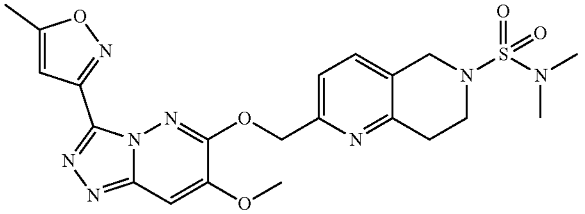 |
| 206 | 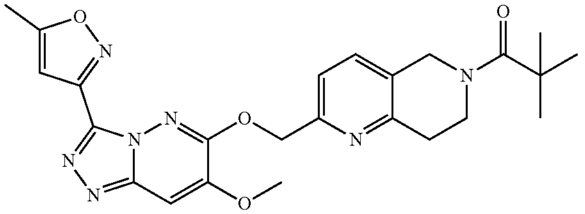 [SMILES: COc1cc2nnc(-c3cc(C)on3)n2nc1OCc1ccc2c(n1)CCN(C(=O)C(C)(C)C)C2] |

-continued
| Embodiment | Structure |
|---|---|
| 207 | 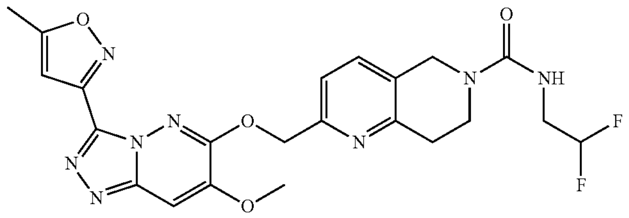 [SMILES: COc1cc2nnc(-c3cc(C)on3)n2nc1OCc1ccc2c(n1)CCN(C(=O)NCC(F)F)C2] |
| 208 | 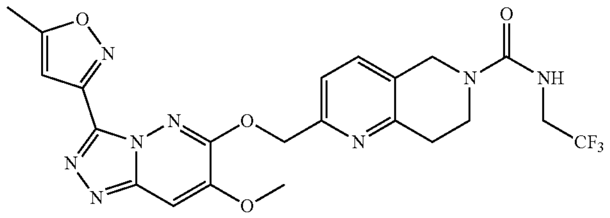 [SMILES: COc1cc2nnc(-c3cc(C)on3)n2nc1OCc1ccc2c(n1)CCN(C(=O)NCC(F)(F)F)C2] |
| 209 | 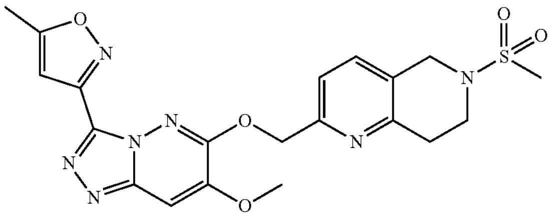 [SMILES: COc1cc2nnc(-c3cc(C)on3)n2nc1OCc1ccc2c(n1)CCN(S(C)(=O)=O)C2] |
| 210 | 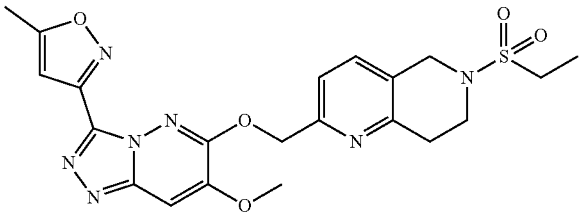 [SMILES: CCS(=O)(=O)N1CCc2nc(COc3nn4c(-c5cc(C)on5)nnc4cc3OC)ccc2C1] |
| 211 | 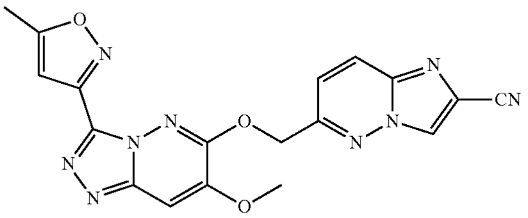 [SMILES: COc1cc2nnc(-c3cc(C)on3)n2nc1OCc1ccc2nc(C#N)cn2n1] |
| 212 | 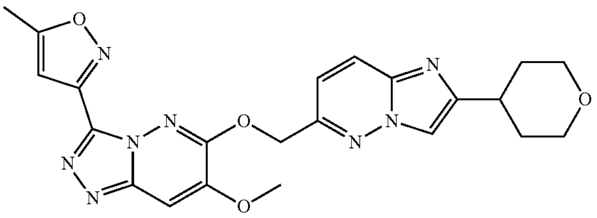 [SMILES: COc1cc2nnc(-c3cc(C)on3)n2nc1OCc1ccc2nc(C3CCOCC3)cn2n1] |
| 213 | 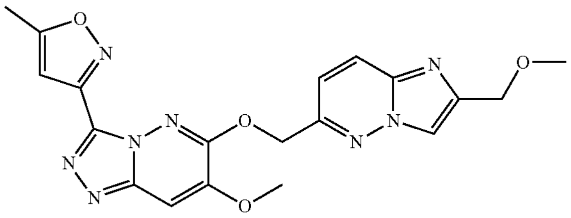 |

-continued
| Embodiment | Structure |
| --- | --- |
| 214 | 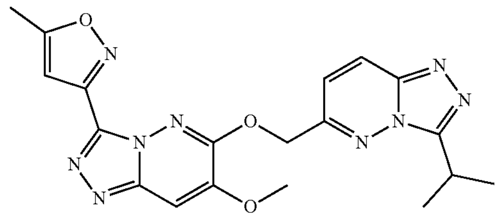 [SMILES: COc1cc2nnc(-c3cc(C)on3)n2nc1OCc1ccc2nnc(C(C)C)n2n1] |
| 215 | 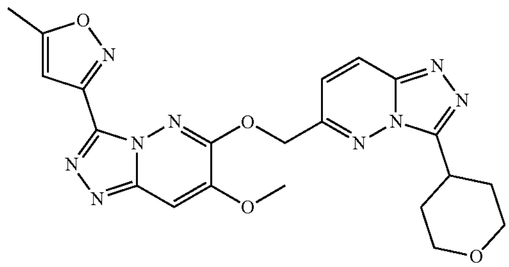 [SMILES: COc1cc2nnc(-c3cc(C)on3)n2nc1OCc1ccc2nnc(C3CCOCC3)n2n1] |
| 216 | 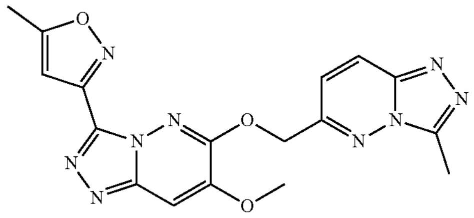 [SMILES: COc1cc2nnc(-c3cc(C)on3)n2nc1OCc1ccc2nnc(C)n2n1] |
| 217 | 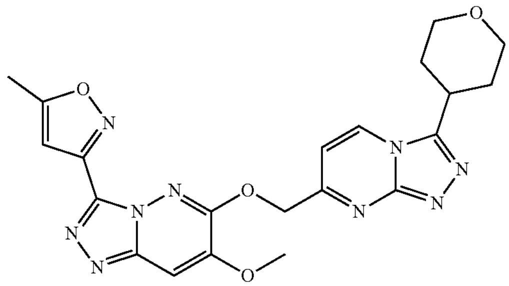 [SMILES: COc1cc2nnc(-c3cc(C)on3)n2nc1OCc1ccn2c(C3CCOCC3)nnc2n1] |
| 218 | 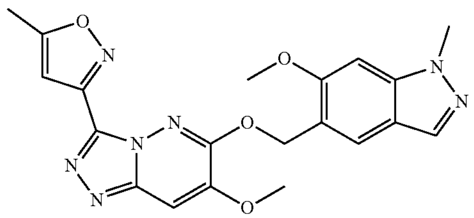 [SMILES: COc1cc2c(cnn2C)cc1COc1nn2c(-c3cc(C)on3)nnc2cc1OC] |
| 219 | 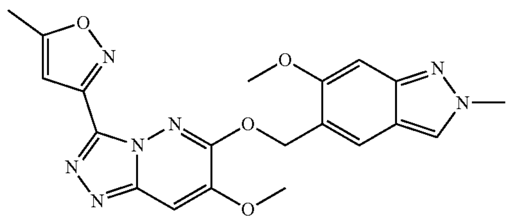 |

-continued
| Embodiment | Structure |
|---|---|
| 220 | 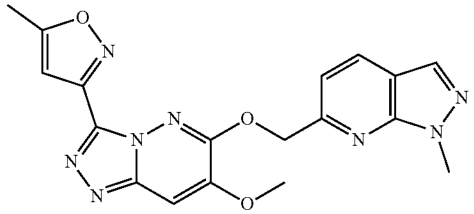 [SMILES: COc1cc2nnc(-c3cc(C)on3)n2nc1OCc1ccc2cnn(C)c2n1] |
| 221 | 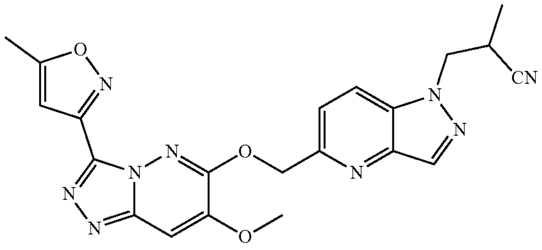 [SMILES: COc1cc2nnc(-c3cc(C)on3)n2nc1OCc1ccc2c(cnn2CC(C)C#N)n1] |
| 222 | 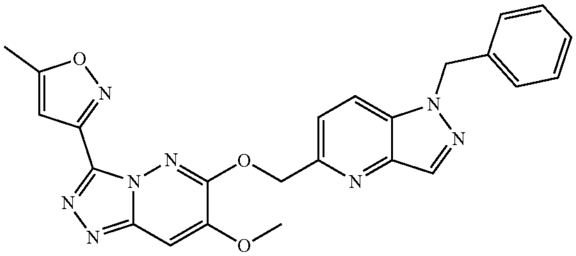 [SMILES: COc1cc2nnc(-c3cc(C)on3)n2nc1OCc1ccc2c(cnn2Cc2ccccc2)n1] |
| 223 | 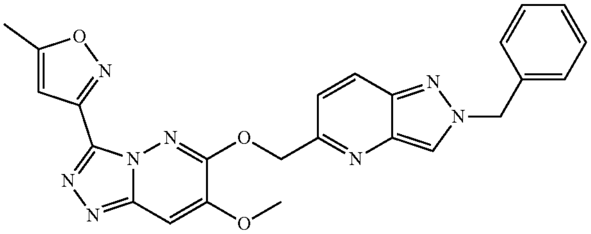 [SMILES: COc1cc2nnc(-c3cc(C)on3)n2nc1OCc1ccc2nn(Cc3ccccc3)cc2n1] |
| 224 | 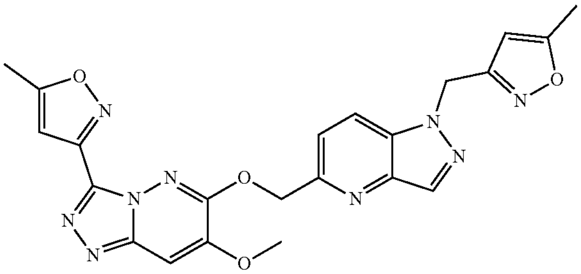 |
| 225 | 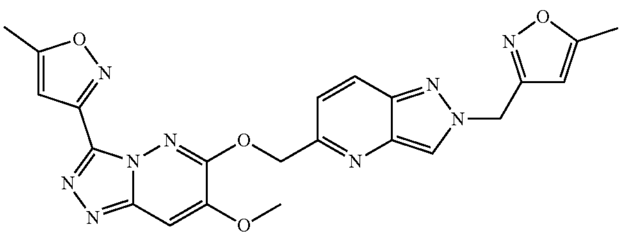 |

-continued
| Embodiment | Structure |
|---|---|
| 226 | 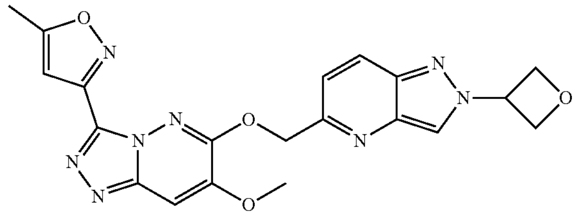 [SMILES: COc1cc2nnc(-c3cc(C)on3)n2nc1OCc1ccc2nn(C3COC3)cc2n1] |
| 227 | 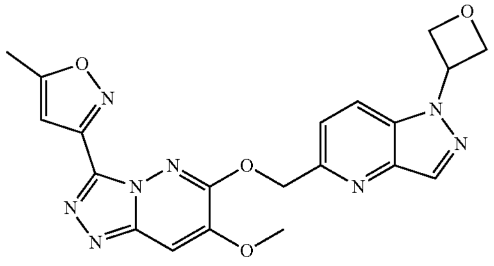 [SMILES: COc1cc2nnc(-c3cc(C)on3)n2nc1OCc1ccc2c(cnn2C2COC2)n1] |
| 228 | 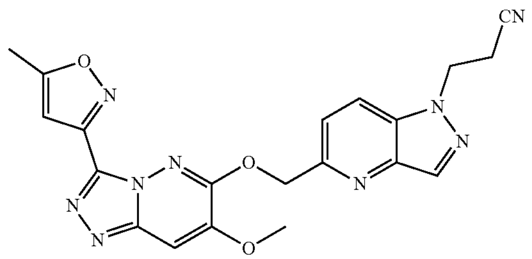 [SMILES: COc1cc2nnc(-c3cc(C)on3)n2nc1OCc1ccc2c(cnn2CCC#N)n1] |
| 229 | 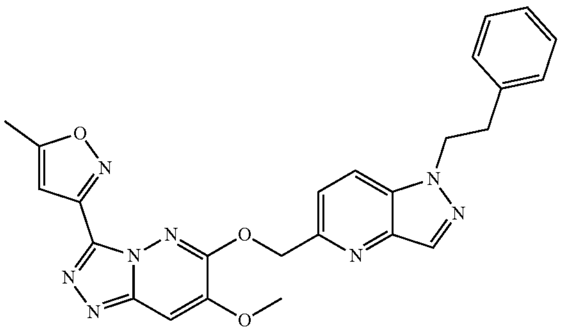 [SMILES: COc1cc2nnc(-c3cc(C)on3)n2nc1OCc1ccc2c(cnn2CCc2ccccc2)n1] |
| 230 | 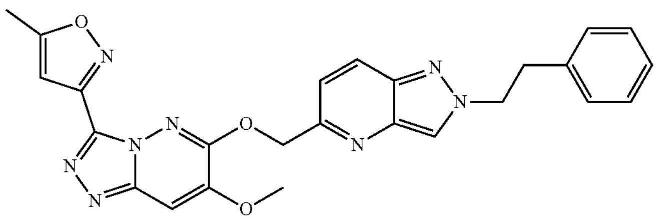 [SMILES: COc1cc2nnc(-c3cc(C)on3)n2nc1OCc1ccc2nn(CCc3ccccc3)cc2n1] |
| 231 | 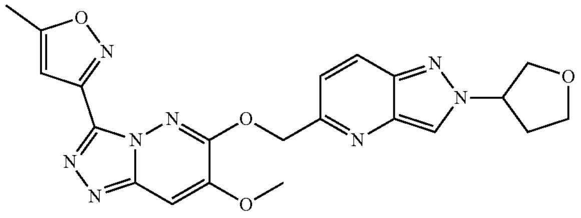 [SMILES: COc1cc2nnc(-c3cc(C)on3)n2nc1OCc1ccc2nn(C3CCOC3)cc2n1] |

-continued
| Embodiment | Structure |
| --- | --- |
| 232 | 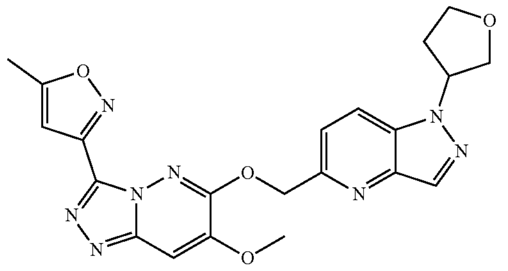 [SMILES: COc1cc2nnc(-c3cc(C)on3)n2nc1OCc1ccc2c(cnn2C2CCOC2)n1] |
| 233 | 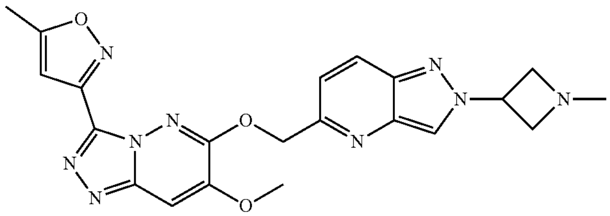 |
| 234 | 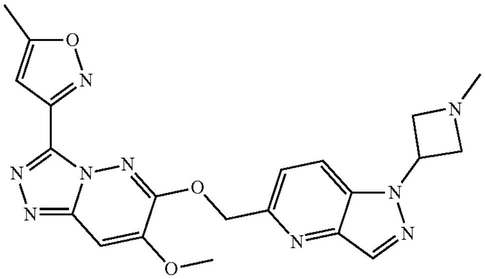 |
| 235 | 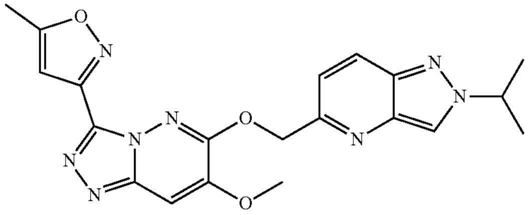 [SMILES: COc1cc2nnc(-c3cc(C)on3)n2nc1OCc1ccc2nn(C(C)C)cc2n1] |
| 236 | 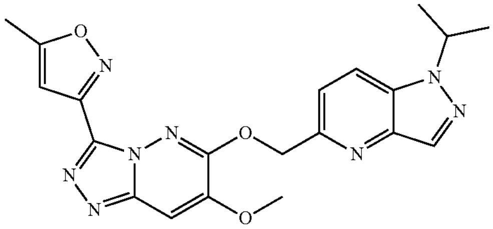 [SMILES: COc1cc2nnc(-c3cc(C)on3)n2nc1OCc1ccc2c(cnn2C(C)C)n1] |
| 237 | 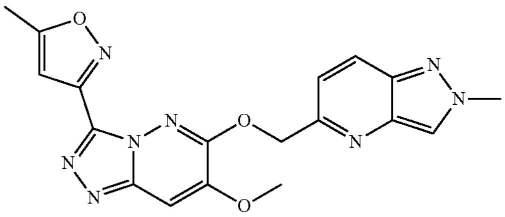 |

-continued
| Embodiment | Structure |
| --- | --- |
| 238 | 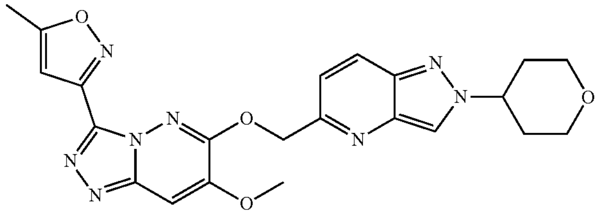 [SMILES: COc1cc2nnc(-c3cc(C)on3)n2nc1OCc1ccc2nn(C3CCOCC3)cc2n1] |
| 239 | 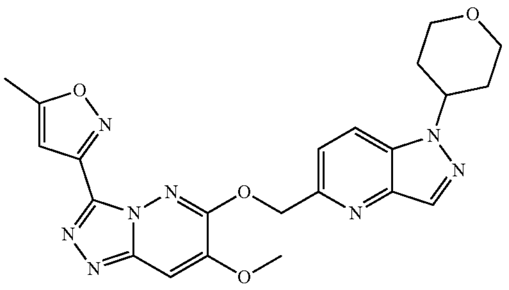 |
| 240 | 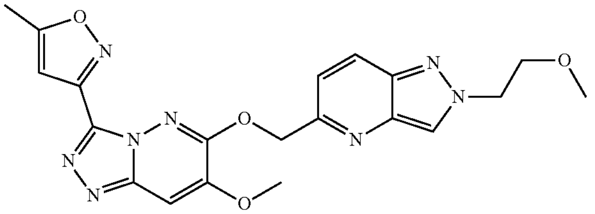 |
| 241 | 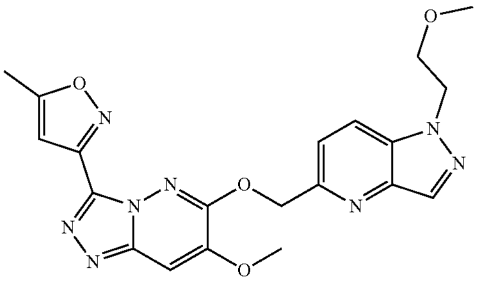 |
| 242 | 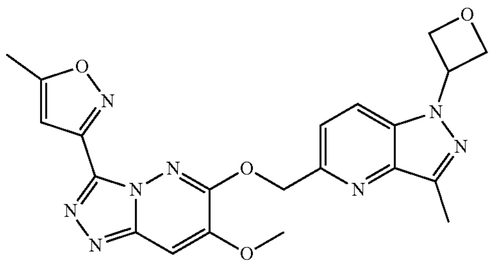 [SMILES: COc1cc2nnc(-c3cc(C)on3)n2nc1OCc1ccc2c(n1)c(C)nn2C1COC1] |
| 243 | 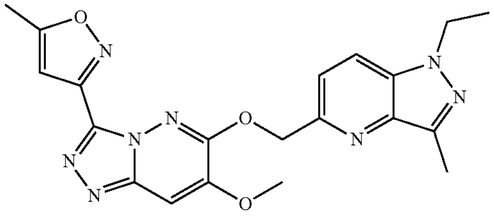 [SMILES: CCn1nc(C)c2nc(COc3nn4c(-c5cc(C)on5)nnc4cc3OC)ccc21] |

-continued
| Embodiment | Structure |
| --- | --- |
| 244 | 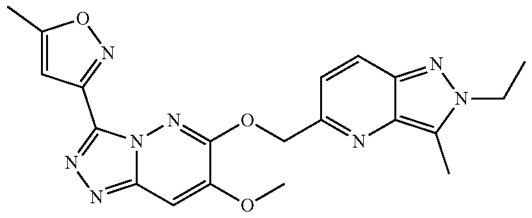 [SMILES: CCn1nc2ccc(COc3nn4c(-c5cc(C)on5)nnc4cc3OC)nc2c1C] |
| 245 | 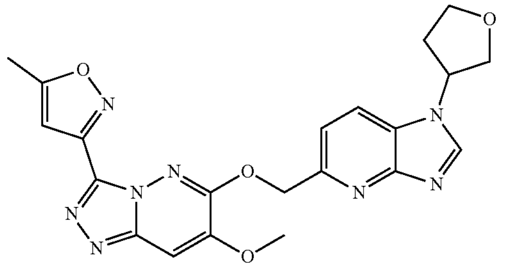 [SMILES: COc1cc2nnc(-c3cc(C)on3)n2nc1OCc1ccc2c(ncn2C2CCOC2)n1] |
| 246 | 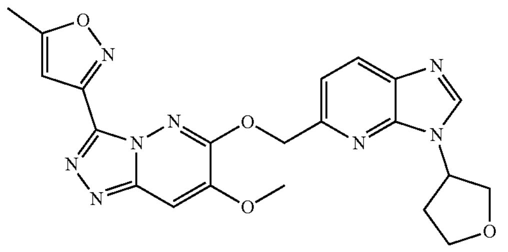 [SMILES: COc1cc2nnc(-c3cc(C)on3)n2nc1OCc1ccc2ncn(C3CCOC3)c2n1] |
| 247 | 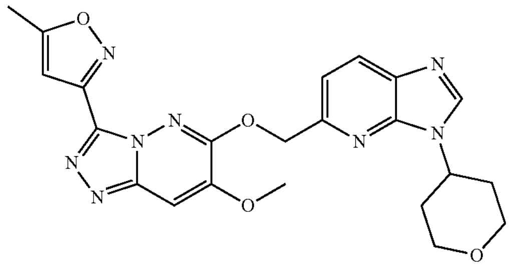 [SMILES: COc1cc2nnc(-c3cc(C)on3)n2nc1OCc1ccc2ncn(C3CCOCC3)c2n1] |
| 248 | 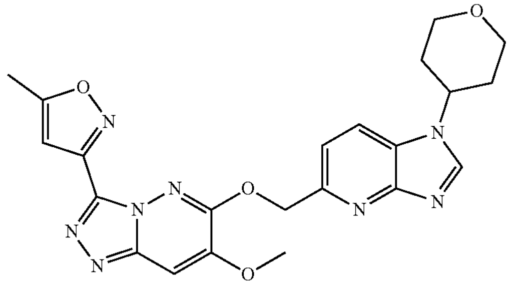 [SMILES: COc1cc2nnc(-c3cc(C)on3)n2nc1OCc1ccc2c(ncn2C2CCOCC2)n1] |
| 249 | 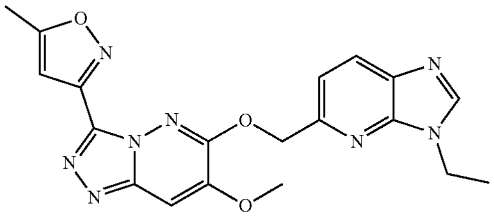 [SMILES: CCn1cnc2ccc(COc3nn4c(-c5cc(C)on5)nnc4cc3OC)nc21] |

-continued
| Embodiment | Structure |
|---|---|
| 250 | 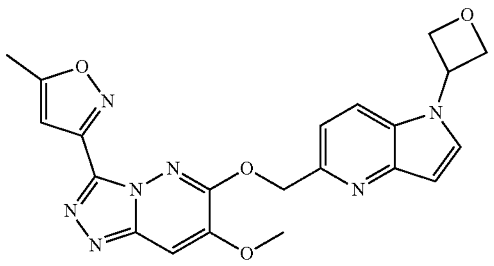 [SMILES: COc1cc2nnc(-c3cc(C)on3)n2nc1OCc1ccc2c(ccn2C2COC2)n1] |
| 251 | 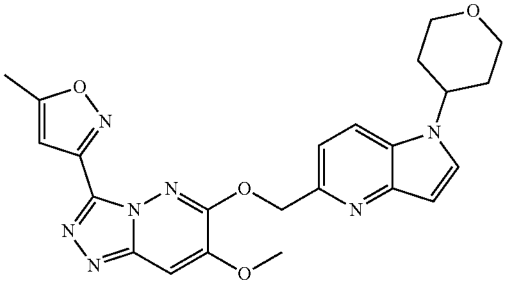 [SMILES: COc1cc2nnc(-c3cc(C)on3)n2nc1OCc1ccc2c(ccn2C2CCOCC2)n1] |
| 252 | 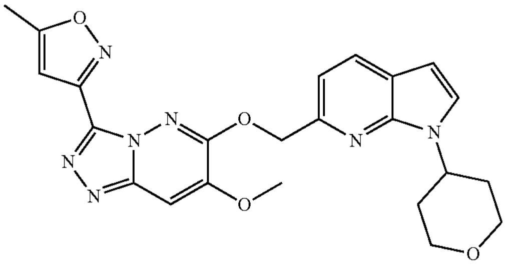 [SMILES: COc1cc2nnc(-c3cc(C)on3)n2nc1OCc1ccc2ccn(C3CCOCC3)c2n1] |
| 253 | 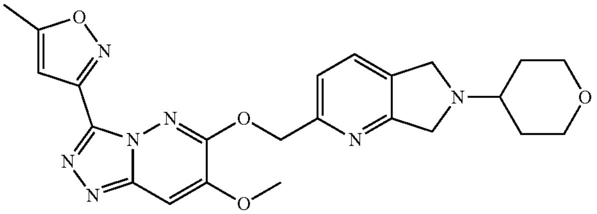 [SMILES: COc1cc2nnc(-c3cc(C)on3)n2nc1OCc1ccc2c(n1)CN(C1CCOCC1)C2] |
| 254 | 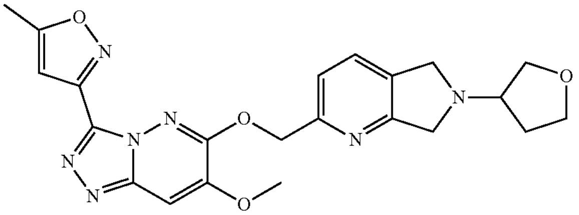 [SMILES: COc1cc2nnc(-c3cc(C)on3)n2nc1OCc1ccc2c(n1)CN(C1CCOC1)C2] |
| 255 | 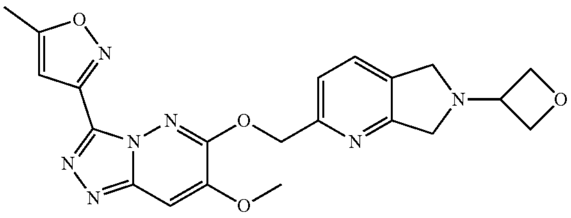 [SMILES: COc1cc2nnc(-c3cc(C)on3)n2nc1OCc1ccc2c(n1)CN(C1COC1)C2] |

-continued
| Embodiment | Structure |
|---|---|
| 256 | 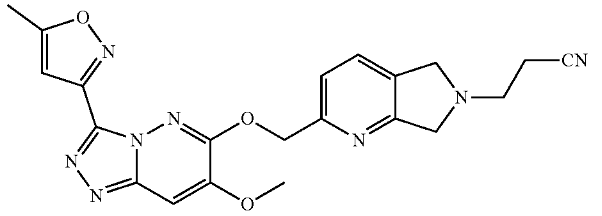 [SMILES: COc1cc2nnc(-c3cc(C)on3)n2nc1OCc1ccc2c(n1)CN(CCC#N)C2] |
| 257 | 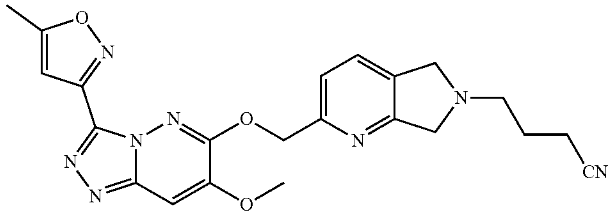 [SMILES: COc1cc2nnc(-c3cc(C)on3)n2nc1OCc1ccc2c(n1)CN(CCCC#N)C2] |
| 258 | 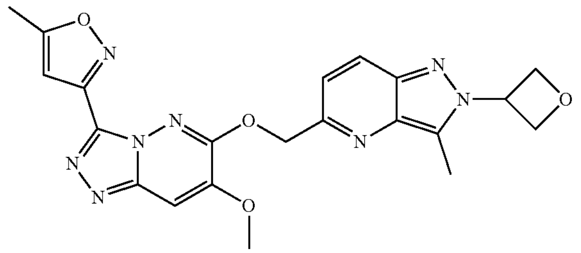 [SMILES: COc1cc2nnc(-c3cc(C)on3)n2nc1OCc1ccc2nn(C3COC3)c(C)c2n1] |
The present disclosure also provides a preparation method of the above-mentioned compound represented by formula I or IL, and the method comprises:
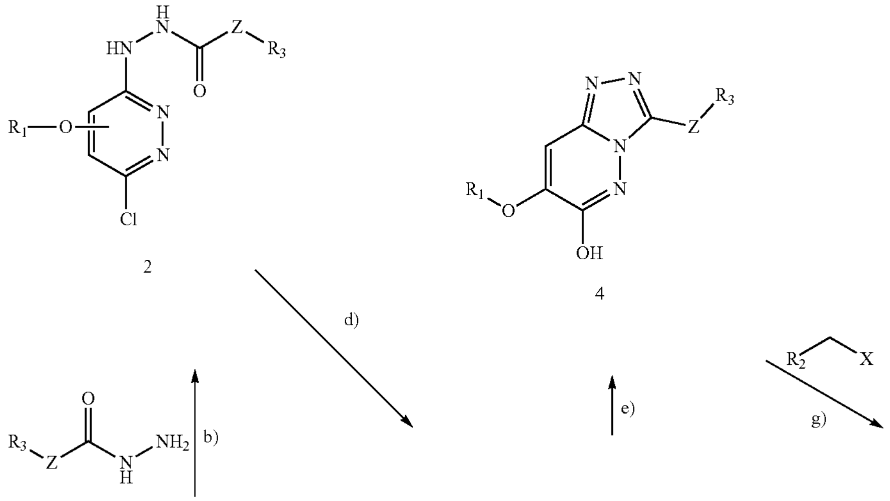

-continued

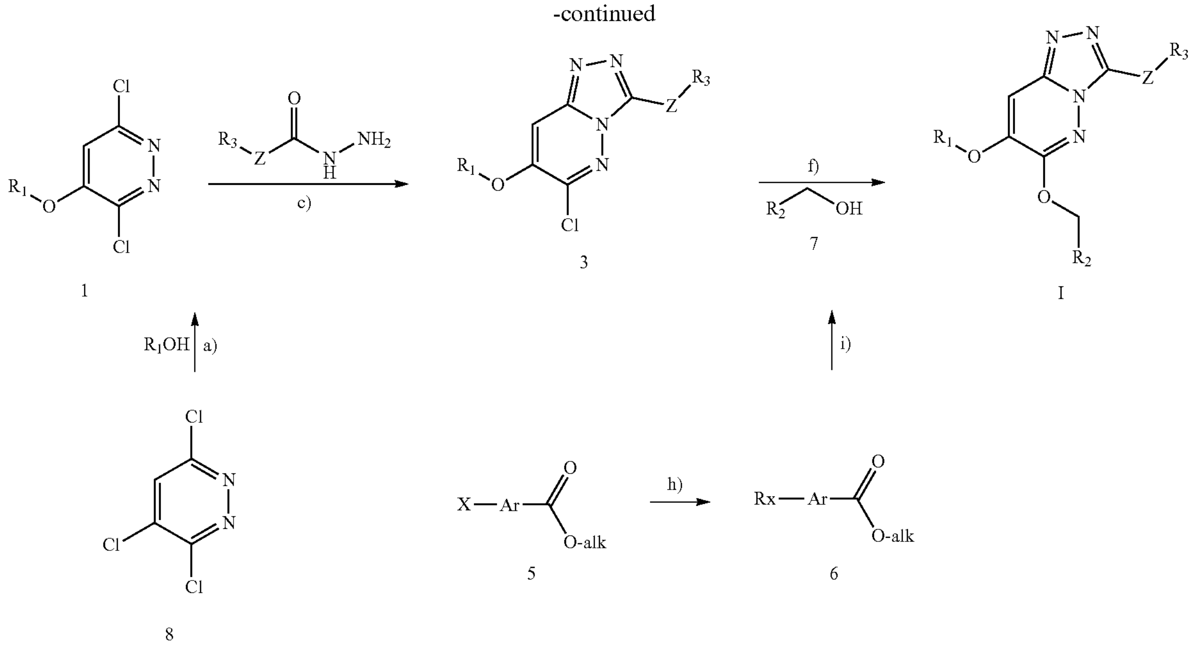

1) generally, compound 1 is provided by commercial raw materials, for compound 1 with a special structure, it can be obtained by a substitution reaction of a corresponding alcohol with compound 8 through step a, generally reacting in ethers or corresponding alcohol solvents in the presence of an alkaline reagent, such as sodium metal, sodium hydride, potassium tert-butanol, etc.;

2) compound 3 can be prepared by step c, directly heating the corresponding hydrazide and compound 1 in various ethers or alcohol solvents under the conditions of acid catalysis, such as p-toluenesulfonic acid, etc., and at the same time, different regioisomers may be produced, which need to be separated; alternatively, for a substrate with weak reactivity, the hydrazide can be reacted with compound 1 through step b under similar conditions as in step c, and then compound 2 can be obtained by separation, and then compound 3 can be further obtained by heating and cyclization in alcohols, acetic acid and other solvents in step d, and then isomer separation;

3) compound 7 can be obtained from the corresponding ester compound 6 by the reduction of, for example, sodium borohydride and lithium aluminum hydride in ethers, alcohols and other solvents through step i; in addition, the ester compound 6 with a complex structure can be obtained from the corresponding halogenated heteroaryl ester or heteroaryl ester substituted by phenolic hydroxyl through step h, substitution, coupling and other reactions;

compound (I) can be directly generated by a substitution reaction of compound 3 and compound 7 in step f, corresponding to alkaline conditions, such as cesium carbonate, potassium phosphate, etc., reacting in various solvents such as DMF, acetonitrile, etc.; alternatively, compound (I) can be obtained by converting compound 3 into the corresponding phenolic compound 4 through alkaline conditions, such as sodium hydroxide, potassium hydroxide, etc., in step e, and then substituting with the corresponding commercially available halogenated compounds through step g under alkaline conditions, such as silver carbonate, cesium carbonate, etc.

The present disclosure also relates to the compound of the general formula (I) or (II) as described above, which is prepared by the method as described above.

If the preparation method is not described in the embodiments, then the compounds represented by general formula (I) or (II) and intermediate products thereof can be prepared according to a similar method or by the method described above. The known raw materials in this art can be commercially available, or can be prepared in known methods or a similar method based on known methods in the art.

It is understandable that the compounds of the general formula (I) or (II) of the present disclosure can be derivatized on the functional group to obtain the derivatives which can be converted into the parent compound in vivo.

If the preparation method is not described in the embodiments, then the compounds represented by general formula (I) or (II) and intermediate products thereof can be prepared according to a similar method or by the method described above. The known raw materials in this art can be commercially available, or can be prepared in known methods or a similar method based on known methods in the art.

The present disclosure also provides a pharmaceutical composition, comprising the compound represented by formula I, the cis-trans isomer thereof, the enantiomer thereof, the diastereomer thereof, the racemate thereof, the solvate thereof, the hydrate thereof, the pharmaceutically acceptable salt thereof or the prodrug thereof, and a pharmaceutically acceptable excipient.

The present disclosure also provides a use of the compound represented by formula I, the cis-trans isomer thereof, the enantiomer thereof, the diastereomer thereof, the racemate thereof, the solvate thereof, the hydrate thereof, the pharmaceutically acceptable salt thereof or the prodrug thereof, or the pharmaceutical composition in the manufacture of a medicament.

In an embodiment, the medicament is used for treating, preventing or ameliorating a disease related to an α5-GABA$_A$ receptor. The disease related to the α5-GABA$_A$ receptor is, for example, one or more of cognitive diseases, Alzheimer's disease, dysmnesia, Down's syndrome, amyotrophic lateral sclerosis (ALS), drug addiction, restless leg syndrome, cognitive deficiency, multi-infarct dementia, pain, stroke, and attention deficit, for another example, pain.

In an embodiment, the medicament is used for treating, preventing or ameliorating one or more of the following diseases: cognitive diseases, Alzheimer's disease, dysmnesia, Down's syndrome, amyotrophic lateral sclerosis (ALS), drug addiction, restless leg syndrome, cognitive deficiency, multi-infarct dementia, pain, stroke, and attention deficit, for another example, pain.

In a preferred embodiment, the pain is one or more of neuropathic pain, inflammatory pain and cancer pain.

In a preferred embodiment, the pain is selected from: headache, facial pain, neck pain, shoulder pain, back pain, thoracic pain, abdominal pain, back pain, waist pain, lower limb pain, muscle and bone pain, vascular pain, gout, arthritis pain, visceral pain, the pain caused by infectious diseases (for example, AIDS pain and postherpetic neuralgia), boniness pain, sickle cell anemia associated pain, autoimmune disease associated pain, multiple sclerosis associated pain or inflammation associated pain, injury or surgery caused chronic pain, nociceptive pain, painful diabetes, trigeminal neuralgia, waist or cervix radiculopathy, glossopharyngeal neuralgia, autonomic nerve reflex pain, reflex sympathetic dystrophy associated pain, nerve root avulsion associated pain, cancer associated pain, chemical injury associated pain, toxin associated pain, nutrition deficiency associated pain, virus or bacteria infection associated pain, and degenerative osteoarthropathy associated pain.

The present disclosure also provides a use of the above-described compound represented by formula I, the cis-trans isomer thereof, the enantiomer thereof, the diastereomer thereof, the racemate thereof, the solvate thereof, the hydrate thereof, the pharmaceutically acceptable salt thereof or the prodrug thereof, or the above-described pharmaceutical composition in the manufacture of a medicament for treating or preventing a disease related to an α5-GABA$_A$ receptor. Herein, the disease related to the α5-GABA$_A$ receptor is described in the present disclosure.

The present disclosure also provides a use of the above-described compound represented by formula I, the cis-trans isomer thereof, the enantiomer thereof, the diastereomer thereof, the racemate thereof, the solvate thereof, the hydrate thereof, the pharmaceutically acceptable salt thereof or the prodrug thereof, or the above-described pharmaceutical composition in the manufacture of a medicament for treating or preventing a disease, wherein the disease is one or more of pain, Alzheimer's disease, multi-infarct dementia, and stroke. Herein, the pain is described in the present disclosure.

The present disclosure also provides a method for treating or preventing a disease related to an α5-GABA$_A$ receptor, comprising administering to a patient an effective dose of the above-described compound represented by formula I, the cis-trans isomer thereof, the enantiomer thereof, the diastereomer thereof, the racemate thereof, the solvate thereof, the hydrate thereof, the pharmaceutically acceptable salt thereof or the prodrug thereof, or the above-described pharmaceutical composition.

In an embodiment, in the composition, use and method of the present disclosure, the above-mentioned compound represented by formula I, the cis-trans isomer thereof, the enantiomer thereof, the diastereomer thereof, the racemate thereof, the solvate thereof, the hydrate thereof, the pharmaceutically acceptable salt thereof or the prodrug thereof may be in an effective dose.

In an embodiment, in the composition, use and method of the present disclosure, the above-mentioned compound represented by formula I, the cis-trans isomer thereof, the enantiomer thereof, the diastereomer thereof, the racemate thereof, the solvate thereof, the hydrate thereof, the pharmaceutically acceptable salt thereof or the prodrug thereof may be used in combination with other medicaments.

The present disclosure also provides a use of the compound or composition described herein in the manufacture of a medicament for treating or preventing the following diseases: pain, Alzheimer's disease, multi-infarct dementia and stroke.

The present disclosure also provides a method for treating or preventing a disease, comprising administering to a patient an effective dose of the above-mentioned compound represented by formula I, the cis-trans isomer thereof, the enantiomer thereof, the diastereomer thereof, the racemate thereof, the solvate thereof, the hydrate thereof, the pharmaceutically acceptable salt thereof or the prodrug thereof, or the above-mentioned pharmaceutical composition, wherein the disease is one or more of pain, Alzheimer's disease, multi-infarct dementia, and stroke. Herein, the pain is described in the present disclosure.

Unless otherwise specified, the following definitions are used to illustrate and define the meaning and scope of various terms used in the description of the present disclosure herein.

The following definitions of the general terms apply irrespective of whether the terms appear alone or in combination.

The nomenclature used in the present disclosure is based on the IUPAC systematic nomenclature generated by ChemDraw. The presence of any open valence bond on a carbon, oxygen, sulfur or nitrogen atom in the structures presented herein indicates the presence of a hydrogen atom.

Some compounds of the present disclosure may have asymmetric carbon atoms (optical centers) or double bonds. Racemates, diastereomers, geometric isomers and individual isomers are included within the scope of the present disclosure.

The term "substituted", unless specifically defined otherwise, means that the specified group or moiety can have 1, 2, 3, 4, 5 or 6 substituents. Where any group carries multiple substituents and a variety of possible substituents is provided, the substituents are independently selected and need not be the same.

The term "unsubstituted" means that the specified group has no substituents.

The term "optionally substituted by . . . " means that the specified group is unsubstituted or substituted by one or more substituents, independently selected from the group consisting of the group of possible substituents.

When indicating the number of substituents, the term "one or more" means from one substituent to the highest possible number of substitution, i.e., replacement of one hydrogen up to replacement of all hydrogens by substituents. 1, 2, 3, 4 or 5 substituents are preferred, unless specifically defined otherwise.

The term "halogen" refers to fluorine, chlorine, bromine and iodine.

The term "cycloalkyl" refers to a monovalent saturated cyclic hydrocarbon group including bridged and spiro rings, preferably having 3-7 ring carbon atoms, such as cyclopropyl, cyclobutyl, cyclopentyl or cyclohexyl, as well as those groups specifically exemplified herein below.

The term "heterocycle" or "heterocyclyl" refers to a cyclic hydrocarbon in which 1 to 4 carbon atoms have been replaced by heteroatoms independently selected from N, N(R), S, S(O), S(O) and O. Heterocycle can be saturated or unsaturated, but are not aromatic. Heterocyclyl may also contain 1, 2 or 3 rings, including bridged ring and spiro ring structures. Examples of suitable heterocyclyl include, but are not limited to: azetidinyl, tetrahydrofuranyl, tetrahydrothienyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiocyclopentadienyl, oxathiocyclopentadienyl, dioxanyl, dioxenyl, dioxazolyl, oxathiozolyl, oxazolonyl, piperazinyl, morpholino, thiomorpholinyl, 3-oxomorpholinyl, dithianyl, trithianyl and oxazinyl.

The term bridged ring compound refers to one or more atoms (i.e., C, O, N, or S) connecting two non-adjacent carbon or nitrogen atoms. Preferred bridged rings include, but are not limited to, one carbon atom, two carbon atoms, one nitrogen atom, two nitrogen atoms and one carbon-nitrogen group. It is worth noting that a bridge always converts a monocyclic ring into a triple ring. In bridged rings, substituents on the ring may also appear on the bridge.

The term spiro ring compound refers to a polycyclic compound in which two monocyclic rings share one carbon atom, and the shared carbon atom is called a spiro atom.

The term "aryl" refers to a monovalent aromatic carbocyclic ring system, comprising 6 to 14, in particular 6 to 10, carbon atoms and having at least one aromatic ring or multiple condensed rings in which at least one ring is aromatic. Examples for aryl are phenyl, naphthyl, biphenyl or indanyl, as well as those groups specifically illustrated by the examples herein below. Preferred aryl is phenyl. Aryl can also be substituted e.g., as defined below and in the claims.

The term "heteroaryl" refers to stable monocyclic, bicyclic, or tricyclic ring containing up to 7 atoms in each ring, wherein at least one ring is an aromatic ring containing 1 to 4 heteroatoms selected from the group consisting of O, N, and S. Heteroaryl within the scope of this definition includes, but is not limited to, acridinyl, carbazolyl, cinnolinyl, quinoxalinyl, quinazolinyl, pyrazolyl, indolyl, isoindolyl, 1H,3H-1-oxoisoindolyl, benzotriazolyl, furanyl, thienyl, pyridomorpholinyl, pyridopiperidinyl, pyridopyrrolidinyl, benzothiophenyl, benzofuranyl, benzodioxanyl, benzodioxaphenyl, quinolyl, isoquinolyl, oxazolyl, isoxazolyl, benzoxazolyl, imidazolyl, pyrazinyl, pyridazinyl, pyridyl, pyrimidinyl, pyrrolyl, tetrahydroquinolyl, thiazolyl, isothiazolyl, 1,2,3-triazolyl, 1,2,4-triazolyl, 1,2,4-oxadiazolyl, 1,2,4-thiadiazolyl, 1,3,5-triazinyl, 1,2,4-triazinyl, 1,2,4,5-tetrazinyl, tetrazolyl, xanthyl, phenazinyl, phenothiazinyl, phenoxazinyl, azepinyl, oxazepinyl, and thiazonyl, Particular heteroaryl has a 5- or 6-membered ring, such as furyl, pyridyl, pyridazinyl, pyrimidinyl, pyrazinyl, thienyl, isoxazolyl, oxazolyl, diazolyl, imidazolyl, pyrrolyl, pyrazolyl, triazolyl, tetrazolyl, thiazolyl, isothiazolyl, thiadiazolyl, pyridomorpholinyl, pyridopiperidinyl, pyridopyrrolidinyl. Heteroaryl may also be substituted, as defined below and in the claims.

Compounds of general formula (I) or (II) can form pharmaceutically acceptable acid addition salts. Examples of such pharmaceutically acceptable salts are salts of compounds of formula (I) or (II) with physiologically compatible inorganic acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salt" refers to such salts. Compounds of formula (I) or (II) which comprise an acidic group, e.g., a COOH group, can further form salts with alkalis. Examples of such salts are alkali metal salts, alkaline earth metal salts and ammonium salts, e.g., Na—, K—, Ca— and trimethylammonium salt. The term "pharmaceutically acceptable salt" also refers to such salts.

The term "prodrug" generally refers to functional group derivatization of the compound represented by general formula (I) or (II), which is easily converted into the compound represented by general formula (I) or (II) in vivo. Selection and preparation of suitable prodrugs can be found in, for example, Design of Prodrug, ed. H. Bundgaard, Elsevier, 1985.

The illustrations of racemates, ambiscalemic and scalemic or the compound in the form of pure enantiomer used herein are from Maehr, J. Che. Ed. 1985, 62:114-120. Unless otherwise specified, wedge-shaped bonds and dashed bonds are used to indicate the absolute configuration of a stereocenter. When the compounds described herein contain olefinic double bonds or other geometric asymmetric centers, unless otherwise specified, they include E and Z geometric isomers. Likewise, all tautomeric forms are included within the scope of the present disclosure.

The compound of the present disclosure may contain an unnatural proportion of atomic isotopes on one or more of the atoms constituting the compound, the isotopes have the same atomic number, but their atomic mass or mass number is different from those that predominantly exist in nature. For example, the compounds can be labeled with radioisotopes, such as deuterium ($^2H$), tritium ($^3H$), iodine-125 ($^{125}I$), or C-14 ($^{14}C$). All isotopic variations of the compound of the present disclosure, whether radioactive or not, are encompassed within the scope of the present disclosure. Isotope variants may improve certain therapeutic advantages, such as deuterium enrichment can increase in vivo half-life or reduce dosage requirements, or provide compounds as standard for the characterization of biological samples. Isotopically enriched compounds within the general formula (I) can be prepared by conventional techniques well known to those skilled in the art, or by methods similar to those described in the routes and embodiments herein, using appropriate isotope-enriched reagents and/or intermediates without redundant experimentation.

As mentioned above, the new compound of the present disclosure and the pharmaceutically acceptable salts thereof and the prodrug have important pharmacological properties and are $\alpha 5GABA_A$ receptor inverse agonists. Therefore, the compound of the present disclosure can be used alone or in combination with other medicaments for treating or preventing diseases mediated by $GABA_A$ receptor ligands containing $\alpha 5$ subunits. These diseases include, but are not limited to, pain, Alzheimer's disease, multi-infarct dementia and stroke.

Therefore, the present disclosure also relates to a pharmaceutical composition comprising the compound as defined above and a pharmaceutically acceptable carrier and/or adjuvant.

Similarly, the present disclosure also provides the compound as described above for use in the manufacture of the medicament for treating or preventing diseases related to the $\alpha 5GABA_A$ receptor, especially for treating or preventing the following diseases: pain, Alzheimer's disease, multi-infarct dementia and stroke.

It is preferred to treat or prevent pain.

It is particularly preferred to treat or prevent neuropathic pain, inflammatory pain, and cancer pain.

As used herein, "cancer pain" refers to the pain occurs during the development process of malignant tumor. Currently, it is thought that there are three mechanisms of cancer pain, i.e., the pain caused directly by cancer development, the pain caused after cancer treatment and the concurrent painful diseases of cancer patients.

As used herein, "neuropathic pain" refers to the pain caused by the primary damage and dysfunction of the nervous system.

As used herein, "inflammatory pain" refers to the pain caused by local acute inflammation or chronic inflammation that stimulates nerves.

As used herein, "treatment" also includes preventive administration, preventing or eliminating the diseases after the establishment of the diseases.

As used herein, "patient" is defined as any warm-blooded animal, including but not limited to mice, cavies, dogs, horses or humans. Preferably, the patient is human.

As used herein, "acute pain" is defined as the pain caused by the injury of skin, body structure or internal organs and/or noxious stimulation of the diseases, or the pain caused by the abnormal function of muscle or internal organs that does not produce a real tissue injury.

As used herein, "chronic pain" is defined as the pain that lasts a period of time that exceeds the common course or healing time of acute diseases, or that is associated with the chronic pathological processes that cause persistent pain, or that relapses for several months or years with certain interval. If pain still exists after treatment that should cure the disease or exceeding the common course, such pain can be regarded as chronic pain. The time duration that the pain lasts depends on the nature of pain and the treatment process associated with pain. If the pain exceeds common treatment process, then this pain is chronic.

The medicaments disclosed by this disclosure can efficiently treat the chronic pain defined as above, and the medicaments disclosed by this disclosure can be used to treat hyperalgia accompanied with other diseases, including hyperalgesia, allodynia, algesia enhancement and pain memory enhancement. The present disclosure will improve the treatment of pain.

As used herein, "headache" can be divided into primary headache and secondary headache. Primary headache includes tension headache, migraine headache and cluster headache, and secondary headache is caused by other diseases. Headache is caused when pain sensitive tissue on head and face undergoes lesion or get stimulated. These pain sensitive tissues are distributed on scalp, face, oral cavity and throat, etc. Since they are mainly muscles and vessels in head with abundant nerve fibers and sensitive to pain, headache is caused when these tissues are injured.

As used herein, "facial pain" includes, but is not limited to trigeminal neuralgia, atypical facial pain, facial palsy and facial spasm.

As used herein, "trigeminal neuralgia" is a unique chronic painful disease, also referred as tic douloureux, representing transient, paroxysmal and repeated electric shock-like severe pain in trigeminal nerve area, or accompanied with ipsilateral facial spasm. Trigeminal neuralgia can be divided into two classes: primary and secondary. Primary trigeminal neuralgia means no neurological sign is found clinically and no organic disease is detected. Secondary trigeminal neuralgia means neurological signs are found clinically and organic diseases such as tumor and inflammation are detected.

As used herein, "atypical facial pain" refers to pain caused by various diseases, appearing as persistent burning pain, non-intermittent and independent of particular action or stimulation. The pain is often bilateral and exceeds the area of trigeminal nerve to even cervical skin. The etiology can be the stimulation of nasosinusitis, malignant tumor, jaw and skull base infection or pain caused by injured trigeminal nerve.

As used herein, "neck pain, back pain, shoulder pain" refer to the pain caused by acute or chronic muscle strain and bone joint degeneration and injury. The common diseases that cause neck, shoulder and upper limb pain include cervicoshoulder myofascitis, neck desmitis, cervical spondylopathy, scapulohumeral periarthritis, thoracic outlet syndrome, external humeral epicondylitis, etc. Alternatively, these terms refer to the pain caused by autoimmune diseases is common in rheumatoid arthritis, ankylosing spondylitis and rheumatic arthritis. Other diseases that can cause neck pain, back pain and shoulder pain are tumors on neck and shoulder, neuritis, arteriovenous disease and various infections as well as referred pain induced by lesions of thoracic and abdominal organs.

As used herein, "thoracic, abdominal, and back pain" refer to the pain caused by diseases in thoracic and abdominal organs, thoracic and abdominal wall tissues.

As used herein, "waist pain, lower limb pain" refer to low back, lumbosacral, sacroiliac, hip, buttocks and lower limb pain.

As used herein, "muscle and bone pain" includes but is not limited to myofascial pain, trauma-caused pain and chronic regional pain syndrome.

As used herein, "diabetic peripheral neuropathy pain" refers to the pain caused by nerve injury complicated by diabetes, and the nerve injury in diabetes is at least partially caused by blood flow reduction and hyperglycemia.

As used herein, "visceral pain" includes but is not limited to the pain of inflammatory bowel syndrome (IBS), with or without chronic fatigue syndrome (CFS), inflammatory bowel disease (IBD) and interstitial cystitis.

As used herein, "vascular pain" refers to the pain generated by the following one or more factors. Firstly, improper perfusion of tissue, resulting in temporary or persistent ischemia, e.g., the ischemia in limb muscles during physical exercise. Secondly, delayed change, e.g., ulcer or gangrene in skin or abdominal organs. Thirdly, the sudden and accelerated change of diameter of great vessels, e.g., the change of arterial aneurysm. Fourthly, aortic rupture, resulting in blood spillover and the stimulation of nociceptive fibers in peritoneum or pleura parietal layers. Fifthly, strong cramp caused by the severe stimulation of artery endothelium by intra-arterial injection. Sixthly, the damage of venous return, leading to a large number of edema of rapidly expanded fascia compartment (Bonica et al., The Management of Pain, Volume 1 (the 2nd version), Philadelphia; Leas & Feboger, 1990).

As used herein, "autonomic nerve reflex pain" refers to the pain caused by "reflex sympathetic atrophy syndrome". For sympathetic atrophy syndrome, after the body suffers an acute or chronic injury, severe spontaneous pain occurs and the body is sensitive to the sense of touch and pain As used herein, "postoperative pain" refers to a complex physiological response of body to the disease itself and the tissue injury caused by operation, showing an unpleasant psychological and behavior experience.

As used herein, "arthritis pain" includes but is not limited to the pain caused by osteoarthritis, rheumatoid arthritis, joint ankylosing spondylitis, psoriatic arthropathy, gout, pseudo gout, infectious arthritis, tendinitis, bursitis, bone damage and joint soft tissue inflammation.

As used herein, "postherpetic neuralgia" refers to the subcutaneously long-standing severe pain in rash site after the healing of the rash of herpes zoster.

As used herein, "nociceptive pain" refers to the pain caused by the tissue injury delivered by nociceptors, or the pain caused by the extended excitement of nociceptors.

On the basis of not violating common knowledge in the art, the above preferred conditions can be combined arbitrarily to obtain preferred examples of the present disclosure.

The reagents and raw materials used in the present disclosure are all commercially available.

The positive progress effect of the present disclosure lies in that the triazolopyridazine derivative in the present disclosure has good inverse agonistic activity, thermodynamic solubility, bioavailability and pharmacokinetic properties for α5-$GABA_A$.

DETAILED DESCRIPTION OF THE PREFERRED EMBODIMENT

Embodiment and Preparation Method

Intermediate 1

3-(6-Chloro-7-methoxy-[1,2,4]triazolo[4,3-b]pyridazin-3-yl)-5-methylisoxazole

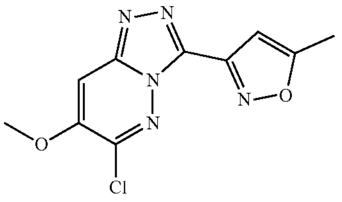

3,6-Dichloro-4-methoxy-pyridazine (9.9 g, 55.6 mmol) and 5-methyl-isoxazole-3-carboxylic acid hydrazide (7.8 g, 55.6 mmol) were sequentially added to 50 mL of n-butanol, heated and refluxed under the protection of argon for 4 hours. The solvent was evaporated to dryness, and a solid was slurried with dichloromethane. An insoluble substance was filtered, and an organic phase was concentrated. A residue was purified by silica chromatography to obtain 500 mg of the title compound as a white solid with a yield of 3%. $^{1}$H NMR (400 MHz, $CDCl_3$) δ=7.35 (s, 1H), 6.82 (s, 1H), 4.07 (s, 3H). LC-MS: m/z $[M+H]^{+*}$=266.

Intermediate 2

(6-Morpholinopyridin-2-yl)methanol

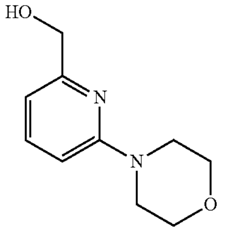 [SMILES: OCc1cccc(N2CCOCC2)n1]

(6-Fluoropyridin-2-yl)methanol (150 mg, 1.2 mmol) and morpholine (1 mL, 12 mmol) were mixed, and the reaction mixture was stirred in a sealed tube at 160° C. for 6 hours. The mixture was concentrated under reduced pressure, and separated by thin layer chromatography to obtain 220 mg of the title compound with a yield of 94% and a pale yellow solid appearance. LC-MS: m/z $[M+H]^{+*}$=195.

Intermediate 3

(6-(Dimethylamino)pyridin-2-yl)methanol

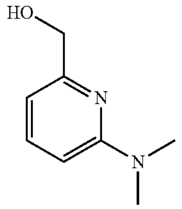

(6-Fluoropyridin-2-yl)methanol (150 mg, 1.2 mmol) and tetrahydrofuran solution of dimethylamine (2 M, 3 mL, 6 mmol) were mixed, and the reaction mixture was stirred in a sealed tube at 90° C. for 16 hours. The mixture was concentrated under reduced pressure to obtain 180 mg of a crude product of the title compound containing the raw material (6-fluoropyridyl-2-yl)methanol with a pale yellow oil appearance. LC-MS: m/z $[M+H]^{+*}$=153.

Intermediate 4

7-Methoxy-3-(5-methylisoxazol-3-yl)-[1,2,4]triazolo[4,3-b]pyridazin-6-ol

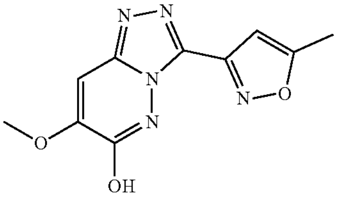

A 10% aqueous potassium hydroxide solution (5 mL) was added to a tetrahydrofuran (5 mL) solution of 3-(6-chloro-7-methoxy-[1,2,4]triazolo[4,3-b]pyridazin-3-yl)-5-methylisoxazole (380 mg, 1.43 mmol), and the mixture was stirred at room temperature for 3 days. The pH was adjusted to 2 with a 1N hydrochloric acid, and the precipitated solid was filtered and dried to obtain 310 mg of the title compound with a yield of 87.6% and a pale yellow solid appearance. LC-MS: m/z $[M+H]^{+}$=248.

Intermediate 5

(5-(2-Methoxyethoxy)pyridin-2-yl)methanol

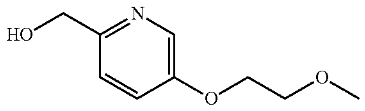

Step 1) Preparation of methyl 5-(2-methoxyethoxy)picolinate

Methyl 5-hydroxypicolinate (2.5 g, 16.3 mmol), 1-bromo-2-methoxyethane (2.7 g, 19.6 mmol) and cesium carbonate (8.0 g, 24.5 mmol) were sequentially added to DMF (30 mL), and the reaction mixture was stirred at room temperature for 16 hours. The mixture was poured into ice water, extracted three times with dichloromethane. The organic phases were combined, washed three times with water and once with saturated brine. The organic phase was dried and concentrated to obtain 3.4 g of methyl 5-(2-methoxyethoxy) picolinate with a yield of 99%. LC-MS: m/z $[M+H]^+$=212.

Step 2) Preparation of (5-(2-methoxyethoxy)pyridin-2-yl)methanol

Methyl 5-(2-methoxyethoxy)picolinate (3.4 g, 16.1 mmol) was dissolved in a mixed solvent of THF (80 mL) and MeOH (20 mL), and $NaBH_4$ (1.2 g, 32.2 mmol) was added in batches, then the reaction mixture was stirred at room temperature for 16 hours. After quenching with ice water, the mixture was extracted three times with dichloromethane, and the organic phases were combined, washed once with water and once with saturated brine. The organic phase was dried and concentrated to obtain 2.31 g of a crude product of the title compound. LC-MS: m/z $[M+H]^+$=184.

Intermediate 6

4-((6-(Hydroxymethyl)pyridin-3-yl)oxy)butanenitrile

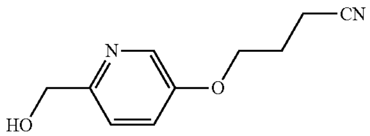 [SMILES: N#CCCCOc1ccc(CO)nc1]

The experimental operation was the same as that of intermediate 5. Methyl 5-hydroxypicolinate (150 mg, 1 mmol), 4-bromobutyronitrile (178 mg, 1.2 mmol) and potassium carbonate (207 mg, 1.5 mmol) were sequentially added to DMF (2 mL). 95 mg of the title compound was obtained by a two-step reaction with a yield of 49%. LC-MS: m/z $[M+H]^+$=193.

Intermediate 7

(5-(3-Methoxypropoxy)pyridin-2-yl)methanol

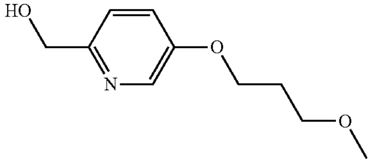

The experimental operation was the same as that of intermediate 5. Methyl 5-hydroxypicolinate (150 mg, 1 mmol), 1-bromo-3-methoxypropane (184 mg, 1.2 mmol) and cesium carbonate (489 mg, 1.5 mmol) were sequentially added to DMF (2 mL). 100 mg of the title compound was obtained by a two-step reaction with a yield of 51%. LC-MS: m/z $[M+H]^+$=198.

Intermediate 8

Methyl 6-(((7-methoxy-3-(5-methylisoxazol-3-yl)-(1,2,4)triazolo[4,3-b]pyridazin-6-yl)oxy)methyl) nicotinate

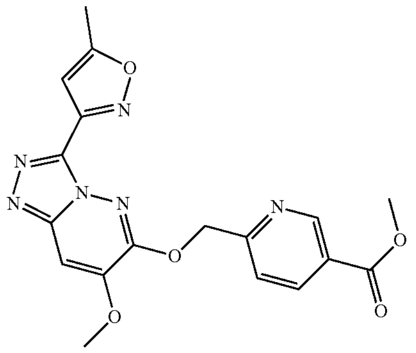 [SMILES: COC(=O)c1ccc(COc2nn3c(-c4cc(C)on4)nnc3cc2OC)nc1]

6-Chloro-7-methoxy-3-(5-methyl-isoxazol-3-yl)-[1,2,4] triazolo[4,3-b]pyridazine (240 mg, 0.9 mmol), methyl 6-(hydroxymethyl)nicotinate (150 mg, 0.9 mmol) and cesium carbonate (585 mg, 1.8 mmol) were sequentially added to 10 mL of acetonitrile, then the mixture was heated to 50° C. and stirred for 2 hours. The cesium carbonate solid was filtered with diatomite, and the organic phase was concentrated. The residue was purified by preparative TLC (dichloromethane/methanol=20/1) to obtain 300 mg of the title compound as a white solid with a yield of 84% and a white solid appearance. LC-MS: m/z $[M+H]^+$=397.

Intermediate 9

(4-(2-Methoxyethoxy)pyridin-2-yl)methanol

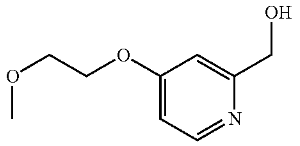

The experimental operation referred to intermediate 5, starting from methyl 4-hydroxypyridine-2-carboxylate (150 mg, 0.98 mmol) and 1-bromo-2-methoxyethane (180 mg, 1.29 mmol), 47 mg of the title compound was obtained with a two-step yield of 26.5%. LC-MS: m/z $[M+H]^+$=184.

Intermediate 10

6-Chloro-7-ethoxy-3-(5-methyl-isoxazol-3-yl)-[1,2,4]triazolo[4,3-b]pyridazine

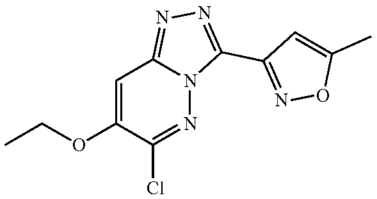 [SMILES: CCOc1cc2nnc(-c3cc(C)on3)n2nc1Cl]

3,6-Dichloro-4-ethoxy-pyridazine (2 g, 10.4 mmol, see Pharmaceutical Bulletin, 1958, vol. 6, p. 641 for synthesis), 5-methyl-isoxazole-3-carboxylic acid hydrazide (1.47 g, 10.4 mmol) were sequentially added to 50 mL of n-butanol, and the synthesis procedure was the same as that of intermediate 1 to obtain 110 mg of the title compound as a white solid with a yield of 4%. LC-MS: m/z $[M+H]^+=280$.

Intermediate 11

N-Ethyl-6-hydroxymethyl-nicotinamide

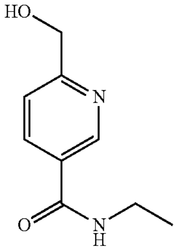

Methyl 6-hydroxymethyl-nicotinate (10 g, 60 mmol) was dissolved in 150 mL of 35% ethanol solution of ethylamine, and the tube was sealed and the mixture was heated to reflux overnight. The solvent was evaporated to dryness to obtain 12 g of a crude product of the title compound, LC-MS: m/z $[M+H]^+=181$.

Intermediate 12

(5-Cyclohex-1-enyl-pyridin-2-yl)-methanol

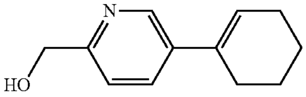 [SMILES: OCc1ccc(C2=CCCCC2)cn1]

(5-Bromo-pyridin-2-yl)-methanol (350 mg, 1.9 mmol), cycloethylene-1-boronic acid pinacol ester (350 mg, 1.9 mmol), [1,1'-bis(diphenylphosphino)ferrocene]palladium dichloride and the catalytic amount of cesium carbonate were dissolved in 10 mL of dioxane, and the mixture was heated to 100° C. overnight. The mixture was filtered, and the filtrate was concentrated. The residue was purified by column chromatography (dichloromethane/ethyl acetate=1/2) to obtain 200 mg of the title compound as a yellow solid with a yield of 55% and a yellow liquid appearance. LC-MS: m/z $[M+H]^+=190$.

Intermediate 13

3,6-Dichloro-4-cyclopropylmethoxy-pyridazine

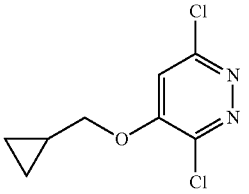 [SMILES: Clc1cc(OCC2CC2)c(Cl)nn1]

Cyclopropylmethanol (400 mg, 5.5 mmol) was dissolved in 20 mL of anhydrous tetrahydrofuran, cooled to 0° C. Sodium hydride (250 mg, 5.5 mmol) was added thereto, and the mixture was stirred for 10 minutes and then 3,4,6-trichloropyridazine (1 g, 5.5 mmol) was added thereto, and the mixture was raised to room temperature and stirred for 1 hour. A drop of water was added to quench the reaction. The mixture was concentrated, and 20 mL of water was added to dissolve the solid, then the mixture was extracted twice with 20 mL of dichloromethane, dried (anhydrous sodium sulfate) and evaporated to obtain 1.2 g of the title compound as a white solid with a yield of 100%. LC-MS: m/z $[M+H]^+=219$.

Intermediate 14

6-Chloro-7-cyclopropylmethoxy-3-(5-methyl-isoxazol-3-yl)-[1,2,4]triazolo[4,3-b]pyridazine

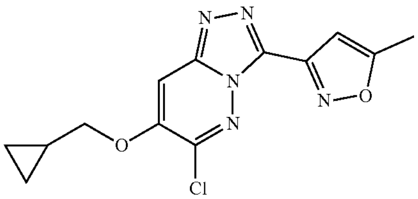 [SMILES: Cc1cc(-c2nnc3cc(OCC4CC4)c(Cl)nn23)no1]

3,6-Dichloro-4-cyclopropylmethoxy-pyridazine (1.2 g, 5.4 mmol) and 5-methyl-isoxazole-3-carboxylic acid hydrazide (770 mg, 5.4 mmol) were sequentially added to 50 mL of n-butanol, and the synthesis procedure was the same as that of intermediate 1 to obtain 100 mg of the title compound as a white solid with a yield of 10%. LC-MS: m/z $[M+H]^+=306$.

Intermediate 15

(5-Ethoxy-pyridin-2-yl)-methanol

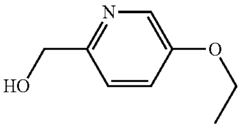

Methyl 5-ethoxy-pyridine-2-carboxylate (4 g, 10 mol) was dissolved in 100 mL of anhydrous tetrahydrofuran, stirred until completely dissolved, and cooled to 0° C. Lithium aluminum hydride (380 mg, 11 mmol) was added thereto, and the mixture was stirred for 15 minutes, and then 400 mg of lithium aluminum hydride was added thereto, and the mixture was stirred for 10 minutes. 0.8 mL of water, 1.5 mL of 15% sodium hydroxide solution, 2.5 ml of water were added thereto sequentially, and the mixture was filtered. The filtrate was dried (anhydrous sodium sulfate) and concentrated, and the residue was purified by column chromatography (dichloromethane/methanol=30/1) to obtain 850 mg of the title compound as a yellow liquid with a yield of 56%. LC-MS: m/z $[M+H]^+$=154.

Intermediate 16

Methyl 5-difluoromethoxy-pyridine-2-carboxylate

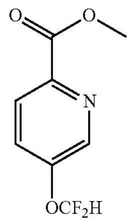

Methyl 5-hydroxyl-pyridine-2-carboxylate (1 g, 6.54 mmol), sodium 2-chloro-2,2-difluoroacetate (2 g, 13.08 mmol) and potassium carbonate (1.1 g, 7.84 mmol) were dissolved in 27 mL (N,N-dimethylformamide/water=8:1), under the protection of argon, the mixture was stirred at 100° C. for 2 hours, quenched and then extracted twice with 100 ml of ethyl acetate. The organic phases were combined, and dried with anhydrous sodium sulfate, concentrated, and subjected to column chromatography to obtain 800 mg of the title compound with a yield of 60% and a white solid appearance. LCMS: m/z $[M+H]^+$=204.

Intermediate 17

Methyl 6-(2-methoxy-ethoxy)-pyridazine-3-carboxylate

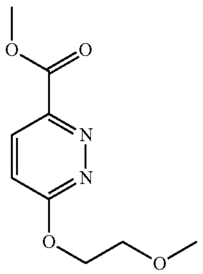

Methyl 6-oxo-1,6-dihydropyridazine-3-carboxylate (500 mg, 3.2 mmol), 2-bromoethyl methyl ether (541 mg, 3.9 mmol) and silver carbonate (1.78 g, 6.5 mmol) were sequentially added to 5 mL of toluene, and then the tube was sealed, and the mixture was heated to 100° C. and stirred overnight. The mixture was filtered and the filtrate was concentrated. The residue was purified by preparative TLC (dichloromethane/methanol=30/1) to obtain 90 mg of the title compound as a colorless oil with a yield of 13%. LC-MS: m/z $[M+H]^+$=213.

Intermediate 18

[6-(2-Methoxy-ethoxy)-pyridazin-3-yl]-methanol

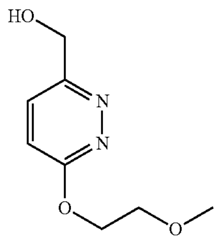

Methyl 6-(2-methoxy-ethoxy)-pyridazine-3-carboxylate (90 mg, 0.42 mol) was dissolved in 10 mL of anhydrous tetrahydrofuran, and sodium borohydride (32 mg, 0.84 mmol) was added thereto and the mixture was stirred for 1 hour. 1 mL of methanol was added to quench, and and the mixture was concentrated, and the residue was purified by preparative TLC (dichloromethane/methanol=30/1) to obtain 40 mg of the title compound as a yellow oil with a yield of 52%. LC-MS: m/z $[M+H]^+$=185.

Intermediate 19

Methyl 6-(3-cyanopropoxy)pyridazine-3-carboxylate

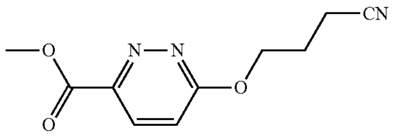 [SMILES: COC(=O)c1ccc(OCCCC#N)nn1]

Methyl 6-oxo-1,6-dihydropyridazine-3-carboxylate (1 g, 6.4 mmol) and 4-bromobutyronitrile (1.5 g, 11.7 mmol) were dissolved in 50 mL of toluene, and silver carbonate (3.6 g, 13.0 mmol) was added, then the mixture was heated to 100° C., and stirred for 5 hours. The reaction solution was cooled, filtered, concentrated, and the residue was purified by preparative TLC (dichloromethane/methanol=20/1) to obtain 100 mg of the target compound as an oil with a yield of 7% and a yellow oil appearance.

LC-MS: m/z $[M+H]^+$=222.

Intermediate 20

4-((6-(Hydroxymethyl)pyridazin-3-yl)oxy)butanenitrile

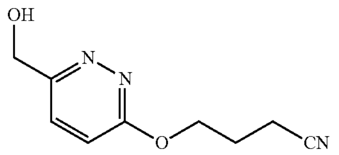 [SMILES: N#CCCCOc1ccc(CO)nn1]

Methyl 6-(3-cyanopropoxy)pyridazine-3-carboxylate (100 mg, 0.45 mol) was dissolved in 5 mL of anhydrous tetrahydrofuran, and sodium borohydride (34 mg, 0.90 mmol) was added thereto, and the mixture was stirred for 1 hour. 1 mL of methanol was added to quench, and the organic phase was concentrated. The residue was purified by preparative TLC (dichloromethane/methanol=20/1) to obtain 20 mg of the title compound as a yellow oil with a yield of 23%. LC-MS: m/z $[M+H]^+$=194.

Intermediate 21

3-Chloro-4-methoxy-6-(pyridine-2-methoxy) pyridazine and an Isomer Thereof

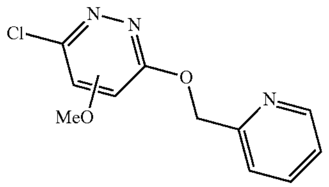

Pyridine-2-methanol (13.7 g, 83.75 mmol) was added to tetrahydrofuran (250 mL), then sodium hydride (5.1 g, 125.6 mmol, 60% in mineral oil) was added thereto, and the reaction was carried out at room temperature for 30 minutes, and then cooled to 0° C. 3,6-Dichloro-4-methoxypyridazine (15 g, 83.75 mmol) was added thereto, and the mixture was stirred at 40° C. for 2 hours. The reaction solution was poured into water, extracted with ethyl acetate, concentrated, and subjected to column chromatography (dichloromethane/methanol=50/1) to obtain a mixture of 3-chloro-4-methoxy-6-(pyridine-2-methoxy)pyridazine and an isomer 6-chloro-4-methoxy-3-(pyridine-2-methoxy)pyridazine (11 g, 52%). The next step reaction was carried out directly without a further purification. $^1$H NMR (400 MHz, $CDCl_3$): δ 8.64-8.62 (m, 1H), 7.73-7.69 (m, 1H), 7.51-7.47 (m, 1H), 7.28-7.22 (m, 1H), 6.80 (s, 1H), 5.67 (s, 2H), 3.95 (s, 3H).

Intermediate 22

N-(5-Methoxy-6-(2-pyridyl-methoxy)pyridazin-3-yl)-5-(methoxymethyl)isoxazole-3-carbohydrazide

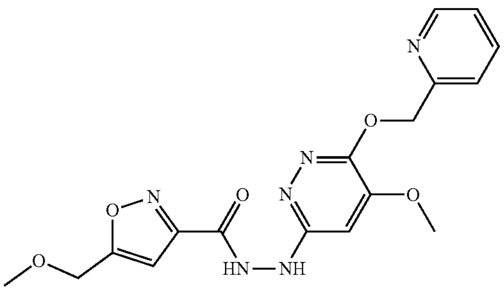 [SMILES: COCc1cc(C(=O)NNc2cc(OC)c(OCc3ccccn3)nn2)no1]

A mixture of 3-chloro-4-methoxy-6-(pyridine-2-methoxy)pyridazine and 6-chloro-4-methoxy-3-(pyridine-2-methoxy)pyridazine (600 mg, 23.84 mmol), 5-(methoxymethyl)isoxazole-3-carboxylhydrazide (605 mg, 35.76 mmol, see CN106854207A for synthesis) and p-toluenesulfonic acid monohydrate (453 mg, 23.84 mmol) were added to dioxane (100 mL), and the reaction was carried out at 120° C. for 3 hours. The reaction solution was diluted with dichloromethane and methanol (10/1). A saturated aqueous sodium carbonate solution was added thereto, and the mixture was extracted with dichloromethane and methanol (10/1), and the organic phases were combined, concentrated, and then subjected to column chromatography (dichloromethane/methanol=10/1) to obtain N-(5-methoxy-6-(2-pyridyl-methoxy)pyridazin-3-yl)-5-(methoxymethyl)isoxazole-3-carbohydrazide (120 mg, 13%). LC-MS: m/z $[M+H]^+$=433.

Intermediate 23

Methyl 6-(((tert-butyldimethylsilyl)oxy)methyl)nicotinate

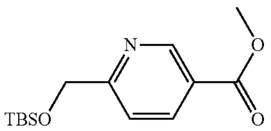 [SMILES: COC(=O)c1ccc(CO[Si](C)(C)C(C)(C)C)nc1]

6-(Hydroxymethyl)nicotinic acid (5.98 g, 38.8 mmol) was dissolved in dichloromethane (200 mL), then imidazole (2.9 g, 42.7 mmol) and tert-butyldimethylsilyl chloride (6.44 g, 42.7 mmol) were added respectively; after the addition was completed, the reaction was carried out at room temperature for 3 hours. The reaction solution was filtered, washed with dichloromethane, and the organic phase was washed with water (50 mL*3 times), then washed with saturated ammonium chloride solution (50 mL) once, and then washed with saturated brine (50 mL*once). The organic phase was dried and concentrated to obtain 2 g of the title compound with a yield of 18.9%. LC-MS: m/z $[M+H]^+$=282.

Intermediate 24

(6-(((tert-Butyldimethylsilyl)oxy)methyl)pyridin-3-yl)methanol

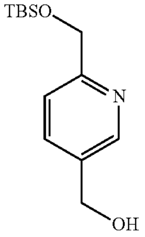 [SMILES: CC(C)(C)[Si](C)(C)OCc1ccc(CO)cn1]

Methyl 6-((tert-butyldimethylsilyl)oxy)methyl)nicotinate (1.28 g, 4.5 mmol) was dissolved in tetrahydrofuran (20 mL), and sodium borohydride (684 mg, 22 mmol) was added thereto, then the reaction was carried out at room temperature for 3 hours. The reaction solution was quenched, concentrated and separated by chromatographic column to obtain 325 mg of the title compound with a yield of 28.6%. LC-MS: m/z $[M+H]^+$=254.2.

Intermediate 25

2-(((tert-Butyldimethylsilyl)oxy)methyl)-5-(methoxymethyl)pyridine

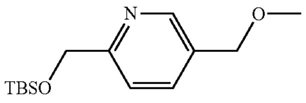

(6-(((tert-Butyldimethylsilyl)oxy)methyl)pyridin-3-yl) methanol (270 mg, 1.06 mmol) was added to tetrahydrofuran (20 mL), under the protection of argon, sodium hydride (51 mg, 1.28 mmol) was added thereto, and the mixture was stirred at 0° C. for 10 minutes. Iodomethane (150 mg, 1.06 mmol) was added thereto; after the addition was completed, the reaction was carried out at room temperature for 3 hours. The reaction solution was quenched with water, extracted with dichloromethane (20 mL*3 times), and the organic phases were combined and then washed with saturated brine (15 mL*1 time). The organic phase was dried and concentrated to obtain 300 mg of the title compound with a yield of 87%. LC-MS: m/z $[M+H]^+$=268.

Intermediate 26

(5-(Methoxymethyl)pyridin-2-yl)methanol

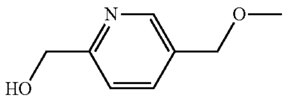

2-(((tert-Butyldimethylsilyl)oxy)methyl)-5-(methoxymethyl)pyridine (300 mg, 1.12 mmol) was dissolved in tetrahydrofuran (10 mL), and then tetrabutylammonium fluoride (783 mg, 3.36 mmol) was added thereto, and the reaction was carried out at room temperature for 3 hours. The reaction solution was concentrated and separated by chromatographic column to obtain 30 mg of the title compound with a yield of 17%. LC-MS: m/z $[M+H]^+$=154.

Intermediate 27

5-Cyclopropyl-2-piconol

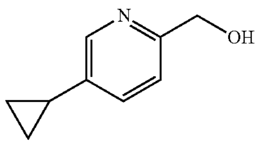 [SMILES: OCc1ccc(C2CC2)cn1]

5-Bromo-2-piconol (1.0 g, 5.32 mmol), cyclopropylboronic acid (1.37 g, 15.96 mmol), tetrakistriphenylphosphine palladium (612 mg, 0.53 mmol) and potassium carbonate (2.2 g, 15.96 mmol) were added to dioxane (15 mL), and the mixture was stirred at 120° C. for 2 hours under the protection of nitrogen. The reaction solution was concentrated and subjected to column chromatography (dichloromethane/methanol=50/1) to obtain the title compound (400 mg, 50%) as an oil. LC-MS: m/z $[M+H]^+$=150.

Intermediate 28

Methyl 1-(3-cyanopropyl)-6-oxo-1,6-dihydropyridazine-3-carboxylate

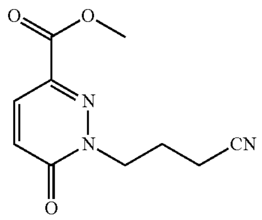 [SMILES: COC(=O)c1ccc(=O)n(CCCC#N)n1]

Methyl 6-oxo-1,6-dihydropyridazine-3-carboxylate (1 g, 6.49 mmol), 4-bromobutyronitrile (960 mg, 6.49 mmol) and cesium carbonate (4.2 g, 13 mmol) were sequentially added to 50 mL of acetonitrile, and then the mixture was stirred at 50° C. for two hours. After quenching, the mixture was filtered and concentrated. The residue was purified by column chromatography (dichloromethane/methanol=20/1) to obtain 1 g of the title compound as a white solid with a yield of 69%. LC-MS: m/z $[M+H]^+$=222.

Intermediate 29

4-(3-(Hydroxymethyl)-6-oxopyridazin-1(6H)-yl) butanenitrile

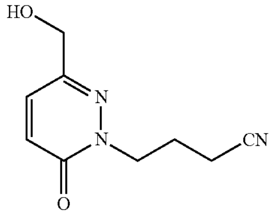 [SMILES: N#CCCCn1nc(CO)ccc1=O]

Methyl 1-(3-cyanopropyl)-6-oxo-1,6-dihydropyridazine-3-carboxylate (400 mg, 1.8 mol) was dissolved in 5 mL of anhydrous tetrahydrofuran, and sodium borohydride (102 mg, 2.7 mmol) was added thereto, then the mixture was stirred for 1 hour. 1 mL of methanol was added to quench, and the mixture was concentrated, and the residue was purified by preparative TLC (dichloromethane/methanol=20/1) to obtain 90 mg of the title compound as a yellow oil with a yield of 26%. LC-MS: m/z $[M+H]^+$=194.

Intermediate 30 tert-Butyl ((6-(hydroxymethyl)pyridin-3-yl)methyl)carbamate

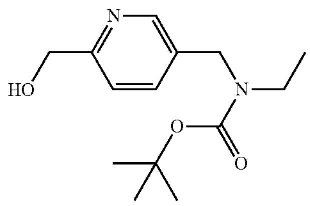 [SMILES: CCN(Cc1ccc(CO)nc1)C(=O)OC(C)(C)C]

(5-((Ethylamino)methyl)pyridin-2-yl)methanol (800 mg of crude product, 5 mmol), di-tert-butyl dicarbonate (1.5 mL, 6 mmol) and triethylamine (2 mL, 10 mmol) were sequentially added to 50 mL of dichloromethane, and the mixture was stirred at room temperature for two hours. 50 mL of water and 50 mL of aqueous ammonium chloride solution were added thereto, and the mixture was extracted twice with 50 ml of dichloromethane, dried with sodium sulfate, and concentrated. The residue was purified by column chromatography (dichloromethane/methanol=40/1) to obtain 120 mg of the title compound as a yellow liquid with a yield of 9%. LC-MS: m/z $[M+H]^+$=267.

Intermediate 31

(5-((Ethylamino)methyl)pyridin-2-yl)methanol

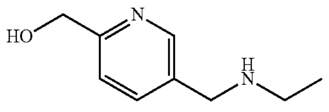

N-Ethyl-6-(hydroxymethyl)nicotinamide (900 mg, 5 mmol) was dissolved in 20 mL of tetrahydrofuran solution of borane, and the container was sealed, and then the mixture was heated to 70° C. overnight. 10 mL of 1M hydrochloric acid was added for quenching, and the solvent was concentrated to obtain 800 mg of a crude product of the title compound as a yellow liquid with a yield of 100%. LC-MS: m/z $[M+H]^+$=167.

Intermediate 32

(5-(Methylsulfonyl)pyridin-2-yl)methanol

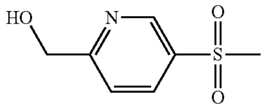

Methyl 5-(methylsulfonyl) picolinate (100 mg, 0.46 mmol) and tetrahydrofuran (20 mL) were added to a single-necked flask, then sodium borohydride (50 mg, 1.4 mmol) was added thereto, and the external temperature was heated to 50° C., and the reaction was carried out for 1 hour. 0.5 mL of water was added to quench excess sodium borohydride, then the mixture was concentrated, and the residue was purified by preparative TLC with dichloromethane/methanol=20/1 as a developing solvent to obtain 35 mg of the title compound with a yield of 40.2% and a yellow solid appearance. LC-MS: m/z $[M+H]^+$=188.

Intermediate 33

3,6-Dichloro-4-(difluoromethoxy)pyridazine

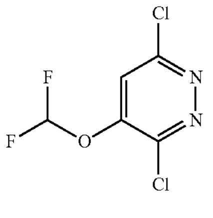 [SMILES: FC(F)Oc1cc(Cl)nnc1Cl]

3,6-Dichloro-4-hydroxypyridazine (1.55 g, 9.5 mmol), potassium carbonate (1.54 g, 11.2 mmol) and sodium 2-chloro-2,2-difluoroacetate (2.88 g, 18.9 mmol) were added to N,N-dimethylformamide (40 mL) and water (5 mL), and the mixture was stirred in an oil bath at 100° C. for 3 hours. Water was added to the system, followed by extraction with ethyl acetate. The organic phase was washed with water, then washed with saturated brine, dried and concentrated. The resultant was separated by column chromatography to obtain 0.83 g of the title compound with a yield of 40.8% as a pale yellow liquid. LC-MS: m/z $[M+H]^+$=215.

Intermediate 34

3-(6-Chloro-7-(difluoromethoxy)-[1,2,4]triazolo[4,3-b]pyridazin-3-yl)-5-methylisoxazole

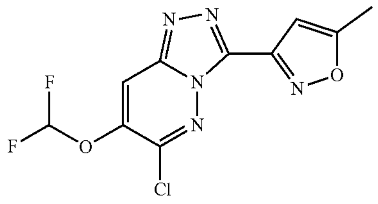 [SMILES: Cc1cc(-c2nnc3cc(OC(F)F)c(Cl)nn23)no1]

3,6-Dichloro-4-(difluoromethoxy)pyridazine (0.82 g, 3.8 mmol) and 5-methylisoxazole-3-carboxyhydrazide (0.54 g, 3.8 mmol) were added to n-butanol (20 mL), and the mixture was stirred in an oil bath at 120° C. for 3 hours under the protection of argon. The insolubles in the system were filtered off, and the filtrate was concentrated and separated by column chromatography. The resultant was further purified by preparative TLC to obtain 124 mg of the title compound with a yield of 10.7% as a yellow solid. LC-MS: m/z $[M+H]^+$=302.

Intermediate 35

Methyl 5-cyclobutylpicolinate

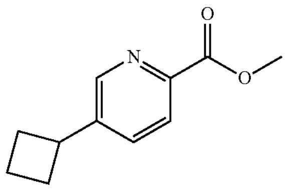

Under an anhydrous and anaerobic condition, a magnesium powder (1.154 g, 48 mmol) was added to a three-necked flask, and THF (2 mL) was added thereto. At 40° C., an initiator isopropylmagnesium chloride lithium chloride complex solution (dissolved in tetrahydrofuran, 1.3 M, 0.96 mL, 0.74 mmol) was added thereto. The raw material bromocyclobutane (5.0 g, 37 mmol) was dissolved in tetrahydrofuran (30 mL) and gradually added to the reaction solution. The reaction was carried out at 40° C. for 2 hours. Zinc chloride (5.54 g, 40.7 mmol) was added thereto at 0° C., and the reaction was carried out at room temperature for 2 hours. The raw materials methyl 5-bromopicolinate (3.98 g, 18.5 mmol), cuprous iodide (351.5 g, 1.85 mmol) and

[1,1'-bis(diphenylphosphino)ferrocene]palladium dichloride (1.35 g, 1.85 mmol) were added to the reaction solution. Then, under the protection of nitrogen, the reaction was carried out overnight at 80° C. A saturated ammonium chloride solution (100 mL) was added to the reaction solution, then the mixture was extracted with ethyl acetate for three times, and the organic phases were collected, dried with anhydrous sodium sulfate, concentrated, and subjected to preparative liquid phase to obtain the title compound as a yellow solid (1.04 g, 14.7%). $^1$H NMR (300 MHz, $CDCl_3$): δ 8.56 (s, 1H), 8.08 (d, J=8.0 Hz, 1H), 7.69 (dd, J=8.0 Hz, 2.4 Hz, 1H), 4.00 (s, 3H), 3.66-3.62 (m, 1H), 2.46-2.39 (m, 2H), 2.22-2.10 (m, 3H), 1.96-1.92 (m, 1H).

Intermediate 36

Methyl 6-(3-methoxypropoxy)pyridazine-3-carboxylate

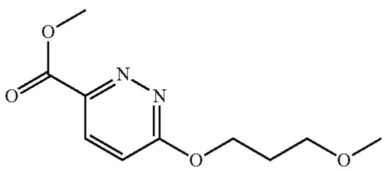 [SMILES: COCCCOc1ccc(C(=O)OC)nn1]

Methyl 6-chloropyridazine-3-carboxylate (2 g, 11.63 mmol), 3-methoxypropanol (1.25 g, 14 mmol) and cesium carbonate (11.34 g, 34.89 mmol) were dissolved in 100 mL of acetonitrile, and the mixture was stirred overnight at room temperature under the protection of argon. The mixture was filtered, and the filtrate was extracted twice with 100 mL of ethyl acetate. The organic phases were combined, dried with anhydrous sodium sulfate, concentrated, and separated by column chromatography to obtain 0.5 g of the title compound as a colorless oil with a yield of 19%. LC-MS: m/z $[M+H]^+$=227.

Intermediate 37

(6-(3-Methoxypropoxy)pyridazin-3-yl)methanol

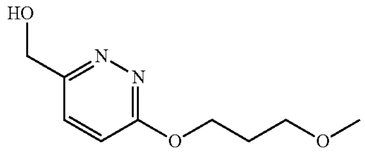

Methyl 6-(3-methoxypropoxy)pyridazine-3-carboxylate (0.5 g, 2.21 mmol) was dissolved in 20 mL of tetrahydrofuran, and sodium borohydride (160 mg, 4.21 mmol) was added thereto, then the mixture was stirred at room temperature for 1 hour. 1 mL of methanol was added for quenching, and the mixture was concentrated, and subjected to column chromatography to obtain 0.3 g of the title compound with a yield of 69% and a colorless oil appearance. LC-MS: m/z $[M+H]^+$=199.

Intermediate 38

(5-Cyclobutylpyridin-2-yl)methanol

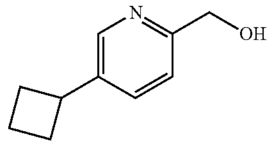 [SMILES: OCc1ccc(C2CCC2)cn1]

Methyl 5-cyclobutylpicolinate (750 mg, 3.92 mmol) was dissolved in methanol (7 mL), and sodium borohydride (430 mg, 11.8 mmol) was slowly added thereto at room temperature, and then the reaction was carried out at room temperature overnight. The reaction solution was directly poured into water, extracted with ethyl acetate. The organic phase was dried with anhydrous sodium sulfate, concentrated and separated by column chromatography (petroleum ether:ethyl acetate=10:1) to obtain the title compound (550 mg, 85%) as a pale yellow oil. $^1$H NMR (400 MHz, $CDCl_3$): δ=8.39 (s, 1H), 7.55 (d, J=6.4 Hz, 1H), 7.19 (d, J=8 Hz, 1H), 4.72 (s, 2H), 3.57-3.53 (m, 1H), 2.41-2.36 (m, 2H), 2.17-1.88 (m, 4H).

Intermediate 39

Methyl 6-iodo-3-methoxypicolinate

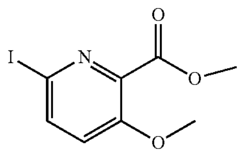

Methyl 6-bromo-3-methoxypyridine-2-carboxylate (500 mg, 2.32 mmol) was dissolved in N,N-dimethylformamide (5 mL), and copper iodide (1320 mg, 6.97 mmol) was added thereto, and the reaction was carried out at 170° C. for 4 hours. The reaction solution was cooled and added with water (30 mL), extracted with ethyl acetate (20 mL*3 times), and the organic phases were combined, and then washed with saturated brine (15 mL*1 time). The organic phase was dried and concentrated to obtain 400 mg of the title compound with a yield of 65%. LC-MS: m/z $[M+H]^+$=293.9.

Intermediate 40

Methyl 3-methoxy-6-(trifluoromethyl)pyridine-2-carboxylate

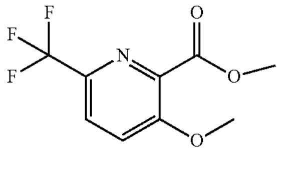 [SMILES: COC(=O)c1nc(C(F)(F)F)ccc1OC]

Methyl 6-iodo-3-methoxypicolinate (106 mg, 0.55 mmol) was dissolved in N,N-dimethylformamide (20 mL), then copper iodide (106 mg, 0.55 mmol) and methyl fluorosulfonyl difluoroacetate (500 mg, 2.6 mmol) were added thereto, and the reaction was carried out at 90° C. for 1 hour. The reaction solution was cooled and added with water (30 mL), extracted with ethyl acetate (20 mL*3 times), and the organic phases were combined, and then washed with saturated brine (15 mL*1 time). The organic phase was dried, concentrated, and separated by column chromatography to obtain 120 mg of the title compound with a yield of 92%. LC-MS: m/z $[M+H]^+$=236.

Intermediate 41

3-Methoxy-6-(trifluoromethyl)pyridine-2-methanol

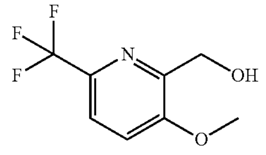

Methyl 3-methoxy-6-(trifluoromethyl)pyridine-2-carboxylate (80 mg, 0.38 mmol) was dissolved in tetrahydrofuran (5 mL), and sodium borohydride (29 mg, 0.76 mmol) was added thereto, then the reaction was carried out at room temperature for 3 hours. The reaction solution was quenched, concentrated and separated by chromatographic column to obtain 20 mg of the title compound with a yield of 25.3%. LC-MS: m/z $[M+H]^+$=208.

Intermediate 42

Pyrazolo[1,5-a]pyrimidin-5-ylmethanol

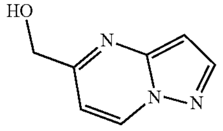 [SMILES: OCc1ccn2nccc2n1]

Triethylamine (84 mg, 84 μL, 0.834 mmol) and isobutyl chloroformate (62 mg, 62 μL, 0.458 mmol) were added to a THF (15 mL) solution of pyrazolo[1,5-a]pyrimidine-5-carboxylic acid (68 mg, 0.417 mmol), and the mixture was fully stirred at room temperature for 1 hour. Then 1 mL of $NaBH_4$ (31 mg, 0.834 mmol) aqueous solution was added dropwise. The mixture was fully stirred and reacted at room temperature for 0.5 hours. LCMS showed that the reaction was completed. The mixture was concentrated and purified by preparative thin layer chromatography to obtain 33 mg of the title compound with a yield of 53%. LC-MS: m/z $[M+H]^+$=210.1.

Intermediate 43

Ethyl (E)-4-ethoxy-2-oxobut-3-enoate

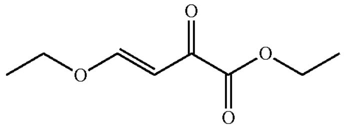

Ethyl vinyl ether (36 g, 263 mmol) was added dropwise to ethyl 2-chloro-2-oxoacetate (10 mL, 263 mmol) under the protection of argon and in an ice bath, and the process was continued for about 20 minutes. The ice bath protection was continued for about 2 hours. Then, the ice bath was removed, and the compound was slowly raised to room temperature. After 15 hours of reaction, the reaction solution was fractionated and the product was collected to obtain 0.5 g of the title compound as a yellow oil. LC-MS: m/z $[M+H]^+$=173.1.

Intermediate 44

Ethyl pyrazolo[1,5-a]pyrimidine-7-carboxylate

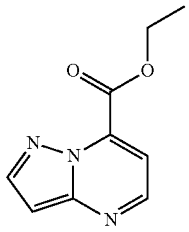

Ethyl (E)-4-ethoxy-2-oxobut-3-enoate (300 mg, 1.74 mmol) was dissolved in 10 mL of ethanol, and then 2-aminopyrazole (100 mg, 1.74 mmol) was added thereto. The reaction solution was reacted at 90° C. for 16 hours. The reaction solution was concentrated, and the residue was separated by a preparative plate to obtain 120 mg of the title compound. LC-MS: m/z $[M+H]^+$=192.1.

Intermediate 45

Pyrazolo[1,5-a]pyrimidin-7-ylmethanol

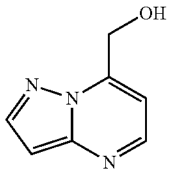 [SMILES: OCc1ccnc2ccnn12]

Ethyl pyrazolo[1,5-a]pyrimidin-7-carboxylate (47.7 mg, 2.5 mmol) was dissolved in 5 mL of tetrahydrofuran and 5 mL of methanol, and then sodium borohydride (22.5 mg, 7.5 mmol) was added thereto. The reaction solution was reacted at room temperature for 16 hours. The reaction solution was concentrated, and the residue was separated by a preparative plate to obtain 27 mg of the title compound. LC-MS: m/z $[M+H]^+$=150.1.

Intermediate 46

Dimethyl 6-methylpyridine-2,5-dicarboxylate

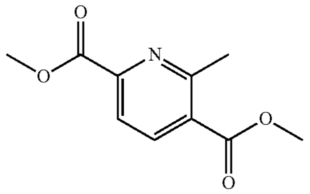

3,6-Dibromo-2-pyridine (7.5 g, 30 mmol) was added to methanol (100 mL), then triethylamine (9.1 g, 90 mmol) and [1,1'-bis(diphenylphosphino)ferrocene]palladium dichloride (1.1 g, 1.5 mmol) were added thereto, and the reaction was carried out overnight at 100° C. under a 5 MPa carbon monoxide atmosphere. The reaction solution was concentrated and separated by column chromatography (petroleum ether/ethyl acetate=10/1-2/1) to obtain the title compound as a pale yellow solid (4.5 g, 72%). $^1H$ NMR (300 MHz, $CDCl_3$) δ 8.31 (d, J=8.1 Hz, 1H), 8.01 (d, J=8.1 Hz, 1H), 4.02 (s, 3H), 3.95 (s, 3H), 4.80 (s, 1H), 2.91 (s, 3H). LC-MS: m/z $[M+H]^+$=210.1.

Intermediate 47

Dimethyl 6-(bromomethyl)pyridine-2,5-dicarboxylate

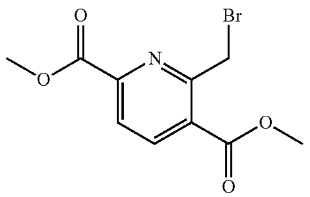

Dimethyl 6-methylpyridine-2,5-dicarboxylate (5.0 g, 23.9 mmol) was added to carbon tetrachloride (60 mL), and N-bromosuccinimide (4.25 g, 23.9 mmol) and dibenzoyl peroxide (291 mg, 1.2 mmol) were added thereto, and the mixture was stirred at 80° C. overnight. The mixture was diluted with water, extracted with ethyl acetate; the organic phase was washed with sodium bicarbonate, washed with saturated brine, dried with anhydrous sodium sulfate, and concentrated to obtain the title compound (5.6 g, 81%) as a yellow oil. LC-MS: m/z $[M+H]^+$=288.0.

Intermediate 48

2-(Hydroxymethyl)-6-(2-methoxyethyl)-6,7-dihydro-5H-pyrrolo[3,4-b]pyridin-5-one

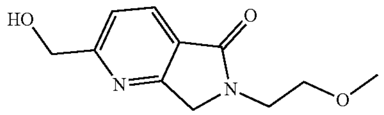 [SMILES: COCCN1Cc2nc(CO)ccc2C1=O]

Dimethyl 6-(bromomethyl)pyridine-2,5-dicarboxylate (1.0 g, 3.47 mmol) was dissolved in acetonitrile (20 mL), 2-methoxyethylamine (260 mg, 3.47 mmol) and triethylamine (701 mg, 6.94 mmol), then the mixture was stirred at room temperature overnight. The mixture was diluted with water, extracted with ethyl acetate, washed with saturated brine, dried with anhydrous sodium sulfate, dried, and separated by column chromatography (dichloromethane:methanol=100:1-50:1) to obtain 130 mg of the compound as a white solid, which was added to methanol (1.5 mL). Sodium borohydride (30 mg, 0.78 mmol) was added thereto at 0° C., and the mixture was stirred at room temperature for 2 hours. A small amount of water was added to quench the reaction, then the mixture was concentrated, and separated by column chromatography (dichloromethane:methanol=100:1-20:1) to obtain the title compound (100 mg, a two-step yield of 13%) as a white solid. $^1H$ NMR (400 MHz, DMSO-$d_6$) δ 8.07 (d, J=7.6 Hz, 1H), 7.58 (d, J=8.0 Hz, 1H), 5.62 (t, J=5.6 Hz, 1H), 4.66 (d, J=5.6 Hz, 2H), 4.52 (s, 2H), 3.70 (t, J=5.6 Hz, 2H), 3.57 (t, J=5.6 Hz, 2H), 3.27 (s, 3H). LC-MS: m/z $[M+H]^+$=223.1.

Intermediate 49

6-Ethyl-2-(hydroxymethyl)-6,7-dihydro-5H-pyrrolo[3,4-b]pyridin-5-one

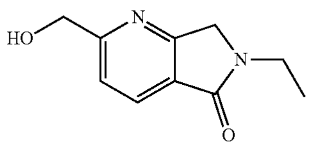

Dimethyl 6-(bromomethyl)pyridine-2,5-dicarboxylate (5.6 g, 19.4 mmol) was dissolved in acetonitrile (60 mL), then ethylamine hydrochloride (1.90 g, 23.28 mmol) and triethylamine (4.91 g, 48.6 mmol) were added thereto, and the mixture was stirred at 40° C. for 2 hours. The mixture was diluted with water, extracted with ethyl acetate and extracted with dichloromethane. The organic phases were combined and evaporated to dryness by rotary evaporation. The residue were mixed with silica gel, and separated by column chromatography (dichloromethane:methanol=100:1-25:1) to obtain the compound (1.0 g, 23%) as a pale yellow solid, which was added to methanol (15 mL). Sodium borohydride (257 mg, 6.75 mmol) was added thereto, and the mixture was stirred at room temperature for 1 hour. The mixture was concentrated, and separated by column chromatography (dichloromethane/methanol=100/1-25/1) to obtain the title compound (430 mg, a two-step yield of 11%) as a pale yellow solid. $^1H$ NMR (400 MHz, DMSO-$d_6$) δ 8.05 (d, J=8.0 Hz, 1H), 7.57 (d, J=8.0 Hz, 1H), 5.62 (t, J=6.0 Hz, 1H), 4.66 (d, J=6.0 Hz, 2H), 4.49 (s, 2H), 3.56 (q, J=7.2 Hz, 2H), 1.18 (t, J=7.2 Hz, 3H). LC-MS: m/z $[M+H]^+$=193.1.

Intermediate 50

Dimethyl 3-cyanopyridine-1,6-dicarboxylate

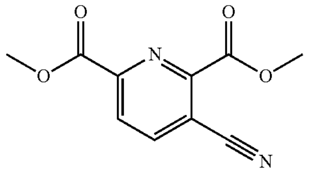

2,6-Dichloronicotinonitrile (10.0 g, 57.8 mmol), [1,1'-bis (diphenylphosphino)ferrocene]palladium chloride (4.23 g, 5.78 mmol) and triethylamine (17.51 g, 173.4 mmol) were sequentially added to methanol (150 mL). Then, the mixture was reacted overnight under a carbon monoxide atmosphere of 5 MPa at 80° C. The mixture was filtered, concentrated and separated by column chromatography (petroleum ether/ethyl acetate=4:1-2:1) to obtain the title compound as a white solid (2.30 g, 18.1%). $^1$H NMR (400 MHz, $CDCl_3$): δ 8.41 (d, J=8.0 Hz, 1H), 8.34 (d, J=8.0 Hz, 1H), 4.10 (s, 3H), 4.07 (s, 3H). LC-MS: m/z $[M+H]^+$=221.

Intermediate 51

Methyl 7-oxo-6,7-dihydro-5H-pyrrolo[3,4-b]pyridine-2-carboxylate

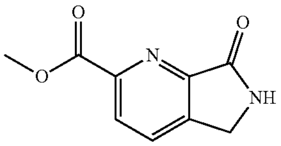

Dimethyl 3-cyanopyridine-1,6-dicarboxylate (2.3 g, 10.5 mmol) and raney nickel (1.24 g, 21.0 mmol) were sequentially added to methanol (300 mL). Then, the mixture was reacted for 5 hours under hydrogen of 50 psi at 40° C. The mixture was filtered under reduced pressure and concentrated to obtain 2.1 g of a crude product of the title compound. LC-MS: m/z $[M+H]^+$=193.

Intermediate 52

6-tert-Butyl-2-methyl-7-oxo-5H-pyrrolo[3,4-b]pyridine-2,6(7H)-dicarboxylate

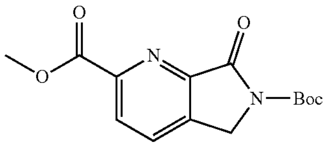 [SMILES: COC(=O)c1ccc2c(n1)C(=O)N(C(=O)OC(C)(C)C)C2]

Methyl 7-oxo-6,7-dihydro-5H-pyrrolo[3,4-b]pyridine-2-carboxylate (2.1 g, 11.0 mmol) and 4-dimethylaminopyridine (201 mg, 1.65 mmol) were sequentially added to dichloromethane (20 mL). Then, the raw material di-tert-butyl dicarbonate (3.6 g, 16.5 mmol) was added dropwise thereto, and the mixture was reacted at 50° C. for 30 minutes. The mixture was concentrated and separated by column chromatography (dichloromethane/methanol=100:1) to obtain the title compound (1.7 g, 53.0%) as a yellow solid. $^1$H NMR (400 MHz, $CDCl_3$): δ 8.36 (d, J=7.6 Hz, 1H), 8.03 (d, J=8.0 Hz, 1H), 4.85 (s, 2H), 4.03 (s, 3H), 1.62 (s, 9H). LC-MS: m/z $[M+H]^+$=293.

Intermediate 53 tert-Butyl 7-hydroxy-2-(hydroxymethyl)-5,7-dihydro-6H-pyrrolo[3,4-b]pyridine-6-carboxylate

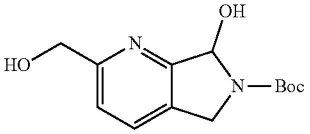 [SMILES: CC(C)(C)OC(=O)N1Cc2ccc(CO)nc2C1O]

At 0° C., the raw material 6-tert-butyl-2-methyl-7-oxo-5H-pyrrolo[3,4-b]pyridine-2,6(7H)-dicarboxylate (930 mg, 3.2 mmol) was added to tetrahydrofuran (10 mL). Under the protection of nitrogen, the raw material diisobutyl aluminum hydride (dissolved in tetrahydrofuran, 9.6 mL, 9.6 mmol, 1 M) was slowly added dropwise to the solution. The mixture was reacted overnight at room temperature. The mixture was added with water to quench the reaction, concentrated, and separated by column chromatography (dichloromethane/methanol=30:1-20:1) to obtain the title compound as a brown solid (376 mg, 44.2%). $^1$H NMR (400 MHz, $CDCl_3$): δ 7.63 (d, J=7.6 Hz, 1H), 7.32 (dd, J=8.0 Hz, 4.0 Hz, 1H), 4.83 (s, 2H), 4.69-4.68 (m, 2H), 4.07-4.03 (m, 1H), 1.55 (s, 9H). LC-MS: m/z $[M+H]^+$=267.

Intermediate 54 tert-Butyl 2-(hydroxymethyl)-5,7-dihydro-6H-pyrrolo[3,4-b]pyridine-6-carboxylate

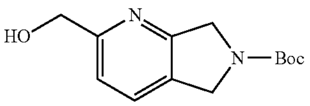 [SMILES: CC(C)(C)OC(=O)N1Cc2ccc(CO)nc2C1]

tert-Butyl 7-hydroxy-2-(hydroxymethyl)-5,7-dihydro-6H-pyrrolo[3,4-b]pyridine-6-carboxylate (376 mg, 1.4 mmol) and sodium cyanoborohydride (97.0 mg, 1.54 mmol) were sequentially added to acetic acid (4 mL). The mixture was reacted at room temperature for 1 hour. The acetic acid was evaporated to dryness by rotary evaporation at low temperature, and the residue was dissolved with dichloromethane/methanol=10:1. The pH of the mixture was adjusted to about 9 with a saturated sodium bicarbonate solution, and the mixture was extracted with dichloromethane/methanol=10:1. The organic phase was collected, dried with anhydrous sodium sulfate, evaporated to dryness by rotary evaporation, and subjected to column chromatography (dichloromethane/methanol=60:1-40:1) to obtain the title compound as a yellow solid (200 mg, 57.1%) as a product. $^1$H NMR (400 MHz, $CDCl_3$): δ 7.60-7.53 (m, 1H), 7.15 (d, J=8.0 Hz, 1H), 4.78-4.77 (m, 2H), 4.71-4.68 (m, 4H), 3.43-3.37 (m, 1H), 1.53 (s, 9H). LC-MS: m/z $[M+H]^+$ =251.

Intermediate 55

(6,7-Dihydro-5H-pyrrolo[3,4-b]pyridin-2-yl)methanol

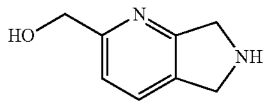 [SMILES: OCc1ccc2c(n1)CNC2]

tert-Butyl 2-(hydroxymethyl)-5,7-dihydro-6H-pyrrolo[3,4-b]pyridine-6-carboxylate (240 mg, 0.96 mmol) and trifluoroacetic acid (3 mL) were sequentially added to dichloromethane (3 mL). The mixture was reacted at room temperature for 30 minutes, and the solution was evaporated to dryness by rotary evaporation at low temperature, dissolved in methanol, added with an ion exchange resin, and stirred for 3 hours until the pH of the solution was alkaline. The mixture was filtered and concentrated to obtain 200 mg of a crude product of the title compound as a reddish brown oil. $^1$H NMR (400 MHz, $CD_3OD$): δ 7.82 (d, J=8.0 Hz, 1H), 7.48 (d, J=8.0 Hz, 1H), 4.70 (s, 2H), 4.54 (s, 2H), 4.30 (s, 2H). LC-MS: m/z $[M+H]^+$=151.

Intermediate 56

(6-Methyl-6,7-dihydro-5H-pyrrolo[3,4-b]pyridin-2-yl)methanol

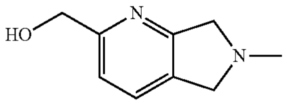

(6,7-Dihydro-5H-pyrrolo[3,4-b]pyridin-2-yl)methanol (150 mg, 1 mmol, crude product) was dissolved in dichloromethane (3 mL), and 1 drop of acetic acid was added dropwise thereto, and then an aqueous formaldehyde solution (0.5 mL) was added thereto; the mixture was reacted at room temperature for 30 minutes, and then sodium triacetoxyborohydride (636 mg, 3 mmol) was added thereto, and the mixture was reacted at room temperature overnight. The reaction solution was concentrated, dissolved in methanol, concentrated, and separated by column chromatography (dichloromethane:methanol=10:1) to obtain the title compound (80 mg, 30%) as a brown oil. JH NMR (400 MHz, $CDCl_3$ & $CD_3OD$) δ 7.63 (d, J=8.0 Hz, 1H), 7.37 (d, J=8.0 Hz, 1H), 4.71 (s, 2H), 4.01-3.99 (m, 4H), 2.66 (s, 3H).

Intermediate 57

(6-Ethyl-6,7-dihydro-5H-pyrrolo[3,4-b]pyridin-2-yl)methanol

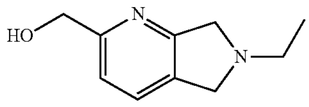

(6,7-Dihydro-5H-pyrrolo[3,4-b]pyridin-2-yl)methanol (200 mg, 1.3 mmol), iodoethane (203 mg, 1.3 mmol) and triethylamine (404 mg, 3.9 mmol) were sequentially added to acetonitrile (2 mL). The mixture was reacted overnight at 85° C. The mixture was concentrated and separated by column chromatography (dichloromethane/methanol=50:1-10:1) to obtain the title compound (120 mg, 70.2%) as a yellow solid. $^1$H NMR (400 MHz, $CD_3OD$): δ 7.59 (d, J=7.6 Hz, 1H), 7.28 (d, J=8.0 Hz, 1H), 4.53 (s, 2H), 4.05-3.99 (m, 4H), 2.90-2.85 (m, 2H), 1.16-1.14 (m, 3H). LC-MS: m/z $[M+H]^+$=179.

Intermediate 58 tert-Butyl 2-(6-(hydroxymethyl)pyridin-3-yl)-1H-pyrrole-1-carboxylate

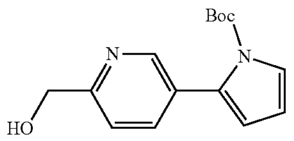 [SMILES: CC(C)(C)OC(=O)n1cccc1-c1ccc(CO)nc1]

(5-Bromopyridin-2-yl)methanol (2.5 g, 13.3 mmol), (1-(tert-butoxycarbonyl)-1H-pyrrol-2-yl) boronic acid (3.37 g. 15.96 mmol), [1,1'-bis(diphenylphosphino)ferrocene]palladium dichloride (974 mg, 1.33 mmol) and potassium carbonate (2.75 g, 39.9 mmol) were added to dioxane (25 mL), and water was added (5 mL) thereto, then the mixture was stirred at 100° C. for 4 hours under the protection of nitrogen. The mixture was concentrated and separated by column chromatography (petroleum ether/ethyl acetate=50/1-10/1) to obtain the title compound as a yellow oil (3.5 g 96%). $^1$H NMR (400 MHz, $CDCl_3$) δ 8.56-8.55 (m, 1H), 7.70-7.67 (m, 1H), 7.40-7.39 (m, 1H), 7.26-7.24 (m, 1H), 6.27-6.24 (m, 2H), 4.79-4.78 (m, 2H), 3.67-3.64 (m, 1H), 1.41 (s, 9H). LC-MS: m/z $[M+H]^+$=275.0.

Intermediate 59 tert-Butyl 2-(6-hydroxymethylpyridin-3-yl)pyrrolidine carboxylate

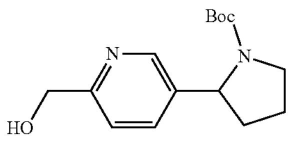 [SMILES: CC(C)(C)OC(=O)N1CCCC1c1ccc(CO)nc1]

tert-Butyl 2-(6-(hydroxymethyl)pyridin-3-yl)-1H-pyrrole-1-carboxylate (4.0 g, 3.65 mmol) was dissolved in methanol (20 mL), then palladium/carbon (10%, 4.0 g) was added thereto, and the mixture was reacted under a hydrogen atmosphere of 50 psi at 50° C. The mixture was filtered, concentrated and separated by column chromatography (dichloromethane/methanol=100:1-20:1) to obtain the title compound (2.3 g, 57%) as a pale yellow oil. AH NMR (400 MHz, $CDCl_3$) δ 8.41 (s, 1H), 7.51-7.48 (m, 1H), 7.20-7.18 (m, 1H), 4.95-4.81 (m, 1H), 4.75 (s, 2H), 3.64-3.49 (m, 2H), 2.40-2.31 (m, 1H), 1.93-1.90 (m, 2H), 1.85-1.77 (m, 1H), 1.45-1.21 (m, 9H). LC-MS: m/z $[M+H]^+$=279.0.

Intermediate 60

2-Bromo-6-((tert-butyldimethylsilyl)oxy)methyl) pyridine

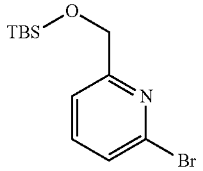

(6-Bromopyridin-2-yl)methanol (9.96 g, 53.0 mmol) was added to dichloromethane (110 mL), then the stirring was started, and imidazole (10.82 g. 159 mmol) was added to the reaction solution. Under an ice bath, tert-butyldimethylsilyl chloride (11.98 g, 79.5 mmol) was slowly added to the reaction solution, and the reaction solution was reacted at room temperature overnight under the protection of nitrogen. The reaction solution was sequentially washed with a saturated ammonium chloride solution, a saturated sodium bicarbonate solution, and a saturated sodium chloride solution. The organic phase was concentrated, and separated by column chromatography (petroleum ether:ethyl acetate=50:1) to obtain the title compound (15.00 g 94%) as a colorless oil. $^1$H NMR (400 MHz, DMSO-$d_6$) δ 7.78 (t, J=8 Hz, 1H), 7.52 (d, J=8 Hz, 1H), 7.45 (d, J=8 Hz, 1H), 4.73 (s, 2H), 0.91 (s, 9H), 0.09 (s, 6H).

Intermediate 61 tert-Butyl 3-hydroxy-3-(6-((tert-butyldimethylsilyl) oxy)methyl)pyridin-2-yl)azetidine-1-carboxylate

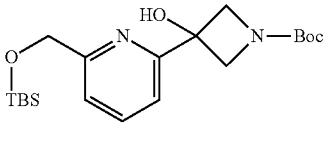

2-Bromo-6-((tert-butyldimethylsilyloxy)methyl)pyridine (5.0 g, 16.6 mmol) was dissolved in tetrahydrofuran (50 mL), then n-butyllithium (2.5 M, 7.3 mL, 18.3 mmol) was added thereto at −78° C.; the mixture was stirred at −78° C. for 30 minutes, and tert-butyl 3-oxoazetidine-1-carboxylate (2.83 g, 16.6 mmol) was added thereto, and the mixture was stirred at −78° C. for 2 hours. The reaction solution was poured into ice water, extracted with ethyl acetate, washed with saturated brine, dried with anhydrous sodium sulfate, concentrated and separated by column chromatography (PE:EA=50:1-5:1) to obtain the title compound (3.8 g, 58%) as a yellow oil. $^1$H NMR (400 MHz, $CDCl_3$) δ 7.86-7.82 (m, 1H), 7.54-7.48 (m, 2H), 5.97 (s, 1H), 4.82 (s, 2H), 4.31-4.29 (m, 2H), 4.11-4.09 (m, 2H), 1.49 (s, 9H), 0.97 (s, 9H), 0.13 (s, 6H). LC-MS: m/z $[M+H]^+$=394.9.

Intermediate 62 tert-Butyl 3-hydroxy-3-(6-(hydroxymethyl)pyridin-2-yl)azetidine-1-carboxylate

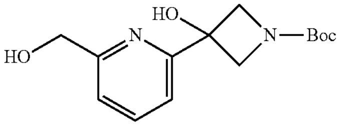 [SMILES: CC(C)(C)OC(=O)N1CC(O)(c2cccc(CO)n2)C1]

tert-Butyl 3-hydroxy-3-(6-((ter-butyldimethylsilyloxy) methyl)pyridin-2-yl)azetidine-1-carboxylate (3.8 g. 9.6 mmol) was dissolved in tetrahydrofuran (30 mL), then tetrabutylammonium fluoride (1 M, 5.8 mL, 5.8 mmol) was added thereto, and the mixture was stirred at room temperature overnight. Ethyl acetate (150 mL) was added thereto, and the mixture was washed with a saturated ammonium chloride solution (50 mL*2), dried and concentrated to obtain the title compound (2.6 g, 96%) as a yellow oil. $^1$H NMR (400 MHz, $CDCl_3$) δ 7.86-7.82 (m, 1H), 7.60-7.58 (m, 1H), 7.35-7.34 (m, 1H), 4.81 (s, 2H), 4.31-4.28 (m, 2H), 4.16-4.12 (m, 2H), 1.49 (s, 9H). LC-MS: m/z $[M+H]^+$=281.0.

Intermediate 63 tert-Butyl 3-hydroxy-3-(6-(acetoxymethyl)pyridin-2-yl)azetidine-1-carboxylate

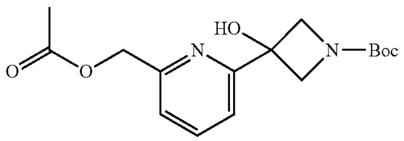 [SMILES: CC(=O)OCc1cccc(C2(O)CN(C(=O)OC(C)(C)C)C2)n1]

tert-Butyl 3-hydroxy-3-(6-(hydroxymethyl)pyridin-2-yl) azetidine-1-carboxylate (2.6 g. 9.3 mmol) was dissolved in dichloromethane (90 mL), then triethylamine (1.88 g, 18.6 mmol) and acetic anhydride (949 mg, 9.3 mmol) were added thereto at 0° C. The mixture was stirred at 0° C. for 1 hour, and then stirred at room temperature for 2 hours. Water (100 mL) was added thereto, and the mixture was extracted with dichloromethane, washed three times with the saturated sodium chloride solution, dried and concentrated to obtain a crude product of the title compound (2.6 g, 87%) as a yellow oil. $^1$H NMR (400 MHz, $CDCl_3$) δ 7.77-7.73 (m, 1H), 7.53-7.52 (m, 1H), 7.26-7.24 (m, 1H), 5.13 (s, 2H), 4.22-4.20 (m, 2H), 4.02-3.99 (m, 2H), 2.01 (s, 3H), 1.39 (s, 9H). LC-MS: m/z $[M+H]^+$=322.9.

Intermediate 64 tert-Butyl 3-fluoro-3-(6-(acetoxymethyl)pyridin-2-yl)azetidine-1-carboxylate

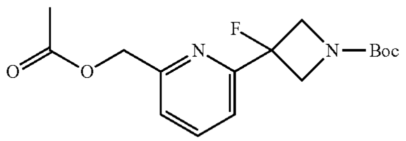 [SMILES: CC(=O)OCc1cccc(C2(F)CN(C(=O)OC(C)(C)C)C2)n1]

tert-Butyl 3-hydroxy-3-(6-(acetoxymethyl)pyridin-2-yl) azetidine-1-carboxylate (2.6 g, 8 mmol) was dissolved in dichloromethane (90 mL), then diethylaminosulfur trifluoride (1.95 g, 12 mmol) was added thereto at 0° C. to react for 5 minutes. The reaction solution was poured into an aqueous solution (100 mL) containing sodium carbonate, extracted with dichloromethane. The organic phases were combined, washed with saturated brine, dried with anhydrous sodium sulfate, concentrated and separated by column chromatography (PE:EA=50:1-5:1) to obtain the title compound (1.5 g, 57%) as a yellow oil. $^1$H NMR (400 MHz, $CDCl_3$) δ 7.77-7.75 (m, 1H), 7.45-7.43 (m, 1H), 7.31-7.29 (m, 1H), 5.25 (s, 2H), 4.54-4.46 (m, 2H), 4.32-4.24 (m, 2H), 2.19 (s, 3H), 1.49 (s, 9H). LC-MS: m/z $[M+H-56]^+$=269.0.

Intermediate 65 tert-Butyl 3-fluoro-3-(6-(hydroxymethyl)pyridin-2-yl)azetidine-1-carboxylate

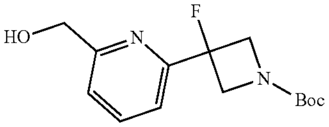 [SMILES: CC(C)(C)OC(=O)N1CC(F)(c2cccc(CO)n2)C1]

tert-Butyl 3-fluoro-3-(6-(acetoxymethyl)pyridin-2-yl) azetidine-1-carboxylate (1.5 g, 4.6 mmol) was dissolved in tetrahydrofuran (20 mL), and then water (10 mL) and lithium hydroxide monohydrate (292 mg, 6.9 mmol) were added thereto. The reaction solution was stirred at room temperature for 2 hours, poured into water, extracted with ethyl acetate, concentrated, and separated by column chromatography (PE:EA=20:1-5:1) to obtain the title compound (1.2 g, 92%) as a yellow solid. $^1$H NMR (400 MHz, $CDCl_3$) δ 7.76-7.72 (m, 1H), 7.44-7.42 (m, 1H), 7.23-7.21 (m, 1H), 4.79-4.78 (m, 2H), 4.52-4.45 (m, 2H), 4.35-4.27 (m, 2H), 3.68-3.69 (m, 1H), 1.48 (s, 9H). LC-MS: m/z $[M+H]^+$ =283.0.

Intermediate 66 tert-Butyl 3-fluoro-3-(6-(hydroxymethyl)pyridin-3-yl)azetidine-1-carboxylate

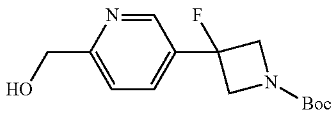 [SMILES: CC(C)(C)OC(=O)N1CC(F)(c2ccc(CO)nc2)C1]

Starting from (5-bromopyridin-2-yl)methanol (10.0 g, 53.4 mmol), the title compound (1.1 g, 63%) obtained by the same synthetic method as intermediate 65 was a yellow oil, which turned into a yellow solid after standing for a period of time. $^1$H NMR (400 MHz, $CDCl_3$) δ 8.69 (s, 1H), 7.79-7.77 (m, 1H), 7.36-7.34 (m, 1H), 4.80 (s, 2H), 4.45-4.41 (m, 2H), 4.29-4.22 (m, 2H), 3.64 (s, 1H), 1.49 (s, 9H).

Intermediate 67

1-Methyl-1H-pyrazolo[4,3-b]pyridine 4-oxide

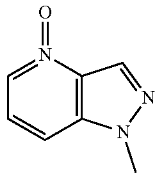

1-Methyl-1H-pyrazolo[4,3-b]pyridine (1.03 g, 7.7 mmol) (referred to document US20140343065A1) and m-chloroperoxybenzoic acid (1.47 g, 8.5 mmol, 85%) were sequentially added to dichloromethane (40 mL), and the reaction mixture was stirred at room temperature for 16 hours. The mixture was adjusted to alkaline with a 4 M aqueous sodium hydroxide solution, extracted with dichloromethane, dried and concentrated to obtain 904 mg of the title compound with a yield of 75%. LC-MS: m/z $[M+H]^+$=150.

Intermediate 68

1-Methyl-1H-pyrazolo[4,3-b]pyridine-5-carbonitrile

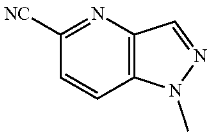

1-Methyl-1H-pyrazolo[4,3-b]pyridine 4-oxide (870 mg, 5.8 mmol), trimethylsilyl cyanide (863 mg, 8.7 mmol) and triethylamine (1.17 g, 11.6 mmol) were sequentially added to acetonitrile (30 mL), and the reaction mixture was stirred at 110° C. for 16 hours. The mixture was concentrated and separated by column chromatography to obtain 958 mg of the title compound with a yield of 100%. $^1$H NMR (400 MHz, DMSO-$d_6$) δ=8.52 (s, 1H), 8.42 (d, J=8.8 Hz, 1H), 7.98 (d, J=8.8 Hz, 1H), 4.15 (s, 3H). LC-MS: m/z $[M+H]^+$ =159.

Intermediate 69

(1-Methyl-1H-pyrazolo[4,3-b]pyridin-5-yl)methanol

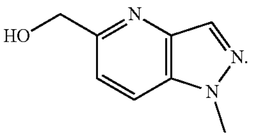

1-Methyl-1H-pyrazolo[4,3-b]pyridine-5-carbonitrile (200 mg, 1.26 mmol) and sodium hydroxide (202 mg, 5.04 mmol) were sequentially added to methanol (20 mL) and water (4 mL), and the reaction mixture was stirred at 100° C. for 16 hours. The mixture was concentrated, and the pH of the residue was adjusted to 3 to 4 with a 1N hydrochloric acid. The precipitated solid was filtered and collected, dried to obtain 208 mg of 1-methyl-1H-pyrazolo[4,3-b]pyridine-5-carboxylic acid. 1-methyl-1H-pyrazolo[4,3-b]pyridine-5-carboxylic acid and trimethylsilyldiazomethane (4.68 mL, 9.36 mmol, 2 M n-hexane solution) were sequentially added to dichloromethane (4 mL) and methanol (0.5 mL), and the reaction mixture was stirred at room temperature for 2 hours. The mixture was poured into water, extracted with dichloromethane, dried, and concentrated to obtain 260 mg of a crude product of the title compound. The crude product and sodium borohydride (206 mg, 5.4 mmol) were sequentially added to tetrahydrofuran (6 mL) and methanol (1.5 mL), and the reaction mixture was stirred at room temperature for 16 hours. The reaction was quenched with water, extracted with ethyl acetate, dried and concentrated to obtain a crude product, and separated by thin layer chromatography to obtain 120 mg of the title compound. LC-MS: m/z $[M+H]^+$=164.

Intermediate 70

1-Methyl-3-(hydroxymethyl)pyridin-2(1H)-one

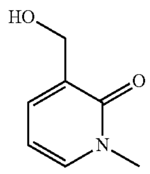

3-(Hydroxymethyl)pyridin-2(1H)-one (100 mg, 0.8 mmol), iodomethane (1.1 g, 8 mmol) and potassium carbonate (442 mg, 3.2 mmol) were sequentially added to methanol (4 mL), and the reaction mixture was stirred at room temperature for 16 hours. The mixture was poured into water, extracted with dichloromethane, dried, concentrated, and separated by thin layer chromatography to obtain 93 mg of the title compound.

Intermediate 71

1-(2-Methoxyethyl)-3-(hydroxymethyl)pyridin-2(1H)-one

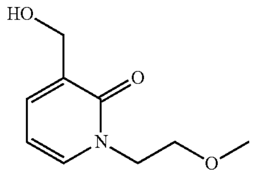

3-(Hydroxymethyl)pyridin-2(1H)-one (100 mg, 0.8 mmol), 1-bromo-2-methoxyethane (667 mg, 4.8 mmol) and potassium carbonate (442 mg, 3.2 mmol) were sequentially added to methanol (4 mL). The experimental operation was the same as that of intermediate 70, and the mixture was separated by thin layer chromatography to obtain 48 mg of the title compound.

Intermediate 72

1-Ethyl-3-(hydroxymethyl)pyridin-2(1H)-one

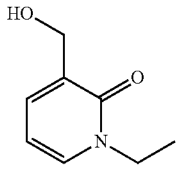

3-(Hydroxymethyl)pyridin-2(1H)-one (150 mg, 1.2 mmol), iodoethane (1.87 g, 12 mmol) and potassium carbonate (663 mg, 4.8 mmol) were sequentially added to methanol (10 mL). The experimental operation was the same as that of intermediate 70 to obtain 75 mg of the title compound.

Intermediate 73

(5,6,7,8-Tetrahydro-1,6-naphthyridin-2-yl)methanol

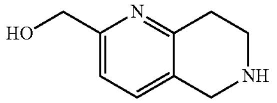 [SMILES: OCc1ccc2c(n1)CCNC2]

Trifluoroacetic acid (10 mL) was added to a dichloromethane solution (10 mL) of tert-butyl 2-(hydroxymethyl)-7,8-dihydro-1,6-naphthyridin-6(5H)-carboxylate (1.1 g, 4.2 mmol), and the mixture was stirred for 16 hours. The mixture was concentrated to obtain 3 g of the title compound with a yield of the crude product more than 99% and a pale yellow oil appearance. LC-MS: m/z $[M+H]^+$=165.

Intermediate 74

2-((tert-Butyldimethylsilyl)oxy)methyl)-5,6,7,8-tetrahydro-1,6-naphthyridine

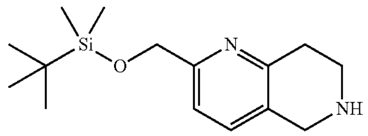 [SMILES: CC(C)(C)[Si](C)(C)OCc1ccc2c(n1)CCNC2]

(5,6,7,8-Tetrahydro-1,6-naphthyridin-2-yl)methanol (2.9 g, 4.2 mmol, crude product) and diisopropylethylamine (11.2 g, 87 mmol) were added to tetrahydrofuran (80 mL), then a solution of tert-butyldimethylsilyl chloride (2.64 g, 17.4 mmol) in THF (20 mL) was added dropwise to the above solution, and the mixture was reacted and stirred overnight. The reaction solution was separated by column chromatography to obtain a mixture of the title compound and diisopropylethylamine (2.5 g, 40% purity) with a yield of 85% and a yellow oil appearance. LC-MS: m/z $[M+H]^+$=279.

Intermediate 75

(6-(2,2,2-Trifluoroethyl)-5,6,7,8-tetrahydro-1,6-naphthyridin-2-yl)methanol

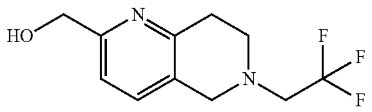 [SMILES: OCc1ccc2c(n1)CCN(CC(F)(F)F)C2]

2-(((tert-Butyldimethylsilyl)oxy)methyl)-5,6,7,8-tetrahydro-1,6-naphthyridine (500 mg, 40% purity, 0.72 mmol), 2,2,2-trifluoroethyl trifluoromethanesulfonate (335 mg, 1.44 mmol) and cesium carbonate (469 mg, 1.44 mmol) were sequentially added to acetonitrile (8 mL), and the reaction mixture was stirred at room temperature for 16 hours. The mixture was poured into water, extracted with ethyl acetate, dried, concentrated to obtain 140 mg of an intermediate. The intermediate and tetrabutylammonium fluoride trihydrate (246 mg, 0.78 mmol) were sequentially added to dichloromethane (5 mL), and the reaction mixture was stirred at room temperature for 16 hours. The mixture was poured into water, extracted with dichloromethane, dried and concentrated to obtain a crude product, and separated by thin layer chromatography to obtain 54 mg of the title compound with a two-step yield of 30.5%. LC-MS: m/z $[M+H]^+$=247.

Intermediate 76

5-(2-Methoxypropoxy)pyrazin-2-yl)methanol

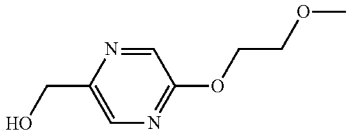

Methy 5-chloropyrazine-2-carboxylate (1 g, 5.8 mmol), ethylene glycol methyl ether (1 g, 11.6 mmol) and cesium carbonate (5.7 g, 17.4 mmol) were sequentially added to 50 mL of acetonitrile, then the mixture was heated to 50° C. and stirred overnight. The cesium carbonate solid was filtered with diatomite, and the reaction solution was diluted with water, extracted with dichloromethane, and the organic phase was concentrated. The residue was purified by silica gel column (petroleum ether/ethyl acetate=5/1) to obtain 180 mg of 2-methoxyethyl 5-(2-methoxyethoxy)pyrazine-2-carboxylate as a yellow liquid, which was dissolved in 20 mL of anhydrous tetrahydrofuran. Sodium borohydride (120 mg, 3.5 mmol) was added thereto, and the mixture was heated to 70° C. and refluxed for 1 hour. 1 mL of methanol was added to quench, then the solid was filtered, and the organic phase was concentrated. The residue was purified by preparative thin layer chromatography (petroleum ether/ethyl acetate=2/1) to obtain 60 mg of the title compound as a colorless oil with a two-step yield of 6%. LC-MS: m/z $[M+H]^+$=185.

Intermediate 77

(5-(3-Methoxypropoxy)pyrazin-2-yl)methanol

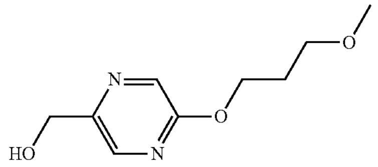

Methy 5-chloropyrazine-2-carboxylate (1 g, 5.8 mmol), 3-methoxy-1-propanol (1 g, 11.6 mmol) and cesium carbonate (5.7 g, mmol) were sequentially added to 50 ml of acetonitrile. The experimental operation was the same as that of intermediate 76 to obtain 120 mg of the title compound as a colorless oil with a two-step yield of 9%. LC-MS: m/z $[M+H]^+$=199.

Intermediate 78

2,5-bis(Methoxycarbonyl)pyridine 1-oxide

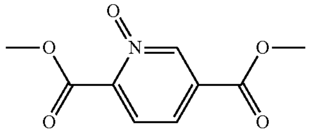

Dimethyl pyridine-2,5-dicarboxylate (4 g. 20 mmol) was dissolved in 200 mL of dichloromethane, then the mixture was cooled to 0° C., and m-chloroperoxybenzoic acid (10.6 g, 61 mmol) was added thereto in batches. The reaction solution was poured into an aqueous solution of sodium thiosulfate, extracted with dichloromethane, and dried with sodium sulfate. The residue was purified by silica gel column (petroleum ether/ethyl acetate=10/1 to 2/1) to obtain 3.5 g of the target compound as a yellow solid with a yield of 81% and a yellow solid appearance. LC-MS: m/z $[M+H]^+$=212.

Intermediate 79

Dimethyl 6-cyanopyridine-2,5-dicarboxylate

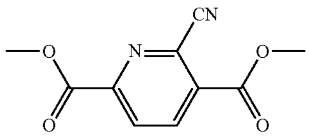

2,5-bis(Methoxycarbonyl)pyridine 1-oxide (3.5 g, 15.8 mmol), TMSCN (3.1 g, 31.7 mmol) and triethylamine (2.4 g, 23.7 mmol) were sequentially added to 100 mL of acetonitrile, then the mixture was heated to 80° C. and stirred overnight. The reaction solution was concentrated. The residue was purified by silica gel column (petroleum ether/ethyl acetate=10/1 to 2/1) to obtain 1.8 g of the target compound as a yellow solid with a yield of 52% and a yellow solid appearance. LC-MS: m/z $[M+H]^+$=221.

Intermediate 80

Methyl 5-oxo-6,7-dihydro-5H-pyrrolo[3,4-b]pyridine-2-carboxylate

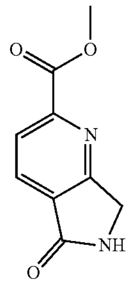

Dimethyl 6-cyanopyridine-2,5-dicarboxylate (1.8 g, 8.1 mol) was dissolved in 100 mL of methanol, then raney nickel was added thereto, and the mixture was stirred overnight at room temperature under a hydrogen atmosphere. The reaction solution was filtered, and the filter cake was dried to obtain 1 g of the title compound as a gray solid with a yield of 64%. LC-MS: m/z $[M+H]^+$=193.

Intermediate 81

2-(Hydroxymethyl)-6,7-dihydro-5H-pyrrolo[3,4-b]pyridin-5-one

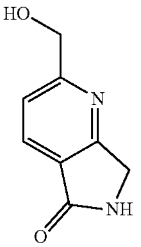

Methyl 5-oxo-6,7-dihydro-5H-pyrrolo[3,4-b]pyridine-2-carboxylate (300 mg, 1.5 mol) was dissolved in 50 mL of anhydrous tetrahydrofuran, the the mixture was cooled to −10° C., and DIBAL-H (1 N, 9 mL, 9 mmol) was added thereto, and the mixture was stirred for 10 min, and then warmed to room temperature and stirred for 1 hour. 1 ml of water was added thereto, abd the reaction solution was concentrated, and the residue was purified by preparative TLC (dichloromethane/methanol=50/1 to 20/1) to obtain 200 mg of the title compound as a gray solid with a yield of 78%. LC-MS: m/z $[M+H]^+$=165.

Intermediate 82

2-Methoxyethyl 1-(2-methoxyethyl)-1H-pyrrolo[2,3-b]pyridine-6-carboxylate

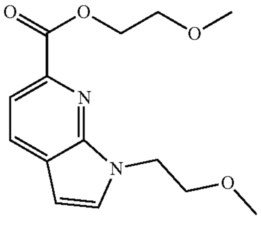 [SMILES: COCCOC(=O)c1ccc2ccn(CCOC)c2n1]

1H-Pyrrolo[2,3-b]pyridine-6-carboxylate (200 mg, 1.23 mmol), 2-bromoethyl methyl ether (514 mg, 3.7 mmol) and potassium carbonate (852 mg, 6.2 mmol) were sequentially added to 50 mL of DMF, then the mixture was heated to 80° C. overnight. The reaction solution was diluted with water, extracted with ethyl acetate, dried and concentrated. The residue was purified by silica gel column (dichloromethane/methanol=50/1 to 20/1). 160 mg of the title compound was obtained as a liquid with a yield of 59% and a yellow oil appearance. LC-MS: m/z $[M+H]^+$=279.

Intermediate 83

(1-(2-Methoxyethyl)-1H-pyrrolo[2,3-b]pyridin-6-yl)methanol

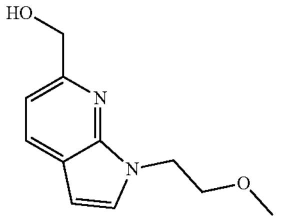

2-Methoxyethyl 1-(2-methoxyethyl)-1H-pyrrolo[2,3-b]pyridine-6-carboxylate (320 mg, 1.2 mol) was dissolved in 10 mL of anhydrous tetrahydrofuran, then the mixture was cooled to 0° C., and lithium aluminum hydride (91 mg, 2.4 mmol) was added thereto; the mixture was stirred for 10 minutes. 0.1 ml of water, 0.1 mL of 15% sodium hydroxide solution, 0.3 mL of water were added sequentially thereto. The solid was filtered, and the organic phase was concentrated. The residue was purified by preparative TLC (dichloromethane/methanol=50/1 to 20/1) to obtain 160 mg of the title compound as a yellow liquid with a yield of 65% and a yellow oil appearance. LC-MS: m/z $[M+H]^+$=207.

Intermediate 84

(1-(3-Methoxypropyl)-1H-pyrrolo[2,3-b]pyridin-6-yl)methanol

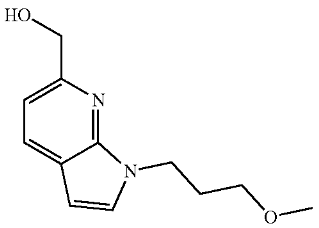 [SMILES: COCCCn1ccc2ccc(CO)nc21]

1H-Pyrrolo[2,3-b]pyridine-6-carboxylate (200 mg, 1.23 mmol), 1-bromo-3-methoxypropane (567 mg, 3.7 mmol) and potassium carbonate (852 mg, 6.2 mmol) were sequentially added to 50 mL of DMF, and the experimental operation was the same as the synthetic method of intermediate 83. A two-step reaction was carried out to obtain 170 mg of the title compound as a yellow liquid with a yield of 65% and a yellow oil appearance. LC-MS: m/z $[M+H]^+$=221.

Intermediate 85

(1-Methyl-1H-pyrazolo[2,3-b]pyridin-6-yl)methanol

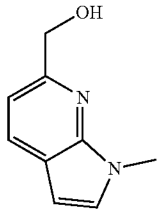

1H-Pyrrolo[2,3-b]pyridine-6-carboxylic acid (250 mg, 1.54 mmol), iodomethane (1.02 g, 7.7 mmol) and potassium carbonate (1.28 g, 9.2 mmol) were sequentially added to 10 mL of DMF, and the experimental operation was the same as the synthesis method of intermediate 83. A two-step reaction was carried out to obtain 150 mg of the title compound as a yellow liquid with a yield of 67% and a yellow oil appearance. LC-MS: m/z $[M+H]^+$=163.

Intermediate 86 tert-Butyl 3-fluoro-3-(6-(hydroxymethyl)pyridin-3-yl)piperidine-1-carboxylate

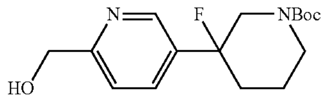

Starting from 5-bromo-2-(((tert-butyldimethylsilyl)oxy)methyl)pyridine (4 g, 13.2 mmol) and tert-butyl 3-oxopiperidine-1-carboxylate (2.6 g, 13.2 mmol), the experimental operation was the same as the synthetic method of intermediate 65 to obtain 130 mg of the title compound as a yellow oil. LC-MS: m/z $[M+H]^+$=311.

Intermediate 87 tert-Butyl 3-(6-(acetoxymethyl)pyridin-3-yl)-3-hydroxypyrrolidine-1-carboxylate

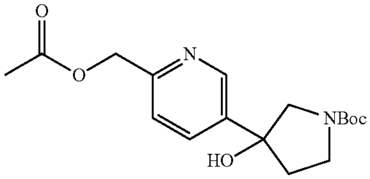 [SMILES: CC(=O)OCc1ccc(C2(O)CCN(C(=O)OC(C)(C)C)C2)cn1]

Starting from 5-bromo-2-(((tert-butyldimethylsilyl)oxy)methyl)pyridine (2 g, 6.6 mmol) and tert-butyl 3-oxopyrrolidine-1-carboxylate (1.2 g, 6.6 mmol) as raw materials, the experimental operation was the same as the synthetic method of intermediate 63 to obtain 300 mg of the title compound as a yellow liquid. LC-MS: m/z $[M+H]^+$=337.

Intermediate 88 tert-Butyl 3-(6-(hydroxymethyl)pyridin-3-yl))-2,5-dihydro-1H-pyrrole-1-carboxylate

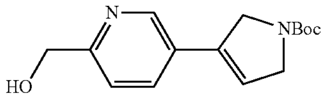 [SMILES: CC(C)(C)OC(=O)N1CC=C(c2ccc(CO)nc2)C1]

tert-Butyl 3-(6-(acetoxymethyl)pyridin-3-yl)-3-hydroxypyrrolidine-1-carboxylate (300 mg, 0.89 mmol) was dissolved in 50 mL of dichloromethane, then the mixture was cooled to 0° C., and DAST (215 mg, 1.33 mmol) was added thereto, and the mixture was stirred at room temperature for 20 minutes. The reaction solution was poured into 20 mL of an aqueous sodium bicarbonate solution to quench, extracted with dichloromethane, dried and concentrated to obtain 300 mg of tert-butyl 3-(6-(acetoxymethyl)pyridin-3-yl)-2,5-dihydro-1H-pyrrole-1-carboxylate as a yellow oil, dissolved in 5 mL of tetrahydrofuran. Lithium hydroxide monohydrate (60 mg, 1.4 mmol) was added thereto, and the mixture was stirred at room temperature for 3 hours. The reaction solution was poured into water, extracted with ethyl acetate, dried and concentrated, and the residue was purified by silica gel column (dichloromethane/methanol=20/1) to obtain 250 mg of the title compound as a yellow oil with a two-step yield of 90%. LC-MS: m/z $[M+H]^+$=277.

Intermediate 89 tert-Butyl 3-(6-(hydroxymethyl)pyridin-3-yl)pyrrolidine-1-carboxylate

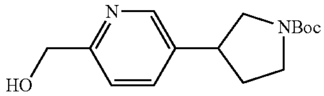 [SMILES: CC(C)(C)OC(=O)N1CCC(c2ccc(CO)nc2)C1]

tert-Butyl 3-(6-(hydroxymethyl)pyridin-3-yl))-2,5-dihydro-1H-pyrrole-1-carboxylate (250 mg, 0.9 mmol) was dissolved in 10 mL of methanol, then a palladium-carbon catalyst (20 mg) was added thereto, and the mixture was stirred overnight at room temperature under a normal pressure hydrogen atmosphere. Palladium-carbon was filtered, and the reaction solution was concentrated to obtain 210 mg of the title compound as a yellow oil with a yield of 90%. LC-MS: m/z $[M+H]^+$=279.

Intermediate 90

Methyl 1-methyl-1H-pyrrolo[3,2-b]pyridine-5-carboxylate

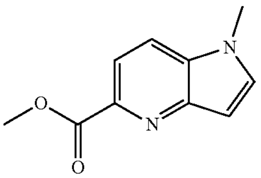

Cesium carbonate (743 mg, 2.28 mmol) and methyl iodide (324 mg, 2.28 mmol) were added to a DMF (3 mL) solution of methyl 1H-pyrrolo[3,2-b]pyridine-5-carboxylate (200 mg, 1.14 mmol), and the mixture was stirred at room temperature for 1 hour. The reaction solution was poured into water (10 mL), extracted with ethyl acetate (4 mL×4), dried with anhydrous sodium sulfate, filtered and concentrated to obtain 210 mg of the title compound with a yield of 97% and a pale yellow oil appearance. LC-MS: m/z $[M+H]^+$=191.

Intermediate 91

(1-Methyl-1H-pyrazolo[3,2-b]pyridin-5-yl)methanol

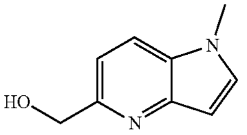

Methyl 1-methyl-1H-pyrrolo[3,2-b]pyridine-5-carboxylate (160 mg, 0.84 mmol) was added to a THF (10 mL) suspension of LiAlH4 (96 mg, 2.53 mmol), and the mixture was stirred for 2 hours. 96 mg of water was added to quench, then the mixture was filtered, and concentrated, then passed through a column to obtain 50 mg of the title compound with a yield of 37% and a pale yellow solid appearance. LC-MS: m/z $[M+H]^+$=163.

Intermediate 92

Dimethyl 3-methylpyridine-2,6-dicarboxylate

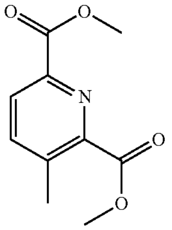

Compound 2,6-dichloro-3-methylpyridine (10.04 g, 62 mmol) was added to 180 mL of anhydrous methanol. Triethylamine (18.78 g. 186 mmol) and [1,1'-bis(diphenylphosphino)ferrocene]dichloride palladium (4.54 g, 6.2 mmol) were sequentially added to the reaction solution. Carbon monoxide was pumped to an internal pressure of 5.0 MPa, then the mixture was heated to 100° C. and reacted overnight. Water and dichloromethane were added to the reaction solution, and the phases was separated. The organic phase was washed with saturated brine, concentrated, and separated by silica gel column chromatography (petroleum ether: ethyl acetate from 8:1 to 2:1) to obtain the title compound (11.7 g, 90.7%) as a gray solid. LC-MS: m/z $[M+H]^+$=210.

Intermediate 93

Dimethyl 3-(bromomethyl)pyridine-2,6-dicarboxylate

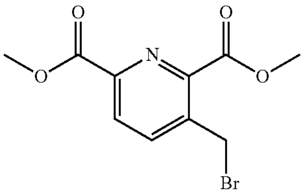

At 0° C., a raw material dimethyl 3-methylpyridine-2,6-dicarboxylate (5.7 g, 27.3 mmol), a raw material N-bromosuccinimide (4.86 g, 27.3 mmol) and benzoyl peroxide (339 mg, 1.4 mmol) were sequentially added to carbon tetrachloride (60 mL). Then, the mixture was refluxed and reacted overnight at 85° C. The mixture was evaporated to dryness by rotary evaporation and subjected to column chromatography (petroleum ether/ethyl acetate=20:1-10:1) to obtain a product as a white solid (6.14 mg, 78.1%). $^1H$ NMR (400 MHz, $CDCl_3$): δ 8.27-8.24 (m, 1H), 8.07-8.05 (m, 1H), 4.94 (s, 2H), 4.04-4.02 (m, 6H). LC-MS: m/z $[M+H]^+$=290.

Intermediate 94

Methyl 6-ethyl-7-oxo-6,7-dihydro-5H-pyrrolo[3,4-b]pyridine-2-carboxylate

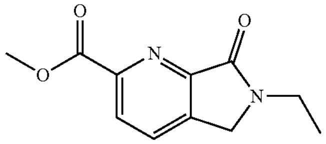 [SMILES: CCN1Cc2ccc(C(=O)OC)nc2C1=O]

A raw material dimethyl 3-(bromomethyl)pyridine-2,6-dicarboxylate (4.44 g, 15.4 mmol), a raw material ethylamine hydrochloride (1.5 g, 18.5 mmol) and potassium carbonate (4.68 g, 34 mmol) were sequentially added to tetrahydrofuran (45 mL). The mixture was reacted overnight at room temperature. Water (100 mL) was added to the reaction solution, and the reaction solution was extracted with ethyl acetate. The organic phase was collected, dried with anhydrous sodium sulfate, evaporated to dryness by rotary evaporation, and subjected to column chromatography (dichloromethane/methanol=100:1-60:1) to obtain the title compound (1.2 g, 35.4%) as a yellow solid. $^1H$ NMR (400 MHz, $CDCl_3$): δ 8.30-8.28 (m, 1H), 7.99-7.97 (m, 1H), 4.49 (s, 2H), 4.03 (s, 3H), 3.80-3.75 (m, 2H), 1.32-1.29 (m, 3H). LC-MS: m/z $[M+H]^+$=221.

Intermediate 95

6-Ethyl-2-(hydroxymethyl)-5H pyrrolo[3,4-b]pyridin-7(6H)-one

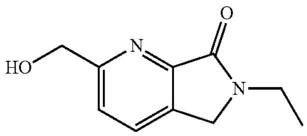

At 0° C., methyl 6-ethyl-7-oxo-6,7-dihydro-5H-pyrrolo[3,4-b]pyridine-2-carboxylate (1.2 g, 5.5 mmol) and a raw material sodium borohydride (627 mg, 16.5 mmol) were sequentially added to methanol (15 mL). The mixture was reacted overnight at room temperature. The reaction solution was concentrated and subjected to column chromatography (dichloromethane/methanol=60:1-50:1) to obtain the title compound (420 mg, 39.8%) as a yellow oil as a product. $^1H$ NMR (400 MHz, $CDCl_3$): δ 7.82 (d, J=8.0 Hz, 1H), 7.45 (d, J=8.0 Hz, 1H), 4.90-4.89 (m, 2H), 4.41 (s, 2H), 3.77-3.75 (m, 2H), 1.33-1.29 (m, 3H). LC-MS: m/z $[M+H]^+$=193.

Intermediate 96 tert-Butyl 6-(hydroxymethyl)-5',6'-dihydro-[2,3'-bipyridine]-1'(2'H)-carboxylate

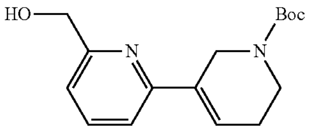 [SMILES: CC(C)(C)OC(=O)N1CCC=C(c2cccc(CO)n2)C1]

(6-Bromopyridin-2-yl)methanol (450 mg, 2.39 mmol), tert-butyl 3-(4,4,5,5-tetramethyl-1,3,2-dioxaborolan-2-yl)-5,6-dihydropyridine-1(2H)-carboxylate (500 mg, 2.39 mmol), $Pd(dppf)Cl_2$ (146 mg, 0.2 mmol) and potassium carbonate (990 mg, 7.17 mmol) were added to dioxane and water (8 mL/2 mL), and the mixture was stirred at 100° C. for 5 hours under the protection of nitrogen. The reaction solution was concentrated and subjected to column chromatography (petroleum ether/ethyl acetate=1/1) to obtain a product (500 mg, 72%). LC-MS: m/z $[M+H]^+$=291.

Intermediate 97 tert-Butyl 3-(6-(hydroxymethyl)pyridin-2-yl)piperidine-1-carboxylate

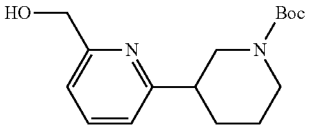 [SMILES: CC(C)(C)OC(=O)N1CCCC(c2cccc(CO)n2)C1]

tert-Butyl 6-(hydroxymethyl)-5',6'-dihydro-[2,3'-bipyridine]-1'(2'H)-carboxylate (500 mg, 1.72 mmol) was dissolved in methanol (10 mL), then 10% palladium carbon (50 mg) was added thereto, and the mixture was stirred at room temperature for 4 hours under the protection of hydrogen. The reaction solution was filtered, concentrated and subjected to column chromatography (petroleum ether/ethyl acetate=2/1) to obtain the title compound (350 mg, 70%). LC-MS: m/z $[M+H]^+$=293.

Intermediate 98

(6-(Piperidin-3-yl)pyridin-2-yl)methanol

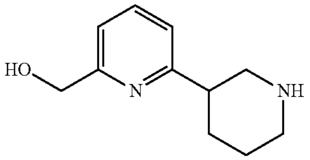 [SMILES: OCc1cccc(C2CCCNC2)n1]

tert-Butyl 3-(6-hydroxymethylpyridin-2-yl)-1-piperidine carboxylate (1.13 g, 3.86 mmol) was dissolved in dichloromethane (10 mL), then trifluoroacetic acid (6 mL) was added thereto, and the mixture was reacted overnight at room temperature. The reaction solution was directly evaporated to dryness by rotary evaporation, dissolved in methanol, and a potassium carbonate solid was added thereto, and the, mixture was stirred for 30 minutes, filtered. The filtrate was added with alkaline alumina and subjected to column chromatography (dichloromethane:methanol=10:1) to obtain the title compound (500 mg, 67%) as a pale yellow oil. LC-MS: m/z $[M+H]^+$=193.

Intermediate 99

(6-(1-Ethylpiperidin-4-yl)pyridin-2-yl)methanol

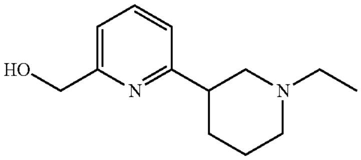 [SMILES: CCN1CCCC(c2cccc(CO)n2)C1]

(6-(Piperidin-3-yl)pyridin-2-yl)methanol (200 g, 1 mmol), iodoethane (468 mg, 3 mmol) and cesium carbonate (1.0 g, 3 mmol) were sequentially added to 10 mL of acetonitrile, then the mixture was stirred at room temperature overnight. The cesium carbonate solid was filtered with diatomite, and the organic phase was concentrated. The residue was purified by preparative TLC (dichloromethane/methanol=5/1) to obtain the title compound (80 mg, 35%) as a colorless oil. LC-MS: m/z $[M+H]^+$=221.

Intermediate 100

Imidazo[1,2-b]pyridazin-6-ylmethanol

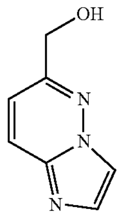

Methyl methylimidazo[1,2-b]pyridazine-6-carboxylate (200 mg, 1.13 mmol) was added to a mixed solution of tetrahydrofuran (5 mL) and methanol (2 mL). Under the protection of argon, sodium borohydride (85 mg, 2.26 mmol) was dissolved in tetrahydrofuran and added dropwise to the above solution in an ice bath, then the mixture was reacted at 0° C. for 2 hours, and the reaction solution was diluted with sodium carbonate solution (30 mL), extracted with ethyl acetate (20 mL*3 times). The organic phases were combined, and then washed with saturated brine (10 mL times). The organic phase was concentrated to obtain 110 mg of the title compound with a yield of 64.9%. LC-MS: m/z $[M+H]^+$=150.

Intermediate 101

(5-((Tetrahydrofuran-2-yl)methoxy)pyridin-2-yl) methanol

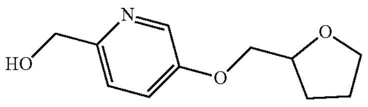 [SMILES: OCc1ccc(OCC2CCCO2)cn1]

Methyl 5-hydroxypicolinate (306 mg, 2 mmol), 2-(bromomethyl)tetrahydrofuran (990 mg, 6 mmol) and potassium carbonate (1.38 g, 10 mmol) were sequentially added to 30 mL of acetonitrile, and the experimental operation was the same as that of intermediate 5 to obtain 40 mg of the title compound as a colorless oil with a yield of 22%. LC-MS: m/z $[M+H]^+$=210.

Intermediate 102

2-(Hydroxymethyl)-6-(3-methoxypropyl)-7,8-dihydro-1,6-naphthyridin-5(6H)-one

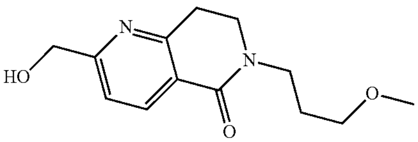 [SMILES: COCCCN1CCc2nc(CO)ccc2C1=O]

(5,6,7,8-Tetrahydro-1,6-naphthyridin-2-yl)methanol (1 g, 6.1 mmol), 1-bromo-3-methoxypropane (1 g, 6.7 mmol) and potassium carbonate (2.52 g, 18.3 mmol) were sequentially added to 30 mL of acetonitrile, and then the mixture was stirred at 70° C. overnight. The mixture was filtered under reduced pressure, and the mother liquor was evaporated to dryness to obtain 820 mg of a yellow oil, which was dissolved in 160 mL of a mixed solvent of THF and water ($THF/H_2O$=2.5/1), then sodium bicarbonate (2.85 g, 33.9 mmol) and iodine (6.46 g, 25.43 mmol) were sequentially added thereto, and then the mixture was stirred overnight at room temperature. The mixture was neutralized with sodium thiosulfate until the color faded, extracted with DCM, and subjected to column chromatography to obtain 400 mg of a colorless oil with a two-step yield of 47%. LC-MS: m/z $[M+H]^+$=251.

Intermediate 103

6-Ethyl-2-(hydroxymethyl)-7,8-dihydro-1,6-naphthyridin-5(6H)-one

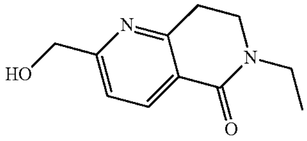

(5,6,7,8-Tetrahydro-1,6-naphthyridin-2-yl)methanol (400 mg, 2.44 mmol), iodoethane (380 mg, 2.44 mmol) and potassium carbonate (1.01 g, 7.32 mmol) were sequentially added to 20 mL of acetonitrile, and the experimental operation was the same as that of intermediate 102 to obtain 60 mg of the title compound as a colorless oil with a two-step yield of 12.5%. LC-MS: m/z $[M+H]^+$=207.

Intermediate 104

(6-(2-Methoxyethyl)-5,6,7,8-tetrahydro-1,6-naphthyridin-2-yl)methanol

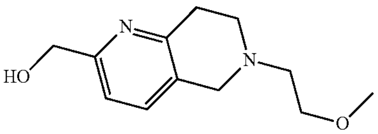 [SMILES: COCCN1CCc2nc(CO)ccc2C1]

(5,6,7,8-Tetrahydro-1,6-naphthyridin-2-yl)methanol (650 mg, 3.96 mmol), 1-bromo-2-methoxyethane (650 mg, 4.76 mmol) and potassium carbonate (1.64 g, 12 mmol) were sequentially added to 20 mL of acetonitrile, and the experimental operation was the same as that of intermediate 102 to obtain 85 mg of the title compound as a colorless oil with a yield of 10%. LC-MS: m/z $[M+H]^+$=237.

Intermediate 105 tert-Butyl 6-(hydroxymethyl)-5',6'-dihydro-[3,4'-bipyridine]-1'(2'H)-carboxylate

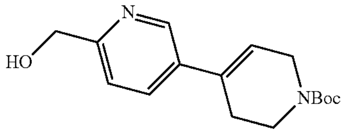 [SMILES: CC(C)(C)OC(=O)N1CC=C(c2ccc(CO)nc2)CC1]

(5-Bromopyridin-2-yl)methanol (1.88 g, 10 mmol), tert-butyl 4-(4,4,5,5-tetramethyl-1,3,2-dioxaborolan-2-yl)-5,6-dihydropyridine-1(2H)-carboxylate (4.5 g, 15 mmol), cesium carbonate (6.5 g, 20 mmol) and $Pd(dppf)_2Cl_2$ (0.8 g, 1 mmol) were sequentially added to 80 mL of dioxane, and then the mixture was stirred at 100° C. overnight under the protection of argon. TLC (dichloromethane:methanol=20:1) showed a complete reaction of raw materials. The mixture was filtered with diatomite under reduced pressure, concentrated and purified by column chromatography (dichloromethane/methanol=20/1) to obtain 3 g of the title compound as a colorless oil. LC-MS: $[M+H]^+=291$.

Intermediate 106 tert-Butyl 4-(6-(hydroxymethyl)pyridin-3-yl)piperidine-1-carboxylate

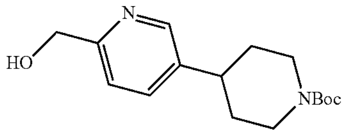

ter-Butyl 6-(hydroxymethyl)-5',6'-dihydro-[3,4'-bipyridine]-1'(2'H)-carboxylate (3 g, 10.3 mmol) was dissolved in 50 mL of methanol, then palladium carbon (200 mg) was added thereto, and the mixture was hydrogenated and stirred overnight at normal temperature and pressure. The mixture was filtered and concentrated to obtain 2 g of the title compound as a yellow oil. LC-MS: $[M+H]^+=293$.

Intermediate 107

Benzyl (2-amino-6-chloropyridin-3-yl)carbamate

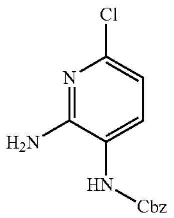 [SMILES: Nc1nc(Cl)ccc1NC(=O)OCc1ccccc1]

6-Chloropyridine-2,3-diamine (2.27 g, 15.8 mmol) was dissolved in 150 mL of 1,4-dioxane. Benzyl chloroformate (2.70 g, 15.8 mmol) was added thereto, and the mixture was stirred overnight in the dark. The reaction solution was filtered, and the solid was dissolved in dichloromethane, washed with a saturated sodium bicarbonate solution and saturated brine, dried with anhydrous sodium sulfate, concentrated and separated by column chromatography (petroleum ether:ethyl acetate=5:1) to obtain 1.20 g of pale yellow solid with a yield of 27%. LC-MS: m/z $[M+H]^+=278$.

Intermediate 108

6-Chloro-$N^3$-methylpyridine-2,3-diamine

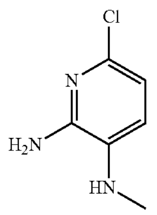

Benzyl (2-amino-6-chloropyridin-3-yl)carbamate (1.20 g 4.60 mmol) was dissolved in tetrahydrofuran (60 mL). Lithium aluminum hydride (0.66 g, 17.5 mmol) was slowly added thereto in three batches, and the mixture was heated to reflux for 15 minutes. The reaction was quenched with water. The solution was adjusted to neutrality with an acetic acid, extracted with ethyl acetate, dried, concentrated, and separated by column chromatography (petroleum ether:ethyl acetate=8:1) to obtain 375 mg of the title compound with a yield of 52%. LC-MS: m/z $[M+H]^+=158$.

Intermediate 109

5-Chloro-1-methyl-1H-imidazo[4,5-b]pyridine

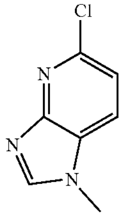

6-Chloro-$N^3$-methylpyridine-2,3-diamine (150 mg, 0.96 mmol) was dissolved in formic acid (7.5 mL), then the mixture was heated to reflux for 3 hours, and the solvent was removed. The residue was dissolved in dichloromethane, washed with saturated sodium bicarbonate and saturated brine, and dried with anhydrous sodium sulfate. After concentration, 150 mg of product was obtained with a yield of 93%. $^1$H NMR (400 MHz, DMSO-$d_6$) □3.88 (s, 3H) 7.37 (d, J=8.31 Hz, 1H) 8.14 (d, J=8.31 Hz, 1H) 8.49 (s, 1H). LC-MS: m/z $[M+H]^+=168$.

Intermediate 110

Methyl 1-methyl-1H-imidazo[4,5-b]pyridine-5-carboxylate

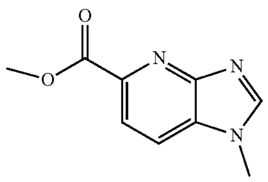

5-Chloro-1-methyl-1H-imidazo[4,5-b]pyridine (100 mg, 0.59 mmol), [1,1'-bis(diphenylphosphino)ferrocene]palladium dichloride (43 mg, 0.059 mmol) and triethylamine (180 mg, 1.78 mmol) were dissolved in methanol (5 mL), and the mixture was reacted under carbon monoxide atmosphere of 5 MPa at 120° C. overnight. Additional [1,1'-bis(diphenylphosphino)ferrocene]palladium dichloride (43 mg, 0.059 mmol) was added, and the mixture was continued to react overnight. The reaction solution was diluted with dichloromethane, concentrated, and separated by column chromatography (dichloromethane:methanol=20:1) to obtain 60 mg of the title compound as an orange oil with a yield of 53%. LC-MS: m/z $[M+H]^+=192$.

Intermediate 111

(1-Methyl-1H-imidazo[4,5-b]pyridin-5-yl)methanol

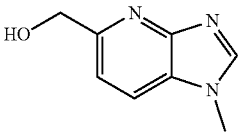

5-Chloro-1-methyl-1H-imidazo[4,5-b]pyridine (100 mg, 0.59 mmol), [1,1'-bis(diphenylphosphino)ferrocene]palladium dichloride (43 mg, 0.059 mmol) and triethylamine (180 mg, 1.78 mmol) were dissolved in methanol (5 mL), and the mixture was reacted under carbon monoxide atmosphere of 5 MPa at 120° C. overnight. Additional [1,1'-bis(diphenylphosphino)ferrocene]palladium dichloride (43 mg, 0.059 mmol) was added, and the mixture was continued to react under carbon monoxide atmosphere of 5 MPa at 120° C. overnight. The reaction solution was diluted with dichloromethane, concentrated, and separated by column chromatography (dichloromethane:methanol=20:1) to obtain an oily compound (60 mg, 53%), which was dissolved in tetrahydrofuran (3 mL) and added with aluminum lithium hydride (48 mg, 1.256 mmol) at 0° C. for reaction at room temperature overnight. The reaction solution was diluted with a small amount of ethyl acetate, then quenched with a small amount of water; the mixture was directly mixed with silica gel and separated by column chromatography (dichloromethane/methanol=30/1) to obtain the title compound as an orange oil (34 mg, yield 66%). $^1$H NMR (400 MHz, $CDCl_3$): δ 8.07 (s, 1H), 7.74-7.72 (m, 1H), 7.22-7.20 (m, 1H), 4.89 (s, 2H), 3.89 (s, 3H). LC-MS: m/z $[M+H]^+$=192.

Intermediate 112 tert-Butyl 6-bromo-2H-pyrido[3,2-b][1,4]oxazine-4 (3H)-carboxylate

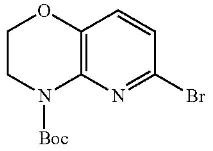 [SMILES: CC(C)(C)OC(=O)N1CCOc2ccc(Br)nc21]

6-Bromo-3,4-dihydro-2H-pyrido[3,2-b][1,4]oxazine (1.86 g, 8.65 mmol), 4-dimethylaminopyridine (0.21 g, 1.73 mmol), triethylamine (1.75 g, 17.3 mmol) were added to dichloromethane (30 mL), and the mixture was cooled to 0 to 10° C. in an ice bath under the protection of nitrogen. BOC anhydride (2.83 g, 12.97 mmol) was slowly added to the reaction solution, then the mixture was stirred at room temperature for 15 minutes, heated to 40° C. and reacted for 3 hours. The reaction solution was quenched by adding water, extracted with dichloromethane, and the organic phase was dried with anhydrous sodium sulfate, and then concentrated, and subjected to column chromatography (petroleum ether/ethyl acetate=12/1) to obtain the title compound as a white solid (2.64 g, 97%). $^1$H NMR (400 MHz, DMSO-$d_6$) δ 7.26-7.21 (m, 2H), 4.24 (t, J=4 Hz, 2H), 3.81 (t, J=4 Hz, 2H), 1.48 (s, 9H).

Intermediate 113

4-tert-Butyl-6-methyl-2H pyrido[3,2-b][1,4]oxazine-4,6(3H)-dicarboxylate

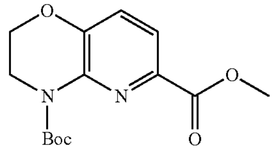 [SMILES: COC(=O)c1ccc2c(n1)N(C(=O)OC(C)(C)C)CCO2]

Methyl tert-butyl-6-bromo-2H-pyrido[3,2-b][1,4]oxazine-4 (3H)-carboxylate (2.32 g, 7.36 mmol) was added to anhydrous methanol (50 mL). Triethylamine (2.23 g, 22.08 mmol), 1,1'-bisdiphenylphosphinoferrocene palladium dichloride (0.54 g, 0.74 mmol) were added sequentially thereto. Carbon monoxide was pumped and ventilated to an internal pressure of 6.0 MPa, and the mixture was heated to 120° C. to react overnight. Water and dichloromethane were added to the reaction solution, and the phases was separated. The organic phases were combined, dried with anhydrous sodium sulfate, concentrated, and subjected to column chromatography (petroleum ether:ethyl acetate=4:1) to obtain the title compound (0.81 g, 37%) as a white solid. $^1$HNMR (400 MHz, DMSO-$d_6$) δ 7.74 (d, J=8 Hz, 1H), 7.38 (d, J=8 Hz, 1H), 4.33 (t, J=4 Hz, 2H), 3.85 (t, J=4 Hz, 2H), 3.83 (s, 1H), 1.50 (s, 9H). LC-MS: m/z $[M+H]^+$=295

Intermediate 114 tert-Butyl 6-(hydroxymethyl)-2-pyrido[3,2-b][1,4] oxazine-4(3H)-carboxylate

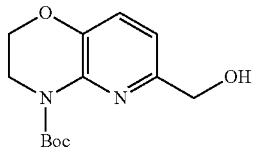 [SMILES: CC(C)(C)OC(=O)N1CCOc2ccc(CO)nc21]

Methyl 4-tert-butyl-6-methyl-2H-pyrido[3,2-b][1,4] oxazine-4,6(3H)-dicarboxylate (590 mg, 2.0 mmol) was added to anhydrous tetrahydrofuran (8 mL), and the mixture was cooled to 0 to 10° C. in an ice bath under the protection of nitrogen. After stirring for 30 minutes, diisobutyl aluminum hydride (1.0 M in n-hexane) (5.0 mL) was slowly added to the reaction solution, and the mixture was reacted in an ice bath for 2 hours. The reaction solution was quenched by adding water, extracted with ethyl acetate, and the organic phase was dried with anhydrous sodium sulfate, concentrated and subjected to column chromatography (petroleum ether/ethyl acetate=5/1) to obtain the title compound (210 mg, 39%) as an off-white solid. LC-MS: m/z $[M+H]^+$=267.

Intermediate 115

2-(2,6-Dichloropyridin-3-yl)acetonitrile

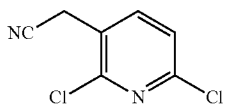 [SMILES: N#CCc1ccc(Cl)nc1Cl]

3-(Bromomethyl)-2,6-dichloropyridine (500 mg, 2.08 mmol) was added to DMF (10 mL), then the mixture was cooled to 0° C., and a solution of sodium cyanide (508 mg, 2.08 mmol) in water (2 mL) was added thereto, and the mixture was stirred at room temperature for 5 hours. The reaction solution was poured into water, extracted with ethyl acetate, and the organic phase was concentrated and subjected to column chromatography (petroleum ether/ethyl acetate=4/1) to obtain the title compound (180 mg, 46%). $^1$H NMR (400 MHz, $CDCl_3$) δ 7.85 (d, J=8.0 Hz, 1H), 7.37 (d, J=8.0 Hz, 1H), 3.84 (s, 2H).

Intermediate 116

Dimethyl 3-(cyanomethyl)pyridine-2,6-dicarboxylate

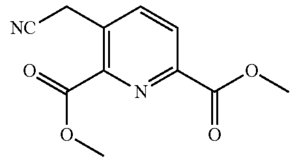 [SMILES: COC(=O)c1ccc(CC#N)c(C(=O)OC)n1]

2-(2,6-Dichloropyridin-3-yl)acetonitrile (180 mg, 0.963 mmol), Pd(dppf)$Cl_2$ (73 mg, 0.1 mmol) and triethylamine (292 mg, 2.89 mmol) were added to methanol (4 mL), then the mixture was reacted overnight under carbon monoxide atmosphere of 5 MPa at 100° C. The reaction solution was concentrated and subjected to column chromatography (petroleum ether/ethyl acetate=4/1) to obtain the title compound (100 mg, 44%). $^1$H NMR (400 MHz, $CDCl_3$) δ 8.34 (d, J=8.0 Hz, 1H), 8.19 (d, J=8.0 Hz, 1H), 4.34 (s, 2H), 4.03 (s, 6H).

Intermediate 117

Methyl 8-oxo-5,6,7,8-tetrahydro-1,7-naphthyridine-2-carboxylate

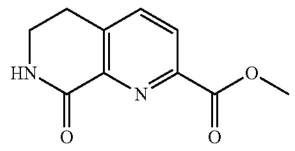

The raw material dimethyl 3-(cyanomethyl)pyridine-2,6-dicarboxylate (100 mg, 0.43 mmol) and raney nickel (51 mg, 0.86 mmol) were sequentially added to methanol (300 mL). The mixture was reacted at 40° C. under hydrogen atmosphere of 50 Psi pressure for 5 hours. The mixture was filtered under reduced pressure, and the filtrate was evaporated to dryness by rotary evaporation to obtain a crude product directly reacted in the next step. LC-MS: m/z $[M+H]^+$=207.

Intermediate 118

(5,6,7,8-Tetrahydro-1,7-naphthyridin-2-yl)methanol

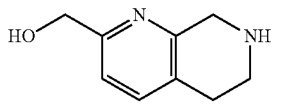 [SMILES: OCc1ccc2c(n1)CNCC2]

Methyl 8-oxo-5,6,7,8-tetrahydro-1,7-naphthyridine-2-carboxylate (500 mg, 2.42 mmol) was added to tetrahydrofuran (10 mL), and the mixture was cooled to 0° C. Tetrahydrofuran solution of lithium aluminum hydride (4.84 mL, 4.84 mmol) was added thereto, and the mixture was stirred at room temperature overnight. The reaction solution was cooled to 0° C., and ethyl acetate was added dropwise, then water was added thereto, and the reaction solution was concentrated to obtain a crude product (1.0 g, 100%).

Intermediate 119 tert-Butyl 2-(hydroxymethyl)-5,6-dihydro-1,7-naphthyridine-7-(8H)-carboxylate

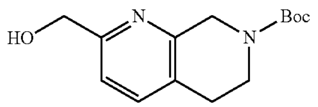 [SMILES: CC(C)(C)OC(=O)N1CCc2ccc(CO)nc2C1]

(5,6,7,8-Tetrahydro-1,7-naphthyridin-2-yl)methanol (1.0 g, 6.1 mmol), di-tert-butyl dicarbonate (1.33 g, 6.1 mmol) and triethylamine (1.85 g, 18.3 mmol) were added to dichloromethane, and the mixture was stirred at room temperature for 3 hours. The reaction solution was concentrated, and subjected to column chromatography to obtain a product (50 mg, 8%). LC-MS: m/z $[M+H]^+$=265.

Intermediate 120

(6-(1-(Oxetan-3-yl)-3-piperidinyl)pyridin-2-yl)methanol

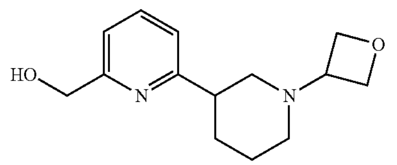 [SMILES: OCc1cccc(C2CCCN(C3COC3)C2)n1]

(6-(Piperidin-3-yl)pyridin-2-yl)methanol (100 mg, 0.52 mmol) was dissolved in dichloromethane (3 mL), and 1 drop of acetic acid was added dropwise thereto. Then oxetan-3-one (116 mg, 1.56 mmol) was added thereto, and the mixture was reacted at room temperature for 30 minutes, and then sodium triacetoxyborohydride (330 mg, 1.56 mmol) was added thereto, and the mixture was reacted at room temperature overnight. The reaction solution was directly filtered, concentrated, and the filtrate was subjected to thin layer chromatography (dichloromethane/methanol=20/1) to obtain the title compound (100 mg, 77%) as a yellow oil. LC-MS: m/z $[M+H]^+$=249.

Intermediate 121

Methyl 6-(1-(tert-butoxycarbonyl)-3-hydroxypyrrolidin-3-yl)picolinate

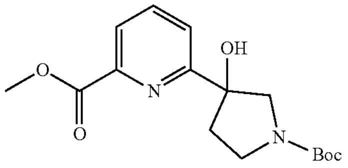 [SMILES: COC(=O)c1cccc(C2(O)CCN(C(=O)OC(C)(C)C)C2)n1]

2,6-Dibromopyridine (7.0 g, 29.55 mmol) was added to tetrahydrofuran (70 mL), and the mixture was cooled to −78° C., then n-butyllithium (13 mL, 32.5 mmol) was added dropwise thereto; the mixture was stirred at −78° C. for 30 minutes, and then tert-butyl 3-oxopyrrolidine-1-carboxylate (5.47 g, 32.5 mmol) was added thereto, and the mixture was naturally warmed to room temperature and reacted for 1 hour. The reaction solution was poured into water, extracted with ethyl acetate, and the organic phase was concentrated, and subjected to column chromatography to obtain a product tert-butyl 3-(6-bromopyridin-2-yl)-3-hydroxypyrrolidine-1-carboxylate (3.0 g); then the product, Pd(dppf)$Cl_2$ (637 mg, 0.87 mmol) and triethylamine (2.65 g, 26.22 mmol) were added to methanol (50 mL), and the mixture was reacted at 80° C. overnight under carbon monoxide atmosphere of 1 MPa. The reaction solution was concentrated and subjected to column chromatography (petroleum ether/ethyl acetate=1/1) to obtain the title compound (1.5 g, a two-step yield of 16%). LC-MS: m/z $[M+H]^+$=323.

Intermediate 122 tert-Butyl 3-(6-(hydroxymethyl)pyridin-2-yl)pyrrolidine-1-carboxylate

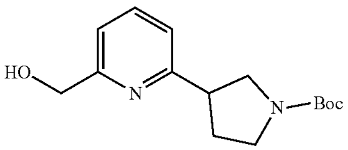 [SMILES: CC(C)(C)OC(=O)N1CCC(c2cccc(CO)n2)C1]

Methyl 6-(1-(tert-butoxycarbonyl)-3-hydroxypyrrolidin-3-yl) picolinate (860 mg, 2.67 mmol) and triethylamine (809 mg, 18.01 mmol) were dissolved in dichloromethane (10 mL), then the mixture was cooled to 0° C., and methanesulfonyl chloride (397 mg, 3.47 mmol) was added thereto, and then the mixture was reacted at room temperature overnight. The reaction solution was poured into water, extracted with dichloromethane, and the organic phase was washed with saturated brine, dried with anhydrous sodium sulfate, concentrated, and subjected to column chromatography (petroleum ether/ethyl acetate=5/1) to obtain 430 mg of a pale yellow solid. The pale yellow solid was dissolved in methanol (8 mL), and palladium/carbon (800 mg) was added thereto, then the mixture was reacted overnight at 50° C. under a hydrogen atmosphere. The reaction solution was filtered to remove palladium/carbon. The filtrate was evaporated to dryness by rotary evaporation to obtain 440 mg of a crude product as a gray oil, and 200 mg of the crude product was taken out and dissolved in tetrahydrofuran (2 mL). Diisobutyl aluminum hydride (1M, 1.95 mL, 1.95 mmol) was added thereto in an ice-ethanol bath, and the mixture was reacted for two hours at 0° C. The reaction solution was poured into water, extracted with dichloromethane. The organic phase was washed with saturated brine, dried with anhydrous sodium sulfate, concentrated, and separated by column chromatography (dichloromethane/methanol=50/1) to obtain 90 mg of a yellow oil with a multistep yield of 25%. LC-MS: m/z $[M+H]^+$=279.

Intermediate 123

(5-(3-Fluoro-1-methylazetidin-3-yl)pyridin-2-yl) methanol

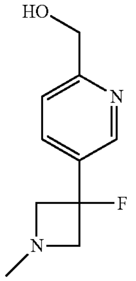

(5-(3-Fluoroazetidin-3-yl)pyridin-2-yl)methanol (600 mg, 3.3 mmol) was dissolved in dichloromethane (6 mL). 1 drop of acetic acid and aqueous formaldehyde solution (1.5 mL) were added thereto, and the mixture was reacted at room temperature for 30 minutes, then sodium triacetoxyborohydride (2 g, 9.9 mmol) was added thereto, and the mixture was reacted at room temperature overnight. The reaction solution was evaporated to dryness by rotary evaporation and dissolved in methanol, and separated by column chromatography (dichloromethane:methanol=10:1) to obtain 100 mg of the title compound as a yellow oil with a yield of 13%. LC-MS: m/z $[M+H]^+$=197.

Intermediate 124 tert-Butyl 3-(6-bromopyridin-2-yl)-3-hydroxypyrrolidine-1-carboxylate

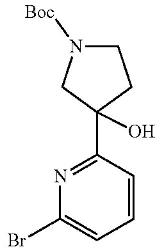 [SMILES: CC(C)(C)OC(=O)N1CCC(O)(c2cccc(Br)n2)C1]

2,6-Dibromopyridine (7.0 g, 29.55 mmol) was added to tetrahydrofuran (70 mL), and the mixture was cooled to −78° C., then n-butyllithium (13 mL, 32.5 mmol) was added dropwise thereto, and the mixture was stirred at −78° C. for 30 minutes, and then 2 (5.47 g, 32.5 mmol) was added thereto, and the mixture was naturally warmed to room temperature and reacted for 1 hour. The reaction solution was poured into water, extracted with ethyl acetate, and the organic phase was concentrated and subjected to column chromatography (petroleum ether:ethyl acetate=3:1) to obtain 3.0 g of the title compound with a yield of 30%. LC-MS: m/z $[M+H-56]^+$=289.

Intermediate 125

Methyl 6-(1-(tert-butoxycarbonyl)-3-hydroxypyrrolidin-3-yl)picolinate

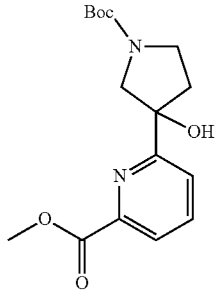 [SMILES: COC(=O)c1cccc(C2(O)CCN(C(=O)OC(C)(C)C)C2)n1]

tert-Butyl 3-(6-bromopyridin-2-yl)-3-hydroxypyrrolidine-1-carboxylate (3.0 g, 8.74 mmol), $Pd(dppf)Cl_2$ (637 mg, 0.87 mmol) and triethylamine (2.65 g, 26.22 mmol) wer added to methanol (50 mL), then the mixture was reacted at 80° C. under carbon monoxide atmosphere of 1 Mpa overnight. The reaction solution was concentrated and separated by column chromatography (petroleum ether:ethyl acetate=1:1) to obtain the title compound (1.5 g, 54%). LC-MS: m/z $[M+H]^+$=323.

Intermediate 126 tert-Butyl 3-fluoro-3-(6-(hydroxymethyl)pyridin-2-yl)pyrrolidine-1-carboxylate

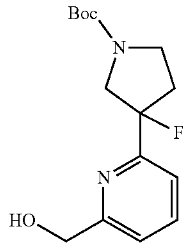 [SMILES: CC(C)(C)OC(=O)N1CCC(F)(c2cccc(CO)n2)C1]

Methyl 6-(1-(tert-butoxycarbonyl)-3-hydroxypyrrolidin-3-yl) picolinate (500 mg, 1.55 mmol) was added to dichloromethane (10 mL), and the mixture was cooled to 0° C. DAST (375 mg, 2.33 mmol) was added dropwise thereto, and the mixture was stirred at room temperature for 2 hours. The reaction solution was poured into water, and the pH was adjusted to 8, then the mixture was extracted with dichloromethane. The organic phase was concentrated, and subjected to column chromatography (petroleum ether:ethyl acetate=3:1) to obtain 300 mg of a compound, which was added to tetrahydrofuran (5 mL), cooled to 0° C. DIBAL-H (2.8 mL, 2.78 mmol) was added dropwise thereto, and the reaction was carried out for 2 hours. The reaction solution was poured into water, extracted with ethyl acetate, and the organic phase was concentrated, and separated by column chromatography (petroleum ether:ethyl acetate=2:1) to obtain the title compound (120 mg, a two-step yield of 26.4%). LC-MS: m/z $[M+H]^+$=297.

Intermediate 127

(5-(3-Fluoroazetidin-3-yl)pyridin-2-yl)methanol

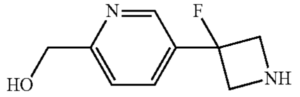 [SMILES: OCc1ccc(C2(F)CNC2)cn1]

tert-Butyl 3-fluoro-3-(6-(hydroxymethyl)pyridin-3-yl) azetidine-1-carboxylate (500 mg, 1.77 mmol) was dissolved in dichloromethane (3 mL), and trifluoroacetic acid (1 mL) was added thereto, then the mixture was reacted at room temperature for 1 hour. Additional trifluoroacetic acid (1 mL) was added thereto to react at room temperature for 2 hours. The reaction solution was directly evaporated to dryness by rotary evaporation, then dissolved in methanol, and a potassium carbonate solid was added thereto, and the mixture was stirred for 30 minutes, filtered, evaporated to dryness by rotary evaporation, subjected to an alkaline alumina column chromatography (dichloromethane/methanol=5/1) to obtain 200 mg of the title compound as a yellow oil with a yield of 62%. $^1H$ NMR (400 MHz, $CDCl_3$) δ 8.78 (s. 1H), 7.90 (d, J=9.6 Hz, 1H), 7.327 (d, J=8.4 Hz, 1H), 4.79 (s, 2H), 4.29-4.21 (m, 2H), 3.91-3.84 (m, 2H), 2.53-2.22 (m, 2H)

Intermediate 128

(5-(3-Fluoro-1-(oxetan-3-yl)azetidin-3-yl)pyridin-2-yl)methanol

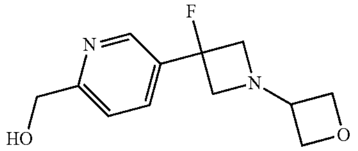 [SMILES: OCc1ccc(C2(F)CN(C3COC3)C2)cn1]

(5-(3-Fluoroazetidin-3-yl)pyridin-2-yl)methanol (150 mg, 0.81 mmol) was dissolved in dichloromethane (3 mL), and 1 drop of acetic acid was added dropwise thereto. Then oxetan-3-one (179.8 mg, 2.43 mmol) was added thereto, and the mixture was reacted at room temperature for 30 minutes, and then sodium triacetoxyborohydride (515 mg, 2.43 mmol) was added thereto, and the mixture was reacted at room temperature overnight. The reaction solution was poured into water, extracted with dichloromethane, dried with anhydrous sodium sulfate, concentrated, and separated by preparative column chromatography (dichloromethane/ methanol=20/1) to obtain 80 mg of the title compound as a yellow solid with a yield of 30%. LC-MS: m/z $[M+H]^+$=239.

Intermediate 129

5-Methyl-1,2,4-oxadiazole-3-carbohydrazide

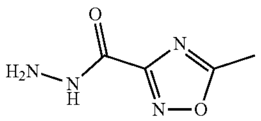

Ethyl 5-methyl-1,2,4-oxadiazole-3-carboxylate (10 g, 64.1 mmol) was dissolved in ethanol (100 mL), and hydrazine hydrate (2.46 g, 76.92 mmol, 99%) was added dropwise thereto in an ice bath and at room temperature for 16 hours. The reaction solution was filtered, and the filter cake was washed with ethanol, dried to obtain 7.2 g of the title compound with a yield of 78.5%. LC-MS: m/z $[M+H]^+$=143.

Intermediate 130

3-(6-Chloro-7-methoxy-[1,2,4]triazolo[4,3-b]pyridazin-3-yl)-5-methyl-1,2,4-oxadiazole

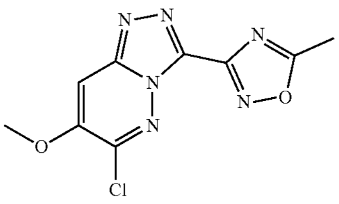

3,6-Dichloro-4-methoxypyridazine (1 g, 5.62 mmol) and 5-methyl-1,2,4-oxadiazole-3-carbohydrazide (797 mg, 5.62 mmol) were dissolved in tert-butanol (20 mL), then methanesulfonic acid (1.08 g, 11.24 mmol) was added thereto, and the mixture was reacted at 85° C. for 16 hours under the protection of argon. The reaction solution was cooled, concentrated, and separated by column chromatography to obtain 36 mg of the title compound with a yield of 2.4%. LC-MS: m/z $[M+H]^+$=267.

Intermediate 131

Methyl 1,6-naphthyridine-2-carboxylate

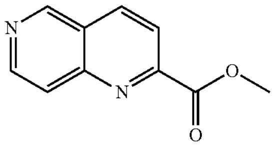

4-Amino-3-pyridinecarbaldehyde (5.0 g, 41 mmol), sodium pyruvate (4.56 g, 41 mmol) and sodium hydroxide (0.62 g, 16 mmol) were dissolved in ethanol (300 mL); after the addition was completed, the mixture was heated to 70° C. and reacted for 5 hours. After the reaction was completed, the reaction solution was filtered, and the filter cake was rinsed with a small amount of ethanol and dried to obtain 7.83 g of a solid compound; the solid compound and concentrated sulfuric acid (9.0 mL) were dissolved in methanol (350 mL). After the addition was completed, the mixture was heated to reflux and reacted for 3 hours. After the reaction was completed, most of the solvent was concentrated, then 150 mL of water was added to the residue, and a saturated sodium bicarbonate solution was added to adjust the pH value of the system to 8-9, then the mixture was extracted with dichloromethane (400 mL*2 times). The organic phases were combined, and then washed with saturated brine (400 mL*1 time). The organic phase was dried and concentrated to obtain 6.4 g of the title compound with a two-step yield of 83%.

LC-MS: m/z $[M+H]^+$=189.07.

Intermediate 132

Methyl 5-oxo-5,6-dihydro-1,6-naphthyridine-2-carboxylate

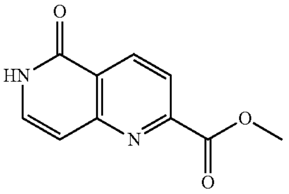

Methyl 1,6-naphthyridine-2-carboxylate (5.1 g, 27 mmol) and m-chloroperoxybenzoic acid (9.36 g. 54 mmol) were added to dichloromethane (75 mL), and the mixture was stirred at room temperature for 2 hours. After the reaction was completed, a saturated sodium bicarbonate solution (150 mL) was added thereto, and the mixture was stirred for 15 minutes, then left to stand for layer separation. The organic phase was separated, then an aqueous phase was extracted with dichloromethane (200 mL*3 times), and the organic phases were combined, then washed with saturated brine (300 mL*1 time). The organic phase was dried and evaporated to dryness by rotary evaporation to obtain a solid compound, which was dissolved in acetic anhydride (110 mL). After the addition was completed, the mixture was heated to 140° C. and stirred for 4 hours, then the system was cooled to 100° C.; water (40 mL) was added thereto, and the mixture was stirred for 0.5 hours, then the system was cooled to room temperature; water (100 mL) was added to the reaction system, followed by extraction with ethyl acetate (250 mL*3 times). The organic phases were combined, and then washed with saturated brine (300 mL*1 time). The organic phase was dried and concentrated to obtain 2.66 g of the title compound with a two-step yield of 48%. LC-MS: m/z $[M+H]^+$=205.11.

Intermediate 133

2-(Hydroxymethyl)-6-(2-methoxyethyl)-1,6-naphthyridin-5(6H)-one

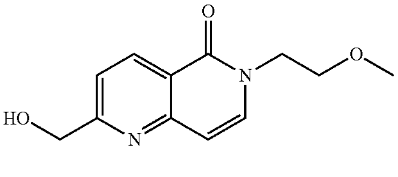 [SMILES: COCCn1ccc2nc(CO)ccc2c1=O]

Methyl 5-oxo-5,6-dihydro-1,6-naphthyridine-2-carboxylate (200 mg, 0.98 mmol) and 1-bromo-2-methoxyethane (135 mg, 0.98 mmol) were dissolved in N,N-dimethylformamide (5 mL), and sodium hydride (58 mg, 1.47 mmol, 60%) was added thereto, then the mixture was reacted at room temperature for 3 hours. The reaction solution was quenched with water, extracted with ethyl acetate (10 mL*3 times), and the organic phases were combined and then washed with saturated brine (15 mL*1 time). The organic phase was dried and concentrated to obtain a solid compound, which was dissolved in a mixed solution of tetrahydrofuran (5 mL) and methanol (5 mL), and sodium borohydride (87 mg, 2.29 mmol) was added thereto, and the mixture was reacted at room temperature for 1 hour. The reaction solution was added with methanol to quench, and separated by column chromatography to obtain 82 mg of the title compound with a two-step yield of 36.2%. LC-MS: m/z $[M+H]^+$=235.

Intermediate 134

Methyl 5-(2-bromoethoxy)picolinate

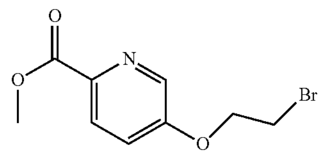

Methyl 5-hydroxypicolinate (3 g, 19.5 mmol) and 1,2-dibromoethane (10.9 g, 58.5 mmol) were dissolved in N,N-dimethylformamide (50 mL), then cesium carbonate (6.3 g, 19.5 mmol) was added thereto, and the mixture was reacted overnight at 60° C. under the protection of argon. The reaction solution was cooled and added with water, extracted with ethyl acetate (20 mL*3 times). The organic phases were combined and then wash with saturated brine (25 mL*1 time). The organic phase was dried and concentrated to obtain 2.5 g of the title compound with a yield of 49.5%. LC-MS: m/z $[M+H]^+$=259.

Intermediate 135

(5-(2-(Azetidin-1-yl)ethoxy)pyridin-2-yl)methanol

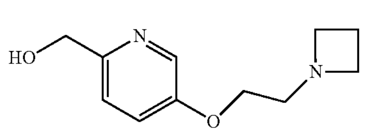 [SMILES: OCc1ccc(OCCN2CCC2)cn1]

Methyl 5-(2-bromoethoxy)picolinate (100 mg, 0.39 mmol) was dissolved in tetrahydrofuran (10 mL), and sodium borohydride (30 mg, 0.78 mmol) was added thereto, then the mixture was reacted at 50° C. for 5 hours. The reaction solution was quenched with methanol, evaporated to dryness by rotary evaporation, extracted with dichloromethane (10 mL*3 times). The organic phases were combined, and then washed with saturated brine (15 mL*1 time). The organic phase was dried and concentrated to obtain 65 mg of compound; the compound and azetidine (48 mg, 0.85 mmol) were dissolved in acetonitrile (10 mL), and then the mixture was reacted at room temperature for 16 hours. The reaction solution was concentrated to obtain 35 mg of the title compound with a two-step yield of 39%. LC-MS: m/z $[M+H]^+$=209.

Intermediate 136

Methyl 5-(azetidin-3-yloxy)picolinate trifluoroacetate

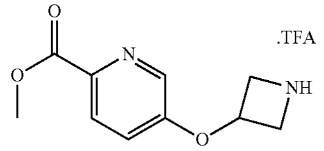

Methyl 5-hydroxypicolinate (2 g, 13.0 mmol) and tert-butyl 3-iodoazetidine-1-carboxylate (7.4 g, 26.0 mmol) were dissolved in N,N-dimethylformamide (100 mL), then cesium carbonate (8.4 g, 26 mmol) and cuprous iodide (2.5 g, 13 mmol) were added thereto respectively, and the mixture was reacted overnight at 100° C. under the protection of argon. The reaction solution was cooled and filtered with diatomite, washed with water and dichloromethane. The filtrate was extracted with dichloromethane (50 mL*3 times), and the organic phases were combined, and then washed with saturated brine (30 mL*1 time). The organic phase was evaporated to dryness by rotary evaporation, and separated by column chromatography to obtain 1.92 g of compound with a yield of 47.8%. 1 g of the compound was taken out and dissolved in dichloromethane (20 mL), then trifluoroacetic acid (5 mL) was added thereto, and the mixture was reacted at room temperature for 3 hours. The reaction solution was evaporated to dryness by rotary evaporation, and added with ethyl acetate, then evaporated to dryness by rotary evaporation, and added with toluene, then evaporated to dryness by rotary evaporation to obtain 1.04 g of the title compound with a yield of 100%. LC-MS: m/z $[M+H]^+$=209.

Intermediate 137

(5-((1-Ethylazetidin-3-yl)oxy)pyridin-2-yl)methanol

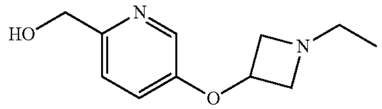

Methyl 5-(azetidin-3-yloxy)picolinate (1.04 g, 3.23 mmol) was dissolved in tetrahydrofuran (10 mL), and a tetrahydrofuran solution of acetaldehyde (6.26 mL, 6.26 mmol) was added thereto, then sodium triacetoxyborohydride (2.05 g, 9.69 mmol) was added thereto, and the mixture was reacted at room temperature for 16 hours after the addition was completed. The reaction solution was concentrated and separated by column chromatography to obtain 283 mg of compound with a yield of 37.0%. The compound (113 mg, 0.55 mmol) was taken out and dissolved in a mixed solution (4 mL) of tetrahydrofuran and methanol, then sodium borohydride (150 mg, 4 mmol) was added to react at room temperature for 6 hours. The reaction solution was quenched by adding an ammonium chloride solution, extracted with ethyl acetate (10 mL*3 times). The organic phases were combined, then washed with saturated saline (15 mL*1 time). The organic phase was dried and concentrated to obtain 25 mg of the title compound with a yield of 21.8%. LC-MS: m/z $[M+H]^+$=209.

Intermediate 138

Imidazo[1,2]pyridin-5-ylmethanol

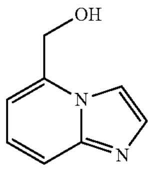 [SMILES: OCc1cccc2nccn12]

Imidazo[1,2]pyridine-5-carboxylate (100 mg, 0.62 mmol) was dissolved in tetrahydrofuran (5 mL), and lithium aluminum hydride (35 mg, 0.93 mmol) was added thereto in an ice bath, then the mixture was reacted at room temperature for 2 hours under the protection of argon. 15 mL of water and 15 mL of 15% sodium hydroxide solution were added to the reaction solution for quenching, and the mixture was extracted with dichloromethane (20 mL*3 times). The organic phases were combined, and then washed with saturated brine (15 mL*1 time). The organic phase was dried, concentrated, and separated by column chromatography to obtain 45 mg of the title compound with a yield of 48.7%. LC-MS: m/z $[M+H]^+$=149.

Intermediate 139

(6-Methoxyquinolin-2-yl)methanol

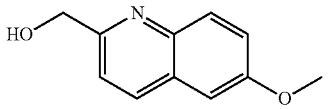

The raw material 6-methoxyquinoline-2-carboxylate (203 mg, 1 mmol) was added to anhydrous tetrahydrofuran (20 mL), then lithium aluminum hydride (60 mg, 1.5 mmol) was added thereto, and the mixture was stirred at room temperature for 1 hour. 3 drops of water were added to quench excess lithium aluminum hydride, and the mixture was thereto filtered under reduced pressure. The filtrate was evaporated to dryness by rotary evaporation, and purified by preparative plate to obtain 30 mg of the title compound as a colorless liquid with a yield of 15.8%. LC-MS: m/z $[M+H]^+$=190.

Intermediate 140

(1,6-Naphthyridin-2-yl)methanol

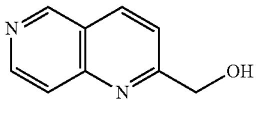 [SMILES: OCc1ccc2cnccc2n1]

Methyl 1,6-naphthyridine-2-carboxylate (200 mg, 1.06 mmol), methanol (4 mL), sodium borohydride (200 mg, 5.26 mmol) were dissolved in tetrahydrofuran (12 mL). After the addition was completed, the mixture was stirred at room temperature for 1.5 hours, and separated by a chromatographic column to obtain 62 mg of the title compound with a yield of 36.5%. LC-MS: m/z $[M+H]^+$=161.10.

Intermediate 141

(6-(Oxetan-3-yl)-5,6,7,8-tetrahydro-1,6-naphthyridin-2-yl)methanol

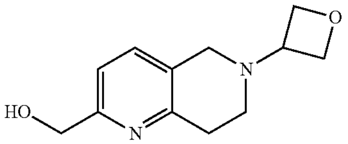

(5,6,7,8-Tetrahydro-1,6-naphthyridin-2-yl)methanol (400 mg, 2.44 mmol), oxetan-3-one (878.4 mg, 12.2 mmol) and sodium triacetoxyborohydride (2.58 g, 12.2 mmol) were added to 1.2-dichloroethane (40 mL), and the mixture was stirred for 15 hours. The mixture was added to a saturated sodium bicarbonate solution and stirred, extracted with dichloromethane (20 mL*5), concentrated, and separated by preparative thin layer chromatography to obtain 140 mg of the title compound with a yield of 26.1% and a yellow solid appearance. LC-MS: m/z $[M+H]^+$=221.

Intermediate 142

2-(Hydroxymethyl)-6-(oxetan-3-yl)-7,8-dihydro-1,6-naphthyridin-5(6H)-one

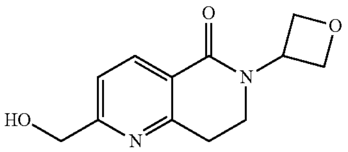 [SMILES: O=C1c2ccc(CO)nc2CCN1C1COC1]

(6-(Oxetan-3-yl)-5,6,7,8-tetrahydro-1,6-naphthalen-2-yl)methanol (140 mg, 0.64 mmol), sodium bicarbonate (537.6 mg, 6.4 mmol), and iodine (1219.4 mg, 4.8 mmol) were sequentially added to 13 mL of a $THF/H_2O$ (2.5:1) solution, and the mixture was stirred at room temperature for 5 hours. A $Na_2S_2O_3$ solution was added dropwise until the reaction solution faded, and the mixture was extracted with dichloromethane (10 mL*5); the organic phases were combined, concentrated, and separated by preparative thin layer chromatography to obtain 30 mg of the title compound with a yield of 20.0% and a colorless solid appearance. LC-MS: m/z $[M+H]^+$=235.

Intermediate 143

2-(Hydroxymethyl)-6-methyl-7,8-dihydro-1,6-naphthyridin-5(6H)-one

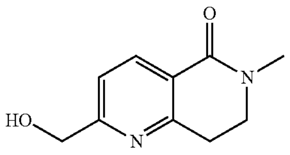

(5,6,7,8-Tetrahydro-1,6-naphthalen-2-yl)methanol (400 mg, 1.68 mmol) and 37 wt % formaldehyde solution (102.28 mg, 3.66 mmol) were added to methanol (10 mL). $NaBH_4$ (369 mg, 9.76 mmol) was added in batches in an ice-water bath, and the mixture was stirred for 1 hour. 5 mL of acetone was added thereto, and the mixture was stirred for 10 min, filtered with diatomite, concentrated, and separated by preparative thin layer chromatography to obtain 230 mg of a yellow solid. 200 mg of the yellow solid, sodium bicarbonate (924 mg, 11 mmol) and iodine (2.1 g, 8.3 mmol) were sequentially added to 35 mL of $THF/H_2O$ (2.5:1) solution, and the mixture was stirred at room temperature for 5 hours. A sodium thiosulfate solution was added dropwise until the reaction solution faded, and the mixture was extracted with dichloromethane (10 mL*5); the organic phases were combined and concentrated to obtain 70 mg of the title compound with a two-step yield of 25% and a yellow solid appearance. LC-MS: m/z $[M+H]^+$=193.

Intermediate 144

2-(Hydroxymethyl)-6-(oxetan-3-yl)-1,6-naphthyridin-5(6H)-one

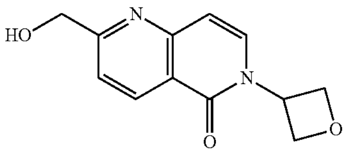 [SMILES: O=c1c2ccc(CO)nc2ccn1C1COC1]

Methyl 5-oxo-5,6-dihydro-1,6-naphthyridine-2-carboxylate (204 mg, 1.0 mmol), sodium hydride (60%) (80 mg, 2.0 mmol), 3-iodo-oxetane (920 mg, 5.0 mmol) were dissolved in DMF (12.0 mL). After the addition was completed, the mixture was heated to 50° C. and stirred for 3 hours. After the reaction was completed, water (50 mL) was added to the reaction system, and then the mixture was extracted with ethyl acetate (50 mL*2 times); the organic phases were combined, and then washed with saturated brine (30 mL*1 time). The organic phase was dried, concentrated and separated by column chromatography to obtain 18.0 mg of compound; with the compound and sodium borohydride (80 mg, 2.35 mmol) were dissolved in a mixed solution of tetrahydrofuran and methanol (tetrahydrofuran:methanol=4:1) (10 mL). After the addition was completed, the mixture was stirred and reacted at room temperature for 1.5 hours. After the reaction was completed, the reaction solution was separated by column chromatography to obtain 10.0 mg of the title compound with a two-step yield of 4.3%. LC-MS: m/z $[M+H]^+$=233.08.

Intermediate 145

(5-Ethoxy-1,6-naphthalen-2-yl)methanol

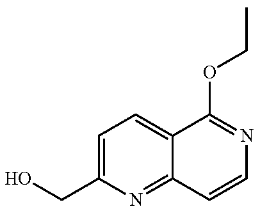

Methyl 5-oxo-5,6-dihydro-1,6-naphthyridine-2-carboxylate (200 mg, 1.0 mmol) was dissolved in phosphorus oxychloride (3.0 mL), and the temperature of the system was raised to 80° C., then the mixture was stirred and reacted for 4 hours. After the reaction was completed, the excess phosphorus oxychloride in the system was distilled off. Then ethanol (20.0 mL) was added to the residue, and the mixture was stirred at room temperature for 2 hours. After the reaction was completed, the excess ethanol in the system was distilled off under reduced pressure. Water (20 mL) was added to the system, followed by extraction with ethyl acetate (40 mL*2 times); the organic phases were combined, and then washed with saturated brine (30 mL*1 time). The organic phase was dried and concentrated to obtain 200 mg of crude product. 170 mg of the crude product and sodium borohydride (140 mg, 3.68 mmol) were dissolved in a mixed solution of tetrahydrofuran and methanol (tetrahydrofuran:methanol=4:1) (10 mL). After the addition was completed, the mixture was stirred and reacted at room temperature for 2.0 hours. After the reaction was completed, the reaction solution was concentrated and separated by column chromatography to obtain 147.0 mg of the title compound with a yield of 98.3%. LC-MS: m/z $[M+H]^+$=205.11.

Intermediate 146

Methyl 3,4-dihydro-2H-pyrido[3,2-b][1,4]oxazine-6-carboxylate

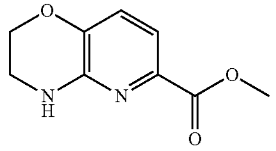

tert-Butyl 6-bromo-2H-pyrido[3,2-b][1,4]oxazine-4(3H)-carboxylate (2.32 g, 7.36 mmol) was added to anhydrous methanol (50 mL). Triethylamine (2.23 g, 22.08 mmol), 1,1'-bisdiphenylphosphinoferrocene palladium dichloride (0.54 g, 0.74 mmol) were added thereto sequentially. Carbon monoxide was pumped and ventilated to an internal pressure of 6.0 MPa, and the mixture was heated to 120° C. and reacted overnight. The reaction solution was added with water and dichloromethane, and the phases were separated. The organic phases were combined, dried with anhydrous sodium sulfate, concentrated, and separated by column chromatography (petroleum ether:ethyl acetate=1:1) to obtain the title compound (0.87 g, 61%) as a white solid. $^1H$ NMR (400 MHz, DMSO-$d_6$) δ 7.26-7.24 (m, 2H), 7.02 (d, J=8 Hz, 1H), 4.17 (t, J=4 Hz, 2H), 3.77 (s, 3H), 3.42-3.40 (m, 2H). LC-MS: m/z $[M+H]^+$=195

Intermediate 147

Methyl 4-methyl-3,4-dihydro-2H-pyrido[3,2-b][1,4]oxazine-6-carboxylate

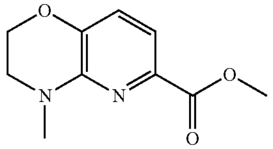

Methyl 3,4-dihydro-2H-pyrido[3,2-b][1,4]oxazine-6-carboxylate (194 mg, 1.0 mmol) was added to N,N-dimethylformamide (3 mL), and the stirring was started. Cesium carbonate (488 mg, 1.5 mmol) and methyl iodide (142 mg, 1.0 mmol) were sequentially added to the reaction solution. under the protection of nitrogen, the reaction was heated to 40° C. and carried out overnight. The reaction solution was quenched by adding water, extracted with ethyl acetate; the organic phase was dried with anhydrous sodium sulfate, concentrated and separated by column chromatography (petroleum ether:ethyl acetate=2:1) to obtain the title compound as a yellow solid (42 mg, 20%). LC-MS: m/z $[M+H]^+$ =209.

Intermediate 148

4-Methyl-3,4-dihydro-2H-pyrido[3,2-b][1,4]oxazin-6-ylmethanol

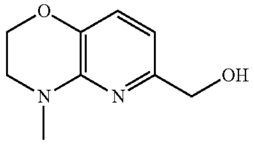

At 0° C., methyl 4-methyl-3,4-dihydro-2H-pyrido[3,2-b][1,4]oxazine-6-carboxylate (71 mg, 0.34 mmol) and lithium aluminum hydride (38.8 mg, 1.02 mmol) were sequentially added to tetrahydrofuran (2 mL). The reaction was carried out for 2 hours. The reaction solution was added with water to quench the reaction, concentrated, and separated by column chromatography (dichloromethane/methanol=100:1-80:1) to obtain the title compound as a yellow oil (53 mg, 86.9%) as a product. $^1H$ NMR (400 MHz, $CDCl_3$): δ 6.89 (d, J=8.0 Hz, 1H), 6.39 (d, J=7.6 Hz, 1H), 4.55 (s, 2H), 4.25-4.23 (m, 2H), 3.65-3.64 (m, 1H), 3.46-3.44 (m, 2H), 3.15 (s, 3H). LC-MS: m/z $[M+H]^+$=181.

Intermediate 149

(6-((3-Methylpyridin-3-yl)methoxy)pyridazin-3-yl)methanol

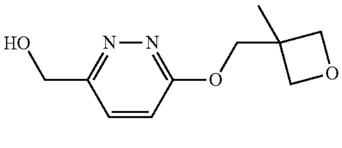

Methyl 6-chloropyridazine-3-carboxylate (500 mg, 2.90 mmol) and (3-methylpyridin-3-yl)methanol (3 g, 29 mmol) were dissolved in acetonitrile (30 mL), and cesium carbonate (1.9 g, 5.8 mmol) was added thereto, then the mixture was reacted at room temperature for 3 hours. 25 mL of water was added to the reaction solution, and the mixture was extracted with ethyl acetate (20 mL*3 times). The organic phases were combined, dried, concentrated, and separated by column chromatography to obtain 250 mg of a colorless oil. The colorless oil was dissolved in a mixed solution of tetrahydrofuran (10 mL) and methanol (10 mL); sodium borohydride (119 mg, 3.15 mmol) was added thereto, and the mixture was reacted at room temperature for 3 hours. The reaction solution was directly concentrated, separated and purified by chromatographic column to obtain the title compound (120 mg, a two-step yield of 20%) as a colorless oil. LC-MS: m/z [M+H]+=211.

Intermediate 150

Ethyl 6-(bromomethyl)pyridazine-3-carboxylate

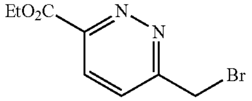 [SMILES: CCOC(=O)c1ccc(CBr)nn1]

Ethyl 6-methylpyridazine-3-carboxylate (460 mg, 2.8 mmol), NBS (605 mg, 3.4 mmol) and AIBN (49 mg, 0.3 mmol) were sequentially added to DMF (6 mL), and the mixture was heated to 80° C. and stirred for 0.5 hours. The reaction mixture was poured into water, extracted three times with ethyl acetate, and the combined organic phase was washed three times with water and washed once with saturated brine. The organic phase was dried and concentrated to obtain a crude product, and the crude product was separated by thin layer chromatography to obtain the title compound (400 mg, 58%) as a reddish brown solid. LC-MS: m/z $[M+H]^+$=245/247.

Intermediate 151

6-(Methoxymethyl)pyridazine-3-carboxylic acid

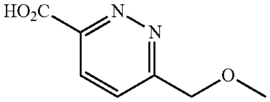

Ethyl 6-(bromomethyl)pyridazine-3-carboxylate (400 mg, 1.6 mmol) and 1.8 M methanol solution of sodium methoxide (3.5 mL, 6.4 mmol) were dissolved in methanol (3.5 mL), and the mixture was stirred at room temperature for 16 hours. The reaction solution was acidified to pH=5 to 6, and dichloromethane (35 mL) was added for dilution, then the mixture was filtered with diatomite, and the filtrate was concentrated to obtain the title compound (340 mg, crude product) as a pale yellow oil. LC-MS: m/z $[M+H]^+$=169.

Intermediate 152

Methyl 6-(methoxymethyl)pyridazine-3-carboxylate

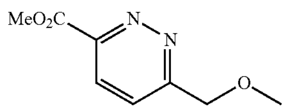

6-(Methoxymethyl)pyridazine-3-carboxylic acid (340 mg, crude product), oxalyl chloride (432 mg, 3.4 mmol) and a catalytic amount of DMF were sequentially added to dichloromethane (5 mL), and the reaction mixture was stirred at room temperature for 0.5 hours. Methanol (5 mL) was added thereto, and the reaction mixture was stirred at room temperature for 16 hours. The reaction mixture was poured into saturated sodium bicarbonate (40 mL), extracted three times with dichloromethane, and the combined organic phase was washed once with saturated brine. The organic phase was dried and concentrated to obtain a crude product, and the crude product was separated by preparative thin layer chromatography (petroleum ether/ethyl acetate=1/1) to obtain the title compound (153 mg, a two-step yield of 51%). LC-MS: m/z $[M+H]^+$=183.

Intermediate 153

(6-(Methoxymethyl)pyridazin-3-yl)methanol

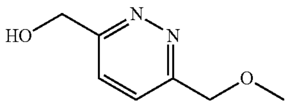

Methyl 6-(methoxymethyl)pyridazine-3-carboxylate (150 mg, 0.82 mmol) was dissolved in tetrahydrofuran (8 mL) and methanol (2 mL), then sodium borohydride (240 mg, 6.3 mmol) was added thereto, and the mixture was stirred at room temperature for 16 hours. The reaction solution was filtered through diatomite, and the filtrate was concentrated, and separated by preparative thin layer chromatography (dichloromethane/methanol=10/1) to obtain the title compound (95 mg, 75%) as a pale yellow oil. LC-MS: m/z $[M+H]^+$=155.

Intermediate 154

(6-((tetrahydro-2H-pyran-4-yl)oxy)pyridazin-3-yl) methanol

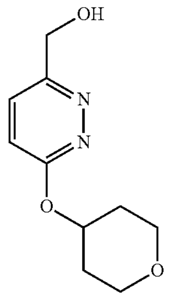 [SMILES: OCc1ccc(OC2CCOCC2)nn1]

Methyl 6-chloropyridazine-3-carboxylate (500 mg, 2.90 mmol) and tetrahydro-2H-pyran-4-ol (1.48 g, 14.5 mmol) were dissolved in acetonitrile (50 mL), and cesium carbonate (1.9 g, 5.8 mmol) was added thereto, and the mixture was reacted at room temperature for 3 hours. 25 mL of water was added to the reaction solution, and the reaction solution was extracted with ethyl acetate (30 mL*3 times). The organic phases were combined, dried, concentrated, and separated by column chromatography to obtain 180 mg of a colorless oil. The colorless oil was dissolved in a mixed solution of tetrahydrofuran (5 mL) and methanol (5 mL), then sodium borohydride (86 mg, 2.27 mmol) was added thereto, and the mixture was reacted at room temperature for 3 hours. The reaction solution was directly concentrated, separated and purified by chromatographic column to obtain the title compound (134 mg, 84%) as a colorless oil. LC-MS: m/z $[M+H]^+$=211.

Intermediate 155

(6-(Oxetan-3-yloxy)pyridazin-3-yl)methanol

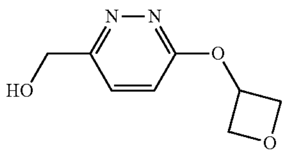 [SMILES: OCc1ccc(OC2COC2)nn1]

Methyl 6-chloropyridazine-3-carboxylate (2.9 g, 16.8 mmol), oxetan-3-ol (2.5 g, 33.7 mmol) and cesium carbonate (17.2 g, 52.8 mmol) were added to acetonitrile (80 mL), and the mixture was stirred at room temperature for 4 hours. The reaction solution was added with dichloromethane (200 mL), stirred for 0.5 hours, and then filtered. The filtrate was concentrated under reduced pressure to obtain 5.0 g of a crude product of ester. 3.5 g of the crude product of of ester and sodium borohydride (1.9 g, 50.0 mmol) were added to methanol (20 mL) and tetrahydrofuran (80 mL), then the mixture was stirred at room temperature for 4 hours. The reaction solution was concentrated, and subjected to column chromatography (dichloromethane/methanol=20/1) to obtain 3.5 g of a crude product of the title compound as a yellow oil. LC-MS: m/z $[M+H]^+$=183.1

Intermediate 156

(6-((Tetrahydrofuran-3-yl)oxy)pyridazin-3-yl)methanol

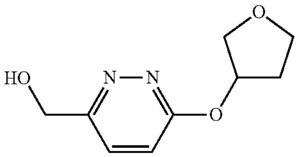 [SMILES: OCc1ccc(OC2CCOC2)nn1]

Methyl 6-chloropyridazine-3-carboxylate (500 mg, 2.90 mmol) and tetrahydrofuran-3-ol (1.3 g, 14.5 mmol) were dissolved in acetonitrile (50 mL), and cesium carbonate (1.9 g, 5.8 mmol) was added thereto, then the mixture was reacted at room temperature for 3 hours. 25 mL of water was added to the reaction solution, and the reaction solution was extracted with ethyl acetate (30 mL*3 times). The organic phases were combined, dried, concentrated, and separated by column chromatography to obtain 130 mg of compound as a colorless oil. The compound was dissolved in a mixed solution of tetrahydrofuran (10 mL) and methanol (5 mL), then sodium borohydride (50 mg, 1.28 mmol) was added thereto, and the mixture was reacted at room temperature for 3 hours. The reaction solution was directly concentrated, separated and purified by chromatographic column to obtain the title compound (83 mg, a two-step yield of 15.6%) as a colorless oil. LC-MS: m/z $[M+H]^+=197$.

Intermediate 157

6-Chloro-3-(3-methoxypropoxy)-4-methylpyridazine and 3-chloro-6-(3-methoxypropoxy)-4-methylpyridazine

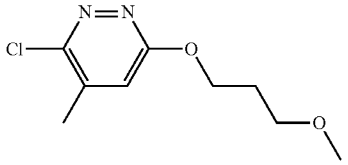

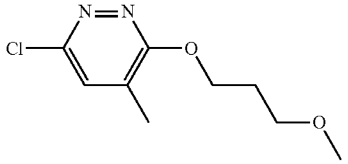

3,6-Dichloro-4-methylpyridazine (3 g, 18.4 mmol) and 3-methoxypropan-1-ol (1.82 g, 20.24 mmol) were dissolved in tetrahydrofuran (50 mL). 60% sodium hydride (736 mg, 18.4 mmol) was added thereto at 0° C., and then the mixture was reacted at room temperature for 1 hour. The reaction solution was poured into water, extracted with ethyl acetate. The organic phase was washed with saturated brine, dried with anhydrous sodium sulfate, concentrated, and separated by column chromatography (petroleum ether:ethyl acetate=10:1) to obtain a mixture (2.4 g, 61%) of 6-chloro-3-(3-methoxypropoxy)-4-methylpyridazine and 3-chloro-6-(3-methoxypropoxy)-4-methylpyridazine as a yellow oil. $^1H$ NMR (400 MHz, $CDCl_3$): δ 7.20 (s, 1H), 6.84 (s, 1H), 4.59-4.53 (m, 4H), 3.57-3.52 (m, 4H), 3.35 (s, 6H), 2.34 (s, 3H), 2.22 (s, 3H), 2.12-2.06 (m, 4H).

Intermediate 158

Methyl 6-(3-methoxypropoxy)-4-methylpyridazine-3-carboxylate and methyl 6-(3-methoxypropoxy)-5-methylpyridazine-3-carboxylate

A

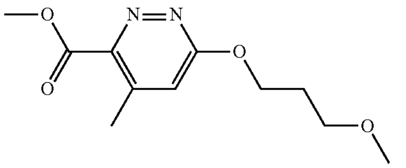

-continued

B

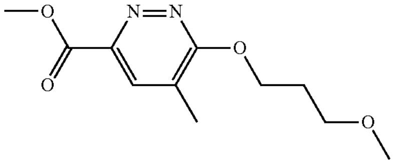

A mixture of 6-chloro-3-(3-methoxypropoxy)-4-methylpyridazine and 3-chloro-6-(3-methoxypropoxy)-4-methylpyridazine (2.4 g, 11.11 mmol), [1,1'-bis(diphenylphosphino)ferrocene]palladium dichloride (813 mg, 1.11 mmol) and triethylamine (3.36 g, 33.33 mmol) were dissolved in methanol (24 mL), and the mixture was reacted overnight at 80° C. under carbon monoxide atmosphere of 5 MPa. The reaction solution was directly concentrated, and part of the residue was subjected to thin layer chromatography (petroleum ether:ethyl acetate=3:1) twice and (petroleum ether: ethyl acetate=2.5:1) twice to obtain methyl 6-(3-methoxypropoxy)-4-methylpyridazine-3-carboxylate (140 mg) as a yellow oil. $^1H$ NMR (400 MHz, $CDCl_3$): δ 6.81 (s, 1H), 4.68-4.65 (m, 2H), 4.00 (s, 3H), 3.56-3.53 (m, 2H), 3.35 (s, 3H), 2.54 (s, 3H), 2.12-2.09 (m, 2H). Methyl 6-(3-methoxypropoxy)-5-methylpyridazine-3-carboxylate (85 mg) as a yellow solid. $^1H$ NMR (400 MHz, $CDCl_3$): δ 7.89 (s, 1H), 4.73-4.69 (m, 2H), 4.01 (s, 3H), 3.58-3.55 (m, 2H), 3.36 (s, 3H), 2.27 (s, 3H), 2.15-2.12 (m, 2H).

Intermediate 159

(6-(3-Methoxypropoxy)-4-methylpyridazin-3-yl)methanol

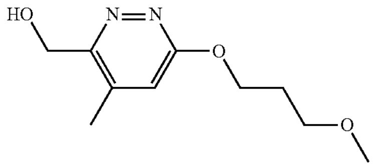

Methyl 6-(3-methoxypropoxy)-4-methylpyridazine-3-carboxylate (140 mg, 0.58 mmol) was dissolved in methanol (2 mL), then sodium borohydride (44.3 mg, 1.167 mmol) was added thereto at 0° C., and the mixture was reacted at room temperature overnight. The reaction solution was quenched by adding 0.5 mL of water, concentrated, then dissolved in dichloromethane, concentrated and separated by column chromatography (dichloromethane:methanol=50:1) to obtain the title compound (90 mg, a yield of 73%) as a yellow oil. LC-MS: m/z $[M+H]^+=213$.

Intermediate 160

(6-(3-Methoxypropoxy)-5-methylpyridazin-3-yl)methanol

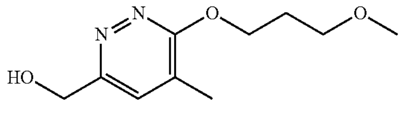

The experimental operation was the same as above, starting from the raw material methyl 6-(3-methoxy-propoxy)-5-methylpyridazine-3-carboxylate (85 mg, 0.35 mmol) to obtain (6-(3-methoxypropoxy)-S-methylpyridazin-3-yl)methanol (56 mg, 75.6%) as a yellow solid. LC-MS: m/z $[M+H]^+$=213.

Intermediate 161

(5-(Oxetan-3-yloxy)pyrazin-2-yl)methanol

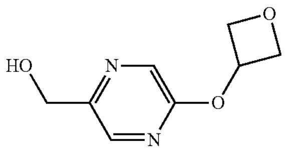 [SMILES: OCc1cnc(OC2COC2)cn1]

Methyl 6-chloropyridazine-3-carboxylate (600 mg, 3.49 mmol) and oxetan-3-ol (774 mg, 10.46 mmol) were dissolved in acetonitrile (50 mL), and cesium carbonate (2.27 g. 6.98 mmol) was added thereto, then the mixture was reacted at room temperature for 3 hours. 25 mL of water was added to the reaction solution, and the the reaction solution was extracted with ethyl acetate (30 mL*3 times). The organic phases were combined, dried, concentrated, and separated by column chromatography to obtain 220 mg of compound as a colorless oil. The compound was dissolved in a mixed solution of tetrahydrofuran (10 mL) and methanol (5 mL), then sodium borohydride (108 mg, 2.86 mmol) was added thereto, and the mixture was reacted at room temperature for 3 hours. The reaction solution was directly concentrated, separated and purified by chromatographic column to obtain the title compound (85 mg, a two-step yield of 14.7%) as a colorless oil. LC-MS: m/z $[M+H]^+$=183.

Intermediate 162

(6-((2-Methoxyethyl)amino)pyridazin-3-yl)methanol

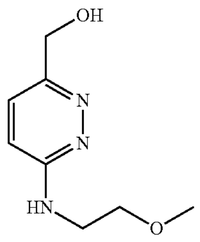

Methyl 6-chloropyridazine-3-carboxylate (500 mg, 2.9 mmol) and 2-methoxyethylamine (2.15 g, 29 mmol) were dissolved in acetonitrile (20 mL), and cesium carbonate (1.9 g, 5.8 mmol) was added thereto, then the mixture was reacted overnight at room temperature. 20 mL of water was added to the reaction solution, and the reaction solution was extracted with ethyl acetate (20 mL*3 times). The organic phases were combined, dried, concentrated, and separated by column chromatography to obtain 230 mg of a crude product as a colorless oil. The compound was dissolved in a mixed solution of tetrahydrofuran (10 mL) and methanol (10 mL), then sodium borohydride (207 mg, 5.45 mmol) was added thereto, and the mixture was reacted at room temperature for 3 hours. The reaction solution was directly concentrated, separated and purified by chromatographic column to obtain the title compound (40 mg, 20%) as a colorless oil. LC-MS: m/z $[M+H]^+$=184.

Intermediate 163

(6-((1-Methoxyprop-2-yl)oxy)pyridazin-3-yl)methanol

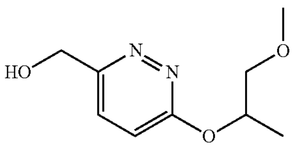

This compound was prepared in the same way as intermediate 154 using 1-methoxypropan-2-ol (607 mg, 6.7 mmol) to obtain a crude product of the title compound (80 mg, 46%) as a yellow oil. LC-MS: m/z $[M+H]^+$=199.

Intermediate 164

(6-((Tetrahydrofuran-3-yl)methoxy)pyridazin-3-yl) methanol

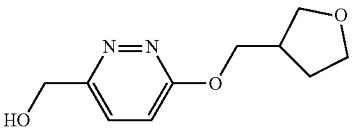 [SMILES: OCc1ccc(OCC2CCOC2)nn1]

This compound was prepared in the same way as intermediate 154 using 3-tetrahydrofuranmethanol (704 mg, 7.0 mmol) to obtain a crude product of the title compound (180 mg, 34%) as a yellow oil. LC-MS: m/z $[M+H]^+$=211.

Intermediate 165 (6-((tetrahydrofuran-2-yl) methoxy)pyridazin-3-yl)methanol

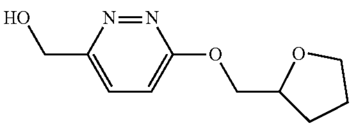 [SMILES: OCc1ccc(OCC2CCCO2)nn1]

This compound was prepared in the same way as intermediate 154 using tetrahydrofurfuryl alcohol (704 mg, 7.0 mmol) to obtain a crude product of the title compound (150 mg, 29%) as a yellow oil. LC-MS: m/z $[M+H]^+$=211.

Intermediate 166 (6-(2-(4-methylpiperazin-1-yl) ethoxy)pyridazin-3-yl)methanol

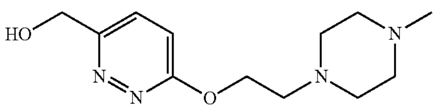 [SMILES: CN1CCN(CCOc2ccc(CO)nn2)CC1]

This compound was prepared in the same way as intermediate 154 using 1-(2-hydroxyethyl)-4-methylpiperazine (1 g, 6.94 mmol) to obtain the title compound (34 mg, 2%) as an oil. LC-MS: m/z $[M+H]^+$=253.16.

Intermediate 167

(6-(2-Morpholinoethoxy)pyridazin-3-yl)methanol

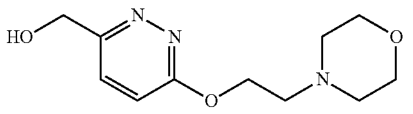 [SMILES: OCc1ccc(OCCN2CCOCC2)nn1]

This compound was prepared in the same way as intermediate 154 using N-(2-hydroxyethyl) morpholine (150 mg, 1.14 mmol) to obtain the title compound (34 mg, 12.2%) as an oil. LC-MS: m/z $[M+H]^+$=239.13.

Intermediate 168 (6-((2-methoxyethoxy)methyl) pyridazin-3-yl)methanol

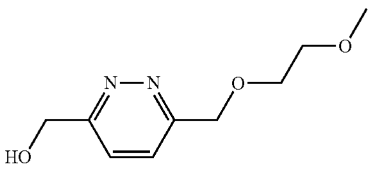

This compound was prepared in the same way as intermediate 153 using ethyl 6-(bromomethyl)pyridazine-3-carboxylate (100 mg, 0.41 mmol) and ethylene glycol monomethyl ether (62 mg, 0.82 mmol) to obtain the title compound (10 mg, 71%) as a pale yellow oil. LC-MS: m/z $[M+H]^+$ =199.

Intermediate 169 (6-(3-ethoxypropoxy)pyridazin-3-yl)methanol

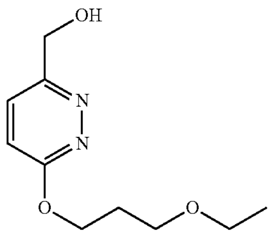

Methyl 6-chloropyridazine-3-carboxylate (500 mg, 2.9 mmol) and 3-ethoxypropan-1-ol (907 mg, 8.72 mmol) were dissolved in acetonitrile (20 mL), and cesium carbonate (1.9 g, 5.8 mmol) was added thereto, then the mixture was reacted overnight at room temperature. 15 mL of water was added to the reaction solution, and the reaction solution was extracted with dichloromethane (20 mL*3 times). The organic phases were combined, dried, concentrated to obtain 300 mg of a yellow oil. The yellow oil was dissolved in a mixed solution of tetrahydrofuran (10 mL) and methanol (5 mL), then sodium borohydride (98 mg, 2.60 mmol) was added thereto, and the mixture was reacted overnight at room temperature. The reaction solution was directly concentrated, separated and purified by chromatographic column to obtain 170 mg of the title compound as a colorless oil with a two-step yield of 27.7%. LC-MS: m/z $[M+H]^+$=213.

Intermediate 170 (6-(((tert-butyldimethylsilyl)oxy) methyl)pyridin-3-yl)methanol

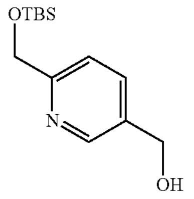 [SMILES: CC(C)(C)[Si](C)(C)OCc1ccc(CO)cn1]

Methyl 6-(hydroxymethyl)nicotinate (2.0 g, 11.98 mmol) and TBSCl (2.2 g, 14.37 mmol) were dissolved in dichloromethane (50 mL), and imidazole (2.44 g, 35.94 mmol) was added thereto at 0° C., then the mixture was reacted for 1 hour at room temperature. The reaction solution was poured into water, extracted with dichloromethane. The organic phase was dried with anhydrous sodium sulfate, concentrated, and subjected to column chromatography (petroleum ether:ethyl acetate=5:1) to obtain a colorless liquid (3.5 g, crude product). The colorless liquid was dissolved in anhydrous tetrahydrofuran (50 mL), and lithium aluminum hydride (455 mg, 11.98 mmol) was added thereto at 0° C., then the mixture was reacted at room temperature for 10 minutes. 0.5 mL of water, 0.5 mL of a 15% aqueous sodium hydroxide solution, and 1.5 mL of water were sequentially added to the reaction solution. The mixture was stirred for 5 minutes, filtered under reduced pressure. A mother liquor was concentrated to obtain the title compound (3 g, crude product) as a light yellow oil, which was directly used in the next step. LC-MS: $[M+H]^+$=254.

Intermediate 171 (5-(azetidin-1-ylmethyl)pyridin-2-yl)methanol

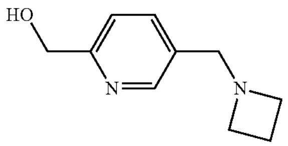 [SMILES: OCc1ccc(CN2CCC2)cn1]

(6-(((tert-Butyldimethylsilyl)oxy)methyl)pyridin-3-yl) methanol (0.5 g, 1.98 mmol) and triethylamine (1 g, 10 mmol) were dissolved in diethylamine (20 mL), and MsCl (338 mg, 2.96 mmol) was added dropwise thereto at 0° C., then the mixture was reacted at room temperature for 2 hours; then azetidine (339 mg, 5.94 mmol) was added thereto, and the mixture was reacted at room temperature for 2 hours. The reaction solution was poured into water, extracted with dichloromethane. The organic phase was dried with anhydrous sodium sulfate and concentrated to obtain a compound (0.5 g, crude product) as a pale yellow oil. The compound was dissolved in dichloromethane (30 mL), and tetrabutylammonium fluoride (893 mg, 3.42 mmol) was added thereto, and the mixture was reacted at 50°

C. for 5 hours. The reaction solution was subjected to column chromatography to obtain the title compound (0.53 g, crude product) as a colorless oil. LC-MS: $[M+H]^+$=179.

Intermediate 172 (5-((3-methylpyridin-3-yl) methoxy)pyridin-2-yl)methanol

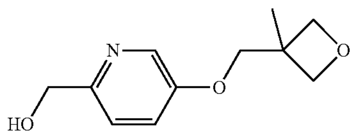

5-Fluoropyridine-2-carbaldehyde (500 mg, 4 mmol) and (3-methylpyridin-3-yl)methanol (1.12 g, 12 mmol) were dissolved in N,N-dimethylformamide (20 mL), and cesium carbonate (2.6 g, 8 mmol) was added thereto, then the mixture was reacted at 100° C. for 2 hours. 25 mL of water was added to the reaction solution, and the reaction solution was extracted with ethyl acetate (20 mL*3 times). The organic phases were combined, dried, concentrated, and separated by column chromatography to obtain a colorless oil. The colorless oil was dissolved in a mixed solution of tetrahydrofuran (10 mL) and methanol (10 mL), then sodium borohydride (200 mg, 5.31 mmol) was added thereto, and the mixture was reacted at room temperature for 3 hours. The reaction solution was directly concentrated, separated and purified by chromatographic column to obtain the title compound (120 mg, 54.2%) as a colorless oil. LC-MS: m/z $[M+H]^+$=210.

Intermediate 173 (6-((tetrahydro-2H-pyran-4-yl) methoxy)pyridazin-3-yl)methanol

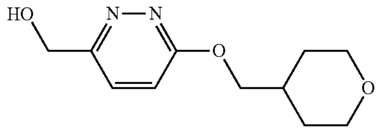 [SMILES: OCc1ccc(OCC2CCOCC2)nn1]

Methyl 6-chloropyridazine-3-carboxylate (500 mg, 2.90 mmol) and (tetrahydro-2H-pyran-4-yl)methanol (1.01 g, 8.72 mmol) were dissolved in acetonitrile (20 mL), and cesium carbonate (1.89 g, 5.8 mmol) was added thereto, then the mixture was reacted at room temperature for 3 hours. 25 mL of water was added to the reaction solution, and the reaction solution was extracted with ethyl acetate (30 mL*3 times). The organic phases were combined, dried, concentrated, and separated by column chromatography to obtain a yellow oil. The yellow oil was dissolved in a mixed solution of tetrahydrofuran (5 mL) and methanol (5 mL), then sodium borohydride (140 mg, 3.69 mmol) was added tehreto, and the mixture was reacted at room temperature for 16 hours. The reaction solution was directly concentrated, separated and purified by chromatographic column to obtain the title compound (97 mg, a two-step yield of 19%) as a colorless oil. LC-MS: m/z $[M+H]^+$=225.

Intermediate 174

(4-(oxetan-3-yloxy)pyridin-2-yl)methanol

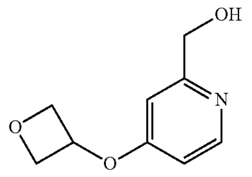 [SMILES: OCc1cc(OC2COC2)ccn1]

Methyl 4-chloropicolinate (380 mg, 2.25 mmol) and oxetan-3-ol (170 mg, 2.25 mmol) were dissolved in acetonitrile (5 mL), and cesium carbonate (1.461 g, 4.50 mmol) was added thereto, and the mixture was reacted at room temperature for 16 hours. The reaction solution was poured into water, extracted with dichloromethane. The organic phase was dried with anhydrous sodium sulfate, concentrated, and subjected to column chromatography (petroleum ether:ethyl acetate=5:1) to obtain a compound as a colorless liquid. The colorless liquid was dissolved in anhydrous tetrahydrofuran (20 mL), and lithium aluminum hydride (114 mg, 3.0 mmol) was added thereto at 0° C., then the mixture was reacted at room temperature for 10 minutes. 0.1 ml of water, 0.1 mL of 15% aqueous sodium hydroxide solution, and 0.3 mL of water were sequentially added to the reaction solution. The mixture was stirred for 5 minutes, filtered under reduced pressure. A mother liquor was concentrated, purified by preparative thin layer chromatography to obtain the title compound (40 mg, 25%) as a pale yellow oil. LC-MS: m/z $[M+H]^+$=182.

Intermediate 175 (5-((tetrahydrofuran-3-yl) methoxy)pyridin-2-yl)methanol

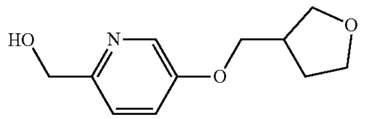 [SMILES: OCc1ccc(OCC2CCOC2)cn1]

5-Fluoropyridine-2-carbaldehyde (380 mg, 3.1 mmol), 3-tetrahydrofuranmethanol (634 mg, 6.3 mmol) and cesium carbonate (4.0 g. 12.6 mmol) were sequentially added to 30 mL of DMF, and the mixture was heated to 100° C. overnight. The mixture was diluted with water, extracted with ethyl acetate, and the organic phase was concentrated, and purified by column chromatography (dichloromethane/methanol=30/1). A yellow oil was obtained, which was dissolved in 5 mL of tetrahydrofuran. 1 mL of methanol and sodium borohydride (72 mg, 1.9 mmol) were added thereto, and after stirring for 15 minutes, additional sodium borohydride (72 mg, 1.9 mmol) was added thereto. 5 mL of methanol was added for quenching, then the organic phase was concentrated, and purified by column chromatography (dichloromethane/methanol=15/1) to obtain the title compound (110 mg, a yield of 57%) as a colorless oil. LC-MS: m/z $[M+H]^+$=210.

Intermediate 176 (5-((tetrahydro-2H-pyran-4-yl)oxy)pyridin-2-yl)methanol

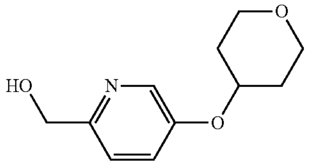 [SMILES: OCc1ccc(OC2CCOCC2)cn1]

5-Fluoropyridine-2-carbaldehyde (330 mg, 2.6 mmol), tetrahydro-2H-pyran-4-ol (809 mg, 7.9 mmol) and cesium carbonate (1.7 g, 5.2 mmol) were sequentially added to DMF (15 mL), and the mixture was heated to 100° C. and stirred for 1.5 hours. The reaction mixture was poured into water, extracted three times with ethyl acetate, and the combined organic phase was washed three times with water and washed once with saturated brine. The organic phase was dried and concentrated to obtain a crude compound, which was dissolved in tetrahydrofuran (4 mL) and methanol (1 mL). Sodium borohydride (86 mg, 2.3 mmol) was added thereto, and the mixture was stirred at room temperature for 16 hours. The reaction solution was concentrated and separated by preparative thin layer chromatography to obtain the title compound (133 mg, a two-step yield of 24%) as a pale yellow oil. LC-MS: m/z $[M+H]^+$=210.

Intermediate 177 (5-(oxetan-3-yloxy)pyridin-2-yl)methanol

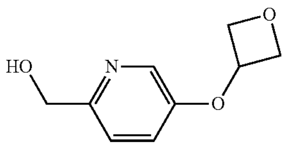 [SMILES: OCc1ccc(OC2COC2)cn1]

Methyl 6-fluoropyridine-3-carboxylate (300 mg, 1.94 mmol) and oxetan-3-ol (430 g, 5.8 mmol) were dissolved in acetonitrile (30 mL), and cesium carbonate (1.26 g, 3.88 mmol) was added thereto, then the mixture was reacted at room temperature for 5 hours. 25 mL of water was added to the reaction solution, and the reaction solution was extracted with ethyl acetate (30 mL*3 times). The organic phases were combined, dried, concentrated, and separated by column chromatography to obtain a yellow oil. The yellow oil was dissolved in a mixed solution of tetrahydrofuran (5 mL) and methanol (5 mL), then sodium borohydride (43 mg, 1.15 mmol) was added thereto, and the mixture was reacted at 50° C. for 16 hours. The reaction solution was directly concentrated, separated and purified by chromatographic column to obtain the title compound (61 mg, a two-step yield of 17.5%) as a colorless oil. LC-MS: m/z $[M+H]^+$=182.

Intermediate 178 (2-ethylimidazo[1,2-b]pyridazin-6-yl)methanol

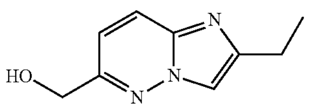

Methyl 6-aminopyridazine-3-carboxylate (153 mg, 1.0 mmol), 1-bromobutan-2-one (222 mg, 1.2 mmol) were added to DMF (10 mL), and the system was heated to 90° C. and stirred for 4 hours. The reaction solution was cooled to room temperature, then dichloromethane (50 mL) and water (40 mL) were added for extraction. The organic phase was subjected to thin layer chromatography (dichloromethane/methanol=20/1) to obtain a solid compound, and the solid compound was added to a mixed solution of tetrahydrofuran (10 mL) and methanol (2.5 mL). Sodium borohydride (55.4 mg, 1.46 mmol) was added thereto, and the mixture was stirred at room temperature for 2 hours. The reaction solution was concentrated, and separated by thin layer chromatography (dichloromethane/methanol=20/1) to obtain the title compound (50.0 mg, a two-step yield of 28%). LC-MS: m/z $[M+H]^+$=178.1.

Intermediate 179 (5-((tetrahydro-2H-pyran-4-yl)oxy)pyrazin-2-yl)methanol

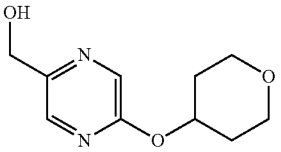 [SMILES: OCc1cnc(OC2CCOCC2)cn1]

Methyl 6-chloropyridazine-3-carboxylate (400 mg, 2.33 mmol) and tetrahydro-2H-pyran-4-ol (711 mg, 6.98 mmol) were dissolved in acetonitrile (30 mL), and cesium carbonate (1.5 g. 4.66 mmol) was added thereto, then the mixture was reacted at room temperature for 16 hours. 25 mL of water was added to the reaction solution, and the reaction solution was extracted with ethyl acetate (30 mL*3 times). The organic phases were combined, dried, concentrated, and separated by chromatographic column to obtain a yellow oil. The yellow oil was dissolved in a mixed solution of tetrahydrofuran (5 mL) and methanol (5 mL), then sodium borohydride (60 mg, 1.56 mmol) was added thereto, and the mixture was reacted at 50° C. for 24 hours. The reaction solution was directly concentrated, separated and purified by chromatographic column to obtain the title compound (60 mg, a two-step yield of 12.2%) as a white solid. LC-MS: m/z $[M+H]^+$=211.

Intermediate 180 (5-((tetrahydrofuran-2-yl)methoxy)pyrazin-2-yl)methanol

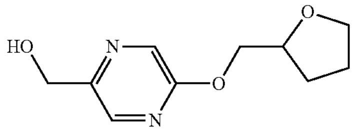 [SMILES: OCc1cnc(OCC2CCCO2)cn1]

Methyl 5-chloropyrazine-2-carboxylate (600 mg, 3.5 mmol), tetrahydrosugar alcohol (711 mg, 7.0 mmol) and cesium carbonate (4.5 g, 13.9 mmol) were sequentially added to 20 mL of acetonitrile, and then the mixture was stirred at room temperature overnight. 30 mL of water was added to dissolve cesium carbonate, and the organic solvent was removed. A large amount of solid was precipitated, and the solid was filtered and dried to obtain an intermediate (600 mg) as a yellow solid. 300 mg of the intermediate was taken and dissolved in 5 mL of tetrahydrofuran. 1 mL of methanol and sodium borohydride (48 mg, 2.6 mmol) were added thereto, and after stirring for 15 minutes, additional sodium borohydride (48 mg, 2.6 mmol) was added thereto. 5 mL of methanol was added thereto for quenching, then the organic phase was concentrated, and purified by column chromatography (dichloromethane/methanol=15/1) to obtain the title compound (180 mg, a two-step yield of 49%) as a colorless oil. LC-MS: m/z $[M+H]^+$=211.

Intermediate 181 (6-((2-oxaspiro[3.3]hept-6-yl)oxy) pyridazin-3-yl)methanol

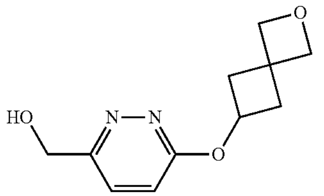 [SMILES: OCc1ccc(OC2CC3(COC3)C2)nn1]

Methyl 6-chloropyridazine-3-carboxylate (300 mg, 1.74 mmol) and 2-oxaspiro[3.3]heptan-6-ol (200 mg, 1.74 mmol) were dissolved in acetonitrile (10 mL), and cesium carbonate (1.13 g, 3.48 mmol) was added thereto, then the mixture was reacted overnight at room temperature. 20 mL of water was added to the reaction solution, and the reaction solution was extracted with ethyl acetate (20 mL*3 times). The organic phases were combined, dried, concentrated, and separated by column chromatography to obtain a crude product as a yellow oil. The crude product was dissolved in a mixed solution of tetrahydrofuran (10 mL) and methanol (10 mL), then sodium borohydride (96 mg, 2.52 mmol) was added thereto, and the mixture was reacted at room temperature for 2 hours. The reaction solution was directly concentrated, separated and purified by chromatographic column to obtain the title compound (48 mg, a two-step yield of 13%) as a white solid. LC-MS: m/z $[M+H]^+$=223.

Intermediate 182 3-chloro-5-(oxetan-3-yloxy)pyridazine

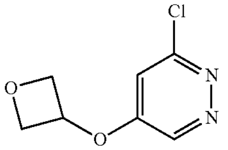 [SMILES: Clc1cc(OC2COC2)cnn1]

3-Oxetanol CAS: 7748-36-9 (550 mg, 6.7 mmol) was dissolved in 20 mL of tetrahydrofuran, then the mixture was cooled to 0° C. Sodium hydride (295 mg, 7 mmol) was added thereto, and the mixture was stirred for 15 minutes. 3,5-Dichloropyridazine CAS: 1837-55-4 (1 g, 6.7 mmol) was added thereto, and the mixture was raised to room temperature and stirred for 1 hour. The reaction solution was quenched with water, extracted with ethyl acetate, dried and concentrated to obtain a crude product of the title compound (800 mg, 64%) as a white solid. LC-MS: m/z $[M+H]^+$=187.

Intermediate 183 5-(oxetan-3-yloxy)pyridazine-3-carbonitrile

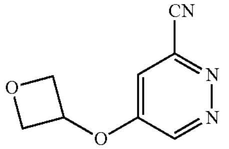 [SMILES: N#Cc1cc(OC2COC2)cnn1]

3-Chloro-5-(oxetan-3-yloxy)pyridazine (700 mg, 3.8 mmol), zinc cyanide (308 mg, 2.6 mmol), $Pd_2(dba)_3$ (103 mg, 0.11 mmol) and DPPF (125 g, 0.22 mmol) were sequentially added to 20 mL of DMF, and the mixture was heated to reflux overnight under the protection of argon. The reaction solution was concentrated and subjected to column chromatography (dichloromethane:methanol=100:1) to obtain the title compound (1.5 g, 100%) as a black solid. LC-MS: m/z $[M+H]^+$=178.

Intermediate 184 oxetan-3-yl 5-(oxetan-3-yloxy)pyridazine-3-carboxylate

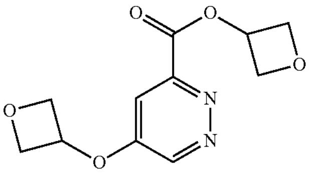 [SMILES: O=C(OC1COC1)c1cc(OC2COC2)cnn1]

5-(Oxetan-3-yloxy)pyridazine-3-carbonitrile (600 mg, 3.4 mmol) was dissolved in 5 mL of 3-oxetanol, and cesium carbonate (1 g, 10 mmol) was added thereto, and then the mixture was stirred at room temperature for 2 days. The reaction solution was poured into water, extracted with ethyl acetate, and the organic phase was dried and concentrated. The residue was purified by preparative TLC (dichloromethane/methanol=20/1) to obtain the title compound (150 mg, 22%) as a white solid. LC-MS: m/z $[M+H]^+$=253.

Intermediate 185 (5-(oxetan-3-yloxy)pyridazin-3-yl)methanol

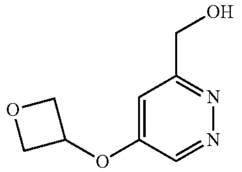 [SMILES: OCc1cc(OC2COC2)cnn1]

Oxetan-3-yl 5-(oxetan-3-yloxy)pyridazine-3-carboxylate (150 mg, 0.7 mol) was dissolved in 5 mL of tetrahydrofuran. 1 mL of methanol was added thereto, and sodium borohydride (54 mg, 1.4 mmol) was added thereto, then the mixture was stirred for 30 minutes. 10 mL of methanol was added to quench, and the organic phase was concentrated. The residue was purified by preparative TLC (dichloromethane/methanol=10/1) to obtain the title compound (30 mg, 24%) as a yellow oil. LC-MS: m/z $[M+H]^+$=183.

Intermediate 186 6-ethyl-2-(hydroxymethyl)-1,6-naphthyridin-5(6)-one

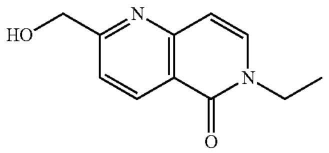

Methyl 5-oxo-5,6-dihydro-1,6-naphthyridine-2-carboxylate (150 mg, 0.735 mmol), sodium hydride (60%) (45 mg, 1.1 mmol), and iodoethane (1.15 g. 7.35 mmol) were dissolved in DMF (6.0 mL). After the addition was completed, the mixture was stirred and reacted at room temperature for 3 hours. After the reaction was completed, water (20 mL) was added to the reaction system, and then the mixture was extracted with ethyl acetate (40 mL*2 times); the organic phases were combined, and then washed with saturated brine (30 mL*1 time). The organic phase was dried, concentrated and dissolved with sodium borohydride (130 mg, 3.5 mmol) into a mixed solution of tetrahydrofuran and methanol (tetrahydrofuran:methanol=4:1) (10 mL). After the addition was completed, the mixture was stirred at room temperature overnight. After the reaction was completed, the reaction solution was separated by chromatographic column to obtain 53 mg of a standard compound with a yield of 40.2%. LC-MS: m/z $[M+H]^+$=205.12.

Intermediate 187

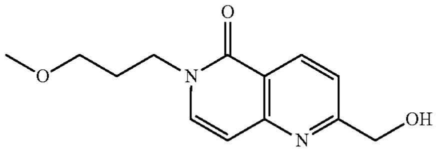 [SMILES: COCCCn1ccc2nc(CO)ccc2c1=O]

Starting from the raw materials of methyl 5-oxo-5,6-dihydro-1,6-naphthyridine-2-carboxylate (100 mg, 0.49 mmol) and 3-bromopropyl methyl ether (380 mg, 2.48 mmol), the experimental operation was the same as that of intermediate 133 to obtain 40 mg of the title compound, LC-MS: m/z $[M+H]^+$=249.

Intermediate 188 (5-(2-methoxyethoxy)pyridin-2-yl)methanol

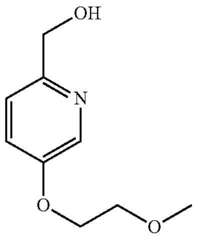

Methyl 5-hydroxypicolinate (1 g, 6.54 mmol) and 2-methoxyethanol (1 g, 13.16 mmol) were dissolved in dry tetrahydrofuran (30 mL), then triphenylphosphine (5.14 g, 19.62 mmol) and diisopropyl azodicarboxylate (3.96 g, 19.62 mmol) were added thereto, and the mixture was reacted at room temperature overnight. The reaction solution was mixed with silica gel, purified by chromatographic column. The filtrate was evaporated to dryness by rotary evaporation to obtain a solid compound, which was dissolved in tetrahydrofuran (20 mL), and then sodium borohydride (180 mg, 4.74 mmol) was added to react at room temperature for 16 hours. The reaction solution was added to methanol to quench, and separated by chromatographic column to obtain 180 mg of the title compound with a two-step yield of 15%.

LC-MS: m/z $[M+H]^+$=184.

Intermediate 187 2-(hydroxymethyl)-6-(2-methoxyethyl)-7,8-dihydro-1,6-naphthyridin-5(6H)-one

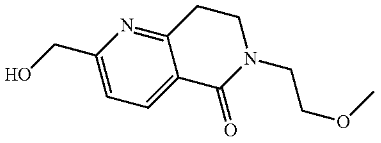 [SMILES: COCCN1CCc2nc(CO)ccc2C1=O]

(6-(2-Methoxyethyl)-5,6,7,8-tetrahydro-1,6-naphthalen-2-yl)methanol (800 mg, 3.6 mmol) was dissolved in THE/$H_2O$) (2.5/1, 35 mL). Sodium bicarbonate (3.027 g, 36 mmol) and iodine (6.685 g, 27 mmol) were sequentially added thereto, followed by stirring at room temperature overnight. TLC (dichloromethane:methanol=20:1) showed a complete reaction of raw materials. The mixture was neutralized with sodium thiosulfate until the color faded, extracted with dichloromethane, and purified by column chromatography to obtain 85 mg of the title compound as a colorless oil with a yield of 10%. LC-MS: $[M+H]^+$=237.

Intermediate 188 [1,2,3]triazolo[1,5-a]pyridine

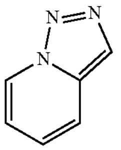

Pyridine-2-carbaldehyde (2.0 g, 18.7 mmol) was added to methanol, then p-toluenesulfonyl hydrazide (3.48 g, 18.7 mmol) was added thereto, and the mixture was stirred at room temperature for 6 hours. The reaction solution was cooled to 0° C., filtered, and the filter cake was washed with a small amount of methanol. The solid was dried to obtain a solid product, which was added to morpholine (30 mL), and the mixture was stirred and reacted at 100° C. for 3 hours. The reaction solution was poured into water, extracted with ethyl acetate, and the organic phase was concentrated, and subjected to column chromatography (petroleum ether/ethyl acetate=1/1) to obtain a yellow oil (900 mg, a two-step yield of 40%). LC-MS: m/z $[M+H]^+$=120.

Intermediate 189 [1,2,3]triazolo[1,5-a]pyridine-7-methanol

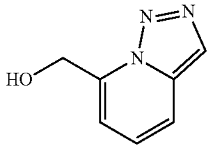 [SMILES: OCc1cccc2cnnn12]

Diisopropylamine (383 mg, 3.78 mmol) was added to tetrahydrofuran (5 mL), the mixture was cooled to −78° C., and n-butyllithium (1.2 mL, 3.02 mmol) was added dropwise thereto, and the mixture was reacted at 0° C. for 20 minutes, and then cooled to −78° C. A tetrahydrofuran solution of [1,2,3]triazolo[1,5-a]pyridine (300 mg, 2.52 mmol) was added dropwise thereto, and the mixture was stirred at −78° C. for 20 minutes, and then DMF (0.5 mL) was added thereto, and the mixture was stirred for 20 minutes. The reaction solution was poured into water, extracted with ethyl acetate, and the organic phase was concentrated and subjected to column chromatography (petroleum ether/ethyl acetate=1/1) to obtain a product (230 mg, 62%). The product was added to methanol (5 mL), and then sodium borohydride (119 mg, 3.13 mmol) was added thereto, and the mixture was stirred at room temperature for 1 hour. The reaction solution was poured into water, extracted with ethyl acetate, and the organic phase was concentrated and subjected to column chromatography (dichloromethane/methanol=30/1) to obtain the title compound (120 mg, 52%). $^1$H NMR (400 MHz, $CDCl_3$): δ 8.27 (s, 1H), 7.92-7.89 (m, 1H), 7.48-7.44 (m, 1H), 7.21-7.19 (m, 1H), 5.92-5.89 (m, 1H), 5.06-5.05 (m, 2H).

Intermediate 190 (3-methyl-3H-imidazo[4,5-b]pyridin-5-yl)methanol

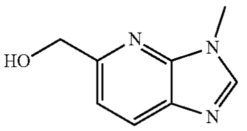

The raw materials of 5-chloro-3-methyl-3H-imidazo[4,5-b]pyridine (200 mg, 1.2 mmol), [1,1'-bis(diphenylphosphino)ferrocene]palladium chloride (88 mg, 0.12 mmol) and triethylamine (364 mg, 3.6 mmol) were sequentially added to methanol (5 mL). Then, the mixture was reacted overnight under carbon monoxide atmosphere of 5 MPa at 120° C. The reaction solution was concentrated and separated by column chromatography to obtain a red solid (180 mg). The red solid and lithium aluminum hydride (107 mg, 2.82 mmol) were sequentially added to tetrahydrofuran (5 mL) at 0° C. The mixture was reacted at room temperature for 12 hours. The reaction solution was added with water to quench the reaction, concentrated, and separated by column chromatography to obtain a yellow solid (100 mg, 65.3%) as a product. $^1$H NMR (400 MHz, $CDCl_3$): δ 8.06-8.01 (m, 2H), 7.20 (d, J=8.4 Hz, 1H), 4.89 (s, 2H), 3.92 (s, 3H). LC-MS: m/z $[M+H]^+$=164.

Intermediate 191 (6-cyclopropylpyridin-2-yl)methanol

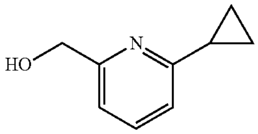 [SMILES: OCc1cccc(C2CC2)n1]

Compound (methyl 6-cyclopropylpicolinate) (1.81 g, 10.2 mmol) was dissolved in 20 mL of methanol, and the mixture was cooled to 0 to 5° C. in an ice bath under the protection of nitrogen. Sodium borohydride (1.15 g, 30.6 mmol) was slowly added to the reaction solution, and after the addition, the mixture was stirred at room temperature for 5 hours. The reaction solution was added with 1.0 ml of water, stirred for 1 hour, concentrated and separated by column chromatography to obtain a colorless oil (1.10 g, 72%). $^1$H NMR (400 MHz, DMSO-$d_6$): δ 7.631-7.593 (m, 1H), 7.203-7.184 (d, J=7.6 Hz, 1H), 7.104-7.084 (d, J=8 Hz, 1H), 5.284-5.256 (m, 1H), 4.464-4.450 (d, J=5.6 Hz, 2H), 2.060-2.028 (m, 1H), 0.916-0.862 (m, 4H). LC-MS: m/z $[M+H]^+$=150.

Intermediate 192 dimethyl 3-cyanopyridine-2,6-dicarboxylate

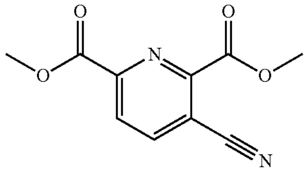

The raw materials of 2,6-dichloronicotinonitrile (17.0 g, 98.7 mmol), [1,1'-bis(diphenylphosphino)ferrocene]palladium chloride (7.2 g, 9.87 mmol) and triethylamine (29.9 g, 296.1 mmol) were sequentially added to methanol (150 mL). Then, the reaction was carried out overnight under carbon monoxide atmosphere of 5 MPa at 80° C. The reaction was combined with NO036-78 for treatment. The reaction solution was filtered under reduced pressure, concentrated and separated by column chromatography (dichloromethane/methanol=300:1) to obtain a white solid (2.16 g, 10.0%) as a product. $^1$H NMR (400 MHz, $CDCl_3$): δ 8.39 (d, J=8.0 Hz, 1H), 8.33 (d, J=8.0 Hz, 1H), 4.10 (s, 3H), 4.07 (s, 3H). LC-MS: m/z $[M+H]^+$=221.

Intermediate 193 6-(tert-butyl) 2-methyl 7-oxo-5,7-dihydro-6H-pyrrolo[3,4-b]pyridine-2,6-dicarboxylate

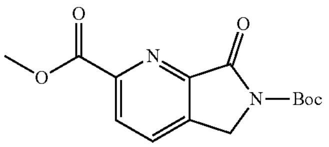 [SMILES: COC(=O)c1ccc2c(n1)C(=O)N(C(=O)OC(C)(C)C)C2]

The raw materials of dimethyl 3-cyanopyridine-2,6-dicarboxylate (2.5 g, 11.4 mmol) and raney nickel (1.4 g, 22.8 mmol) were sequentially added to methanol (300 mL). Then, the reaction was carried out under hydrogen atmosphere of 50 psi at 40° C. for 8 hours. The reaction solution was concentrated to obtain a gray solid, and the gray solid and 4-dimethylaminopyridine (124 mg, 1.02 mmol) were sequentially added to dichloromethane (10 mL). Then, the raw material di-tert-butyl dicarbonate (2.2 g, 10.2 mmol) was added thereto, and the reaction was carried out at 50° C. for 30 minutes. The reaction solution was concentrated, and separated by column chromatography to obtain a reddish brown solid (1.25 g, 63.0%) as a product. $^1$H NMR (400 MHz, $CDCl_3$): δ 8.36 (d, J=8.0 Hz, 1H), 8.03 (d, J=8.0 Hz, 1H), 4.85 (s, 2H), 4.04 (s, 3H), 1.62 (s, 9H). LC-MS: m/z $[M+H]^+$=293.

Intermediate 194 tert-butyl 7-hydroxy-2-(hydroxymethyl)-5H-pyrrolo[3,4-b]pyridine-6 (7H)-carboxylate

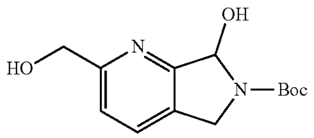 [SMILES: CC(C)(C)OC(=O)N1Cc2ccc(CO)nc2C1O]

At 0° C., the raw material 6-(tert-butyl) 2-methyl 7-oxo-5,7-dihydro-6H-pyrrolo[3,4-b]pyridine-2,6-dicarboxylate (900 mg, 3.1 mmol) was added to tetrahydrofuran (10 mL). Then, under the protection of nitrogen, the raw material diisobutyl aluminum hydride (dissolved in tetrahydrofuran, 6.2 mL, 6.2 mmol, 1 M) was added dropwise to the solution. After 2 hours of reaction, additional raw material diisobutyl aluminum hydride (6.2 mL, 6.2 mmol, 1 M) was added thereto. The mixture was reacted at room temperature for 3 hours. Water (10 mL) was added dropwise to the reaction solution to quench excess diisobutyl aluminum hydride, and the mixture was filtered and concentrated, and separated by column chromatography to obtain the title compound (320 mg, 37.6%) as a yellow solid. $^1$H NMR (400 MHz, $CDCl_3$): δ 7.63 (d, J=7.6 Hz, 1H), 7.31 (d, J=8.0 Hz, 1H), 4.83 (s, 2H), 4.68-4.61 (m, 2H), 3.70 (s, 1H), 1.59 (s, 9H). LC-MS: m/z $[M+H]^+$=267.

Intermediate 195 tert-butyl 2-(hydroxymethyl)-5H-pyrrolo[3,4-b]pyridine-6(7H)-carboxylate

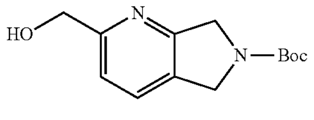 [SMILES: CC(C)(C)OC(=O)N1Cc2ccc(CO)nc2C1]

The raw materials tert-butyl 7-hydroxy-2-(hydroxymethyl)-5H-pyrrolo[3,4-b]pyridine-6(7H)-carboxylate (320 mg, 1.2 mmol) and sodium cyanoborohydride (83.2 mg, 1.32 mmol) were sequentially added to acetic acid (5 mL). The mixture was reacted at room temperature for 1 hour. The acetic acid was evaporated to dryness by rotary evaporation at low temperature, and the residue was dissolved with dichloromethane/methanol=10:1. The pH of the mixture was adjusted to about 9 with a saturated sodium carbonate solution, and the mixture was extracted with dichloromethane/methanol=10:1. The organic phase was collected, dried with anhydrous sodium sulfate, concentrated, and separated by column chromatography to obtain the title compound (190 mg, 63.3%) as a yellow solid. $^1$H NMR (400 MHz, $CDCl_3$): δ 7.60-7.53 (m, 1H), 7.15 (d, J=8.0 Hz, 1H), 4.78-4.77 (m, 2H), 4.71-4.67 (m, 4H), 1.50 (s, 9H). LC-MS: m/z $[M+H]^+$=251.

Intermediate 196 (6,7-dihydro-5H-pyrrolo[3,4-b]pyridin-2-yl)methanol

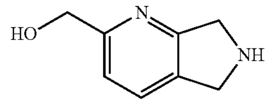 [SMILES: OCc1ccc2c(n1)CNC2]

tert-Butyl 2-(hydroxymethyl)-5H-pyrrolo[3,4-b]pyridine-6 (7H)-carboxylate (300 mg, 1.2 mmol) was dissolved in dichloromethane (2 mL), and trifluoroacetic acid (1 mL) was added thereto, and the mixture was reacted at room temperature for 1 hour. The reaction solution was directly concentrated, dissolved in methanol, added with ion resin and stirred for 30 minutes, filtered and concentrated to obtain the title compound (180 mg, crude product) as a brown solid. LC-MS: m/z $[M+H]^+$=151.

Intermediate 197 (6-methyl-6,7-dihydro-5H-pyrrolo[3,4-b]pyridin-2-yl)methanol

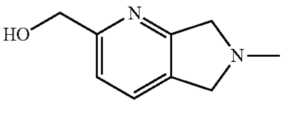

(6,7-Dihydro-5H-pyrrolo[3,4-b]pyridin-2-yl)methanol (150 mg, 1 mmol, crude product) was dissolved in dichloromethane (3 mL), and 1 drop of acetic acid was added dropwise thereto, and then an aqueous formaldehyde solution (0.5 mL) was added thereto, and the mixture was reacted at room temperature for 30 minutes; sodium triacetoxyborohydride (636 mg, 3 mmol) was added thereto, and the mixture was reacted at room temperature overnight. The reaction solution was concentrated, dissolved in methanol, concentrated, and separated by column chromatography to obtain the title compound (80 mg, 30%) as a brown oil. $^1$H NMR (400 MHz, $CDCl_3$ & $CD_3OD$) δ 7.63 (d, J=8.0 Hz, 1H), 7.37 (d, J=8.0 Hz, 1H), 4.71 (s, 2H), 4.01-3.99 (m, 4H), 2.66 (s, 3H).

Intermediate 198 (5-(2-methoxyethoxy)-1,6-naphthyridin-2-yl)methanol

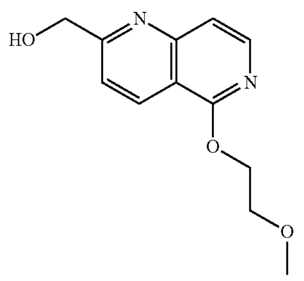 [SMILES: COCCOc1nccc2nc(CO)ccc12]

Methyl 5-oxo-5,6-dihydro-1,6-naphthyridine-2-carboxylate (200 mg, 1.0 mmol) was dissolved in phosphorus oxychloride (3.0 mL), and the temperature of the system was raised to 80° C., and the mixture was stirred and reacted for 4 hours. After the reaction was completed, the system was cooled to room temperature. Then, ethylene glycol monomethyl ether (30.0 mL) was added to the system and the mixture was stirred at room temperature for 0.5 hours. After the reaction was completed, the pH of the reaction system was adjusted to 8-9 with saturated sodium bicarbonate solution. Water (20 mL) was added to the reaction system, followed by extraction with ethyl acetate (40 mL*2 times); the organic phases were combined, and then washed with saturated brine (30 mL*1 time). The organic phase was dried, concentrated and dissolved with sodium borohydride (433 mg, 11.4 mmol) into a mixed solution of tetrahydrofuran and methanol (tetrahydrofuran:methanol=4:1) (20 mL). After the addition was completed, the mixture was stirred and reacted at room temperature for 2.0 hours. After the reaction was completed, the reaction solution was separated by column chromatography to obtain the title compound (105.0 mg, 19.6%). LC-MS: m/z $[M+H]^+$=235.10.

Intermediate 199 ethyl 2-(2-(hydroxymethyl)-7,8-dihydro-1,6-naphthyridin-6(5H)-yl)-2-methylpropanoate

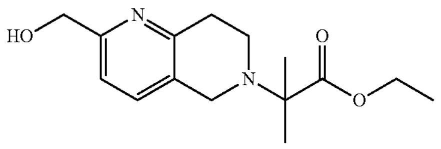 [SMILES: CCOC(=O)C(C)(C)N1CCc2nc(CO)ccc2C1]

(5,6,7,8-Tetrahydro-1,6-naphthyridin-2-yl)methanol (1 g, 6.1 mmol), ethyl 2-bromoisobutyrate (CAS: 600-00-0, 2 g, 12 mmol) and potassium carbonate (2.5 g, 218 mmol) were dissolved in 10 mL of acetonitrile, then the mixture was heated to 80° C. and stirred overnight. The solid was filtered, then the reaction solution was concentrated, and purified by preparative plate (dichloromethane:methanol=10:1) to obtain the title compound (1 g, 59%) as a colorless liquid. LC-MS: m/z $[M+H]^+$=279.

Intermediate 200 ethyl 2-(2-((tert-butyldimethylsilyl)oxy)methyl)-7,8-dihydro-1,6-naphthyridin-6(5H)-yl)-2-methylpropanoate

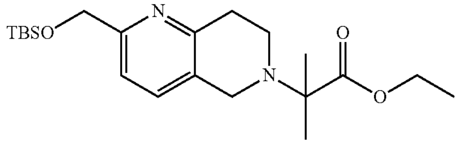 [SMILES: CCOC(=O)C(C)(C)N1CCc2nc(CO[Si](C)(C)C(C)(C)C)ccc2C1]

Ethyl 2-(2-(hydroxymethyl)-7,8-dihydro-1,6-naphthyridin-6(5H)-yl)-2-methylpropanoate (1 g, 4 mmol), and imidazole (900 mg, 6 mmol) were dissolved in 10 mL of dichloromethane, then the mixture was cooled to 0° C. TBSCl (1 g, 15 mmol) was added thereto, and the mixture was stirred at room temperature for 2 hours. The solid was filtered, then the reaction solution was concentrated, and purified by column chromatography (petroleum ether:ethyl acetate=30:1) to obtain the title compound (400 mg, 28%) as a yellow liquid. LC-MS: m/z $[M+H]^+$=393.

Intermediate 201 2-(2-((tert-butyldimethylsilyl)oxy)methyl)-7,8-dihydro-1,6-naphthyridin-6(5H)-yl)-2-methylpropan-1-ol

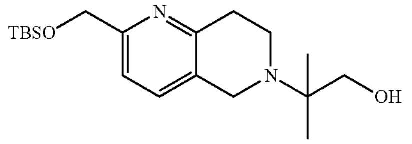 [SMILES: CC(C)(CO)N1CCc2nc(CO[Si](C)(C)C(C)(C)C)ccc2C1]

Ethyl 2-(2-(((tert-butyldimethylsilyl)oxy)methyl)-7,8-dihydro-1,6-naphthyridin-6(5H)-yl)-2-methylpropanoate (400 mg, 1 mmol) was dissolved in 10 mL of tetrahydrofuran, then the mixture was cooled to 0° C., added with lithium aluminum hydride (80 mg, 2 mmol) and stirred at room temperature for 30 minutes. Sodium sulfate decahydrate was added to quench. The solid was filtered, and the reaction solution was concentrated, and purified by preparative plate (dichloromethane:methanol=10:1) to obtain the title compound (300 mg, 90%) as a colorless liquid. LC-MS: m/z $[M+H]^+$=351.

Intermediate 202 2-(((tert-butyldimethylsilyl)oxy)methyl)-6-(1-methoxy-2-methylpropan-2-yl)-5,6,7,8-tetrahydro-1,6-naphthyridine

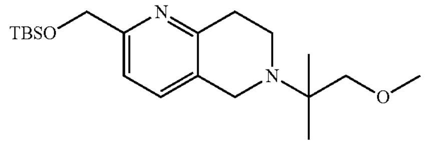 [SMILES: COCC(C)(C)N1CCc2nc(CO[Si](C)(C)C(C)(C)C)ccc2C1]

2-(2-(((tert-Butyldimethylsilyl)oxy)methyl)-7,8-dihydro-1,6-naphthyridin-6(5H)-yl)-2-methylpropan-1-ol (300 mg, 0.8 mmol) was dissolved in 10 mL of tetrahydrofuran, then the mixture was cooled to 0° C., added with lithium sodium hydride (40 mg, 1 mmol) and stirred for 30 minutes. 0.5 mL of iodomethane was added thereto, and the mixture was stirred at room temperature for 2 hours. The solid was filtered, the reaction solution was concentrated, and purified by preparative plate (dichloromethane:methanol=10:1) to obtain the title compound (300 mg, 100%) as a colorless liquid. LC-MS: m/z $[M+H]^+$=365.

Intermediate 203 (6-(1-methoxy-2-methylpropan-2-yl)-5,6,7,8-tetrahydro-1,6-naphthyridin-2-yl)methanol

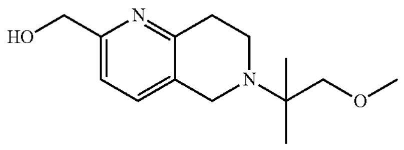 [SMILES: COCC(C)(C)N1CCc2nc(CO)ccc2C1]

2-(((tert-Butyldimethylsilyl)oxy)methyl)-6-(1-methoxy-2-methylpropan-2-yl)-5,6,7,8-tetrahydro-1,6-naphthyridine (300 mg, 0.8 mmol) was dissolved in 5 mL of tetrahydrofuran, then 1M tetrahydrofuran solution of tetrabutyl ammonium fluoride (5 mL) was added thereto, and the mixture was stirred at room temperature overnight. The reaction solution was concentrated, and purified by preparative plate (dichloromethane:methanol=10:1) to obtain the title compound (200 mg, 95%) as a colorless liquid. LC-MS: m/z $[M+H]^+=251$.

Intermediate 204 (6-(5-methylisoxazol-3-yl)-5,6,7,8-tetrahydro-1,6-naphthyridin-2-yl)methanol

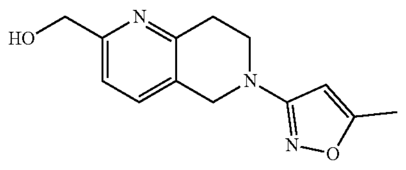 [SMILES: Cc1cc(N2CCc3nc(CO)ccc3C2)no1]

3-Bromo-5-methylisothiazole (CAS: 25741-97-3, 330 mg, 2 mmol) and methyl trifluoromethanesulfonate (1 mL) were heated to 80° C., and the mixture was stirred for 1 hour, cooled, concentrated, and dissolved in methanol, added with (5,6,7,8-tetrahydro-1,6-naphthyridin-2-yl)methanol (330 mg, 2 mmol), stirred at room temperature for 1 hour. Then the reaction solution was concentrated, then DMF was added thereto to dissolve, and triphenyl phosphine (500 mg, 2 mmol) was added thereto, then the mixture was heated to 120° C. overnight under the protection of argon. Water was added thereto, and the mixture was extracted with dichloromethane, concentrated, and purified by preparative plate (dichloromethane:methanol=10:1 then ethyl acetate) to obtain the title compound (100 mg, 20%) as a yellow oil. LC-MS: m/z $[M+H]^+=246$.

Intermediate 205 tert-butyl 3-(2-((((7-methoxy-3-(5-methylisoxazol-3-yl)-[1,2,4]triazolo[4,3-b]pyridazin-6-yl]oxy)methyl)-7,8-dihydro-1,6-naphthyridin-6(5H)-yl)azetidine-1-carboxylate

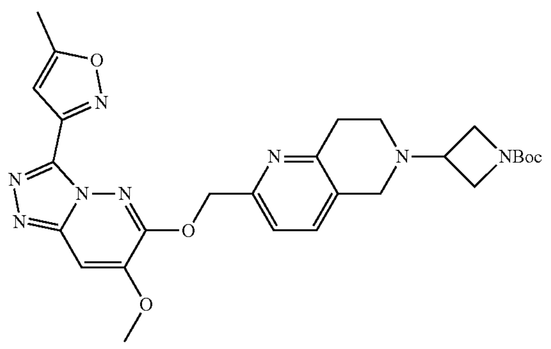 [SMILES: COc1cc2nnc(-c3cc(C)on3)n2nc1OCc1ccc2c(n1)CCN(C1CN(C(=O)OC(C)(C)C)C1)C2]

3-(7-Methoxy-6-(((5,6,7,8-tetrahydro-1,6-naphthopyridin-2-yl)methoxy)-[1,2,4]triazolo[4,3-b]pyridazin-3-yl)-5-methylisoxazole (300 mg, 0.7 mmol) and 1-(tert-butoxycarbonyl)-3-azetidinone (CAS: 398489-26-4, 171 mg, 1 mmol) were dissolved in 10 mL of methanol, then sodium cyanoborohydride (200 mg, 3 mmol) was added thereto, and the mixture was stirred at room temperature overnight. Water was added thereto, and the mixture was extracted with dichloromethane, separated, concentrated, and purified by preparative plate (dichloromethane:methanol=10:1) to obtain the title compound (300 mg, 78%) as a white solid. LC-MS: m/z $[M+H]^+=549$.

Intermediate 206 3-(6-((6-(azetidin-3-yl)-5,6,7,8-tetrahydro-1,6-naphthyridine-2-yl)methoxy)-7-methoxy-[1,2,4]triazolo[4,3-b]pyridazin-3-yl)-5-methylisoxazole hydrochloride

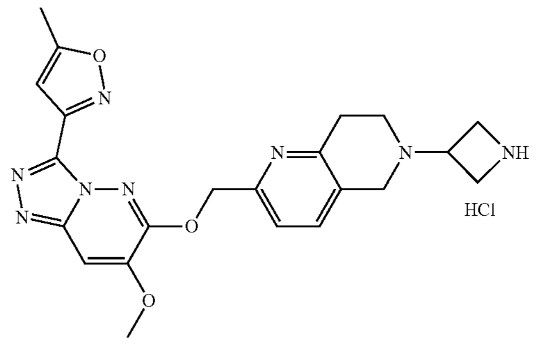 [SMILES: COc1cc2nnc(-c3cc(C)on3)n2nc1OCc1ccc2c(n1)CCN(C1CNC1)C2 ; Cl]

tert-Butyl 3-(2-((((7-methoxy-3-(5-methylisoxazol-3-yl)-[1,2,4]triazolo[4,3-b]pyridazin-6-yl]oxy)methyl)-7,8-dihydro-1,6-naphthyridin-6(5H)-yl)azetidine-1-carboxylate (300 mg, 0.6 mmol) was dissolved in 10 mL of dichloromethane, then 10 mL of an ethyl acetate solution of hydrochloride was added thereto, and the mixture was stirred at room temperature for 30 minutes. The reaction solution was concentrated, dissolved in methanol, neutralized by adding solid sodium bicarbonate to neutral, filtered, and the organic phase was concentrated to obtain the title compound (300 mg, 100%) as a white solid. LC-MS: m/z $[M+H]^+=449$.

Intermediate 207 6-chloroimidazo[1,2-b]pyridazine-2-carboxamide

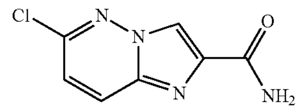 [SMILES: NC(=O)c1cn2nc(Cl)ccc2n1]

Under the protection of nitrogen, methyl 6-chloroimidazo[1,2-b]pyridazine-2-carboxylate (2.0 g, 9.45 mmol) was dispersed in acetonitrile (30 mL) at 40° C., and ammonia water (100 mL) was added thereto, and the reaction solution was stirred for 2 hours. After the reaction was completed, the reaction solution was cooled to room temperature, filtered, and the solid was dried to obtain the title product (1.6 g, white solid) with a yield of 86%. LC-MS: m/z $[M+H]^+=197$.

Intermediate 208 methyl 2-carbamoylimidazo[1,2-b]pyridazine-6-carboxylate

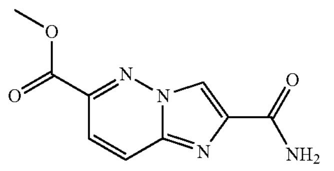 [SMILES: COC(=O)c1ccc2nc(C(N)=O)cn2n1]

In an autoclave, 6-chloroimidazo[1,2-b]pyridazine-2-carboxamide (937 mg, 4.8 mmol) was dispersed in methanol (30 mL). [1,1'-bis(Diphenylphosphino)ferrocene]palladium dichloride (936 mg, 1.15 mmol) and triethylamine (9 mL) were added thereto, and the reaction solution was reacted at 80° C. for 16 hours under carbon monoxide atmosphere of 3 Mpa. After the reaction was completed, the temperature was lowered to room temperature, and the reaction solution was filtered. The filtrate was concentrated, and the residue was purified by column chromatography (dichloromethane/methanol=10/1) to obtain the title product (1 g, brown solid) with a yield of 99%. LC-MS: m/z $[M+H]^+$=221.

Intermediate 209 methyl 2-cyanoimidazo[1,2-b]pyridazine-6-carboxylate

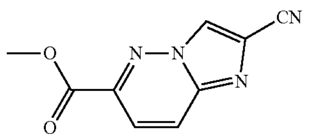

Under the protection of nitrogen at room temperature, methyl 2-chloroimidazo[1,2-b]pyridazine-6-carboxylate (1 g, 4.55 mmol) was dissolved in tetrahydrofuran (20 mL), then triethylamine (920 mg, 9.10 mmol) and trifluoroacetic anhydride (3.81 g, 18.20 mmol) were added thereto. The reaction solution was stirred for 2 hours. After the reaction was completed, the reaction solution was concentrated, and the residue was purified by column chromatography (dichloromethane/methanol=10/1) to obtain the title product (645 mg, white solid) with a yield of 70%. LC-MS: m/z $[M+H]^+$ =203.

Intermediate 210 6-(hydroxymethyl)imidazo[1,2-b]pyridazine-2-carbonitrile

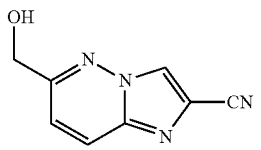 [SMILES: N#Cc1cn2nc(CO)ccc2n1]

Under the protection of nitrogen at 30° C., methyl 2-cyanoimidazo[1,2-b]pyridazine-6-carboxylate (550 mg, 2.72 mmol) was dissolved in tetrahydrofuran (15 mL). Anhydrous calcium chloride (604 mg, 5.45 mmol) and sodium borohydride (206 mg, 5.45 mmol) were added thereto, and the reaction solution was stirred for 2 hours. After the reaction was completed, the reaction solution was cooled and concentrated, and the residue was purified by column chromatography (dichloromethane/methanol=10/1) to obtain the title product (350 mg, white solid) with a yield of 73%. LC-MS: m/z $[M+H]^+$=175.

Intermediate 211 2-bromo-1-(tetrahydro-2H-pyran-4-yl)ethan-1-one

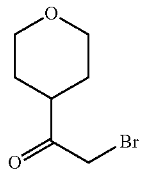

1-(Tetrahydro-2H-pyran-4-yl)ethan-1-one was put into anhydrous methanol (5 ml), and the mixture was cooled to 0° C. Liquid bromine (0.4 mL) was added dropwise to the reaction solution at 0° C., the mixture was kept at 0° C. for 45 minutes, and then heated to room temperature and reacted for 45 minutes. Then, concentrated sulfuric acid (2.7 mL) was added to the reaction solution, and the reaction was carried out at room temperature overnight. A saturated aqueous sodium bisulfite solution (5 mL) was added to the reaction solution, then ethyl acetate (200 mL) was added thereto. The ethyl acetate was washed three times with water, and then dried with anhydrous sodium sulfate, and then evaporated to dryness by rotary evaporation to obtain the title compound (677 mg, 41.9%) as a yellow oil. LC-MS: m/z $[M+H]^+$=208.

Intermediate 212 methyl 2-(tetrahydro-2H-pyran-4-yl)imidazo[1,2-b]pyridazine-6-carboxylate

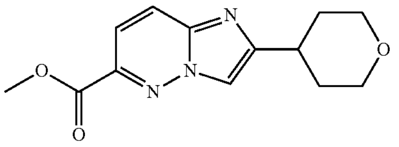 [SMILES: COC(=O)c1ccc2nc(C3CCOCC3)cn2n1]

2-Bromo-1-(tetrahydro-2H-pyran-4-yl)ethan-1-one (677 mg, 3.27 mmol) and methyl 6-aminopyridazine-3-carboxylate (500 mg, 3.27 mmol) were put into ethylene glycol dimethyl ether (10 mL), and the mixture was reacted at 90° C. for 2 hours. The reaction solution was directly subjected to thin layer chromatography (dichloromethane/anhydrous methanol=20/1) to obtain the title compound (430 mg, 50.4%) as a yellow solid. LC-MS: m/z $[M+H]^+$=262.

Intermediate 213 (2-(tetrahydro-2H-pyran-4-yl)imidazo[1,2-b]pyridazin-6-yl)methanol

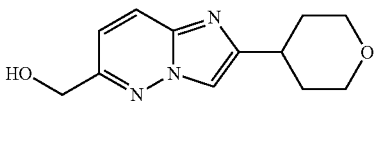

The experimental operation was the same as that of (2-(oxetan-3-yl)-2H-pyrazolo[4,3-b]pyridin-5-yl)methanol using raw material methyl 2-(tetrahydro-2H-pyrman-4-yl) imidazo[1,2-b]pyridazine-6-carboxylate (430 mg, 1.6 mmol) to obtain the title compound (200 mg, 52.1%) as a yellow solid. LC-MS: m/z $[M+H]^+$=234.

Intermediate 214 methyl 2-(bromomethyl)imidazo [1,2-b]pyridazine-6-carboxylate

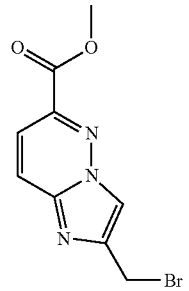

Methyl 6-aminopyridazine-3-carboxylate (300 mg, 2 mmol) and 1,2-dibromoacetone (440 mg, 2.2 mmol) were added to 1,2-dimethoxyethane (2 mL), and the mixture was reacted at 90° C. for 2 hours. The mixture was subjected to preparative thin layer chromatography (dichloromethane/methanol=30/1) to obtain the title compound (193 mg, 35.9%) as a yellow solid. LC-MS: m/z $[M+H]^+$=270, 272.

Intermediate 215 2-(methoxymethyl)imidazo[1,2-b] pyridazine-6-carboxylic acid

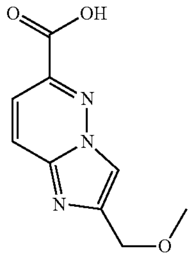

Methyl 2-(bromomethyl)imidazo[1,2-b]pyridazine-6-carboxylate (190 mg, 0.72 mmol) was added to a mixed solution of tetrahydrofuran (2 mL) and methanol (1 mL), and potassium carbonate (200 mg, 1.45 mmol) was added to the reaction solution, and the mixture was reacted at 55° C. for 2 hours. The pH of the reaction solution was adjusted to about 5 with glacial acetic acid, and the mixture was concentrated, and purified by reverse-phase chromatographic column to obtain a crude product.

Intermediate 216 methyl 2-(methoxymethyl)imidazo [1,2-b]pyridazine-6-carboxylate

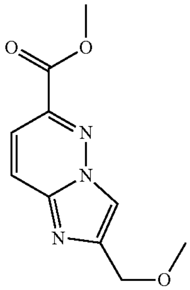 [SMILES: COCc1cn2nc(C(=O)OC)ccc2n1]

2-(Methoxymethyl)imidazo[1,2-b]pyridazine-6-carboxylic acid (the crude product from the previous step) was added to methanol (5 mL), and thionyl chloride (1 mL) was slowly added dropwise to the reaction solution, and the mixture was reacted at 60° C. for 1 hour. The mixture was subjected to preparative thin layer chromatography (dichloromethane/methanol=30/1) to obtain the title compound (87 mg, a two-step yield of 54.9%) as a brownish yellow solid. LC-MS: m/z $[M+H]^+$=222.

Intermediate 217 (2-(methoxymethyl)imidazo[1,2-b] pyridazin-6-yl)methanol

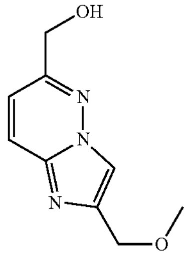

Methyl 2-(methoxymethyl)imidazo[1,2-b]pyridazine-6-carboxylate (87 mg, 0.40 mmol) was added to a mixed solution of tetrahydrofuran (2 mL) and methanol (0.5 mL). Sodium borohydride (45 mg, 1.2 mmol) was added to the reaction solution in two batches, and the mixture was stirred at room temperature for 1 hour. Methanol (20 mL) was added to the reaction solution to quench, and the mixture was concentrated, and subjected to preparative thin layer chromatography (dichloromethane/methanol=20/1) to obtain the title compound (68 mg, 88%) as a yellow solid. LC-MS: m/z $[M+H]^+$=194.

Intermediate 218 methyl 3-isopropyl-[1,2,4]triazolo [4,3-b]pyridazine-6-carboxylate

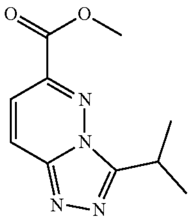 [SMILES: COC(=O)c1ccc2nnc(C(C)C)n2n1]

Methyl 6-hydrazinopyridazine-3-carboxylate dihydrochloride (400 mg, 1.659 mmol), isobutyraldehyde (239 mg, 3.32 mmol) and potassium acetate (326 mg, 3.32 mmol) were added to anhydrous ethanol (3 mL), and the mixture was stirred at room temperature for 30 minutes. Copper bromide (407 mg, 1.83 mmol) was added to the reaction solution, and potassium peroxosulfate complex salt (1.123 g, 1.83 mmol) dissolved in water (2 mL) was added to the reaction solution, and the mixture was stirred at room temperature for 1 hour. The reaction solution was filtered under reduced pressure, then the organic phase was concentrated, and subjected to preparative thin layer chromatography (dichloromethane/methanol=40/1) to obtain the title compound (280 mg, 76.7%) as a yellow solid. LC-MS: m/z $[M+H]^+=221$.

Intermediate 219 (3-isopropyl-[1,2,4]triazolo[4,3-b]pyridazin-6-yl)methanol

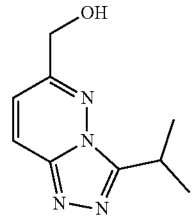

Methyl 3-isopropyl-[1,2,4]triazolo[4,3-b]pyridazine-6-carboxylate (280 mg, 1.280 mmol) was added to tetrahydrofuran (2 mL), and the mixture was stirred at −20° C. for 15 minutes. At −20° C., lithium aluminum hydride (99 mg, 2.56 mmol) was added to the reaction solution in three batches, and the reaction was carried out at −20° C. for 30 minutes after the addition was completed. Sodium sulfate decahydrate (5 g) was added to the reaction solution, and the reaction solution was filtered under reduced pressure. The organic phase was concentrated, and subjected to preparative thin layer chromatography (dichloromethane/methanol=25/1) to obtain the title compound (62 mg, 25.2%) as a brown oily liquid. LC-MS: m/z $[M+H]^+=193$.

Intermediate 220 methyl 3-(tetrahydro-2H-pyran-4-yl)-[1,2,4]triazolo[4,3-b]pyridazine-6-carboxylate

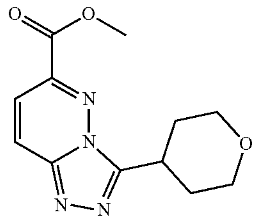 [SMILES: COC(=O)c1ccc2nnc(C3CCOCC3)n2n1]

Methyl 6-hydrazinopyridazine-3-carboxylate dihydrochloride (300 mg, 1.25 mmol), potassium acetate (366 mg, 3.74 mmol) and tetrahydropyran 4-carbaldehyde (284 mg, 2.49 mmol) were added to ethanol (2 ml), and the mixture was stirred at room temperature for 30 minutes. Copper bromide (305 mg, 1.37 mmol) was added to the reaction solution, and potassium peroxosulfate complex salt (842 mg, 1.37 mmol) dissolved in water (1.5 mL) was added to the reaction solution, and the mixture was stirred at room temperature for 1 hour. The reaction solution was filtered under reduced pressure, concentrated, and subjected to preparative thin layer chromatography (dichloromethane/methanol=20/1) to obtain the title compound (184 mg, 56.4%) as a yellow solid. LC-MS: m/z $[M+H]^+=263$.

Intermediate 221 (3-(tetrahydro-2H-pyran-4-yl)-[1,2,4]triazolo[4,3-b]pyridazin-6-yl)methanol

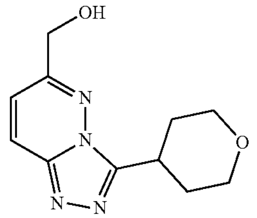 [SMILES: OCc1ccc2nnc(C3CCOCC3)n2n1]

Methyl 3-(tetrahydro-2H-pyran-4-yl)-[1,2,4]triazolo[4,3-b]pyridazine-6-carboxylate (168 mg, 0.641 mmol) was added to tetrahydrofuran (2 mL), and the mixture was stirred at −20° C. for 15 minutes. At −20° C., lithium aluminum hydride (49 mg, 1.282 mmol) was added to the reaction solution in three batches, and the reaction was carried out at −20° C. for 30 minutes after the addition was completed. Sodium sulfate decahydrate (5 g) was added to the reaction solution, and the reaction solution was filtered under reduced pressure. The organic phase was concentrated, and subjected to preparative thin layer chromatography (dichloromethane/methanol=20/1) to obtain the title compound (86 mg, 57.3%) as a brown oily liquid. LC-MS: m/z $[M+H]^+=235$.

Intermediate 222 methyl 3-methyl-[1,2,4]triazolo[4,3-b]pyridazine-6-carboxylate

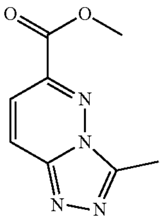

Methyl 6-hydrazinopyridazine-3-carboxylate dihydrochloride (484 mg, 2 mmol) and potassium acetate (588 mg) were added to triethyl orthoformate (2 mL), and the mixture was reacted at 90° C. overnight. The reaction solution was subjected to preparative thin layer chromatography (dichloromethane/methanol=30/1) to obtain the title compound (321 mg, 99.2%) as a yellow solid. LC-MS: m/z $[M+H]^+=193$.

Intermediate 223 (3-methyl-[1,2,4]triazolo[4,3-b]pyridazin-6-yl)methanol

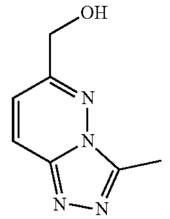

Methyl 3-methyl-[1,2,4]triazolo[4,3-b]pyridazine-6-carboxylate (300 mg, 1.562 mmol) was added to tetrahydrofuran (4 mL), and the mixture was stirred at −20° C. 15 minutes. Lithium aluminum hydride (54 mg, 1.406 mmol) was added to the reaction solution in three batches at −20° C., and the mixture was stirred at −20° C. for 30 minutes. The reaction solution was added with sodium sulfate decahydrate (5 g), filtered under reduced pressure; the organic phase was concentrated, and subjected to preparative plate (dichloromethane/methanol=30/1) to obtain the title compound (88 mg, 34.3%) as a yellow solid. LC-MS: m/z $[M+H]^+$=165.

Intermediate 224 (2-chloropyrimidin-4-yl)methanol

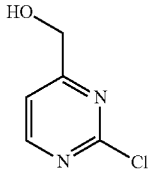

Methyl 2-chloropyrimidine-4-carboxylate (500 mg, 2.89 mmol) was added to tetrahydrofuran (4 mL), and the mixture was stirred at −20° C. for 15 minutes. At −20° C., lithium aluminum hydride (99 mg, 2.6 mmol) was added to the reaction solution in three batches, and the reaction was carried out at −20° C. for 30 minutes after the addition was completed. Sodium sulfate decahydrate (10 g) was added to the reaction solution, and the mixture was filtered under reduced pressure. The organic phase was concentrated, and subjected to preparative thin layer chromatography (dichloromethane/methanol=30/1) to obtain the title compound (168 mg, 40.3%) as a brownish black solid. LC-MS: m/z $[M+H]^+$=145, 147.

Intermediate 225 (2-hydrazinopyrimidin-4-yl)methanol

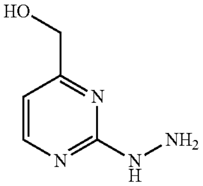

(2-Chloropyrimidin-4-yl)methanol (168 mg, 1.16 mmol) and hydrazine hydrate (64 mg, 1.27 mmol) were added to anhydrous ethanol (2 mL), and the mixture was reacted at 90° C. for 1.5 hours. The mixture was subjected to preparative thin layer chromatography (dichloromethane/methanol=10/1) to obtain the title compound (141 mg, 86.9%) as a tan oily liquid. LC-MS: m/z $[M+H]^+$=141.

Intermediate 226 (3-(tetrahydro-2H-pyran-4-yl)-[1,2,4]triazolo[4,3-a]pyrimidin-7-yl)methanol

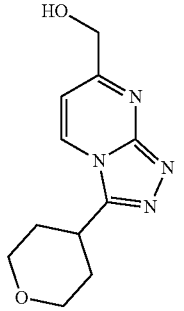 [SMILES: OCc1ccn2c(C3CCOCC3)nnc2n1]

(2-Hydrazinopyrimidin-4-yl)methanol (141 mg, 1.0 mmol) and tetrahydropyran 4-carbaldehyde (228 mg, 2.0 mmol) were added to ethanol (2 mL), and the mixture was stirred at room temperature for 1 hour. Copper bromide (246 mg, 1.1 mmol) was added to the reaction solution, and potassium peroxosulfate complex salt (681 mg, 1.1 mmol) dissolved in water (1.5 mL) was added to the reaction solution, and the mixture was stirred at room temperature for 1 hour. The reaction solution was filtered under reduced pressure; the organic phase was concentrated, and subjected to preparative thin layer chromatography (dichloromethane/methanol=30/1) to obtain the title compound (101 mg, 43.1%) as a brown oily liquid. LC-MS: m/z $[M+H]^+$=235.

Intermediate 227
5-bromo-6-methoxy-1-methyl-1H-indazole (Intermediate 227-A)

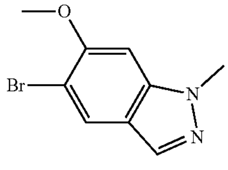

5-Bromo-6-methoxy-2-methyl-2H-indazole (Intermediate 227-B)

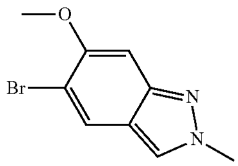

Under the protection of nitrogen at 0° C., 5-bromo-6-methoxy-1H-indazole (2.27 g, 10 mmol) was dissolved in N,N-dimethylformamide (100 mL), and sodium hydride (0.48 g, 12 mmol, 60% dispersed in mineral oil) was added slowly thereto. The reaction mixture was stirred at room temperature for 0.5 hours, and then iodomethane (2.13 g, 15 mmol) was added thereto. The mixture was continued to be stirred at room temperature for 2 hours. The reaction was quenched with saturated aqueous sodium chloride solution and extracted with ethyl acetate (50 mL×3). The organic phase was concentrated and purified by column chromatography (petroleum ether/ethyl acetate=2/1) to obtain a small polar component 5-bromo-6-methoxy-1-methyl-1H-indazole (1.5 g, a pale yellow solid) with a yield of 62.5%. LC-MS: m/z [M+H]+=241; a large polar component 5-bromo-6-methoxy-2-methyl-2H-indazole (800 mg, a pale yellow solid) with a yield of 33% was obtained. LC-MS: m/z $[M+H]^+=241$.

Intermediate 228

6-Methoxy-1-methyl-1H-indazole-5-carboxylic Acid

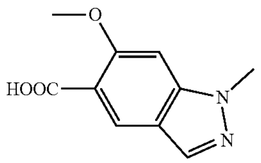

Under the protection of nitrogen, S-bromo-6-methoxy-1-methyl-1H-indazole (1.4 g, 5.8 mmol) was dissolved in 20 mL of tetrahydrofuran, and the solution was cooled to −78° C. under the protection of nitrogen. At this temperature, n-butyllithium (2.6 mL, 6.4 mmol, 2.5 M in n-hexane solution) was added slowly thereto. After stirring at this temperature for 0.5 hours, carbon dioxide gas was introduced. After stirring the reaction solution at this temperature for 1 hour, the temperature was naturally raised to room temperature, and stirring was continued for 12 hours. The pH was adjusted to 5-6 with 1N hydrochloric acid. The reaction solution was extracted with dichloromethane (50 mL×3). The organic phase was concentrated and purified by column chromatography (petroleum ether/ethyl acetate=1/1) to obtain the title product (700 mg, a yellow solid) with a yield of 59%. LC-MS: m/z $[M+H]^+=207$.

Intermediate 229

(6-methoxy-1-methyl-1H-indazol-5-yl)methanol

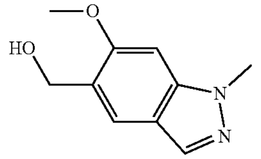

Under the protection of nitrogen, 6-methoxy-1-methyl-1H-indazole-5-carboxylic acid (100 mg, 0.49 mmol) was dissolved in 5 mL of tetrahydrofuran, and the solution was cooled to 0° C. under the protection of nitrogen. At this temperature, lithium aluminum hydride (55 mg, 1.46 mmol) was added slowly thereto. After stirring at this temperature for 2 hours. The reaction was quenched with water, and the mixture was filtered. The filtrate was extracted with dichloromethane (50 mL×3). The organic phase was concentrated and purified by column chromatography (petroleum ether/ethyl acetate=1/1) to obtain the title product (70 mg, a white solid) with a yield of 75%. LC-MS: m/z $[M+H]^+=193$.

Intermediate 330

6-methoxy-2-methyl-2H-indazole-5-carboxylic Acid

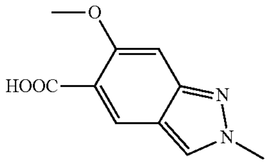

Under the protection of nitrogen, 5-bromo-6-methoxy-2-methyl-2H-indazole (300 mg, 1.24 mmol) was dissolved in 10 mL of tetrahydrofuran, and the solution was cooled to −78° C. under the protection of nitrogen. At this temperature, n-butyllithium (0.55 mL, 6.4 mmol, 2.5M in n-hexane solution) was added slowly thereto. After stirring at this temperature for 0.5 hours, carbon dioxide gas was introduced. After stirring the reaction solution at this temperature for 1 hour, the temperature was naturally raised to room temperature, and stirring was continued for 12 hours. The pH was adjusted to 5-6 with 1N hydrochloric acid. The reaction solution was extracted with dichloromethane (50 mL×3). The organic phase was concentrated and purified by column chromatography (petroleum ether/ethyl acetate=1/1) to obtain the title product (250 mg, a yellow solid) with a yield of 97%. LC-MS: m/z $[M+H]^+=207$.

Intermediate 231

(6-methoxy-2-methyl-2H-indazol-5-yl)methanol

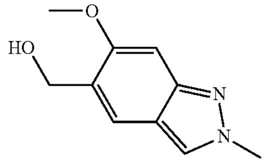

Under the protection of nitrogen, 6-methoxy-2-methyl-2H-indazole-5-carboxylic acid (100 mg, 0.49 mmol) was dissolved in 5 mL of tetrahydrofuran, and the solution was cooled to 0° C. under the protection of nitrogen. At this temperature, lithium aluminum hydride (55 mg, 1.46 mmol) was added slowly thereto. After stirring for 2 hours at this temperature, the reaction was quenched with water, and the mixture was filtered. The filtrate was extracted with dichloromethane (50 mL×3). The organic phase was concentrated and purified by column chromatography (petroleum ether/ethyl acetate=1/1) to obtain the title product (60 mg, a white solid) with a yield of 65%. LC-MS: m/z $[M+H]^+=193$.

Intermediate 232 methyl 1-(2-cyanopropyl)-1H-pyrazolo[4,3-b]pyridine-5-carboxylate

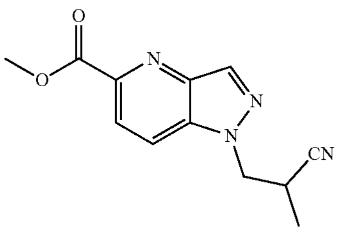 [SMILES: COC(=O)c1ccc2c(cnn2CC(C)C#N)n1]

Methyl 1H-pyrazolo[4,3-b]pyridine-5-carboxylate (CAS: 1033772-23-4, 400 mg, 2.3 mmol), 2-iodo-2-methylpropionitrile (CAS: 19481-79-9, 800 mg, 4 mmol) and cesium carbonate (1.6 g, 5 mmol) were dissolved in 10 mL of acetonitrile, then the mixture was heated to 70° C. and stirred overnight. The solid was filtered, then the reaction solution was concentrated, and purified by preparative plate (dichloromethane:methanol=20:1) to obtain the title compound (350 mg, 64%) as a white solid. LC-MS: m/z $[M+H]^+$ =245.

Intermediate 233 3-(5-(hydroxymethyl)-1H-pyrazolo[4,3-b]pyridin-1-yl)-2-methylpropionitrile

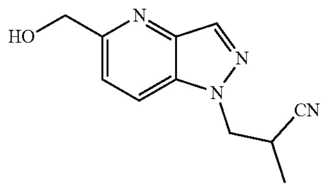 [SMILES: CC(C#N)Cn1ncc2nc(CO)ccc21]

Methyl 1-(2-cyanopropyl)-1H-pyrazolo[4,3-b]pyridine-5-carboxylate (200 mg, 0.9 mmol) was dissolved in 5 mL of tetrahydrofuran, then 5 mL of methanol and sodium borohydride (100 mg, 3 mmol) were added thereto, and the mixture was stirred at room temperature for 30 minutes. The reaction solution was concentrated, and purified by preparative plate (dichloromethane:methanol=10:1) to obtain the title compound (100 mg, 45%) as a white solid. LC-MS: m/z $[M+H]^+$=217.

Intermediate 234 methyl 2-benzyl-2H-pyrazolo[4,3-b]pyridine-5-carboxylate (Intermediate 234-A)

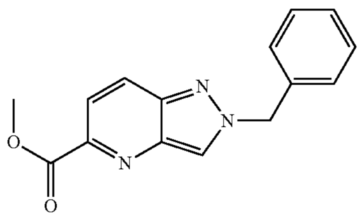 [SMILES: COC(=O)c1ccc2nn(Cc3ccccc3)cc2n1]

Methyl 1-benzyl-1H-pyrazolo[4,3-b]pyridine-5-carboxylate (Intermediate 234-B)

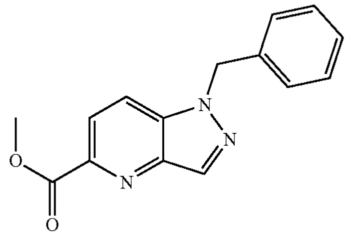 [SMILES: COC(=O)c1ccc2c(cnn2Cc2ccccc2)n1]

The experimental operation was the same as the synthesis method of intermediate 232. From raw materials methyl 2H-pyrazolo[4,3-b]pyridine-5-carboxylate (500 mg, 2.82 mmol), (bromomethyl)benzene (960 mg, 5.65 mmol), the title compound as a yellow solid was obtained; a large polar component methyl 2-benzyl-2H-pyrazolo[4,3-b]pyridine-S-carboxylate (170 mg, 22.5%), a small polar component methyl 1-benzyl-1H-pyrazolo[4,3-b]pyridine-5-carboxylate (300 mg, 39.8%) were obtained. LC-MS: m/z $[M+H]^+$=268.

Intermediate 235

(1-Benzyl-1H-pyrazolo[4,3-b]pyridin-5-yl)methanol

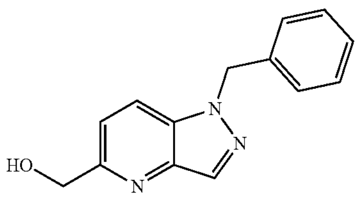 [SMILES: OCc1ccc2c(cnn2Cc2ccccc2)n1]

The experimental operation was the same as the synthesis method of intermediate 233. The title compound (300 mg, crude product) as a yellow oil was obtained form a raw material methyl 1-benzyl-1H-pyrazolo[4,3-b]pyridine-5-carboxylate (300 mg, 1.1 mmol). LC-MS: m/z $[M+H]^+$=240.

Intermediate 236

(2-Benzyl-2H-pyrazolo[4,3-b]pyridin-5-yl)methanol

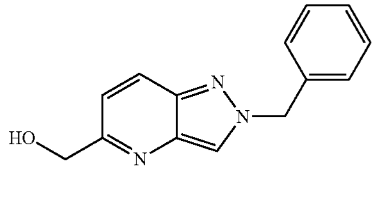 [SMILES: OCc1ccc2nn(Cc3ccccc3)cc2n1]

The experimental operation was the same as the synthesis method of intermediate 233. The title compound (100 mg, 65.7%) as a yellow solid was obtained from a raw material methyl 2-benzyl-2H-pyrazolo[4,3-b]pyridine-5-carboxylate (170 mg, 0.64 mmol). LC-MS: m/z $[M+H]^+$=240.

Intermediate 237

Methyl 1-((5-methylisoxazol-3-yl)methyl)-1H-pyrazolo[4,3-b]pyridine-5-carboxylate (Intermediate 237-A)

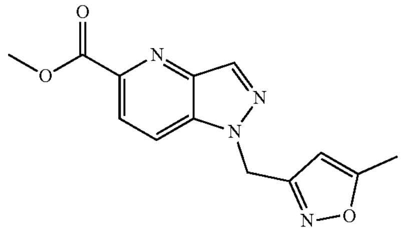

Methyl 2-(5-methylisoxazol-3-yl)methyl)-2H-pyrazolo[4,3-b]pyridine-5-carboxylate (Intermediate 237-B)

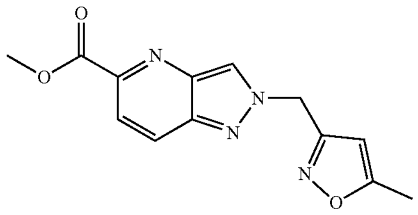

Methyl 1H-pyrazolo[4,3-b]pyridine-5-carboxylate (300 mg, 1.65 mmol), cesium carbonate (1.6 g, 4.95 mmol) and 3-(chloromethyl)-5-methyl isothiazole (217 mg, 1.65 mmol) were added to acetonitrile (10 mL), and the mixture was stirred at 85° C. overnight. The reaction solution was directly separated and purified by preparative plate (dichloromethane/methanol=20/1) to obtain methyl 2-((5-methylisoxazol-3-yl)methyl)-2H-pyrazolo[4,3-b]pyridine-5-carboxylate (130 mg, 29%) and methyl 1-((5-methylisoxazol-3-yl)methyl)-1H-pyrazolo[4,3-b]pyridine-5-carboxylate (250 mg, 56%). LC-MS: m/z $[M+H]^+$=273.

Intermediate 238

(1-(((5-Methylisoxazol-3-yl)methyl)-1H-pyrazolo[4,3-b]pyridin-5-yl)methanol

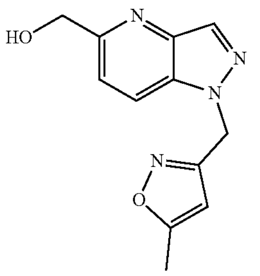 [SMILES: Cc1cc(Cn2ncc3nc(CO)ccc32)no1]

Methyl 1-((5-methylisoxazol-3-yl)methyl)-1H-pyrazolo[4,3-b]pyridine-5-carboxylate (230 mg, 0.84 mmol) and $NaBH_4$ (300 mg, 8 mmol) were added to THF/MeOH (6/3 mL), and the mixture was stirred at room temperature for 1 hour. The reaction solution was concentrated and purified by preparative plate (dichloromethane/methanol=15/1) to obtain the title compound (160 mg, 78.4%). LC-MS: m/z $[M+H]^+$=246.

Intermediate 239

(2-(((5-Methylisoxazol-3-yl)methyl)-2H-pyrazolo[4,3-b]pyridin-5-yl)methanol

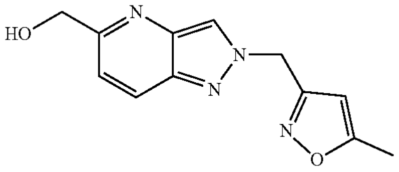 [SMILES: Cc1cc(Cn2cc3nc(CO)ccc3n2)no1]

Methyl 2-((5-methylisoxazol-3-yl)methyl)-2H-pyrazolo[4,3-b]pyridine-5-carboxylate (130 mg, 0.48 mmol) and $NaBH_4$ (200 mg, 10 mmol) were added to THF/MeOH (6/3 mL), and the mixture was stirred at room temperature for 1 hour. The reaction solution was concentrated and purified by preparative plate (dichloromethane/methanol=15/1) to obtain the title compound (90 mg, 76.3%). LC-MS: m/z $[M+H]^+$=246.

Intermediate 240

Methyl 2-(oxetan-3-yl)-2H-pyrazolo[4,3-b]pyridine-5-carboxylate (Intermediate 240-A)

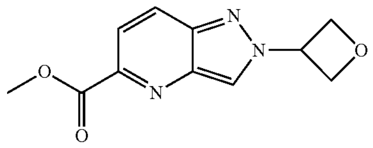 [SMILES: COC(=O)c1ccc2nn(C3COC3)cc2n1]

Methyl 1-(oxetan-3-y))-1H-pyrazolo[4,3-b]pyridine-5-carboxylate (Intermediate 240-B)

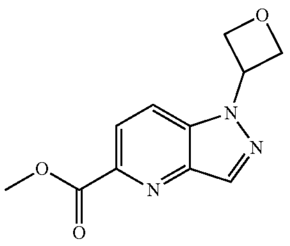 [SMILES: COC(=O)c1ccc2c(cnn2C2COC2)n1]

Methyl 2H-pyrazolo[4,3-b]pyridine-5-carboxylate (400 mg, 2.2 mmol), 3-iodooxetane (500 mg, 2.6 mmol) and cesium carbonate (2.20 g, 6.6 mmol) were added to N,N-dimethylformamide (20 ml), then the mixture was reacted overnight at 60° C. The reaction solution was directly purified by thin layer chromatography (petroleum ether/ethyl acetate=1/1) to obtain the title compound as a white solid, with a large polar component of methyl 2-(oxetan-3-yl)-2H-pyrazolo[4,3-b]pyridine-5-carboxylate (100 mg, 19%), and a small polar component of methyl 1-(oxetan-3-yl)-1H-pyrazolo[4,3-b]pyridine-5-carboxylate. m/z $[M+H]^+$ =234.

Intermediate 241

(2-(Oxetan-3-yl)-2H-pyrazolo[4,3-b]pyridin-5-yl) methanol

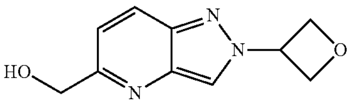 [SMILES: OCc1ccc2nn(C3COC3)cc2n1]

The experimental operation was the same as the synthesis method of intermediate 233. The title compound (20 mg, 28.5%) as a white oil was obtained from raw material methyl 2-(oxetan-3-yl)-2H-pyrazolo[4,3-b]pyridine-5-carboxylate (100 mg, 0.43 mmol). LC-MS: m/z $[M+H]^+$=206.

Intermediate 242

(1-(Oxetan-3-yl)-2H-pyrazolo[4,3-b]pyridin-5-yl) methanol

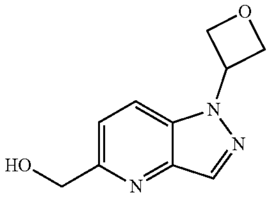 [SMILES: OCc1ccc2c(cnn2C2COC2)n1]

The experimental operation was the same as the synthesis method of intermediate 233. The title compound (100 mg, 75.8%) as a yellow solid was obtained from raw material methyl 1-(oxetan-3-yl)-1H-pyrazolo[4,3-b]pyridine-5-carboxylate (150 mg, 0.64 mmol). LC-MS: m/z $[M+H]^+$=206.

Intermediate 243

Methyl 1-(2-cyanoethyl)-1H-pyrazolo[4,3-b]pyridine-5-carboxylate

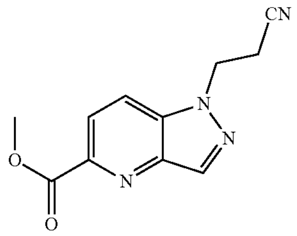 [SMILES: COC(=O)c1ccc2c(cnn2CCC#N)n1]

The experimental operation was the same as the synthesis method of intermediate 232. The title compound (570 mg, 87.7%) as a yellow solid was obtained from raw materials of methyl 2H-pyrazolo[4,3-b]pyridine-S-carboxylate (500 mg, 2.82 mmol) and 3-bromopropanenitrile (680 mg, 5.65 mmol). LC-MS: m/z [M+H]+=231.

Intermediate 244

3-(5-(Hydroxymethyl)-1H-pyrazolo[4,3-b]pyridin-1-yl)propionitrile

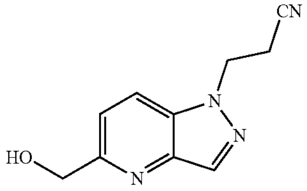 [SMILES: N#CCCn1ncc2nc(CO)ccc21]

The experimental operation was the same as the synthesis method of intermediate 233. The title compound (200 mg, 40%) as a yellow solid was obtained from raw material methyl 1-(2-cyanoethyl)-1H-pyrazolo[4,3-b]pyridine-5-carboxylate (570 mg, 2.5 mmol). LC-MS: m/z $[M+H]^+$=203.

Intermediate 245

Methyl 2-phenethyl-2H-pyrazolo[4,3-b]pyridine-5-carboxylate (Intermediate 245-A)

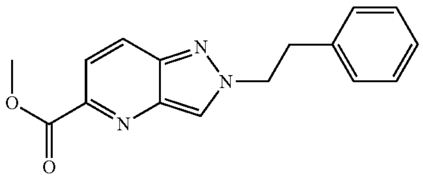 [SMILES: COC(=O)c1ccc2nn(CCc3ccccc3)cc2n1]

Methyl 1-phenethyl-1H-pyrazolo[4,3-b]pyridine-5-carboxylate (Intermediate 245-B)

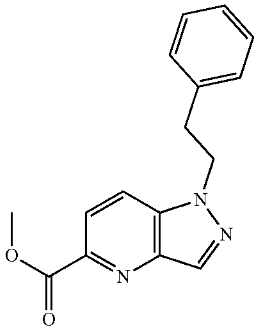 [SMILES: COC(=O)c1ccc2c(cnn2CCc2ccccc2)n1]

The experimental operation was the same as the synthesis method of intermediate 232. From raw materials methyl 2H-pyrazolo[4,3-b]pyridine-5-carboxylate (500 mg, 2.82 mmol) and (2-iodoethyl)benzene (1300 mg, 5.65 mmol), the title compound a mixture of methyl 2-phenethyl-2H-pyrazolo[4,3-b]pyridine-5-carboxylate/methyl 1-phenethyl-1H-pyrazolo[4,3-b]pyridine-5-carboxylate (600 mg, 75.6%) as a yellow solid was obtained. LC-MS: m/z [M+H]+=282.

Intermediate 246

(2-Phenethyl-2H-pyrazolo[4,3-b]pyridin-5-yl)methanol (Intermediate 246-A)

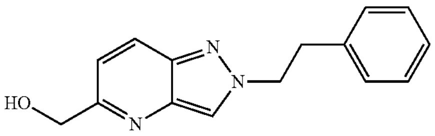 [SMILES: OCc1ccc2nn(CCc3ccccc3)cc2n1]

(1-Phenethyl-1H-pyrazolo[4,3-b]pyridin-5-yl)methanol (Intermediate 246-B)

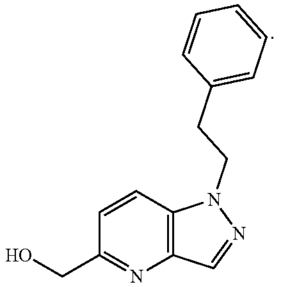 [SMILES: OCc1ccc2c(cnn2CCc2ccccc2)n1]

The experimental operation was the same as the synthesis method of intermediate 233. From raw material a mixture of methyl 2-phenethyl-2H-pyrazolo[4,3-b]pyridine-5-carboxylate/methyl 1-phenethyl-1H-pyrazolo[4,3-b]pyridine-5-carboxylate (600 mg, 2.14 mmol), the title compound a mixture of (2-phenethyl-2H-pyrazolo[4,3-b]pyridin-5-yl)methanol/(1-phenethyl-1H-pyrazolo[4,3-b]pyridin-5-yl)methanol (500 mg, 92.6%) as a yellow oil was obtained. LC-MS: LC-MS: m/z $[M+H]^+=254$.

Intermediate 247

Methyl 2-(tetrahydrofuran-3-yl)-2H-pyrazolo[4,3-b]pyridine-5-carboxylate (Intermediate 247-A)

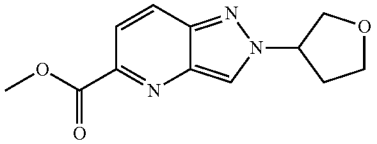 [SMILES: COC(=O)c1ccc2nn(C3CCOC3)cc2n1]

Methyl 1-(tetrahydrofuran-3-yl)-1H-pyrazolo[4,3-b]pyridine-5-carboxylate (Intermediate 247-B)

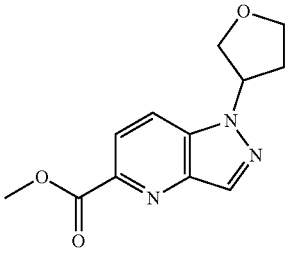 [SMILES: COC(=O)c1ccc2c(cnn2C2CCOC2)n1]

The experimental operation was the same as the synthesis method of intermediate 232. From raw materials methyl 2H-pyrazolo[4,3-b]pyridine-5-carboxylate (500 mg, 2.82 mmol) and 3-iodotetrahydrofuran (1100 mg, 5.65 mmol), the title compound as a yellow solid was obtained, and a large polar component methyl 2-(tetrahydrofuran-3-yl)-2H-pyrazolo[4,3-b]pyridine-5-carboxylate (230 mg, 33%) and a small polar component methyl methyl 1-(tetrahydrofuran-3-yl)-1H-pyrazolo[4,3-b]pyridine-5-carboxylate (330 mg, 47.3%) were obtained. LC-MS: m/z $[M+H]^+=248$.

Intermediate 248

(2-(Tetrahydrofuran-3-yl)-2H-pyrazolo[4,3-b]pyridin-5-yl)methanol

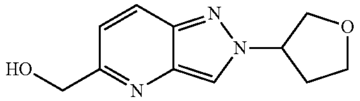 [SMILES: OCc1ccc2nn(C3CCOC3)cc2n1]

The experimental operation was the same as the synthesis method of intermediate 233. The title compound (150 mg, 73.5%) as a yellow solid was obtained from raw material methyl 2-(tetrahydrofuran-3-yl)-2H-pyrazolo[4,3-b]pyridine-5-carboxylate (230 mg, 1.1 mmol). LC-MS: m/z $[M+H]^+=220$.

Intermediate 249

(1-(Tetrahydrofuran-3-yl)-1H-pyrazolo[4,3-b]pyridin-5-yl)methanol

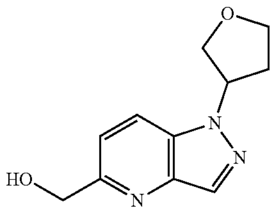 [SMILES: OCc1ccc2c(cnn2C2CCOC2)n1]

The experimental operation was the same as the synthesis method of intermediate 233. The title compound (100 mg, 37.6%) as a yellow solid was obtained from raw material methyl 1-(tetrahydrofuran-3-yl)-1H-pyrazolo[4,3-b]pyridine-5-carboxylate (300 mg, 1.21 mmol). LC-MS: m/z $[M+H]^+=220$.

Intermediate 250

Methyl 2-(1-(tert-butoxycarbonyl)azetidin-3-yl)-2H-pyrazolo[4,3-b]pyridine-5-carboxylate (Intermediate 250-A)

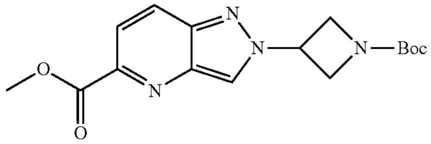 [SMILES: COC(=O)c1ccc2nn(C3CN(C(=O)OC(C)(C)C)C3)cc2n1]

Methyl 1-(1-(tert-butoxycarbonyl)azetidin-3-yl)-1H-pyrazolo[4,3-b]pyridine-5-carboxylate (Intermediate 250-B)

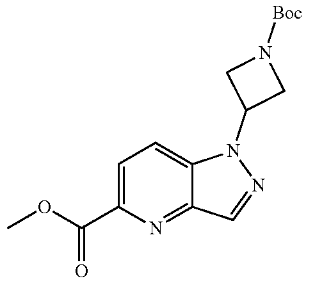 [SMILES: COC(=O)c1ccc2c(cnn2C2CN(C(=O)OC(C)(C)C)C2)n1]

The experimental operation was the same as the synthesis method of intermediate 232. From raw materials methyl 2H-pyrazolo[4,3-b]pyridine-5-carboxylate (500 mg, 2.82 mmol) and tert-butyl 3-(toluenesulfonyloxy) azetidine-1-carboxylate (1600 mg, 5.65 mmol), the title compound as a colorless oil was obtained, and a large polar component methyl 2-(1-(tert-butoxycarbonyl)azetidin-3-yl)-2H-pyrazolo[4,3-b]pyridine-5-carboxylate (300 mg, 32%) and a small polar component methyl 1-(1-(tert-butoxycarbonyl) azetidin-3-yl)-1H-pyrazolo[4,3-b]pyridine-5-carboxylate (400 mg, 42.6%) were obtained. LC-MS: m/z [M+H]+=333.

Intermediate 251 tert-Butyl 3-(5-(hydroxymethyl)-2H-pyrazolo[4,3-b] pyridin-2-yl) azetidine-1-carboxylate

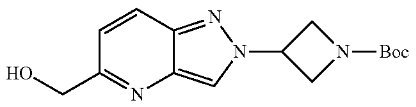 [SMILES: CC(C)(C)OC(=O)N1CC(n2cc3nc(CO)ccc3n2)C1]

The experimental operation was the same as the synthesis method of intermediate 233. The title compound (170 mg, 62.9%) as a colorless oil was obtained from raw material methyl 2-(1-(tert-butoxycarbonyl)azetidin-3-yl)-2H-pyrazolo[4,3-b]pyridine-5-carboxylate (300 mg, 0.9 mmol). LC-MS: m/z $[M+H]^+$=305.

Intermediate 252 tert-Butyl 3-(5-((((7-methoxy-3-(5-methylisoxazol-3-yl)-[1,2,4]triazolo[4,3-b]pyridazin-6-yl]oxy) methyl)-2H-pyrazolo[4,3-b]pyridin-2-yl)azetidine-1-carboxylate

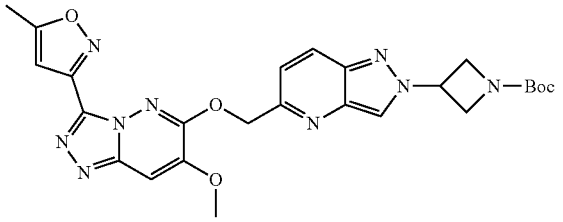 [SMILES: COc1cc2nnc(-c3cc(C)on3)n2nc1OCc1ccc2nn(C3CN(C(=O)OC(C)(C)C)C3)cc2n1]

The experimental operation was the same as that of embodiment 226. The title compound ((130 mg, 43.6%) as a yellow solid was obtained from raw materials tert-butyl 3-(5-(hydroxymethyl)-2H-pyrazolo[4,3-b]pyridin-2-yl)azetidine-1-carboxylate (170 mg, 0.56 mmol) and 3-(6-chloro-7-methoxy-[1,2,4]triazolo[4,3-b]pyridazin-3-yl)-5-methyl-isoxazole (150 mg, 0.56 mmol). LC-MS: m/z $[M+H]^+$=534.

Intermediate 253

3-(6-((2-(Azetidin-3-yl)-2H-pyrazolo[4,3-b]pyridin-5-yl)methoxy)-7-methoxy-[1,2,4]triazolo[4,3-b] pyridazin-3-yl)-5-methylisoxazole

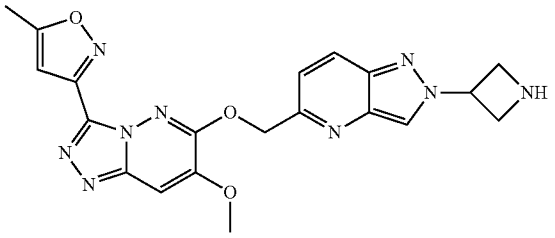 [SMILES: COc1cc2nnc(-c3cc(C)on3)n2nc1OCc1ccc2nn(C3CNC3)cc2n1]

tert-Butyl 3-(5-((((7-methoxy-3-(5-methylisoxazol-3-yl)-[1,2,4]triazolo[4,3-b]pyridazin-6-yl]oxy)methyl)-2H-pyrazolo[4,3-b]pyridin-2-yl)azetidine-1-carboxylate (130 mg, 0.24 mmol) was put into ethyl acetate (5 mL), and self-made hydrochloric acid/ethyl acetate (2 mL, 4M) was dropped into the reaction solution, and the reaction was carried out at room temperature for 4 hours. The reaction solution was adjusted to alkaline with the saturated aqueous sodium bicarbonate solution, and a solid was precipitated. After filtration, the filter cake was washed with water for three times to obtain the title compound (100 mg, 94.7%) as a yellow solid. LC-MS: m/z $[M+H]^+$=434.

Intermediate 254 tert-Butyl 3-(5-(hydroxymethyl)-1H-pyrazolo[4,3-b] pyridin-2-yl)azetidine-1-carboxylate

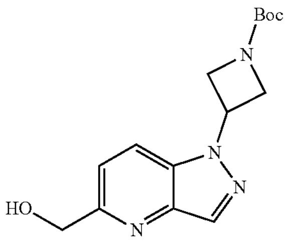 [SMILES: CC(C)(C)OC(=O)N1CC(n2ncc3nc(CO)ccc32)C1]

The experimental operation was the same as the synthesis method of intermediate 233. The title compound (260 mg, 71%) as a colorless oil was obtained from raw material methyl 1-(1-(tert-butoxycarbonyl)azetidin-3-yl)-1H-pyrazolo[4,3-b]pyridine-5-carboxylate (400 mg, 1.2 mmol). LC-MS: m/z $[M+H]^+$=305.

Intermediate 255 tert-Butyl 3-(5-((((7-methoxy-3-(5-methylisoxazol-3-yl)-[1,2,4]triazolo[4,3-b]pyridazin-6-yl)oxy)methyl)-1H-pyrazolo[4,3-b]naphthalen-1-yl)azetidine-1-carboxylate

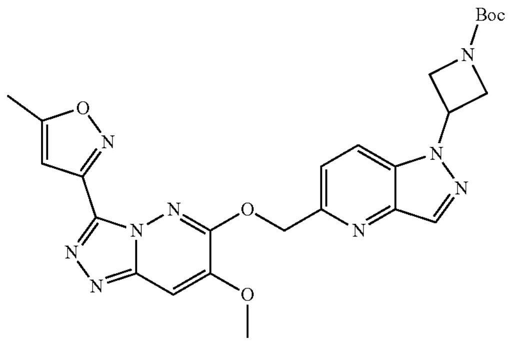 [SMILES: COc1cc2nnc(-c3cc(C)on3)n2nc1OCc1ccc2c(cnn2C2CN(C(=O)OC(C)(C)C)C2)n1]

The experimental operation was the same as that of embodiment 226. The title compound ((260 mg, 57%) as a yellow solid was obtained from raw materials tert-butyl 3-(5-(hydroxymethyl)-1H-pyrazolo[4,3-b]pyridin-2-yl)azetidine-1-carboxylate (260 mg, 0.86 mmol) and 3-(6-chloro-7-methoxy-[1,2,4]triazolo[4,3-b]pyridazin-3-yl)-5-methylisoxazole (230 mg, 0.86 mmol). LC-MS: m/z $[M+H]^+$=534.

Intermediate 256

3-(6-((1-(Azetidin-3-yl)-1H-pyrazolo[4,3-b]pyridin-5-yl)methoxy)-7-methoxy-[1,2,4]triazolo[4,3-b]pyridazin-3-yl)-5-methylisoxazole

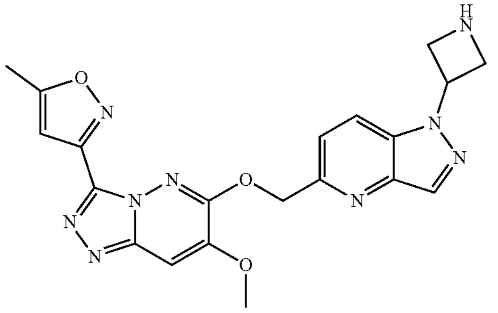 [SMILES: COc1cc2nnc(-c3cc(C)on3)n2nc1OCc1ccc2c(cnn2C2CNC2)n1]

The experimental operation was the same as that of intermediate 253. The title compound (170 mg, 80.5%) as a yellow solid was obtained from raw material tert-butyl 3-(5-((((7-methoxy-3-(5-methylisoxazol-3-yl)-[1,2,4]triazolo[4,3-b]pyridazin-6-yl)oxy)methyl)-1H-pyrazolo[4,3-b]naphthalen-1-yl)azetidine-1-carboxylate (260 mg, 0.49 mmol). LC-MS: m/z $[M+H]^+$=434.

Intermediate 257

Methyl 2-isopropyl-2H-pyrazolo[4,3-b]pyridine-5-carboxylate (Intermediate 257-A)

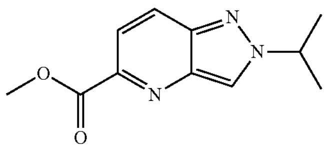 [SMILES: COC(=O)c1ccc2nn(C(C)C)cc2n1]

Methyl 1-isopropyl-1H-pyrazolo[4,3-b]pyridine-5-carboxylate (Intermediate 257-B)

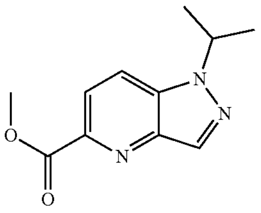 [SMILES: COC(=O)c1ccc2c(cnn2C(C)C)n1]

The experimental operation was the same as the synthesis method of intermediate 232. From raw materials methyl 2H-pyrazolo[4,3-b]pyridine-5-carboxylate (500 mg, 2.82 mmol) and 2-iodopropane (960 mg, 5.65 mmol), the title compound as a yellow liquid was obtained, and a large polar component methyl 2-isopropyl-2H-pyrazolo[4,3-b]pyridine-5-carboxylate (260 mg, 42%) and a small polar component methyl 1-isopropyl-1H-pyrazolo[4,3-b]pyridine-5-carboxylate (350 mg, 56.6%) were obtained. LC-MS: m/z $[M+H]^+$=220.

Intermediate 258

(2-isopropyl-2H-pyrazolo[4,3-b]pyridin-5-yl)methanol

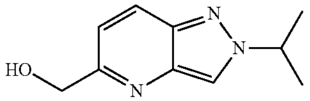

The experimental operation was the same as the synthesis method of intermediate 233. The title compound (120 mg, 55%) as a yellow solid was obtained from raw material methyl 2-isopropyl-2H-pyrazolo[4,3-b]pyridine-5-carboxylate (250 mg, 1.14 mmol). LC-MS: m/z $[M+H]^+$=192.

Intermediate 259

(1-Isopropyl-1H-pyrazolo[4,3-b]pyridin-5-yl)methanol

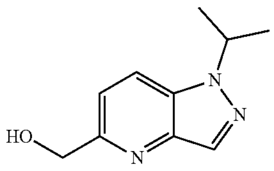

The experimental operation was the same as the synthesis method of intermediate 233. The title compound (220 mg, 72%) as a yellow oil was obtained from raw material methyl 1-isopropyl-1H-pyrazolo[4,3-b]pyridine-5-carboxylate (350 mg, 1.6 mmol). LC-MS: m/z $[M+H]^+$=192.

Intermediate 260

Methyl 1-methyl-1H-pyrazolo[4,3-b]pyridine-5-carboxylate (intermediate 260-A)

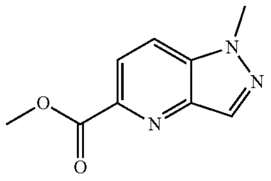

Methyl 2-methyl-2H-pyrazolo[4,3-b]pyridine-5-carboxylate (intermediate 260-B)

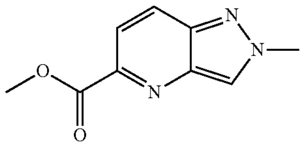

The experimental operation was the same as the synthesis method of intermediate 232. From raw materials methyl 2H-pyrazolo[4,3-b]pyridine-5-carboxylate (500 mg, 2.82 mmol) and iodomethane (800 mg, 5.65 mmol), the title compound as a yellow solid was obtained, and a large polar component methyl 2-methyl-2H-pyrazolo[4,3-b]pyridine-5-carboxylate (270 mg, 50%) and a small polar component methyl 1-methyl-1H-pyrazolo[4,3-b]pyridine-5-carboxylate (200 mg, 37%) were obtained. LC-MS: m/z $[M+H]^+$=192.

Intermediate 261

(2-Methyl-2H-pyrazolo[4,3-b]pyridin-5-yl)methanol

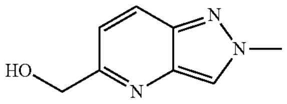

The experimental operation was the same as the synthesis method of intermediate 233. The title compound (200 mg, 117%) as a yellow oil was obtained from raw material methyl 2-methyl-2H-pyrazolo[4,3-b]pyridine-5-carboxylate (200 mg, 1.05 mmol). LC-MS: m/z $[M+H]^+$=164.

Intermediate 262

Methyl 2-(tetrahydro-2H-pyran-4-yl)-2H-pyrazolo[4,3-b]pyridine-5-carboxylate (Intermediate 262-A)

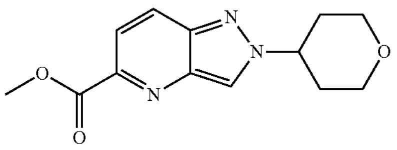 [SMILES: COC(=O)c1ccc2nn(C3CCOCC3)cc2n1]

Methyl 1-(tetrahydro-2H-pyran-4-yl)-1H-pyrazolo[4,3-b]pyridine-5-carboxylate (Intermediate 262-B)

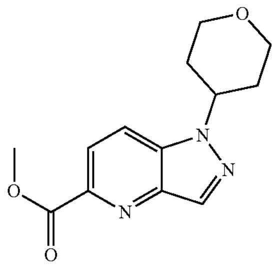 [SMILES: COC(=O)c1ccc2c(cnn2C2CCOCC2)n1]

The experimental operation was the same as the synthesis method of intermediate 232. From raw materials methyl 2H-pyrazolo[4,3-b]pyridine-S-carboxylate (500 mg, 2.82 mmol) and tetrahydro-2H-pyran-4-yl-4-methylbenzene-sulfonate (1400 mg, 5.65 mmol), the title compound as a yellow solid was obtained, and a large polar component methyl 2-(tetrahydro-2H-pyran-4-yl)-2H-pyrazolo[4,3-b]pyridine-5-carboxylate (220 mg, 29.8%) and a small polar component methyl 1-(tetrahydro-2H-pyran-4-yl)-1H-pyrazolo[4,3-b]pyridine-5-carboxylate (220 mg, 29.8%) were obtained. LC-MS: m/z $[M+H]^+$=262.

Intermediate 263

(2-(Tetrahydro-2H-pyran-4-yl)-2H-pyrazolo[4,3-b]pyridin-5-yl)methanol

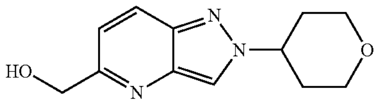

The experimental operation was the same as the synthesis method of intermediate 233. The title compound (60 mg, 30.6%) as a white solid was obtained from raw material methyl 2-(tetrahydro-2H-pyran-4-yl)-2H-pyrazolo[4,3-b]pyridine-5-carboxylate (220 mg, 0.84 mmol). LC-MS: m/z $[M+H]^+$=234.

Intermediate 264

(1-(Tetrahydro-2H-pyran-4-yl)-1H-pyrazolo[4,3-b]pyridin-5-yl)methanol

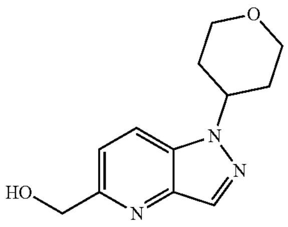 [SMILES: OCc1ccc2c(cnn2C2CCOCC2)n1]

The experimental operation was the same as the synthesis method of intermediate 233. The title compound (100 mg, 51%) as a white solid was obtained from raw material methyl 1-(tetrahydro-2H-pyran-4-yl)-1H-pyrazolo[4,3-b]pyridine-5-carboxylate (220 mg, 0.84 mmol). LC-MS: m/z $[M+H]^+$=234.

Intermediate 265

Methyl 2-(2-methoxyethyl)-2H-pyrazolo[4,3-b]pyridine-5-carboxylate (Intermediate 265-A)

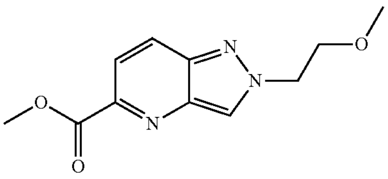

Methyl 1-(2-methoxyethyl)-1H-pyrazolo[4,3-b]pyridine-5-carboxylate (Intermediate 265-B)

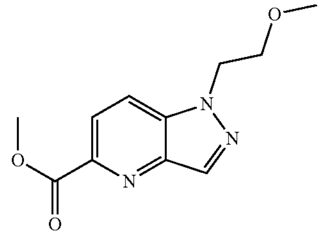 [SMILES: COCCn1ncc2nc(C(=O)OC)ccc21]

The experimental operation was the same as the synthesis method of intermediate 232. From raw materials methyl 2H-pyrazolo[4,3-b]pyridine-5-carboxylate (500 mg, 2.82 mmol) and 1-bromo-2-methoxyethane (780 mg, 5.65 mmol), the title compound as a yellow solid was obtained, and a large polar component methyl 2-(2-methoxyethyl)-2H-pyrazolo[4,3-b]pyridine-5-carboxylate (290 mg, 43.7%) and a small polar component methyl 1-(2-methoxyethyl)-1H-pyrazolo[4,3-b]pyridine-5-carboxylate (340 mg, 51.2%) were obtained.

LC-MS: m/z $[M+H]^+$=236.

Intermediate 266

(2-(2-Methoxyethyl)-2H-pyrazolo[4,3-b]pyridin-5-yl)methanol

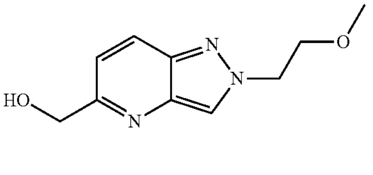

The experimental operation was the same as the synthesis method of intermediate 233. The title compound (100 mg, 39%) as a yellow oil was obtained from raw material methyl 2-(2-methoxyethyl)-2H-pyrazolo[4,3-b]pyridine-5-carboxylate (290 mg, 1.23 mmol). LC-MS: m/z $[M+H]^+$=208.

Intermediate 267

(1-(2-Methoxyethyl)-1H-pyrazolo[4,3-b]pyridin-5-yl)methanol

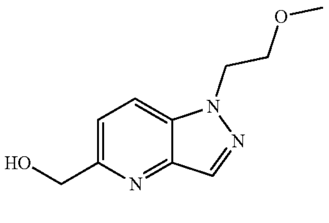

The experimental operation was the same as the synthesis method of intermediate 233. The title compound (200 mg, 66.7%) as a yellow oil was obtained from raw material methyl 1-(2-methoxyethyl)-1H-pyrazolo[4,3-b]pyridine-5-carboxylate (340 mg, 1.45 mmol). LC-MS: m/z $[M+H]^+$=208.

Intermediate 268

3-Methyl-1-(oxetan-3-yl)-1H-pyrazolo[4,3-b]pyridine (Intermediate 268-A)

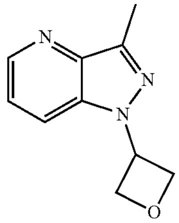

3-Methyl-2-(oxetan-3-yl)-2H-pyrazolo[4,3-b]pyridine (Intermediate 268-B)

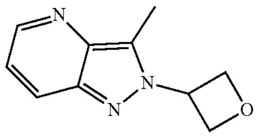

Under the protection of nitrogen and at 80° C., 3-methyl-1H-pyrazolo[4,3-b]pyridine (3.0 g, 22.5 mmol), 3-iodooxetane (4.97 g, 27.0 mmol) and cesium carbonate (8.81 g, 27.0 mmol) were dissolved in N,N-dimethylformamide (40 mL), and the reaction solution was stirred for 3 hours. After the reaction was completed, the reaction solution was concentrated, and the residue was purified by preparative liquid phase to obtain a small polar component 3-methyl-1-(oxetan-3-yl)-1H-pyrazolo[4,3-b]pyridine (2.3 g, a white solid) with a yield of 54%, LC-MS: m/z $[M+H]^+$=190; and to obtain a large polar component 3-methyl-2-(oxetan-3-yl)-

2H-pyrazolo[4,3-b]pyridine (0.5 g, a white solid) with a yield of 11.7%. LC-MS: m/z $[M+H]^+=190$.

Intermediate 269

3-Methyl-1-(oxetan-3-yl)-1H-pyrazolo[4,3-b]pyridine 4-oxide

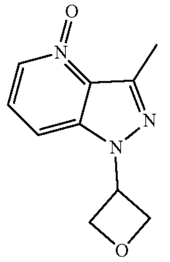

3-Methyl-1-(oxetan-3-yl)-1H-pyrazolo[4,3-b]pyridine (1.6 g, 8.72 mmol) was dissolved in dichloromethane (20 mL), then m-chloroperoxybenzoic acid (3.8 g, 21.8 mmol) was added thereto, and the reaction solution was stirred at room temperature for 16 hours. After the reaction was completed, the reaction solution was concentrated, and the residue was purified by column chromatography (dichloromethane/methanol=10/1) to obtain the title product (1.7 g, a pale yellow solid) with a yield of 99%. LC-MS: m/z $[M+H]^+=206$.

Intermediate 270

3-Methyl-1-(oxetan-3-yl)-1H-pyrazolo[4,3-b]pyridine-5-carbonitrile

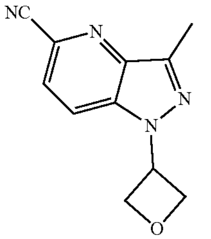 [SMILES: Cc1nn(C2COC2)c2ccc(C#N)nc12]

3-Methyl-1-(oxetan-3-yl)-1H-pyrazolo[4,3-b]pyridine 4-oxide (1.7 g, 8.8 mmol) was dissolved in dichloromethane (25 mL). Trimethylsilyl cyanide (1.61 g, 16.4 mmol) and dimethylcarbamoyl chloride (1.77 g, 16.4 mmol) were added thereto, and the reaction solution was stirred at 30° C. for 16 hours. The reaction solution was concentrated, and the residue was purified by column chromatography (dichloromethane/methanol=10/1) to obtain the title product (1.2 g, a white solid) with a yield of 69%. LC-MS: m/z $[M+H]^+=215$.

Intermediate 271

3-Methyl-1-(oxetan-3-yl)-1H-pyrazolo[4,3-b]pyridine-5-carboxylic acid

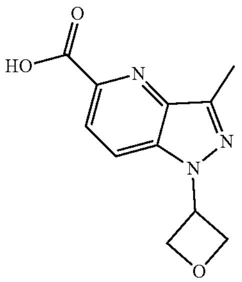 [SMILES: Cc1nn(C2COC2)c2ccc(C(=O)O)nc12]

3-Methyl-1-(oxetan-3-yl)-1H-pyrazolo[4,3-b]pyridine-5-carbonitrile (500 mg, 2.3 mmol) was dissolved in ethanol (20 mL), then a saturated aqueous solution of sodium hydroxide (934 mg, 23.4 mmol) was added thereto, and the reaction solution was stirred at 90° C. for 2 hours. After the reaction was completed, the reaction solution was cooled to room temperature; the pH of the reaction solution was adjusted to <7 with 1 N hydrochloric acid, then the reaction solution was extracted with ethyl acetate, and the organic phase was dried, and concentrated to obtain the title product (437 mg, a white solid) with a yield of 54%. LC-MS: m/z $[M+H]^+=234$.

Intermediate 272

Methyl 3-methyl-1-(oxetan-3-yl)-1H-pyrazolo[4,3-b]pyridine-5-carboxylate

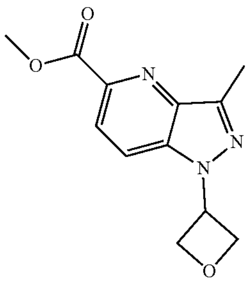

Under the condition of nitrogen, 3-methyl-1-(oxetan-3-yl)-1H-pyrazolo[4,3-b]pyridine-5-carboxylic acid (280 mg, 1.2 mmol) was dissolved in methanol/toluene=1/4 (7.5 mL), then (trimethylsilyl) diazomethane (466 mg, 4.1 mmol) was added thereto, and the reaction solution was stirred at room temperature for 2 hours. After the reaction was completed, the reaction solution was concentrated to obtain the title product (130 mg, a white solid) with a yield of 44%. LC-MS: m/z $[M+H]^+=248$.

Intermediate 273

(3-Methyl-1-(oxetan-3-yl)-1H-pyrazolo[4,3-b]pyridine-5-yl)methanol

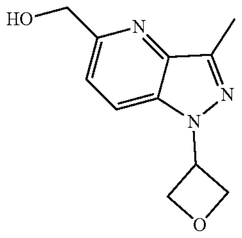 [SMILES: Cc1nn(C2COC2)c2ccc(CO)nc12]

Under the condition of nitrogen, methyl 3-methyl-1-(oxetan-3-yl)-1H-pyrazolo[4,3-b]pyridine-5-carboxylate (130 mg, 0.52 mmol) was dissolved in tetrahydrofuran (5 mL). Anhydrous calcium chloride (117 mg, 1.04 mmol) and sodium borohydride (40 mg, 1.04 mmol) were added thereto, and the reaction solution was stirred at 60° C. for 8 hours. After the reaction was completed, the reaction solution was concentrated, and the residue was purified by column chromatography to obtain the title product (90 mg, a white solid) with a yield of 78%. LC-MS: m/z $[M+H]^+$=220.

Intermediate 274

3-Methyl-2-(oxetan-3-yl)-2H-pyrazolo[4,3-b]pyridine 4-oxide

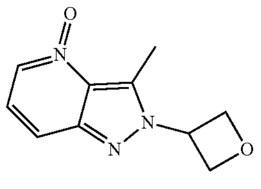

3-Methyl-2-(oxetan-3-yl)-2H-pyrazolo[4,3-b]pyridine (0.5 g, 2.65 mmol) was dissolved in dichloromethane (10 mL), then m-chloroperoxybenzoic acid (1.14 g, 6.6 mmol) was added thereto, and the reaction solution was stirred at 24° C. for 16 hours. After the reaction was completed, the reaction solution was concentrated, and the residue was purified by column chromatography (dichloromethane/methanol=10/1) to obtain the title product (380 mg, a pale yellow solid) with a yield of 70%. LC-MS: m/z $[M+H]^+$=206.

Intermediate 275

3-Methyl-2-(oxetan-3-yl)-2H-pyrazolo[4,3-b]pyridine-5-carbonitrile

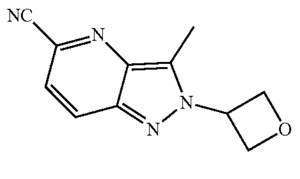 [SMILES: Cc1c2nc(C#N)ccc2nn1C1COC1]

3-Methyl-2-(oxetan-3-yl)-2H-pyrazolo[4,3-b]pyridine 4-oxide (330 mg, 1.61 mmol) was dissolved in dichloromethane (10 mL). Trimethylsilyl cyanide (320 mg, 3.2 mmol) and dimethylcarbamoyl chloride (346 mg, 3.2 mmol) were added thereto, and the reaction solution was stirred at 30° C. for 16 hours. The reaction solution was concentrated, and the residue was purified by column chromatography (dichloromethane/methanol=10/1) to obtain the title product (280 mg, a white solid) with a yield of 80%. LC-MS: m/z $[M+H]^+$=215.

Intermediate 276

3-Methyl-2-(oxetan-3-yl)-2H-pyrazolo[4,3-b]pyridine-5-carboxylic acid

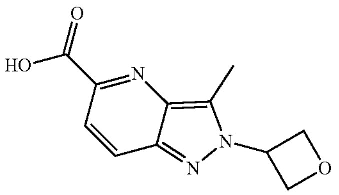 [SMILES: Cc1c2nc(C(=O)O)ccc2nn1C1COC1]

3-Methyl-2-(oxetan-3-yl)-2H-pyrazolo[4,3-b]pyridine-5-carbonitrile (280 mg, 1.3 mmol) was dissolved in ethanol (20 mL), then a saturated aqueous solution of sodium hydroxide (523 mg, 13.1 mmol) was added thereto, and the reaction was stirred at 90° C. for 2 hours. After the reaction was completed, the reaction solution was cooled to room temperature, and the pH of the reaction solution was adjusted to <7 with 1 N hydrochloric acid; the reaction solution was extracted with ethyl acetate, and the organic phase was dried, and concentrated to obtain the title product (110 mg, a white solid) with a yield of 34%. LC-MS: m/z $[M+H]^+$=234.

Intermediate 277

Methyl 3-methyl-2-(oxetan-3-yl)-2H-pyrazolo[4,3-b]pyridine-5-carboxylate

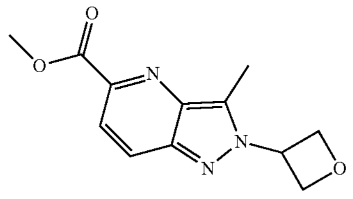 [SMILES: COC(=O)c1ccc2nn(C3COC3)c(C)c2n1]

Under the condition of nitrogen, 3-methyl-2-(oxetan-3-yl)-2H-pyrazolo[4,3-b]pyridine-5-carboxylic acid (130 mg, 0.56 mmol) was dissolved in methanol/toluene=1/4 (7.5 mL), then (trimethylsilyl) diazomethane (191 mg, 1.67 mmol) was added thereto, and the reaction solution was stirred at room temperature for 2 hours. After the reaction was completed, the reaction solution was concentrated to obtain the title product (110 mg, a white solid) with a yield of 79%. LC-MS: m/z $[M+H]^+$=248.

Intermediate 278

(3-Methyl-2-(oxetan-3-yl)-2H-pyrazolo[4,3-b]pyridine-5-yl)methanol

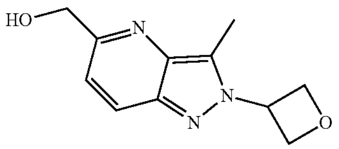 [SMILES: Cc1c2nc(CO)ccc2nn1C1COC1]

Under the condition of nitrogen, methyl 3-methyl-2-(oxetan-3-yl)-2H-pyrazolo[4,3-b]pyridine-5-carboxylate (110 mg, 0.44 mmol) was dissolved in tetrahydrofuran (5 mL). Anhydrous calcium chloride (99 mg, 0.88 mmol) and sodium borohydride (34 mg, 1.04 mmol) were added thereto, and the reaction solution was stirred at 60° C. for 8 hours. After the reaction was completed, the reaction solution was concentrated, and the residue was purified by column chromatography to obtain the title product (30 mg, a white solid) with a yield of 34%. LC-MS: m/z $[M+H]^+$ =220.

Intermediate 279

1-Ethyl-3-methyl-1H-pyrazolo[4,3-b]pyridine (Intermediate 279-A)

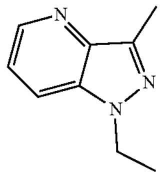

2-Ethyl-3-methyl-2H-pyrazolo[4,3-b]pyridine (Intermediate 279-B)

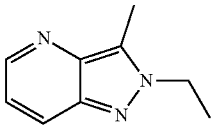

3-Methyl-1H-pyrazolo[4,3-b]pyridine (2.0 g, 15 mmol) was dissolved in N,N-dimethylformamide (20 mL), and the reaction solution was added with sodium hydride (720 mg, 18.0 mmol, 60% dispersed in mineral oil) after cooling in an ice bath. The reaction solution was stirred for 30 minutes, then iodoethane (2.8 g, 18.0 mmol) was added thereto, and the reaction solution was stirred for 16 hours. The reaction solution was quenched by adding water, extracted with ethyl acetate, washed with saturated sodium chloride. The organic phase was dried, concentrated, and the residue was purified by preparative liquid phase to obtain a small polar component of a white solid 1-ethyl-3-methyl-1H-pyrazolo[4,3-b]pyridine (1.0 g, a yield of 43%). MS m/z (ESI): 162 [M+1]. A large polar component 2-ethyl-3-methyl-2H-pyrazolo[4,3-b]pyridine (0.8 g, a white solid) with a yield of 34% was obtained. MS m/z (ESI): 162 [M+1].

Intermediate 280

1-Ethyl-3-methyl-1H-pyrazolo[4,3-b]pyridine 4-oxide

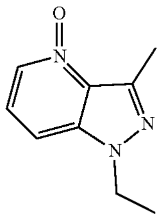

1-Ethyl-3-methyl-1H-pyrazolo[4,3-b]pyridine (1.0 g, 6.2 mmol) was dissolved in dichloromethane (20 mL), then m-chloroperoxybenzoic acid (2.14 g, 12.4 mmol) was added thereto, and the reaction solution was stirred at room temperature for 16 hours. The reaction solution was concentrated, and the residue was purified by column chromatography (dichloromethane/methanol=10/1) to obtain the title product (0.8 g, a pale yellow solid) with a yield of 73%. MS m/z (ESI): 178 [M+1].

Intermediate 281

1-Ethyl-3-methyl-1H-pyrazolo[4,3-b]pyridine-5-carbonitrile

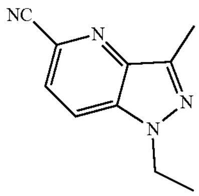

1-Ethyl-3-methyl-1H-pyrazolo[4,3-b]pyridine 4-oxide (0.4 g, 2.26 mmol) was dissolved in dichloromethane (8 mL). Trimethylsilyl cyanide (0.45 g, 4.5 mmol) and dimethylcarbamoyl chloride (0.24 g, 2.26 mmol) were added thereto, and the reaction solution was stirred at 30° C. for 16 hours. The reaction solution was concentrated, and the residue was purified by column chromatography (dichloromethane/methanol=10/1) to obtain the title product (0.3 g, a white solid) with a yield of 71%. MS m/z (ESI): 187 [M+1].

Intermediate 282

1-Ethyl-3-methyl-1H-pyrazolo[4,3-b]pyridine-5-carboxylic acid

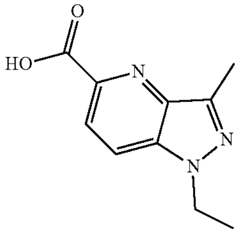

1-Ethyl-3-methyl-1H-pyrazolo[4,3-b]pyridine-5-carbonitrile (300 mg, 1.61 mmol) was dissolved in concentrated hydrochloric acid (5 mL), and the reaction solution was stirred at 100° C. for 2 hours. The reaction solution was cooled to room temperature, and the pH of the reaction solution was adjusted to 6 to 7 with aqueous sodium bicarbonate solution; the reaction solution was extracted with ethyl acetate, and the organic phase was dried, and concentrated to obtain the title product (200 mg, a white solid) with a yield of 61%. MS m/z (ESI): 206 [M+1].

Intermediate 283

Methyl 1-ethyl-3-methyl-1H-pyrazolo[4,3-b]pyridine-5-carboxylate

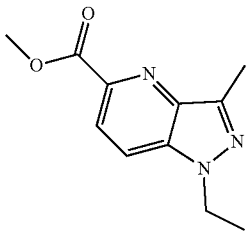

Under the condition of nitrogen, 1-ethyl-3-methyl-1H-pyrazolo[4,3-b]pyridine-5-carboxylic acid (200 mg, 0.97 mmol) was dissolved in methanol/toluene=1/4 (7.5 mL), then (trimethylsilyl) diazomethane (336 mg, 2.9 mmol) was added thereto, and the reaction solution was stirred at room temperature for 2 hours. The reaction solution was concentrated, and the residue was purified to obtain the title product (200 mg, a white solid) with a yield of 93.6%. MS m/z (ESI): 220 [M+1].

Intermediate 284

(1-Ethyl-3-methyl-1H-pyrazolo[4,3-b]pyridin-5-yl) methanol

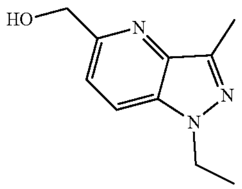

Under the condition of nitrogen, methyl 1-ethyl-3-methyl-1H-pyrazolo[4,3-b]pyridine-5-carboxylate (200 mg, 0.9 mmol) was dissolved in tetrahydrofuran (6 mL). Anhydrous calcium chloride (0.2 g, 1.8 mmol) and sodium borohydride (70 mg, 1.8 mmol) were added thereto, and the reaction solution was stirred at 60° C. for 8 hours. The reaction solution was concentrated, and the residue was purified by column chromatography (petroleum ether/ethyl acetate=10/1) to obtain the title product (80 mg, a white solid) with a yield of 46%. MS m/z (ESI): 193 [M+1].

Intermediate 285

2-Ethyl-3-methyl-2H-pyrazolo[4,3-b]pyridine 4-oxide

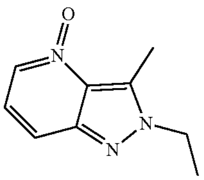

2-Ethyl-3-methyl-2H-pyrazolo[4,3-b]pyridine (0.8 g, 5.0 mmol) was dissolved in dichloromethane (16 mL), then m-chloroperoxybenzoic acid (1.72 g, 9.92 mmol) was added thereto, and the reaction solution was stirred at room temperature for 16 hours. The reaction solution was concentrated, and the residue was purified by column chromatography (dichloromethane/methanol=10/1) to obtain the title product (0.64 g, a pale yellow solid) with a yield of 73%. MS m/z (ESI): 178 [M+1].

Intermediate 286

2-Ethyl-3-methyl-2H-pyrazolo[4,3-b]pyridine-5-carbonitrile

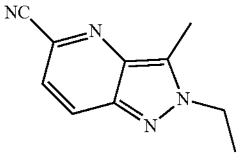

2-Ethyl-3-methyl-2H-pyrazolo[4,3-b]pyridine 4-oxide (0.4 g, 2.26 mmol) was dissolved in dichloromethane (8 mL). Trimethylsilyl cyanide (0.45 g, 4.5 mmol) and dimethylcarbamoyl chloride (0.24 g, 2.26 mmol) were added thereto, and the reaction solution was stirred at 30° C. for 16 hours. The reaction solution was concentrated, and the residue was purified by column chromatography (dichloromethane/methanol=10/1) to obtain the title product (0.3 g, a white solid) with a yield of 71%. MS m/z (ESI): 187 [M+1].

Intermediate 287

2-Ethyl-3-methyl-2H-pyrazolo[4,3-b]pyridine-5-carboxylic acid

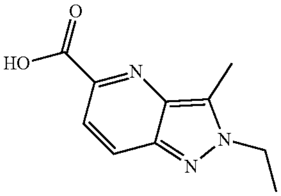

2-Ethyl-3-methyl-2H-pyrazolo[4,3-b]pyridine-5-carbonitrile (300 mg, 1.61 mmol) was dissolved in concentrated hydrochloric acid (5 mL), and the reaction solution was stirred at 100° C. for 2 hours. The reaction solution was cooled to room temperature, and the pH of the reaction solution was adjusted to 6 to 7 with aqueous sodium bicarbonate solution; the reaction solution was extracted with ethyl acetate, and the organic phase was dried, and concentrated to obtain the title product 2-ethyl-3-methyl-2H-pyrazolo[4,3-b]pyridine-5-carboxylic acid (200 mg, a white solid) with a yield of 61%. MS m/z (ESI): 206 [M+1].

Intermediate 288

Methyl 2-ethyl-3-methyl-2H-pyrazolo[4,3-b]pyridine-5-carboxylate

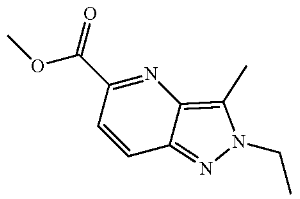 [SMILES: CCn1nc2ccc(C(=O)OC)nc2c1C]

Under the condition of nitrogen, 2-ethyl-3-methyl-2H-pyrazolo[4,3-b]pyridine-5-carboxylic acid (200 mg, 0.97 mmol) was dissolved in methanol/toluene=1/4 (7.5 mL), then (trimethylsilyl) diazomethane (336 mg, 2.9 mmol) was added thereto, and the reaction solution was stirred at room temperature for 2 hours. The reaction solution was concentrated, and the title product (200 mg, a white solid) with a yield of 93.6% was obtained from the residue. MS m/z (ESI): 220 [M+1].

Intermediate 289

(2-Ethyl-3-methyl-2H-pyrazolo[4,3-b]pyridine-5-yl) methanol

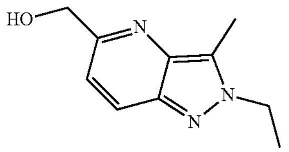

Under the condition of nitrogen, methyl 2-ethyl-3-methyl-2H-pyrazolo[4,3-b]pyridine-5-carboxylate (200 mg, 0.9 mmol) was dissolved in tetrahydrofuran (6 mL). Anhydrous calcium chloride (0.2 g. 1.8 mmol) and sodium borohydride (70 mg, 1.8 mmol) were added thereto, and the reaction solution was stirred at 60° C. for 8 hours. The reaction solution was concentrated, and the residue was purified by column chromatography (petroleum ether/ethyl acetate=10/1) to obtain the title product (80 mg, a white solid) with a yield of 46%. MS m/z (ESI): 193 [M+1].

Intermediate 290

Methyl 3H-imidazo[4,5-b]pyridine-5-carboxylate

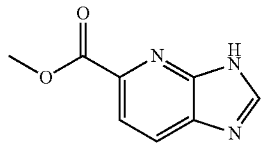

3H-Imidazo[4,5-b]pyridine-5-carboxylic acid (0.50 g, 3.07 mmol) and thionyl chloride (1 mL) were sequentially added to methanol (10 mL), and the mixture was stirred at 80° C. for 2 hours. The reaction solution was evaporated to dryness by rotary evaporation to obtain the title compound (0.60 g, a crude product). LC-MS: m/z $[M+H]^+$=178.

Intermediate 291

Methyl 3-(tetrahydrofuran-3-yl)-3H-imidazo[4,5-b]pyridine-5-carboxylate (Intermediate 291-A)

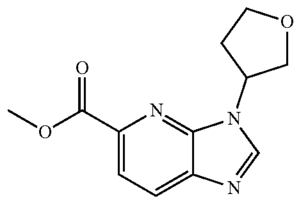 [SMILES: COC(=O)c1ccc2ncn(C3CCOC3)c2n1]

Methyl 1-(tetrahydrofuran-3-yl)-1H-pyrazolo[4,5-b]pyridine-5-carboxylate (Intermediate 291-B)

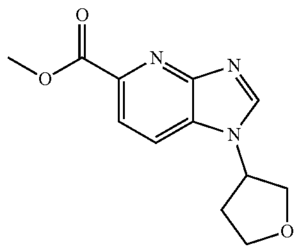 [SMILES: COC(=O)c1ccc2c(ncn2C2CCOC2)n1]

Methyl 3H-imidazo[4,5-b]pyridine-5-carboxylate (600 mg, 3.39 mmol), 3-iodotetrahydrofuran (1008 mg, 5.09 mmol) and potassium carbonate (1403 mg, 10.17 mmol) were added into N,N-dimethylformamide (10 mL), and the mixture was stirred at 80° C. for 16 hours. The mixture was separated by preparative thin layer chromatography (petroleum ether/ethyl acetate=1/1) to obtain a mixture of the two title compounds (1000 mg, a crude product) as a pale yellow oily liquid. LC-MS: m/z $[M+H]^+$=248.

Intermediate 292

(3-(Tetrahydrofuran-3-yl)-3H-imidazo[4,5-b]pyridin-5-yl)methanol (Intermediate 292-A)

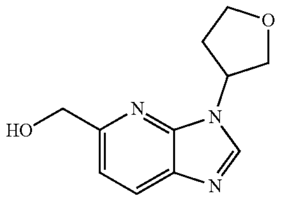 [SMILES: OCc1ccc2ncn(C3CCOC3)c2n1]

(1-(Tetrahydrofuran-3-yl)-1H-imidazo[4,5-b]pyridin-5-yl)methanol (Intermediate 292-B)

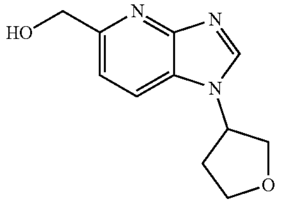 [SMILES: OCc1ccc2c(ncn2C2CCOC2)n1]

Tetrahydrofuran (10 mL), a mixture of methyl 3-(tetrahydrofuran-3-yl)-3H-imidazo[4,5-b]pyridine-5-carboxylate and methyl 1-(tetrahydrofuran-3-yl)-1H-pyrazolo[4,5-b]pyridine-5-carboxylate (1000 mg, 4.05 mmol), and sodium borohydride (770 mg, 20.25 mmol) were sequentially added to methanol (10 mL), and the mixture was stirred at room temperature for 16 hours. The solid in the reaction solution was filtered out, and the filtrate was concentrated and then separated by preparative thin layer chromatography (dichloromethane/methanol=20/1) to obtain a pale yellow oily liquid (3-(tetrahydrofuran-3-yl)-3H-imidazo[4,5-b]pyridin-5-yl)methanol (90 mg, 10.1%), and a pale yellow oily liquid (1-(tetrahydrofuran-3-yl)-1H-imidazo[4,5-b]pyridin-5-yl) methanol (40 mg, 4.5%). LC-MS: m/z $[M+H]^+$=220.

Intermediate 293

Methyl 3-(tetrahydro-2H-pyran-4-yl)-3H-imidazo[4,5-b]pyridine-5-carboxylate (Intermediate 293-A)

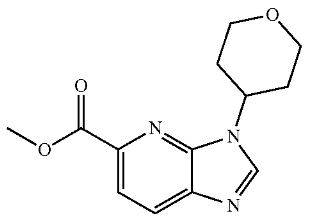 [SMILES: COC(=O)c1ccc2ncn(C3CCOCC3)c2n1]

Methyl 1-(tetrahydro-2H-pyran-4-yl)-1H-pyrazolo[4,5-b]pyridine-5-carboxylate (Intermediate 293-B)

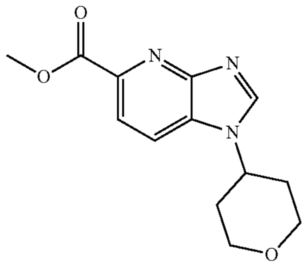 [SMILES: COC(=O)c1ccc2c(ncn2C2CCOCC2)n1]

Methyl 3H-imidazo[4,5-b]pyridine-5-carboxylate (700 mg, 3.95 mmol), tetrahydro-2H-pyran-4-yl-4-methylbenzenesulfonate (2022 mg, 7.90 mmol) and potassium carbonate (1635 mg, 11.85 mmol) were added to N,N-dimethylformamide (20 mL), and the mixture was stirred at 80° C. for 16 hours. The reaction solution was added dropwise to an aqueous solution (50 mL), extracted with ethyl acetate (30 mL*3). The aqueous phase was concentrated, and then separated by preparative thin layer chromatography (dichloromethane/methanol=30/1) to obtain a white solid methyl 1-(tetrahydro-2H-pyran-4-yl)-1H-pyrazolo[4,5-b]pyridine-5-carboxylate (400 mg, 38.7%). The organic phase was concentrated, and then separated by preparative thin layer chromatography (dichloromethane/methanol=30/1) to obtain a pale yellow oily liquid methyl 3-(tetrahydro-2H-pyran-4-yl)-3H-imidazo[4,5-b]pyridine-5-carboxylate (300 mg, 29.0%). LC-MS: m/z $[M+H]^+$=262.

Intermediate 294

(3-(Tetrahydro-2H-pyran-4-yl)-3H-imidazo[4,5-b]pyridin-5-yl)methanol

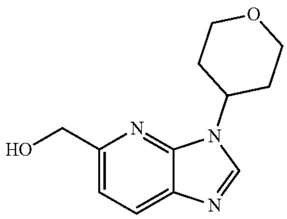 [SMILES: OCc1ccc2ncn(C3CCOCC3)c2n1]

Tetrahydrofuran (5 mL), methyl 3-(tetrahydro-2H-pyran-4-yl)-3H-imidazo[4,5-b]pyridine-5-carboxylate (250 mg, 0.96 mmol), and sodium borohydride (182 mg, 4.80 mmol) were sequentially added to methanol (5 mL), and the mixture was stirred at room temperature for 16 hours. The solid in the reaction solution was filtered out, and the filtrate was concentrated, and then separated by preparative thin layer chromatography (dichloromethane/methanol=20/1) to obtain the title compound (70 mg, 31.4%) as a pale yellow oily liquid. LC-MS: m/z $[M+H]^+$=234.

Intermediate 295

(1-(Tetrahydro-2H-pyran-4-yl)-1H-imidazo[4,5-b]pyridin-5-yl)methanol

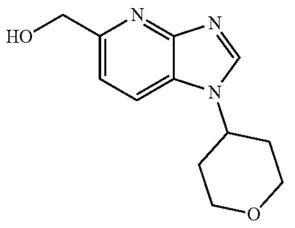 [SMILES: OCc1ccc2c(ncn2C2CCOCC2)n1]

Tetrahydrofuran (5 mL), methyl 1-(tetrahydro-2H-pyran-4-yl)-1H-imidazo[4,5-b]pyridine-5-carboxylate (400 mg, 1.54 mmol), and sodium borohydride (293 mg, 7.70 mmol) were sequentially added to methanol (5 mL), and the mixture was stirred at room temperature for 16 hours. The solid in the reaction solution was filtered out, and the filtrate was concentrated, and then separated by preparative thin layer chromatography (dichloromethane/methanol=20/1) to obtain the title compound (200 mg, 55.6%) as a pale yellow oily liquid. LC-MS: m/z $[M+H]^+$=234.

Intermediate 296

Ethyl 3-ethyl-3H-imidazo[4,5-b]pyridine-5-carboxylate

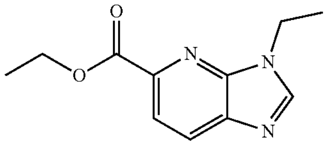 [SMILES: CCOC(=O)c1ccc2ncn(CC)c2n1]

3H-Imidazo[4,5-b]pyridine-5-carboxylic acid (500 mg, 3.07 mmol), iodoethane (1437 mg, 9.21 mmol) and potassium carbonate (1271 mg, 9.21 mmol) were added to N,N-dimethylformamide (10 mL), and the mixture was stirred at 80° C. for 4 hours. The mixture was separated by preparative thin layer chromatography (petroleum ether/ethyl acetate=1/1) to obtain the title compound (600 mg, a crude product) as a pale yellow oily liquid. LC-MS: m/z $[M+H]^+$=220.

Intermediate 297

(3-Ethyl-3H-imidazo[4,5-b]pyridin-5-yl)methanol

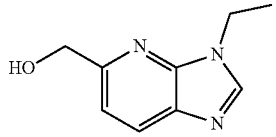

Tetrahydrofuran (5 mL), ethyl 3-ethyl-3H-imidazo[4,5-b]pyridine-5-carboxylate (600 mg, 2.75 mmol), and sodium borohydride (868 mg, 22.85 mmol) were sequentially added to methanol (5 mL), and the mixture was stirred at room temperature for 16 hours. The solid in the reaction solution was filtered out, and the filtrate was concentrated, and then separated by preparative thin layer chromatography (dichloromethane/methanol=20/1) to obtain the title compound (100 mg, 20.7%) as a white solid. LC-MS: m/z $[M+H]^+$=178.

Intermediate 298

Methyl 1-(oxetan-3-yl)-1H-pyrrolo[3,2-b]pyridine-5-carboxylate

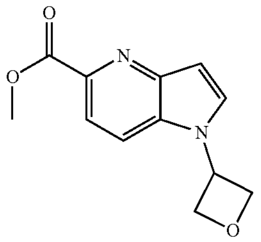 [SMILES: COC(=O)c1ccc2c(ccn2C2COC2)n1]

Methyl 1H-pyrrolo[3,2-b]pyridine-5-carboxylate (300 mg, 1.70 mmol), 3-iodooxetane (627 mg, 3.41 mmol) and potassium carbonate (440 mg, 3.41 mmol) were added to N,N-dimethylformamide (4 mL), and the mixture was reacted at 105° C. for 24 hours. The reaction solution was filtered under reduced pressure, concentrated, and subjected to preparative thin layer chromatography (dichloromethane/methanol=45/1) to obtain the title compound (68 mg, 17.2%) as a white solid. LC-MS: m/z $[M+H]^+$=233.

Intermediate 299

(1-(Oxetan-3-yl)-1H-pyrrolo[3,2-b]pyridin-5-yl)methanol

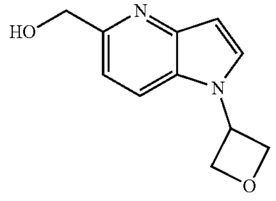 [SMILES: OCc1ccc2c(ccn2C2COC2)n1]

Methyl 1-(oxetan-3-yl)-1H-pyrrolo[3,2-b]pyridine-S-carboxylate (65 mg, 0.29 mmol) was added to a mixed solution of tetrahydrofuran (2 mL) and methanol (0.5 mL). Sodium borohydride (50 mg, 1.32 mmol) was added to the reaction solution in two batches, and the reaction was carried out at room temperature for 1 hour. Methanol (20 mL) was added to the reaction solution to quench, and the mixture was concentrated, and subjected to preparative thin layer chromatography (dichloromethane/methanol=15/1) to obtain the title compound (22 mg, 37.2%) as a yellow liquid. LC-MS: m/z $[M+H]^+$=205.

Intermediate 300

Methyl 1-(tetrahydro-2H-pyran-4-yl)-1H-pyrrolo[3,2-b]pyridine-5-carboxylate

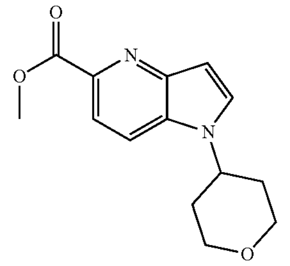 [SMILES: COC(=O)c1ccc2c(ccn2C2CCOCC2)n1]

Methyl 1H-pyrrolo[3,2-b]pyridine-5-carboxylate (300 mg, 1.71 mmol), tetrahydro-2H-pyran-4-yl-4-methylbenzenesulfonate (877 mg, 3.41 mmol) and potassium carbonate (470 mg, 3.41 mmol) were added to DMF (3.5 mL), and the mixture was reacted at 105° C. for 24 hours. The reaction solution was filtered under reduced pressure, concentrated, and subjected to preparative thin layer chromatography (dichloromethane/methanol=40/1) to obtain the title compound (105 mg, 23.7%) as a yellow solid. LC-MS: m/z $[M+H]^+$=261.

Intermediate 301

(1-(Tetrahydro-2H-pyran-4-yl)-1H-pyrrolo[3,2-b]pyridin-5-yl)methanol

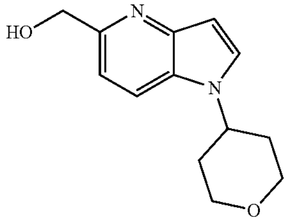 [SMILES: OCc1ccc2c(ccn2C2CCOCC2)n1]

Methyl 1-(tetrahydro-2H-pyran-4-yl)-1H-pyrrolo[3,2-b]pyridine-5-carboxylate (105 mg, 0.40 mmol) was added to a mixed solution of tetrahydrofuran (2 mL) and methanol (0.5 mL). Sodium borohydride (31 mg, 0.81 mmol) was added to the reaction solution, and the mixture was stirred at room temperature for 30 minutes. The reaction solution was quenched by adding methanol (10 mL), concentrated, and subjected to preparative thin layer chromatography (dichloromethane/methanol=10/1) to obtain the title compound (52 mg, 55.4%) as a yellow oily liquid. LC-MS: m/z $[M+H]^+$=233.

Intermediate 302

Methyl 1-(tetrahydro-2H-pyran-4-yl)-1H-pyrrolo[2,3-b]pyridine-6-carboxylate

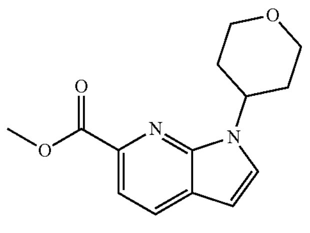 [SMILES: COC(=O)c1ccc2ccn(C3CCOCC3)c2n1]

Methyl 1H-pyrrolo[2,3-b]pyridine-6-carboxylate (200 mg, 1.14 mmol), tetrahydro-2H-pyran-4-yl 4-methylbenzenesulfonate (438 mg, 1.71 mmol) and potassium carbonate (472 mg, 3.42 mmol) were added to N,N-dimethylformamide (5 mL), and the mixture was stirred at 100° C. for 16 hours. The reaction mixture was added dropwise to an aqueous solution (50 mL), extracted with ethyl acetate (30 mL*3), and the organic phases were combined and washed with saturated brine (50 mL). The organic phase was concentrated and then separated by preparative thin layer chromatography (petroleum ether/ethyl acetate=3/1) to obtain the title compound (120 mg, 40.5%) as a pale yellow oily liquid. LC-MS: m/z $[M+H]^+$=261.

Intermediate 303

(1-(Tetrahydro-2H-pyran-4-yl)-1H-pyrrolo[2,3-b]pyridin-6-yl)methanol

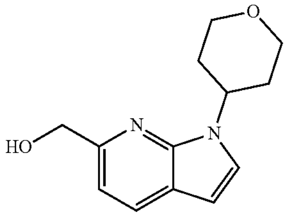 [SMILES: OCc1ccc2ccn(C3CCOCC3)c2n1]

Tetrahydrofuran (2 mL), methyl 1-(tetrahydro-2H-pyran-4-yl)-1H-pyrrolo[2,3-b]pyridine-6-carboxylate (120 mg, 0.46 mmol) and sodium borohydride (35 mg, 0.92 mmol) were sequentially added to methanol (2 mL), and the mixture was stirred at room temperature for 16 hours. The solid in the reaction solution was filtered out, and the filtrate was concentrated, and then separated by preparative thin layer chromatography (dichloromethane/methanol=20/1) to obtain the title compound (50 mg, 47.2%) as a white solid. LC-MS: m/z $[M+H]^+$=233.

Embodiment 1 (Method A)

3-(7-Methoxy-6-((1-methyl-1H-1,2,4-triazol-5-yl)methoxy)-[1,2,4]triazolo[4,3-b]pyridazin-3-yl)-5-methylisoxazole

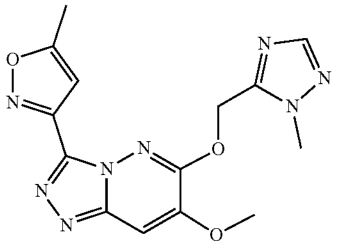 [SMILES: COc1cc2nnc(-c3cc(C)on3)n2nc1OCc1ncnn1C]

3-(6-Chloro-7-methoxy-[1,2,4]triazolo[4,3-b]pyridazin-3-yl)-5-methylisoxazole (60 mg, 0.23 mmol), (1-methyl-1H-1,2,4-triazol-5-yl)methanol (26 mg, 0.23 mmol) and cesium carbonate (147 mg, 0.45 mmol) were sequentially added to acetonitrile (3 mL), then the reaction mixture was stirred at 50° C. for 16 hours. The mixture was poured into ice water, and the precipitated solid was collected by filtration and dried to obtain 51.0 mg of the title compound as a white solid with a yield of 66%. $^1$H NMR (400 MHz, DMSO-$d_6$) δ 7.98 (s, 1H), 7.77 (s, 1H), 7.09 (s, 1H), 5.66 (s, 2H), 3.98 (s, 3H), 3.94 (s, 3H), 2.56 (s, 3H). LC-MS: m/z [M+H]$^+$=343.

Embodiment 11

6-(((7-Methoxy-3-(5-methylisoxazol-3-yl)-[1,2,4]triazolo[4,3-b]pyridazin-6-yl)oxy)methyl)-N-(2,2,2-trifluoroethyl)nicotinamide

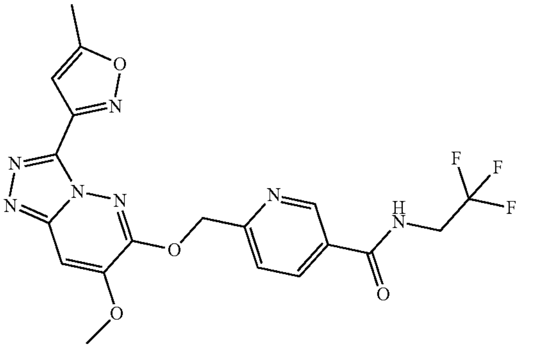 [SMILES: COc1cc2nnc(-c3cc(C)on3)n2nc1OCc1ccc(C(=O)NCC(F)(F)F)cn1]

6-[7-Methoxy-3-(5-methyl-isoxazol-3-yl)-[1,2,4]triazolo[4,3-b]pyridazin-6-yloxymethyl]-nicotinic acid (200 mg, 0.52 mmol), HOBT (210 mg, 1.56 mmol) and EDCI (210 mg, 1.56 mmol) were sequentially added to 5 mL of DMF. 2,2,2-Trifluoro ethylamine (1410 mg, 1.0 mmol) and triethylamine (0.5 mL) were sequentially added to the mixture, and then the mixture was stirred at room temperature overnight. The mixture was diluted with ethyl acetate (10 mL), washed once with brine (20 mL), dried with anhydrous sodium sulfate, and concentrated. The residue was purified by preparative TLC (dichloromethane/methanol=15/1) to obtain 8 mg of the target compound as a white solid with a yield of 3% and a white solid appearance. $^1$H NMR (400 MHz, DMSO-$d_6$) δ 9.37-9.29 (m, 1H), 9.06 (d, J=2.0 Hz, 1H), 8.29 (dd, J=2.2, 8.1 Hz, 1H), 7.77 (s, 1H), 7.75 (d, J=7.8 Hz, 1H), 6.81 (s, 1H), 5.63 (s, 2H), 4.18-4.06 (m, 2H), 4.00 (s, 3H), 2.53 (s, 3H). LC-MS: m/z [M+H]$^+$=464.

Embodiment 12 (Method B)

6-(((7-Ethoxy-3-(5-methylisoxazol-3-yl)-[1,2,4]triazolo[4,3-b]pyridazin-6-yl)oxy)methyl)-N-ethylnicotinamide

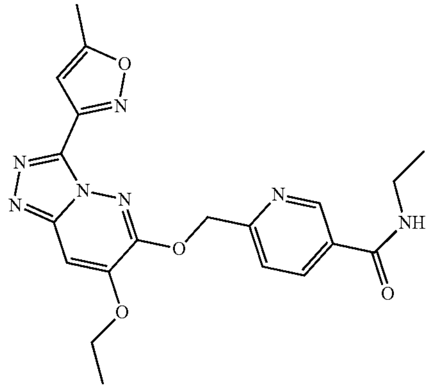 [SMILES: CCNC(=O)c1ccc(COc2nn3c(-c4cc(C)on4)nnc3cc2OCC)nc1]

6-Chloro-7-ethoxy-3-(5-methyl-isoxazol-3-yl)-[1,2,4]triazolo[4,3-b]pyridazine (110 mg, 0.39 mmol), N-ethyl-6-hydroxymethyl-nicotinamide (71 mg, 0.39 mmol) and cesium carbonate (252 mg, 0.78 mmol) were sequentially added to 20 mL of acetonitrile, then the mixture was heated to 50° C. and stirred for 2 hours, and filtered. The filtrate was concentrated, and the residue was purified by preparative thin layer chromatography plate (dichloromethane/methanol=20/1) or column chromatography to obtain 30 mg of the title compound as a white solid with a yield of 18% and a white solid appearance. $^1$H NMR (400 MHz, DMSO-$d_6$) δ 9.01 (br. s., 1H), 8.68-8.69 (m, 1H), 8.20-8.25 (m, 1H), 7.75 (s, 2H), 6.78 (s, 1H), 5.62 (br. s., 2H), 4.28 (d, J=6.85 Hz, 2H), 3.25-3.31 (m, 2H), 2.53 (br. s., 3H), 1.42 (t, J=6.60 Hz, 3H), 1.12 (t, J=6.85 Hz, 3H). LC-MS: m/z [M+H]$^+$=424.

Embodiment 28

3-(7-Methoxy-6-(pyridin-2-ylmethoxy)-[1,2,4]triazolo[4,3-b]pyridazin-3-yl)-5-(methoxymethyl)isoxazole

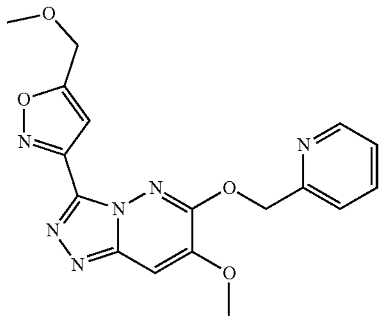 [SMILES: COCc1cc(-c2nnc3cc(OC)c(OCc4ccccn4)nn23)no1]

N-(5-Methoxy-6-(2-pyridyl-methoxy)pyridazin-3-yl)-5-(methoxymethyl)isoxazole-3-carbohydrazide (120 mg, 0.31 mmol) was added to acetic acid (3 mL), and the mixture was stirred at 100° C. for 5 hours. The reaction solution was concentrated, then diluted with dichloromethane and methanol (10/1), washed with saturated aqueous sodium carbonate solution, concentrated, and subjected to column chromatography (dichloromethane/methanol=30/1) to obtain the title compound (45 mg, 6%) as a pale yellow solid. $^1$H NMR (400 MHz, DMSO-$d_6$): δ 8.62-8.60 (m, 1H), 7.88-7.84 (m, 1H), 7.78 (s, 1H), 7.63-7.61 (m, 1H), 7.40-7.37 (m, 1H), 7.17 (s, 1H), 5.56 (s, 2H), 4.69 (s, 2H), 4.00 (s, 3H), 3.38 (s, 3H). LC-MS: m/z [M+H]$^+$=369.

Embodiment 33 (Method C)

3-(7-Methoxy-6-(pyridinyl-2-methoxy)-[1,2,4]-triazolo[4,3-b]pyridazin-3-yl)-5-methylisoxazole

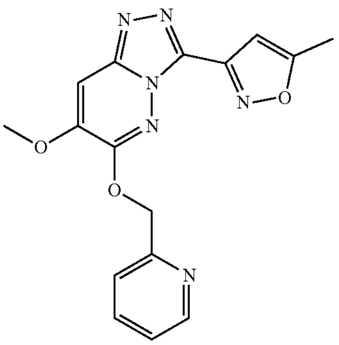

The raw material 2-piconol (314 mg, 2.88 mmol) was dissolved in tetrahydrofuran (5 mL), and bistrimethylsilyl amide lithium (tetrahydrofuran solution, 1 M, 3.6 mL, 3.6 mmol) was added to the solution at 0° C. The mixture was reacted at 0° C. for 30 minutes, and then the raw material 3-(6-chloro-7-methoxy-[1,2,4]triazolo[4,3-b]pyridazin-3-yl)-5-methylisoxazole (636 mg, 2.4 mmol) was added thereto. Then, the reaction was carried out at 50° C. overnight. After the reaction was completed, water (100 mL) was added to the reaction solution, then the mixture was extracted with dichloromethane/methanol=10/1. The organic phase was collected, dried with anhydrous sodium sulfate, concentrated, and subjected to column chromatography (dichloromethane/methanol=100/1 to 90/1 to 80/1) to obtain the title compound as a yellow solid (650 mg, 80.1%). $^1$H NMR (400 MHz, DMSO-$d_6$): δ 8.63-8.61 (m, 1H), 7.89-7.85 (m, 1H), 7.76 (s, 1H), 7.63-7.61 (m, 1H), 7.41-7.38 (m, 1H), 6.88 (s, 1H), 5.55 (s, 2H), 4.00 (s, 3H), 2.55 (s, 3H). LC-MS: m/z $[M+H]^+$=339.

Embodiment 46

(3-(7-Methoxy-6-(pyridin-2-ylmethoxy)-[1,2,4]triazolo[4,3-b]pyridazin-3-yl]isoxazol-5-yl)methanol

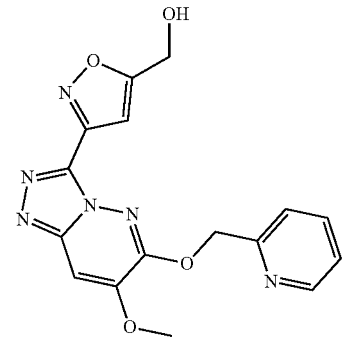 [SMILES: COc1cc2nnc(-c3cc(CO)on3)n2nc1OCc1ccccn1]

6-Chloro-4-methoxy-3-(pyridine-2-methoxy)pyridazine and an isomer thereof (500 mg, 2 mmol), referring to intermediate 21, 5-(hydroxymethyl)isoxazole-3-formylhydrazide (470 mg, 3 mmol) and p-toluenesulfonic acid monohydrate (380 mg, 2 mmol) were dissolved in 1,4-dioxane (9 mL), and the mixture was reacted at 120° C. for 3 hours. The reaction solution was mixed directly with silica gel and subjected to column (dichloromethane:methanol=100/1-10/1) to obtain a brown solid. Then the brown solid was subjected to thin layer chromatography (dichloromethane/methanol=15/1) to obtain an orange solid, and the orange solid was then separated by thin layer chromatography (dichloromethane:methanol=15:1) to obtain the title compound (17 mg, a yield of 2%) as a yellow solid. $^1$H NMR (400 MHz, $CD_3OD$): δ 8.579 (d, J=5.6 Hz, 1H), 7.91-7.88 (m, 1H), 7.734 (d, J=7.6 Hz, 1H), 7.50 (s, 1H), 7.42-7.39 (m, 1H), 7.07 (s, 1H), 5.63 (s, 2H), 4.80 (s, 2H), 4.07 (s, 3H). LC-MS: m/z $[M+H]^+$=355.

Embodiment 47

(3-(7-Methoxy-6-((5-methoxypyridin-2-yl)methoxy)-[1,2,4]triazolo[4,3-b]pyridazine-3-yl)isoxazol-5-yl)methanol

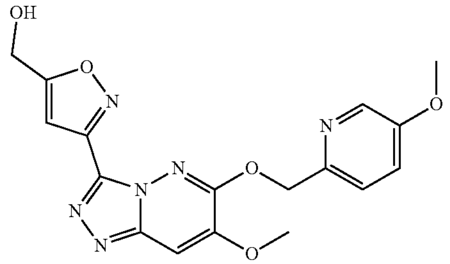 [SMILES: COc1ccc(COc2nn3c(-c4cc(CO)on4)nnc3cc2OC)nc1]

6-Chloro-4-methoxy-3-((5-methoxypyridin-2-yl)methoxy)pyridazine and an isomer thereof (200 mg, 0.71 mmol, prepared with reference to intermediate 21), 5-(hydroxymethyl)isoxazole-3-formylhydrazide (167 mg, 1.06 mmol) and p-toluenesulfonic acid (122 mg, 0.71 mmol) were dissolved in 1,4-dioxane (4 mL), and the mixture was reacted at 120° C. for 3 hours. The reaction solution was diluted with a sodium bicarbonate solution, extracted with (dichloromethane/methanol=10/1), and the organic phase was dried with anhydrous sodium sulfate, and concentrated to obtain a brown solid. 5 mL of acetic acid was added thereto at 90° C., and the mixture was reacted for 2 hours. The reaction solution was directly concentrated, dissolved in (dichloromethane/methanol=10/1), washed with sodium bicarbonate solution, dried with anhydrous sodium sulfate, concentrated, and separated by thin layer chromatography (dichloromethane:methanol=20:1) to obtain the title compound (17 mg, 6.2%) as a yellow solid. $^1$H NMR (400 MHz, $CD_3OD$): δ=8.28 (s, 1H), 7.724 (d, J=8.8 Hz, 1H), 7.50-7.46 (m, 2H), 7.15 (s, 1H), 5.58 (s, 2H), 4.71 (s, 2H), 4.07 (s, 3H), 3.91 (s, 3H). LC-MS: m/z $[M+H]^+$=385.

Embodiment 48

3-(7-Methoxy-6-((5-methoxypyridin-2-yl)methoxy)-[1,2,4]triazolo[4,3-b]pyridazine-3-yl)-5-(methoxymethyl)isoxazole

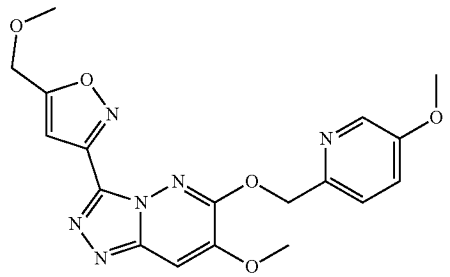 [SMILES: COCc1cc(-c2nnc3cc(OC)c(OCc4ccc(OC)cn4)nn23)no1]

6-Chloro-4-methoxy-3-((5-methoxypyridin-2-yl)methoxy)pyridazine and an isomer thereof (200 mg, 2 mmol, synthesized with reference to intermediate 21), 5-(methoxymethyl)isoxazole-3-formylhydrazide (182 mg, 1.06 mmol) and p-toluenesulfonic acid (122 mg, 0.71 mmol) were dissolved in 1,4-dioxane (4 mL). The experimental operation was shown in Embodiment 47 to obtain the title compound (16 mg, 5.6%) as a white solid. $^1H$ NMR (400 MHz, $CD_3OD$): δ=8.28 (d, J=2.4 Hz, 1H), 7.72 (d, J=8.8 Hz, 1H), 7.51-7.45 (m, 2H), 7.19 (s, 1H), 5.58 (s, 2H), 4.73 (s, 2H), 4.07 (s, 3H), 3.90 (s, 3H), 3.50 (s, 3H). LC-MS: m/z $[M+H]^+$=399.

Embodiment 63

6-(((7-Methoxy-3-(5-methylisoxazol-3-yl)-[1,2,4] triazolo[4,3-b]pyridazin-6-yl)oxy)methyl)nicotinate

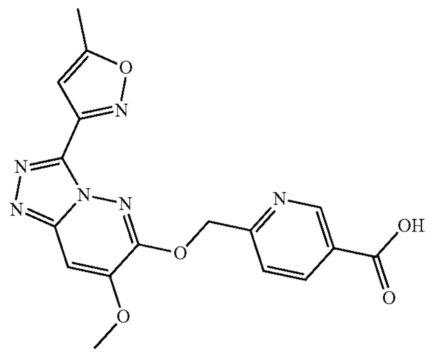 [SMILES: COc1cc2nnc(-c3cc(C)on3)n2nc1OCc1ccc(C(=O)O)cn1]

Methyl 6-[7-methoxy-3-(5-methyl-isoxazol-3-yl)-[1,2,4] triazolo[4,3-b]pyridazin-6-yloxymethyl]-nicotinate (300 mg, 0.75 mmol), 1M lithium hydroxide (1.5 mL, 1.5 mmol) were sequentially added to 10 mL of ethanol, and the mixture was stirred at room temperature for 1 hour. The mixture was added with 0.5 M hydrochloric acid to neutralize to pH=7, diluted with water, extracted with ethyl acetate. It was found that the product had good water solubility, so the water phase was evaporated to dryness to obtain 200 mg of the title compound as a yellow solid, with a yield of 70% and a yellow solid appearance. LC-MS: m/z $[M+H]^+$=383.

Embodiment 69 (Method D)

3-(7-Methoxy-6-((5-(pyrrolidin-2-yl)pyridin-2-yl) methoxy)-[1,2,4]triazolo[4,3-b]pyridazin-3-yl)-5-methylisoxazole

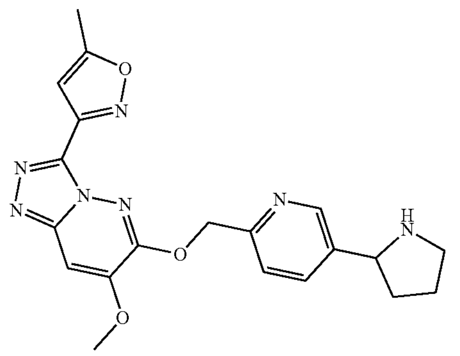 [SMILES: COc1cc2nnc(-c3cc(C)on3)n2nc1OCc1ccc(C2CCCN2)cn1]

From tert-butyl 2-(6-hydroxymethylpyridin-3-yl)pyrrolidine carboxylate (188 mg, 0.68 mmol), 3-(6-chloro-7-methoxy-[1,2,4]triazolo[4,3-b]pyridazin-3-yl)-5-methylisoxazole (150 mg, 0.56 mmol), same as method C, a product tert-butyl 2-(6-(((7-methoxy-3-(5-methylisoxazol-3-yl)-[1,2,4]-triazolo[4,3-b]pyridazin-6-yl)oxy)methyl) pyridin-3-yl)pyrrolidine-1-carboxylate (120 mg, 42%) was obtained as a pale yellow solid, which was dissolved in dichloromethane (3 mL). Trifluoroacetic acid (1 mL) was added thereto, and the mixture was stirred at room temperature for 3 hours. The reaction solution was poured into water; the pH of the reaction solution was adjusted to >=11 with 1M sodium hydroxide solution, and the reaction solution was extracted, dried, concentrated and separated by column chromatography (dichloromethane/methanol=30/1-8/1) to obtain the title compound (26.6 mg, a two-step yield of 11%) as an off-white solid. $^1H$ NMR (400 MHz, DMSO-$D_6$) δ 8.59 (s, 1H), 7.84-7.82 (m, 1H), 7.76 (s, 1H), 7.59-7.57 (m, 1H), 6.91 (s, 1H), 4.17-4.14 (m, 1H), 3.99 (s, 3H), 3.04-3.00 (m, 1H), 2.97-2.93 (m, 1H), 2.56 (s, 3H), 2.19-2.15 (m, 1H), 1.81-1.76 (m, 2H), 1.54-1.51 (m, 1H). LC-MS: m/z $[M+H]^+$=408.0.

Embodiment 78

3-(6-(5,6,7,8-Tetrahydro-1,6-naphthyridin-2-yl) methoxy)-7-methoxy-[1,2,4]triazolo[4,3-b] pyridazin-3-yl)-5-methylisoxazole Intermediates tert-butyl 2-(hydroxymethyl)-7,8-dihydro-1,6-naphthyridine-6(5H)-carboxylate (0.50 g/1.89 mmol) and 3-(6-chloro-7-methoxy-[1,2,4]triazolo[4,3-b]pyridazin-3-yl)-5-methylisoxazole (0.53 g/1.05 mmol) (the synthesis method referred to: method B) were reacted to obtain a crude product (0.88 g) as a white solid. The above crude product was added to 20 mL of HCl/EtOAc (2.6 mol/L/4.04 mmol) solution, and the mixture was stirred and reacted at 25 to 30° C. for 3 hours. Sampling was controlled, the reaction was complete; the reaction solution was filtered, and the filter cake was dried to obtain a white solid (0.57 g) with a yield of 93.07%. $^1H$ NMR (400 MHz, DMSO-$d_6$) δ 7.74 (s, 1H), 7.49 (d, J=7.8 Hz, 1H), 7.38 (d, J=7.8 Hz, 1H), 6.99 (s, 1H), 5.46 (s, 2H), 3.98 (s, 3H), 3.87 (s, 2H), 3.04 (t, J=5.9 Hz, 2H), 2.85-2.75 (m, 2H), 2.56 (s, 3H); LC-MS: m/z $[M+H]^+$=395.

Embodiment 79 (Method E)

3-(6-(6-Ethyl-5,6,7,8-tetrahydro-1,6-naphthalen-2-yl)methoxy)-7-methoxy-[1,2,4]triazolo[4,3-b] pyridazin-3-yl)-5-methylisoxazole

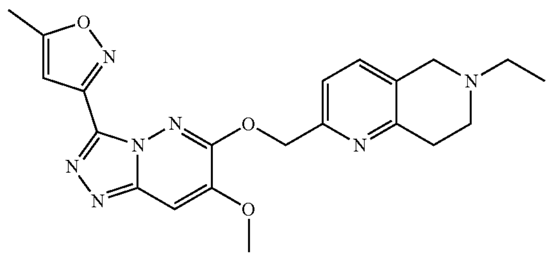 [SMILES: CCN1CCc2nc(COc3nn4c(-c5cc(C)on5)nnc4cc3OC)ccc2C1]

3-(7-Methoxy-6-((5,6,7,8-tetrahydro-1,6-naphthalen-2-yl)methoxy)-[1,2,4]triazolo[4,3-b]pyridazinpyridin-3-yl)-5-methylisoxazole (Embodiment 78) (40 mg, 0.1 mmol), iodoethane (23 mg, 0.15 mmol) and potassium carbonate (28 mg, 0.2 mmol) were sequentially added to DMF (1 mL), and the reaction mixture was stirred at room temperature overnight. The mixture was poured into water, extracted with ethyl acetate, dried, and concentrated to obtain a crude product, and separated by thin layer chromatography to obtain 14.7 mg of the title compound with a yield of 35% and a white solid appearance. $^1$H NMR (400 MHz, DMSO-$d_6$) δ 7.76 (s, 1H), 7.57 (d, J=7.8 Hz, 1H), 7.41 (d, J=7.8 Hz, 1H), 6.98 (d, J=1.0 Hz, 1H), 5.47 (s, 2H), 3.98 (s, 3H), 3.63 (m, 2H), 2.93 (m, 2H), 2.81 (m, 2H), 2.67 (m, 2H), 2.56 (s, 3H), 1.11 (t, J=6.8 Hz, 3H). LC-MS: m/z $[M+H]^+$=422.

Embodiment 84

3-(7-Methoxy-6-((6-(oxetan-3-yl)-5,6,7,8-tetrahydro-1,6-naphthyridin-2-yl)methoxy)-[1,2,4]triazolo[4,3-b]pyridazin-3-yl)-5-methylisoxazole

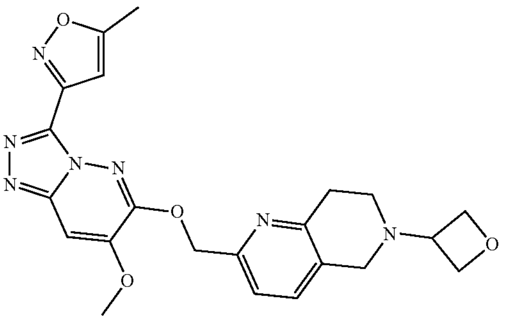 [SMILES: COc1cc2nnc(-c3cc(C)on3)n2nc1OCc1ccc2c(n1)CCN(C1COC1)C2]

3-(7-Methoxy-6-((5,6,7,8-tetrahydro-1,6-naphthyridin-2-yl)methoxy)-[1,2,4]triazolo[4,3-b]pyridazin-3-yl)-5-methylisoxazole (25 mg, 0.064 mmol), oxetan-3-one (23 mg, 0.32 mmol) and sodium triacetoxyborohydride (68 mg, 0.32 mmol) were sequentially added to 1,2-dichloroethane (3 mL), and the reaction mixture was stirred at room temperature overnight. The mixture was poured into saturated sodium bicarbonate solution, extracted with dichloromethane, dried, concentrated to obtain a crude product, purified by thin layer chromatography to obtain 24.1 mg of the title compound with a yield of 84% and a white solid appearance. $^1$H NMR (400 MHz, $CDCl_3$) δ 7.47 (d, J=7.8 Hz, 1H), 7.39 (d, J=7.8 Hz, 1H), 7.26 (s, 1H), 6.79 (s, 1H), 5.57 (s, 2H), 4.80-4.63 (m, 4H), 4.00 (s, 3H), 3.71 (t, J=6.6 Hz, 1H), 3.52 (s, 2H), 3.08 (t, J=5.9 Hz, 2H), 2.71 (t, J=6.1 Hz, 2H), 2.55 (s, 3H) LC-MS: m/z $[M+H]^+$=450.

Embodiment 84

3-(7-Methoxy-6-((6-(oxetan-3-yl)-5,6,7,8-tetrahydro-1,6-naphthyridin-2-yl)methoxy)-[1,2,4]triazolo[4,3-b]pyridazin-3-yl)-5-methylisoxazole

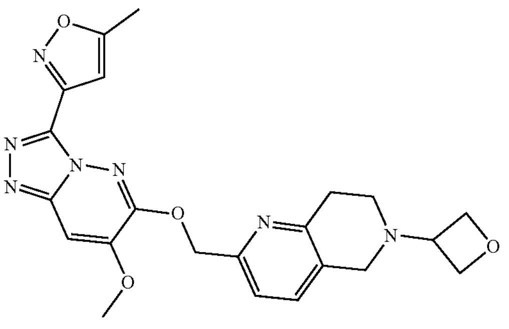 [SMILES: COc1cc2nnc(-c3cc(C)on3)n2nc1OCc1ccc2c(n1)CCN(C1COC1)C2]

Method 1: intermediate 141: (6-(oxetan-3-yl)-5,6,7,8-tetrahydro-1,6-naphthyridin-2-yl)methanol and intermediate 1:3-(6-chloro-7-methoxy-[1,2,4]triazolo[4,3-b]pyridazin-3-yl)-5-methylisoxazole were prepared to obtain Embodiment 84 (the synthetic method referred to Embodiment 12: method B).

Method 2:

3-(7-Methoxy-6-((5,6,7,8-tetrahydro-1,6-naphthyridin-2-yl)methoxy)-[1,2,4]triazolo[4,3-b]pyridazin-3-yl)-5-methylisoxazole (compound of Embodiment 78) (25 mg, 0.064 mmol), oxetan-3-one (23 mg, 0.32 mmol) and sodium triacetoxyborohydride (68 mg, 0.32 mmol) were sequentially added to 1,2-dichloroethane (3 mL), and the reaction mixture was stirred at room temperature overnight. The mixture was poured into saturated sodium bicarbonate solution, extracted with dichloromethane, dried, concentrated to obtain a crude product, purified by thin layer chromatography to obtain 24.1 mg of the title compound with a yield of 84% and a white solid appearance. $^1$H NMR (400 MHz, $CDCl_3$) δ 7.47 (d, J=7.8 Hz, 1H), 7.39 (d, J=7.8 Hz, 1H), 7.26 (s, 1H), 6.79 (s, 1H), 5.57 (s, 2H), 4.80-4.63 (m, 4H), 4.00 (s, 3H), 3.71 (t, J=6.6 Hz, 1H), 3.52 (s, 2H), 3.08 (t, J=5.9 Hz, 2H), 2.71 (t, J=6.1 Hz, 2H), 2.55 (s, 3H).

LC-MS: m/z $[M+H]^+$=450.

Embodiment 87

3-(7-Methoxy-6-((6-phenyl-5,6,7,8-tetrahydro-1,6-naphthalen-2-yl)methoxy)-[1,2,4]triazolo[4,3-b]pyridazin-3-yl)-5-methylisoxazole

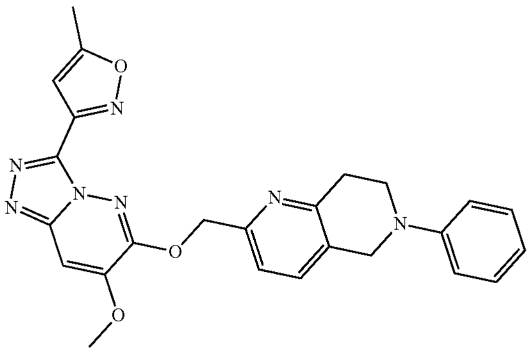 [SMILES: COc1cc2nnc(-c3cc(C)on3)n2nc1OCc1ccc2c(n1)CCN(c1ccccc1)C2]

3-(7-Methoxy-6-((5,6,7,8-tetrahydro-1,6-naphthalen-2-yl)methoxy)-[1,2,4]triazolo[4,3-b]pyridazinpyridin-3-yl)-5-methylisoxazole (Embodiment 78) (200 mg, 0.5 mmol), triphenylbismuth (440 mg, 1 mmol) and copper acetate (181 mg, 1 mmol) were sequentially added to 50 mL of dichloromethane, and the mixture was stirred at room temperature overnight. The solid was filtered through celite and the organic phase was concentrated. The residue was purified by preparative TLC (dichloromethane/methanol=20/1) to obtain 110 mg of the target compound as a white solid with a yield of 47% and a white solid appearance. $^1$H NMR (400 MHz, $CDCl_3$) δ 7.54 (d, J=2.93 Hz, 2H) 7.28-7.33 (m, 2H) 7.24 (br. s., 1H) 7.01 (d, J=8.31 Hz, 2H) 6.88 (s, 1H) 6.81 (s, 1H) 5.62 (s, 2H) 4.42 (s, 2H) 4.02 (s, 3H) 3.69 (t, J=5.87 Hz, 2H) 3.19 (t, J=5.87 Hz, 2H) 2.57 (s, 3H). LC-MS: m/z $[M+H]^+$=470.

Embodiment 88 (Method F)

2-(((7-Methoxy-3-(5-methylisoxazol-3-yl)-[1,2,4]triazolo[4,3-b]pyridazin-6-yl)oxy)methyl)-6-(pyrimidin-2-ylmethyl)-7,8-dihydro-1,6-naphthyridin-5(6H)-one

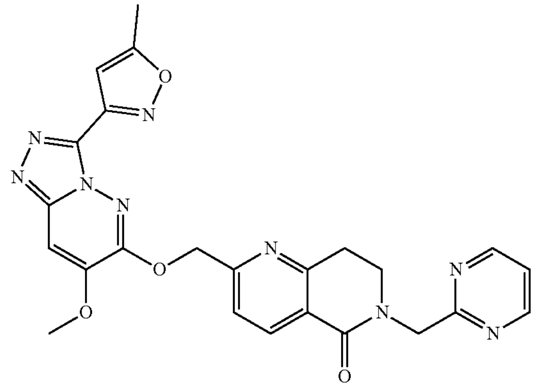 [SMILES: COc1cc2nnc(-c3cc(C)on3)n2nc1OCc1ccc2c(n1)CCN(Cc1ncccn1)C2=O]

3-(7-Methoxy-6-((5,6,7,8-tetrahydro-1,6-naphthalen-2-yl)methoxy)-[1,2,4]triazolo[4,3-b]pyridazinpyridin-3-yl)-5-methyl-isoxazole (120 mg, 0.64 mmol), pyrimidine-2-methylmethanesulfonate (274 mg, 0.64 mmol) and triethylamine (193 mg, 1.9 mmol) were sequentially added to 10 mL of dichloromethane, and then the mixture was stirred at room temperature overnight. The reaction solution was diluted with water, extracted with dichloromethane, dried and concentrated. The residue was purified by preparative TLC (dichloromethane/methanol=20/1) to obtain 150 mg of 3-(7-methoxy-6-((6-(pyrimidin-2-ylmethyl)-5,6,7,8-tetrahydro-1,6-naphthalen-2-yl)methoxy)-[1,2,4]triazolo[4,3-b]pyridazin-3-yl)-5-methylisoxazole as a white solid, which was dissolved in 20 mL of tetrahydrofuran and water 3:1. Sodium bicarbonate (260 mg, 3.1 mmol) and iodine particles (590 mg, 2.3 mmol) were added thereto, and the mixture was stirred at room temperature overnight. 2 mL of aqueous sodium thiosulfate solution and 10 ml of water was added thereto, then the mixture was extracted with dichloromethane and ethyl acetate once each, dried, and the organic phase was concentrated. The residue was purified by preparative TLC to obtain 62 mg of the title compound as a white solid with a two-step yield of 22%. $^1$H NMR (400 MHz, $CDCl_3$) δ 8.70 (d, J=4.89 Hz, 2H) 8.44 (d, J=7.83 Hz, 1H) 7.70 (d, J=7.83 Hz, 1H) 7.26 (br. s., 1H) 7.20 (t, J=4.89 Hz, 1H) 6.79 (s, 1H) 5.68 (s, 2H) 5.06 (s, 2H) 4.05 (s, 3H) 3.85 (t, J=6.85 Hz, 2H) 3.33 (t, J=6.85 Hz, 2H) 2.57 (s, 3H). LC-MS: m/z $[M+H]^+$=500.

Embodiment 108 (Method G)

1-(2-(((7-Methoxy-3-(5-methylisoxazol-3-yl)-[1,2,4]triazolo[4,3-b]pyridazin-6-yl)oxy)methyl)-7,8-dihydro-1,6-naphthyridin-6(5H)-yl)prop-2-en-1-one

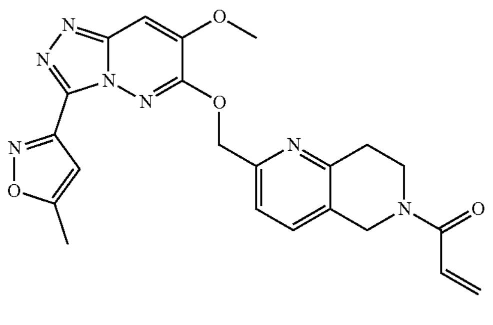 [SMILES: C=CC(=O)N1CCc2nc(COc3nn4c(-c5cc(C)on5)nnc4cc3OC)ccc2C1]

3-(7-Methoxy-6-((5,6,7,8-tetrahydro-1,6-naphthalen-2-yl)methoxy)-[1,2,4]triazolo[4,3-b]pyridazinpyridin-3-yl)-5-methyl-isoxazole (Embodiment 78) (100 mg, 0.254 mmol), 3-fluoropropionic acid (50 mg, 0.508 mmol), HBTU (191 mg, 0.504 mmol) and triethylamine (128 mg, 1.27 mmol) were sequentially added to 20 mL of dichloromethane, and then the mixture was stirred at room temperature overnight. TLC (dichloromethane:methanol=20:1) showed a complete reaction of raw materials. The reaction solution was extracted with aqueous ammonium chloride solution, and the organic phase was concentrated. The residue was purified by preparative TLC (dichloromethane/methanol=20/1) to obtain 10 mg of the target compound as a white solid with a yield of 9% and a white solid appearance. $^1$H NMR (400 MHz, $CDCl_3$) δ 7.59 (d, J=7.9 Hz, 1H), 7.56-7.46 (m, 1H), 7.23 (s, 1H), 6.80 (s, 1H), 6.65 (d, J=10.9 Hz, 1H), 6.35 (d, J=16.3 Hz, 1H), 5.77 (d, J=10.2 Hz, 1H), 5.61 (s, 2H), 4.94-4.70 (m, 2H), 4.01 (s, 3H), 3.97-3.77 (m, 2H), 3.11 (s, 2H), 2.57 (s, 3H). LC-MS: m/z $[M+H]^+$=448.

Embodiment 111

Ethyl 2-(((7-methoxy-3-(5-methylisoxazol-3-yl)-[1,2,4]triazolo[4,3-b]pyridazin-6-yl)oxy)methyl)7,8-dihydro-1,6-naphthyridine-6(5H)-carboxylate

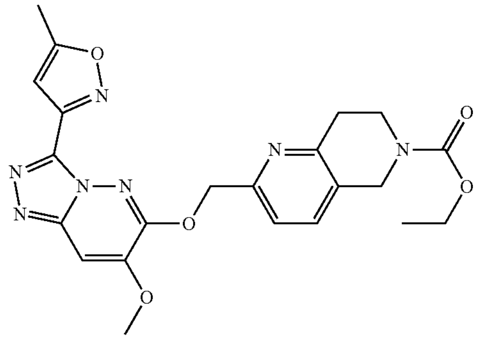 [SMILES: CCOC(=O)N1CCc2nc(COc3nn4c(-c5cc(C)on5)nnc4cc3OC)ccc2C1]

3-(7-Methoxy-6-((5,6,7,8-tetrahydro-1,6-naphthalen-2-yl)methoxy)-[1,2,4]triazolo[4,3-b]pyridazinpyridin-3-yl)-5-methylisoxazole (Embodiment 78) (200 mg, 0.508 mmol) and triethylamine (257 mg, 2.54 mmol) were dissolved in 20 mL of dichloromethane, and the mixture was cooled to 0° C., and added with triphosgene (200 mg, 0.330 mmol), stirred at low temperature for 10 minutes, and then stirred at room temperature for 30 minutes. The solvent was evaporated, ethanol (10 mL) and triethylamine (257 mg, 2.54 mmol) were added thereto, and the mixture was refluxed at 70° C. overnight. The reaction solution was extracted with aqueous ammonium chloride solution, and the organic phase was concentrated. The residue was purified by preparative thin layer chromatography (dichloromethane/methanol=20/1) to obtain 60 mg of the title compound as a white solid with a yield of 51%. $^1$H NMR (400 MHz, DMSO-$d_6$) δ 7.75 (s, 1H), 7.69 (d, J=7.9 Hz, 1H), 7.48 (d, J=7.9 Hz, 1H), 6.97 (s, 1H), 5.49 (s, 2H), 4.60 (s, 2H), 4.09 (q, J=7.1 Hz, 2H), 3.99 (s, 3H), 3.72 (t, J=5.8 Hz, 2H), 2.91 (t, J=5.8 Hz, 2H), 2.55 (s, 3H), 1.21 (t, J=7.1 Hz, 3H). LC-MS: m/z $[M+H]^+$=466.

Embodiment 113

3-(7-Methoxy-6-((6-(2-(methylsulfonyl)ethyl)-5,6,7,8-tetrahydro-1,6-naphthalen-2-yl)methoxy)-[1,2,4]triazolo[4,3-b]pyridazin-3-yl)-5-methylisoxazole

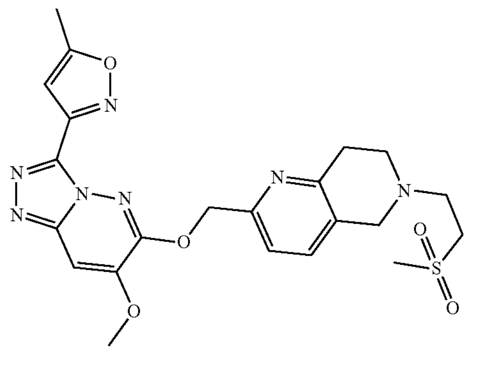 [SMILES: COc1cc2nnc(-c3cc(C)on3)n2nc1OCc1ccc2c(n1)CCN(CCS(C)(=O)=O)C2]

3-(7-Methoxy-6-((5,6,7,8-tetrahydro-1,6-naphthalen-2-yl)methoxy)-[1,2,4]triazolo[4,3-b]pyridazinpyridin-3-yl)-5-methyl-isoxazole (80 mg, 0.204 mmol), (methylsulfonyl) ethylene (108 mg, 1.02 mmol) and triethylamine (411 mg, 4.04 mmol) were sequentially added to 20 mL of MeOH, then the mixture was stirred at room temperature overnight. The mixture was concentrated and filtered to obtain 30 mg of the title compound as a white solid with a yield of 30%. $^1$H NMR (400 MHz, DMSO-$d_6$) δ 7.76 (s, 1H), 7.68 (d, J=7.7 Hz, 1H), 7.55 (d, J=7.8 Hz, 1H), 6.99 (s, 1H), 5.51 (s, 2H), 4.54-4.49 (m, 2H), 3.98 (s, 3H), 3.75-3.70 (m, 6H), 3.15-3.10 (m, 5H), 2.55 (s, 3H). LC-MS: m/z $[M+H]^+$=500.

Embodiment 114

2-(3-(2-(((7-Methoxy-3-(5-methylisoxazol-3-yl)-[1,2,4]triazolo[4,3-b]pyridazin-6-yl)oxy)methyl)-7,8-dihydro-1,6-naphthyridin-6(5H)-yl)oxetan-3-yl)acetonitrile

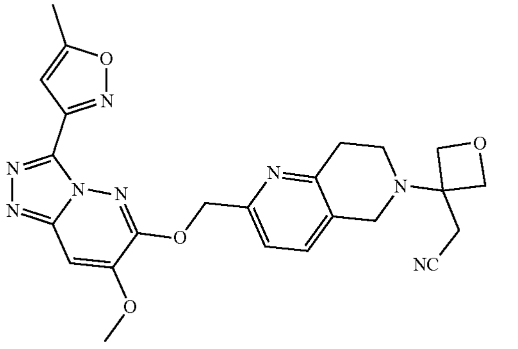 [SMILES: COc1cc2nnc(-c3cc(C)on3)n2nc1OCc1ccc2c(n1)CCN(C1(CC#N)COC1)C2]

3-(7-Methoxy-6-((5,6,7,8-tetrahydro-1,6-naphthalen-2-yl)methoxy)-[1,2,4]triazolo[4,3-b]pyridazinpyridin-3-yl)-5-methyl-isoxazole (80 mg, 0.204 mmol), 2-(oxetan-3-ylidene)acetonitrile and triethyamine (60 mg, 0.612 mmol) were sequentially added to 5 mL of MeOH, then the mixture was heated to reflux for 2 days. The mixture was acidified with acetic acid, concentrated, and the residue was purified by preparative thin layer chromatography (dichloromethane/methanol=20/1) to obtain 37 mg of the title compound as a white solid with a yield of 37%. $^1$H NMR (400 MHz, DMSO-$d_6$) δ 7.74 (s, 1H), 7.52 (d, J=7.9 Hz, 1H), 7.39 (d, J=7.8 Hz, 1H), 6.95 (s, 1H), 5.46 (s, 2H), 4.56 (d, J=6.5 Hz, 2H), 4.44 (d, J=6.5 Hz, 2H), 3.97 (s, 3H), 3.65 (s, 2H), 3.09 (s, 2H), 2.91 (d, J=5.3 Hz, 2H), 2.75 (t, J=5.6 Hz, 2H), 2.55 (s, 3H). LC-MS: m/z $[M+H]^+$=489.

Embodiment 137

5-(6-(((7-Methoxy-3-(5-methylisoxazol-3-yl)-[1,2,4]triazolo[4,3-b]pyridazin-6-yl)oxy)methyl)pyridin-3-yl)-3-methyl-1,2,4-oxadiazole

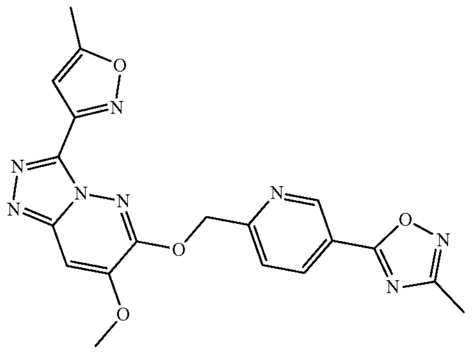 [SMILES: COc1cc2nnc(-c3cc(C)on3)n2nc1OCc1ccc(-c2nc(C)no2)cn1]

The raw materials 6-(((7-methoxy-3-(5-methylisoxazol-3-yl)-[1,2,4]triazolo[4,3-b]pyridazin-6-yl)oxy)methyl)nicotinic acid (382 mg, 1 mmol), N-hydroxyacetamidine (74 mg, 1 mmol), EDCI (300 mg, 1.5 mmol), HOBt (200 mg, 1.5 mmol), and DIPEA (260 mg, 2 mmol) were added to DMF (10 mL), and the mixture was stirred at 50° C. overnight. The reaction solution was cooled to room temperature, then the solvent was evaporated, and the residue was purified by column chromatography to obtain 140 mg of nicotinamide compound with a yield of 31.9%. The nicotinamide compound and triethylamine hydrochloride (10 mg, 0.07 mmol) were added to xylene (15 mL), then the mixture was stirred at 140° C. for 2 hours. The reaction solution was cooled to room temperature, then the solvent was evaporated, and the residue was purified by a preparative plate to obtain 19 mg of the title compound with a yield of 14.1% as a white solid. $^1$H NMR (400 MHz, DMSO-$d_6$) 9.23-9.32 (m, 1H) 8.52 (dd, J=8.07, 2.20 Hz, 1H) 7.76-7.89 (m, 2H) 6.84 (s, 1H) 5.68 (s, 2H) 4.02 (s, 3H) 2.54 (s, 3H) 2.44 (s, 3H). LC-MS: m/z $[M+H]^+$=421.

Embodiment 160

3-(7-Methoxy-6-((6-methyl-6,7-dihydro-5H-pyrrolo[3,4-b]pyridin-2-yl)methoxy)-[1,2,4]triazolo[4,3-b]pyridazin-3-yl)-5-methylisoxazole

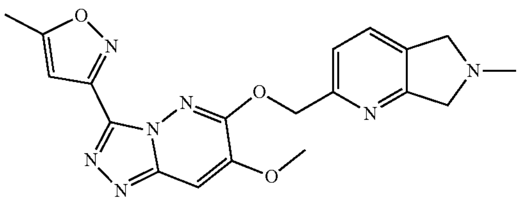

(6-Methyl-6,7-dihydro-5H-pyrrolo[3,4-b]pyridin-2-yl) methanol (90 mg, 0.545 mmol) was dissolved in tetrahydrofuran (3 mL). Lithium hexamethyldisilazide (1 M) (0.57 mL, 0.572 mmol) was added thereto at 0° C., and the reaction was carried out at room temperature for half an hour. Then 3-(6-chloro-7-methoxy-[1,2,4]triazolo[4,3-b]pyridazin-3-yl)-5-methylisoxazole (159 mg, 0.599 mmol) was added thereto at 0° C., then the mixture was heated to 50° C. and reacted overnight. The reaction solution was poured into water, extracted with dichloromethane, dried, concentrated, and separated by column chromatography (dichloromethane:methanol=30:1) to obtain the title compound (45 mg, 21%) as a white solid. $^1$H NMR (400 MHz, $CDCl_3$) δ 7.52 (d, J=3.2 Hz, 2H), 7.20 (s, 1H), 6.80 (s, 1H), 5.61 (s, 2H), 4.00-3.96 (m, 7H), 2.63 (s, 3H), 2.57 (s, 3H). LC-MS: m/z $[M+H]^+$=394.

The Remaining Embodiments Interface the Mother Nucleus with the Corresponding Fragment According to Similar Methods Described Above.

| Embodiment | Structure | Synthesis method | Mass spectrum $[M + H]^+$ | $^1$H NMR (400 MHz) |
|---|---|---|---|---|
| 2 | 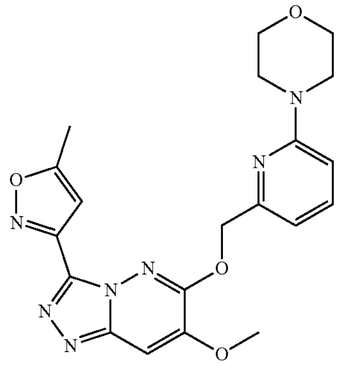 [SMILES: COc1cc2nnc(-c3cc(C)on3)n2nc1OCc1cccc(N2CCOCC2)n1] | A | 424 | ($DMSO-d_6$) δ 7.75 (s, 1 H), 7.61 (dd, J = 7.3, 8.3 Hz, 1 H), 6.92-6.76 (m, 3 H), 5.38 (s, 2 H), 3.99 (s, 3 H), 3.74-3.63 (m, 4 H), 3.47-3.41 (m, 4 H), 2.54 (d, J = 1.0 Hz, 3 H) |
| 3 | 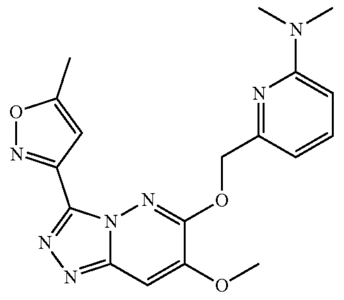 [SMILES: COc1cc2nnc(-c3cc(C)on3)n2nc1OCc1cccc(N(C)C)n1] | A | 382 | ($DMSO-d_6$) δ 7.74 (s, 1 H), 7.53 (t, J = 7.8 Hz, 1 H), 6.83 (s, 1 H), 6.74 (d, J = 6.8 Hz, 1 H), 6.60 (d, J = 8.3 Hz, 1 H), 5.35 (s, 2 H), 3.99 (s, 3 H), 3.01 (s, 6H), 2.52 (s, 3 H) |
| 4 | 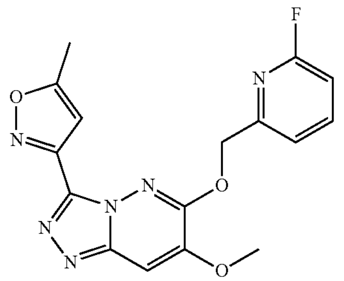 [SMILES: COc1cc2nnc(-c3cc(C)on3)n2nc1OCc1cccc(F)n1] | A | 357 | ($DMSO-d_6$) δ 8.06 (q, J = 8.0 Hz, 1 H), 7.78 (s, 1 H), 7.58 (dd, J = 2.0, 7.3 Hz, 1 H), 7.19 (dd, J = 2.2, 8.1 Hz, 1 H), 6.89 (s, 1 H), 5.51 (s, 2 H), 4.00 (s, 3 H), 2.55 (s, 3 H) |
| 5 | 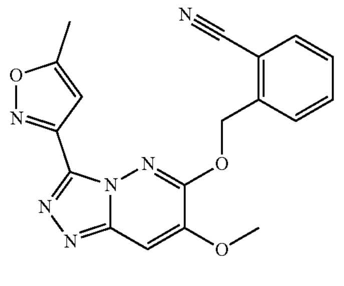 [SMILES: COc1cc2nnc(-c3cc(C)on3)n2nc1OCc1ccccc1C#N] | A | 363 | ($DMSO-d_6$) δ 7.98-7.94 (m, 1 H), 7.86-7.81 (m, 1 H), 7.80-7.74 (m, 2 H), 7.62 (dt, J = 1.2, 7.7 Hz, 1 H), 6.96 (d, J = 1.0 Hz, 1 H), 5.66 (s, 2 H), 3.97 (s, 3 H), 2.56 (s, 3 H) |

-continued

| Embodiment | Structure | Synthesis method | Mass spectrum $[M + H]^+$ | $^1H$ NMR (400 MHz) |
|---|---|---|---|---|
| 6 | 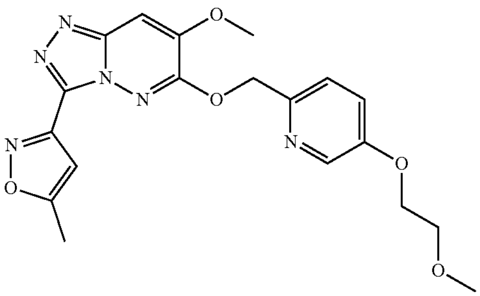 [SMILES: COCCOc1ccc(COc2nn3c(-c4cc(C)on4)nnc3cc2OC)nc1] | A | 413 | ($CDCl_3$) δ 8.37 (d, J = 2.9 Hz, 1 H), 7.67 (d, J = 8.8 Hz, 1 H), 7.25 (d, J = 2.9 Hz, 1 H), 7.20 (s, 1 H), 6.81 (d, J = 1.0 Hz, 1 H), 5.59 (s, 2 H), 4.20-4.15 (m, 2 H), 3.99 (s, 3 H), 3.79-3.74 (m, 2 H), 3.45 (s, 3H), 2.57 (d, J = 1.0 Hz, 3 H) |
| 7 | 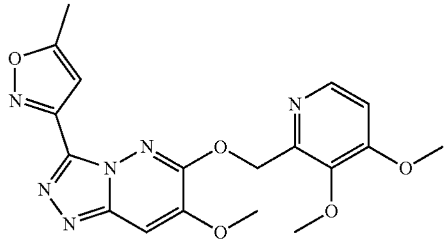 [SMILES: COc1cc2nnc(-c3cc(C)on3)n2nc1OCc1nccc(OC)c1OC] | A | 399 | ($DMSO-d_6$) δ 8.21 (d, J = 5.4 Hz, 1 H), 7.70 (s, 1 H), 7.17 (d, J = 5.9 Hz, 1 H), 6.95 (d, J = 1.0 Hz, 1 H), 5.52 (s, 2 H), 3.95 (s, 3 H), 3.91 (s, 3 H), 3.80 (s, 3 H), 2.53 (s, 3 H) |
| 8 | 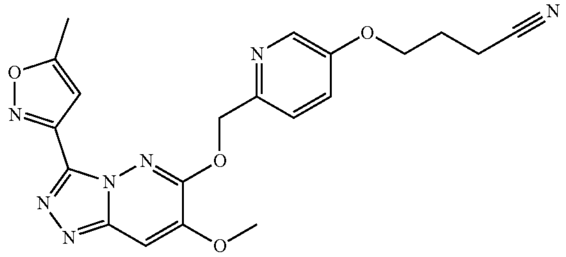 [SMILES: COc1cc2nnc(-c3cc(C)on3)n2nc1OCc1ccc(OCCCC#N)cn1] | A | 422 | ($DMSO-d_6$) δ 8.33 (d, J = 2.9 Hz, 1 H), 7.72 (s, 1 H), 7.62 (d, J = 8.8 Hz, 1 H), 7.46 (dd, J = 2.9, 8.3 Hz, 1 H), 6.98 (d, J = 1.0 Hz, 1 H), 5.48 (s, 2 H), 4.13 (t, J = 6.1 Hz, 2 H), 3.97 (s, 3 H), 2.66 (t, J = 7.1 Hz, 2 H), 2.60-2.51 (m, 3H), 2.08-2.00 (m, 2H) |
| 9 | 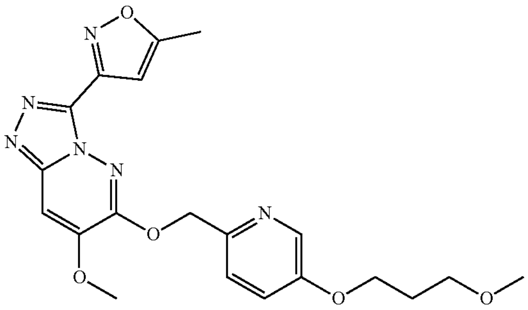 [SMILES: COCCCOc1ccc(COc2nn3c(-c4cc(C)on4)nnc3cc2OC)nc1] | A | 427 | ($DMSO-d_6$) δ 8.30 (d, J = 2.9 Hz, 1 H), 7.73 (s, 1 H), 7.60 (d, J = 8.8 Hz, 1 H), 7.44 (dd, J = 2.9, 8.3 Hz, 1 H), 6.98 (d, J = 1.0 Hz, 1 H), 5.47 (s, 2 H), 4.11 (t, J = 6.4 Hz, 2 H), 3.97 (s, 3 H), 3.48-3.45 (m, 2 H), 3.28-3.21 (m, 3 H), 2.56 (s, 3 H), 1.96 (quin, J = 6.2 Hz, 2 H) |
| 10 | 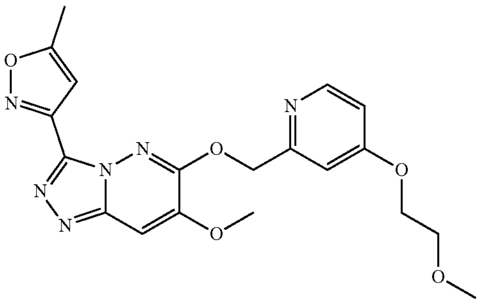 [SMILES: COCCOc1ccnc(COc2nn3c(-c4cc(C)on4)nnc3cc2OC)c1] | A | 413 | ($DMSO-d_6$) δ 8.41 (d, J = 5.9 Hz, 1 H), 7.75 (s, 1 H), 7.20 (d, J = 2.0 Hz, 1 H), 6.97 (dd, J = 2.4, 5.4 Hz, 1 H), 6.90 (s, 1 H), 5.49 (s, 2 H), 4.22-4.14 (m, 2 H), 4.00 (s, 3 H), 3.70-3.60 (m, 2 H), 3.28 (s, 3 H), 2.55 (s, 3 H) |

-continued
| Em-bodi-ment | Structure | Synthesis method | Mass spectrum [M + H]+ | $^1$H NMR (400 MHz) |
|---|---|---|---|---|
| 13 | 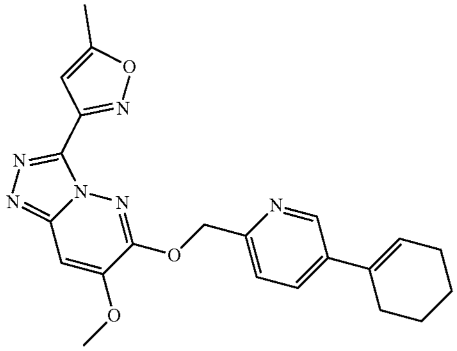 [SMILES: COc1cc2nnc(-c3cc(C)on3)n2nc1OCc1ccc(C2=CCCCC2)cn1] | B | 419 | (DMSO-$d_6$) δ 8.66 (s, 1 H), 7.82-7.91 (m, 1 H), 7.76 (s, 1 H), 7.51-7.61 (m, 1 H), 6.91 (s, 1 H), 6.22-6.35 (m, 1 H), 5.53 (s, 2 H), 3.99 (s, 3 H), 2.55 (s, 3 H), 2.38 (br. s., 2H), 2.19 (br. s., 2 H), 1.68-1.79 (m, 2 H), 1.55-1.65 (m, 2 H) |
| 14 | 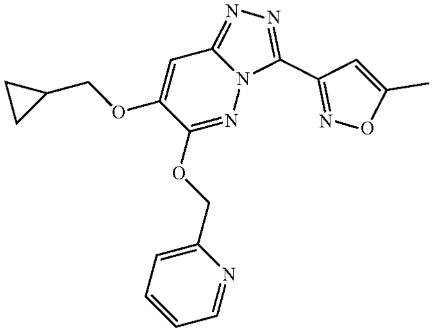 [SMILES: Cc1cc(-c2nnc3cc(OCC4CC4)c(OCc4ccccn4)nn23)no1] | B | 379 | (DMSO-$d_6$) δ 8.62 (d, J = 4.40 Hz, 1 H), 7.84-7.90 (m, 1 H), 7.70 (s, 1 H), 7.63 (d, J = 7.83 Hz, 1 H), 7.39 (dd, J = 6.85, 5.38 Hz, 1 H), 6.82 (s, 1 H), 5.59 (s, 2 H), 4.08 (d, J = 6.85 Hz, 2 H), 2.54 (s, 3H), 1.30-1.35 (m, 1 H), 0.64 (dd, J = 7.83, 1.47 Hz, 2 H), 0.39 (d, J = 4.89 Hz, 2 H) |
| 15 | 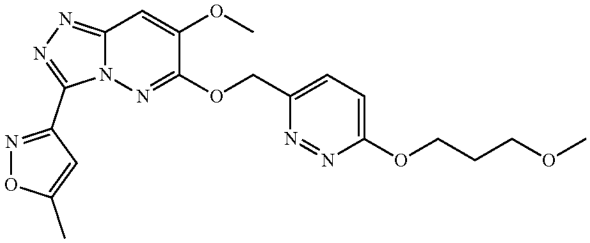 [SMILES: COCCCOc1ccc(COc2nn3c(-c4cc(C)on4)nnc3cc2OC)nn1] | B | 428 | (DMSO-$d_6$) δ 7.87 (d, J = 9.1 Hz, 1 H), 7.76 (s, 1 H), 7.27 (d, J = 9.0 Hz, 1 H), 6.99 (d, J = 0.8 Hz, 1 H), 5.67 (s, 2 H), 4.49 (t, J = 6.6 Hz, 2 H), 3.98 (s, 3 H), 3.48 (t, J = 6.3 Hz, 2 H), 3.24 (s, 3 H), 2.57 (s, 3 H), 2.01 (t, J = 6.4 Hz, 2 H) |
| 16 | 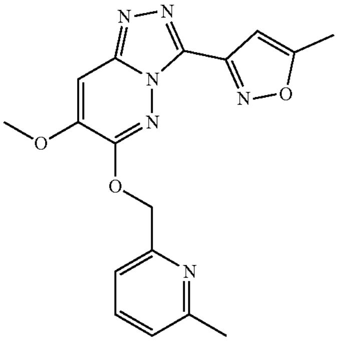 | B | 353 | (DMSO-$d_6$) δ 7.72-7.80 (m, 2 H), 7.39-7.45 (m, 1 H), 7.23-7.29 (m, 1 H), 6.94 (s, 1 H), 5.49 (s, 2 H), 3.99 (s, 3 H), 2.56 (s, 3 H), 2.50-2.52 (m, 3 H) |

-continued
| Embodiment | Structure | Synthesis method | Mass spectrum [M + H]$^+$ | $^1$H NMR (400 MHz) |
|---|---|---|---|---|
| 17 | 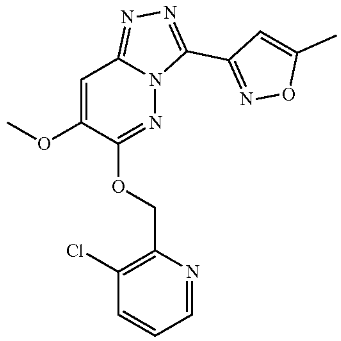 | B | 373 | (DMSO-$d_6$) δ 8.54 (d, J = 3.42 Hz, 1 H), 8.05 (d, J = 1.47 Hz, 1 H), 7.76 (s, 1 H), 7.44-7.51 (m, 1 H), 6.81 (s, 1 H), 5.69 (s, 2 H), 3.98(s, 3 H), 2.53 (s, 3 H) |
| 18 | 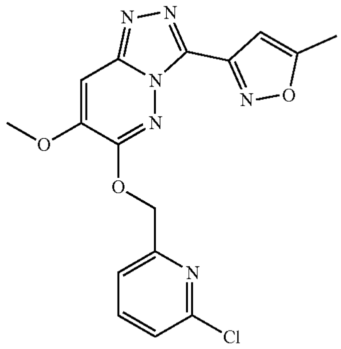 | B | 373 | (DMSO-$d_6$) δ 7.90-7.98 (m, 1 H), 7.75-7.81 (m, 1 H), 7.61-7.68 (m, 1 H), 7.49-7.57 (m, 1 H), 6.85-6.93 (m, 1 H), 5.47-5.58(m, 2 H), 3.98-4.03 (m, 3 H), 2.55-2.57 (m, 3 H) |
| 19 | 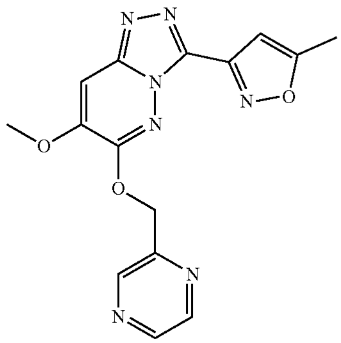 | B | 340 | (DMSO-$d_6$) δ 8.95 (d, J = 0.98 Hz, 1 H), 8.64-8.75 (m, 2 H), 7.77 (s, 1 H), 6.90 (s, 1 H), 5.63 (s, 2 H), 3.99 (s, 3 H), 2.55 (s, 3 H) |
| 20 | 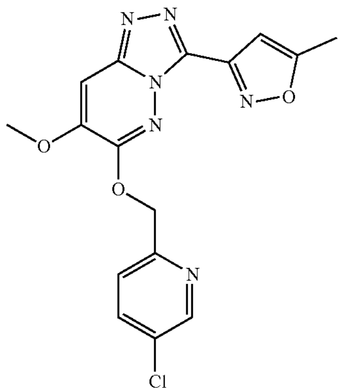 | B | 373 | (DMSO-$d_6$) δ 8.67 (br. s., 1 H), 8.01 (d, J = 6.36 Hz, 1 H), 7.62-7.80 (m, 2 H), 6.88 (s, 1 H), 5.56 (s, 2 H), 3.99 (s, 3 H), 2.55 (s, 3 H) |

-continued
| Embodiment | Structure | Synthesis method | Mass spectrum $[M + H]^+$ | $^1H$ NMR (400 MHz) |
| --- | --- | --- | --- | --- |
| 21 | 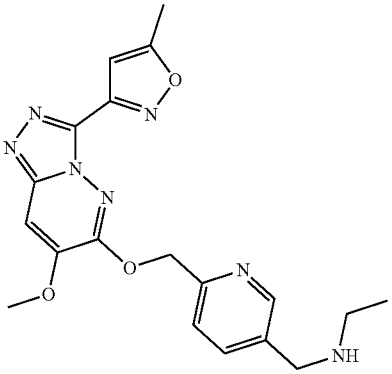 [SMILES: CCNCc1ccc(COc2nn3c(-c4cc(C)on4)nnc3cc2OC)nc1] | B | 396 | (DMSO-$d_6$) δ 9.61 (br. s., 2 H), 8.83 (d, J = 1.47 Hz, 1 H), 8.24 (dd, J = 8.31, 1.96 Hz, 1 H), 7.74-7.81 (m, 2H), 6.94 (s, 1 H), 5.62 (s, 2H), 3.99 (s, 3 H), 2.88-2.97 (m, 2 H), 2.55 (s, 3 H), 1.22 (t, J = 7.34 Hz, 3 H) |
| 22 | 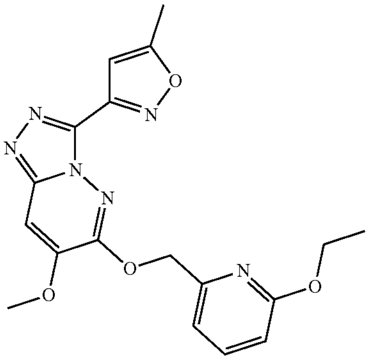 [SMILES: CCOc1cccc(COc2nn3c(-c4cc(C)on4)nnc3cc2OC)n1] | B | 383 | (DMSO-$d_6$) δ 7.68-7.81 (m, 2 H), 7.17 (d, J = 7.34 Hz, 1 H), 6.71-6.87 (m, 2 H), 5.45 (s, 2H), 4.28 (d, J = 6.85 Hz, 2 H), 4.00 (s, 3 H), 2.53 (s, 3 H), 1.28 (t, J = 6.85 Hz, 3 H) |
| 23 | 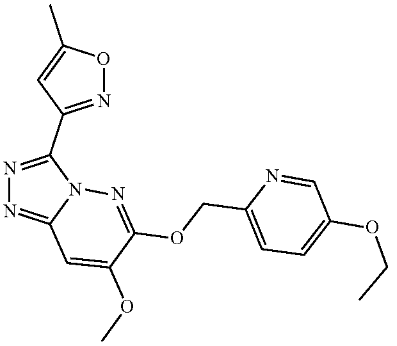 [SMILES: CCOc1ccc(COc2nn3c(-c4cc(C)on4)nnc3cc2OC)nc1] | B | 383 | (DMSO-$d_6$) δ 8.29 (d, J = 2.93 Hz, 1 H), 7.73 (s, 1 H), 7.60 (d, J = 8.80 Hz, 1 H), 7.42 (dd, J = 8.56, 2.69 Hz, 1 H), 6.98 (s, 1 H), 5.46 (s, 2 H), 4.11 (q, J = 6.85 Hz, 2 H), 3.97 (s, 3 H), 2.55 (s, 3 H), 1.34 (t, J = 6.85 Hz, 3 H) |
| 24 | 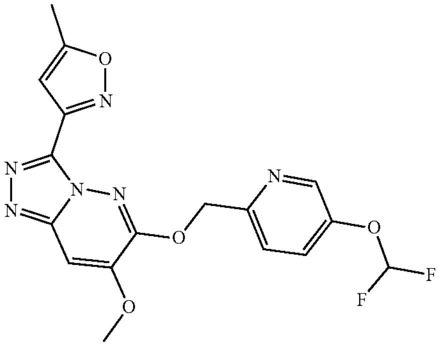 [SMILES: COc1cc2nnc(-c3cc(C)on3)n2nc1OCc1ccc(OC(F)F)cn1] | B | 405 | (DMSO-$d_6$) δ 8.53 (s, 1 H), 7.67-7.83 (m, 3H), 7.14-7.55 (t, J = 72 Hz, 1 H), 6.91 (s, 1 H), 5.55 (s, 2 H), 3.99 (s, 3 H), 2.55 (s, 3 H) |

-continued
| Embodiment | Structure | Synthesis method | Mass spectrum $[M + H]^+$ | $^1H$ NMR (400 MHz) |
|---|---|---|---|---|
| 25 | 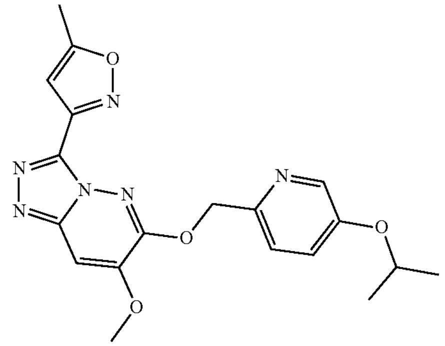 [SMILES: COc1cc2nnc(-c3cc(C)on3)n2nc1OCc1ccc(OC(C)C)cn1] | B | 397 | (DMSO-$d_6$) δ 8.27 (d, J = 2.45 Hz, 1 H), 7.74 (s, 1 H), 7.59 (d, J = 8.80 Hz, 1 H), 7.40-7.48 (m, 1 H), 6.98 (s, 1 H), 5.46 (s, 2 H), 4.65-4.76 (m, 1 H), 3.97 (s, 3 H), 2.56 (s, 3 H), 1.28 (d, J = 5.87 Hz, 6 H) |
| 26 | 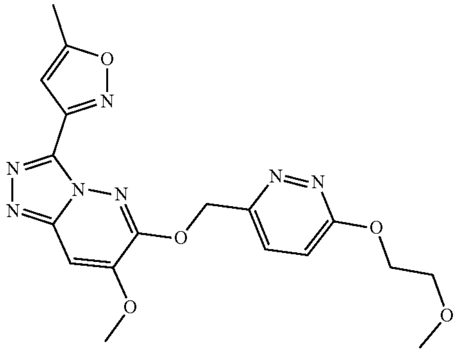 [SMILES: COCCOc1ccc(COc2nn3c(-c4cc(C)on4)nnc3cc2OC)nn1] | B | 414 | ($CDCl_3$) δ 7.95 (d, J = 8.80 Hz, 1 H), 7.25 (br. s., 1 H), 7.08 (d, J = 9.29 Hz, 1 H), 6.82 (s, 1 H), 5.78 (s, 2 H), 4.68-4.74(m, 2 H), 4.01 (s, 3 H), 3.77-3.84 (m, 2 H), 3.45 (s, 3 H), 2.58 (s, 3 H) |
| 27 | 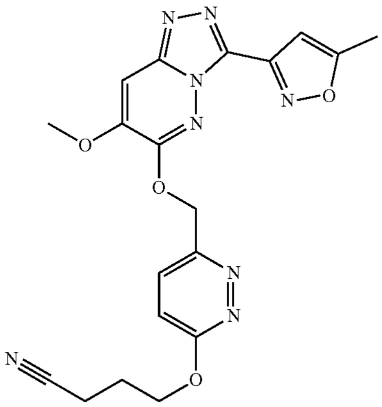 [SMILES: COc1cc2nnc(-c3cc(C)on3)n2nc1OCc1ccc(OCCCC#N)nn1] | B | 423 | ($CDCl_3$) δ 8.02 (d, J = 9.29 Hz, 1 H), 7.25 (s, 1 H), 7.03 (d, J = 9.29 Hz, 1 H), 6.82 (s, 1 H), 5.78 (s, 2 H), 4.67 (t, J = 5.87 Hz, 2 H), 4.01 (s, 3 H), 2.58 (s, 3 H), 2.53-2.57 (m, 2 H), 2.22 (quin, J = 6.48 Hz, 2 H) |
| 29 | 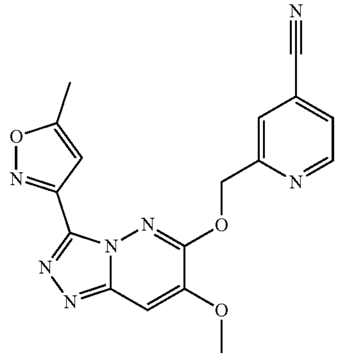 [SMILES: COc1cc2nnc(-c3cc(C)on3)n2nc1OCc1cc(C#N)ccn1] | A | 364 | (DMSO-$d_6$) δ 8.86 (d, J = 4.89 Hz, 1 H), 8.11 (s, 1 H), 7.91-7.83 (m, 1 H), 7.77 (s, 1 H), 6.82 (s, 1 H), 5.63 (s, 2 H), 4.01 (s, 3 H), 2.55 (s, 3 H) |

-continued
| Embodiment | Structure | Synthesis method | Mass spectrum $[M + H]^+$ | $^1H$ NMR (400 MHz) |
|---|---|---|---|---|
| 30 | 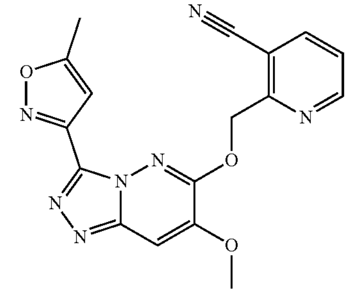 [SMILES: COc1cc2nnc(-c3cc(C)on3)n2nc1OCc1ncccc1C#N] | B | 364 | (DMSO-$d_6$) δ 8.88-8.81 (m, 1 H), 8.41 (dd, J = 7.83, 1.47 Hz, 1 H), 7.77 (s, 1 H), 7.61 (dd, J = 7.83, 4.89 Hz, 1 H), 6.82 (s, 1 H), 5.75 (s, 2 H), 3.98 (s, 3 H), 2.53 (s, 3 H) |
| 31 | 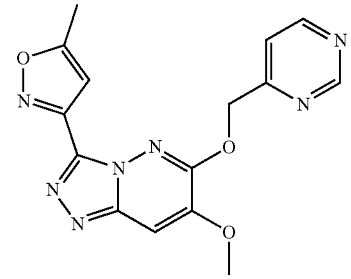 [SMILES: COc1cc2nnc(-c3cc(C)on3)n2nc1OCc1ccncn1] | B | 340 | (DMSO-$d_6$) δ 9.26-9.12 (m, 1 H), 8.83 (d, J = 4.89 Hz, 1 H), 7.78 (s, 1 H), 7.67 (d, J = 4.89 Hz, 1 H), 6.74 (s, 1 H), 5.58 (s, 2 H), 4.01 (m, 3 H), 2.52 (s, 3 H) |
| 32 | 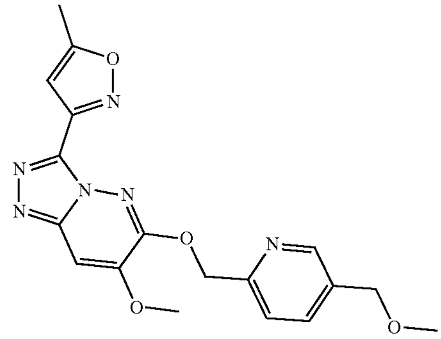 [SMILES: COCc1ccc(COc2nn3c(-c4cc(C)on4)nnc3cc2OC)nc1] | B | 383 | (DMSO-$d_6$) δ 8.56 (s, 1 H), 7.80 (d, J = 5.9 Hz, 1 H), 7.76 (s, 1 H), 7.62 (d, J = 7.8 Hz, 1 H), 6.88 (s, 1 H), 5.55 (s, 2 H), 4.47 (s, 2 H), 3.99 (s, 3 H), 3.30 (s, 3 H), 2.55 (s, 3 H) |
| 34 | 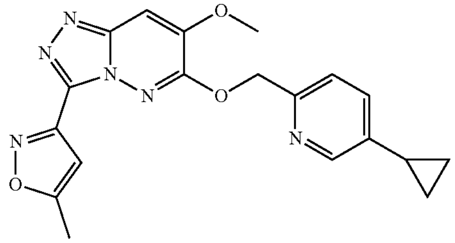 [SMILES: COc1cc2nnc(-c3cc(C)on3)n2nc1OCc1ccc(C2CC2)cn1] | C | 339 | (DMSO-$d_6$): δ 8.63-8.61(m, 1H), 7.89-7.85 (m, 1H), 7.76 (s, 1H), 7.63-7.61 (m, 1H), 7.41-7.38 (m, 1H), 6.88 (s, 1H), 5.55 (s, 2H), 4.00 (s, 3H), 2.55 (s, 3H) |
| 35 | 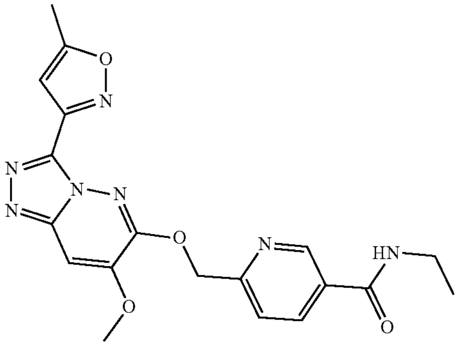 [SMILES: CCNC(=O)c1ccc(COc2nn3c(-c4cc(C)on4)nnc3cc2OC)nc1] | B | 410 | (DMSO-$d_6$) δ 9.00 (d, J = 1.7 Hz, 1H), 8.68 (s, 1H), 8.22 (dd, J = 8.1, 2.1 Hz, 1H), 7.75 (s, 1H), 7.70 (d, J = 8.1 Hz, 1H), 6.83 (s, 1H), 5.60 (s, 2H), 4.00 (s, 3H), 3.30-3.27 (m, 2H), 2.53 (s, 3H), 1.12 (t, J = 7.2 Hz, 3H) |

-continued
| Em-bodi-ment | Structure | Synthesis method | Mass spectrum $[M + H]^+$ | $^1H$ NMR (400 MHz) |
|---|---|---|---|---|
| 36 | 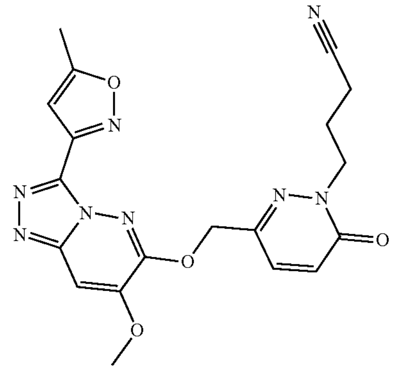 [SMILES: COc1cc2nnc(-c3cc(C)on3)n2nc1OCc1ccc(=O)n(CCCC#N)n1] | B | 423 | ($CDCl_3$) δ 7.81 (d, J = 9.78 Hz, 1 H) 7.25 (s, 1 H) 6.94 (d, J = 9.29 Hz, 1 H) 6.79 (s, 1 H) 5.42-5.48 (m, 2 H) 4.29 (t, J = 6.60 Hz, 2 H) 4.02 (s, 3 H) 2.52-2.61 (m, 3 H) 2.39-2.47 (m, 2 H) 2.20 (quin, J = 6.97 Hz, 2 H) |
| 37 | 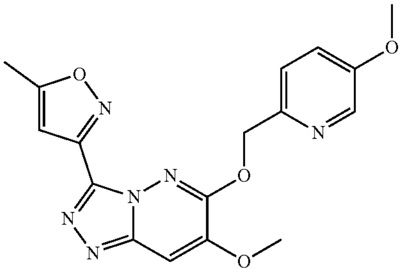 | B | 369 | (DMSO-$d_6$) δ 8.30 (d, J = 2.7 Hz, 1H), 7.72 (s, 1H), 7.61 (d, J = 8.6 Hz, 1H), 7.43 (dd, J = 8.6, 2.8 Hz, 1H), 6.97 (s, 1H), 5.46 (s, 2H), 3.95 (s, 3H), 3.82 (s, 3H), 2.54 (s, 3H) |
| 38 | 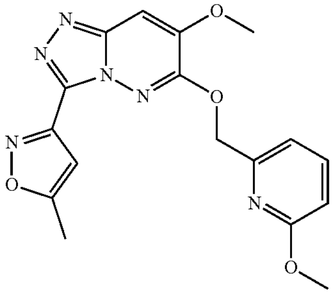 [SMILES: COc1cccc(COc2nn3c(-c4cc(C)on4)nnc3cc2OC)n1] | B | 369 | (DMSO-$d_6$) δ 7.78-7.71 (m, 2H), 7.18 (d, J = 7.2 Hz, 1H), 6.84-6.77 (m, 2H), 5.44 (s, 2H), 3.98 (s, 3H), 3.83 (s, 3H), 2.52 (s, 3H) |
| 39 | 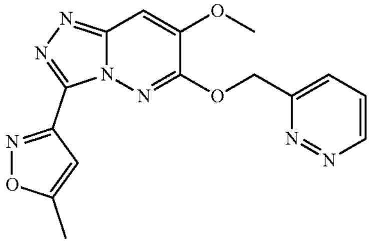 [SMILES: COc1cc2nnc(-c3cc(C)on3)n2nc1OCc1cccnn1] | B | 340 | (DMSO-$d_6$) δ 9.23 (dd, J = 4.9, 1.5 Hz, 1H), 7.92 (dd, J = 8.5, 1.5 Hz, 1H), 7.76 (dd, J = 7.8, 5.6 Hz, 2H), 6.87 (d, J = 0.6 Hz, 1H), 5.76 (s, 2H), 3.98 (s, 3H), 2.53 (s, 3H) |
| 40 | 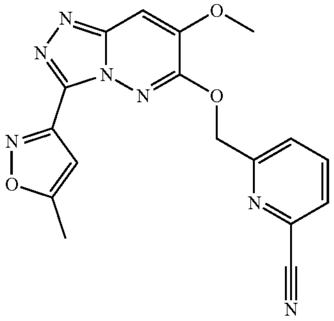 [SMILES: COc1cc2nnc(-c3cc(C)on3)n2nc1OCc1cccc(C#N)n1] | B | 364 | (DMSO-$d_6$) δ 8.11 (t, J = 7.8 Hz, 1H), 8.03 (d, J = 7.5 Hz, 1H), 7.94 (d, J = 7.9 Hz, 1H), 7.76 (s, 1H), 6.86 (s, 1H), 5.60 (s, 2H), 3.99 (s, 3H), 2.54 (s, 3H) |

-continued
| Embodiment | Structure | Synthesis method | Mass spectrum [M + H]+ | 1H NMR (400 MHz) |
|---|---|---|---|---|
| 41 | 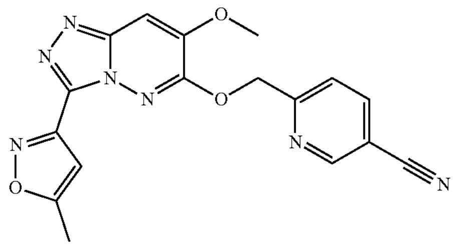 [SMILES: COc1cc2nnc(-c3cc(C)on3)n2nc1OCc1ccc(C#N)cn1] | B | 364 | ($DMSO-d_6$) δ 9.05 (s, 1H), 8.37 (dd, J = 8.2, 2.1 Hz, 1H), 7.82-7.77 (m, 2H), 6.80 (s, 1H), 5.64 (s, 2H), 4.00 (s, 3H), 2.53 (s, 3H) |
| 42 | 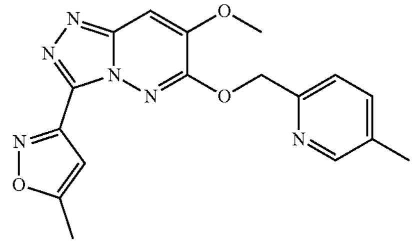 [SMILES: COc1cc2nnc(-c3cc(C)on3)n2nc1OCc1ccc(C)cn1] | B | 353 | ($DMSO-d_6$) δ 8.43 (s, 1H), 7.73 (s, 1H), 7.66 (d, J = 7.9 Hz, 1H), 7.51 (d, J = 7.9 Hz, 1H), 6.91 (s, 1H), 5.48 (s, 2H), 3.97 (s, 3H), 2.54 (s, 3H), 2.29 (s, 3H) |
| 43 | 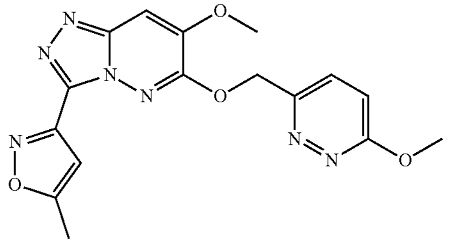 [SMILES: COc1ccc(COc2nn3c(-c4cc(C)on4)nnc3cc2OC)nn1] | B | 370 | ($DMSO-d_6$) δ 7.87 (d, J = 9.1 Hz, 1H), 7.75 (s, 1H), 7.28 (d, J = 9.1 Hz, 1H), 6.97 (s, 1H), 5.65 (s, 2H), 4.03 (s, 3H), 3.96 (s, 3H), 2.55 (s, 3H) |
| 44 | 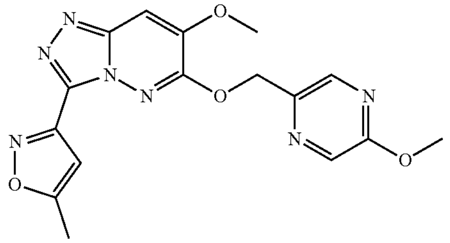 [SMILES: COc1cnc(COc2nn3c(-c4cc(C)on4)nnc3cc2OC)cn1] | B | 370 | ($DMSO-d_6$) δ 8.55 (s, 1H), 8.34 (s, 1H), 7.72 (s, 1H), 7.00 (s, 1H), 5.51 (s, 2H), 3.94 (s, 3H), 3.91 (s, 3H), 2.55 (s, 3H) |
| 45 | 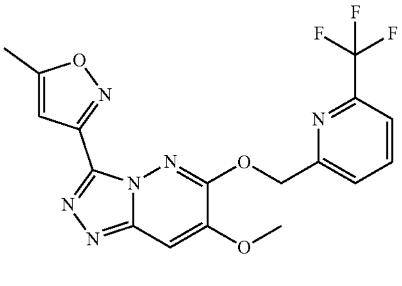 [SMILES: COc1cc2nnc(-c3cc(C)on3)n2nc1OCc1cccc(C(F)(F)F)n1] | C | 407 | ($DMSO-d_6$): 8.20-8.16 (m, 1H), 7.96-7.91 (m, 2H), 7.78 (s, 1H), 6.88 (s, 1H), 5.65 (s, 2H), 4.00 (s, 3H), 2.53-2.50 (m, 3H) |
| 49 | 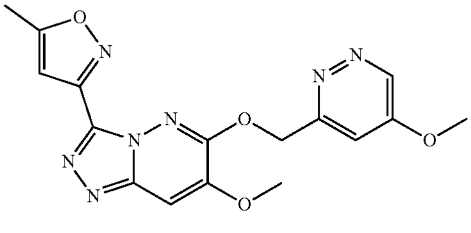 | C | 370 | ($DMSO-d_6$): δ 9.00 (d, J = 2.4 Hz, 1H), 7.77 (s, 1H), 7.53 (d, J = 2.4 Hz, 1H), 6.91 (s, 1H), 5.70 (s, 2H), 3.99 (s, 3H), 3.90 (s, 3H), 2.55 (s, 3H) |

-continued
| Embodiment | Structure | Synthesis method | Mass spectrum $[M + H]^+$ | $^1H$ NMR (400 MHz) |
|---|---|---|---|---|
| 50 | 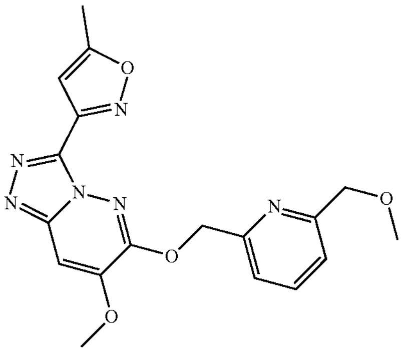 [SMILES: COCc1cccc(COc2nn3c(-c4cc(C)on4)nnc3cc2OC)n1] | B | 383 | (DMSO-$d_6$) 7.87 (t, J = 7.8 Hz, 1H), 7.75 (s, 1H), 7.52 (d, J = 7.8 Hz, 1H), 7.40 (d, J = 7.8 Hz, 1H), 6.90 (s, 1H), 5.52 (s, 2H), 4.50 (s, 2H), 3.98 (s, 3H), 2.54 (s, 3H) |
| 51 | 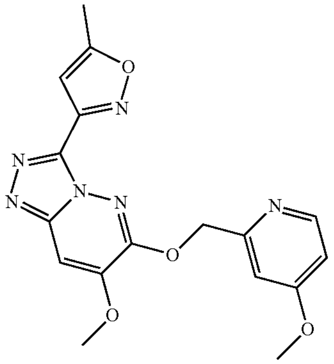 [SMILES: COc1ccnc(COc2nn3c(-c4cc(C)on4)nnc3cc2OC)c1] | B | 369 | (DMSO-$d_6$) 8.41 (d, J = 5.4 Hz, 1 H), 7.74 (s, 1 H), 7.19 (d, J = 2.0 Hz, 1 H), 6.96 (dd, J = 2.4, 5.4 Hz, 1 H), 6.89 (s, 1 H), 5.47 (s, 2 H), 3.98 (s, 3 H), 3.81 (s, 3 H), 2.53 (s, 3 H) |
| 52 | 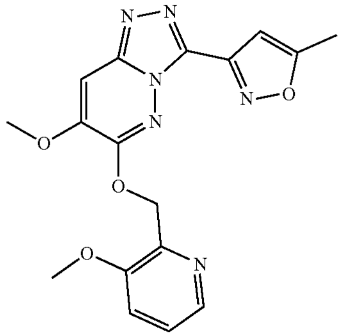 | B | 369 | (DMSO-$d_6$) 8.14 (d, J = 3.9 Hz, 1 H), 7.72 (s, 1 H), 7.55 (d, J = 8.3 Hz, 1 H), 7.42 (dd, J = 4.4, 8.3 Hz, 1 H), 6.89 (s, 1 H), 5.52 (s, 2 H), 3.94 (s, 3 H), 3.86 (s, 3 H), 2.52 (s, 3 H) |
| 53 | 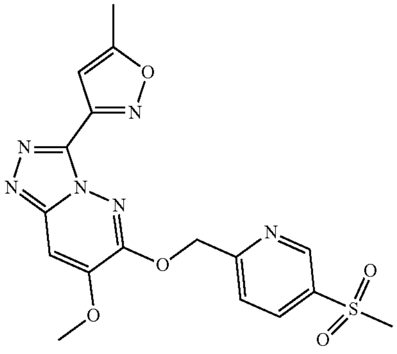 [SMILES: COc1cc2nnc(-c3cc(C)on3)n2nc1OCc1ccc(S(C)(=O)=O)cn1] | B | 417 | (DMSO-$d_6$) 9.09 (d, J = 2.0 Hz, 1 H), 8.37 (dd, J = 2.4, 8.3 Hz, 1 H), 7.86 (d, J = 7.8 Hz, 1 H), 7.78 (s, 1 H), 6.78 (s, 1 H), 5.67 (s, 2 H), 4.00 (s, 3 H), 3.27 (s, 3 H), 2.53 (s, 3 H) |

-continued
| Em-bodi-ment | Structure | Synthesis method | Mass spectrum [M + H]+ | $^1$H NMR (400 MHz) |
|---|---|---|---|---|
| 54 | 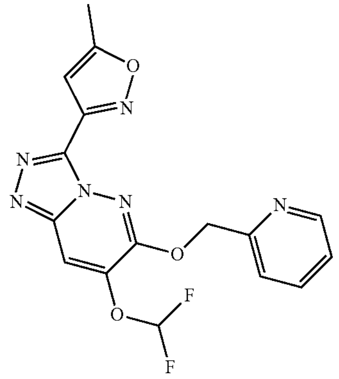 [SMILES: Cc1cc(-c2nnc3cc(OC(F)F)c(OCc4ccccn4)nn23)no1] | B | 375 | (DMSO-$d_6$) δ 8.61 (d, J = 4.6 Hz, 1H), 8.20 (s, 1H), 7.86 (td, J = 7.7, 1.5 Hz, 1H), 7.62 (d, J = 8.2 Hz, 1H), 7.45 (s, 1H), 7.38 (dd, J = 7.1, 5.2 Hz, 1H), 6.88 (s, 1H), 5.62(s, 2H), 2.57(s, 3H) |
| 55 | 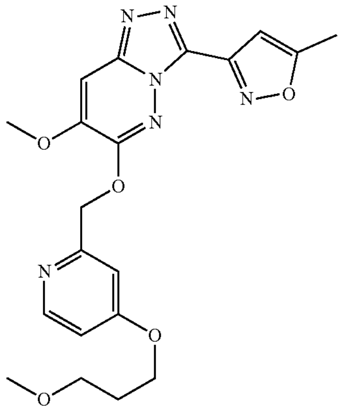 | B | 427 | (DMSO-$d_6$) δ 8.40 (d, J = 5.4 Hz, 1 H), 7.76 (s, 1 H), 7.20 (d, J = 2.4 Hz, 1 H), 6.96 (dd, J = 2.4, 5.4 Hz, 1 H), 6.91 (d, J = 1.0 Hz, 1 H), 5.49 (s, 2H), 4.10 (s, 2 H), 4.00 (s, 3 H), 3.46-3.41 (m, 2H), 3.22 (s, 3 H), 2.55 (s, 3 H), 1.94 (quin, J = 6.4 Hz, 2 H) |
| 56 | 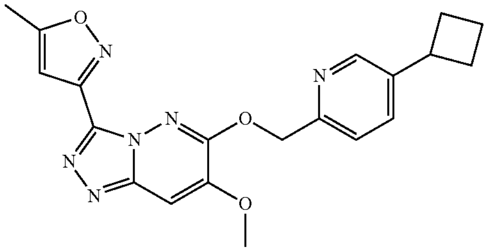 [SMILES: COc1cc2nnc(-c3cc(C)on3)n2nc1OCc1ccc(C2CCC2)cn1] | C | 393 | (DMSO-$d_6$): δ 8.48 (s, 1H), 7.77 (s, 2H), 7.59-7.57 (d, J = 7.6 Hz, 1H), 6.91 (s, 1H), 5.51 (s, 2H), 3.99 (s, 3H), 3.58-3.56 (m, 1H), 2.55 (s, 3H), 2.33-2.32 (m, 2H), 2.15-2.10 (m, 2H), 2.02-1.99 (m, 1H), 1.86-1.83 (m, 1H) |
| 57 | 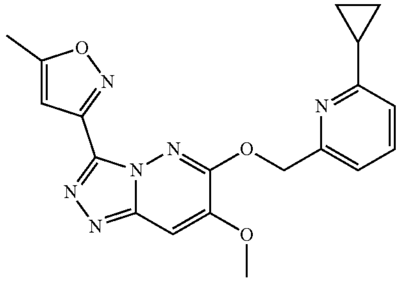 [SMILES: COc1cc2nnc(-c3cc(C)on3)n2nc1OCc1cccc(C2CC2)n1] | C | 379 | (DMSO-$d_6$): δ 7.77 (s, 1H), 7.72-7.68 (t, J = 7.8 Hz, 1H), 7.34-7.32 (d, J = 7.6 Hz, 1H), 7.27-7.25 (d, J = 8 Hz, 1H), 6.83 (s, 1H), 5.46 (s, 2H), 3.99 (s, 3H), 2.54 (s, 3H), 2.13-2.10 (m, 1H), 0.95-0.93 (m, 2H), 0.89-0.88 (m, 2H) |

-continued
| Em-bodi-ment | Structure | Synthesis method | Mass spectrum $[M + H]^+$ | $^1H$ NMR (400 MHz) |
|---|---|---|---|---|
| 58 | 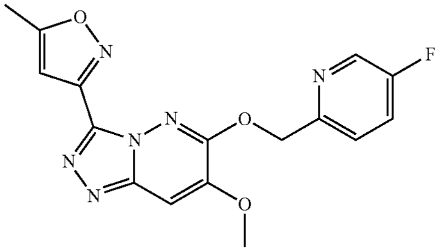 [SMILES: COc1cc2nnc(-c3cc(C)on3)n2nc1OCc1ccc(F)cn1] | C | 357 | (DMSO-$d_6$): δ 8.63-8.63 (m, 1H), 7.84-7.79 (m, 1H), 7.77 (s, 1H), 7.76-7.73 (m, 1H), 6.94 (s, 1H), 5.55 (s, 2H), 3.99 (s, 3H), 2.56 (s, 3H) |
| 59 | 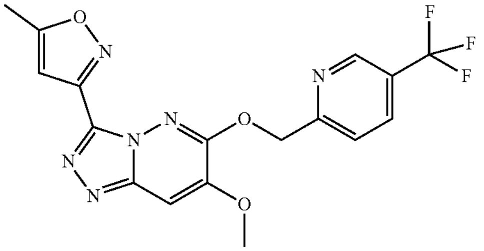 [SMILES: COc1cc2nnc(-c3cc(C)on3)n2nc1OCc1ccc(C(F)(F)F)cn1] | C | 407 | (DMSO-$d_6$): δ 9.02 (s, 1H), 8.31-8.29 (d, J = 10 Hz, 1H), 7.85-7.83 (d, J = 8.4 Hz, 1H), 7.79 (s, 1H), 6.79 (s, 1H), 5.68 (s, 2H), 4.02 (s, 3H), 2.54 (s, 3H) |
| 60 | 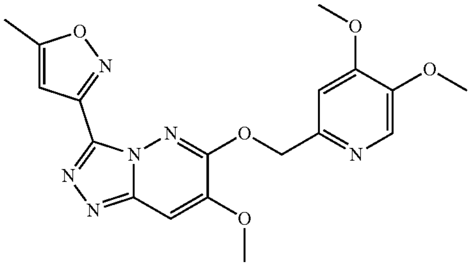 | C | 399 | (DMSO-$d_6$): δ 8.19 (s, 1H), 7.76 (s, 1H), 7.36 (s, 1H), 7.00 (s, 1H), 5.44 (s, 2H), 3.97 (s, 3H), 3.85 (s, 3H), 3.81 (s, 3H), 2.56 (s, 3H) |
| 61 | 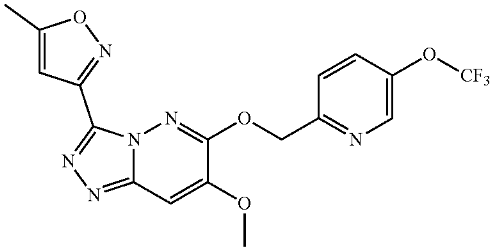 [SMILES: COc1cc2nnc(-c3cc(C)on3)n2nc1OCc1ccc(OC(F)(F)F)cn1] | C | 423 | (DMSO-$d_6$): δ 8.77 (s, 1H), 8.00-7.98 (d, J = 10.4 Hz, 1H), 7.81-7.78 (m, 2H), 6.87 (s, 1H), 5.61 (s, 2H), 4.00 (s, 3H), 2.55 (s, 3H) |
| 62 | 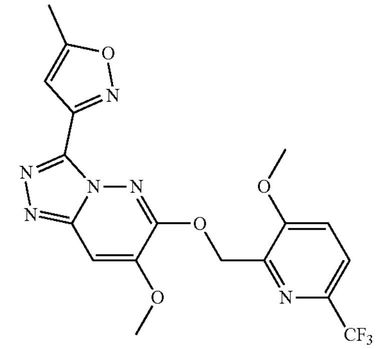 [SMILES: COc1ccc(C(F)(F)F)nc1COc1nn2c(-c3cc(C)on3)nnc2cc1OC] | B | 437 | (DMSO-$d_6$) δ 7.96 (d, J = 8.8 Hz, 1 H), 7.80-7.73 (m, 2 H), 6.95 (s, 1 H), 5.59 (s, 2 H), 3.97 (d, J = 2.9 Hz, 6 H), 2.54 (s, 3 H) |

-continued
| Embodiment | Structure | Synthesis method | Mass spectrum [M + H]+ | $^1H$ NMR (400 MHz) |
|---|---|---|---|---|
| 64 | 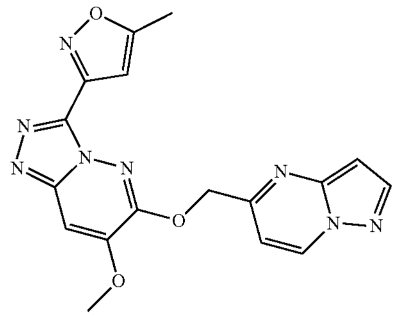 [SMILES: COc1cc2nnc(-c3cc(C)on3)n2nc1OCc1ccn2nccc2n1] | B | 379 | (DMSO-$d_6$) δ 9.14 (d, J = 7.1 Hz, 8 H), 8.24 (d, J = 2.2 Hz, 9 H), 7.78 (s, 8 H), 7.20 (d, J = 7.1 Hz, 9 H), 6.86 (s, 7 H), 6.72 (d, J = 1.5 Hz, 8 H), 5.62 (s, 13 H), 4.02 (s, 21 H), 2.51 (br. s., 18 H) |
| 65 | 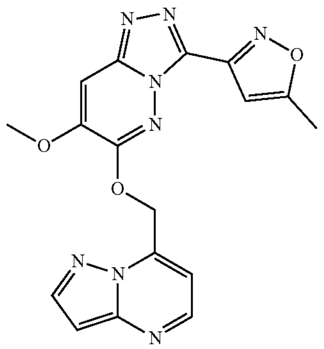 | B | 379 | (DMSO-$d_6$) δ 8.66-8.36 (m, 1 H), 7.50-7.22 (m, 7 H), 7.15-7.04 (m, 2 H), 4.94 (s, 2 H), 4.07-3.99 (m, 1 H), 3.85 (s, 3 H), 3.71 (s, 3H), 1.99 (s, 1 H), 1.36 (br. s., 9 H), 1.20-1.14 (m, 1 H) |
| 66 | 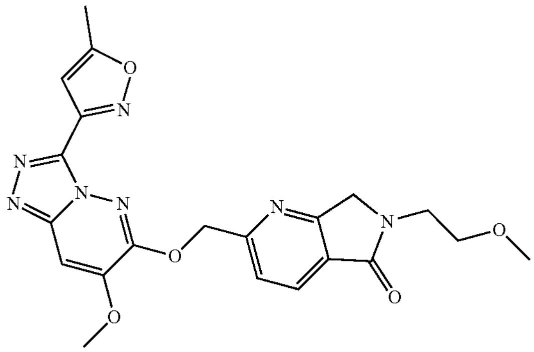 [SMILES: COCCN1Cc2nc(COc3nn4c(-c5cc(C)on5)nnc4cc3OC)ccc2C1=O] | B | 452 | (DMSO-$d_6$) δ 8.16 (d, J = 7.6 Hz, 1H), 7.79 (s, 1H), 7.74 (d, J = 8.0 Hz, 1H), 6.92 (s, 1H), 5.68 (s, 2H), 4.59 (s 2H), 4.01 (s, 3H), 3.72 (t, J = 5.2 Hz, 2H), 3.58 (t, J = 5.2 Hz, 2H), 3.26 (s , 3H), 2.55 (s, 3H) |
| 67 | 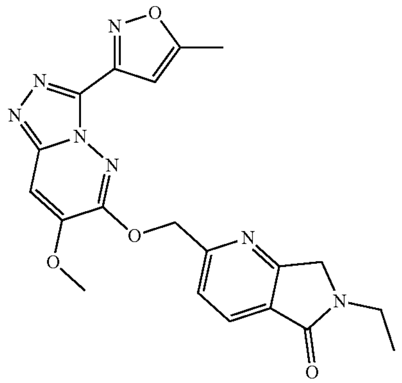 [SMILES: CCN1Cc2nc(COc3nn4c(-c5cc(C)on5)nnc4cc3OC)ccc2C1=O] | C | 422 | (DMSO-$d_6$) δ 8.14 (d, J = 8.0 Hz, 1H), 7.78 (s, 1H), 7.74 (d, J = 8.0 Hz, 1H), 6.92 (s, 1H), 5.67 (s, 2H), 4.56 (s, 2H), 4.01 (s, 3H), 3.58 (q, J = 7.2 Hz, 2H), 2.55 (s, 3H) 1.19 (t, J = 7.2 Hz, 3H) |

-continued
| Embodiment | Structure | Synthesis method | Mass spectrum [M + H]+ | $^1$H NMR (400 MHz) |
|---|---|---|---|---|
| 68 | 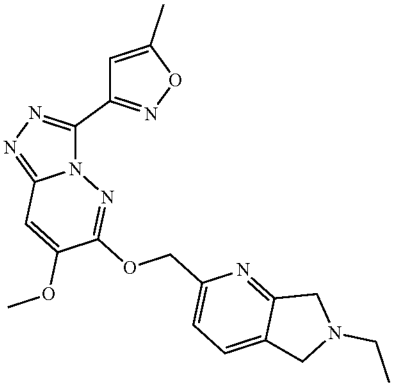 [SMILES: CCN1Cc2ccc(COc3nn4c(-c5cc(C)on5)nnc4cc3OC)nc2C1] | C | 408 | (DMSO-$d_6$): δ 7.76 (s, 1H), 7.71 (d, J = 8.0 Hz, 1H), 7.46 (d, J = 8.0 Hz, 1H), 6.98 (s, 1H), 5.51 (s, 2H), 3.98 (s, 3H), 3.90(d, J = 11.6 Hz, 4H), 2.75-7.73 (m, 2H), 2.56 (s, 3H), 1.12-1.10 (m, 3H) |
| 70 | 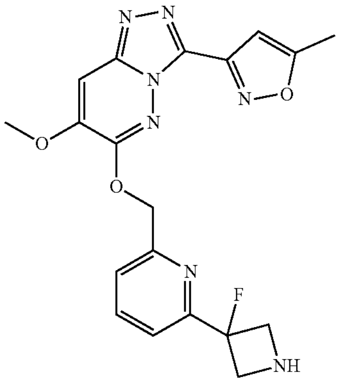 | D | 412 | (DMSO-$d_6$) δ 7.99-7.95 (m, 1H), 7.78 (s, 1H), 7.66-7.64 (m, 1H), 7.56-7.54 (m, 1H), 6.89 (s, 1H), 5.61 (s, 2H), 4.11-4.08 (m, 1H), 4.06-4.03 (m, 1H), 4.00 (s, 3H), 3.88-3.85 (m, 1H), 3.83-3.80 (m, 1H), 2.54 (s, 3H) |
| 71 | 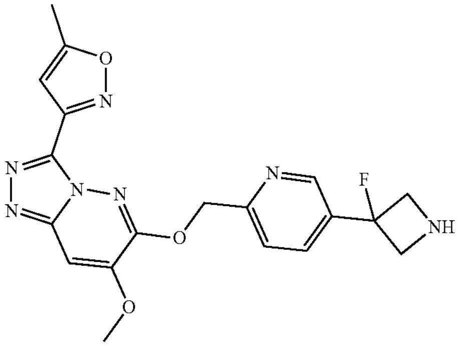 [SMILES: COc1cc2nnc(-c3cc(C)on3)n2nc1OCc1ccc(C2(F)CNC2)cn1] | D | 412 | (DMSO-$d_6$): δ 8.81(s, 1H), 8.04-8.02 (m, 1H), 7.77 (s, 1H), 7.73-7.71 (m, 1H), 6.87 (s, 1H), 5.59 (s, 2H), 4.00-3.95 (m, 5H), 3.82-3.78 (m, 2H), 2.55 (s, 3H) |
| 72 | 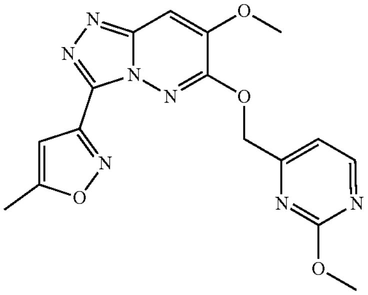 | B | 370 | (DMSO-$d_6$) δ 8.63 (d, J = 4.9 Hz, 1 H), 7.78 (s, 1 H), 7.27 (d, J = 5.4 Hz, 1 H), 6.76 (d, J = 1.0 Hz, 1 H), 5.51 (s, 2 H), 4.02 (s, 3 H), 3.92 (s, 3 H), 2.53 (d, J = 1.0 Hz, 3 H) |

-continued
| Embodiment | Structure | Synthesis method | Mass spectrum $[M + H]^+$ | $^1H$ NMR (400 MHz) |
|---|---|---|---|---|
| 73 | 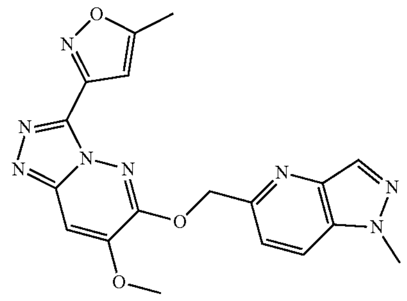 [SMILES: COc1cc2nnc(-c3cc(C)on3)n2nc1OCc1ccc2c(cnn2C)n1] | B | 393 | (DMSO-$d_6$) δ 8.27 (s, 1 H), 8.19 (d, J = 8.8 Hz, 1 H), 7.70 (s, 1 H), 7.67 (d, J = 8.8 Hz, 1 H), 6.94 (s, 1 H), 5.66 (s, 2 H), 4.07 (s, 3 H), 3.97 (s, 3 H), 2.53 (s, 3 H) |
| 74 | 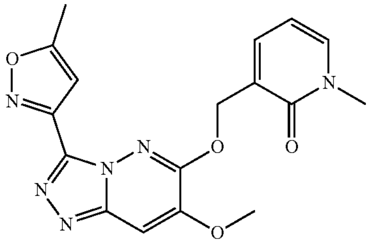 [SMILES: COc1cc2nnc(-c3cc(C)on3)n2nc1OCc1cccn(C)c1=O] | B | 369 | (DMSO-$d_6$) δ 7.75 (t, J = 7.1 Hz, 2 H), 7.70 (s, 1 H), 6.99 (s, 1 H), 6.27 (t, J = 6.8 Hz, 1 H), 5.30 (s, 2 H), 3.96 (s, 3 H), 3.48 (s, 3 H), 2.55 (s, 3 H) |
| 75 | 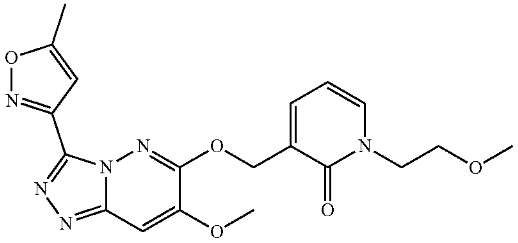 [SMILES: COCCn1cccc(COc2nn3c(-c4cc(C)on4)nnc3cc2OC)c1=O] | B | 413 | (DMSO-$d_6$) δ 7.75 (dd, J = 2.0, 6.8 Hz, 1 H), 7.71 (s, 1 H), 7.68 (dd, J = 2.4, 6.8 Hz, 1 H), 7.00 (d, J = 1.0 Hz, 1 H), 6.27 (t, J = 6.6 Hz, 1 H), 5.31 (s, 2 H), 4.11 (t, J = 5.4 Hz, 2 H), 3.96 (s, 3 H), 3.59 (t, J = 5.4 Hz, 2 H), 3.24 (s, 3 H), 2.55 (d, J = 1.0 Hz, 3 H) |
| 76 | 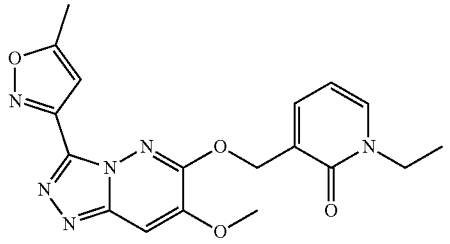 [SMILES: CCn1cccc(COc2nn3c(-c4cc(C)on4)nnc3cc2OC)c1=O] | B | 383 | (DMSO-$d_6$) δ 7.81-7.70 (m, 2 H), 7.67 (s, 1 H), 6.99 (s, 1 H), 6.30 (t, J = 6.8 Hz, 1 H), 5.30 (s, 2 H), 3.98-3.93 (m, 2 H), 3.55 (s, 3 H), 2.52 (d, J = 12.7 Hz, 3 H), 1.27-1.16 (m, 3 H) |
| 77 | 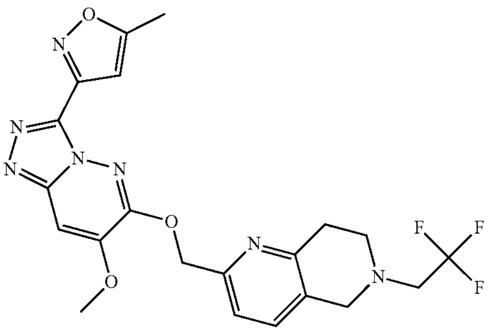 [SMILES: COc1cc2nnc(-c3cc(C)on3)n2nc1OCc1ccc2c(n1)CCN(CC(F)(F)F)C2] | B | 476 | ($CDCl_3$) δ 7.49 (d, J = 8.3 Hz, 1 H), 7.39 (d, J = 7.8 Hz, 1 H), 7.21 (s, 1 H), 6.80 (s, 1 H), 5.60 (s, 2 H), 4.01 (s, 3 H), 3.91 (s, 2 H), 3.20 (q, J = 9.5 Hz, 2 H), 3.11 (s, 4 H), 2.58 (s, 3 H) |

-continued
| Embodiment | Structure | Synthesis method | Mass spectrum [M + H]+ | $^1$H NMR (400 MHz) |
|---|---|---|---|---|
| 78 | 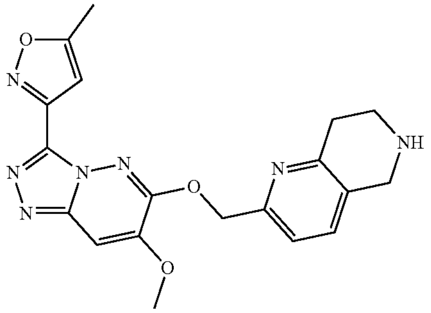 [SMILES: COc1cc2nnc(-c3cc(C)on3)n2nc1OCc1ccc2c(n1)CCNC2] | D | 394 | (DMSO-$d_6$) δ 7.74 (s, 1 H), 7.49 (d, J = 7.8 Hz, 1 H), 7.38 (d, J = 7.8 Hz, 1 H), 6.99 (s, 1 H), 5.46 (s, 2 H), 3.98 (s, 3 H), 3.87 (s, 2 H), 3.04 (t, J = 5.9 Hz, 2 H), 2.85-2.75 (m, 2 H), 2.56 (s, 3 H) |
| 80 | 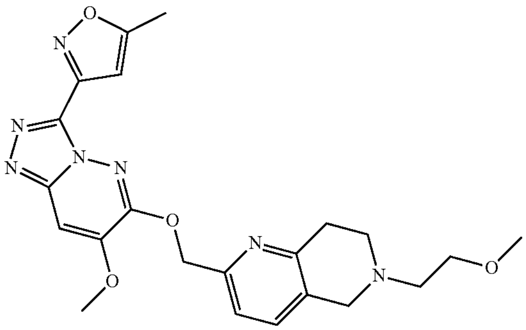 [SMILES: COCCN1CCc2nc(COc3nn4c(-c5cc(C)on5)nnc4cc3OC)ccc2C1] | E | 452 | ($CDCl_3$) δ 7.43 (d, J = 7.8 Hz, 1 H), 7.38 (d, J = 7.8 Hz, 1 H), 7.23 (s, 1 H), 6.79 (s, 1 H), 5.55 (s, 2 H), 3.99 (s, 3 H), 3.70 (s, 2 H), 3.59 (t, J = 5.6 Hz, 2 H), 3.40-3.32 (m, 3 H), 3.06 (t, J = 6.1 Hz, 2 H), 2.90 (t, J = 6.1 Hz, 2 H), 2.76 (t, J = 5.4 Hz, 2 H), 2.55 (s, 3 H) |
| 81 | 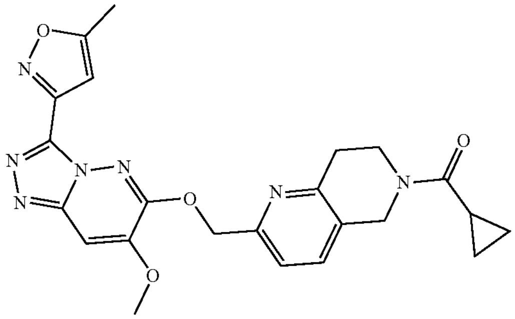 [SMILES: COc1cc2nnc(-c3cc(C)on3)n2nc1OCc1ccc2c(n1)CCN(C(=O)C1CC1)C2] | E | 462 | ($CDCl_3$) δ 7.55 (d, J = 7.3 Hz, 1 H), 7.50 (d, J = 7.8 Hz, 1 H), 7.24 (s, 1 H), 6.79 (s, 1 H), 5.58 (s, 2 H), 4.86-4.73 (m, 2 H), 4.00 (s, 3 H), 3.91 (m, 2 H), 3.12-3.02 (m, 2 H), 2.54 (s, 3 H), 1.83 (m, 1 H), 1.07-0.92 (m, 2 H), 0.81 (m, 2 H) |
| 82 | 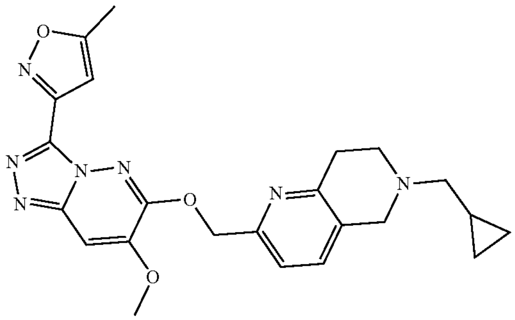 [SMILES: COc1cc2nnc(-c3cc(C)on3)n2nc1OCc1ccc2c(n1)CCN(CC1CC1)C2] | E | 448 | ($CDCl_3$) δ 7.51-7.36 (m, 2 H), 7.23 (s, 1 H), 6.79 (s, 1 H), 5.57 (s, 2 H), 4.00 (s, 3 H), 3.76 (s, 2 H), 3.09 (d, J = 5.4 Hz, 2 H), 2.97 (d, J = 5.4 Hz, 2 H), 2.55 (s, 3 H), 2.48 (d, J = 6.4 Hz, 2 H), 0.97 (m, 1 H), 0.59 (m, 2 H), 0.19 (m, 2 H) |

-continued
| Embodiment | Structure | Synthesis method | Mass spectrum [M + H]+ | $^1$H NMR (400 MHz) |
|---|---|---|---|---|
| 83 | 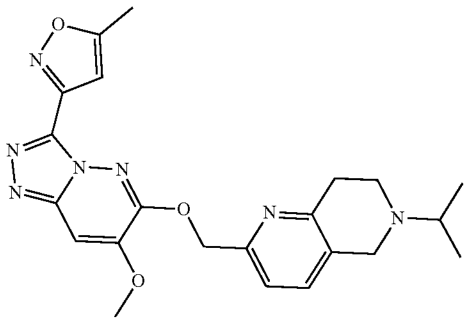 [SMILES: COc1cc2nnc(-c3cc(C)on3)n2nc1OCc1ccc2c(n1)CCN(C(C)C)C2] | E | 436 | ($CDCl_3$) δ 7.48-7.38 (m, 2 H), 7.24 (s, 1 H), 6.79 (s, 1 H), 5.56 (s, 2 H), 3.99 (s, 3 H), 3.78 (m, 2 H), 3.09-2.94 m, 5 H), 2.55 (s, 3 H), 1.17 (d, J = 6.4 Hz, 6 H) |
| 85 | 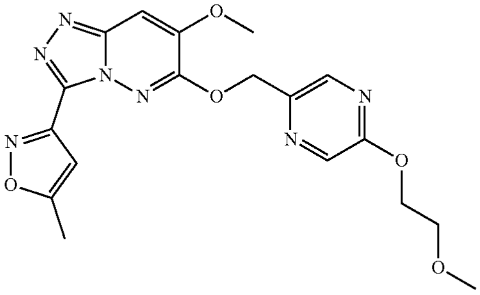 [SMILES: COCCOc1cnc(COc2nn3c(-c4cc(C)on4)nnc3cc2OC)cn1] | B | 414 | (DMSO-$d_6$) δ 8.53 (d, J = 0.98 Hz, 1 H) 8.37 (s, 1 H) 7.74 (s, 1 H) 7.00 (s, 1 H) 5.53 (s, 2 H) 4.38-4.48 (m, 2 H) 3.96 (s, 3 H) 3.62-3.72 (m, 2 H) 3.29 (s, 3 H) 2.57 (s, 3 H) |
| 86 | 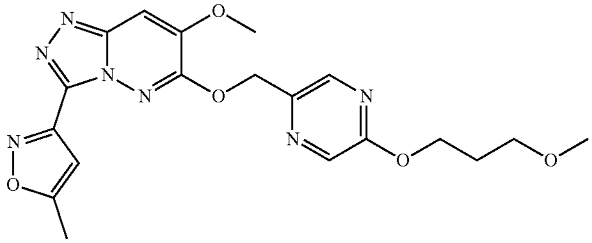 [SMILES: COCCCOc1cnc(COc2nn3c(-c4cc(C)on4)nnc3cc2OC)cn1] | B | 428 | (DMSO-$d_6$) δ 8.53 (s, 1 H) 8.33 (s, 1 H) 7.73 (s, 1 H) 7.01 (s, 1 H) 5.52 (s, 2 H) 4.35 (t, J = 6.36 Hz, 2 H) 3.96 (s, 3 H) 3.45 (t, J = 6.11 Hz, 2 H) 3.23 (s, 3 H) 2.56 (s, 3 H) 1.90-2.05 (m, 2 H) |
| 89 | 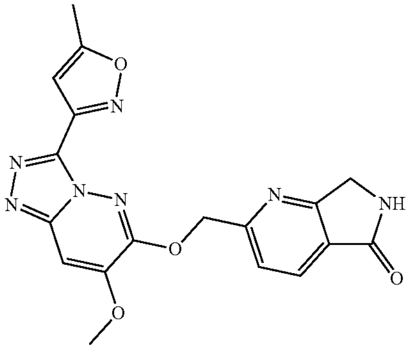 [SMILES: COc1cc2nnc(-c3cc(C)on3)n2nc1OCc1ccc2c(n1)CNC2=O] | B | 394 | (DMSO-$d_6$) δ 8.77-8.86 (m, 1 H) 8.13-8.19 (m, 1 H) 7.78 (s, 1 H) 7.71-7.76 (m, 1 H) 6.85-6.96 (m, 1 H) 5.67 (s, 2 H) 4.45 (s, 2 H) 4.01 (s, 3 H) 2.55 (s, 3 H) |
| 90 | 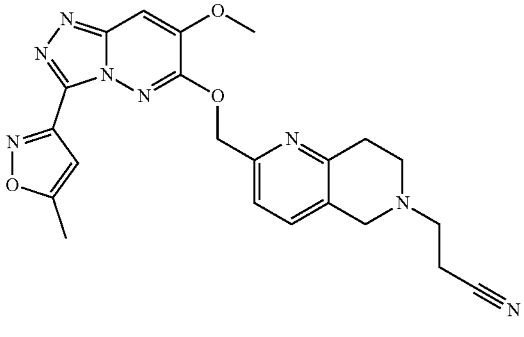 [SMILES: COc1cc2nnc(-c3cc(C)on3)n2nc1OCc1ccc2c(n1)CCN(CCC#N)C2] | E | 447 | (DMSO-$d_6$) δ 7.74 (s, 1H), 7.52 (d, J = 7.9 Hz, 1H), 7.39 (d, J = 7.9 Hz, 1H), 6.94 (s, 1H), 5.46 (s, 2H), 3.97 (s, 3H), 3.66 (s, 2H), 2.89 (d, J = 5.4 Hz, 2H), 2.83 (t, J = 5.7 Hz, 2H), 2.76 (s, 4H), 2.54 (s, 3H) |

-continued
| Embodiment | Structure | Synthesis method | Mass spectrum [M + H]+ | $^{1}$H NMR (400 MHz) |
|---|---|---|---|---|
| 91 | 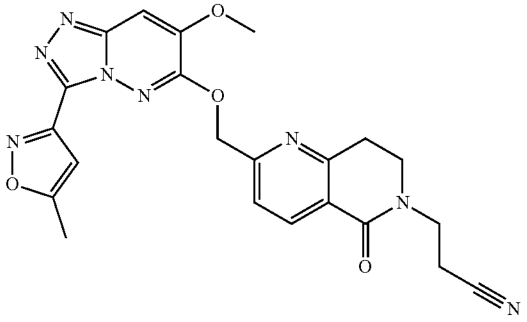 [SMILES: COc1cc2nnc(-c3cc(C)on3)n2nc1OCc1ccc2c(n1)CCN(CCC#N)C2=O] | F | 461 | (DMSO-$d_6$) δ 8.22-8.31 (m, 1 H) 7.77 (s, 1 H) 7.59-7.66 (m, 1 H) 6.91 (s, 1 H) 5.59 (s, 2 H) 4.01 (s, 3 H) 3.75 (d, J = 8.80 Hz, 3H) 3.16 (t, J = 6.60 Hz, 2 H) 2.86 (t, J = 6.60 Hz, 2 H) 2.55 (s, 3 H) |
| 92 | 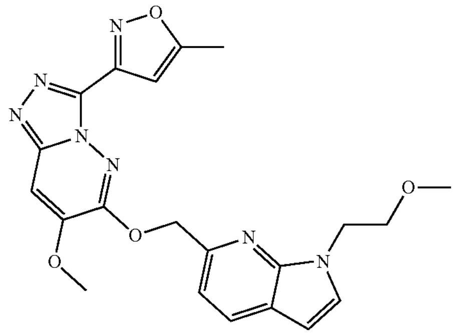 [SMILES: COCCn1ccc2ccc(COc3nn4c(-c5cc(C)on5)nnc4cc3OC)nc21] | B | 436 | (DMSO-$d_6$) δ 8.01-8.05 (m, 1 H) 7.73-7.76 (m, 1 H) 7.57-7.60 (m, 1 H) 7.35-7.39 (m, 1 H) 6.94 (s, 1 H) 6.49 (d, J = 3.42 Hz, 1H) 5.61 (s, 2 H) 4.41 (t, J = 5.62 Hz, 2 H) 3.97 (s, 3 H) 3.68 (t, J = 5.38 Hz, 2 H) 3.20 (s, 3 H) 2.53 (s, 3 H) |
| 93 | 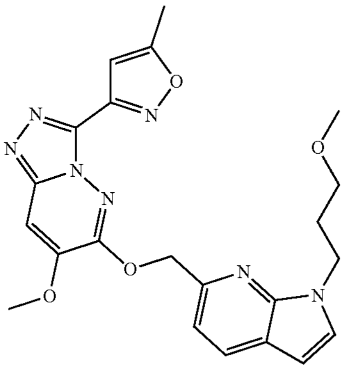 | B | 450 | (DMSO-$d_6$) δ 8.02 (d, J = 7.83 Hz, 1 H) 7.74 (s, 1 H) 7.58 (d, J = 3.42 Hz, 1 H) 7.36 (d, J = 7.83 Hz, 1 H) 6.92 (s, 1 H) 6.50 (d, J = 3.42 Hz, 1 H) 5.60 (s, 2 H) 4.29 (t, J = 7.09 Hz, 2 H) 3.97 (s, 3 H) 3.25 (t, J = 6.11 Hz, 2 H) 3.18-3.20 (m, 3 H) 2.52 (s, 3 H) 1.94-2.04 (m, 2 H) |
| 94 | 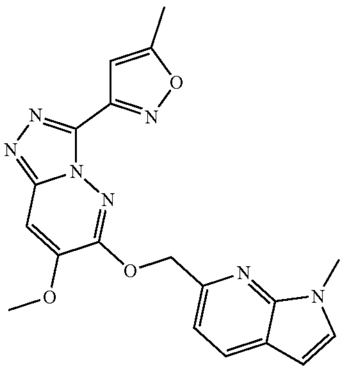 | B | 392 | (DMSO-$d_6$) δ 7.97-8.06 (m, 1 H) 7.74 (s, 1 H) 7.51-7.62 (m, 1 H) 7.30-7.41 (m, 1 H) 6.95 (s, 1 H) 6.39-6.53 (m, 1 H) 5.60 (s, 2 H) 3.97 (s, 3 H) 3.83 (s, 3 H) 2.52 (s, 3 H) |

-continued
| Embodiment | Structure | Synthesis method | Mass spectrum [M + H]+ | 1H NMR (400 MHz) |
| --- | --- | --- | --- | --- |
| 95 | 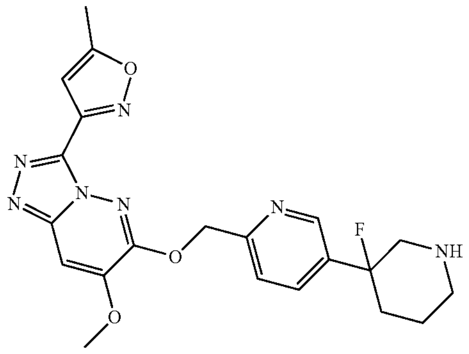 [SMILES: COc1cc2nnc(-c3cc(C)on3)n2nc1OCc1ccc(C2(F)CCCNC2)cn1] | D | 440 | (DMSO-$d_6$) δ 8.71 (d, J = 1.47 Hz, 1 H) 7.92 (dd, J = 8.07, 2.20 Hz, 1 H) 7.76 (s, 1 H) 7.66 (d, J = 8.31 Hz, 1 H) 6.87 (s, 1 H) 5.48-5.61 (m, 2 H) 3.99 (s, 3 H) 2.92-3.07 (m, 3 H) 2.64 (t, J = 12.47 Hz, 1 H) 2.55 (s, 3 H) 2.08-2.25 (m, 1 H) 1.93-2.07 (m, 2 H) 1.69-1.82 (m, 1 H) 1.56 (d, J = 13.21 Hz, 1 H) |
| 96 | 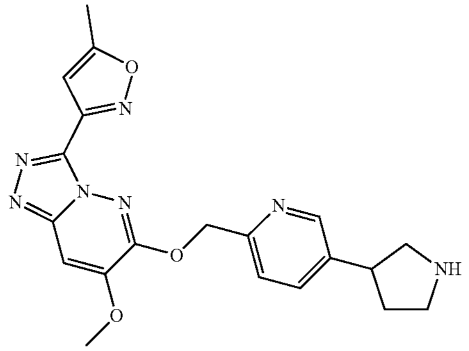 [SMILES: COc1cc2nnc(-c3cc(C)on3)n2nc1OCc1ccc(C2CCNC2)cn1] | D | 408 | (DMSO-$d_6$) δ 8.60 (d, J = 1.96 Hz, 1 H) 7.89 (dd, J = 8.07, 2.20 Hz, 1 H) 7.74 (s, 1 H) 7.63 (d, J = 8.31 Hz, 1 H) 6.90 (s, 1 H) 5.52 (s, 2 H) 3.91-4.03 (m, 3 H) 3.62 (dd, J = 10.76, 8.31 Hz, 2 H) 3.47-3.53 (m, 2 H) 3.40 (ddd, J = 11.37, 8.44, 3.18 Hz, 3 H) 3.06-3.13 (m, 1 H) 2.55 (s, 3 H)2.38 (ddd, J = 19.44, 7.21, 3.18 Hz, 1 H) 1.88-2.01 (m, 1 H) |
| 97 | 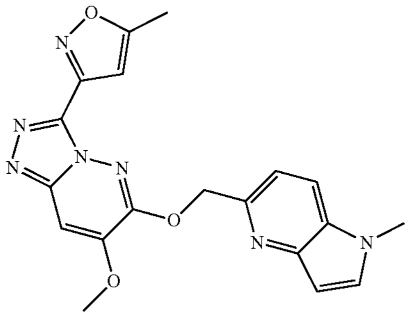 [SMILES: COc1cc2nnc(-c3cc(C)on3)n2nc1OCc1ccc2c(ccn2C)n1] | B | 392 | (DMSO-$d_6$) δ7.88-7.97 (d, J = 8.3 Hz, 1 H), 7.73 (s, 1 H), 7.67 (d, J = 3.4 Hz, 1 H), 7.43 (d, J = 8.8 Hz, 1 H) 7.02 (s, 1 H) 6.57 (d, J = 2.9 Hz, 1 H) 5.61 (s, 2 H) 3.97 (s, 3 H) 3.83 (s, 3 H) 2.56 (s, 3 H) |
| 98 | 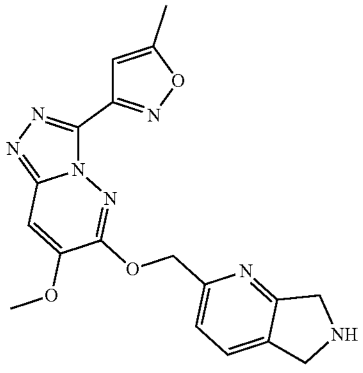 [SMILES: COc1cc2nnc(-c3cc(C)on3)n2nc1OCc1ccc2c(n1)CNC2] | D | 380 | (DMSO-$d_6$): δ 7.78 (d, J = 8.0 Hz, 1H), 7.58 (d, J = 8.0 Hz, 1H), 7.50 (s, 1H), 6.94 (s, 1H), 5.63 (s, 2H), 4.26 (s, 2H), 4.20 (s, 2H), 4.06 (d, J = 7.6 Hz, 3H), 2.60 (s, 3H) |

-continued
| Embodiment | Structure | Synthesis method | Mass spectrum [M + H]+ | $^1H$ NMR (400 MHz) |
|---|---|---|---|---|
| 99 | 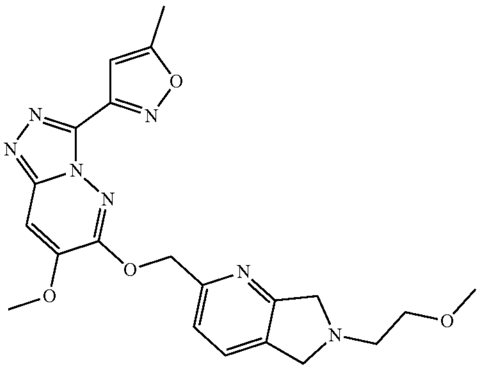 | E | 438 | ($CD_3OD$): δ 7.74 (d, J = 8.0 Hz, 1H), 7.58 (d, J = 7.6 Hz, 1H), 7.50 (s, 1H), 6.94 (s, 1H), 5.62 (s, 2H), 4.08-4.05 (m, 7H), 3.65-3.62 (m, 2H), 3.40 (s, 3H), 3.02-2.99 (m, 2H), 2.60 (s, 3H) |
| 100 | 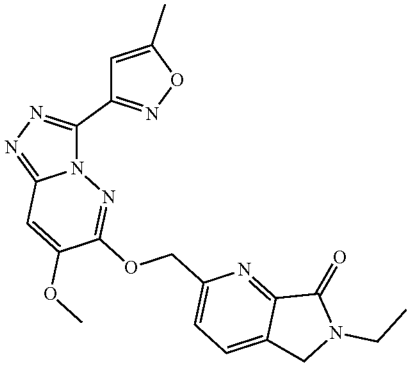 [SMILES: CCN1Cc2ccc(COc3nn4c(-c5cc(C)on5)nnc4cc3OC)nc2C1=O] | C | 422 | ($CD_3OD$): δ 7.99 (d, J = 8.0 Hz, 1H), 7.77 (d, J = 8.0 Hz, 1H), 7.41 (s, 1H), 6.77 (s, 1H), 5.65 (s, 2H), 4.47 (s, 2H), 3.98 (s, 3H), 3.66-3.60 (m, 2H), 2.48 (s, 3H), 1.23-1.17 (m, 3H) |
| 101 | 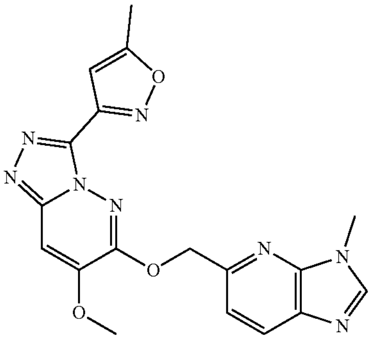 [SMILES: COc1cc2nnc(-c3cc(C)on3)n2nc1OCc1ccc2ncn(C)c2n1] | C | 393 | (DMSO-$d_6$): δ 8.48 (s, 1H), 8.14 (d, J = 8.0 Hz, 1H), 7.76 (s, 1H), 7.57 (d, J = 8.0 Hz, 1H), 6.98 (s, 1H), 5.65 (s, 2H), 3.98 (s, 3H), 3.86 (s, 3H), 2.54 (s, 3H) |
| 102 | 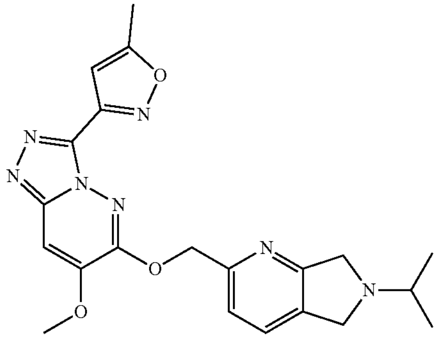 [SMILES: COc1cc2nnc(-c3cc(C)on3)n2nc1OCc1ccc2c(n1)CN(C(C)C)C2] | E | 422 | ($CD_3OD$): δ 7.66 (d, J = 8.0 Hz, 1H), 7.50 (d, J = 8.0 Hz, 1H), 7.39 (s, 1H), 6.82 (s, 1H), 5.52 (s, 2H), 4.02 (s, 2H), 3.99 (s, 2H), 3.96 (s, 3H), 2.87-2.82 (m, 1H), 2.49 (s, 3H), 1.15-1.14 (m, 6H) |

-continued
| Embodiment | Structure | Synthesis method | Mass spectrum [M + H]+ | $^1$H NMR (400 MHz) |
|---|---|---|---|---|
| 103 | 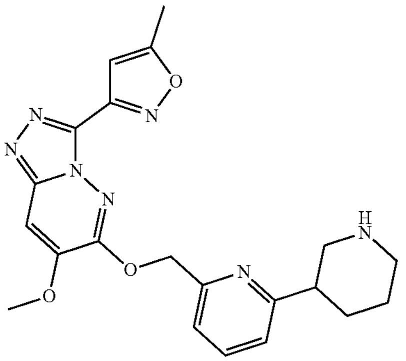 [SMILES: COc1cc2nnc(-c3cc(C)on3)n2nc1OCc1cccc(C2CCCNC2)n1] | D | 422 | (DMSO-$d_6$): δ 7.79-7.75 (m, 2H), 7.42 (d, J = 7.6 Hz,, 1H), 7.75 (d, J = 8.0 Hz, 1H), 6.93 (s, 1H), 5.52 (s, 2H), 4.00 (m, 3H), 3.03-3.00 (m, 1H), 2.92-2.90 (m, 1H), 2.76-2.74 (m, 1H), 2.67-2.61 (m, 1H), 2.58 (s, 3H), 2.45-2.42 (m, 1H), 1.91-1.88 (m, 1H), 1.66-1.43 (m, 3H) |
| 104 | 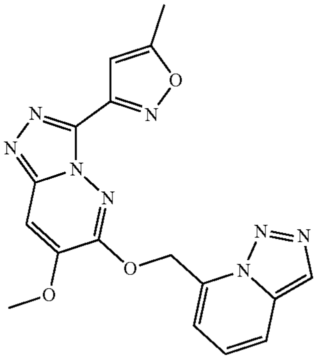 [SMILES: COc1cc2nnc(-c3cc(C)on3)n2nc1OCc1cccc2cnnn12] | C | 379 | (DMSO-$d_6$): δ 8.36 (s, 1H), 8.26 (d, J = 7.6 Hz, 1H), 7.81 (s, 1H), 7.48 (d, J = 8.0 Hz, 2H), 6.89 (s, 1H), 6.10 (s, 2H), 3.97 (s, 3H), 2.50 (s, 3H) |
| 105 | 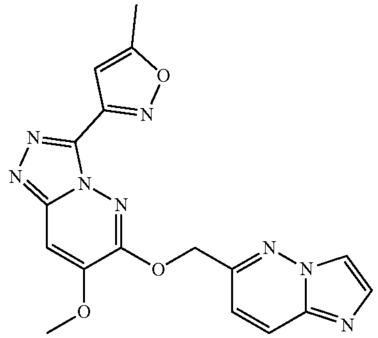 [SMILES: COc1cc2nnc(-c3cc(C)on3)n2nc1OCc1ccc2nccn2n1] | B | 379 | (DMSO-$d_6$) δ 8.31 (s, 1 H), 8.18 (d, J = 9.3 Hz, 1 H), 7.81 (s, 1 H), 7.77 (s, 1 H), 7.46 (d, J = 9.3 Hz, 1 H), 6.96 (s, 1 H), 5.64 (s, 2 H), 3.97 (s, 3 H), 2.54 (s, 3 H) |
| 106 | 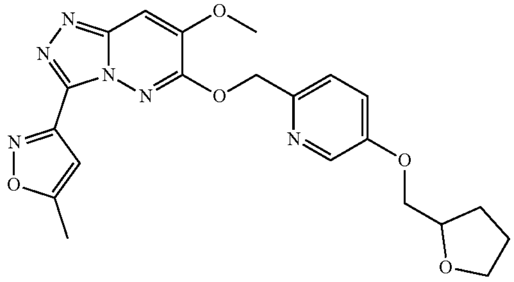 [SMILES: COc1cc2nnc(-c3cc(C)on3)n2nc1OCc1ccc(OCC2CCCO2)cn1] | B | 439 | (DMSO-$d_6$) δ 8.32 (d, J = 2.6 Hz, 1H), 7.73 (s, 1H), 7.60 (d, J = 8.6 Hz, 1H), 7.45 (dd, J = 8.5, 2.7 Hz, 1H), 6.98 (s, 1H), 5.47 (s, 2H), 4.15 (dt, J = 10.4, 5.3 Hz, 1H), 4.11-4.00 (m, 2H), 3.97 (s, 3H), 3.83-3.63 (m, 2H), 2.56 (s, 3H), 2.05-1.97 (m, 1H), 1.94-1.78 (m, 2H), 1.72-1.62 (m, 1H) |

-continued
| Em-bodi-ment | Structure | Synthesis method | Mass spectrum [M + H]+ | $^1$H NMR (400 MHz) |
|---|---|---|---|---|
| 107 | 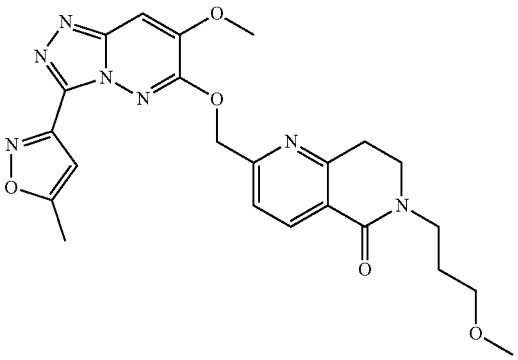 [SMILES: COCCCN1CCc2nc(COc3nn4c(-c5cc(C)on5)nnc4cc3OC)ccc2C1=O] | B | 480 | (DMSO-$d_6$) δ 8.23 (d, J = 8.0 Hz, 1H), 7.78 (s, 1H), 7.61 (d, J = 8.0 Hz, 1H), 6.92 (s, 1H), 5.58 (s, 2H), 4.00 (s, 3H), 3.64 (t, J = 6.7 Hz, 2H), 3.52 (t, J = 7.1 Hz, 2H), 3.36 (t, J = 6.2 Hz, 2H), 3.22 (s, 3H), 3.14 (d, J = 6.6 Hz, 2H), 2.55 (s, 3H), 1.82-1.78 (m, 2H) |
| 109 | 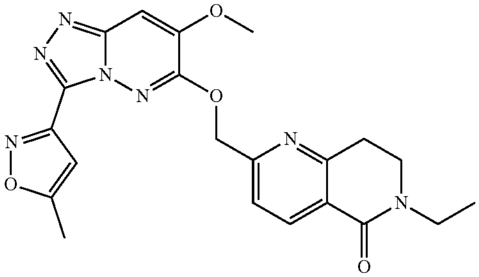 [SMILES: CCN1CCc2nc(COc3nn4c(-c5cc(C)on5)nnc4cc3OC)ccc2C1=O] | B | 436 | (DMSO-$d_6$) δ 8.22 (d, J = 7.9 Hz, 1H), 7.74 (s, 1H), 7.59 (d, J = 8.0 Hz, 1H), 6.90 (s, 1H), 5.55 (s, 2H), 3.99 (s, 3H), 3.64 (t, J = 6.7 Hz, 2H), 3.51 (dd, J = 14.2, 7.1 Hz, 2H), 3.12 (t, J = 6.7 Hz, 2H), 2.53 (s, 3H), 1.11 (t, J = 7.1 Hz, 3H) |
| 110 | 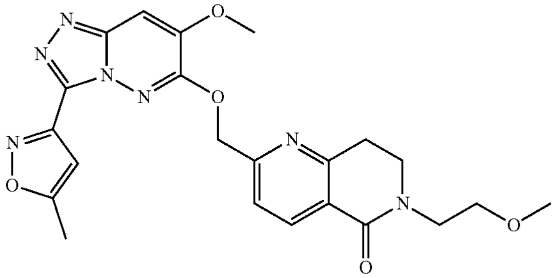 [SMILES: COCCN1CCc2nc(COc3nn4c(-c5cc(C)on5)nnc4cc3OC)ccc2C1=O] | B | 466 | (DMSO-$d_6$) δ 8.23 (d, J = 8.0 Hz, 1H), 7.76 (s, 1H), 7.61 (d, J = 8.0 Hz, 1H), 6.91 (s, 1H), 5.58 (s, 2H), 4.01 (s, 3H), 3.74-3.62 (m, 4H), 3.53 (t, J = 5.5 Hz, 2H), 3.26 (s, 3H), 3.11 (t, J = 6.7 Hz, 2H), 2.55 (s, 3H) |
| 112 | 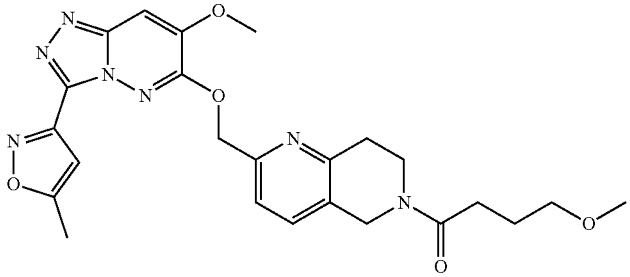 [SMILES: COCCCC(=O)N1CCc2nc(COc3nn4c(-c5cc(C)on5)nnc4cc3OC)ccc2C1] | G | 494 | (DMSO-$d_6$) δ 7.74 (s, 1H), 7.68 (t, J = 7.2 Hz, 1H), 7.48 (t, J = 6.5 Hz, 1H), 6.97 (s, 1H), 5.48 (s, 2H), 4.67 (d, J = 18.3 Hz, 2H), 3.97 (s, 3H), 3.77 (d, J = 4.9 Hz, 2H), 3.32-3.28 (m, 2H), 3.20-3.16 (m, 3H), 2.93-2.88 (m, 2H), 2.54 (s, 3H), 2.46-2.37 (m, 2H), 1.75-1.70 (m, 2H) |

-continued
| Em-bodi-ment | Structure | Synthesis method | Mass spectrum [M + H]+ | $^1$H NMR (400 MHz) |
|---|---|---|---|---|
| 115 | 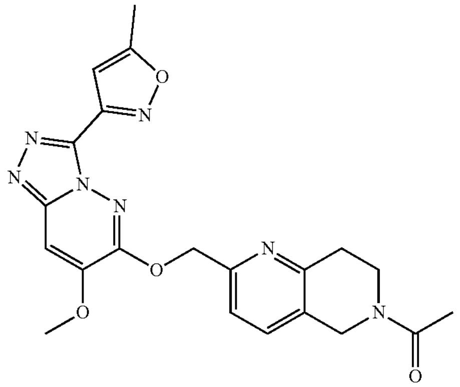 [SMILES: COc1cc2nnc(-c3cc(C)on3)n2nc1OCc1ccc2c(n1)CCN(C(C)=O)C2] | G | 436 | (DMSO-$d_6$) δ 7.72-7.75 (m, 1 H) 7.64-7.71 (m, 1 H) 7.44-7.51 (m, 1 H) 6.94-7.01 (m, 1 H) 5.44-5.51 (m, 2 H) 4.61-4.72(m, 2 H) 3.98 (s, 3 H) 3.74-3.80 (m, 2 H) 2.96-3.02 (m, 1 H) 2.82-2.90 (m, 1 H) 2.55 (s, 3 H) 2.11 (s, 3H) |
| 116 | 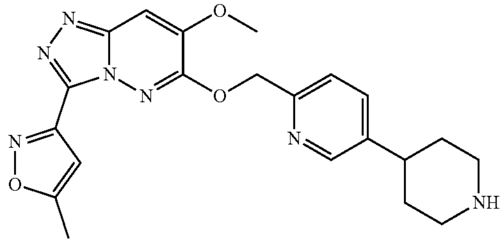 [SMILES: COc1cc2nnc(-c3cc(C)on3)n2nc1OCc1ccc(C2CCNCC2)cn1] | D | 422 | (DMSO-$d_6$) δ 8.50 (s, 1H), 7.79-7.67 (m, 2H), 7.60 (d, J = 8.0 Hz, 1H), 6.88 (s, 1H), 5.51 (s, 2H), 3.97 (s, 3H), 3.30 (m. 2H), 2.94 (dd, J = 12.1, 9.3 Hz, 4H), 2.54 (s, 3H), 1.87 (d, J = 22.5 Hz, 4H) |
| 117 | 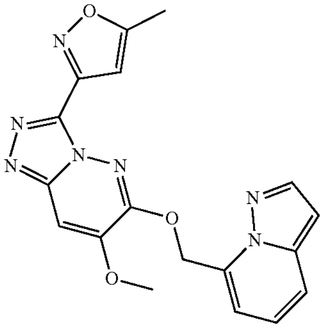 [SMILES: COc1cc2nnc(-c3cc(C)on3)n2nc1OCc1cccc2ccnn12] | B | 378 | (DMSO-$d_6$) δ 8.08 (d, J = 2.2 Hz, 1H), 7.81-7.75 (m, 2H), 7.26 (dd, J = 8.8, 6.9 Hz, 1H), 7.19 (d, J = 6.1 Hz, 1H), 6.83 (d, J = 0.7 Hz, 1H), 6.75 (d, J = 2.2 Hz, 1H), 5.95 (s, 2H), 3.95 (s, 3H), 2.48 (s, 3H) |
| 118 | 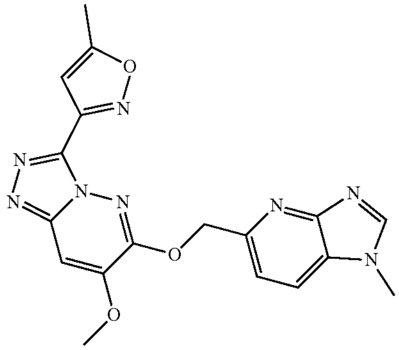 [SMILES: COc1cc2nnc(-c3cc(C)on3)n2nc1OCc1ccc2c(ncn2C)n1] | C | 393 | ($CD_3OD$) δ 8.40 (s, 1H), 8.10-8.07 (m, 1H), 7.69-7.67 (m, 1H), 7.48 (s, 1H), 6.87 (s, 1H), 5.75 (s, 2H), 4.06 (s, 3H), 3.95 (s, 3H), 2.57 (s, 3H) |
| 119 | 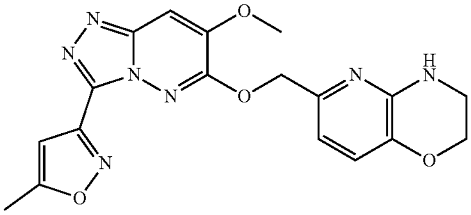 [SMILES: COc1cc2nnc(-c3cc(C)on3)n2nc1OCc1ccc2c(n1)NCCO2] | D | 396 | ($CDCl_3$) δ 7.18 (s, 1H), 6.98-6.96 (m, 1H), 6.91-6.89 (m, 1H), 6.79 (s, 1H), 5.39 (s, 2H), 4.91 (s, 1H), 4.24-4.22 (m, 2H), 3.98 (s, 3H), 3.58-3.55 (m, 2H), 2.56 (s, 3H). |

-continued
| Em-bodi-ment | Structure | Synthesis method | Mass spectrum [M + H]+ | $^1$H NMR (400 MHz) |
|---|---|---|---|---|
| 120 | 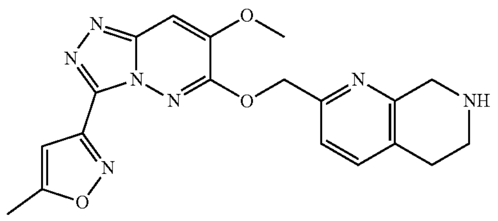 [SMILES: COc1cc2nnc(-c3cc(C)on3)n2nc1OCc1ccc2c(n1)CNCC2] | D | 394 | ($CD_3OD$) δ 7.63 (s, 1H), 7.54-7.52 (m, 1H), 7.51 (s, 1H), 6.96 (s, 1H), 5.57 (s, 2H), 4.08 (s, 3H), 4.04 (s, 2H), 3.14-3.10 (m, 2H), 2.91-2.88 (m, 2H), 2.61 (s, 3H) |
| 121 | 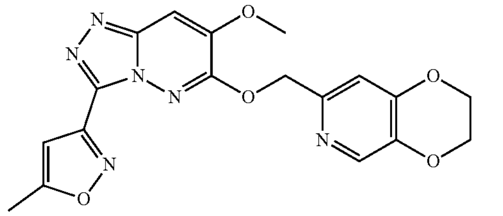 [SMILES: COc1cc2nnc(-c3cc(C)on3)n2nc1OCc1cc2c(cn1)OCCO2] | C | 397 | ($CD_3OD$) δ 8.08 (s, 1H), 7.41 (s, 1H), 7.24 (s, 1H), 6.86 (s, 1H), 5.50 (s, 2H), 4.38-4.32 (m, 4H), 4.06 (s, 3H), 2.60 (s, 3H) |
| 122 | 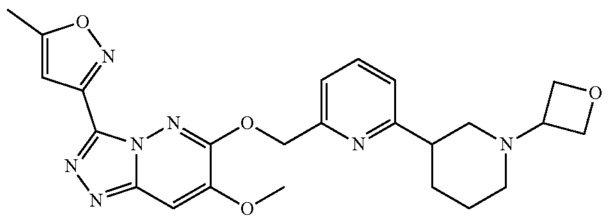 [SMILES: COc1cc2nnc(-c3cc(C)on3)n2nc1OCc1cccc(C2CCCN(C3COC3)C2)n1] | C | 478 | (DMSO-$d_6$) δ 7.80-7.77 (m, 2H), 7.45-7.43 (m, 1H), 7.31-7.29 (m, 1H), 6.90 (s, 1H), 5.52 (s, 2H), 4.53-4.36 (m, 4H), 3.99 (s, 3H), 3.38-3.35 (m, 1H), 2.94-2.88 (m, 1H), 2.75-2.69 (m, 2H), 2.54 (s, 3H), 1.94-1.85 (m, 2H), 1.75-1.68 (m, 2H), 1.56-1.48 (m, 2H) |
| 123 | 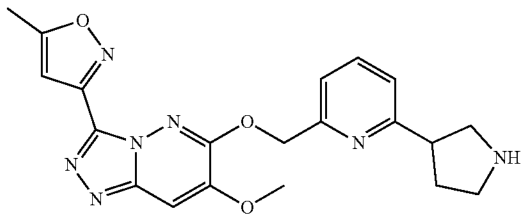 [SMILES: COc1cc2nnc(-c3cc(C)on3)n2nc1OCc1cccc(C2CCNC2)n1] | D | 408 | ($CD_3OD$) δ 7.88-7.84 (m, 1H), 7.63-7.61 (m, 1H), 7.51 (s, 1H), 7.39-7.37 (m, 1H), 6.87 (s, 1H), 5.62 (s, 2H), 4.09 (s, 3H), 3.86-3.83 (m, 1H), 3.74-3.70 (m, 1H), 3.5-3.58 (m, 2H), 3.49-3.42 (m, 1H), 2.59 (s, 3H), 2.54-2.47 (m, 1H), 2.24-2.19 (m, 1H) |
| 124 | 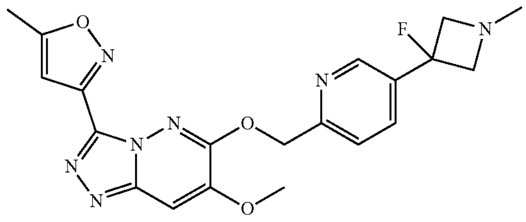 | C | 426 | ($CD_3OD$) δ 8.72 (s, 1H), 8.03-8.00 (m, 1H), 7.76-7.74 (m. 1H), 7.44 (s, 1H), 6.80 (s, 1H), 5.61 (s, 2H), 4.03 (s, 3H), 3.79-3.64 (m, 4H), 2.53 (s, 3H), 2.42 (s, 3H) |
| 125 | 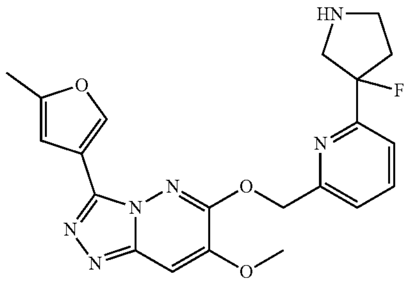 [SMILES: COc1cc2nnc(-c3coc(C)c3)n2nc1OCc1cccc(C2(F)CCNC2)n1] | D | 426 | ($CD_3OD$) δ 7.80-7.76 (m, 1H), 7.52-7.50 (m, 2H), 7.39 (s, 1H), 6.74 (s, 1H), 5.52 (s, 2H), 3.97 (s, 3H), 3.23-3.15 (m, 4H), 2.46 (s, 3H), 2.30-2.20 (m, 2H) |

-continued
| Em-bodi-ment | Structure | Synthesis method | Mass spectrum $[M + H]^+$ | $^1H$ NMR (400 MHz) |
|---|---|---|---|---|
| 126 | 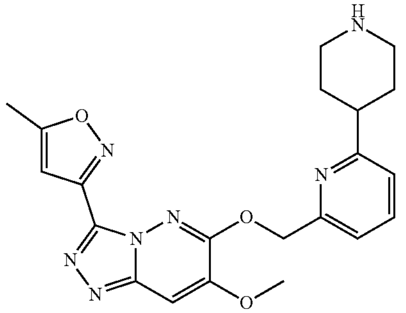 [SMILES: COc1cc2nnc(-c3cc(C)on3)n2nc1OCc1cccc(C2CCNCC2)n1] | D | 422 | ($CD_3OD$) δ 7.84-7.80 (m, 1H), 7.55-7.54 (m, 1H), 7.50 (s, 1H), 7.31-7.29 (m, 1H), 6.90 (s, 1H), 5.60 (s, 2H), 4.08 (s, 3H), 3.23-3.19 (m, 2H), 2.95-2.89 (m, 1H), 2.84-2.77 (m, 2H), 2.59 (s, 3H), 1.96-1.92 (m, 2H), 1.81-1.77 (m, 2H) |
| 127 | 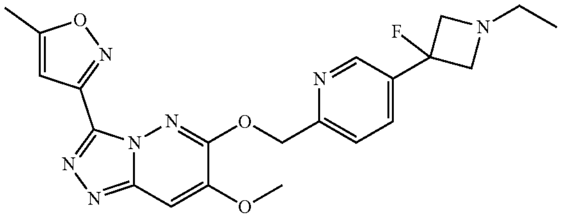 [SMILES: CCN1CC(F)(c2ccc(COc3nn4c(-c5cc(C)on5)nnc4cc3OC)nc2)C1] | C | 440 | ($CD_3OD$) δ 8.77 (s, 1H), 8.07-8.05 (m, 1H), 7.81-7.79 (m, 1H), 7.50 (s, 1H), 6.85 (s, 1H), 5.66 (s, 2H), 4.07 (s, 3H), 3.86-3.74 (m, 4H), 2.75-7.72 (m, 2H), 2.57 (s, 3H), 1.08-1.04 (m, 3H) |
| 128 | 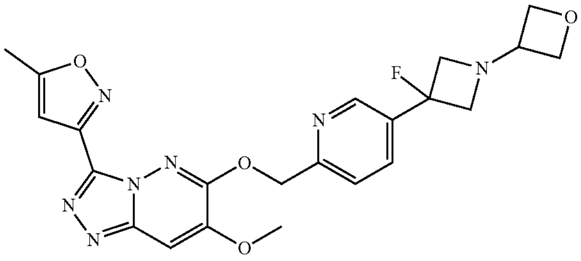 [SMILES: COc1cc2nnc(-c3cc(C)on3)n2nc1OCc1ccc(C2(F)CN(C3COC3)C2)cn1] | C | 468 | (DMSO-$d_6$) δ 8.82-8.81 (m, 1H), 8.06-8.04 (m, 1H), 7.77 (s, 1H), 7.73-7.71 (m, 1H), 6.86 (s, 1H), 5.59 (s, 2H), 4.61-4.58 (m, 2H), 4.41-4.38 (m, 2H), 4.00 (s, 3H), 3.92-3.86 (m, 1H), 3.79-3.64 (m, 4H), 2.55 (s, 3H) |
| 129 | 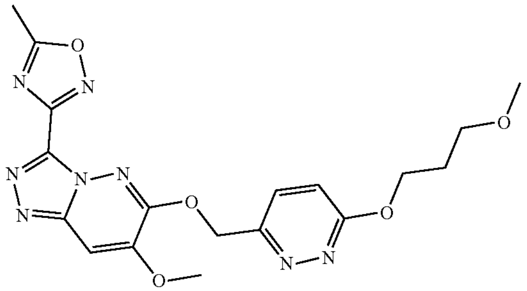 [SMILES: COCCCOc1ccc(COc2nn3c(-c4noc(C)n4)nnc3cc2OC)nn1] | B | 429 | (DMSO-$d_6$) δ 7.93 (d, J = 9.3 Hz, 1 H), 7.79 (s, 1 H), 7.25 (d, J = 9.3 Hz, 1 H), 5.61 (s, 2 H), 4.47 (t, J = 6.4 Hz, 2 H), 3.97 (s, 3 H), 3.46 (t, J = 6.4 Hz, 2 H), 3.23 (s, 3 H), 2.74 (s, 3 H), 1.99 (t, J = 6.4 Hz, 2 H) |
| 130 | 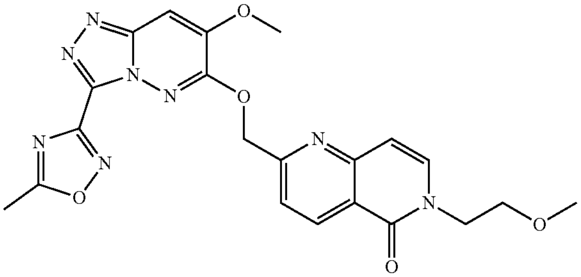 | B | 465 | (DMSO-$d_6$) δ 8.58 (d, J = 8.3 Hz, 1 H), 7.83 (s, 1 H), 7.71 (t, J = 8.1 Hz, 3 H), 6.68 (d, J = 7.3 Hz, 1 H), 5.65 (s, 2 H), 4.15 (t, J = 5.1 Hz, 2 H), 4.03 (s, 3 H), 3.62 (t, J = 5.1 Hz, 2 H), 3.24 (s, 3 H), 2.73 (s, 3 H) |

-continued
| Embodiment | Structure | Synthesis method | Mass spectrum $[M + H]^+$ | $^1H$ NMR (400 MHz) |
|---|---|---|---|---|
| 131 | 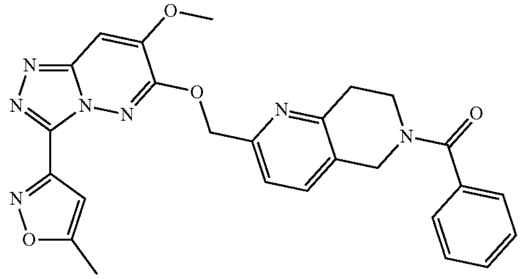 [SMILES: COc1cc2nnc(-c3cc(C)on3)n2nc1OCc1ccc2c(n1)CCN(C(=O)c1ccccc1)C2] | G | 498 | (DMSO-$d_6$) δ 7.94 (d, J = 7.3 Hz, 1 H), 7.74 (s, 1 H), 7.70-7.56 (m, 1 H), 7.54-7.37 (m, 5 H), 6.97 (s, 1 H), 5.49 (s, 2 H), 4.81 (br. s., 1 H), 4.64 (br. s., 1 H), 3.98 (s, 3 H), 3.67 (br. s., 2 H), 2.98 (br. s., 2 H), 2.55 (s, 3 H) |
| 132 | 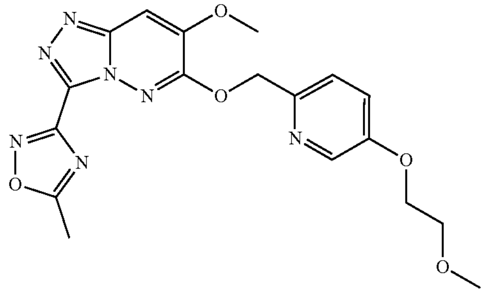 [SMILES: COCCOc1ccc(COc2nn3c(-c4noc(C)n4)nnc3cc2OC)nc1] | B | 414 | ($CDCl_3$) δ 7.80 (d, J = 2.4 Hz, 1 H), 7.20 (d, J = 8.3 Hz, 1 H), 6.86 (s, 1 H), 6.83 (s, 1 H), 6.79 (dd, J = 2.9, 8.8 Hz, 1 H), 5.08 (s, 2 H), 3.69-3.66 (m, 2 H), 3.52 (s, 2 H), 2.94 (s, 3 H), 2.26 (s, 3 H) |
| 133 | 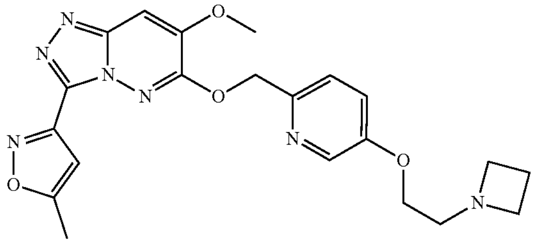 [SMILES: COc1cc2nnc(-c3cc(C)on3)n2nc1OCc1ccc(OCCN2CCC2)cn1] | C | 438 | (DMSO-$d_6$) δ 8.32 (s, 1 H), 7.75 (s, 1 H), 7.63 (d, J = 8.8 Hz, 1 H), 7.46 (dd, J = 2.9, 8.8 Hz, 1 H), 6.99 (s, 1 H), 5.49 (s, 2 H), 4.16 (br. s., 2 H), 3.98 (s, 3 H), 3.65 (br. s., 4 H), 3.15 (br. s., 2 H), 2.57 (s, 3 H), 2.21-2.10 (m, 2 H) |
| 134 | 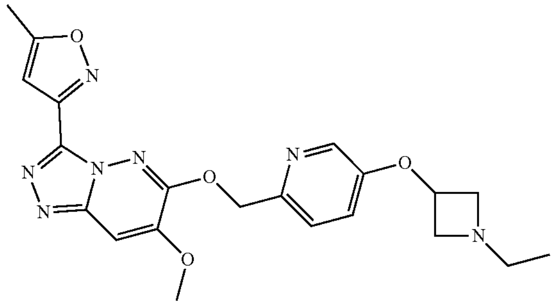 [SMILES: CCN1CC(Oc2ccc(COc3nn4c(-c5cc(C)on5)nnc4cc3OC)nc2)C1] | B | 438 | (DMSO-$d_6$) δ 8.25 (d, J = 2.9 Hz, 1 H), 7.74 (s, 1 H), 7.61 (d, J = 8.3 Hz, 1 H), 7.37 (dd, J = 2.9, 8.3 Hz, 1 H), 6.98 (s, 1 H), 5.49 (s, 2 H), 5.13 (t, J = 6.1 Hz, 1 H), 4.07-4.00 (m, 2 H), 3.97 (s, 3 H), 3.80-3.73 (m, 2 H), 2.93 (q, J = 7.2 Hz, 2 H), 2.56 (s, 3 H), 1.10 (t, J = 7.1 Hz, 3 H) |
| 135 | 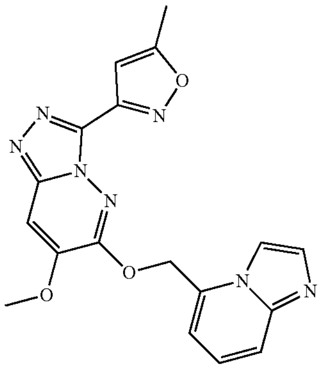 [SMILES: COc1cc2nnc(-c3cc(C)on3)n2nc1OCc1cccc2nccn12] | B | 378 | (DMSO-$d_6$) δ 8.07 (s, 1 H), 7.74 (s, 1 H), 7.70-7.62 (m, 2H), 7.33-7.21 (m, 2 H), 7.03 (s, 1 H), 5.82 (s, 2 H), 3.92 (s, 3 H), 2.53 (s, 3 H) |

-continued
| Embodiment | Structure | Synthesis method | Mass spectrum $[M + H]^+$ | $^1H$ NMR (400 MHz) |
| --- | --- | --- | --- | --- |
| 136 | 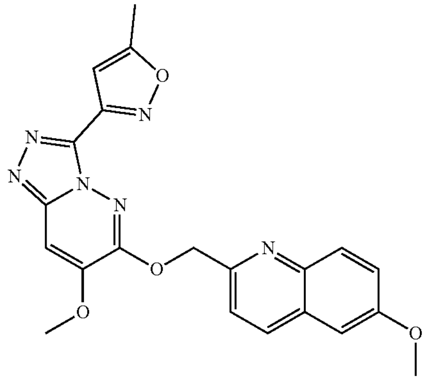 [SMILES: COc1ccc2nc(COc3nn4c(-c5cc(C)on5)nnc4cc3OC)ccc2c1] | B | 419 | (DMSO-$d_6$) □ 8.31 (d, J = 8.80 Hz, 1H), 7.93 (d, J = 8.80 Hz, 1H), 7.76 (s, 1H), 7.68 (d, J = 8.31 Hz, 1H), 7.35-7.45 (m, 2H), 6.85 (s, 1H), 5.67 (s, 2H), 3.99 (s, 4H), 3.88 (s, 4H) |
| 138 | 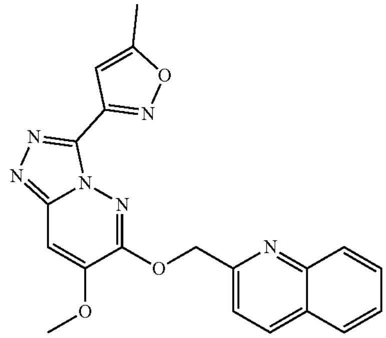 [SMILES: COc1cc2nnc(-c3cc(C)on3)n2nc1OCc1ccc2ccccc2n1] | B | 389 | (DMSO-$d_6$) □ 8.44 (d, J = 8.31 Hz, 1H), 8.01 (d, J = 8.31 Hz, 1H), 8.05 (d, J = 8.31 Hz, 1H), 7.72-7.84 (m, 3H), 7.64 (s, 1H), 6.80 (s, 1H), 5.75 (s, 2H), 4.02 (s, 3H), 2.46 (s, 3H) |
| 139 | 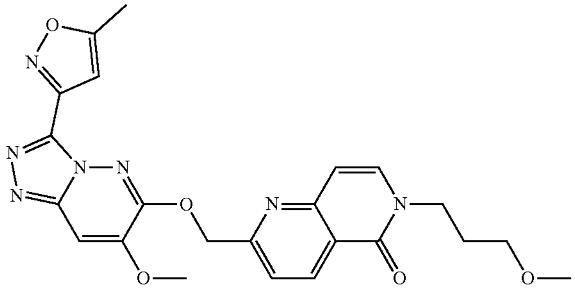 [SMILES: COCCCn1ccc2nc(COc3nn4c(-c5cc(C)on5)nnc4cc3OC)ccc2c1=O] | B | 478 | (DMSO-$d_6$) □ 8.56 (s, 1H), 7.77 (s, 1H), 7.72 (d, J = 7.34 Hz, 1H), 7.67 (d, J = 8.31 Hz, 1H), 6.76 (s, 1H), 6.71 (d, J = 7.34 Hz, 1H), 5.68 (s, 2H), 3.94-4.10 (m, 5H), 3.29-3.32 (m, 2H), 3.21 (s, 3H), 2.49 (s, 5H), 1.90 (quin, J = 6.60 Hz, 2H) |
| 140 | 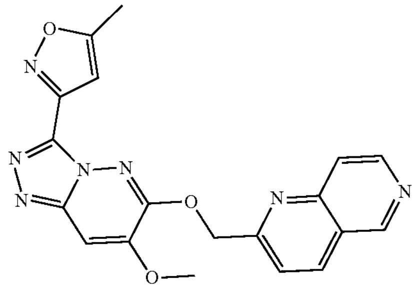 [SMILES: COc1cc2nnc(-c3cc(C)on3)n2nc1OCc1ccc2cnccc2n1] | B | 390 | (DMSO-$d_6$) □ 9.42 (s, 1H), 8.77 (d, J = 5.87 Hz, 1H), 8.65 (d, J = 8.31 Hz, 1H), 7.93 (d, J = 5.87 Hz, 1H), 7.89 (d, J = 8.80 Hz, 1H), 7.79 (s, 1H), 6.72 (s, 1H), 5.80 (s, 2H), 4.03 (s, 4H), 2.45 (s, 4H) |

-continued
| Em-bodi-ment | Structure | Synthesis method | Mass spectrum [M + H]+ | $^1$H NMR (400 MHz) |
|---|---|---|---|---|
| 141 | 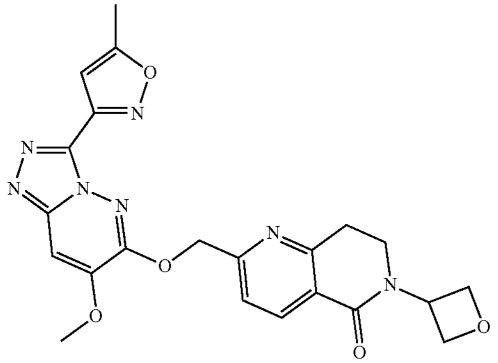 [SMILES: COc1cc2nnc(-c3cc(C)on3)n2nc1OCc1ccc2c(n1)CCN(C1COC1)C2=O] | B | 464 | (DMSO-$d_6$) δ 8.19-8.27 (m, 1 H) 7.78 (s, 1 H) 7.58-7.64 (m, 1 H) 6.93 (s, 1 H) 5.60 (s, 2 H) 5.46 (m, 1 H) 4.72-4.79 (m, 4 H) 4.01 (s, 3 H) 3.81 (t, J = 6.60 Hz, 2 H) 3.18-3.24 (t, J = 6.60 Hz, 2 H) 2.55 (s, 3 H) |
| 142 | 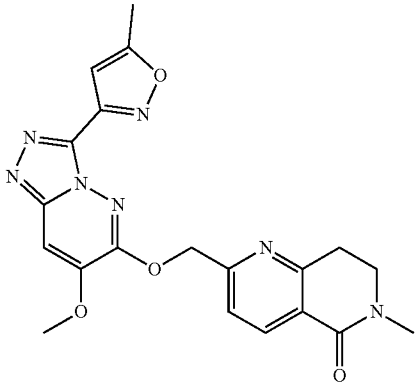 [SMILES: COc1cc2nnc(-c3cc(C)on3)n2nc1OCc1ccc2c(n1)CCN(C)C2=O] | B | 422 | (DMSO-$d_6$) δ 8.23 (m, 1H), 7.77 (s, 1 H), 7.60 (m, 1 H), 6.92 (s, 1 H), 5.58 (s, 2 H), 4.00 (s, 3 H), 3.64 (t, J = 6.85 Hz, 2 H), 3.14 (t, J = 6.85 Hz, 2 H), 3.03 (s, 3 H), 2.54 (s, 3 H) |
| 143 | 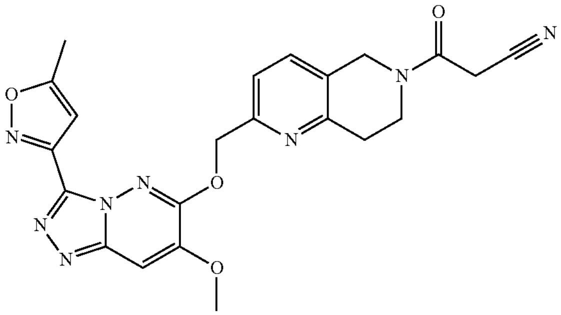 [SMILES: COc1cc2nnc(-c3cc(C)on3)n2nc1OCc1ccc2c(n1)CCN(C(=O)CC#N)C2] | G | 461 | (DMSO-$d_6$) δ 7.61-7.78 (m, 2 H), 7.46-7.54 (m, 1 H), 6.99 (s, 1 H), 5.49 (s, 2 H), 4.60-4.71 (m, 2 H), 4.12-4.20 (m, 2 H), 3.98 (s, 3 H), 3.66-3.84 (m, 2 H), 2.86-3.05 (m, 2 H), 2.55 (s, 3 H) |
| 144 | 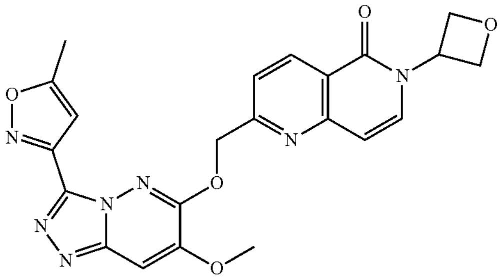 [SMILES: COc1cc2nnc(-c3cc(C)on3)n2nc1OCc1ccc2c(=O)n(C3COC3)ccc2n1] | B | 462 | (DMSO-$d_6$) □ 8.56 (d, J = 8.31 Hz, 1H), 7.91 (d, J = 7.83 Hz, 1H), 7.79 (s, 1H), 7.69 (d, J = 8.31 Hz, 1H), 6.76-6.86 (m, 2H), 5.70 (s, 2H), 5.60-5.68 (m, 1H), 4.87-4.98 (m, 2H), 4.80 (t, J = 6.85 Hz, 2H), 4.02 (s, 3H) |

-continued
| Em-bodi-ment | Structure | Synthesis method | Mass spectrum $[M + H]^+$ | $^1H$ NMR (400 MHz) |
|---|---|---|---|---|
| 145 | 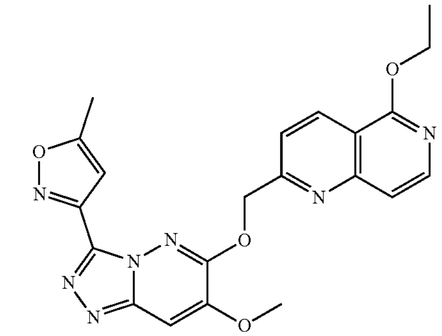 [SMILES: CCOc1nccc2nc(COc3nn4c(-c5cc(C)on5)nnc4cc3OC)ccc12] | B | 434 | (DMSO-$d_6$) □ 8.55-8.63 (m, 1H), 8.20-8.28 (m, 1H), 7.79 (s, 2H), 7.43-7.49 (m, 1H), 6.73 (s, 1H), 5.76 (s, 2H), 4.52-4.57 (m, 4H), 4.03 (s, 3H), 2.47 (s, 4H), 1.39-1.46 (m, 5H) |
| 146 | 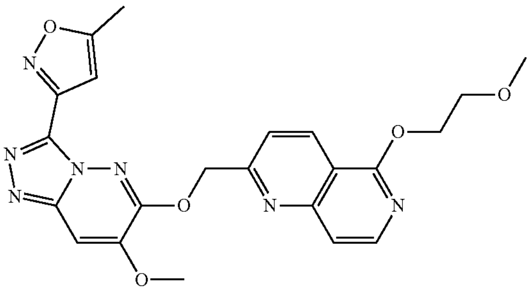 [SMILES: COCCOc1nccc2nc(COc3nn4c(-c5cc(C)on5)nnc4cc3OC)ccc12] | B | 464 | $^1H$ NMR (400 MHz, DMSO-$d_6$) □ 8.60 (d, J = 8.31 Hz, 1H), 8.26 (d, J = 5.87 Hz, 1H), 7.74-7.91 (m, 2H), 7.49 (d, J = 5.87 Hz, 1H), 6.73 (br. s., 1H), 5.77 (br. s., 2H), 4.62 (br. s., 2H), 4.04 (br. s., 2H), 3.78 (br. s., 1H) |
| 147 | 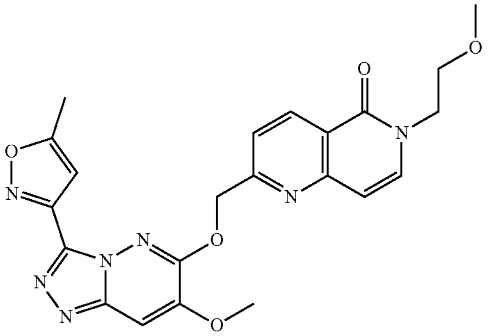 [SMILES: COCCn1ccc2nc(COc3nn4c(-c5cc(C)on5)nnc4cc3OC)ccc2c1=O] | B | 464 | (DMSO-$d_6$) □ 8.58 (d, J = 8.31 Hz, 1H), 7.78 (s, 1H), 7.67 (d, J = 8.31 Hz, 1H), 7.71 (d, J = 7.83 Hz, 1H), 6.74 (s, 1H), 6.70 (d, J = 7.83 Hz, 1H), 5.68 (s, 2H), 4.15 (t, J = 5.38 Hz, 2H), 4.02 (s, 3H), 3.62 (t, J = 5.38 Hz, 2H), 3.24 (s, 3H) |
| 148 | 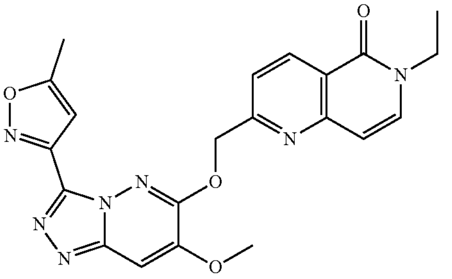 [SMILES: CCn1ccc2nc(COc3nn4c(-c5cc(C)on5)nnc4cc3OC)ccc2c1=O] | B | 434 | $^1H$ NMR (400 MHz, DMSO-$d_6$) □ 8.59 (d, J = 8.31 Hz, 1H), 7.76-7.88 (m, 2H), 7.68 (d, J = 8.31 Hz, 1H), 6.68-6.84 (m, 2H), 5.69 (s, 2H), 3.94-4.10 (m, 5H), 2.52-2.59 (m, 2H), 1.25-1.32 (m, 3H) |
| 149 | 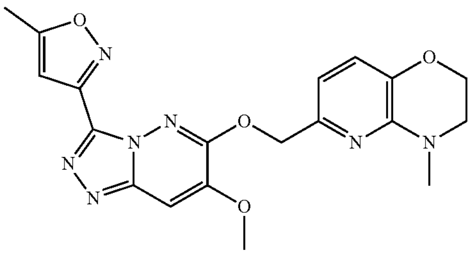 [SMILES: COc1cc2nnc(-c3cc(C)on3)n2nc1OCc1ccc2c(n1)N(C)CCO2] | C | 410 | (DMSO-$d_6$) δ 7.74(s, 1H), 6.97-6.94(m, 2H), 6.76(d, 1H), 5.29(s, 2H), 4.21(t, J = 4 Hz, 2H), 3.97(s, 3H), 3.44(t, J = 4 Hz, 2H), 3.01(s, 3H), 2.55(s, 3H) |

-continued
| Embodiment | Structure | Synthesis method | Mass spectrum $[M + H]^+$ | $^1H$ NMR (400 MHz) |
|---|---|---|---|---|
| 150 | 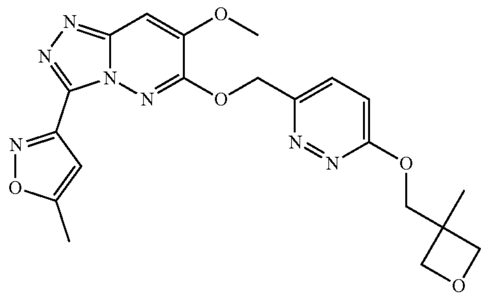 [SMILES: COc1cc2nnc(-c3cc(C)on3)n2nc1OCc1ccc(OCC2(C)COC2)nn1] | B | 440 | (DMSO-$d_6$) δ 7.88 (d, J = 9.3 Hz, 1 H), 7.75 (s, 1 H), 7.32 (d, J = 8.8 Hz, 1 H), 6.98 (s, 1 H), 5.66 (s, 2 H), 4.53 (s, 2 H), 4.51 (d, J = 5.9 Hz, 2 H), 4.30 (d, J = 5.9 Hz, 2 H), 3.96 (s, 3 H), 2.55 (s, 3 H), 1.36 (s, 3 H) |
| 151 | 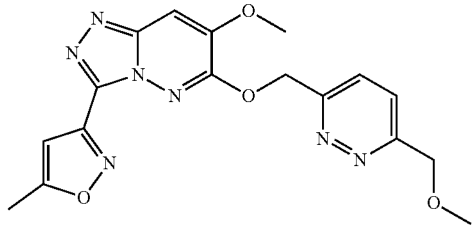 | B | 384 | ($CDCl_3$) □ 8.10 (d, J = 8.3 Hz, 1 H), 7.72 (d, J = 8.8 Hz, 1 H), 7.31 (s, 1 H), 6.81 (s, 1 H), 5.90 (s, 2 H), 4.85 (s, 2 H), 4.05 (s, 3 H), 3.51 (s, 3 H), 2.61 (s, 3 H) |
| 152 | 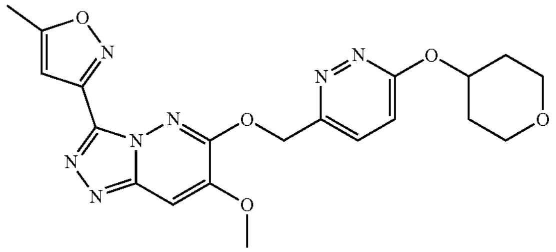 [SMILES: COc1cc2nnc(-c3cc(C)on3)n2nc1OCc1ccc(OC2CCOCC2)nn1] | B | 440 | (DMSO-$d_6$) □ 7.87 (d, J = 9.3 Hz, 1 H), 7.75 (s, 1 H), 7.25 (d, J = 9.3 Hz, 1 H), 6.99 (s, 1 H), 5.64 (s, 2 H), 5.45-5.33 (m, 1 H), 3.96 (s, 3 H), 3.90-3.82 (m, 2 H), 3.50 (t, J = 9.5 Hz, 2 H), 2.54 (s, 3 H), 2.05 (d, J = 12.7 Hz, 2 H), 1.67 (dd, J = 3.9, 12.7 Hz, 2 H) |
| 153 | 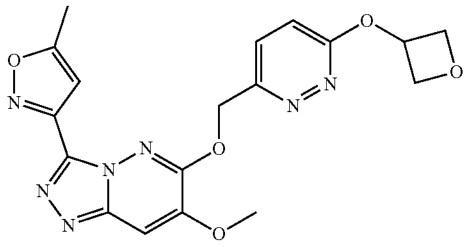 [SMILES: COc1cc2nnc(-c3cc(C)on3)n2nc1OCc1ccc(OC2COC2)nn1] | B | 412 | ($CD_3OD$) δ 8.06 (d, 1H), 7.21 (s, 1H), 7.08 (d, 1H), 6.80(s, 1H), 5.81 (m, 1H), 5.75 (s, 2H), 5.05 (t, 2H), 4.75 (dd, 2H), 3.99 (s, 3H), 2.56 (s, 3H) |
| 154 | 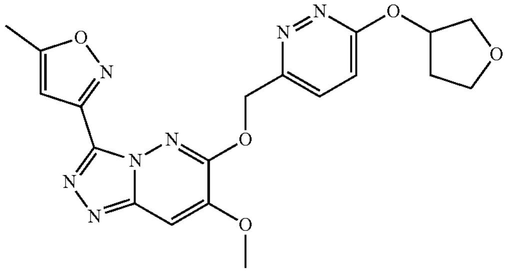 [SMILES: COc1cc2nnc(-c3cc(C)on3)n2nc1OCc1ccc(OC2CCOC2)nn1] | B | 426 | (DMSO-$d_6$) δ 7.87 (d, J = 9.3 Hz, 1 H), 7.75 (s, 1 H), 7.28 (d, J = 8.8 Hz, 1 H), 6.99 (s, 1 H), 5.70-5.66 (m, 1 H), 5.65 (s, 2 H), 3.96 (s, 3 H), 3.95-3.91 (m, 1 H), 3.89-3.84 (m, 1 H), 3.81 (d, J = 6.8 Hz, 1 H), 3.78-3.72 (m, 1 H), 2.55 (s, 3 H), 2.35-2.23 (m, 1 H), 2.08-1.99 (m, 1 H) |

-continued
| Embodiment | Structure | Synthesis method | Mass spectrum $[M + H]^+$ | $^1H$ NMR (400 MHz) |
|---|---|---|---|---|
| 155 | 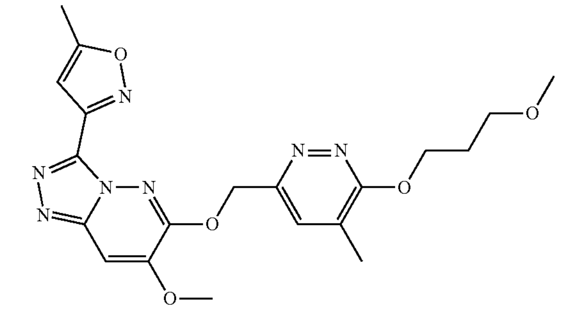 [SMILES: COCCCOc1nnc(COc2nn3c(-c4cc(C)on4)nnc3cc2OC)cc1C] | C | 442 | ($DMSO-d_6$) δ 7.79 (s, 1H), 7.76 (s, 1H), 7.00(s, 1H), 5.61 (s, 2H), 4.52-4.49(m, 2H), 3.98 (s, 3H), 3.51-3.48 (m, 2H), 3.25 (s, 3H), 2.57 (s, 3H), 2.18 (s, 3H), 2.03-2.00 (m, 2H) |
| 156 | 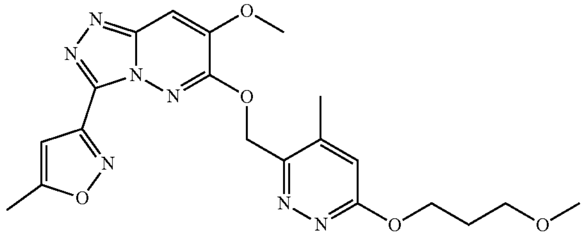 | C | 442 | ($CDCl_3$) δ 7.21 (s, 1H), 6.85 (s, 1H), 6.82 (s, 1H), 5.78 (s, 2H), 4.61-4.58 (m, 2H), 3.97 (s, 3H), 3.55-3.52 (m, 2H), 3.35 (s, 3H), 2.57 (s, 3H), 2.42 (s, 3H), 2.10-2.07 (m, 2H) |
| 157 | 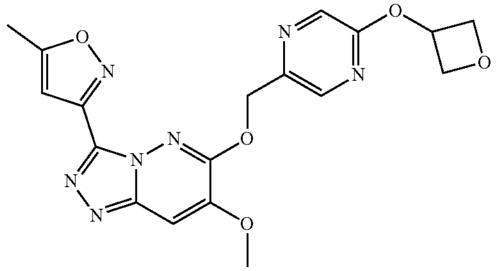 | B | 412 | ($DMSO-d_6$) δ 8.47 (s, 1 H), 8.43 (s, 1 H), 7.73 (s, 1 H), 6.99 (s, 1 H), 5.59 (quin, J = 5.6 Hz, 1 H), 5.51 (s, 2H), 4.89 (t, J = 6.8 Hz, 2 H), 4.60-4.55 (m, 2 H), 3.94 (s, 3 H), 2.55 (s, 3 H) |
| 158 | 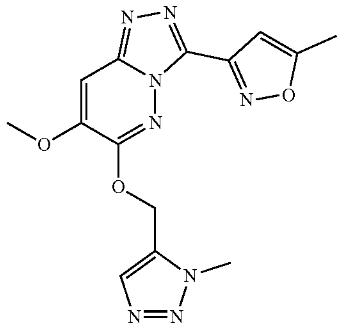 | B | 343 | ($CDCl_3$) δ 8.07 (s, 1 H) 7.21 (s, 1 H) 6.83 (s, 1 H) 5.63 (s, 2 H) 4.19 (s, 3 H) 3.93-4.03 (m, 3 H) 2.57 (s, 3 H) |
| 159 | 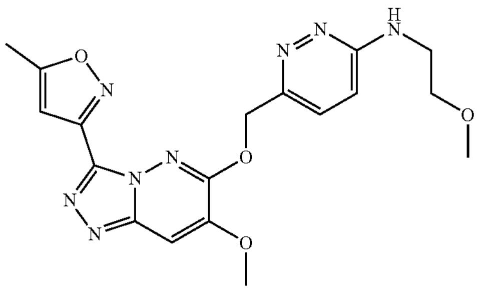 | B | 413 | ($DMSO-d_6$) δ 7.71 (s, 1 H), 7.49 (d, J = 9.3 Hz, 1 H), 7.17 (br. s., 1 H), 7.03 (s, 1 H), 6.90 (d, J = 9.3 Hz, 1 H), 5.48 (s, 2H), 3.94 (s, 3 H), 3.49.3.48 (m, 4 H), 3.24 (s, 3 H), 2.54 (s, 3 H) |

-continued

| Embodiment | Structure | Synthesis method | Mass spectrum [M + H]+ | $^1$H NMR (400 MHz) |
|---|---|---|---|---|
| 161 | 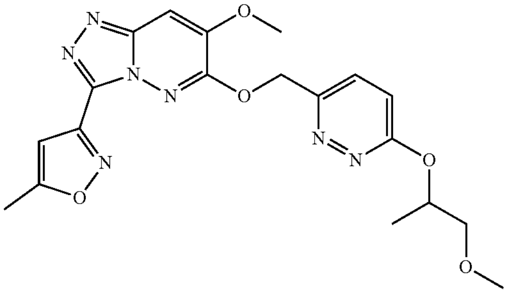 | B | 428 | (DMSO-$d_6$) □ 7.87 (d, J = 9.0 Hz, 1 H), 7.77 (s, 1 H), 7.25 (d, J = 9.0 Hz, 1 H), 7.00 (d, J = 0.8 Hz, 1 H), 5.66 (s, 2 H), 5.59-5.50 (m, 1 H), 3.98 (s, 3 H), 3.61-3.48 (m, 2 H), 3.30-3.25 (m, 3 H), 2.60-2.54 (m, 3 H), 1.31 (d, J = 6.5 Hz, 3 H) |
| 162 | 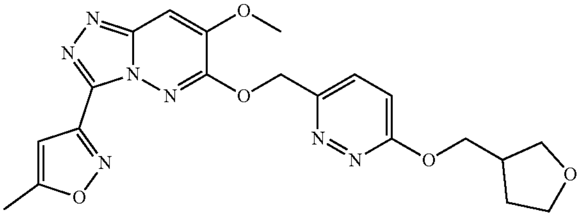 [SMILES: COc1cc2nnc(-c3cc(C)on3)n2nc1OCc1ccc(OCC2CCOC2)nn1] | B | 440 | (DMSO-$d_6$) □ 7.89 (d, J = 9.0 Hz, 1 H), 7.77 (s, 1 H), 7.29 (d, J = 9.0 Hz, 1 H), 6.99 (d, J = 1.0 Hz, 1 H), 5.66 (s, 2H), 4.43 (dd, J = 6.8, 10.5 Hz, 1 H), 4.35 (dd, J = 7.8, 10.5 Hz, 1 H), 4.01-3.93 (m, 3 H), 3.82-3.73 (m, 2 H), 3.70-3.62 (m, 1 H), 3.56 (dd, J = 5.5, 8.8 Hz, 1 H), 2.78-2.66 (m, 1 H), 2.59-2.54 (m, 3 H), 2.08-1.96 (m, 1 H), 1.74-1.63 (m, 1 H) |
| 163 | 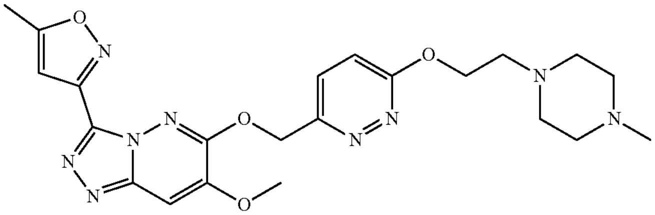 | B | 482 | ($CDCl_3$) □ 7.99 (d, 1 H) 7.19-7.24 (m, 1 H) 7.02 (d, 1 H) 6.81 (s, 1 H) 6.77-6.86 (m, 1 H) 5.77 (s, 2H) 4.67 (t, 2 H) 3.99 (s, 3 H) 3.08 (br. s., 2 H) 2.89-3.02 (m, 4 H) 2.73-2.82 (m, 2 H) 2.62 (s, 5 H) 2.57 (s, 3 H) |
| 164 | 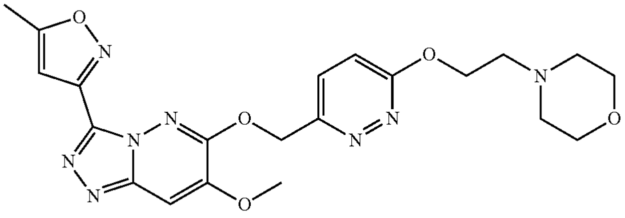 [SMILES: COc1cc2nnc(-c3cc(C)on3)n2nc1OCc1ccc(OCCN2CCOCC2)nn1] | B | 469 | ($CDCl_3$) □ □ 7.96 (d, 1 H) 7.23 (s, 1 H) 7.03 (d, 1 H) 6.80 (s, 1 H) 5.76 (s, 2 H) 4.68 (t, 2 H) 3.99 (s, 3 H) 3.64-3.82 (m, 4 H) 2.84 (t, 2 H) 2.57 (s, 7 H) |
| 165 | 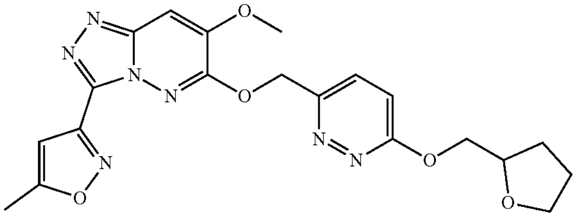 [SMILES: COc1cc2nnc(-c3cc(C)on3)n2nc1OCc1ccc(OCC2CCCO2)nn1] | B | 440 | (DMSO-$d_6$) δ 7.88 (d, J = 8.80 Hz, 1H), 7.76 (s, 1 H), 7.30 (d, J = 9.29 Hz, 1H), 6.98 (s, 1H), 5.66 (s, 2H), 4.42-4.49 (m, 1H), 4.34-4.40 (m, 1H), 4.21 (dd, J = 6.85, 3.91 Hz, 1H), 3.97 (s, 3H), 3.78 (q, J = 7.01 Hz, 1H), 3.63-3.71 (m, 1H), 2.56 (s, 3H), 1.95-2.06 (m, 1H), 1.90-1.80 (m, 2H), 1.75-1.60 (m, 1 H) |
| 166 | 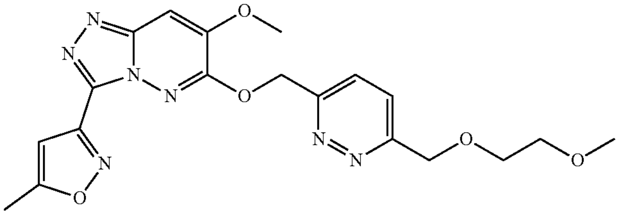 | B | 428 | (DMSO-$d_6$) □ 7.97 (d, J = 8.8 Hz, 1 H), 7.84-7.72 (m, 2 H), 6.88 (s, 1 H), 5.78 (s, 2 H), 4.81 (s, 2 H), 3.99 (s, 3 H), 3.70-3.61 (m, 2 H), 3.53-3.47 (m, 2 H), 3.24 (s, 3 H), 2.55 (s, 3 H) |

-continued

| Embodiment | Structure | Synthesis method | Mass spectrum $[M + H]^+$ | $^1H$ NMR (400 MHz) |
|---|---|---|---|---|
| 167 | 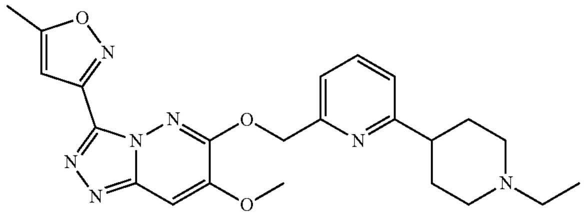 [SMILES: CCN1CCC(c2cccc(COc3nn4c(-c5cc(C)on5)nnc4cc3OC)n2)CC1] | B | 450 | ($CDCl_3$) □ 7.69-7.76 (m, 1 H) 7.55 (d, J = 7.34 Hz, 1 H) 7.25 (t, J = 3.67 Hz, 2 H) 6.80 (s, 1 H) 5.63 (s, 2 H) 4.03 (s, 3H) 3.44 (br. s., 2H) 2.91 (br. s., 3 H) 2.57 (s, 4 H) 2.09-2.41 (m, 5 H) 1.37-1.43 (m, 3H) |
| 168 | 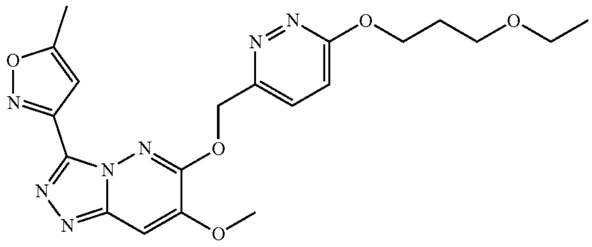 [SMILES: CCOCCCOc1ccc(COc2nn3c(-c4cc(C)on4)nnc3cc2OC)nn1] | B | 442 | (DMSO-$d_6$) □ 7.87 (d, J = 9.1 Hz, 1 H), 7.77 (s, 1 H), 7.27 (d, J = 9.1 Hz, 1 H), 6.99 (d, J = 0.8 Hz, 1 H), 5.67 (s, 2H), 4.50 (t, J = 6.5 Hz, 2 H), 3.98 (s, 3 H), 3.51 (t, J = 6.3 Hz, 2 H), 3.42 (q, J = 7.0 Hz, 2 H), 2.57 (s, 3 H), 2.00 (t, J = 6.4 Hz, 2 H), 1.09 (t, J = 7.0 Hz, 3 H) |
| 169 | 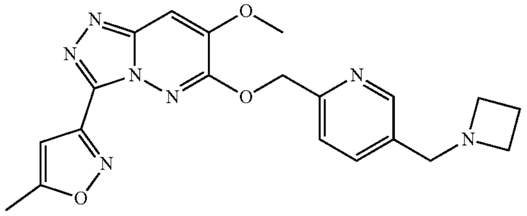 [SMILES: COc1cc2nnc(-c3cc(C)on3)n2nc1OCc1ccc(CN2CCC2)cn1] | B | 408 | ($CDCl_3$) δ 8.55 (s, 1H), 7.81 (d, J = 7.4 Hz, 1H), 7.66 (d, J = 8.0 Hz, 1H), 7.22 (s, 1H), 6.76 (s, 1H), 5.63 (s, 2H), 4.01 (s, 3H), 3.72 (s, 2H), 3.40-3.36 (s, 4H), 2.56 (s, 3H), 2.26-2.12 (m, 2H) |
| 170 | 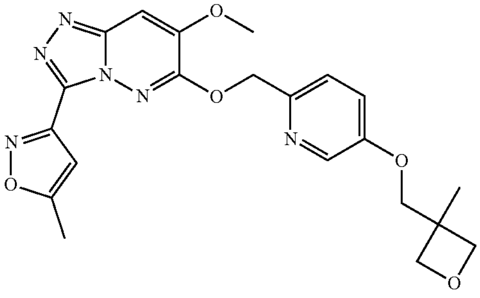 [SMILES: COc1cc2nnc(-c3cc(C)on3)n2nc1OCc1ccc(OCC2(C)COC2)cn1] | B | 439 | (DMSO-$d_6$) δ 8.34 (d, J = 2.4 Hz, 1 H), 7.72 (s, 1 H), 7.61 (d, J = 8.3 Hz, 1 H), 7.48 (dd, J = 2.7, 8.6 Hz, 1 H), 6.97 (s, 1 H), 5.46 (s, 2 H), 4.47 (d, J = 5.9 Hz, 2 H), 4.29 (d, J = 5.9 Hz, 2 H), 4.13 (s, 2 H), 3.95 (s, 3 H), 2.54 (s, 3 H), 1.35 (s, 3 H) |
| 171 | 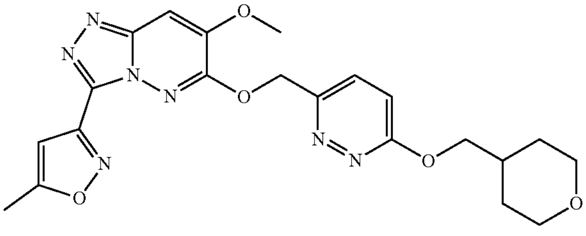 [SMILES: COc1cc2nnc(-c3cc(C)on3)n2nc1OCc1ccc(OCC2CCOCC2)nn1] | B | 454 | (DMSO-$d_6$) δ 7.88 (d, J = 9.1 Hz, 1 H), 7.77 (s, 1 H), 7.28 (d, J = 9.1 Hz, 1 H), 6.99 (d, J = 0.9 Hz, 1 H), 5.67 (s, 2 H), 4.32 (d, J = 6.5 Hz, 2 H), 3.98 (s, 3H), 3.87 (dd, J = 3.4, 10.7 Hz, 2 H), 3.32 (br. s., 1 H), 3.29 (d, J = 4.4 Hz, 1 H), 2.56 (s, 3 H), 2.15-2.01 (m, 1 H), 1.67 (dd, J = 1.8, 12.9 Hz, 2 H), 1.41-1.28 (m, 2 H) |
| 172 | 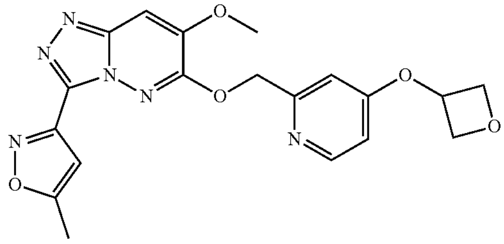 [SMILES: COc1cc2nnc(-c3cc(C)on3)n2nc1OCc1cc(OC2COC2)ccn1] | B | 411 | ($CDCl_3$) δ 8.46 (d, J = 5.7 Hz, 1H), 7.21 (s, 1H), 7.10 (d, J = 2.4 Hz, 1H), 6.80 (s, 1H), 6.61 (dd, J = 5.1, 2.4 Hz, 1H), 5.59 (s, 2H), 5.30 (t, J = 5.5 Hz, 1H), 4.98 (t, J = 6.8 Hz, 2H), 4.76-4.72 (m, 2H), 4.02 (s, 3H), 2.58 (s, 3H). |

-continued

| Embodiment | Structure | Synthesis method | Mass spectrum $[M + H]^+$ | $^1H$ NMR (400 MHz) |
|---|---|---|---|---|
| 173 | 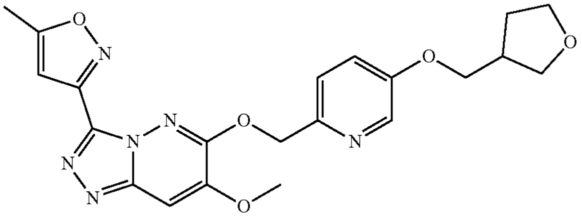 [SMILES: COc1cc2nnc(-c3cc(C)on3)n2nc1OCc1ccc(OCC2CCOC2)cn1] | B | 439 | ($CDCl_3$) δ 8.33 (d, J = 2.45 Hz, 1 H) 7.70 (d, J = 8.31 Hz, 1 H) 7.17-7.24 (m, 2 H) 6.82 (s, 1 H) 5.60 (s, 2 H) 4.00 (s, 3H) 3.97 (d, J = 6.85 Hz, 1 H) 3.88-3.95 (m, 3 H) 3.79 (d, J = 7.83 Hz, 1 H) 3.72 (dd, J = 8.80, 4.89 Hz, 1 H) 2.72-2.82 (m, 1 H) 2.58 (s, 3 H) 2.07-2.19 (m, 1H) 1.66-1.83 (m, 1 H) |
| 174 | 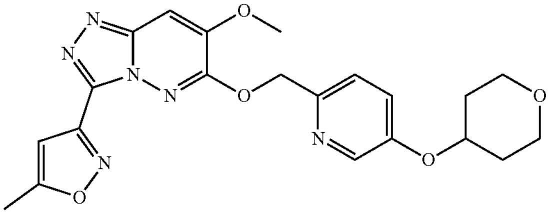 [SMILES: COc1cc2nnc(-c3cc(C)on3)n2nc1OCc1ccc(OC2CCOCC2)cn1] | B | 439 | ($CDCl_3$) δ 8.34 (d, J = 2.9 Hz, 1 H), 7.70 (d, J = 8.3 Hz, 1 H), 7.24 (dd, J = 2.9, 8.8 Hz, 1 H), 7.20 (s, 1 H), 6.85-6.78 (m, 1 H), 5.60 (s, 2 H), 4.60-4.47 (m, 1 H), 4.00 (s, 3 H), 4.00-3.91 (m, 2 H), 3.64-3.52 (m, 2 H), 2.58 (s, 3 H), 2.10-2.01 (m, 2 H), 1.85-1.75 (m, 2H) |
| 175 | 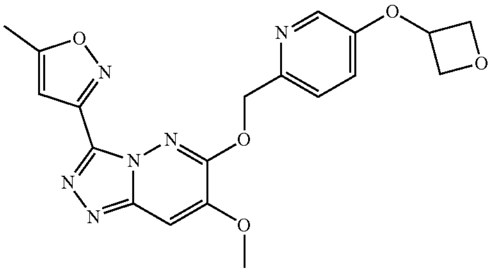 [SMILES: COc1cc2nnc(-c3cc(C)on3)n2nc1OCc1ccc(OC2COC2)cn1] | B | 411 | (DMSO-$d_6$) δ 8.23 (d, J = 2.9 Hz, 1 H), 7.74 (s, 1 H), 7.61 (d, J = 8.6 Hz, 1 H), 7.29 (dd, J = 3.0, 8.5 Hz, 1 H), 6.98 (s, 1 H), 5.48 (s, 2 H), 5.39 (t, J = 5.3 Hz, 1 H), 4.94 (t, J = 6.8 Hz, 2 H), 4.56 (dd, J = 4.8, 7.4 Hz, 2 H), 3.97 (s, 3 H), 2.56 (s, 3 H) |
| 176 | 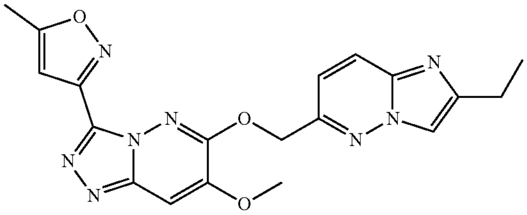 [SMILES: CCc1cn2nc(COc3nn4c(-c5cc(C)on5)nnc4cc3OC)ccc2n1] | B | 407 | ($CDCl_3$) δ 7.87 (d, 1 H) 7.76 (s, 1 H) 7.44 (d, 1 H) 7.23 (s, 1 H) 6.80 (s, 1 H) 5.67 (s, 2 H) 4.01 (s, 3H) 2.87 (d, 2 H) 2.57 (s, 3 H) 1.36 (t, 3 H) |
| 177 | 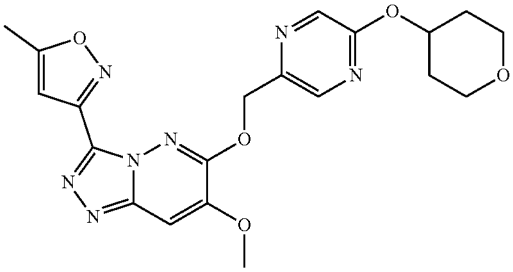 [SMILES: COc1cc2nnc(-c3cc(C)on3)n2nc1OCc1cnc(OC2CCOCC2)cn1] | B | 452 | (DMSO-$d_6$) δ 7.86 (d, J = 9.3 Hz, 1 H), 7.75 (s, 1 H), 7.23 (d, J = 8.8 Hz, 1 H), 6.98 (s, 1 H), 5.63 (s, 2H), 5.15 (t, J = 6.8 Hz, 1 H), 4.63 (s, 2 H), 4.53 (s, 2 H), 3.96 (s, 3 H), 2.79 (ddd, J = 2.9, 7.2, 10.4 Hz, 2 H), 2.55 (s, 3 H), 2.28 (d, J = 6.4 Hz, 2 H) |
| 178 | 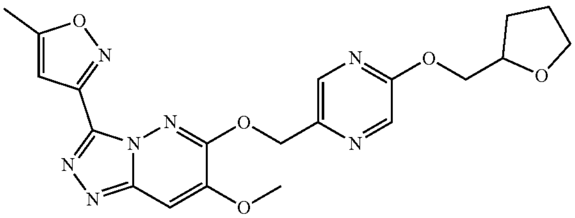 [SMILES: COc1cc2nnc(-c3cc(C)on3)n2nc1OCc1cnc(OCC2CCCO2)cn1] | B | 440 | ($CDCl_3$) δ 8.53 (s, 1 H) 8.31 (s, 1 H) 7.24 (s, 1 H) 6.81 (s, 1 H) 5.62 (s, 2 H) 4.38-4.46 (m, 1 H) 4.22-4.33 (m, 2 H)3.99 (s, 3 H) 3.90-3.96 (m, 1 H) 3.80-3.87 (m, 1 H) 2.58 (s, 3 H) 2.03-2.12 (m, 1 H) 1.91-2.01 (m, 2 H) 1.71 (d, J = 4.40 Hz, 1 H) |

-continued

| Embodiment | Structure | Synthesis method | Mass spectrum [M + H]$^+$ | $^1$H NMR (400 MHz) |
|---|---|---|---|---|
| 179 | 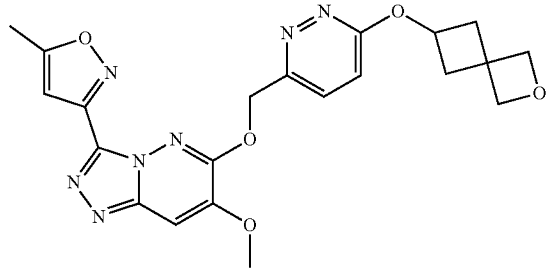 [SMILES: COc1cc2nnc(-c3cc(C)on3)n2nc1OCc1ccc(OC2CC3(COC3)C2)nn1] | B | 452 | (DMSO-$d_6$) δ 7.86 (d, J = 9.3 Hz, 1 H), 7.75 (s, 1 H), 7.23 (d, J = 8.8 Hz, 1 H), 6.98 (s, 1 H), 5.63 (s, 2H), 5.15 (t, J = 6.8 Hz, 1 H), 4.63 (s, 2 H), 4.53 (s, 2 H), 3.96 (s, 3 H), 2.79 (ddd, J = 2.9, 7.2, 10.4 Hz, 2 H), 2.55 (s, 3 H), 2.28 (d, J = 6.4 Hz, 2 H) |
| 180 | 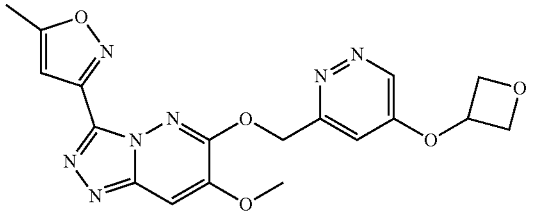 [SMILES: COc1cc2nnc(-c3cc(C)on3)n2nc1OCc1cc(OC2COC2)cnn1] | B | 412 | ($CDCl_3$) δ 8.86 (d, J = 2.93 Hz, 1 H) 7.41 (d, J = 2.45 Hz, 1 H) 7.23 (s, 1 H) 6.84 (s, 1 H) 5.81 (s, 2 H) 5.37-5.44 (m, 1 H) 4.98 (t, J = 6.60 Hz, 2 H) 4.74 (dd, J = 7.34, 4.89 Hz, 2 H) 4.02 (s, 3 H) 2.61 (s, 3 H) |

Embodiment 181

(S)-3-(7-Methoxy-6-((6-(tetrahydrofuran-3-yl)-5,6,7,8-tetrahydro-1,6-naphthyridin-2-yl)methoxy)-[1,2,4]triazolo[4,3-b]pyridazin-3-yl)-5-methylisoxazole

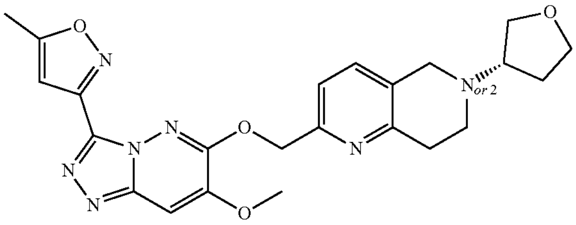

Embodiment 182

(R)-3-(7-methoxy-6-((6-(tetrahydrofuran-3-yl)-5,6,7,8-tetrahydro-1,6-naphthyridin-2-yl)methoxy)-[1,2,4]triazolo[4,3-b]pyridazin-3-yl)-5-methylisoxazole

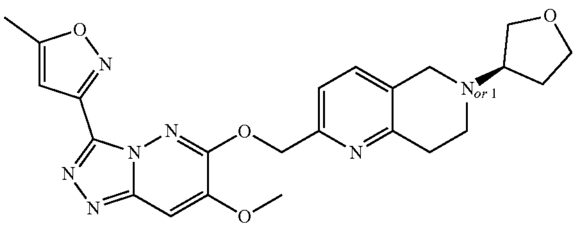

3-(7-Methoxy-6-(((5,6,7,8-tetrahydro-1,6-naphthopyridin-2-yl)methoxy)-[1,2,4]triazolo[4,3-b]pyridazin-3-yl)-5-methylisoxazole (800 mg, 2.03 mmol) and dihydrofuran-3(2H)-one (CAS: 22929-52-8, 500 mg, 5.8 mmol) were dissolved in 100 mL of methanol, then sodium cyanoborohydride (630 mg, 10 mmol) was added thereto, and the mixture was stirred at room temperature for 2 hours. The reaction solution was concentrated, dissolved in water (100 mL), extracted with dichloromethane (200 mL*2), separated, and the organic phase was concentrated to obtain 900 mg of pale yellow solid (crude product), which was chiral resolved to obtain a white solid (under the chiral separation method, retention time of 5.316 min) (S)-3-(7-methoxy-6-((6-(tetrahydrofuran-3-yl)-5,6,7,8-tetrahydro-1,6-naphthyridin-2-yl)methoxy)-[1,2,4]triazolo[4,3-b]pyridazin-3-yl)-5-methylisoxazole (308 mg, 33%); to obtain a white solid (under chiral resolution method, retention time of 4.327 min) (R)-3-(7-methoxy-6-((6-(tetrahydrofuran-3-yl)-5,6,7,8-tetrahydro-1,6-naphthyridin-2-yl)methoxy)-[1,2,4]triazolo[4,3-b]pyridazin-3-yl)-5-methylisoxazole (314 mg, 33%).

Chiral resolution method:
Instrument: Waters UPC2 analytical SFC (SFC—H)
Column: ChiralPak AD, 150×4.6 mm I.D., 3 μm
Mobile phase: A for $CO_2$ and B for Methanol (0.05% DEA)
Gradient: B 50%
Flow rate: 2.5 mL/min
Back pressure: 100 bar
Column temperature: 35° C.
Wavelength: 220 nm Embodiment 181: $^1$H NMR (400 MHz, CHLOROFORM-$d_6$) ppm 7.47-7.41 (m, 2H), 7.40 (br. s., 1H), 7.20 (s, 1H), 6.79 (s, 2H)-5.57 (m, 1H), 4.03 (br. s., 1H), 3.82 (t, J=8.0 Hz, 1H), 3.76-3.68 (m, 2H), 3.65-3.56 (m, 2H), 3.21-3.49 (m, 1H), 3.07-2 (m, 2H) (t, J=5.62 Hz, 2H), 2.84-2.87-2.75 (s, 1H) 2.55 (br. s., 1H), 2.17 (br. s., 2H) 1.97 (d, J=6.85 Hz, 2H); LC-MS: m/z [M+H]$^+$=464.

Embodiment 182: $^1$H NMR (400 MHz, CHLOROFORM-d) 7.46-7.35 (m, 2H), 7.20 (s, 1H), 6.79 (s, 1H), 5.56 (s, 2H), 4.02-3.92 (m, 5H), 3.86-3.78 (m, 1H), 3.76-3.69 (m, 2H), 3.67-3.57 (m, 1H), 3.21 (quin, J=7.0 Hz, 1H), 3.07 (t, J=5.9 Hz, 2H), 2.92 (td, J=5.9, 11.7 Hz, 1H), 2.79 (td, J=5.7, 11.6 Hz, 1H), 2.55 (s, 3H), 2.19-2.11 (m, 1H), 1.98-1.91 (m, 1H); LC-MS: m/z $[M+H]^+$=464.

Embodiment 183 (Method H)

3-(7-Methoxy-6-(((6-(tetrahydrofuran-3-yl)-5,6,7,8-tetrahydro-1,6-naphthyridin-2-yl)methoxy)-[1,2,4]triazolo[4,3-b]pyridazin-3-yl)-5-methylisoxazole

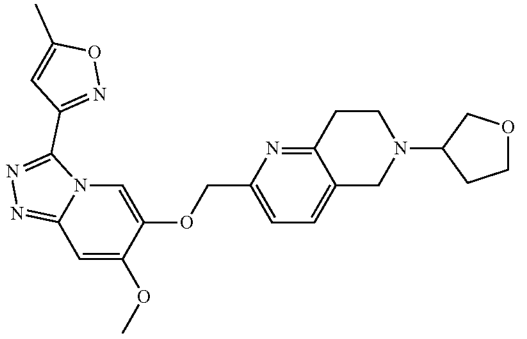 [SMILES: COc1cc2nnc(-c3cc(C)on3)n2cc1OCc1ccc2c(n1)CCN(C1CCOC1)C2]

3-(7-Methoxy-6-(((5,6,7,8-tetrahydro-1,6-naphthopyridin-2-yl)methoxy)-[1,2,4]triazolo[4,3-b]pyridazin-3-yl)-5-methylisoxazole (300 mg, 0.7 mmol) and dihydrofuran-3(2H)-one (CAS: 22929-52-8, 100 mg, 1 mmol) were dissolved in 10 mL of methanol, then sodium cyanoborohydride (200 mg, 3 mmol) was added thereto, and the mixture was stirred at room temperature overnight. Water was added thereto, and the mixture was extracted with dichloromethane, separated, concentrated, and purified by preparative plate (dichloromethane:methanol=10:1) to obtain the title compound (168 mg, 52%) as a white solid.

$^1H$ NMR (400 MHz, CHLOROFORM-$d_6$) δ ppm 7.44-7.49 (m, 1H) 7.36-7.42 (m, 1H) 7.21 (s, 1H) 6.81 (s, 1H) 5.59 (s, 2H) 4.01 (m, 5H) 3.78-3.66 (m, 4H) 3.23 (t, J=6.85 Hz, 1H) 3.05-3.15 (m, 2H) 2.95 (dt, J=11.62, 5.69 Hz, 1H) 2.76-2.87 (m, 1H) 2.57 (s, 3H) 2.09-2.23 (m, 1H) 1.93-2.05 (m, 1H); LC-MS: m/z $[M+H]^+$=464.

Embodiment 187 (Method I)

3-((2-((((7-Methoxy-3-(5-methylisoxazol-3-yl)-[1,2,4]triazolo[4,3-b]pyridazin-6-yl)oxy)methyl)-7,8-dihydro-1,6-naphthyridin-6(5H)-yl)methyl)-5-methylisoxazole

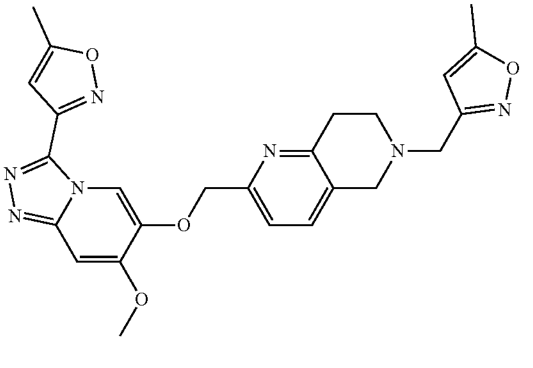 [SMILES: COc1cc2nnc(-c3cc(C)on3)n2cc1OCc1ccc2c(n1)CCN(Cc1cc(C)on1)C2]

3-(7-Methoxy-6-(((5,6,7,8-tetrahydro-1,6-naphthopyridin-2-yl)methoxy)-[1,2,4]triazolo[4,3-b]pyridazin-3-yl)-5-methylisoxazole (120 mg, 0.3 mmol), 3-chloromethyl-5-methylisoxazole (CAS: 35166-37-1, 100 mg, 0.9 mmol) and potassium carbonate (300 mg, 2.5 mmol) were dissolved in 5 mL of acetonitrile, then the mixture was heated to 70° C. and stirred for 2 hours. The solid was filtered, the reaction solution was concentrated, and purified by preparative plate (dichloromethane:methanol=10:1) to obtain the title compound (23 mg, 15%) as a white solid.

$^1H$ NMR (400 MHz, CHLOROFORM-$d_6$) δ ppm 7.45 (d, J=7.34 Hz, 1H) 7.36 (d, J=7.34 Hz, 1H) 7.21 (s, 1H) 6.80 (br. s., 1H) 6.05 (br. s., 1H) 5.58 (br. s., 2H) 4.00 (s, 3H) 3.77 (br. s., 2H) 3.68 (br. s., 2H) 3.08 (br. s., 2H) 2.92 (br. s., 2H) 2.57 (s, 3H) 2.42 (s, 3H); LC-MS: m/z $[M+H]^+$=489.

Embodiment 192

2-(2-((((7-Methoxy-3-(5-methylisoxazol-3-yl)-(1,2,4)triazolo[4,3-b]pyridazin-6-yl)oxy)methyl)-7,8-dihydro-1,6-naphthyridin-6(5H)-yl)-5-methyl-1,3,4-oxadiazole

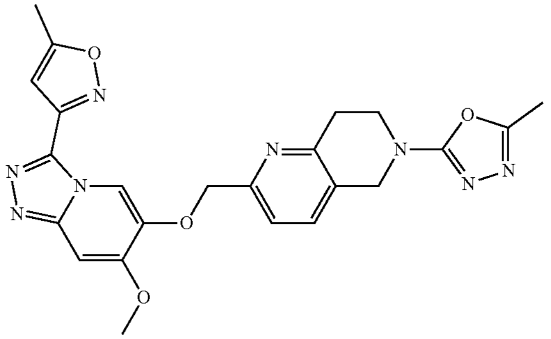 [SMILES: COc1cc2nnc(-c3cc(C)on3)n2cc1OCc1ccc2c(n1)CCN(c1nnc(C)o1)C2]

3-(7-Methoxy-6-(((5,6,7,8-tetrahydro-1,6-naphthopyridin-2-yl)methoxy)-[1,2,4]triazolo[4,3-b]pyridazin-3-yl)-5-methylisoxazole (100 mg, 0.23 mmol), 2-bromo-5-methyl-1,3,4-oxadiazole (CAS: 864750-58-3, 38 mg, 0.23 mmol) and sodium bicarbonate (84 mg, 1 mmol) were dissolved in 5 mL of DMF, then the mixture was heated to 80° C. and stirred for 3 hours. The sodium bicarbonate solid was filtered, and the reaction solution was concentrated, and purified by preparative plate (dichloromethane:methanol=10:1) to obtain the title compound (13 mg, 12%) as a white solid.

$^1H$ NMR (400 MHz, CHLOROFORM-$d_6$) δ ppm 7.56-7.64 (m, 1H) 7.49-7.54 (m, 1H) 7.24 (s, 1H) 6.80 (s, 1H) 5.61 (s, 2H) 5.30 (s, 3H) 4.68 (s, 2H) 3.88 (t, J=5.62 Hz, 2H) 3.16 (t, J=5.14 Hz, 2H) 2.57 (s, 3H) 2.42 (s, 3H); LC-MS: m/z $[M+H]^+$=476.

Embodiment 194

3-((2-((((7-Methoxy-3-(5-methylisoxazol-3-yl)-[1,2,4]triazolo[4,3-b]pyridazin-6-yl)oxy)methyl)-7,8-dihydro-1,6-naphthyridin-6(5H)-yl)methyl)bicyclo[1.1.1]pentane-1-carbonitrile

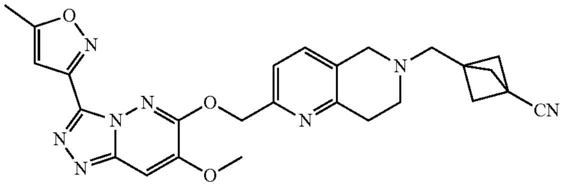 [SMILES: COc1cc2nnc(-c3cc(C)on3)n2nc1OCc1ccc2c(n1)CCN(CC13CC(C#N)(C1)C3)C2]

3-(Hydroxymethyl)bicyclo[1.1.1]pentane-1-carbonitrile (cas: 1370705-39-7, 200 mg, 1.63 mmol) was dissolved in dichloromethane (10 mL). Triethyamine (600 mg, 6 mmol) and p-toluenesulfonyl chloride (310 mg, 1.63 mmol) were sequentially added thereto, and the mixture was stirred at room temperature for 4 hours, washed with an aqueous ammonium chloride solution (10 mL*2), and the organic phase was concentrated to obtain 400 mg of a pale yellow solid (a crude product). The resulting crude product was then dissolved in acetonitrile (5 mL). 3-(7-Methoxy-6-((((5,6,7,8-tetrahydro-1,6-naphthpyridin-2-yl)methoxy)-[1,2,4]triazolo[4,3-b]pyridazin-3-yl)-5-methylisoxazole (100 mg, 0.25 mmol) and potassium carbonate (138 mg, 1 mmol) were sequentially added thereto, and the mixture was heated and stirred at 80° C. for 16 hours, prepared by a preparative plate to obtain the title compound (24 mg, 19%) with a pale yellow solid appearance.

$^1$H NMR (400 MHz, CHLOROFORM-d)=7.45 (d, J=7.8 Hz, 1H), 7.35 (d, J=7.8 Hz, 1H), 7.22 (s, 1H), 6.79 (s, 1H), 5.56 (s, 2H), 3.99 (s. 3H), 3.63 (s, 2H), 3.03 (t, J=5.1 Hz, 2H), 2.82 (t, J=5.6 Hz, 2H), 2.61 (s, 2H), 2.55 (s, 3H), 2.24 (s, 6H); LC-MS: m/z $[M+H]^+$=499.

Embodiment 195

3-(2-((((7-Methoxy-3-(5-methylisoxazol-3-yl)-[1,2,4]triazolo[4,3-b]pyridazin-6-yl)oxy)methyl)-7,8-dihydro-1,6-naphthyridin-6(5H)-yl)cyclobutane-1-carbonitrile

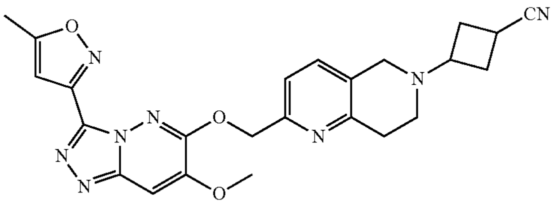 [SMILES: COc1cc2nnc(-c3cc(C)on3)n2nc1OCc1ccc2c(n1)CCN(C1CC(C#N)C1)C2]

3-Hydroxycyclobutane-1-carbonitrile (cas: 20249-17-6, 200 mg, 2.15 mmol) was dissolved in dichloromethane (10 mL). At 0° C., triethylamine (1 g, 10 mmol) and trifluoromethanesulfonic anhydride (608 mg, 2.15 mmol) were sequentially added dropwise thereto, and the mixture was stirred at room temperature for 4 hours. Then 3-(7-methoxy-6-((((5,6,7,8-tetrahydro-1,6-naphthpyridin-2-yl)methoxy)-[1,2,4]triazolo[4,3-b]pyridazin-3-yl)-5-methylisoxazole (100 mg, 0.25 mmol) was added thereto, and the mixture was stirred at room temperature for 16 hours, prepared by a preparative plate to obtain the title compound (10 mg, 8%) with a pale yellow solid appearance.

$^1$H NMR (400 MHz, CHLOROFORM-d)=7.45 (d, J=14.7 Hz, 2H), 7.23 (s, 1H), 6.75 (s, 1H), 5.52 (s, 2H), 3.96 (s, 3H), 3.65-3.57 (m, 2H), 3.29 (br. s., 1H), 3.12-3.02 (m, 2H), 2.55-2.49 (m, 6H), 1.32 (d, J=6.8 Hz, 4H); LC-MS: m/z $[M+H]^+$=473.

Embodiment 196

2,2-Difluoro-3-(2-((((((7-methoxy-3-(5-methylisoxazol-3-yl)-[1,2,4]triazolo[4,3-b]pyridazin-6-yl)oxy)methyl)-7,8-dihydro-1,6-naphthyridin-6(5H)-yl)propan-1-ol

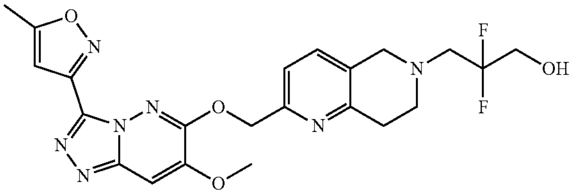 [SMILES: COc1cc2nnc(-c3cc(C)on3)n2nc1OCc1ccc2c(n1)CCN(CC(F)(F)CO)C2]

2,2-Difluoropropane-1,3-diol (cas: 428-63-7, 150 mg, 1.34 mmol) was dissolved in dichloromethane (10 mL). At 0° C., triethylamine (500 mg, 5 mmol) and trifluoromethanesulfonic anhydride (280 mg, 1 mmol) were sequentially added dropwise thereto, and the mixture was stirred at room temperature for 4 hours. Then 3-(7-methoxy-6-((((5,6,7,8-tetrahydro-1,6-naphthpyridin-2-yl)methoxy)-[1,2,4]triazolo[4,3-b]pyridazin-3-yl)-5-methylisoxazole (80 mg, 0.20 mmol) was added thereto, and the mixture was stirred at room temperature for 16 hours, prepared by a preparative plate to obtain the title compound (8 mg, 8%) with a pale yellow solid appearance.

$^1$H NMR (400 MHz, CHLOROFORM-d) 7.48 (s, 1H), 7.39 (s, 1H), 7.26 (s, 1H), 6.80 (d, J=0.8 Hz, 1H), 5.58 (s, 2H), 4.01 (s, 3H), 3.91 (s, 2H), 3.85 (s, 2H), 3.13-3.04 (m, 6H), 2.56 (d, J=0.8 Hz, 3H); LC-MS: m/z $[M+H]^+$=488.

Embodiment 197

2-(2-((((7-Methoxy-3-(5-methylisoxazol-3-yl)-[1,2,4]triazolo[4,3-b]pyridazin-6-yl)oxy)methyl)-7,8-dihydro-1,6-naphthyridin-6(5H)-yl)cyclobutyl)acetonitrile

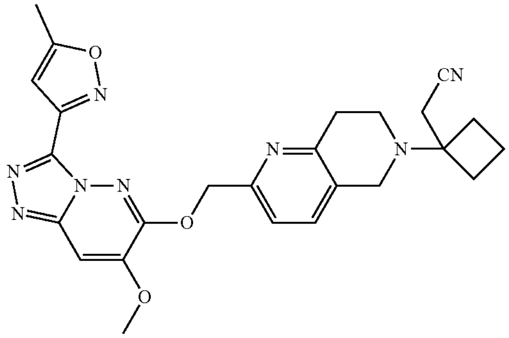 [SMILES: COc1cc2nnc(-c3cc(C)on3)n2nc1OCc1ccc2c(n1)CCN(C1(CC#N)CCC1)C2]

3-(7-Methoxy-6-(((5,6,7,8-tetrahydro-1,6-naphthopyridin-2-yl)methoxy)-[1,2,4]triazolo[4,3-b]pyridazin-3-yl)-5-methylisoxazole (100 mg, 0.25 mmol), 2-cyclobutylideneacetonitrile (CAS: 27784-69-6, 100 mg, 1 mmol) and triethylamine (200 mg, 2 mmol) were dissolved in 10 mL of methanol, then the mixture was heated to 80° C. and stirred overnight. The reaction solution was concentrated, and purified by preparative plate (dichloromethane:methanol=10:1) to obtain the title compound (22 mg, 18%) as a white solid.

$^1$H NMR (400 MHz, DMSO-d$_6$) δ ppm 7.68-7.79 (m, 1H) 7.51-7.58 (m, 1H) 7.35-7.43 (m, 1H) 6.91-7.00 (m, 1H) 5.42-5.50 (m, 2H) 3.98 (s, 3H) 3.61-3.71 (m, 2H) 2.88 (br. s., 4H) 2.73-2.80 (m, 2H) 2.56 (s, 3H) 2.09-2.19 (m, 2H) 1.94-2.03 (m, 2H) 1.82-1.91 (m, 1H) 1.72-1.80 (m, 1H); LC-MS: m/z [M+H]$^+$=487.

Embodiment 198

Cyclopropyl(3-(2-((((7-methoxy-3-(5-methylisoxazol-3-yl)-[1,2,4]triazolo[4,3-b]pyridazin-6-yl]oxy]methyl)-7,8-dihydro-1,6-naphthyridin-6(5H)-yl)azetidin-1-yl)methanone

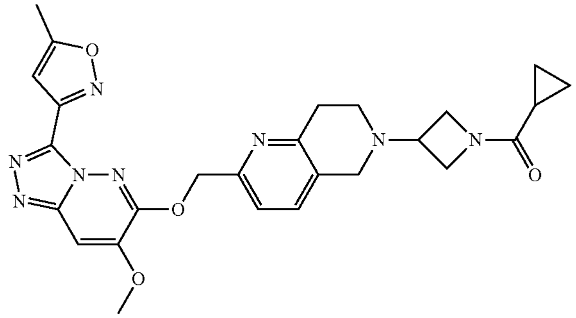 [SMILES: COc1cc2nnc(-c3cc(C)on3)n2nc1OCc1ccc2c(n1)CCN(C1CN(C(=O)C3CC3)C1)C2]

3-(6-((6-(Azetidin-3-yl)-5,6,7,8-tetrahydro-1,6-naphthyridin-2-yl)methoxy)-7-methoxy-[1,2,4]triazolo[4,3-b]pyridazin-3-yl)-5-methylisoxazole hydrochloride (100 mg, 0.22 mmol) was dissolved in 10 mL of dichloromethane, then triethylamine (1 mL) and cyclopropanecarbonyl chloride (CAS: 4023-34-1, 330 mg, 0.33 mmol) were added thereto, and the mixture was stirred at room temperature for 2 hours. An aqueous ammonium chloride solution was added thereto, and the mixture was extracted with dichloromethane, separated, concentrated, and purified by preparative plate (dichloromethane:methanol=10:1) to obtain the title compound (16 mg, 14%) as a white solid.

$^1$H NMR (400 MHz, CHLOROFORM-d$_6$) δ ppm 7.37-7.53 (m, 2H) 7.24 (br. s., 1H) 6.81 (s, 1H) 5.60 (s, 2H) 4.34-4.42 (m, 1H) 4.23 (br. s., 1H) 4.13 (t, J=8.56 Hz, 1H) 3.95-4.04 (m, 4H) 3.54-3.68 (m, 2H) 3.40-3.49 (m, 1H) 3.07-3.16 (m, 2H) 2.81 (t, J=5.62 Hz, 2H) 2.57 (s, 3H) 1.42 (br. s., 1H) 0.97 (br. s., 2H) 0.76 (d, J=6.85 Hz, 2H); LC-MS: m/z [M+H]$^+$=517.

Embodiment 199

1-(3-(2-(((7-Methoxy-3-(5-methylisoxazol-3-yl)-[1,2,4]triazolo[4,3-b]pyridazin-6-yl)oxy)methyl)-7,8-dihydro-1,6-naphthyridin-6(5H)-yl)azetidin-1-yl)ethan-1-one

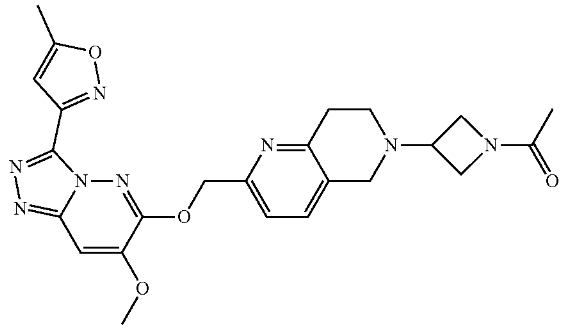 [SMILES: COc1cc2nnc(-c3cc(C)on3)n2nc1OCc1ccc2c(n1)CCN(C1CN(C(C)=O)C1)C2]

3-(6-((6-(Azetidin-3-yl)-5,6,7,8-tetrahydro-1,6-naphthyridin-2-yl)methoxy)-7-methoxy-[1,2,4]triazolo[4,3-b]pyridazin-3-yl)-5-methylisoxazole hydrochloride (100 mg, 0.22 mmol) was dissolved in 10 mL of dichloromethane, then triethylamine (1 mL) and acetic anhydride (300 mg, 0.33 mmol) were added thereto, and the mixture was stirred at room temperature for 2 hours. An aqueous ammonium chloride solution was added thereto, and the mixture was extracted with dichloromethane, separated, concentrated, and purified by preparative plate (dichloromethane:methanol=10:1) to obtain the title compound (36 mg, 33%) as a white solid.

$^1$H NMR (400 MHz, DMSO-d$_6$) δ ppm 7.49-7.61 (m, 1H) 7.39-7.45 (m, 1H) 6.92-7.03 (m, 1H) 5.53-5.54 (m, 1H) 5.42-5.55 (m, 2H) 4.15-4.21 (m, 1H) 4.03-4.08 (m, 1H) 3.98 (s, 3H) 3.88-3.94 (m, 1H) 3.72-3.78 (m, 1H) 3.52-3.62 (m, 2H) 3.23-3.28 (m, 1H) 2.88-2.97 (m, 2H) 2.66-2.79 (m, 2H) 2.56 (s, 3H) 1.76 (s, 3H); LC-MS: m/z [M+H]$^+$=491.

Embodiment 201 (Method J)

N-(3,3-Difluorocyclobutyl)-2-(((7-methoxy-3-(5-methylisoxazol-3-yl)-[1,2,4]triazolo[4,3-b]pyridazin-6-yl)oxy)methyl)-7,8-dihydro-1,6-naphthyridine-6(5H)-carboxamide

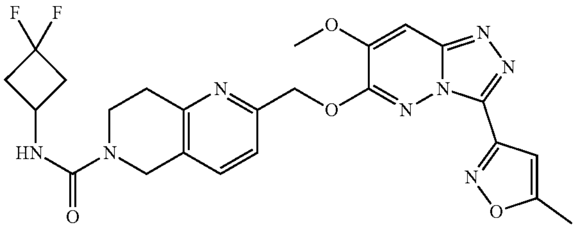 [SMILES: COc1cc2nnc(-c3cc(C)on3)n2nc1OCc1ccc2c(n1)CCN(C(=O)NC1CC(F)(F)C1)C2]

3-(7-Methoxy-6-(((5,6,7,8-tetrahydro-1,6-naphthopyridin-2-yl)methoxy)-[1,2,4]triazolo[4,3-b]pyridazin-3-yl)-5-methylisoxazole hydrochloride (233 mg, 0.54 mmol), triethylamine (154 mg, 1.5 mmol) and dichloromethane (3 mL) were mixed and stirred in an ice bath, and then added dropwise to a stirred mixture of 3,3-difluorocyclobutylamine hydrochloride (144 mg, 1.0 mmol), triphosgene (99 mg, 0.33 mmol), triethylamine (250 mg, 2.5 mmol) and dichloromethane (3 mL); and the mixture was stirred overnight after the addition was completed. Water was added to the reaction solution, then the phases were separated, and an organic layer was directly separated by column chromatography to obtain the title compound (53 mg) as a white solid. $^1$H NMR (400 MHz, CHLOROFORM-d) d ppm 2.44-2.60 (m, 5H) 2.94-3.09 (m, 4H) 3.72 (t, J=5.87 Hz, 2H) 4.01 (s, 3H) 4.21 (br. s., 1H) 4.61 (s, 2H) 5.07 (d, J=5.87 Hz, 1H) 5.60 (s, 2H) 6.80 (s, 1H) 7.21 (s, 1H) 7.44-7.59 (m, 2H); LC-MS: m/z $[M+H]^+$=527.

Embodiment 205 (Method K)

2-(((7-Methoxy-3-(5-methylisoxazol-3-yl)-[1,2,4]triazolo[4,3-b]pyridazin-6-yl)oxy)methyl)-N,N-dimethyl-7,8-dihydro-1,6-naphthyridine-6(5H)-sulfonamide

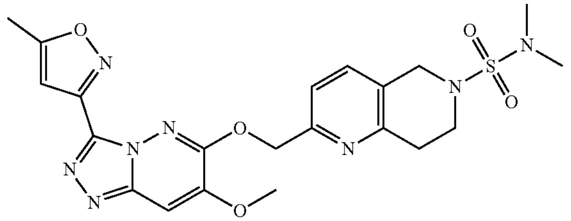

3-(7-Methoxy-6-(((5,6,7,8-tetrahydro-1,6-naphthyridin-2-yl)methoxy)-[1,2,4]triazolo[4,3-b]pyridazin-3-yl)-5-methylisoxazole hydrochloride (100 mg, 0.25 mmol), triethylamine (150 mg, 1.5 mmol) and dimethylsulfamoyl chloride (73 mg, 0.51 mmol) were added to DCM (4 mL), and the mixture was stirred at room temperature overnight. The reaction solution was directly separated and purified by a preparative plate (dichloromethane/methanol=10/1) to obtain the title compound (25 mg, 24%).

$^1$H NMR (400 MHz, $CDCl_3$)=7.56 (d, J=8.2 Hz, 1H), 7.45 (d, J=7.8 Hz, 1H), 7.22 (s, 1H), 6.80 (s, 1H), 5.60 (s, 2H), 4.44 (s, 2H), 4.01 (s, 3H), 3.62 (t, J=6.1 Hz, 2H), 3.12 (t, J=5.9 Hz, 2H), 2.84 (s, 6H), 2.56 (s, 3H). LC-MS: m/z $[M+H]^+$=501.

Embodiment 211 (Method L)

6-(((7-Methoxy-3-(5-methylisoxazol-3-yl)-[1,2,4]triazolo[4,3-b]pyridazin-6-yl)oxy)methyl)imidazo[1,2-b]pyridazine-2-carbonitrile

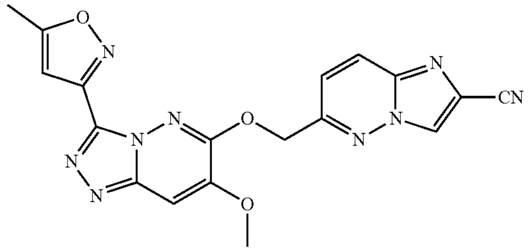 [SMILES: COc1cc2nnc(-c3cc(C)on3)n2nc1OCc1ccc2nc(C#N)cn2n1]

Under the protection of nitrogen at room temperature, 6-(hydroxymethyl)imidazo[1,2-b]pyridazine-2-carbonitrile (60 mg, 0.34 mmol) was dissolved in tetrahydrofuran (3 mL), and tert-butanol potassium was added thereto, and the mixture was stirred at room temperature for 15 minutes. 3-(6-Chloro-7-methoxy-[1,2,4]triazolo[4,3-b]pyridazin-3-yl)-5-methylisoxazole (68 mg, 0.26 mmol) was added thereto, and the reaction solution was stirred for 2 hours. After the reaction was completed, the reaction solution was concentrated, and the residue was purified by column chromatography (dichloromethane/methanol=10/1) to obtain the title product (7.5 mg, a white solid) with a yield of 5%. LC-MS: m/z $[M+H]^+$=404.

$^1$H NMR (400 MHz, DMSO-$d_6$) δ 9.23 (s, 1H), 8.32 (d, J=9.4 Hz, 1H), 7.80 (s, 1H), 7.69 (d, J=9.5 Hz, 1H), 6.94 (s, 1H), 5.69 (s, 2H), 4.00 (s, 3H), 2.55 (s, 3H).

Embodiment 220

3-(7-Methoxy-6-(((1-methyl-1H-pyrazolo[3,4-b]pyridin-6-yl)methoxy)-[1,2,4]triazolo[4,3-b]pyridazin-3-yl)-5-methylisoxazole

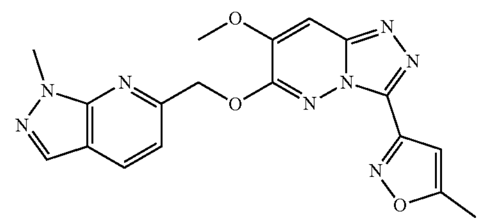 [SMILES: COc1cc2nnc(-c3cc(C)on3)n2nc1OCc1ccc2cnn(C)c2n1]

3-(7-Methoxy-6-(((5,6,7,8-tetrahydro-1,6-naphthopyridin-2-yl)methoxy)-[1,2,4]triazolo[4,3-b]pyridazin-3-yl)-5-methylisoxazole hydrochloride (150 mg, 0.56 mmol), (1-methyl-1H-pyrazolo[3,4-b]pyridin-6-yl)methanol (92 mg, 0.56 mmol), potassium phosphate (179 mg, 0.85 mmol) and acetonitrile (5 mL) were added to a reaction flask, respectively, and the mixture was reacted at 50° C. overnight. The reaction solution was filtered, and the filter cake was washed with water to obtain the title compound (87 mg) as a white solid. $^1$H NMR (400 MHz, DMSO-$d_6$) d ppm 2.58 (br. s., 3H) 3.93 (br. s., 3H) 4.06 (br. s., 3H) 5.65 (br. s., 2H) 7.03 (br. s., 1H) 7.68 (br. s., 1H) 8.16 (br. s., 1H) 8.51 (br. s., 1H) 8.82 (br. s., 1H); LC-MS: m/z $[M+H]^+$=393.

Embodiment 226 (Method M)

3-(7-Methoxy-6-((2-(oxetan-3-yl)-2H-pyrazolo[4,3-b]pyridin-5-yl)methoxy)-[1,2,4]triazolo[4,3-b]pyridazin-3-yl)-5-methylisoxazole

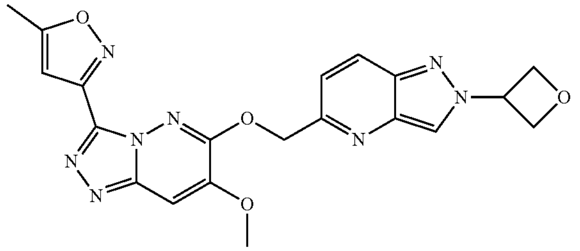 [SMILES: COc1cc2nnc(-c3cc(C)on3)n2nc1OCc1ccc2nn(C3COC3)cc2n1]

(2-(Oxetan-3-yl)-2H-pyrazolo[4,3-b]pyridin-5-yl)methanol (20 mg, 0.1 mmol) was added to tetrahydrofuran (4 mL), and sodium hydride (12 mg, 0.5 mmol) was added thereto, and the mixture was stirred at room temperature for 5 minutes. Then 3-(6-chloro-7-methoxy-[1,2,4]triazolo[4,3-b]pyridazin-3-yl)-5-methylisoxazole (27 mg, 0.1 mmol) was added to the reaction solution, and the reaction was carried out at room temperature for 1 hour. The reaction solution was directly purified by thin layer chromatography (dichloromethane/anhydrous methanol=20/1) to obtain the title compound (23.6 mg, 55.7%) as a white solid.

$^1$H NMR (400 MHz, DMSO-$d_6$) d ppm 2.51-2.54 (m, 3H) 3.96-4.01 (m, 3H) 4.99-5.07 (m, 4H) 5.60-5.65 (m, 2H) 5.90-5.97 (m, 1H) 6.91-6.94 (m, 1H) 7.51-7.56 (m, 1H) 7.72-7.76 (m, 1H) 8.19-8.25 (m, 1H) 8.81-8.84 (m, 1H); LC-MS: m/z $[M+H]^+$=435.

Embodiment 229

3-(7-Methoxy-6-(((1-phenethyl-1H-pyrazolo[4,3-b]pyridin-5-yl]methoxy])-[1,2,4]triazolo[4,3-b]pyridazin-3-yl)-5-methylisoxazole

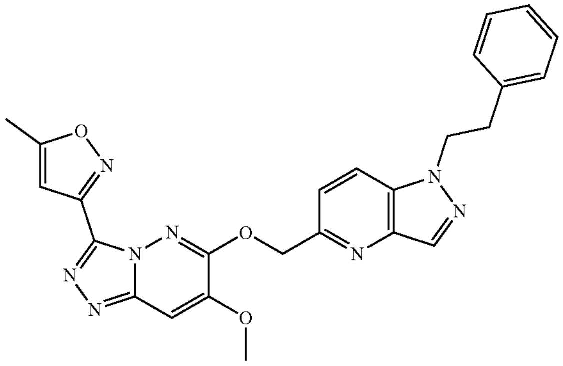 [SMILES: COc1cc2nnc(-c3cc(C)on3)n2nc1OCc1ccc2c(cnn2CCc2ccccc2)n1]

Embodiment 230

3-(7-Methoxy-6-(((2-phenethyl-2H-pyrazolo[4,3-b]pyridin-5-yl]methoxy])-[1,2,4]triazolo[4,3-b]pyridazin-3-yl)-5-methylisoxazole

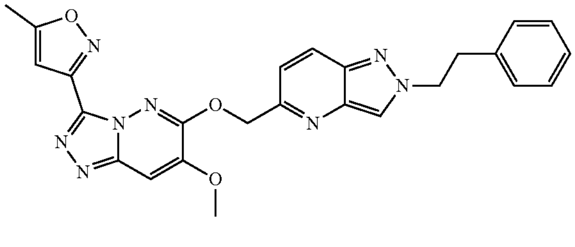 [SMILES: COc1cc2nnc(-c3cc(C)on3)n2nc1OCc1ccc2nn(CCc3ccccc3)cc2n1]

The experimental operation was the same as that of 3-(7-methoxy-6-((2-(oxetan-3-yl)-2H-pyrazolo[4,3-b]pyridin-5-yl)methoxy)-[1,2,4]triazolo[4,3-b]pyridazin-3-yl)-5-methylisoxazole. From the raw material a mixture of (2-phenethyl-2H-pyrazolo[4,3-b]pyridin-5-yl)methanol/(1-phenethyl-1H-pyrazolo[4,3-b]pyridin-5-yl)methanol (500 mg, 1.98 mmol) and 3-(6-chloro-7-methoxy-[1,2,4]triazolo[4,3-b]pyridazin-3-yl)-5-methylisoxazole (525 mg, 1.98 mmol), the title compound (360 mg) as a yellow solid was obtained. Then the title compound 3-(7-methoxy-6-(((2-phenethyl-2H-pyrazolo[4,3-b]pyridin-5-yl]methoxy])-[1,2,4]triazolo[4,3-b]pyridazin-3-yl)-5-methylisoxazole (52 mg, 5.5%) as a white solid was prepared.

$^1$H NMR (400 MHz, CHLOROFORM-d) d ppm 2.54 (s, 3H) 3.33 (t, J=7.09 Hz, 2H) 4.02 (s, 3H) 4.69 (t, J=7.09 Hz, 2H) 5.72 (s, 2H) 6.79 (s, 1H) 7.08 (d, J=6.36 Hz, 2H) 7.23 (d, J=5.38 Hz, 3H) 7.25-7.26 (m, 1H) 7.59 (d, J=8.80 Hz, 1H) 7.95 (s, 1H) 8.12 (d, J=8.80 Hz, 1H); LC-MS: m/z $[M+H]^+$=483.

The title compound as a white solid 3-(7-methoxy-6-(((1-phenethyl-1H-pyrazolo[4,3-b]pyridin-5-yl]methoxy])-[1,2,4]triazolo[4,3-b]pyridazin-3-yl)-5-methylisoxazole (152 mg, 16%). $^1$H NMR (400 MHz, CHLOROFORM-d) d ppm 2.57 (s, 3H) 3.21 (t, J=7.09 Hz, 2H) 4.01 (s, 3H) 4.60 (t, J=7.09 Hz, 2H) 5.74 (s, 2H) 6.79 (s, 1H) 7.03 (d, J=5.87 Hz, 2H) 7.13-7.19 (m, 3H) 7.21 (s, 1H) 7.45 (s, 1H) 7.60 (d, J=8.80 Hz, 1H) 8.26 (s, 1H), LC-MS: m/z $[M+H]^+$=483.

Embodiment 253 (Method N)

3-(7-Methoxy-6-((6-(tetrahydro-2H-pyran-4-yl)-6,7-dihydro-5H-pyrrolo 3,4-b]pyridin-2-yl)methoxy)-[1,2,4]triazolo[4,3-b]pyridazin-3-yl)-5-methylisoxazole

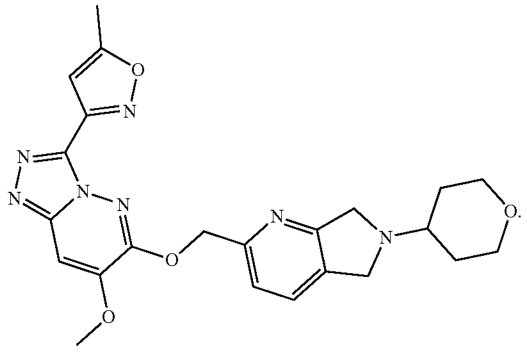 [SMILES: COc1cc2nnc(-c3cc(C)on3)n2nc1OCc1ccc2c(n1)CN(C1CCOCC1)C2]

3-(6-((6,7-Dihydro-5H-pyrrolo[3,4-b]pyridin-2-yl)methoxy)-7-methoxy-[1,2,4]triazolo[4,3-b]pyridazin-3-yl)-5-methylisoxazole (30 mg, 0.079 mmol) was dissolved in dichloromethane (10 mL). 50 mg of acetic acid was added dropwise thereto, and then tetrahydro-4H-pyran-4-one (32 mg, 0.32 mmol) was added thereto, and the mixture was reacted at room temperature for 30 minutes, and then sodium triacetoxyborohydride (67 mg, 0.316 mmol) was added thereto, and the mixture was reacted at room temperature for 3 hours. After the reaction was completed, a saturated aqueous sodium bicarbonate solution was added dropwise to the reaction solution until the pH of the solution was weakly alkaline. A crude product of the title compound was obtained by filtration. The crude product was subjected to column chromatography (dichloromethane/methanol=10/1) to obtain the title compound (22 mg, 71%) as an off-white solid. LC-MS: m/z $[M+H]^+$=464. $^1$H NMR (400 MHz, $CDCl_3$) δ 7.56 (q, J=7.7 Hz, 2H), 7.21 (s, 1H), 6.80 (s, 1H), 5.62 (s, 2H), 4.05 (d, J=8.9 Hz, 6H), 4.00 (s, 3H), 3.47 (t, J=11.2 Hz, 2H), 2.73 (s, 1H), 2.57 (s, 3H), 1.91 (d, J=12.0 Hz, 2H), 1.69 (d, J=10.1 Hz, 2H).

Embodiment 256

3-(2-(((7-Methoxy-3-(5-methylisoxazol-3-yl)-[1,2,4]triazolo[4,3-b]pyridazin-6-yl)oxy)methyl)-5,7-dihydro-6H-pyrrolo[3,4-b]pyridin-6-yl)propanenitrile

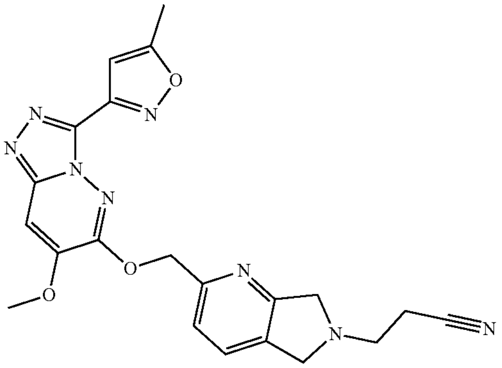 [SMILES: COc1cc2nnc(-c3cc(C)on3)n2nc1OCc1ccc2c(n1)CN(CCC#N)C2]

3-(6-((6,7-Dihydro-5H-pyrrolo[3,4-b]pyridin-2-yl)methoxy)-7-methoxy-[1,2,4]triazolo[4,3-b]pyridazin-3-yl)-5-methylisoxazole (30 mg, 0.079 mmol) was dissolved in ethanol (2 mL), and triethylamine (50 mg, 0.079 mmol) was added dropwise thereto. Then acrylonitrile (21 mg, 0.316 mmol) was added thereto, and the reaction was carried out at 100° C. for 30 minutes under microwave irradiation. The mixture was subjected to column chromatography (dichloromethane/methanol=10/1), then the title compound (20 mg, 58%) as off-white solid was obtained. LC-MS: m/z $[M+H]^+$ =433. $^1H$ NMR (400 MHz, $CDCl_3$) δ 7.56 (s, 2H), 7.22 (s, 1H), 6.80 (s, 1H), 5.62 (s, 2H), 4.10 (s, 4H), 4.00 (s, 3H), 3.11 (t, J=6.9 Hz, 2H), 2.63 (t, J=6.9 Hz, 2H), 2.57 (s, 3H).

| Embodiment | Structure | Synthesis method | Mass spectrum $[M + H]^+$ | $^1H$ NMR (400 MHz) |
|---|---|---|---|---|
| 184 | 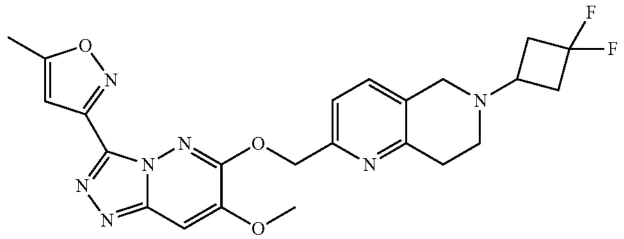 [SMILES: COc1cc2nnc(-c3cc(C)on3)n2nc1OCc1ccc2c(n1)CCN(C1CC(F)(F)C1)C2] | H | 484 | (400 MHz, DMSO-$d_6$ ) ppm 2.55 (s, 3 H) 2.69 (br. s., 2 H) 2.77 (br. s., 1 H) 2.90 (br. s., 2 H) 3.55-3.40 (m, 4H) 3.62 (s, 3 H) 3.97 (br. s., 2 H) 5.47 (s, 2 H) 6.96 (br. s., 1 H) 7.40 (br. s., 1 H) 7.54 (br. s., 1 H) 7.71 (br. s., 1 H) |
| 185 | 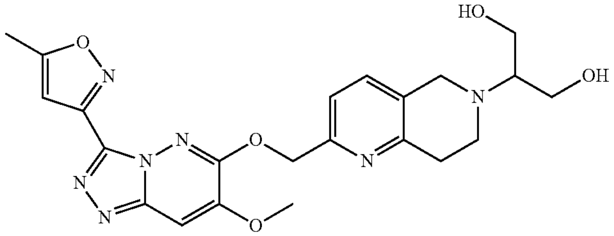 [SMILES: COc1cc2nnc(-c3cc(C)on3)n2nc1OCc1ccc2c(n1)CCN(C(CO)CO)C2] | H | 468 | (400 MHz, DMSO-$d_6$) δ ppm 7.68-7.78 (m, 1 H) 7.47-7.56 (m, 1 H) 7.33-7.41 (m, 1 H) 6.92-7.01 (m, 1 H) 5.37-5.50 (m, 2H) 4.33-4.45(m, 2 H)3.98 (s, 3 H) 3.82-3.92 (m, 2 H) 3.49-3.64 (m, 4 H) 2.97-3.03 (m, 2 H) 2.84-2.91 (m, 2 H) 2.68-2.75 (m, 1 H) 2.55 (s, 3 H) |
| 186 | 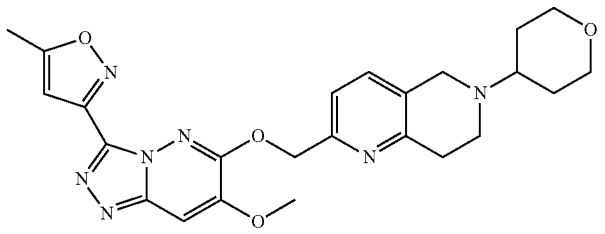 [SMILES: COc1cc2nnc(-c3cc(C)on3)n2nc1OCc1ccc2c(n1)CCN(C1CCOCC1)C2] | H | 478 | (400 MHz, $CDCl_3$) δ ppm 7.44 (d, J = 8.0 Hz, 1H), 7.39 (d , J = 8.0 Hz, 1H), 7.20 (s, 1H), 6.80 (s, 1H), 5.57 (s, 2H), 4.05-4.08 (m, 2H), 3.99 (s, 3H), 3.80 (s, 2H), 3.39-3.45 (t, J = 7.6 Hz, 2H), 3.06-3.09(t, J = 5.6 Hz, 2H), 2.95-2.97 (t, J = 5.6 Hz, 2H), 2.71-2.73 (m, 1H), 2.56 (s, 3H), 1.68-1.86 (m, 4H) |
| 188 | 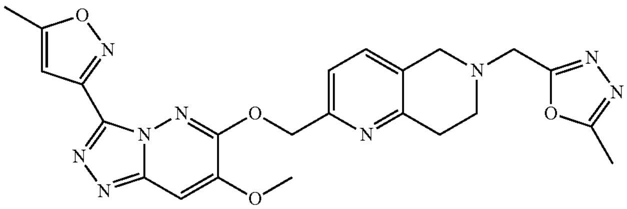 [SMILES: COc1cc2nnc(-c3cc(C)on3)n2nc1OCc1ccc2c(n1)CCN(Cc1nnc(C)o1)C2] | I | 490 | (400 MHz, CHLOROFORM-$d_6$) δ ppm 7.44-7.49 (m, 1 H) 7.38 (d, J = 7.83 Hz, 1 H) 7.20-7.23 (m, 1 H) 6.80 (s, 1 H) 5.58 (s, 2 H) 4.00-4.02 (m, 3 H) 3.99 (s, 2 H) 3.78 (s, 2 H) 3.08-3.15 (m, 2 H) 2.97-3.04 (m, 2 H) 2.57 (s, 3 H) 2.53-2.56 (m, 3H) |

-continued

| Embodiment | Structure | Synthesis method | Mass spectrum $[M + H]^+$ | $^1H$ NMR (400 MHz) |
|---|---|---|---|---|
| 189 | 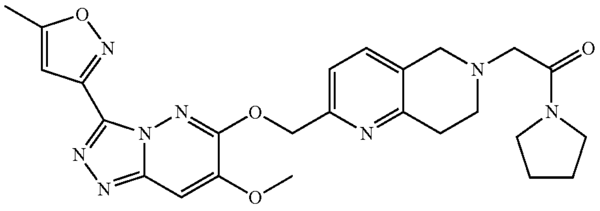 [SMILES: COc1cc2nnc(-c3cc(C)on3)n2nc1OCc1ccc2c(n1)CCN(CC(=O)N1CCCC1)C2] | I | 505 | (400 MHz, CHLOROFORM-$d_6$) δ ppm7.45 (s, 1 H) 7.35-7.41 (m, 1 H) 7.20 (s, 1 H) 6.82 (s, 1 H) 5.59 (s, 2 H) 4.01 (s, 3 H) 3.83 (s, 2 H) 3.52 (d, J = 5.38 Hz, 4 H) 3.38 (s, 2 H) 3.11 (d, J = 5.38 Hz, 2 H) 3.01 (br. s., 2 H) 2.58 (s, 3 H) 1.92-1.99 (m, 2H) 1.83-1.90 (m, 2 H) |
| 190 | 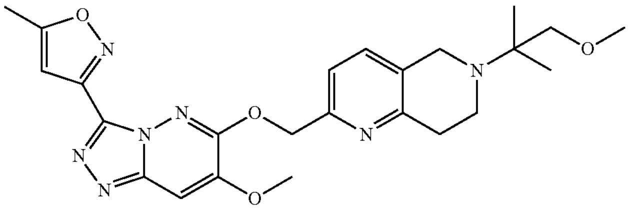 | B | 480 | (400 MHz, CHLOROFORM-$d_6$) δ ppm 7.40 (q, J = 7.83 Hz, 2 H) 7.20 (s, 1 H) 6.82 (s, 1 H) 5.58 (s, 2 H) 4.00 (s, 3 H) 3.88 (s, 2 H) 3.37 (br. s., 2 H) 3.36 (s, 3 H) 3.04 (d, J = 4.89 Hz, 2 H) 2.98 (d, J = 4.89 Hz, 2 H) 2.58 (s, 3H) 1.18 (s, 6H) |
| 191 | 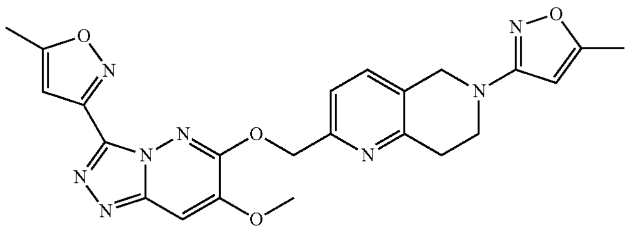 | B | 475 | (400 MHz, DMSO-$d_6$) δ ppm 7.71-7.77 (m, 1 H) 7.65-7.70 (m, 1 H) 7.43-7.50 (m, 1 H) 6.94-7.01 (m, 1 H) 6.12-6.17 (m, 1 H) 5.43-5.54(m, 2 H) 4.39-4.46 (m, 2 H) 3.96-3.98 (m, 3 H) 3.60-3.65 (m, 2 H) 2.91-3.01 (m, 2 H) 2.53-2.55 (m, 3 H) 2.24-2.30 (m, 3 H) |
| 193 | 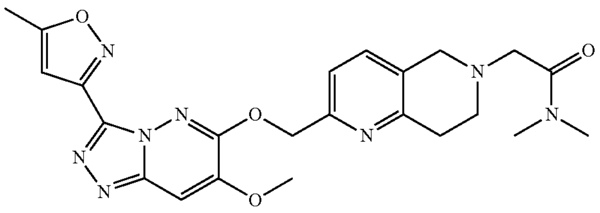 | I | 479 | (400 MHz, CHLOROFORM-$d_6$) δ ppm 7.44-7.50 (m, 1 H) 7.35-7.41 (m, 1 H) 7.22 (s, 1 H) 6.82 (s, 1 H) 5.59 (s, 2 H) 4.01 (s, 3 H) 3.80 (s, 2 H)3.43 (s, 2H) 3.11 (s, 4H) 2.98 (s, 6 H) 2.58 (s, 3H) |
| 200 | 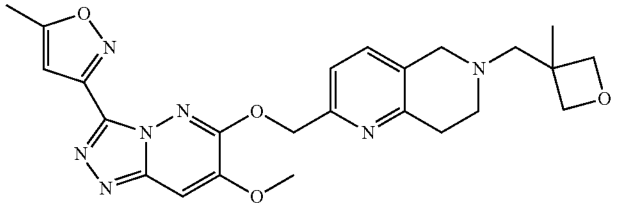 [SMILES: COc1cc2nnc(-c3cc(C)on3)n2nc1OCc1ccc2c(n1)CCN(CC1(C)COC1)C2] | H | 478 | (400 MHz, CHLOROFORM-d) d = 7.46 (d, J = 7.8 Hz, 1 H), 7.36 (d, J = 7.8 Hz, 1 H), 7.21 (s, 1 H), 6.80 (s, 1 H), 5.59 (s, 2H), 4.55 (d, J = 5.4 Hz, 2 H), 4.40 (d, J = 5.4 Hz, 2 H), 4.01 (s, 3 H), 3.58 (s, 2 H), 3.09-3.02 (m, 2 H), 2.79-2.72 (m, 4 H), 2.57 (s, 3 H), 1.44 (s, 3 H) |
| 202 | 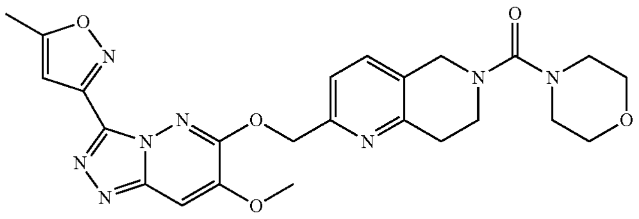 [SMILES: COc1cc2nnc(-c3cc(C)on3)n2nc1OCc1ccc2c(n1)CCN(C(=O)N1CCOCC1)C2] | J | 507 | (400 MHz, CHLOROFORM-d) d ppm 2.56 (s, 3 H) 3.08 (t, J = 5.62 Hz, 2 H) 3.28-3.36 (m, 4H) 3.59 (t, J = 5.62 Hz, 2 H) 3.66-3.75 (m, 4H) 4.00 (s, 3 H) 4.44 (s, 2 H) 5.58 (s, 2 H) 6.79 (s, 1 H) 7.24 (s, 1 H) 7.46 (d, J = 8.31 Hz, 1 H) 7.54 (d, J = 7.83 Hz, 1 H) |
| 203 | 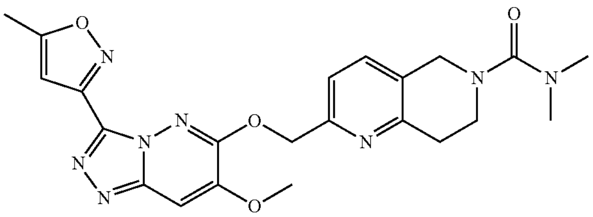 | J | 465 | (400 MHz, CHLOROFORM-d) d ppm 2.56 (s, 3 H) 2.89 (s, 6 H) 3.07-3.12 (m, 2 H) 3.56 (t, J = 5.38 Hz, 2 H) 4.00 (s, 3 H) 4.40 (s, 2 H) 5.59 (s, 2 H) 6.80 (s, 1 H) 7.22 (s, 1 H) 7.40-7.60 (m, 2 H) |

-continued

| Embodiment | Structure | Synthesis method | Mass spectrum [M + H]$^+$ | $^1$H NMR (400 MHz) |
|---|---|---|---|---|
| 204 | 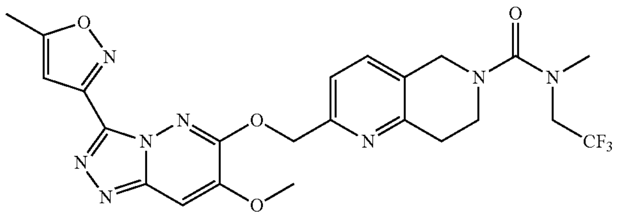 [SMILES: COc1cc2nnc(-c3cc(C)on3)n2nc1OCc1ccc2c(n1)CCN(C(=O)N(C)CC(F)(F)F)C2] | J | 533 | (400 MHz, $CDCl_3$) = 7.62-7.47 (m, 2 H), 7.25-7.24 (m, 1 H), 6.80 (s, 1 H), 5.60 (s, 2 H), 4.45 (s, 2 H), 4.01 (s, 3 H), 3.98-3.88 (m, 2 H), 3.63 (t, J = 5.6 Hz, 2 H), 3.16-3.11 (m, 2 H), 3.09 (s, 3 H), 2.56 (s, 3 H) |
| 206 | 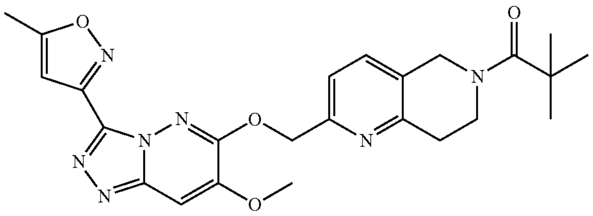 [SMILES: COc1cc2nnc(-c3cc(C)on3)n2nc1OCc1ccc2c(n1)CCN(C(=O)C(C)(C)C)C2] | K | 478 | (400 MHz, $CDCl_3$) = 7.57-7.46 (m, 2 H), 7.26 (s, 1 H), 6.79 (s, 1 H), 5.59 (s, 2 H), 4.76 (s, 2H), 4.01 (s, 3 H), 3.96 (t, J = 5.6 Hz, 2 H), 3.07 (t, J = 5.6 Hz, 2H), 2.56 (s, 3 H), 1.32 (s, 9H) |
| 207 | 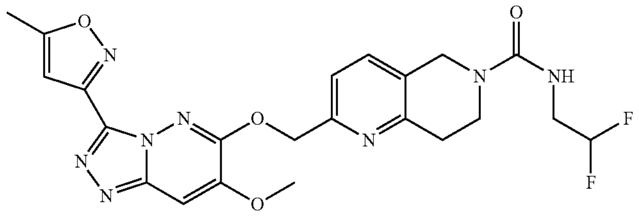 [SMILES: COc1cc2nnc(-c3cc(C)on3)n2nc1OCc1ccc2c(n1)CCN(C(=O)NCC(F)F)C2] | J | 501 | (400 MHz, CHLOROFORM-d) d = 7.57 (d, J = 7.8 Hz, 1 H), 7.50 (d, J = 7.8 Hz, 1 H), 7.21 (s, 1 H), 6.81 (s, 1 H), 5.73 (br. s., 1 H), 5.61 (s, 2 H), 4.96 (br. s., 1 H), 4.64 (s, 2 H), 4.02 (s, 3 H), 3.74 (t, J = 5.6 Hz, 2 H), 3.63 (d, J = 18.1 Hz, 2H), 3.10 (t, J = 5.4 Hz, 2H), 2.58 (s, 3 H) |
| 208 | 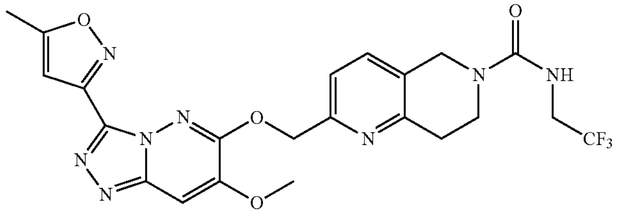 [SMILES: COc1cc2nnc(-c3cc(C)on3)n2nc1OCc1ccc2c(n1)CCN(C(=O)NCC(F)(F)F)C2] | J | 519 | (400 MHz, CHLOROFORM-d) d = 7.59 (d, J = 7.3 Hz, 1 H), 7.51 (d, J = 7.8 Hz, 1 H), 7.22 (s, 1 H), 6.81 (s, 1 H), 5.62 (s, 2 H), 4.93 (br. s., 1 H), 4.66 (s, 2 H), 4.02 (s, 3 H), 3.97 (d, J = 7.8 Hz, 2 H), 3.76 (t, J = 5.6 Hz, 2 H), 3.11 (t, J = 5.4 Hz, 2 H), 2.58 (s, 3 H) |
| 209 | 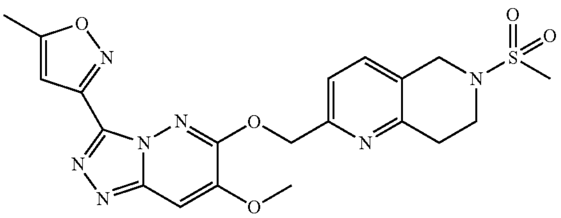 [SMILES: COc1cc2nnc(-c3cc(C)on3)n2nc1OCc1ccc2c(n1)CCN(S(C)(=O)=O)C2] | K | 472 | (400 MHz, DMSO-$d_6$) δ ppm 7.63-7.77 (m, 2 H) 7.49 (s, 1 H) 6.95 (s, 1 H) 5.48 (s, 2 H) 4.42 (s, 2 H) 3.98 (s, 3 H) 3.54 (t, J = 5.62 Hz, 2 H) 3.01 (t, J = 5.62 Hz, 2 H) 2.98 (s, 3 H) 2.54 (s, 3 H) |
| 210 | 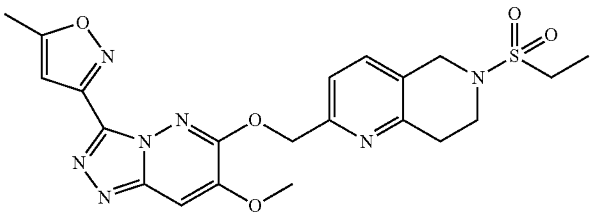 [SMILES: CCS(=O)(=O)N1CCc2nc(COc3nn4c(-c5cc(C)on5)nnc4cc3OC)ccc2C1] | K | 486 | (400 MHz, DMSO-$d_6$) δ ppm 7.74 (s, 1 H) 7.64-7.71 (m, 1 H) 7.45-7.53 (m, 1 H) 6.92-7.01 (m, 1 H) 5.49 (s, 2 H) 4.48 (s, 2 H) 3.98 (s, 3 H) 3.61 (br. s., 2 H) 3.12-3.19 (m, 2 H) 2.93-3.04 (m, 2 H) 2.55 (s, 3 H) 1.22 (d, J = 6.85 Hz, 3 H) |

-continued

| Embodiment | Structure | Synthesis method | Mass spectrum [M + H]$^+$ | $^1$H NMR (400 MHz) |
|---|---|---|---|---|
| 212 | 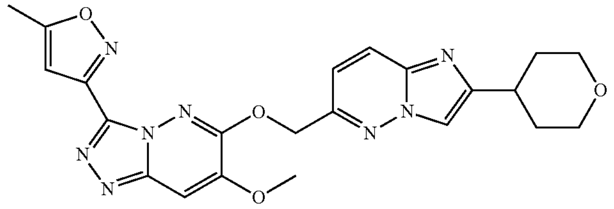 [SMILES: COc1cc2nnc(-c3cc(C)on3)n2nc1OCc1ccc2nc(C3CCOCC3)cn2n1] | B | 463 | (400 MHz, CHLOROFORM-d) d ppm 1.71-1.82 (m, 2 H) 1.94 (d, J = 13.21 Hz, 2H) 2.49 (s, 3 H) 2.97 (br. s., 1 H) 3.50 (t, J = 11.25 Hz, 2 H) 3.95 (s, 3 H) 3.98 (d, J = 12.23 Hz, 2 H) 5.60 (s, 2 H) 6.72 (s, 1 H) 7.25 (s, 1 H) 7.40 (d, J = 9.29 Hz, 1 H) 7.69 (s, 1 H) 7.83 (d, J = 9.29 Hz, 1 H) |
| 213 | 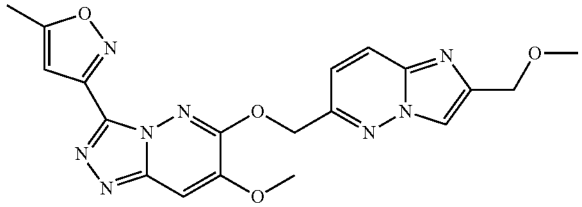 | B | 423 | (400 MHz, CHLOROFORM-d) d = 7.97 (s, 1 H), 7.92 (d, J = 9.3 Hz, 1 H), 7.51 (d, J = 9.3 Hz, 1 H), 7.24 (s, 1 H), 6.80 (s, 1 H), 5.70 (s, 2 H), 4.68 (s, 2 H), 4.02 (s, 3 H), 3.49 (s, 3 H), 2.57 (s, 3 H) |
| 214 | 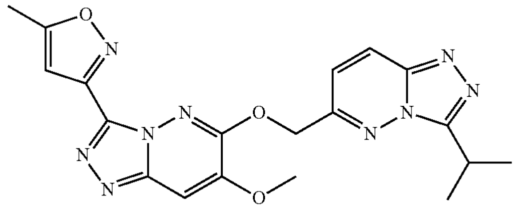 [SMILES: COc1cc2nnc(-c3cc(C)on3)n2nc1OCc1ccc2nnc(C(C)C)n2n1] | B | 422 | (400 MHz, CHLOROFORM-d) d = 8.11 (d, J = 9.3 Hz, 1 H), 7.55 (d, J = 9.3 Hz, 1 H), 7.28 (s, 1 H), 6.78 (s, 1 H), 5.71 (s, 2 H), 4.03 (s, 3 H), 3.67 (td, J = 7.0, 13.8 Hz, 1 H), 2.55 (s, 3 H), 1.52 (d, J = 6.8 Hz, 6 H) |
| 215 | 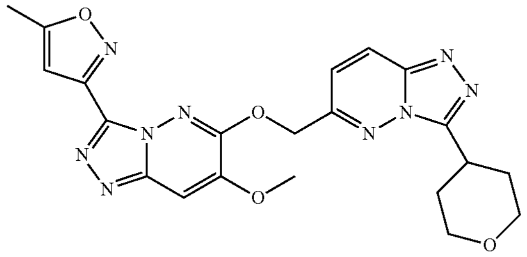 [SMILES: COc1cc2nnc(-c3cc(C)on3)n2nc1OCc1ccc2nnc(C3CCOCC3)n2n1] | B | 464 | (400 MHz, CHLOROFORM-d) d = 8.12 (d, J = 9.8 Hz, 1 H), 7.58 (d, J = 9.8 Hz, 1 H), 7.29 (s, 1 H), 6.78 (s, 1 H), 5.72 (s, 2H), 4.18-4.10 (m, 2 H), 4.04 (s, 3 H), 3.70-3.64 (m, J = 2.0 Hz, 3 H), 2.56 (s, 3 H), 2.30-2.16 (m, 2 H), 2.13-2.04 (m, 2 H) |
| 216 | 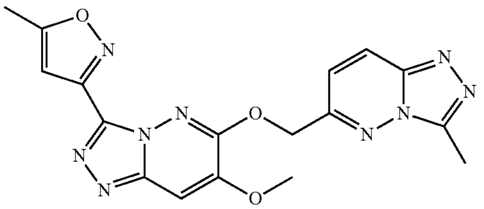 [SMILES: COc1cc2nnc(-c3cc(C)on3)n2nc1OCc1ccc2nnc(C)n2n1] | B | 394 | (400 MHz, CHLOROFORM-d) d = 8.10 (d, J = 9.3 Hz, 1 H), 7.61 (d, J = 9.3 Hz, 1 H), 7.28 (br. s., 1 H), 6.78 (s, 1 H), 5.72 (s, 2 H), 4.03 (s, 3 H), 2.84 (s, 3 H), 2.56 (s, 3 H). |
| 217 | 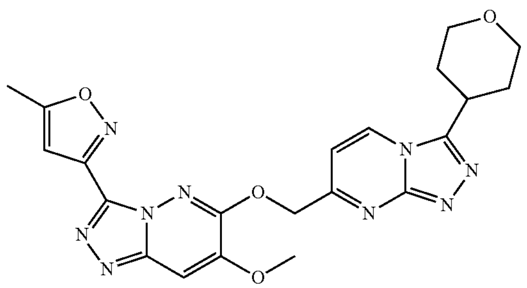 [SMILES: COc1cc2nnc(-c3cc(C)on3)n2nc1OCc1ccn2c(C3CCOCC3)nnc2n1] | B | 464 | (400 MHz, CHLOROFORM-d) d = 8.78 (d, J = 7.3 Hz, 1 H), 7.50 (d, J = 6.8 Hz, 1 H), 7.26 (s, 1 H), 6.76 (s, 1 H), 5.74 (s, 2H), 4.11-3.99 (m, 5 H), 3.64-3.55 (m, 2 H), 3.28-3.15 (m, 1 H), 2.57 (s, 3 H), 2.0-2.04 (m, 4 H). |

-continued

| Embodi-ment | Structure | Synthesis method | Mass spectrum [M + H]+ | 1H NMR (400 MHz) |
|---|---|---|---|---|
| 218 | 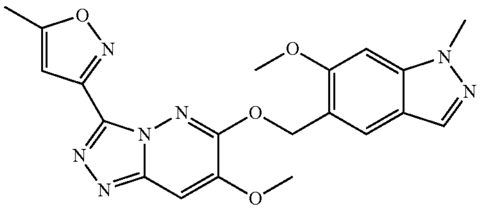 [SMILES: COc1cc2c(cnn2C)cc1COc1nn2c(-c3cc(C)on3)nnc2cc1OC] | L | 422 | (400 MHz, DMSO-$d_6$) δ 7.94 (s, 2H), 7.72 (s, 1H), 7.22 (s, 1H), 7.01 (d, J = 0.8 Hz, 1H), 5.52 (s, 2H), 4.02 (s, 3H), 3.93 (m, 6H), 2.57 (s, 3H) |
| 219 | 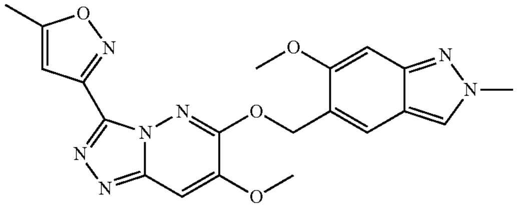 | L | 422 | (400 MHz, DMSO-$d_6$) δ 7.75 (m, J = 9.5 Hz, 2H), 7.12 (s, 1H), 6.94 (s, H), 6.72 (m, 1H), 5.93 (s, 2H), 4.14 (s, 3H), 3.94 (s, 3H), 3.79 (s, 3H), 2.58 (s, 3H) |
| 221 | 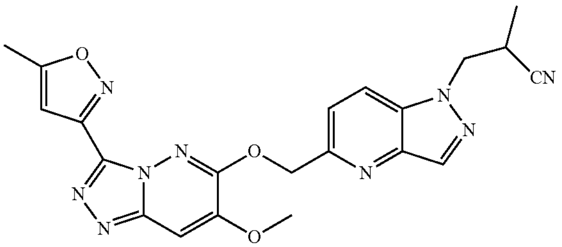 [SMILES: COc1cc2nnc(-c3cc(C)on3)n2nc1OCc1ccc2c(cnn2CC(C)C#N)n1] | B | 446 | (400 MHz, CHLOROFORM-$d_6$) δ ppm 8.29 (s, 1 H) 7.89-7.96 (m, 1 H) 7.80-7.87 (m, 1 H) 7.23 (s, 1 H) 6.80 (s, 1 H) 5.77 (s, 2H) 4.45-4.69 (m, 2 H) 4.01 (s, 3 H) 3.30-3.44 (m, 1 H) 2.57 (s, 3 H) 1.38 (d, J = 6.85 Hz, 3 H) |
| 222 | 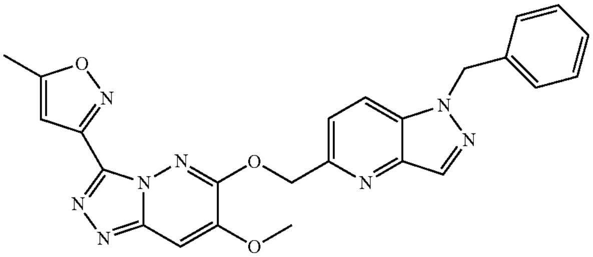 [SMILES: COc1cc2nnc(-c3cc(C)on3)n2nc1OCc1ccc2c(cnn2Cc2ccccc2)n1] | M | 469 | (400 MHz, CHLOROFORM-d) d ppm 2.55 (s, 3 H) 3.99 (s, 3 H) 5.60 (s, 2H) 5.75 (s, 2 H) 6.78 (s, 1 H) 7.15-7.23 (m, 3 H) 7.27-7.33 (m, 3 H) 7.69 (s, 2 H) 8.28 (s, 1 H) |
| 223 | 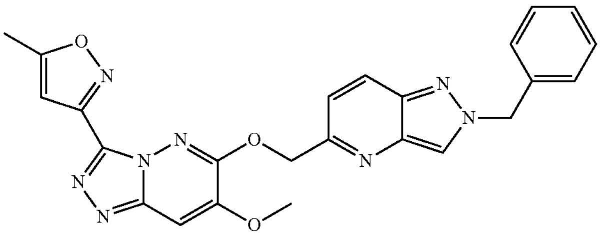 [SMILES: COc1cc2nnc(-c3cc(C)on3)n2nc1OCc1ccc2nn(Cc3ccccc3)cc2n1] | M | 469 | (400 MHz, CHLOROFORM-d) d ppm 2.52 (s, 3 H) 3.99-4.03 (m, 3 H) 5.62 (s, 2 H) 5.71 (s, 2H) 6.76 (s, 1 H) 7.22 (s, 1 H) 7.28-7.32 (m, 2 H) 7.33-7.40 (m, 3 H) 7.57 (d, J = 8.80 Hz, 1 H) 8.10 (d, J = 8.80 Hz, 1 H) 8.17 (s, 1 H) |
| 224 | 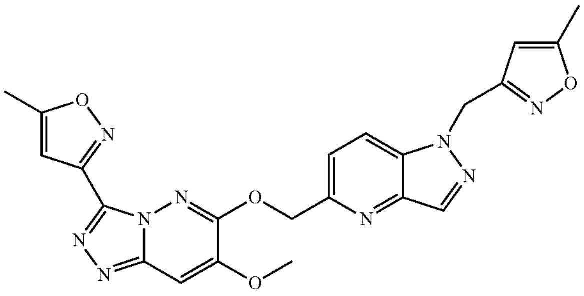 | B | 474 | (400 MHz, $CDCl_3$) = 8.22 (s, 1 H), 7.88 (d, J = 8.8 Hz, 1 H), 7.72 (d, J = 8.8 Hz, 1 H), 7.22 (s, 1 H), 6.75 (s, 1 H), 5.83 (s, 1 H), 5.71 (s, 2 H), 5.56 (s, 2 H), 3.97 (s, 3 H), 2.53 (s, 3 H), 2.30 (s, 3 H) |

-continued

| Embodiment | Structure | Synthesis method | Mass spectrum $[M + H]^+$ | $^1H$ NMR (400 MHz) |
|---|---|---|---|---|
| 225 | 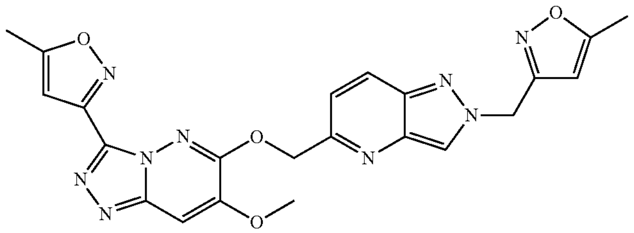 | B | 474 | (400 MHz, $CDCl_3$) = 8.28 (s, 1 H), 8.11 (d, J = 8.8 Hz, 1 H), 7.61 (d, J = 8.8 Hz, 1 H), 7.23 (s, 1 H), 6.78 (s, 1 H), 5.96 (s, 1 H), 5.79-5.61 (m, 4 H), 4.02 (s, 3 H), 2.62-2.32 (m, 6 H) |
| 227 | 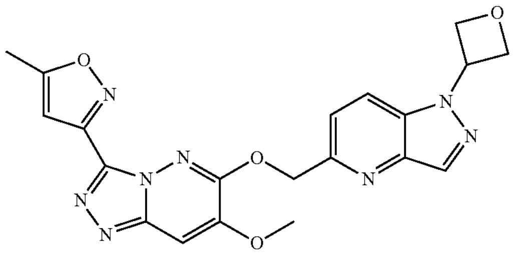 [SMILES: COc1cc2nnc(-c3cc(C)on3)n2nc1OCc1ccc2c(cnn2C2COC2)n1] | M | 435 | (400 MHz, DMSO-$d_6$) d ppm 2.52-2.56 (m, 3 H) 3.94-4.00 (m, 3 H) 4.96-5.04 (m, 4 H) 5.63-5.68 (m, 2 H) 6.05-6.09 (m, 1 H) 6.93-6.96 (m, 1 H) 7.68-7.74 (m, 2 H) 8.22-8.26 (m, 1 H) 8.45-8.48 (m, 1 H) |
| 228 | 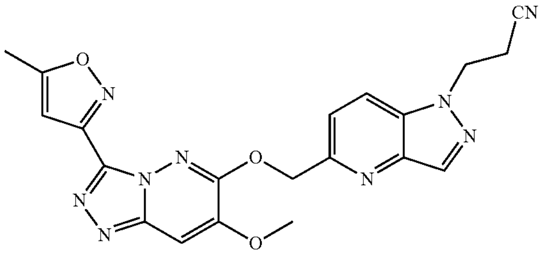 [SMILES: COc1cc2nnc(-c3cc(C)on3)n2nc1OCc1ccc2c(cnn2CCC#N)n1] | M | 432 | (400 MHz, CHLOROFORM-d) d ppm 2.51 (s, 3 H) 2.98 (t, J = 6.60 Hz, 2 H) 3.97 (s, 3 H) 4.62 (t, J = 6.36 Hz, 2 H) 5.71 (s, 2 H) 6.75 (s, 1 H) 7.26 (s, 1 H) 7.77 (s, 1 H) 7.90 (s, 1 H) 8.23 (s, 1 H) |
| 231 | 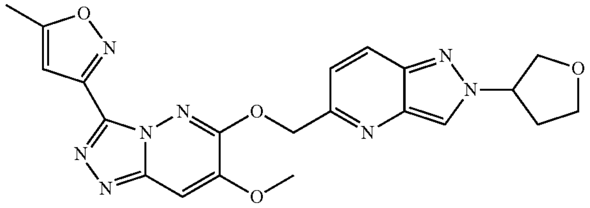 [SMILES: COc1cc2nnc(-c3cc(C)on3)n2nc1OCc1ccc2nn(C3CCOC3)cc2n1] | M | 449 | (400 MHz, CHLOROFORM-d) d ppm 2.47 (d, J = 7.83 Hz, 1 H) 2.55 (s, 3 H) 2.58-2.67 (m, 1 H) 4.01 (s, 3 H) 4.13-4.28 (m, 4 H) 5.29 (br. s., 1 H) 5.72 (s, 2 H) 6.78 (s, 1 H) 7.23 (s, 1 H) 7.57 (d, J = 8.80 Hz, 1 H) 8.09 (d, J = 8.80 Hz, 1 H) 8.29 (s, 1 H) |
| 232 | 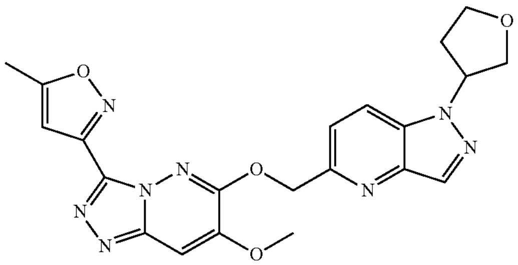 [SMILES: COc1cc2nnc(-c3cc(C)on3)n2nc1OCc1ccc2c(cnn2C2CCOC2)n1] | M | 449 | (400 MHz, CHLOROFORM-d) d ppm 2.57 (s, 5 H) 4.01 (s, 5 H) 4.12-4.22 (m, 2 H) 4.22-4.29 (m, 1 H) 5.78 (s, 2 H) 6.81 (s, 1 H) 7.77 (d, J = 8.80 Hz, 1 H) 7.94 (d, J = 8.80 Hz, 1 H) 8.25 (s, 1 H) |
| 233 | 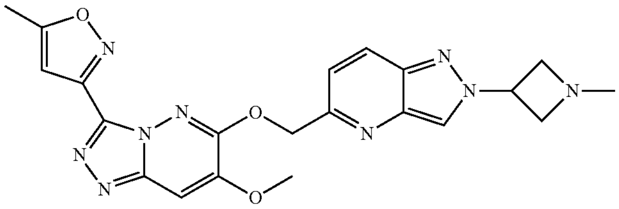 | H | 448 | (400 MHz, CHLOROFORM-d) d ppm 2.54 (s, 3 H) 2.56 (s, 3 H) 3.72-3.78 (m, 2 H) 4.02 (s, 5 H) 5.25-5.30 (m, 1 H) 5.73 (s, 2 H) 6.79 (s, 1 H) 7.23 (s, 1 H) 7.56-7.63 (m, 1 H) 8.10-8.14 (m, 1 H) 8.34 (s, 1 H) |

-continued

| Embodi-ment | Structure | Synthesis method | Mass spectrum [M + H]+ | 1H NMR (400 MHz) |
|---|---|---|---|---|
| 234 | 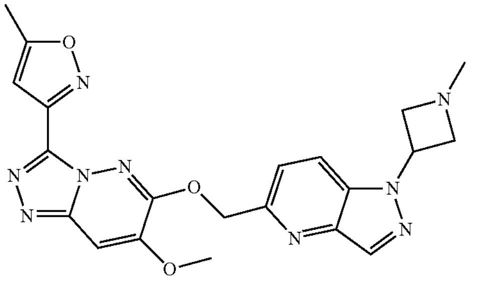 | H | 448 | (400 MHz, CHLOROFORM-d) d ppm 2.58 (s, 6 H) 3.81 (t, J = 7.58 Hz, 2 H) 4.00 (s, 3 H) 4.06 (t, J = 7.58 Hz, 2H) 5.34 (t, J = 7.34 Hz, 1 H) 5.77 (s, 2H) 6.81 (s, 1 H) 7.22 (s, 1 H) 7.79 (d, J = 8.31 Hz, 1 H) 7.93 (d, J = 8.80 Hz, 1 H) 8.31 (s, 1 H) |
| 235 | 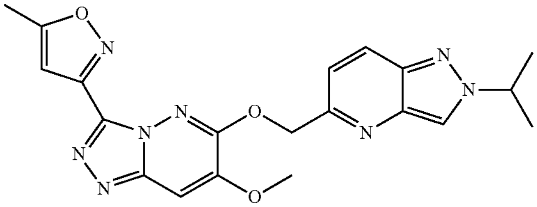 [SMILES: COc1cc2nnc(-c3cc(C)on3)n2nc1OCc1ccc2nn(C(C)C)cc2n1] | M | 421 | (400 MHz, CHLOROFORM-d) d ppm 1.64 (d, J = 6.85 Hz, 6 H) 2.52 (s, 3 H) 3.98 (s, 3 H) 4.80 (dt, J = 13.33, 6.79 Hz, 1 H) 5.69 (s, 2 H) 6.74 (s, 1 H) 7.21 (s, 1 H) 7.53 (d, J = 8.80 Hz, 1 H) 8.07 (d, J = 9.29 Hz, 1 H) 8.19 (s, 1 H) |
| 236 | 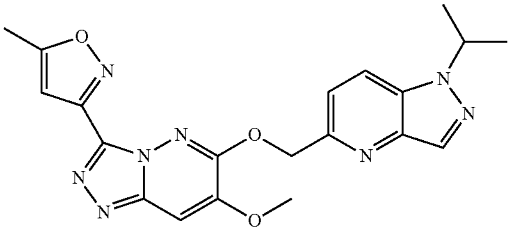 [SMILES: COc1cc2nnc(-c3cc(C)on3)n2nc1OCc1ccc2c(cnn2C(C)C)n1] | M | 421 | (400 MHz, CHLOROFORM-d) d ppm 1.59 (d, J = 6.85 Hz, 6 H) 2.55 (s, 3 H) 4.01 (s, 3 H) 4.83 (dt, J = 13.21, 6.60 Hz, 1 H) 5.75 (s, 2 H) 6.79 (s, 1 H) 7.39 (s, 1 H) 7.71 (d, J = 8.80 Hz, 1 H) 7.83 (d, J = 8.80 Hz, 1 H) 8.23 (s, 1 H) |
| 237 | 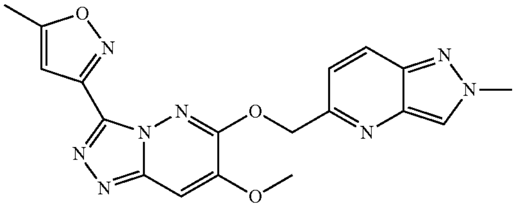 | M | 393 | (400 MHz, CHLOROFORM-d) d ppm 2.56 (s, 3 H) 4.01 (s, 3 H) 4.28 (s, 3 H) 5.73 (s, 2 H) 6.78 (s, 1 H) 7.25 (d, J = 8.80 Hz, 1 H) 7.59 (d, J = 8.80 Hz, 1 H) 8.06-8.12 (m, 1 H) 8.18 (s, 1 H) |
| 238 | 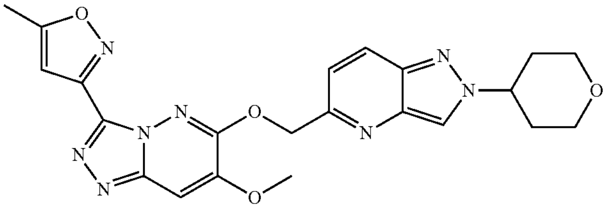 [SMILES: COc1cc2nnc(-c3cc(C)on3)n2nc1OCc1ccc2nn(C3CCOCC3)cc2n1] | M | 463 | (400 MHz, CHLOROFORM-d) d ppm 2.19-2.31 (m, 4 H) 2.55 (s, 3 H) 3.61 (t, J = 11.00 Hz, 2 H) 4.01 (s, 3 H) 4.18 (d, J = 11.25 Hz, 2 H) 4.62-4.74 (m, 1 H) 5.72 (s, 2 H) 6.77 (s, 1 H) 7.20-7.24 (m, 1 H) 7.58 (d, J = 8.31 Hz, 1 H) 8.09 (d, J = 8.80 Hz, 1 H) 8.24 (s, 1 H) |
| 239 | 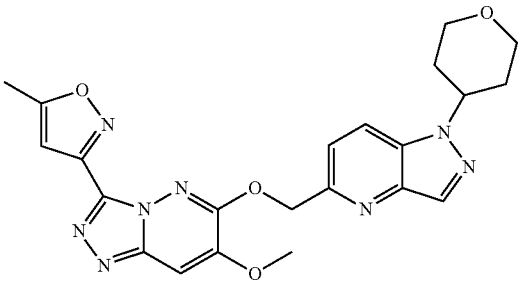 [SMILES: COc1cc2nnc(-c3cc(C)on3)n2nc1OCc1ccc2c(cnn2C2CCOCC2)n1] | M | 463 | (400 MHz, CHLOROFORM-d) d ppm 1.97 (d, J = 12.72 Hz, 2 H) 2.32-2.46 (m, 2 H) 2.56 (s, 3 H) 3.60 (t, J = 11.98 Hz, 2 H) 3.99 (s, 3 H) 4.16 (d, J = 10.76 Hz, 2 H) 4.64 (t, J = 11.49 Hz, 1 H) 5.77 (s, 2 H) 6.80 (s, 1 H) 7.21 (s, 1 H) 7.75-7.81 (m, 1 H) 7.84-7.90 (m, 1 H) 8.24 (s, 1 H) |

-continued

| Embodi-ment | Structure | Synthesis method | Mass spectrum [M + H]+ | 1H NMR (400 MHz) |
|---|---|---|---|---|
| 240 | 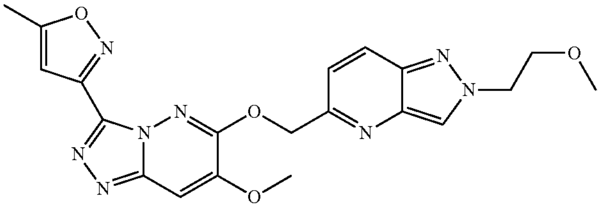 | M | 437 | (400 MHz, CHLOROFORM-c) d ppm 2.54 (br. s., 3 H) 3.32 (br. s., 3 H) 3.87 (br. s, 2 H) 4.00 (br. s., 3 H) 4.61 (br. s., 2 H) 5.71 (br. s., 2 H) 6.77 (br. s., 1 H) 7.18-7.23 (m, 1 H) 7.56 (d, J = 8.80 Hz, 1 H) 8.07 (d, J = 8.80 Hz, 1 H) 8.29 (br. s., 1 H) |
| 241 | 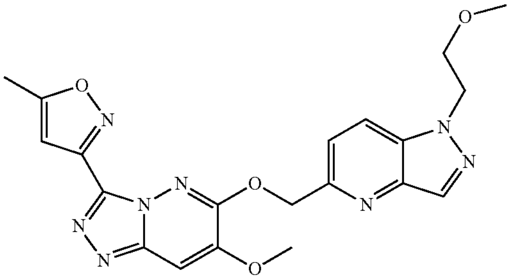 | M | 437 | (400 MHz, CHLOROFORM-d) d ppm 2.55 (s, 3 H) 3.25 (s, 3 H) 3.80 (t, J = 5.14 Hz, 2 H) 4.00 (s, 3 H) 4.54 (t, J = 5.14 Hz, 2 H) 5.76 (s, 2 H) 6.78 (s, 1 H) 7.23 (s, 1 H) 7.72 (d, J = 8.80 Hz, 1 H) 7.89 (d, J = 8.80 Hz, 1 H) 8.23 (s, 1 H) |
| 242 | 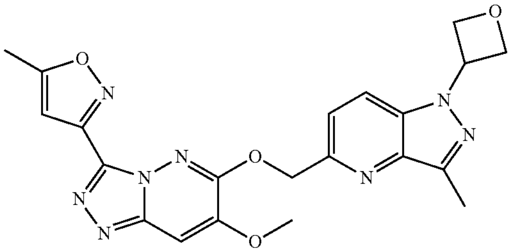 [SMILES: COc1cc2nnc(-c3cc(C)on3)n2nc1OCc1ccc2c(n1)c(C)nn2C1COC1] | L | 449 | (400 MHz, $CDCl_3$) δ 7.90 (d, J = 8.7 Hz, 1H), 7.81 (d, J = 8.7 Hz, 1H), 7.22 (s, 1H), 6.81 (d, J = 0.8 Hz, 1H), 5.79 (s, 2H), 5.68 (m, 1H), 5.24 (t, J = 6.6 Hz, 2H), 5.13 (t, J = 7.4 Hz, 2H), 4.01 (s, 3H), 2.71 (s, 3H), 2.58 (s, 3H) |
| 243 | 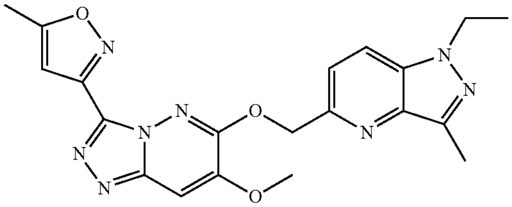 [SMILES: CCn1nc(C)c2nc(COc3nn4c(-c5cc(C)on5)nnc4cc3OC)ccc21] | L | 421 | (400 MHz, $CDCl_3$) 7.74 (m, 2H), 7.22 (s, 1H), 6.81 (s, 1H), 5.78 (s, 2H), 4.37 (d, J = 6.9 Hz, 2H), 4.00 (s, 3H), 2.68 (s, 3H), 2.57 (s,3H), 1.49 (t, J = 6.7 Hz, 3H). |
| 244 | 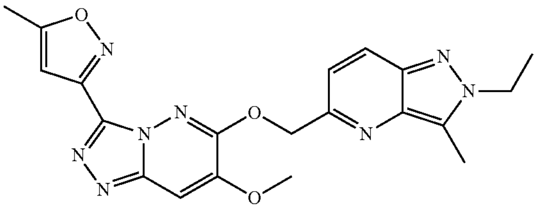 [SMILES: CCn1nc2ccc(COc3nn4c(-c5cc(C)on5)nnc4cc3OC)nc2c1C] | L | 421 | (400 MHz, $CDCl_3$) δ 8.02 (d, J = 8.9 Hz, 1H), 7.54 (d, J = 8.9 Hz, 1H), 7.22 (s, 1H), 6.80 (d, J = 0.8 Hz, 1H), 5.73 (s, 2H), 4.45 (q, J = 7.3 Hz, 2H), 4.01 (s, 3H), 2.74 (s, 3H), 2.56 (s, 3H), 1.55 (m, 3H) |
| 245 | 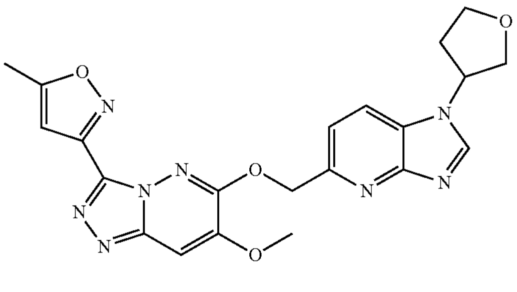 [SMILES: COc1cc2nnc(-c3cc(C)on3)n2nc1OCc1ccc2c(ncn2C2CCOC2)n1] | B | 449 | (400 MHz, CHLOROFORM-d) δ = 8.24 (s, 1 H), 7.93 (d, J = 8.3 Hz, 1 H), 7.65 (d, J = 8.3 Hz, 1 H), 7.23 (s, 1 H), 6.81 (s, 1 H), 5.75 (s, 2 H), 5.10-5.04 (m, 1 H), 4.26-4.17 (m, 2 H), 4.03 (dd, J = 5.9, 10.3 Hz, 1 H), 3.99 (s, 3 H), 3.90 (d, J = 7.3 Hz, 1 H), 2.66 (s, 1 H), 2.57-2.56 (m, 3 H), 2.24-2.15 (m, 1 H) |

-continued

| Embodiment | Structure | Synthesis method | Mass spectrum [M + H]$^+$ | $^1$H NMR (400 MHz) |
|---|---|---|---|---|
| 246 | 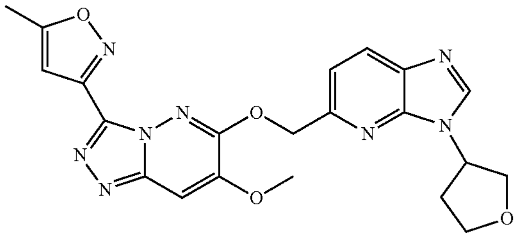 [SMILES: COc1cc2nnc(-c3cc(C)on3)n2nc1OCc1ccc2ncn(C3CCOC3)c2n1] | B | 449 | (400 MHz, CHLOROFORM-d) δ = 8.23 (s, 1 H), 8.10 (d, J = 8.3 Hz, 1 H), 7.67 (d, J = 8.3 Hz, 1 H), 7.27 (s, 1 H), 7.23 (s, 1 H), 6.80 (s, 1 H), 5.77 (s, 2 H), 5.50 (dt, J = 2.9, 5.1 Hz, 1 H), 4.27-4.19 (m, 1 H), 4.18-4.12 (m, 1 H), 4.12-4.06 (m, 1 H), 4.05-3.98 (m, 4 H), 2.68-2.60 (m, 1 H), 2.57 (s, 3 H), 2.31-2.22 (m, 1 H). |
| 247 | 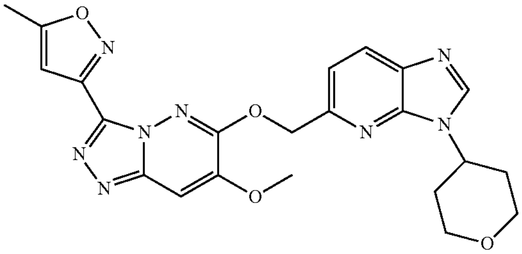 [SMILES: COc1cc2nnc(-c3cc(C)on3)n2nc1OCc1ccc2ncn(C3CCOCC3)c2n1] | B | 463 | (400 MHz, CHLOROFORM-d) δ = 8.17 (s, 1 H), 8.11 (d, J = 7.8 Hz, 1 H), 7.67 (d, J = 7.8 Hz, 1 H), 7.24 (br. s., 1 H), 6.79 (s, 1 H), 5.77 (s, 2 H), 4.87 (br. s., 1 H), 4.17 (d, J = 10.8 Hz, 2 H), 4.03 (s, 3 H), 3.67 (t, J = 11.5 Hz, 2H), 2.57 (s, 3H), 2.26-2.13 (m, 4 H) |
| 248 | 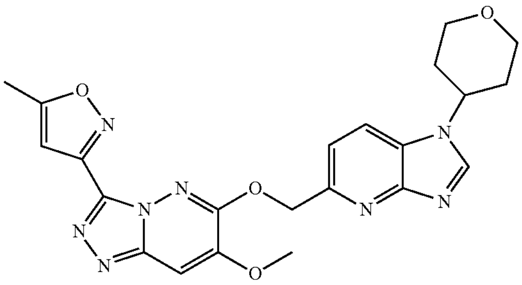 [SMILES: COc1cc2nnc(-c3cc(C)on3)n2nc1OCc1ccc2c(ncn2C2CCOCC2)n1] | B | 463 | (400 MHz, CHLOROFORM-d) δ = 8.25 (s, 1 H), 7.85 (d, J = 8.3 Hz, 1 H), 7.67 (d, J = 7.8 Hz, 1 H), 7.23 (s, 1 H), 6.80 (s, 1 H), 5.75 (s, 2 H), 4.45 (br. s., 1 H), 4.15 (d, J = 8.3 Hz, 2 H), 3.99 (s, 3H), 3.58 (t, J = 12.0 Hz, 2 H), 2.56 (s, 3 H), 2.25-2.05 (m, 4 H) |
| 249 | 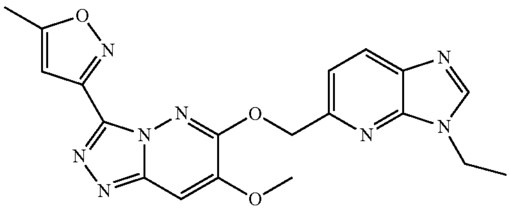 [SMILES: CCn1cnc2ccc(COc3nn4c(-c5cc(C)on5)nnc4cc3OC)nc21] | B | 407 | (400 MHz, CHLOROFORM-d) δ = 8.16 (s, 1 H), 8.12 (d, J = 8.3 Hz, 1 H), 7.65 (d, J = 7.8 Hz, 1 H), 7.25 (s, 1 H), 6.79 (s, 1 H), 5.76 (s, 2 H), 4.38 (q, J = 7.3 Hz, 2 H), 4.01 (s, 3 H), 2.56 (s, 3 H), 1.57 (t, J = 7.3 Hz, 3 H) |
| 250 | 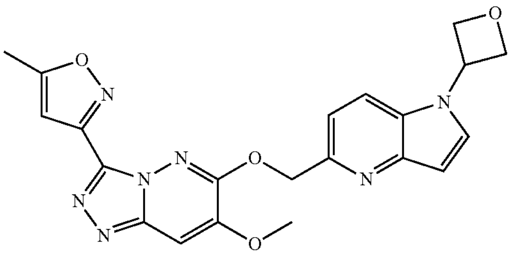 | B | 434 | (400 MHz, CHLOROFORM-d) d = 7.91 (d, J = 8.3 Hz, 1 H), 7.67 (d, J = 3.4 Hz, 1 H), 7.59 (d, J = 8.3 Hz, 1 H), 7.21 (s, 1 H), 6.84-6.81 (m, 2 H), 5.76 (s, 2 H), 5.55-5.48 (m, 1 H), 5.20 (t, J = 7.3 Hz, 2H), 5.08-5.04 (m, 2 H), 4.00 (s, 3 H), 2.58 (s, 3 H) |
| 251 | 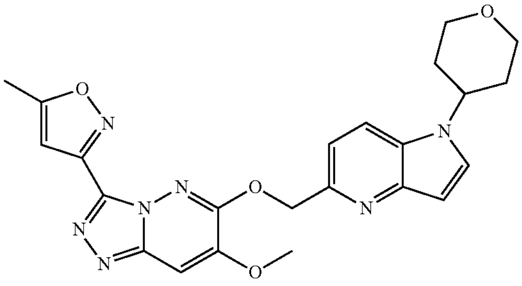 [SMILES: COc1cc2nnc(-c3cc(C)on3)n2nc1OCc1ccc2c(ccn2C2CCOCC2)n1] | B | 462 | (400 MHz, CHLOROFORM-d) d = 7.72 (d, J = 8.8 Hz, 1 H), 7.48 (br. s., 2H), 7.21 (s, 1 H), 6.75 (s, 1 H), 6.66 (br. s., 1 H), 5.66 (s, 2 H), 4.39 (br. s., 1 H), 4.09 (d, J = 9.3 Hz, 2H), 3.94 (s, 3 H), 3.59-3.53 (m, 2 H), 2.50 (s, 3 H), 2.13-2.01 (m, 2 H), 1.98-1.92 (m, 2 H) |

-continued

| Embodi-ment | Structure | Synthesis method | Mass spectrum [M + H]+ | 1H NMR (400 MHz) |
|---|---|---|---|---|
| 252 | 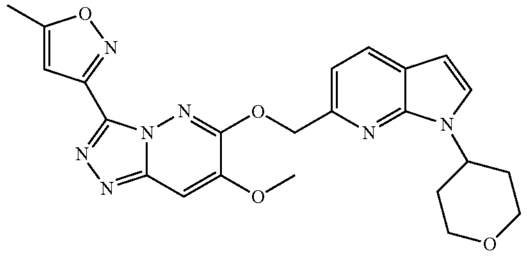 | B | 462 | (400 MHz, CHLOROFORM-d) δ = 7.93 (d, J = 8.3 Hz, 1H), 7.42 (d, J = 7.8 Hz, 1 H), 7.34 (d, J = 3.4 Hz, 1 H), 7.24 (s, 1 H), 6.77 (s, 1 H), 6.49 (d, J = 2.9 Hz, 1 H), 5.74 (s, 2 H), 5.11-5.02 (m, 1 H), 4.12 (d, J = 10.8 Hz, 2 H), 4.01 (s, 3H), 3.66 (t, J = 11.7 Hz, 2H), 2.55 (s, 3H), 2.12-2.00 (m, 4H) |
| 254 | 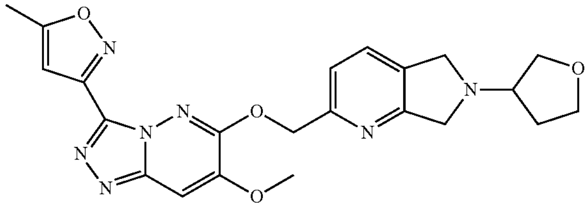 [SMILES: COc1cc2nnc(-c3cc(C)on3)n2nc1OCc1ccc2c(n1)CN(C1CCOC1)C2] | N | 450 | (400 MHz, $CDCl_3$ & $CD_3OD$) δ 7.57-7.49 (m, 2H), 7.20 (s, 1H), 6.80 (s, 1H), 5.62 (s, 2H), 4.03 (m, 2H), 3.99 (m, 6H), 3.93 (m, 1H), 3.90-3.83 (m, 1H), 3.79 (m, 1H), 3.42-3.35 (m, 1H), 2.57 (s, 3H), 2.19-2.09 (m, 1H), 2.07-1.97 (m, 1H) |
| 255 | 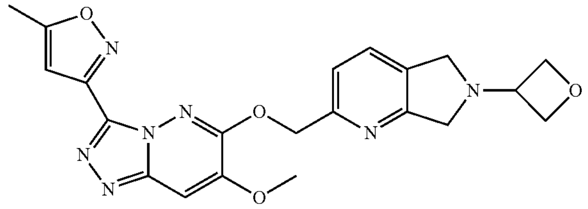 [SMILES: COc1cc2nnc(-c3cc(C)on3)n2nc1OCc1ccc2c(n1)CN(C1COC1)C2] | N | 436 | (400 MHz, $CDCl_3$) δ7.60-7.54 (m, 2H), 7.21 (s, 1H), 6.80 (s, 1H), 5.63 (s, 2H), 4.81 (t, J = 6.7 Hz, 2H), 4.75 (t, J = 6.1 Hz, 2H), 4.10 (m, 1H), 4.04 (m, 4H), 4.01 (s, 3H), 2.57 (s, 3H) |
| 257 | 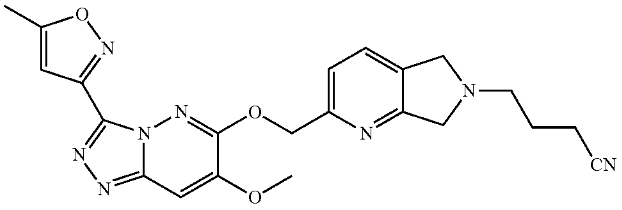 [SMILES: COc1cc2nnc(-c3cc(C)on3)n2nc1OCc1ccc2c(n1)CN(CCCC#N)C2] | N | 447 | (400 MHz, $CDCl_3$) δ 7.56 (s, 2H), 7.21 (s, 1H), 6.80 (d, J = 0.8 Hz, 1H), 5.62 (s, 2H), 4.00 (m, 7H), 2.92 (m, 2H), 2.57 (s, 3H), 2.53 (m, 2H), 1.95 (m, 2H) |
| 258 | 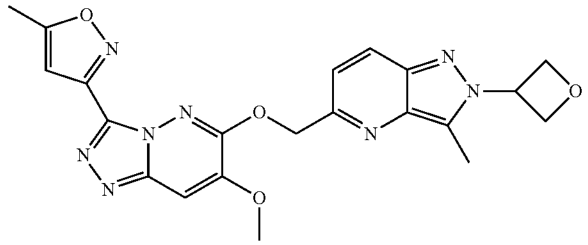 [SMILES: COc1cc2nnc(-c3cc(C)on3)n2nc1OCc1ccc2nn(C3COC3)c(C)c2n1] | L | 449 | (400 MHz, $CDCl_3$) δ 8.14 (d, J = 8.9 Hz, 1H), 7.62 (d, J = 8.9 Hz, 1H), 7.26 (s, 1H), 6.82 (s, 1H), 5.82-5.74 (m, 3H), 5.35 (t, J = 6.5 Hz, 2H), 5.13 (t, J = 7.2 Hz, 2H), 4.02 (s, 3H), 2.72 (s, 3H), 2.57 (s, 3H) |

Biological Experiment Method:

Previous studies have revealed that the $GABA_A$ receptors mediate at least two modes of inhibition, the phasic inhibition and the tonic inhibition. When the GABA increases to the millimole level, the $GABA_A$ receptors will be desensitized rapidly, show low affinity for GABA and form phasic inhibition. When the GABA activates $GABA_A$ receptors at several hundred nanomolar to several tens of micromolar level, the high affinity extrasynaptic $GABA_A$ receptors will mediate tonic inhibition and regulate neuronal excitability and signal transmission. (Farrant M et al. (2005) Variations on an inhibitory theme: phasic and tonic activation of GABA(A) receptors. Nat Rev Neurosci 6:215-229Y). Yeung J Y et al disclose that low concentrations of GABA are more likely to activate the α5-$GABA_A$ receptor (Yeung J Y et al (2003). Tonically activated $GABA_A$ receptors in hippocampal neurons are high-affinity, low-conductance sensors for extracellular GABA. Mol Pharmacol; 63:2-8). K. Y LEE et al reported that low concentrations of GABA-activated, sustained high affinity $GABA_A$ currents were detected on isolated DRG cells cultured for 24 hours, 20 μM GABA-activated high affinity GABAA current was up to about 100 pA/pF. (Lee K Y et al. Upregulation of high-affinity GABA (A) receptors in cultured rat dorsal root ganglion neurons. Neuroscience 208 (2012) 133-142). In 2013, I. Lecker et al reported that L-655,708, an α5-$GABA_A$ receptor inverse agonist, dose-dependently inhibited the current included by low concentrations of GABA (5, 50 and 500 nM). When the GABA concentration was increased to 1 μM, the highest concentration of L-655,708 could only suppress 15% of the current. When the GABA concentration continued to increase, L-655,708 had no inhibitory effect on the current induced by GABA. (I. Lecker et al (2013). Potentiation of $GABA_A$ receptor activity by volatile anaesthetics is reduced by α5-GABAA receptor-preferring inverse agonists. British Journal of Anaesthesia 110 (S1): i73-i81).

Cell-Level Screening

The inventors used electrophysiological methods to determine the inverse agonist efficacy of the drugs to be tested on the α5-$GABA_A$ receptor. The detailed methods are as follows:

Different subunits of $GABA_A$ receptors were expressed in human kidney epithelial cell line 293 (HEK293) cell line. The cells were cultured in a culture medium and used as a cell model for screening pain inhibiting drugs. The α, β and γ subunits are necessary to form complete functional $GABA_A$ receptors. In this embodiment, the inventors had established the following cell model: α5 subunit (see GenBank Accession No. NM_000810.3 for protein sequences), β3 subunit (see GenBank Accession No. NM_000814.5 for protein sequences) and γ2 subunit (see GenBank Accession No. NM_000816.3 for protein sequences) were expressed in HEK293 cell line at the same time, followed by screening the monoclonal cell line. This cell line contained α5-$GABA_A$ receptor and had complete $GABA_A$ receptor function.

The monoclonal stably transfected HEK-293 cells expressing α5-$GABA_A$ receptor were cultured in 10 cm culture dishes and passaged when the cells grew to 80%-90%. During passaging, the culture medium was aspirated first, then 3 mL of DPBS phosphate buffer salt (Gibco™) was added to the culture dishes, and the culture dishes were shaken slightly, and DPBS was aspirated. 1 mL of trypsin (TrypLE Express, Gibco™) was added thereto, and the cells were digested at 37° C. for 1-2 minutes. Then 3 mL of complete medium (DMEM+10% FBS (Gibco™)) was added and the cells at the bottom of the culture dishes were dispersed. The cell suspension were transferred to a 15 mL centrifugal tube (Corning) and then centrifuged at 200 g for 3 minutes. The supernatant was discarded, 4 mL of complete medium was added, and the cells were gently blown and resuspended for use. If cell passaging was performed, the cell suspension was diluted at a ratio of 1:5 or 1:10. If cells for electrophysiology use were prepared, the cell suspension was diluted in a ratio of 1:12, then added into a 24-well dish (Corning™) in which glass slides were placed and pre-treated with Poly-D-Lysine, and the cells were tested after being attached to the walls. The culture time of cells for electrophysiology use was no more than 48 hours.

Drug concentration setting: the final drug concentration used in drug screening was 100 nM, and the GABA concentration range was 0.05 μM. The final drug concentrations used in the dose-inversal agonistic efficiency (%) test were 0.3 nM, 3 nM, 10 nM, 30 nM, 100 nM and 300 nM. The whole cell patch clamp technique was used in electrophysiological experiments, which could refer to the literature (I. Lecker, Y. Yin, D. S. Wang and B. A. Orser, (2013) Potentiation of GABAA receptor activity by volatile anaesthetics is reduced by α5-GABAA receptor-preferring inverse agonists, British Journal of Anaesthesia 110 (S1): i73-i81). The components of extracellular solution (ECS) for electrophysiology use were as follows: 150 mM NaCl, 5 mM KCl, 2.5 mM $CaCl_2$), 1 mM $MgCl_2$, 10 mM HEPES and 10 mM glucose (pH 7.4); electrode internal solutions for electrophysiology use were as follows: 140 mM CsCl, 11 mM EGTA, 10 mM HEPES, 2 mM $CaCl_2$), 1 mM $MgCl_2$, 4 mM MgATP, 2 mM TEA (pH 7.3). The signal acquisition used an EPC-10 amplifier and the PatchMaster software (HEKA). The recording electrode was drawn using borosilicate glass, and the electrode resistance was 4 to 6 MΩ. The ALA-VC3-8PP™ system was used for extracellular administration. Separate cells that grew independently was selected for recording. During recording, the cell membrane potential was clamped at −60 mV. During experiment, an extracellular solution was applied to the cells for about 20 seconds. When the baseline reached to a stable state, the extracellular solution was switched to GABA. Then the current induced by GABA could be detected. After about 20 to 40 seconds, after the current was stable, extracellular solution was switched to a corresponding drug solution to detect the effect of the drug. At last, the solution was switched to extracellular solution, and the test was terminated when the baseline returned to the level before administration. Only data with a baseline of less than −120 pA that could be recovered after administration would be analyzed subsequently. GABA was diluted at a final concentration of 0.05 μM in extracellular solution. Then, drugs were diluted at the desired concentration in GABA-containing extracellular solution.

The experimental results were analyzed with the PatchMaster software. During the analysis, the leakage currents ($I_{leak}$), the GABA currents before ($I_{pre}$) and after ($I_{post}$) administration were recorded respectively. The effects of drugs were calculated by the following equation: inverse agonism efficacy (%)=100−100*($I_{post}$−$I_{leak}$)/($I_{pre}$−$I_{leak}$).

The screening results of the compounds are shown in Table 1.

TABLE 1

| Embodiment | Compound inverse agonist efficacy % |
|---|---|
| 1 | 41.9 |
| 2 | 26.6 |
| 3 | 37.1 |
| 4 | 40.8 |
| 5 | 31.5 |
| 6 | 42.2 |
| 7 | 30.1 |
| 8 | 57.8 |
| 9 | 40.6 |
| 10 | 37.1 |
| 11 | 35.4 |
| 12 | 29.6 |
| 13 | 29.0 |
| 14 | 19.4 |
| 15 | 45.8 |
| 16 | 31.1 |
| 17 | 47.7 |
| 18 | 23.0 |
| 19 | 35.4 |
| 20 | 42.9 |
| 21 | 36.3 |
| 22 | 22.1 |
| 23 | 41.2 |
| 24 | 35.0 |
| 25 | 34.1 |
| 26 | 41.7 |
| 27 | 42.0 |
| 28 | 35.4 |
| 29 | 66.9 |
| 30 | 29.4 |
| 31 | 34.1 |
| 32 | 41.6 |
| 33 | 40.4 |
| 34 | 38.0 |
| 35 | 39.3 |

TABLE 1-continued

| Embodiment | Compound inverse agonist efficacy % |
|---|---|
| 36 | 25.9 |
| 37 | 42.1 |
| 38 | 32.0 |
| 39 | 36.5 |
| 40 | 39.0 |
| 41 | 39.4 |
| 42 | 44.9 |
| 43 | 44.2 |
| 44 | 44.8 |
| 45 | 42.4 |
| 46 | 48.7 |
| 47 | 45.2 |
| 48 | 34.7 |
| 49 | 37.2 |
| 50 | 38.8 |
| 51 | 46.2 |
| 52 | 38.0 |
| 53 | 48.8 |
| 54 | 43.5 |
| 55 | 25.1 |
| 56 | 21.6 |
| 57 | 17.6 |
| 58 | 38.5 |
| 59 | 35.7 |
| 60 | 45.8 |
| 61 | 45.8 |
| 62 | 35.7 |
| 63 | 24.2 |
| 64 | 40.0 |
| 65 | 55.4 |
| 66 | 62.0 |
| 67 | 58.0 |
| 68 | 51.3 |
| 69 | 50.0 |
| 70 | 31.7 |
| 71 | 40.7 |
| 72 | 54.3 |
| 73 | 34.5 |
| 74 | 40.4 |
| 75 | 44.3 |
| 76 | 41.6 |
| 77 | 44.8 |
| 78 | 43.4 |
| 79 | 47.6 |
| 80 | 47.2 |
| 81 | 45.9 |
| 82 | 47.9 |
| 83 | 39.9 |
| 84 | 39.6 |
| 85 | 57.3 |
| 86 | 41.8 |
| 87 | 39.7 |
| 88 | 32.5 |
| 89 | 47.2 |
| 90 | 64.9 |
| 91 | 47.8 |
| 92 | 52.8 |
| 93 | 36.5 |
| 94 | 32.9 |
| 95 | 48.1 |
| 96 | 38.8 |
| 97 | 32.6 |
| 98 | 38.0 |
| 99 | 33.7 |
| 100 | 35.3 |
| 101 | 32.9 |
| 102 | 47.3 |
| 103 | 43.9 |
| 104 | 48.2 |
| 105 | 49.3 |
| 106 | 60.4 |
| 107 | 39.3 |
| 108 | 54.9 |
| 109 | 47.3 |
| 110 | 58.6 |

TABLE 1-continued

| Embodiment | Compound inverse agonist efficacy % |
|---|---|
| 111 | 59.6 |
| 112 | 52.4 |
| 113 | 36.7 |
| 114 | 36.0 |
| 115 | 32.9 |
| 116 | 44.9 |
| 117 | 32.3 |
| 118 | 63.7 |
| 119 | 35.9 |
| 120 | 42.6 |
| 121 | 37.4 |
| 122 | 31.9 |
| 123 | 36.7 |
| 124 | 43.9 |
| 125 | 41.8 |
| 126 | 38.3 |
| 127 | 41.8 |
| 128 | 41.2 |
| 129 | 45.8 |
| 130 | 39.9 |
| 131 | 52.2 |
| 132 | 57.3 |
| 133 | 36.9 |
| 134 | 30.4 |
| 135 | 39.5 |
| 136 | 37.3 |
| 137 | 47.2 |
| 138 | 42.9 |
| 139 | 49.0 |
| 140 | 49.3 |
| 141 | 40.6 |
| 142 | 50.2 |
| 143 | 49.6 |
| 144 | 42.0 |
| 145 | 51.3 |
| 146 | 33.4 |
| 147 | 39.8 |
| 148 | 69.6 |
| 149 | 71.7 |
| 150 | 46.2 |
| 151 | 55.8 |
| 152 | 39.3 |
| 153 | 49.4 |
| 154 | 45.2 |
| 155 | 50.1 |
| 156 | 40.5 |
| 157 | 46.8 |
| 158 | 53.1 |
| 159 | 50.4 |
| 160 | 49.3 |
| 161 | 53.1 |
| 162 | 36.6 |
| 163 | 45.2 |
| 164 | 33.9 |
| 165 | 49.8 |
| 166 | 49.9 |
| 167 | 42.5 |
| 168 | 37.5 |
| 169 | 40.7 |
| 170 | 32.9 |
| 171 | 53.1 |
| 172 | 47.6 |
| 173 | 58.8 |
| 174 | 43.5 |
| 175 | 36.0 |
| 176 | 50.1 |
| 177 | 56.5 |
| 178 | 36.7 |
| 179 | 39.0 |
| 180 | 65.4 |
| 181 | 59 |
| 182 | 53.8 |
| 183 | 55.8 |
| 184 | 33.9 |
| 185 | 45.6 |

TABLE 1-continued

| Embodiment | Compound inverse agonist efficacy % |
|---|---|
| 186 | 56 |
| 187 | 50.4 |
| 188 | 52.4 |
| 189 | 52.4 |
| 190 | 38.3 |
| 191 | 44 |
| 192 | 40.8 |
| 193 | 32.6 |
| 194 | 41.5 |
| 195 | 45.8 |
| 196 | 50.8 |
| 198 | 55.9 |
| 199 | 56.8 |
| 200 | 37.4 |
| 201 | 48.3 |
| 202 | 57.4 |
| 203 | 63.6 |
| 204 | 49.7 |
| 205 | 52.5 |
| 206 | 44.7 |
| 207 | 49.3 |
| 208 | 52.2 |
| 209 | 48.8 |
| 210 | 43.4 |
| 211 | 64.7 |
| 212 | 72.6 |
| 213 | 59.5 |
| 214 | 34.9 |
| 215 | 36.8 |
| 216 | 52.1 |
| 217 | 45.6 |
| 220 | 51.8 |
| 222 | 44.3 |
| 224 | 46.7 |
| 225 | 74.4 |
| 226 | 45.9 |
| 227 | 61.5 |
| 228 | 44.7 |
| 229 | 30.8 |
| 230 | 57.2 |
| 231 | 40.3 |
| 232 | 53.4 |
| 233 | 41.3 |
| 234 | 53.2 |
| 235 | 43.5 |
| 236 | 54.8 |
| 237 | 57.9 |
| 239 | 48 |
| 241 | 51.3 |
| 242 | 54.7 |
| 243 | 50.5 |
| 244 | 75.1 |
| 246 | 46.6 |
| 247 | 60.4 |
| 248 | 31.4 |
| 249 | 51.2 |
| 250 | 47.4 |
| 252 | 42.2 |
| 253 | 56.1 |
| 254 | 39 |
| 255 | 45.4 |
| 256 | 40.2 |
| 257 | 50 |
| 258 | 54.7 |

Effect Embodiment 2 Solubility of the Compounds

Experimental Materials and Instrument 50 mM phosphate buffer solution pH=7.4:0.39 g of $NaH_2PO_4·2H_2O$, and 1.4025 g of $Na_2HPO_4$ were weighted and placed in an erlenmeyer flask, then 240 mL of water was added thereto. The solid was dissolved and mixed thoroughly, and the pH value was adjusted to 7.4 with 10M NaOH solution, and the resulting solution was transferred to a 250 mL volumetric flask, followed by dilution to scale with water.

Simulated intestinal fluid FaSSIF: 54.76 mg of FaSSIF-V2 (Biorelevant, batch. V2FAS-0619-A, lot. V2FAS01) was weighed and added to 15 mL of a buffer solution. After dissolving, the solution was supplemented to 30 mL, and put at room temperature for 1 hour before use.

Waters e2695 HPLC high performance liquid chromatography, Mettler XSE105 analytical balance.

Experimental Method

Firstly, a 10 mM stock solution was prepared with DMSO, and was diluted with a diluent (ACN: PB buffer 50:50) into 1 μM-200 μM as a standard solution.

Thermodynamic solubility in intestinal fluid (TS in FaSSIF) was simulated. About 0.3 mg of each sample was weighed and added to 1.5 mL of FaSSIF solution, with two parts in parallel, shaken at 1000 rpm at 37° C. for 4 hours, filtered. 1 mL of an initial filtrate was discarded, and 400 μL of the subsequent filtrate was taken. The filtrate was detected by high performance liquid chromatograph (UV). The test results of the compounds of the present disclosure are shown in Table 2 below.

TABLE 2

| Compound No. | Thermodynamic solubility μg/mL |
|---|---|
| 1 | 146.30 |
| 6 | 46.90 |
| 7 | 37.79 |
| 9 | 60.30 |
| 19 | 49.20 |
| 21 | 519.10 |
| 28 | 55.20 |
| 31 | 43.80 |
| 32 | 262.40 |
| 33 | 32.30 |
| 36 | 122.70 |
| 39 | 180.30 |
| 43 | 48.70 |
| 47 | 40.40 |
| 49 | 142.60 |
| 50 | 83.00 |
| 55 | 38.00 |
| 63 | 306.90 |
| 66 | 145.60 |
| 68 | 145.70 |
| 75 | 52.40 |
| 78 | 254.90 |
| 80 | 195.20 |
| 84 | 197.00 |
| 85 | 53.90 |
| 88 | 60.30 |
| 90 | 84.90 |
| 99 | 222.40 |
| 100 | 70.00 |
| 102 | 30.80 |
| 103 | 322.20 |
| 107 | 212.50 |
| 109 | 54.00 |
| 110 | 46.60 |
| 112 | 317.90 |
| 113 | 191.10 |
| 114 | 138.80 |
| 115 | 137.00 |
| 122 | 48.39 |
| 124 | 365.41 |
| 126 | 202.90 |
| 127 | 223.40 |
| 128 | 118.10 |

TABLE 2-continued

| Compound No. | Thermodynamic solubility µg/mL |
|---|---|
| 129 | 85.40 |
| 130 | 30.90 |
| 135 | 35.40 |
| 141 | 63.90 |
| 150 | 262.96 |
| 151 | 174.98 |
| 152 | 43.98 |
| 153 | 189.08 |
| 154 | 177.01 |
| 156 | 73.80 |
| 158 | 38.17 |
| 160 | 245.82 |
| 162 | 236.53 |
| 163 | 179.45 |
| 164 | 309.04 |
| 166 | 300.01 |
| 167 | 407.92 |
| 168 | 59.90 |
| 169 | 306.36 |
| 170 | 66.14 |
| 173 | 32.78 |
| 174 | 35.43 |
| 179 | 44.90 |
| 180 | 146.30 |
| 185 | 238.90 |
| 186 | 95.40 |
| 187 | 176.11 |
| 189 | 75.81 |
| 193 | 200.00 |
| 198 | 204.03 |
| 200 | 228.50 |
| 202 | 32.57 |
| 203 | 264.44 |
| 206 | 34.75 |
| 208 | 33.97 |
| 210 | 47.00 |
| 213 | 30.17 |
| 214 | 236.89 |
| 216 | 167.06 |
| 217 | 57.57 |
| 231 | 30.55 |
| 232 | 58.97 |
| 233 | 244.78 |
| 234 | 265.62 |
| 240 | 43.50 |
| 241 | 91.76 |
| 247 | 32.73 |
| 253 | 38.88 |

Thermodynamic solubility in phosphate buffer solution (TS in PBS). 1 mg of the sample was weighed, and 1.5 mL of 50 mM phosphate buffer solution (pH 7.4) was added thereto, then the mixture was shaken at room temperature for 24 hours to ensure that the sample was saturated, and filtered. The filtrate was detected with the high performance liquid chromatograph (UV). The compounds of the present disclosure and comparative compounds are tested by this method, and the results are shown in Table 3 below:

TABLE 3

| Compound No. | Thermo-dynamic solubility µg/ mL | Comparative compound | Thermo-dynamic solubility µg/mL |
|---|---|---|---|
| 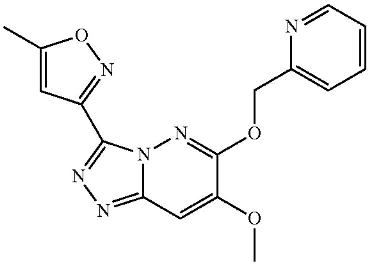 Embodiment 33 | 20.1 | 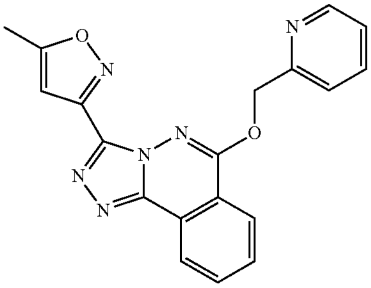 α5IA-II | 0.3 |
| | | 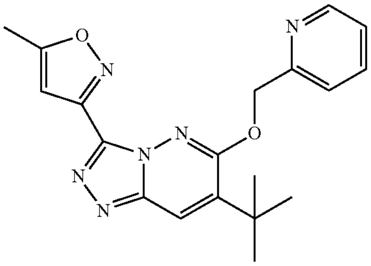 [SMILES: Cc1cc(-c2nnc3cc(C(C)(C)C)c(OCc4ccccn4)nn23)no1] | 2.6 |

TABLE 3-continued

| Compound No. | Thermo-dynamic solubility μg/ mL | Comparative compound | Thermo-dynamic solubility μg/mL |
|---|---|---|---|
| 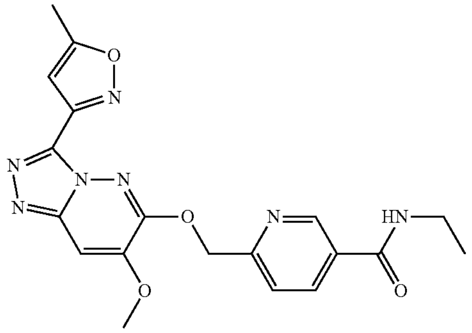 Embodiment 35 | 14.2 | 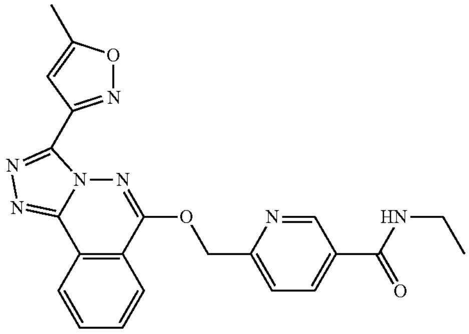 Compound 07 in CN106854207A | 0.8 |
| | | 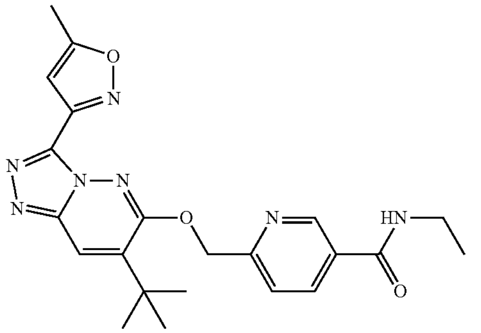 Compound 42 in CN107344936A | 2.5 |

Conclusion: Compared with a triazolophthalazine mother nucleus and a 7-tert-butyltriazolopyridazine mother nucleus, the thermodynamic solubility of the compound of the present disclosure is greatly increased, which can significantly reduce the difficulty of formulation development in preclinical and clinical studies, and improve oral bioavailability.

Effect embodiment 3 Rat liver microsome stability (RLM) experiment

Experimental Materials

Rat liver microsomes (Xenotech, item No. R1000, lot No. 1310030), 100 mM potassium phosphate buffer solution (pH 7.4), 10 mM magnesium chloride.

Compound preparation: 5 μL of compound DMSO mother liquor (10 mM) was added to 495 μL of methanol to obtain an intermediate solution with a compound concentration of 100 μM. Then 50 μL of the intermediate solution was taken and dissolved in 450 μL of potassium phosphate buffer solution to obtain a test solution with a final concentration of 10 μM.

NADPH regeneration system (concentration of isocitrate dehydrogenase 1 unit/mL).

Liver microsomes (final concentration 0.5 mg protein/mL).

Reaction termination solution: cold acetonitrile containing 100 ng/mL Tolbutamide and 100 ng/mL Labetalol as an internal standard.

Experimental Method (1) Preparation of buffer solution:

Buffer solution A: 1.0 L of 0.1 M potassium phosphate buffer solution containing 1.0 mM EDTA Buffer solution B: 1.0 L of 0.1 M dipotassium phosphate buffer solution containing 1.0 mM EDTA Buffer solution C: 0.1 M potassium phosphate buffer, 1.0 mM EDTA, pH 7.4, titrated with 700 mL of buffer solution B and buffer solution A, monitored by pH meter.

(2) Preparation of reference substance (ketanserin) and concentration of administration solution of the test substance:

5000 administration solution: 10 μ0 10 mM DMSO reference substance stock solution and test substance stock solution were added to 190 μL of ACN, respectively. 1.5 μM administration solution (containing 0.75 mg/mL liver microsomes): 1.5 g/mL μM administration solution and 18.75 μL of 20 mg/mL liver microsomes were added to 479.75 μL of buffer C on a wet ice.

(3) NADPH was added to buffer solution C to obtain a NADPH stock solution (6 mM).

(4) 30 μL of 1.5 μM administration solution (containing 0.75 mg/mL of liver microsomes) was taken on the wet ice and added to the wells of the test plate at different time points (0-, 5-, 15-, 30-, 45-min), respectively.

(5) Firstly, 135 μL of ACN containing IS was added to the wells of a 0 min test plate, and then 15 μL of the NADPH stock solution (6 mM) was added.

(6) The test plate at other time points and the NADPH stock solution were pre-heated in a 37° C. water bath for 5 minutes.

(7) 15 μL of the NADPH stock solution (6 mM) was taken and added to a pre-incubated test plate, and the reaction was started and timed.

(8) At 5 min, 15 min, 30 min and 45 min, 135 μL of CAN containing IS was added to the corresponding test plate respectively, and the test was completed.

(9) Test plates were shaken with a shaker (IKA, MTS 2/4) for 10 min (600 rpm/min) and then centrifuged for 15 min (Thermo Multifuge×3R, 5594 g).

(10) 50 μL of supernatant from each well was added to a 96-well sample plate containing 50 μL of ultrapure water (Millipore, ZMQS50F01), and the samples were analyzed by LC/MS.

The rat liver microsomal stability data for the compounds of the present disclosure are shown in Table 4 below:

TABLE 4

| Compound No. | RLM μL/min/mg |
|---|---|
| 84 | 0 |
| 128 | 6 |

TABLE 4-continued

| Compound No. | RLM μL/min/mg |
|---|---|
| 129 | 14 |
| 151 | 1 |
| 152 | 23 |
| 153 | 5 |
| 154 | 1 |
| 160 | 6 |
| 166 | 0 |
| 183 | 5 |
| 185 | 9 |
| 186 | 22 |
| 187 | 15 |
| 211 | 5 |
| 213 | 10 |
| 253 | 10 |

The rat liver microsomal stability data for the compounds of the present disclosure and the comparative compounds are shown in Table 5 below.

TABLE 5

| Compound No. | RLM μL/min/mg | Comparative compound | RLM μL/min/mg |
|---|---|---|---|
| 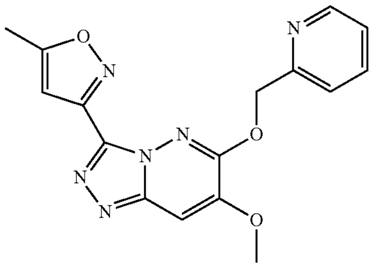 33 | 0.3 | 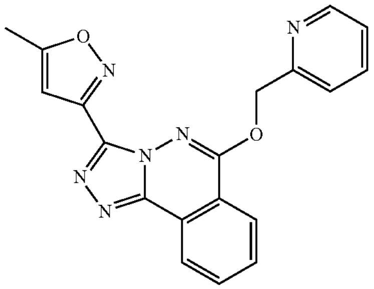 α5IA-II | 28.2 |
| | | 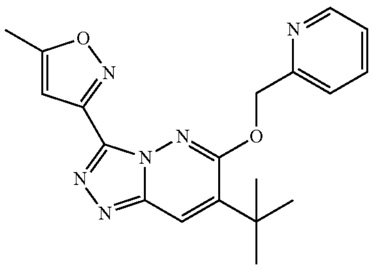 [SMILES: Cc1cc(-c2nnc3cc(C(C)(C)C)c(OCc4ccccn4)nn23)no1] | 33.6 |

TABLE 5-continued

| Compound No. | RLM µL/min/mg | Comparative compound | RLM µL/min/mg |
|---|---|---|---|
| 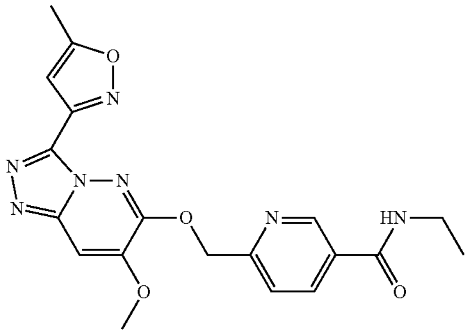 35 | 11.4 | 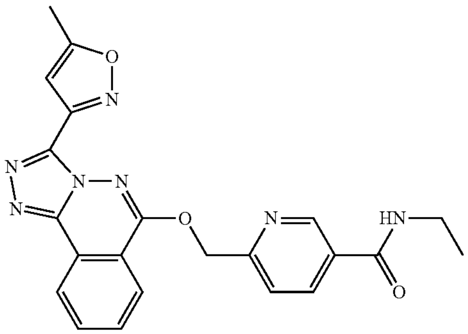 Compound 07 in CN106854207A | 26 |
| | | 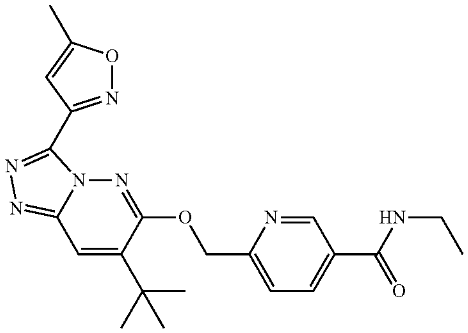 Compound 42 in CN107344936A | 142.6 |

Conclusion: Compared with a triazolophthalazine mother nucleus and a 7-tert-butyltriazolopyridazine mother nucleus, the compounds of the present disclosure have better rat liver microsomal stability, can significantly reduce the clearance rate in vivo and improve oral bioavailability.

Effect Embodiment 4 Pharmacokinetic Experiment on Rats

In the pharmacokinetic experiment on rats, the maximum plasma drug concentration ($C_{max}$) was used to evaluate the absorption of the compounds in rats. All rats fasted overnight before administration; the test compounds were dissolved and administered orally (po) to male SD rats, with 3 rats in each group. After administration of the test compounds, blood was collected by jugular vein puncture at 0.25, 0.5, 1.2, and 4.8 hours with about 0.25 mL per sample. The plasma drug concentration was determined by LC-MS/MS method, and the pharmacokinetic parameters were calculated by Phoenix WinNonlin7.0. The dosage was 10 mg/kg, and the vehicle was 5% CMC-Na aqueous solution.

The drug concentration ratio of plasma and brain tissue in the pharmacokinetic experiment on rats was used to evaluate the entry of compounds into brain. All rats fasted overnight before administration; the test compounds were dissolved and administered orally (po) to male SD rats, with 3 rats in each group. After administration of the test compounds, blood was collected by jugular vein puncture at 0.5 hours with about 0.25 mL per sample. The whole brain was taken at the same time. The plasma and brain tissue drug concentration were determined by LC-MS/MS method, and the pharmacokinetic parameters were calculated by Phoenix WinNonlin7.0. The dosage was 10 mg/kg, and the vehicle was 5% CMC-Na aqueous solution. Table 6 below shows the maximum plasma drug concentration and brain entry ratios (brain tissue/plasma concentration ratios) of the compounds of the present disclosure and comparative compounds.

TABLE 6

| Compound No. | 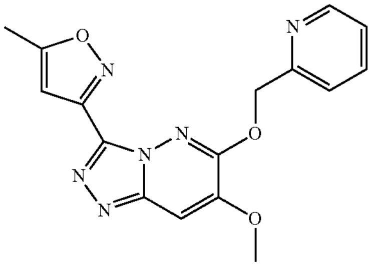 33 | 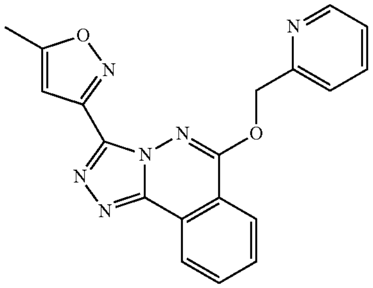 α5IA-II |
|---|---|---|
| Maximum plasma drug concentration | 1778 ng/mL | 25.7 ng/ mL |
| Brain entry ratio | 7% | 151% |

| | Compound No. | 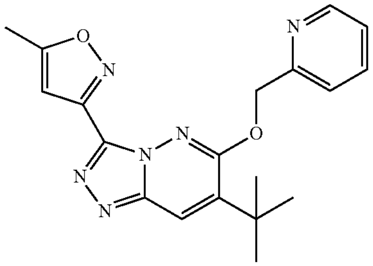 [SMILES: Cc1cc(-c2nnc3cc(C(C)(C)C)c(OCc4ccccn4)nn23)no1] |
|---|---|---|
| | Maximum plasma drug concentration | 216 ng/mL |
| | Brain entry ratio | 65.1% |

Conclusion: Compared with a triazolophthalazine mother nucleus and a 7-tert-butyltriazolopyridazine mother nucleus, the compounds of the present disclosure has better absorption and is more conducive to drug formation. Moreover, the compounds of the present disclosure have lower brain entry ratio and fewer central nervous system (CNS) side effects.

Data on the brain entry ratio (ratio of brain tissue/plasma concentration) in rats for the compounds of the present disclosure are shown in Table 7 below.

TABLE 7

| Compound No. | Brain entry ratio |
|---|---|
| 84 | 0.45% |
| 128 | 3.2% |
| 129 | 4.7% |
| 151 | 2% |
| 152 | 2.43% |
| 153 | 2% |
| 154 | 2.57% |
| 160 | 4.41% |
| 166 | 1% |
| 183 | 1.83% |
| 185 | 0 |
| 186 | 4.42% |
| 187 | 2.93% |
| 211 | 1.8% |

TABLE 7-continued

| Compound No. | Brain entry ratio |
|---|---|
| 213 | 1.79% |
| 253 | 1.33% |

Although the specific embodiments of the present disclosure have been described above, those skilled in the art should understand that these are only embodiments, various changes or modifications can be made to these embodiments without departing from the principle and essence of the present disclosure. Therefore, the protection scope of the present disclosure is defined by the appended claims.

Biological Experiment Method:

Previous studies have revealed that the $GABA_A$ receptors mediate at least two modes of inhibition, the phasic inhibition and the tonic inhibition. When the GABA increases to the millimole level, the $GABA_A$ receptors will be desensitized rapidly, show low affinity for GABA and form phasic inhibition. When the GABA activates $GABA_A$ receptors at several hundred nanomolar to several tens of micromolar level, the high affinity extrasynaptic $GABA_A$ receptors will mediate tonic inhibition and regulate neuronal excitability and signal transmission. (Farrant M et al. (2005) Variations on an inhibitory theme: phasic and tonic activation of GABA(A) receptors. Nat Rev Neurosci 6:215-229Y). Yeung J Y et al disclose that low concentrations of GABA are more likely to activate the α5-$GABA_A$ receptor (Yeung J Y et al (2003). Tonically activated $GABA_A$ receptors in hippocampal neurons are high-affinity, low-conductance sensors for extracellular GABA. Mol Pharmacol; 63:2-8). K. Y LEE et al reported that low concentrations of GABA-activated, sustained high affinity $GABA_A$ currents were detected on isolated DRG cells cultured for 24 hours, 20 μM GABA-activated high affinity GABAA current was up to about 100 pA/pF. (Lee K Y et al. Upregulation of high-affinity GABA (A) receptors in cultured rat dorsal root ganglion neurons. Neuroscience 208 (2012) 133-142). In 2013, I. Lecker et al reported that L-655,708, an α5-$GABA_A$ receptor inverse agonist, dose-dependently inhibited the current included by low concentrations of

The invention claimed is:

1. A compound represented by formula I:

I

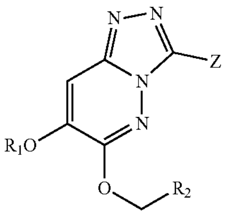

or a pharmaceutically acceptable salt or stereoisomer thereof, wherein:

$R_1$ is H, $C_{1-6}$ alkyl, $C_{1-6}$ alkylene-$OC_{1-6}$ alkyl, $C_{1-6}$ alkylene-$C_{3-6}$ cycloalkyl, $C_{3-6}$ cycloalkyl, or $C_{3-7}$ heterocycloalkyl;

wherein any $C_{1-6}$ alkyl, $C_{1-6}$ alkylene, and $OC_{1-6}$ alkyl is optionally and independently substituted by one, two, three, or four substituents independently selected from the group consisting of halogen, CN, $NHC_{1-6}$ alkyl, OH, and $OC_{1-6}$ alkyl; and wherein any $C_{3-6}$ cycloalkyl and $C_{3-7}$ heterocycloalkyl is optionally and independently substituted by one, two, three, or four substituents independently selected from the group consisting of halogen, CN, $C_{1-6}$ alkyl, $NHC_{1-6}$ alkyl, OH, and $OC_{1-6}$ alkyl;

$R_2$ is heterocyclyl, phenyl, or heteroaryl;

wherein the heterocyclyl, phenyl, or heteroaryl is optionally substituted by one, two, three, or four substituents independently selected from the group consisting of halogen, CN, $C_{1-6}$ alkyl, $C_{2-6}$ alkenyl, C(O)R, $C(O)NR_4R_5$, C(O)OH, $NHC_{2-6}$ alkenyl, $NH(C_{3-6}$ cycloalkenyl), NH(heterocyclyl), NH(aryl), NH(heteroaryl), $NR_4R_5$, OR, =O, $S(O)_2C_{1-6}$ alkyl, $S(O)_2NR_6R_7$, $C_{3-6}$ cycloalkyl, $C_{3-6}$ cycloalkenyl, heterocyclyl, aryl, and heteroaryl; and wherein any $C_{1-6}$ alkyl, $C_{2-6}$ alkenyl, $C_{3-6}$ cycloalkyl, $C_{3-6}$ cycloalkenyl, heterocyclyl, aryl, and heteroaryl substituent is optionally and independently substituted by one, two, or three independently selected R' substituents;

each $R_4$ is independently H, $C_{1-6}$ alkyl, or $C_{3-6}$ cycloalkyl;

wherein each $C_{1-6}$ alkyl is optionally and independently substituted by one, two, three, four, or five substituents independently selected from the group consisting of halogen, $NH_2$, OH, and $OC_{1-6}$ alkyl; and wherein each $C_{3-6}$ cycloalkyl is optionally and independently substituted by one, two, three, four, or five substituents independently selected from the group consisting of halogen, $C_{1-6}$ alkyl, $NH_2$, OH, and $OC_{1-6}$ alkyl:

each $R_5$ is independently H, $C_{1-6}$ alkyl, or $C_{3-6}$ cycloalkyl;

wherein each $C_{1-6}$ alkyl is optionally and independently substituted by one, two, three, four, or five substituents independently selected from the group consisting of halogen, $NH_2$, OH, and $OC_{1-6}$ alkyl; and wherein each $C_{3-6}$ cycloalkyl is optionally and independently substituted by one, two, three, four, or five substituents independently selected from the group consisting of halogen, $C_{1-6}$ alkyl, $NH_2$, OH, and $OC_{1-6}$ alkyl; or any $R_4$ and $R_5$, together with the nitrogen heteroatom to which they are attached, independently forms a 5- or 6-membered heterocycloalkyl, wherein each 5- or 6-membered heterocycloalkyl optionally and independently contains 1 or 2 additional heteroatoms independently selected from the group consisting of nitrogen, oxygen, and sulfur;

each $R_6$ is independently $C_{1-6}$ alkyl;

each $R_7$ is independently $C_{1-6}$ alkyl;

each R is independently H, $C_{1-6}$ alkyl, $C_{2-6}$ alkenyl, $C_{3-6}$ cycloalkyl, $C_{3-6}$ cycloalkenyl, heterocyclyl, aryl, or heteroaryl;

wherein each $C_{1-6}$ alkyl and $C_{2-6}$ alkenyl is optionally and independently substituted by one, two, or three substituents independently selected from the group consisting of halogen, CN, $NHC_{1-6}$ alkyl, $C(O)R'^{-2}$, $C(O)NR_8R_9$, OH, $OC_{1-6}$ alkyl, $S(O)_2R_{10}$, $C_{3-6}$ cycloalkyl, heterocyclyl, substituted 3- to 9-membered heterocyclyl, $C_{6-18}$ aryl, heteroaryl, and substituted 5- to 10-membered heteroaryl;

wherein each $C_{3-6}$ cycloalkyl substituent is optionally and independently substituted by one, two, or three CN substituents;

wherein each substituted 3- to 9-membered heterocyclyl substituent is independently substituted by one, two, or three independently selected $R'^{-3}$ substituents;

wherein each substituted 5- to 10-membered heteroaryl substituent is independently substituted by one, two, or three independently selected $R'^{-1}$ substituents; and wherein each $C_{3-6}$ cycloalkyl, $C_{3-6}$ cycloalkenyl, heterocyclyl, aryl, and heteroaryl is optionally and independently substituted by one, two, or three independently selected R' substituents:

each R' is independently halogen, CN, $C_{1-6}$ alkyl, $C_{1-3}$ haloalkyl, $C_{1-3}$ cyanoalkyl, $NHC_{1-6}$ alkyl, $C(O)R'^{-2}$, $C(O)NR_8R_9$, OH, $OC_{1-6}$ alkyl, $S(O)_2R_{10}$, $C_{3-6}$ cycloalkyl, heterocyclyl, substituted 3- to 9-membered heterocyclyl, $C_{6-18}$ aryl, heteroaryl, or substituted 5- to 10-membered heteroaryl;

wherein each $C_{3-6}$ cycloalkyl is optionally substituted by one, two, or three CN substituents;

wherein each substituted 3- to 9-membered heterocyclyl is independently substituted by one, two, or three independently selected $R'^{-3}$ substituents; and wherein each substituted 5- to 10-membered heteroaryl is independently substituted by one, two, or three independently selected $R'^{-1}$ substituents;

each $R_8$ is independently H or $C_{1-6}$ alkyl;

each $R_9$ is independently H or $C_{1-6}$ alkyl; or any $R_8$ and $R_9$, together with the nitrogen heteroatom to which they are attached, independently forms a 5- or 6-membered heterocyclyl, wherein each 5- or 6-membered heterocyclyl optionally and independently contains 1 or 2 additional heteroatoms independently selected from the group consisting of nitrogen, oxygen, and sulfur;

each $R_{10}$ is independently $C_{1-6}$ alkyl;

each $R'^{-1}$ is independently $C_{1-6}$ alkyl;

each $R'^{-2}$ is independently $C_{1-6}$ alkyl or $C_{3-6}$ cycloalkyl;

each $R'^{-3}$ is independently $C_{1-6}$ alkyl;

Z is a 5- or 6-membered heteroaryl;

wherein the 5- or 6-membered heteroaryl contains 1, 2, or 3 heteroatoms independently selected from the group consisting of nitrogen, oxygen, and sulfur; and wherein the 5- or 6-membered heteroaryl is optionally substituted by one or more independently selected $R_3$ substituents; and each $R^3$ is independently halogen, CN, $C_{1-6}$ alkyl, $C_{1-6}$ alkylene-$OC_{1-6}$ alkyl, $C_{1-6}$ alkylene-$OC_{1-6}$ alkylene-$C_{3-6}$ cycloalkyl, $C_{1-6}$ alkylene-$C_{3-7}$ heterocycloalkyl, $OC_{1-6}$ alkylene-$C_{3-6}$ cycloalkyl, or $C_{3-7}$ heterocycloalkyl;

wherein any $C_{1-6}$ alkyl, $C_{1-6}$ alkylene, $OC_{1-6}$ alkylene, and $OC_{1-6}$ alkyl is optionally and independently substituted by one, two, three, or four substituents independently selected from the group consisting of halogen, CN, $NHC_{1-6}$ alkyl, and OH; and wherein any $C_{3-6}$ cycloalkyl and $C_{3-7}$ heterocycloalkyl is optionally and independently substituted by one, two, three, or four substituents independently selected from the group consisting of halogen, CN, $C_{1-6}$ alkyl, $NHC_{1-6}$ alkyl, and OH.

2. The compound as claimed in claim 1, or a pharmaceutically acceptable salt or stereomer thereof, wherein, $R_2$ is heterocyclyl, phenyl or heteroaryl;

wherein heterocyclyl, phenyl or heteroaryl is optionally substituted by one, two, three, or four substituents independently selected from the group consisting of halogen, CN, $C_{1-6}$ alkyl, $C_{2-6}$ alkenyl, —C(O)R, —$C(O)NR_4R_5$, —C(O)OH, $NHC_{2-6}$ alkenyl, $NH(C_{3-6}$ cycloalkenyl), NH(heterocyclyl), NH(aryl), NH(heteroaryl), —$NR_4R_5$, —OR, =O, —$S(O)_2C_{1-6}$ alkyl, —$S(O)_2NR_6R_7$, $C_{3-6}$ cycloalkyl, $C_{3-6}$ cycloalkenyl, heterocyclyl, aryl and heteroaryl; and wherein any $C_{1-6}$ alkyl, $C_{2-6}$ alkenyl, $C_{3-6}$ cycloalkyl, $C_{3-6}$ cycloalkenyl, heterocyclyl, aryl, and heteroaryl substituent is optionally and independently substituted by one by one, two, or three independently selected R' substituents;

each $R_4$ is independently H or $C_{1-6}$ alkyl; wherein each $C_{1-6}$ alkyl is optionally and independently substituted by one, two, three, four, or five substituents independently selected from the the group consisting of halogen, $NH_2$, OH, and $OC_{1-6}$ alkyl;

each $R_5$ is independently H or $C_{1-6}$ alkyl; wherein each $C_{1-6}$ alkyl is optionally and independently substituted by one, two, three, four, or five substituents independently selected from the the group consisting of halogen, $NH_2$, OH, and $OC_{1-6}$ alkyl; and each R is independently H, $C_{1-6}$ alkyl, $C_{2-6}$ alkenyl, $C_{3-6}$ cycloalkyl, heterocyclyl, aryl or heteroaryl;

wherein each $C_{1-6}$ alkyl and $C_{2-6}$ alkenyl is optionally and independently substituted by one, two, or three substituents independently selected from the group consisting of halogen, CN, $NHC_{1-6}$ alkyl, OH, $OC_{1-6}$ alkyl, —$SO_2R_{10}$, $C_{3-6}$ cycloalkyl, heterocyclyl and heteroaryl; and wherein each $C_{3-6}$ cycloalkyl, heterocyclyl, aryl, or heteroaryil is optionally and independently substituted by one, two, or three independently selected R' substituents; and each R' is independently halogen, CN, $C_{1-6}$ alkyl, $C_{1-3}$ haloalkyl, $C_{1-3}$ cyanoalkyl, $NHC_{1-6}$ alkyl, OH, $OC_{1-6}$ alkyl, $S(O)_2R_{10}$, $C_{3-6}$ cycloalkyl, heterocyclyl, substituted 3- to 6-membered heterocyclyl, heteroaryl, or substituted 5- to 10-membered heteroaryl;

wherein each substituted 3- to 6-membered heterocyclyl is substituted by one, two, or three independently selected $R'^{-3}$ substituents; and wherein each substituted 5- to 10-membered heteroaryl is independently substituted by one, two, or three independently selected $R'^{-1}$ substituents.

3. The compound represented as claimed in claim 2, or a pharmaceutically acceptable salt or stereomer thereof, wherein, $R_1$ is H, $C_{1-6}$ alkyl, $C_{1-6}$ alkylene-$OC_{1-6}$ alkyl, $C_{1-3}$ alkylene-$C_{3-6}$cycloalkyl, $C_{3-6}$ cycloalkyl, or $C_{3-7}$ heterocycloalkyl;

wherein any $C_{1-6}$ alkyl, $C_1$-3 alkylene, $C_{1-6}$ alkylene, and $OC_{1-6}$ alkyl is optionally and independently substituted by one, two, three, or four substituents independently selected from the group consisting of halogen, CN, $NHC_{1-6}$ alkyl, OH, and $OC_{1-6}$ alkyl; and wherein any $C_{3-6}$ cycloalkyl and $C_{3-7}$ heterocycloalkyl is optionally and independently substituted by one, two, three, or four substituents independently selected from the group consisting of halogen, CN, $C_{1-6}$ alkyl, $NHC_{1-6}$ alkyl, OH, and $OC_{1-6}$ alkyl;

(i) $R_2$ is heterocyclyl or phenyl;

wherein the heterocyclyl or phenyl is optionally substituted by one, two, three, or four substituents independently selected from the group consisting of halogen, CN, $C_{1-6}$ alkyl, $C_{2-6}$ alkenyl, C(O)R, —$C(O)NR_4R_5$, C(O)OH, $NHC_{2-6}$ alkenyl, $NH(C_{3-6}$ cycloalkyl), NH(heterocyclyl), NH(aryl), NH(heteroaryl), —$NR_4R_5$, —OR, =O, —$S(O)_2C_{1-6}$ alkyl, $C_{3-6}$ cycloalkyl, $C_{3-6}$ cycloalkenyl, heterocycly, aryl, and heteroaryl; and wherein any $C_{1-6}$ alkyl, $C_{2-6}$ alkenyl, $C_{3-6}$ cycloalkyl, heterocyclyl, aryl, heteroaryl substituent is optionally and independently substituted by one, two, or three independently selected R substituents; or (ii) $R_2$ is

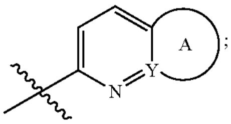

;

wherein $R_2$ is optionally substituted on a heteroatom of A by one, two, three, or four substituents independently selected from the group consisting of halogen, CN, $C_{1-6}$ alkyl, $C_{2-6}$ alkenyl, C(O)R, —$C(O)NR_4R_5$, C(O)OH, $NHC_{2-6}$ alkenyl, $NH(C_{3-6}$ cycloalkyl), NH(heterocyclyl), NH(aryl), NH(heteroaryl), $NR_4R_5$, OR, =O, $S(O)_2C_{1-6}$ alkyl, $C_{3-6}$ cycloalkyl, $C_{3-6}$ cycloalkenyl, heterocyclyl, aryl, and heteroaryl; and wherein any $C_{1-6}$ alkyl, $C_{2-6}$ alkenyl, $C_{3-6}$ cycloalkyl, heterocyclyl, aryl, and heteroaryl substituent is optionally and independently substituted by one, two, or three independently selected R' substituents;

Y is Cor N;

A is a 5- or 6-membered heterocyclyl or a 5- or 6-membered heteroaryl, wherein the 5- or 6-membered heterocyclyl or 5- or 6-membered heteroaryl contains 1 or 2 nitrogerheteroatoms;

each $R_4$ is independently H, $C_{1-6}$ alkyl, or $CH_2CF_3$, wherein each $C_{1-6}$ alkyl is optionally and independently substituted by one, two, three, four, or five substituents independently selected from the group consisting of Cl, Br, I, $NH_2$, OH, and $OC_{1-6}$ alkyl;

each $R_5$ is independently H, $C_{1-6}$ alkyl, or $CH_2CF_3$, wherein each $C_{1-6}$ alkyl is optionally and independently substituted by one, two, three, four, or five substituents independently selected from the group consisting of Cl, Br, I, $NH_2$, OH, and $OC_{1-6}$ alkyl;

each R' is independently halogen, CN, $C_{1-6}$ alkyl, $C_{1-3}$ haloalkyl, $C_{1-3}$ cyanoalkyl, $NHC_{1-6}$ alkyl, OH, $OC_{1-6}$ alkyl, $S(O)_2R_{10}$, $C_{3-6}$ cycloalkyl, heterocyclyl, 4-methylpiperazin-1-yl, 3-methyloxetan-3-yl, heteroaryl, 5-methylisoxazol-3-yl, or 2-methyl-1,3,4-oxadiazolyl;

each $R_3$ is independently halogen, CN, $C_{1-6}$ alkyl, $CH_2OH$, $C_{1-3}$ alkylene-$OC_{1-3}$ alkyl, $C_{1-6}$ alkylene-$OC_{1-6}$ alkylene-$C_{3-6}$ cycloalkyl, $C_{1-6}$ alkylene-$C_{3-7}$ heterocycloalkyl, $OC_{1-6}$ alkylene-$C_{3-6}$ cycloalkyl, or $C_{3-7}$ heterocycloalkyl;

wherein any $C_{1-6}$ alkyl is optionally and independently substituted by one, two, three, or four substituents independently selected from the group consisting of halogen, CN, and $NHC_{1-6}$ alkyl;

wherein any $C_{1-3}$ alkylene, $C_{1-6}$ alkylene, $OC_{1-3}$ alkyl, and $OC_{1-6}$ alkyl is optionally and independently substituted by one, two, three, or four substituents independently selected from the group consisting of halogen, CN, $NHC_{1-6}$ alkyl, and OH; and wherein any $C_{3-6}$ cycloalkyl and $C_{3-7}$ heterocycloalkyl is optionally and independently substituted by one, two, three, or four substituents independently selected from the group consisting of halogen, CN, $C_{1-6}$ alkyl, $NHC_1$-6 alkyl, and OH.

4. The compound as claimed in claim 1, wherein the compound is represented by formula II:

II

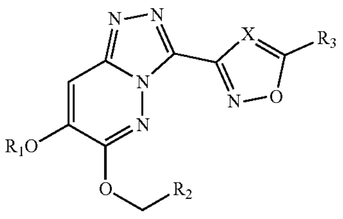

or a pharmaceutically acceptable salt or stereoisomer thereof, wherein:

X is CH or N.

5. The compound as claimed in claim 4, wherein the compound is represented by formula III:

III

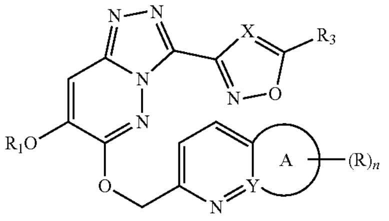

or

III

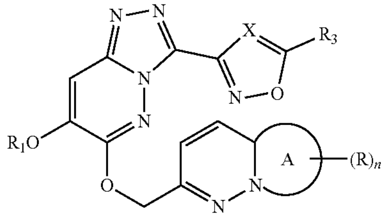

or a pharmaceutically acceptable salt or stereoisomer thereof, wherein:

A is absent, a 5- or 6-membered heterocyclyl, or a 5- or 6-membered heteroaryl, wherein the 5- or 6-membered heterocyclyl or 5- or 6-membered heteroaryl contains 1 or 2 nitrogen heteroatoms;

Y is C;

each R is independently H, $C_{1-6}$ alkyl, $C_{2-6}$ alkenyl, $C_{3-6}$ cycloalkyl, $C_{3-6}$ cycloalkenyl, heterocyclyl, aryl, or heteroaryl;

wherein each $C_{1-6}$ alkyl and $C_{2-6}$ alkenyl is optionally and independently substituted by one, two, or three substituents independently selected from the group consisting of halogen, CN, $NHC_{1-6}$ alkyl, $C(O)R'^{-2}$, $C(O)NR_8R_9$, OH, $OC_{1-6}$ alkyl, $S(O)_2R_{10}$, $C_{3-6}$ cycloalkyl, heterocyclyl, substituted 3- to 9-membered heterocyclyl, $C_{6-18}$ aryl, heteroaryl, and substituted 5- to 10-membered heteroaryl;

wherein each $C_{3-6}$ cycloalkyl substituent is optionally and independently substituted by one, two, or three CN substituents;

wherein each substituted 3- to 9-membered heterocyclyl substituent is independently substituted by one, two, or three independently selected $R'^{-3}$ substituents;

wherein each substituted 5- to 10-membered heteroaryl substituent is independently substituted by one, two, or three independently selected $R'^{-1}$ substituents; and wherein each $C_{3-6}$ cycloalkyl, $C_{3-6}$ cycloalkenyl, heterocyclyl, aryl, and heteroaryl is optionally and independently substituted by one, two, or three independently selected R' substituents; and n is 0, 1, 2, 3, or 4.

6. The compound as claimed in claim 1, or a pharmaceutically acceptable salt or stereomer thereof, wherein, $R_1$ is H, $C_{1-6}$ alkyl, or $C_{1-6}$ alkylene-$C_{3-6}$ cycloalky, wherein $C_{1-6}$ alkyl or $C_{1-6}$ alkylene-$C_{3-6}$ cycloalky is optionally substituted by one, two, three, or four independently selected from halogen substituents;

$R_2$ is phenyl or heteroaryl, wherein phenyl or heteroaryl is optionally substituted by one, two, three, or four substituents independently selected from the group consisting of halogen, CN, $C_{1-6}$ alkyl, $C_{2-6}$ alkenyl, —$C(O)C_{1-6}$ alkyl, —C(O)$C_{2-6}$ alkenyl, —$C(O)NR_4R_5$, —C(O)OH, —C(O)

$C_{3-6}$ cycloalky, —C(O)aryl, —$NR_4R_5$, $OC_{1-6}$ alkyl, O(heterocyclyl), =O, —$S(O)_2C_{1-6}$ alkyl, —$S(O)_2NR_6R_7$, $C_{3-6}$ cycloalkyl, $C_{3-6}$ cycloalkenyl, heterocyclyl, aryl and heteroaryl; and each $R^3$ is independently $C_{1-6}$ alkyl or $C_{1-6}$ alkylene-$OC_{1-6}$ alkyl, wherein each $C_{1-6}$ alkyl and $C_{1-6}$ alkylene-$OC_{1-6}$ alkyl is optionally and independently substituted by one, two, three, or four OH substituents.

7. The compound represented as claimed in claim 1, or a pharmaceutically acceptable salt or stereomer thereof, wherein, $R_1$ is $C_{1-6}$ alkyl, or $C_{1-6}$ alkylene-$C_{3-6}$ cycloalky, wherein $C_{1-6}$ alkyl or or $C_{1-6}$ alkylene-$C_{3-6}$ cycloalky is optionally substituted by one, two, three, or four independently selected from halogen substituents;

$R_2$ is phenyl, a monocyclic 5- or 6-membered heteroaryl, or a bicyotic 9- or 10-membered heteroaryl;

wherein the bicyclic 9- or 10-membered heteroaryl is a bicyclic heteroaryl of a 5- or 6-membered heteroaryl fused to a 5- or 6-membered heteroaryl; and wherein the phenyl, monocyclic 5- or 6-membered heteroaryl, or bicyclic 9- or 10-membered heteroaryl is optionally substituted by one, two, three, or four substituents independently selected from the group consisting of halogen, CN, $C_{1-6}$ alkyl, $C_{2-6}$ alkenyl, $C(O)C_{1-6}$ alkyl, $C(O)C_{2-6}$ alkenyl, $C(O)C_{3-6}$cycloalkyl, C(O)aryl, $NR_4R_5$, $OC_{1-6}$ alkyl, O(heterocyclyl), =O, $S(O)_2C_{1-6}$ alkyl, $S(O)_2NR_6R_7$, $C_{3-6}$ cycloalkyl, $C_{3-6}$ cycloalkenyl, heterocyclyl, aryl, and heteroaryl; and each $R^3$ is independently $C_{1-6}$ alkyl or $C_{1-6}$ alkylene-$OC_{1-6}$ alkyl, wherein each $C_{1-6}$ alkyl and $C_{1-6}$ alkylene-$OC_{1-6}$ alkyl is optionally and independently substituted by one, two, three, or four OH substituents.

8. The compound as claimed in claim 1, or a pharmaceutically acceptable salt or stereomer thereof, wherein, $R_1$ is $C_{1-6}$ alkyl or $C_{1-6}$ alkylene-$C_{3-6}$ cycloalky, wherein the $C_{1-6}$ alkyl or $C_{1-6}$ alkylene-$C_{3-6}$ cycloalky is optionally and independently substituted by one, two, three, or four substituents independently selected from the halogen substituents;

$R_2$ is phenyl or a monocyclic or bicyclic 5- to 10-membered heteroaryl;

wherein the monocyclic or bicyclic 5- to 10-membered heteroaryl contains 1, 2, 3, or 4 heteroatoms independently selected from the group consisting of nitrogen and oxygen; and wherein the phenyl or monocyclic or bicyclic 5- to 10-membered heteroaryl heteroaryl is optionally substituted by one, two, three, or four substituents independently selected from the group consisting of halogen, CN, $C_{1-6}$ alkyl, $C_{2-6}$ alkenyl, $NHC_{2-6}$ alkenyl, $NH(C_{3-6}$ cycloalkenyl), NH(heterocyclyl), NH(aryl), NH(heteroaryl), $NR_4R_5$, OR, =O, $S(O)_2C_{1-6}$ alkyl, $S(O)_2NR_6R_7$, $C_{3-6}$ cycloalkyl, $C_{3-6}$ cycloalkenyl, heterocyclyl, aryl, and heteroaryl;

Z is a 5-membered heteroaryl, wherein the 5-membered heteroaryl contains 2 heteroatoms independently selected from the group consisting of nitrogen and oxygen; and each $R^3$ is independently $C_{1-6}$ alkyl or $C_{1-6}$ alkylene-$OC_{1-6}$ alkyl, wherein each $C_{1-6}$ alkyl and $C_{1-6}$ alkylene-$OC_{1-6}$ alkyl is optionally and independently substituted by one, two, three, or four OH substituents.

9. The compound as claimed in claim 1, or a pharmaceutically acceptable salt or stereomer thereof, wherein, $R_1$ is $C_{1-6}$ alkyl;

$R_2$ is a monocyclic or bicyclic 5- to 10-membered heteroaryl;

wherein the monocyclic or bicyclic 5- to 10-membered heteroaryl contains 1, 2, or 3 nitrogen heteroatoms;

wherein the monocyclic or bicyclic 5- to 10-membered heteroaryl is optionally substituted by one, two, three, or four substituents independently selected from the group consisting of CN, $C_{1-6}$ alkyl, $OC_{1-6}$ alkyl, O(heterocyclyl), and heterocyclyl; and wherein any $C_{1-6}$ alkyl, and heterocyclyl substituent is optionally and independently substituted by one, two, or three independently selected R' substituents;

each R' is independently halogen, OH, $OC_{1-6}$ alkyl, substituted 3- to 9-membered heterocyclyl, or substituted 5- to 10-membered heteroaryl;

wherein each substituted 3- to 9-membered heterocyclyl is substituted by one, two, or three independently selected R-3 substituents; and wherein each substituted 5- to 10-membered heteroaryl is independently substituted by one, two, or three independently selected $R'^{-1}$ substituents; and each $R^3$ is independently $C_{1-6}$ alkyl.

10. The compound as claimed in claim 9, or a pharmaceutically acceptable salt or stereoisomer thereof, wherein:

$R_2$ is

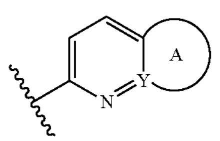

or

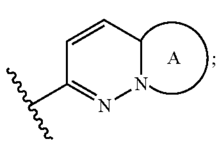

;

wherein $R_2$ is optionally substituted on a heteroatom of A by one, two, three, or four substituents independently selected from the group consisting of $C_{1-6}$ alkyl and heterocyclyl; and wherein any $C_{1-6}$ alkyl and heterocyclyl substituent is optionally and independently substituted by one, two, or three independently selected R' substituents:

Y is C;

A is a 5- or 6-membered heterocyclyl, wherein the 5- or 6-membered heterocyclyl contains 1 or 2 nitrogen heteroatoms; and each R' is independently OH or substituted 5- to 10-membered heteroaryl, wherein each substituted 5- to 10-membered heteroaryl is independently substituted by one, two, or three independently selected $R'^{-1}$ substituents.

11. The compound represented by formula I as claimed in claim 1, or a pharmaceutically acceptable salt or stereomer thereof, wherein, $R_1$ is $C_{1-6}$ alkyl;

$R_2$ is a bicyotic 9- or 10-membered heteroaryl;

wherein the bicyclic 9- or 10-membered heteroaryl is a bicyclic heteroaryl of a 5- or 6-membered heteroaryl fused to a 5- or 6-membered heteroaryl; and wherein the bicyclic 9- or 10-membered heteroaryl is optionally substituted by one, two, three, or four substituents independently selected from the group consisting of halogen, CN, $C_{1-6}$ alkyl, $C_{2-6}$ alkenyl, $C(O)C_{1-6}$ alkyl, $C(O)C_{2-6}$ alkenyl, $C(O)C_{3-6}$ cycloalkyl, C(O)aryl, $NR_4R_5$, $OC_{1-6}$ alkyl, O(heterocyclyl), =O, $S(O)_2C_{1-6}$ alkyl, $S(O)_2NR_6R_7$, $C_{3-6}$ cycloalkyl, $C_{3-6}$ cycloalkenyl, heterocyclyl, aryl, and heteroaryl; and each $R^3$ is independently $C_{1-6}$ alkyl.

12. The compound as claimed in claim 1, or a pharmaceutically acceptable salt or stereomer thereof, wherein $R_1$ is H, $C_{1-4}$ alkyl, $C_{1-6}$ alkylene-$OC_{1-6}$ alkyl, $C_{1-4}$ alkylene-$C_{3-6}$ cycloalkyl, $C_{3-6}$ cycloalkyl, or $C_{3-7}$ heterocycloalkyl;

wherein any $C_{1-4}$ alkyl, $C_{1-6}$ alkylene, and $OC_{1-6}$ alkyl is optionally and independently substituted by one, two, three, or four substituents independently selected from the group consisting of F, Cl, Br, I, CN, $NHC_{1-6}$ alkyl, OH, and $OC_{1-6}$ alkyl; and wherein any $C_{3-6}$ cycloalkyl and $C_{3-7}$ heterocycloalkyl is optionally and independently substituted by one, two, three, or four substituents independently selected from the group consisting of F, Cl, Br, I, CN, $C_{1-6}$ alkyl, $NHC_{1-6}$ alkyl, OH, and $OC_{1-6}$ alkyl;

$R_2$ is heterocyclyl, phenyl, or a monocyclic or bicyclic 5- to 10-membered heteroaryl;

wherein the monocyclic or bicyclic 5- to 10-membered heteroaryl contains 1, 2, 3, or 4 heteroatoms independently selected from the group consisting of nitrogen and oxygen;

wherein the heterocyclyl, phenyl, or monocyclic or bicyclic 5- to 10-membered heteroaryl is optionally substituted by one, two, three, or four substituents independently selected from the group consisting of F, Cl, Br, I, CN, $C_{1-6}$ alkyl, $C_{2-6}$ alkenyl, $C(O)C_{1-6}$ alkyl, $C(O)C_{2-4}$ alkenyl, $C(O)NR_4R5$, C(O)OH, $C(O)C_{3-6}$ cycloalkyl, C(O)aryl, $NHC_{2-6}$ alkenyl, $NH(C_{3-6}$ cycloalkenyl), NH(heterocyclyl), NH(aryl), NH(heteroaryl), $NR_4R_5$, $OC_{1-6}$ alkyl, O(heterocyclyl), =O, $S(O)_2C_{1-4}$ alkyl, $S(O)_2NR_6R_7$, $C_{3-6}$ cycloalkyl, $C_{3-6}$ cycloalkenyl, heterocyclyl, aryl, and heteroaryl; and wherein any $C_{1-6}$ alkyl, $C_{2-6}$ alkenyl, $C_{3-6}$ cycloalkyl, $C_{3-6}$ cycloalkenyl, heterocyclyl, aryl, and heteroaryl substituent is optionally and independently substituted by one, two, or three independently selected R' substituents;

each $R_4$ is independently H, $C_{1-4}$ alkyl, or $C_{3-6}$ cycloalkyl;

wherein each $C_{1-4}$ alkyl is optionally and independently substituted by one, two, or three substituents independently selected from the group consisting of halogen, $NH_2$, OH, and $OC_{1-6}$ alkyl; and wherein each $C_{3-6}$ cycloalkyl is optionally and independently substituted by one, two, or three substituents independently selected from the group consisting of F, Cl, Br, I, $C_{1-6}$ alkyl, $NH_2$, OH, and $OC_{1-6}$ alkyl;

each $R_5$ is independently H, $C_{1-4}$ alkyl, or $C_{3-6}$ cycloalkyl;

wherein each $C_{1-4}$ alkyl is optionally and independently substituted by one, two, or three substituents independently selected from the group consisting of F, Cl, Br, I, $NH_2$, OH, and $OC_{1-6}$ alkyl; and wherein each $C_{3-6}$ cycloalkyl is optionally and independently substituted by one, two, or three substituents independently selected from the group consisting of F, Cl, Br, I, $C_{1-6}$ alkyl, $NH_2$, OH, and $OC_{1-6}$ alkyl; or any $R_4$ and $R_5$, together with the nitrogen heteroatom to which they are attached, independently forms morpholin-4-yl;

each $R_6$ is independently $C_{1-4}$ alkyl;

each $R_7$ is independently $C_{1-4}$ alkyl;

each R is independently H, $C_{1-4}$ alkyl, $C_2$-3 alkenyl, $C_{3-6}$ cycloalkyl, cyclopropenyl, cyclobutenyl, cyclohexenyl, 3- to 10-membered heterocyclyl, $C_{6-14}$ aryl, or 5- to 10-membered heteroaryl;

wherein each 3- to 10-membered heterocyclyl and 5- to 10-membered heteroaryl independently contains 1, 2, or 3 heteroatoms independently selected from the group consisting of nitrogen and oxygen;

wherein each $C_{1-4}$ alkyl and $C_{2-3}$ alkenyl is optionally and independently substituted by one, two, or three substituents independently selected from the group consisting of halogen, CN, $NHC_{1-6}$ alkyl, —$C(O)R'^{-2}$, $C(O)NR_8R_9$, OH, $OC_{1-6}$ alkyl, $S(O)_2R_{10}$, $S(O)_2C_{1-6}$ alkyl, $C_{3-6}$ cycloalkyl, heterocyclyl, substituted 3- to 9-membered heterocyclyl, $C_{6-18}$ aryl, heteroaryl, and 5- to 10-membered heteroaryl;

wherein each $C_{3-6}$ cycloalkyl substituent is optionally and independently substituted by one, two, or three CN substituents;

wherein each 3- to 9-membered heterocyclyl substituent is independently substituted by one, two, or three independently selected $R'^{-3}$ substituents;

wherein each 5- to 10-membered heteroaryl substituent is independently substituted by one, two, or three independently selected $R'^{-1}$ substituents; and wherein each $C_{3-6}$ cycloalkyl, cyclopropenyl, cyclobutenyl, cyclohexonyl, 3- to 10-membered heterocyclyl, $C_{6-14}$ aryl, and 5- to 10-membered heteroaryl is optionally and independently substituted by one, two, or three independently selected R' substituents;

each R' is independently F, Cl, Br, I, CN, $C_{1-4}$ alkyl, $C_{1-3}$ haloalkyl, $C_{1-3}$ cyanoalkyl, $NHC_{1-3}$ alkyl, $C(O)R'^{-2}$, $C(O)NR_8R_9$, OH, $OC_{1-6}$ alkyl, $S(O)_2R_{10}$, $C_{3-6}$ cycloalkyl, bicyclic bridged 5-membered cycloalkyl, monocyclic 3- to 6-membered heterocyclyl, substituted monocyclic 4- to 6-membered heterocyclyl, phenyl, naphthyl, phenanthryl, anthranyl, monocyclic or bicyclic 5- to 10-membered heteroanyl, or substituted 5- or 6-membered heteroaryl;

wherein each monocyclic 3- to 6-membered heterocyclyl and substituted monocyclic 4- to 6-membered heterocyclyl independently contains 1 or 2 heteroatoms independently selected from the group consisting of nitrogen and oxygen;

wherein each monocyclic or bicyclic 5- to 10-membered heteroaryl and substituted 5- or 6-membered heteroaryl independently contains 1, 2, or 3 heteroatoms independently selected from the group consisting of nitrogen and oxygen;

wherein each bicyclic bridged 5-membered cycloalkyl is substituted by one, two, or three CN substituents;

wherein each substituted monocyclic 4- to 6-membered heterocyclyl is substituted by one, two, or three independently selected $R'^{-3}$ substituents; and wherein each substituted 5- or 6-membered heteroaryl is independently substituted by one, two, or three independently selected $R'^{-1}$ substituents;

each $R_8$ is independently H or $C_{1-4}$ alkyl;

each $R_9$ is independently H or $C_{1-4}$ alkyl; or any $R_8$ and $R_9$, together with the nitrogen heteroatom to which they are attached, independently forms pyrrolidin-1-yl;

each $R_{10}$ is independently $C_{1-4}$ alkyl;

each $R'^{-1}$ is independently $C_{1-4}$ alkyl;

each $R'^{-2}$ is independently $C_{1-6}$ alkyl or $C_{3-6}$ cycloalkyl;

each $R'^{-3}$ independently $C_{1-4}$ alkyl;

Z is a 5-membered heteroaryl;

wherein the 5-membered heteroaryl contains 2 heteroatoms independently selected from the group consisting of nitrogen, oxygen, and sulfur; and wherein the 5-membered heteroaryl is optionally substituted by one or two independently selected $R_3$ substituents; and each $R^3$ is independently halogen, CN, $C_{1-4}$ alkyl, $C_{1-4}$ alkylene-$OC_{1-4}$ alkyl, $C_{1-6}$ alkylene-$OC_{1-6}$ alkylene-$C_{3-6}$ cycloalkyl, $C_{1-6}$ alkylene-$C_{3-7}$ heterocycloalkyl, $OC_{1-4}$ alkylene-$C_{3-6}$ cycloalkyl, or $C_{3-7}$ heterocycloalkyl;

wherein any $C_{1-4}$ alkyl, $C_{1-4}$ alkylene, $C_{1-6}$ alkylene, and $OC_{1-4}$ alkyl is optionally and independently substituted by one, two, three, or four substituents independently selected from the group consisting of halogen, CN, $NHC_{1-6}$ alkyl, and OH; and wherein any $C_{3-6}$ cycloalkyl and $C_{3-7}$ heterocycloalkyl is optionally and independently substituted by one, two, three, or four substituents independently selected from the group consisting of halogen, CN, $C_{1-6}$ alkyl, $NHC_{1-6}$ alkyl, and OH.

13. The compound as claimed in claim 12, or a pharmaceutically acceptable salt or stereomer thereof, wherein, $R_1$ is H, $C_{1-4}$ alkyl, $C_{1-6}$ alkylene-$OC_{1-6}$ alkyl, $CH_2$—$C_{3-4}$ cycloalkyl, $C_{3-6}$cycloalkyl, or $C_{3-7}$ heterocycloalkyl;

wherein any $C_{1-4}$ alkyl, $C_{1-6}$ alkylene, and $OC_{1-6}$ alkyl is optionally and independently substituted by one or two substituents independently selected from the group consisting of F, CN, $NHC_{1-6}$ alkyl, OH, and $OC_{1-6}$ alkyl; and wherein any $C_{3-4}$ cycloalkyl, $C_{3-6}$ cycloalkyl, and $C_{3-7}$ heterocycloalkyl is optionally and independently substituted by one or two substituents independently selected from the group consisting of F, CN, $C_{1-6}$ alkyl, $NHC_{1-6}$ alkyl, OH, and $OC_{1-6}$ alkyl;

$R_2$ is heterocyclyl, phenyl, a monocyclic 5- or 6-membered heteroaryl, or a bicyclic 9- or 10-membered heteroaryl;

wherein the monocyclic 5- or 6-membered heteroaryl or bicyclic 9- or 10-membered heteroaryl contains 1,2,3, or 4 heteroatoms independently selected from the group consisting of nitrogen and oxygen;

wherein the heterocyclyl, phenyl, monocyclic 5- or 6-membered heteroaryl, or bicyclic 9- or 10-membered heteroaryl is optionally substituted by one or two substituents independently selected from the group consisting of F, CI, CN, $C_{1-6}$ alkyl, $C_{2-6}$ alkenyl, $C(O)C_{1-6}$ alkyl, $C(O)C_{2-6}$ alkenyl, $C(O)NR_4R_5$, C(O)OH, $C(O)C_{3-6}$ cycloalkyl, C(O)aryl, $NHC_{2-6}$ alkenyl, NH($C_{3-6}$ cycloalkenyl), NH(heterocyclyl), NH(aryl), NH(heteroaryl), $NR_4R_5$, $OC_{1-6}$ alkyl, O(heterocyclyl), =O, $S(O)_2C_{1-3}$ alkyl, $S(O)_2NR_6R_7$, $C_{3-6}$ cycloalkyl, cyclohexen-1-yl, heterocyclyl, aryl, and heteroaryl; and wherein any $C_{1-6}$ alkyl, $C_{2-6}$ alkenyl, $C_{3-6}$ cycloalkyl, cyclohexene-1-yl, heterocyclyl, aryl, and heteroaryl substituent is optionally and independently substituted by one, two or three independently selected R substituents;

each $R_4$ is independently H, $CH_3$, $CH_2CH_2$, $CH_2CH_2CH_2CH_3$, or cyclohexyl;

wherein each $CH_3$, $CH_2CH_2$, and $CH_2CH_2CH$ $CH_3$ is optionally and independently substituted by one, two or three substituents independently selected from the group consisting of F, $NH_2$, OH, and $OC_{1-6}$ alkyl; and wherein each cyclohexyl is optionally and independently substituted by one, two, or three substituents independently selected from the group consisting of F, $C_{1-6}$ alkyl, $NH_2$, OH, and $OC_{1-6}$ alkyl;

each $R_5$ is independently H, $CH_3$, $CH_2CH_2$, $CH_2CH_2CH_2CH_3$, or cyclohexyl;

wherein each $CH_3$, $CH_2CH_2$, and $CH_2CH_2CH_2CH_3$ is optionally and independently substituted by one, two or three substituents independently selected from the group consisting of F, $NH_2$, OH, and $OC_{1-6}$ alkyl; and wherein each cyclohexyl is optionally and independently substitutes by one, two, or three substituents independently selected from the group consisting of F, $C_{1-6}$ alkyl, $NH_2$, OH, and $OC_{1-6}$ alkyl;

any $R_4$ and $R_5$, together with the nitrogen heteroatom to which they are attached, independently forms morpholin-4-yl;

each $R_6$ is independently $C_{1-3}$ alkyl;

each $R_7$ is independently $C_{1-3}$ alkyl;

each R is independently H, $C_{1-4}$ alkyl, $C_{2-3}$ alkenyl, $C_{3-4}$ cycloalkyl, cyclohexen-1-yl, monocyclic 5- or 6-membered heterocyclyl, spirocyclic 7- or 8-membered heterocyclyl, phenyl, phthyl, phenanthryl, anthranyl, or a monocyclic 5-membered heteroaryl;

wherein each monocyclic 5- or 6-membered heterocyclyl and spirocyclic 7- or 8-membered heterocyclyl independently contains 1 or 2 heteroatoms independently selected from the group consisting of nitrogen and oxygen;

wherein each monocyclic 5-membered heteroaryl independently contains 2 or 3 heteroatoms independently selected from the group consisting of nitrogen and oxygen;

wherein each $C_{1-4}$ alkyl and $C_{2-3}$ alkenyl is optionally and independently substituted by one, two, or three substituents independently selected from the group consisting of halogen, CN, $NHC_{1-6}$ alkyl, —$C(O)R'^{-2}$, $C(O)NR_8R_9$, OH, $OC_{1-6}$ alkyl, $S(O)_2R_{10}$, $S(O)_2C_{1-6}$ alkyl, $C_{3-6}$ cycloalkyl, $C_{3-6}$ cycloalkyl, heterocyclyl, substituted 3- to 9-membered heterocyclyl, C6-18 aryl, heteroaryl, and 5- to 10-membered heteroaryl;

wherein each $C_{3-6}$ cycloalkyl substituent is optionally and independently substituted by one, two, or three CN substituents;

wherein each 3- to 9-membered heterocyclyl substituent is independently substituted by one, two, or three independently selected $R'^{-3}$ substituents;

wherein each 5- to 10-membered heteroaryl substituent is independently substituted by one, two, or three independently selected $R'^{-1}$ substituents; and wherein each $C_{3-4}$ cycloalkyl, cyclohexen-1-yl, monocyclic 5- or 6-membered heterocycly, spirocyclic 7- or 8-membered heterocyclyl, phenyl, naphthyl, phenanthryl, anthranyl, anholocyclic 5-membered heteroaryl is optionally and independently substituted by one, two, or three independently selected R' substituents:

each R' is independently F, CN, $C_{1-3}$ alkyl, $C(halo)_{1-3}$, $C(cyano)_{1-3}$, $NHCH_2CH_3$, $C(O)R'^{-2}$, $C(O)NR_8R_9$, OH, $OC_{1-3}$ alkyl, $S(O)_2R_{10}$, cyclopropyl, bicyclo[1.1.1]pentan-1-yl, azetidinyl, oxetanyl, tetrahydrofuranyl, piperazinyl, morpholinyl, substituted oxetanyl, substituted piperazinyl, phenyl, monocyclic 5-membered heteroaryl, or substituted oxadiazolyl;

wherein each monocyclic 5-membered heteroaryl independently contains 1, 2, or 3 heteroatoms independently selected from the group consisting of nitrogen and oxygen;

wherein each bicyclo[1.1.1]pentan-1-yl is substituted by one, two, or three CN substituents;

wherein each substituted oxetanyl and substituted piperazinyl is substituted by one, two, or three independently selected $R'^{-3}$ substituents; and wherein each substituted oxadiazolyl is independently substituted by one, two, or three independently selected $R'^{-1}$ substituents:

each $R_8$ is independently H or $C_{1-3}$ alkyl;

each $R_9$ is independently H or $C_{1-3}$ alkyl; or any $R_8$ and $R_9$, together with the nitrogen heteroatom to which they are attached, independently forms pyrrolidin-1-yl;

each $R_{10}$ is independently $C_{1-3}$ alkyl;

each $R'^{-1}$ is independently $C_{1-3}$ alkyl;

each $R'^{-2}$ is independently $C_{1-6}$ alkyl or $C_{3-6}$ cycloalkyl;

each $R'^{-3}$ independently $C_{1-3}$ alkyl;

Z is isoxazolyl, wherein the isoxazolyl is optionally substituted by one or two independently selected R3 substituents; and each $R_3$ is independently halogen, CN, $C_{1-3}$ alkyl, $C_{1-3}$ alkylene-$OC_{1-3}$ alkyl, $C_{1-6}$ alkylene-$OC_{1-6}$ alkylene-$C_{3-6}$ cycloalkyl, $C_{1-6}$ alkylene-$C_{3-7}$ heterocycloalkyl, $OC_{1-6}$ alkylene-$C_{3-6}$ cycloalkyl, or $C_{3-7}$ heterocycloalkyl;

wherein any $C_{1-3}$ alkyl, $C_{1-3}$ alkylene, $C_{1-6}$ alkylene, and $OC_{1-3}$ alkyl is optionally and independently substituted by one or two substituents independently selected from the group consisting of halogen, CN, $NHC_{1-6}$ alkyl, and OH; and wherein any $C_{3-6}$ cycloalkyl and $C_{3-7}$ heterocycloalkyl is optionally and independently substituted by one or two substituents independently selected from the group consisting of halogen, CN, $C_{1-6}$ alkyl, $NHC_{1-6}$ alkyl, and OH.

14. The compound as claimed in claim 12, or a pharmaceutically acceptable salt or stereomer thereof, wherein, $R_2$ is heterocyclyl, phenyl, triazolyl, pyridinonyl, pyridinyl, pyrridazinonyl, pyridazinyl, pyrimidinyl, pyrazinyl, indolyl, pyrrolopyridinyl, oxopyrrolopyridinyl, pyrazolopyricdinyl, imidazopyridinyl, triazolopyridinyl, imidazopyridazinyl, triazolopyridazinyl, pyrazolopyrimidinyl, quinolinyl, diazanaphthalenyl, tetrahydronaphthyridinyl, naphthyridinonyl, naphthyridinyl, pyridooxazinyl, or dioxinopyridinyl;

wherein the heterocyclyl, phenyl, triazolyl, pyridinonyl, pyridinyl, pyridazinonyl, pyridazinyl, pyrimidinyl, pyrazinyl, indolyl, pyrrolopyridinyl, oxopyrrolopyridinyl, pyrazolopyridinyl, imidazopyridinyl, triazolopyridinyl, imidazopyridazinyl, triazolopyridazinyl, |pyrazolopyrimidinyl, quinolinyl, diazanaphthalenyl, tetrahydronaphthyridinyl, naphthyridinonyl, naphthyridinyl, pyridooxazinyl, or dioxinopyridinyl is optionally substituted by one or two substituents independently selected from the group consisting of F, CI, CN, $C_{1-6}$ alkyl, $C_{2-6}$ alkenyl, $C(O)C_{1-6}$ alkyl, $C(O)C_{2-6}$ alkenyl, $C(O)NR_4R_5$, C(O)OH, $C(O)C_{3-6}$ cycloalkyl, C(O)aryl, $NHC_{2-6}$ alkenyl, $NH(C_{3-6}$ cycloalkenyl), NH(heterocyclyl), NH(aryl), NH(heteroaryl), NR4R5, $OC_{1-6}$ alkyl, O(heterocyclyl), =O, $S(O)_2CH_3$, $S(O)_2CH_2CH_3$, $S(O)_2NR_6R_7$, $C_{3-6}$ cycloalkyl, cyclohexen-1-yl, heterocyclyl, aryl, and heteroaryl; and wherein any $C_{1-6}$ alkyl, $C_{2-6}$ alkenyl, $C_{3-6}$ cycloalkyl, cyclohexen-1-yl, heterocyclyl, aryl, and heteroaryl substituent is optionally and independently substituted by one, two, or three independently selected R' substituents;

each $R_6$ is independently $CH_3$;

each $R_7$ is independently $CH_3$;

each R is independently H, $C_{1-4}$ alkyl, $C_{2-3}$ alkenyl, $C_{3-4}$ cycloalkyl, cyclohexen-1-yl, azetidinyl, oxetanyl, pyrrolidinyl, tetrahydrofuranyl, piperidinyl, tetrahydropyranyl, morpholinyl, 2-oxaspiro[3,3]heptanyl, phenyl, isoxazolyl, oxadiazolyl, or pyrimidinyl;

wherein each $C_{1-4}$ alkyl and $C_{2-3}$ alkenyl is optionally and independently substituted by one, two, or three substituents independently selected from the group consisting of halogen, CN, $NHC_{1-6}$ alkyl, —$C(O)R'^{-2}$, $C(O)NR_8R_9$, OH, $OC_{1-6}$ alkyl, $S(O)_2R_{10}$, $S(O)_2C_{1-6}$ alkyl, $C_{3-6}$ cycloalkyl, heterocyclyl, substituted 3- to 9-membered heterocyclyl, $C_{6-18}$ aryl, heteroaryl, and 5- to 10-membered heteroaryl;

wherein each $C_{3-6}$ cycloalkyl substituent is optionally and independently substituted by one, two, or three CN substituents;

wherein each 3- to 9-membered heterocyclyl substituent is independently substituted by one, two, or three independently selected $R'^{-3}$ substituents;

wherein each 5- to 10-membered heteroaryl substituent is independently substituted by one, two, or three independently selected $R'^{-1}$ substituents; and wherein each $C_{3-4}$ cycloalkyl, cyclohexen-1-yl, azetidinyl, oxetanyl, pyrrolidinyl, tetrahydrofuranyl, piperidinyl, tetrahydropyranyl, morpholinyl, 2-oxaspiro[3,3]heptanyl, phenyl, isoxazolyl, oxadiazolyl, and pyrimidinyl is optionally and independently substituted by one, two, or three independently selected R' substituents;

each R' is independently F, CN, $CH_3$, $C(halo)_{1-3}$, $C(cyano)_{1-3}$, $NHCH_2CH_3$, $C(O)R'^{-2}$, $C(O)NR_8R_9$, OH, $OCH_3$, $S(O)_2R_{10}$, cyclopropyl, bicyclo[1.1.1]pentan-1-yl, azetidin-3-yl, oxetan-3-yl, tetrahydrofuran-3-yl, piperazin-1-yl, morpholin-4-yl, substituted oxetan-3-yl, substituted piperazin-1-yl, phenyl, isoxazolyl, oxadiazolyl, pyrimidinyl, substituted isoxazol-3-yl, or substituted 1,3,4-oxadiazol-2-yl;

wherein each bicyclo[1.1.1]pentan-1-yl is substituted by one, two, or three CN substituents;

wherein each substituted oxetan-3-yl and substituted piperazin-1-yl is substituted by one, two, or three independently selected $R'^{-3}$ substituents; and wherein each substituted isoxazol-3-yl and substituted 1,3,4-oxadiazol-2-yl is independently substituted by one, two, or three independently selected $R'^{-1}$ substituents;

each $R_8$ is independently H or $CH_3$;

each $R_9$ is independently H or $CH_3$; or any $R_8$ and $R_9$, together with the nitrogen heteroatom to which they are attached, independently forms pyrrolidin-1-yl;

each $R_{10}$ is independently $CH_3$;

each $R'^{-1}$ is independently $CH_3$;

each $R'^{-3}$ independently $CH_3$;

Z is isoxazol-3-yl or isoxazol-5-yl, wherein the isoxazol-3-yl or isoxazol-5-yl is optionally substituted by one or two independently selected $R_3$ substituents; and each $R_3$ is independently halogen, CN, $CH_3$, $CH_2OCH_3$, $C_{1-6}$ alkylene-$OC_{1-6}$ alkylene-$C_{3-6}$ cycloalkyl, $C_{1-6}$ alkylene-$C_{3-7}$ heterocycloalkyl, $OC_{1-6}$ alkylene-$C_{3-6}$ cycloalkyl, or $C_{3-7}$ heterocycloalkyl;

wherein any $C_{1-6}$ alkylene is optionally and independently substituted by one or two substituents independently selected from the group consisting of halogen, CN, $NHC_{1-6}$ alkyl, and OH; and wherein any $C_{3-6}$ cycloalkyl and $C_{3-7}$ heterocycloalkyl is optionally and independently substituted by one or two substituents independently selected from the group consisting of halogen, CN, $C_{1-6}$ alkyl, $NHC_{1-6}$ alkyl, and OH.

15. The compound as claimed in claim 14, or a pharmaceutically acceptable salt or stereomer thereof, wherein $R_2$ is

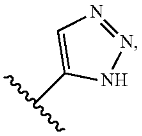,
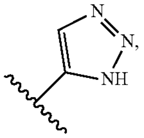,
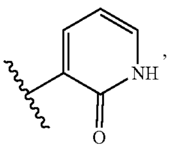,
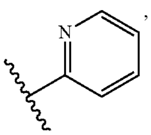,
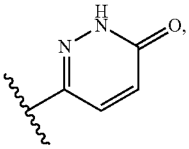,
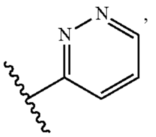,
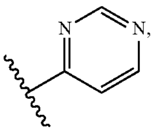,
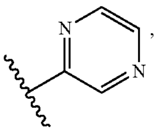,
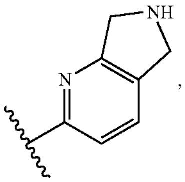,
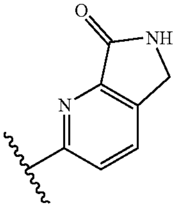,
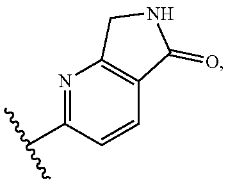,
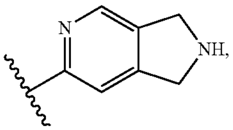,
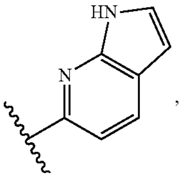,
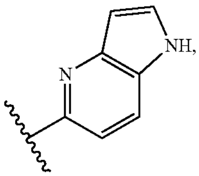,
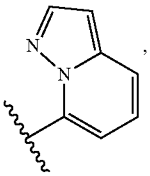,
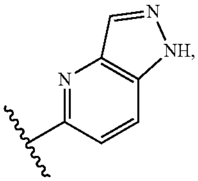,
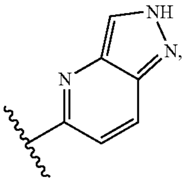,
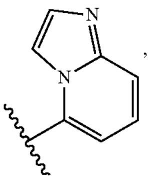,
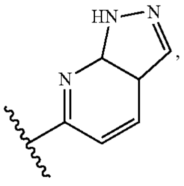, -continued

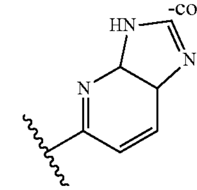,
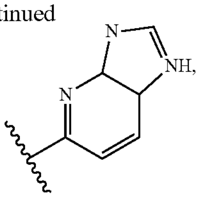,
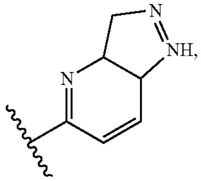,
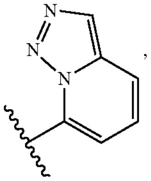,
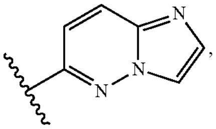,
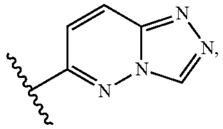,
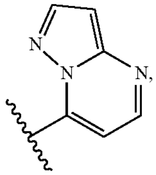,
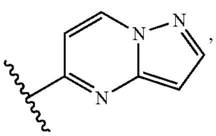,
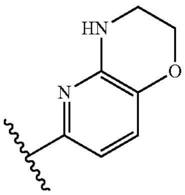
or,
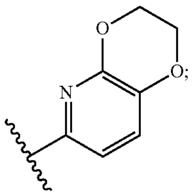;

each R is independently H, $C_{1-4}$ alkyl, $C_{2-3}$ alkenyl, $C_{3-4}$ cycloalkyl, cyclohexen-1-yl, azetidin-3-yl, oxetan-3-yl, pyrrolidin-2-yl, pyrrolidin-3-yl, tetrahydrofuran-3-yl, piperidin-4-yl, tetrahydropyran-4-yl, morpholin-4-yl, 2-oxaspiro[3,3]heptan-6-yl, phenyl, isoxazol-3-yl, 1,3,4-oxadiazol-2-yl, or pyrimidin-2-yl;

wherein each $C_{1-4}$ alkyl and $C_{2-3}$ alkenyl is optionally and independently substituted by one, two, or three substituents independently selected from the group consisting of halogen, CN, $NHC_{1-6}$ alkyl, —C(O)$R'^{-2}$, C(O)$NR_8R_9$, OH, $OC_{1-6}$ alkyl, $S(O)_2R_{10}$, $S(O)_2C_{1-6}$ alkyl, $C_{3-6}$ cycloalkyl, heterocyclyl, substituted 3- to 9-membered heterocyclyl, $C_{6-18}$ aryl, heteroaryl, and 5- to 10-membered heteroaryl;

wherein each $C_{3-6}$ cycloalkyl substituent is optionally and independently substituted by one, two, or three CN substituents;

wherein each 3- to 9-membered heterocyclyl substituent is independently substituted by one, two, or three independently selected $R'^{-3}$ substituents;

wherein each 5- to 10-membered heteroaryl substituent is independently substituted by one, two, or three independently selected $R'^{-1}$ substituents;

wherein each 2-oxaspiro[3,3]heptan-6-yl is optionally and independently substituted by one or two independently selected R' substituents; and wherein each $C_{3-4}$ cycloalkyl, cyclohexen-1-yl, azetidin-3-yl, oxetan-3-yl, pyrrolidin-2-yl, pyrrolidin-3-yl, tetrahydrofuran-3-yl, piperidin-4-yl, tetrahydropyran-4-yl, morpholin-4-yl, phenyl, isoxazol-3-yl, 1,3,4-oxadiazol-2-yl, and pyrimidin-2-yl is optionally and independently substituted by one, two, or three independently selected R' substituents;

each R' is independently F, CN, $CH_3$, $C(halo)_{1-3}$, $C(cyano)_{1-3}$, $NHCH_2CH_3$, $C(O)R'^{-2}$, $C(O)NR_8R_9$, OH, $OCH_3$, $S(O)_2R_{10}$, cyclopropyl, bicyclo[1.1]pentan-1-yl, oxetan-3-yl, substituted oxetan-3-yl, substituted piperazin-1-yl, phenyl, isoxazol-3-yl, 1,3,4-oxadiazol-2-yl, or pyrimidin-2-yl substituted isoxazol-3-yl, or substituted 1,3,4-oxadiazol-2-yl;

wherein each bicyclo[1.1.1]pentan-1-yl is substituted by one, two or three CN substituents;

wherein each substituted oxetan-3-yl and substituted piperazin-1-yl is substituted by one, two, or three independently selected $R'^{-3}$ substituents; and wherein each substituted isoxazol-3-yl and substituted 1,3,4-oxadiazol-2-yl is independently substituted by one, two, or three independently selected $R'^{-1}$ substituents; and Z is isoxazol-3-yl, wherein the isoxazol-3-yl is optionally substituted at position 5 by one $R_3$ substituent.

16. The compound as claimed in claim 1, wherein the compound is selected from the group consisting of

| Embodiment | Structure |
|---|---|
| 1 | 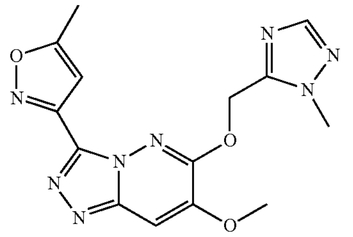 [SMILES: COc1cc2nnc(-c3cc(C)on3)n2nc1OCc1ncnn1C] |
| 2 | 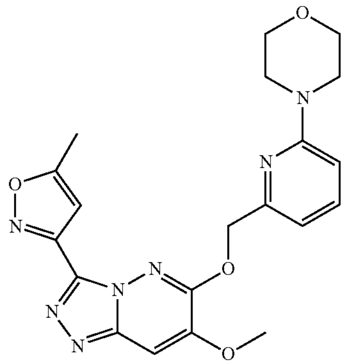 [SMILES: COc1cc2nnc(-c3cc(C)on3)n2nc1OCc1cccc(N2CCOCC2)n1] |
| 3 | 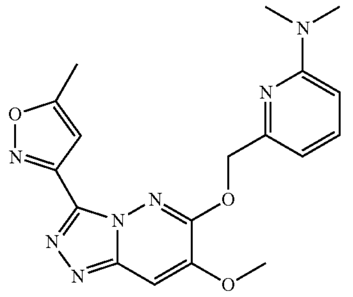 [SMILES: COc1cc2nnc(-c3cc(C)on3)n2nc1OCc1cccc(N(C)C)n1] |
| 4 | 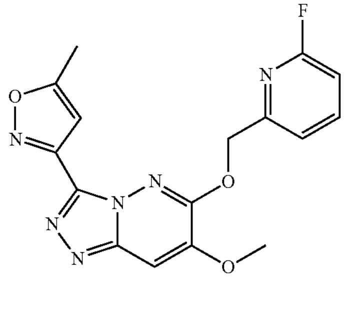 [SMILES: COc1cc2nnc(-c3cc(C)on3)n2nc1OCc1cccc(F)n1] |

-continued
| Embodiment | Structure |
| --- | --- |
| 5 | 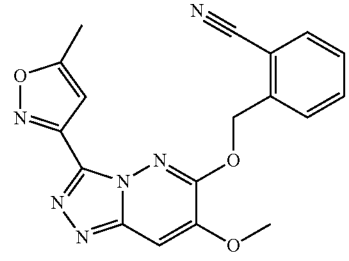 [SMILES: COc1cc2nnc(-c3cc(C)on3)n2nc1OCc1ccccc1C#N] |
| 6 | 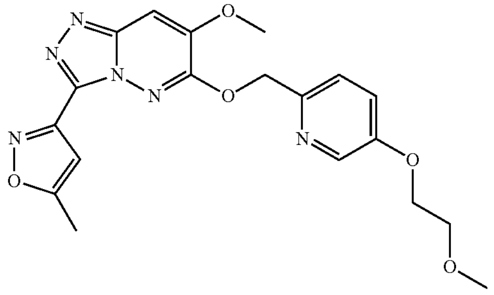 [SMILES: COCCOc1ccc(COc2nn3c(-c4cc(C)on4)nnc3cc2OC)nc1] |
| 7 | 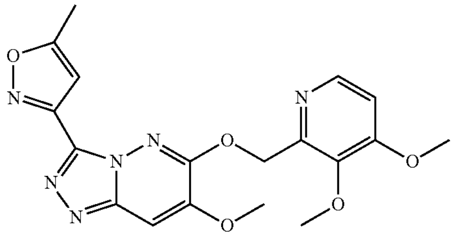 [SMILES: COc1cc2nnc(-c3cc(C)on3)n2nc1OCc1nccc(OC)c1OC] |
| 8 | 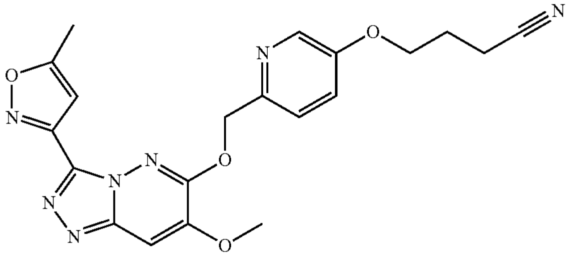 [SMILES: COc1cc2nnc(-c3cc(C)on3)n2nc1OCc1ccc(OCCCC#N)cn1] |
| 9 | 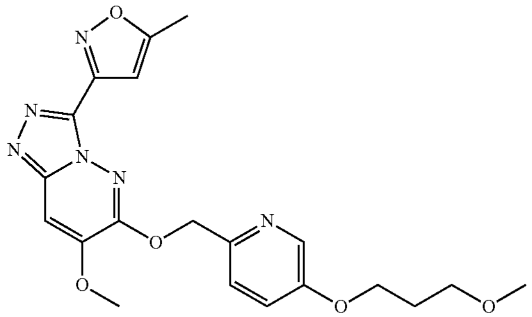 [SMILES: COCCCOc1ccc(COc2nn3c(-c4cc(C)on4)nnc3cc2OC)nc1] |

-continued
| Embodiment | Structure |
|---|---|
| 10 | 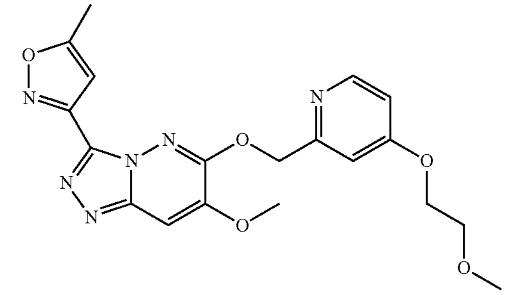 [SMILES: COCCOc1ccnc(COc2nn3c(-c4cc(C)on4)nnc3cc2OC)c1] |
| 11 | 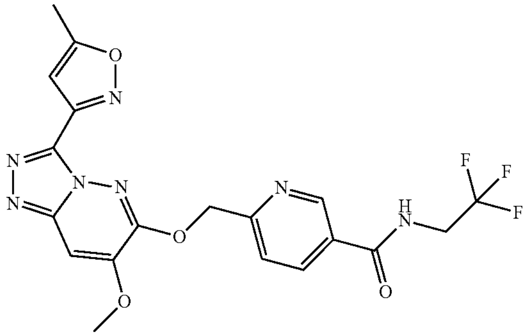 [SMILES: COc1cc2nnc(-c3cc(C)on3)n2nc1OCc1ccc(C(=O)NCC(F)(F)F)cn1] |
| 12 | 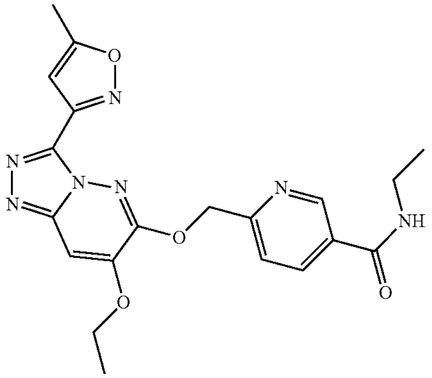 [SMILES: CCNC(=O)c1ccc(COc2nn3c(-c4cc(C)on4)nnc3cc2OCC)nc1] |
| 13 | 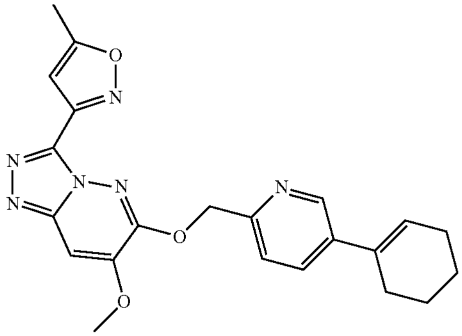 [SMILES: COc1cc2nnc(-c3cc(C)on3)n2nc1OCc1ccc(C2=CCCCC2)cn1] |

-continued
| Embodiment | Structure |
| --- | --- |
| 14 | 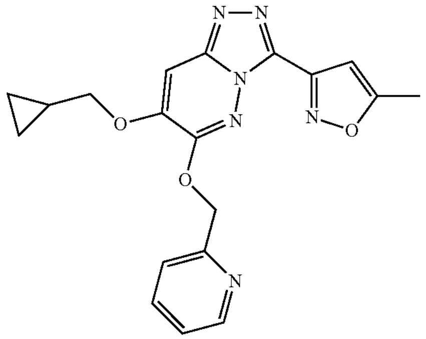 [SMILES: Cc1cc(-c2nnc3cc(OCC4CC4)c(OCc4ccccn4)nn23)no1] |
| 15 | 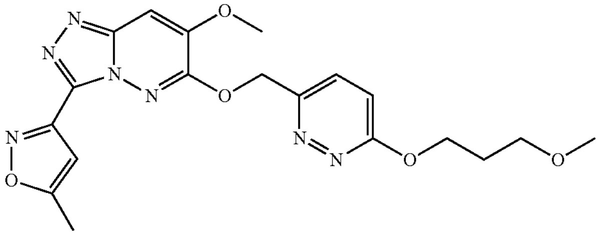 [SMILES: COCCCOc1ccc(COc2nn3c(-c4cc(C)on4)nnc3cc2OC)nn1] |
| 16 | 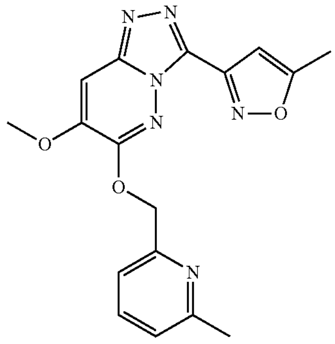 |
| 17 | 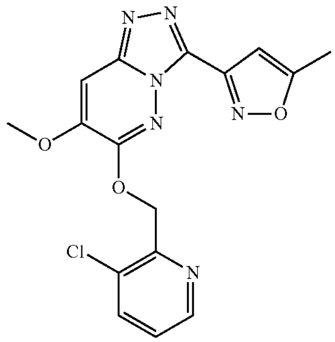 |

-continued
| Embodiment | Structure |
|---|---|
| 18 | 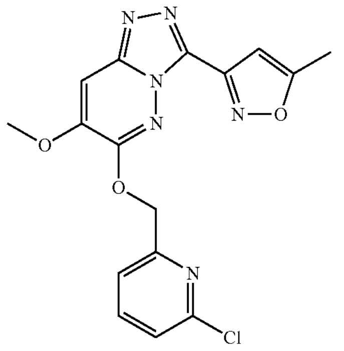 |
| 19 | 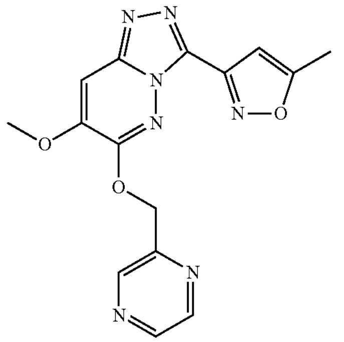 |
| 20 | 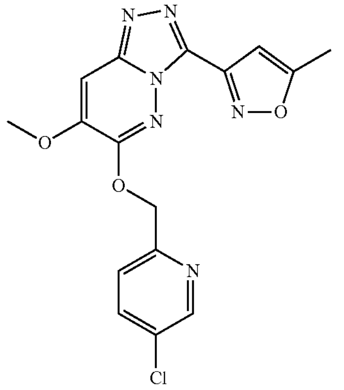 |
| 21 | 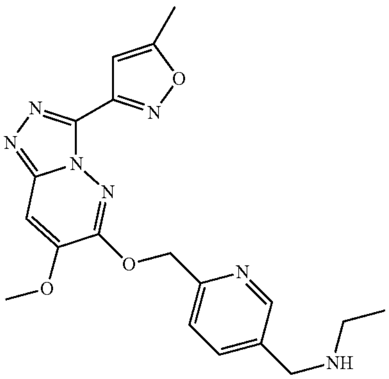 [SMILES: CCNCc1ccc(COc2nn3c(-c4cc(C)on4)nnc3cc2OC)nc1] |

-continued
| Embodiment | Structure |
| --- | --- |
| 22 | 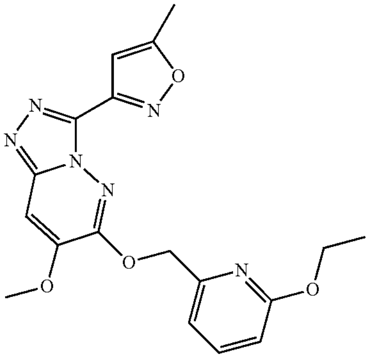 [SMILES: CCOc1cccc(COc2nn3c(-c4cc(C)on4)nnc3cc2OC)n1] |
| 23 | 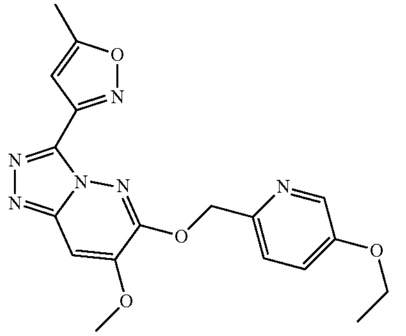 [SMILES: CCOc1ccc(COc2nn3c(-c4cc(C)on4)nnc3cc2OC)nc1] |
| 24 | 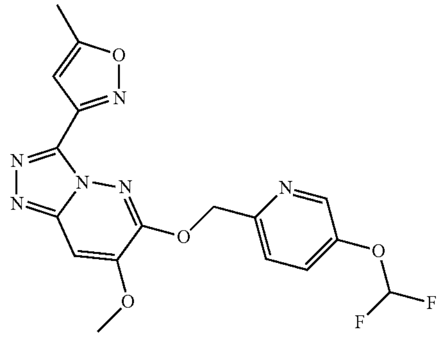 [SMILES: COc1cc2nnc(-c3cc(C)on3)n2nc1OCc1ccc(OC(F)F)cn1] |
| 25 | 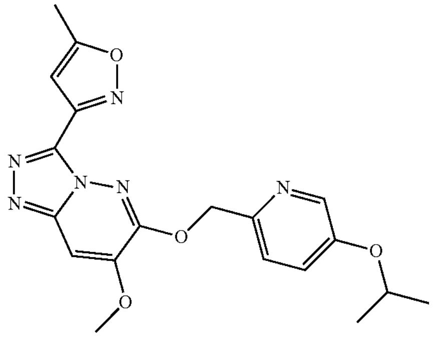 [SMILES: COc1cc2nnc(-c3cc(C)on3)n2nc1OCc1ccc(OC(C)C)cn1] |

-continued
| Embodiment | Structure |
|---|---|
| 26 | 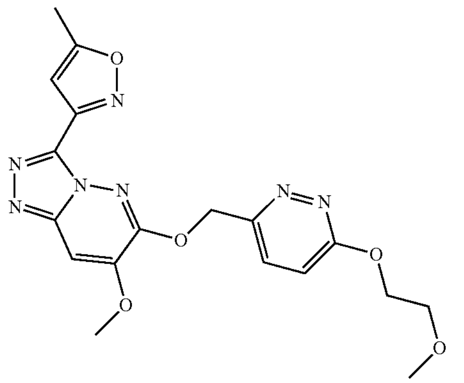 [SMILES: COCCOc1ccc(COc2nn3c(-c4cc(C)on4)nnc3cc2OC)nn1] |
| 27 | 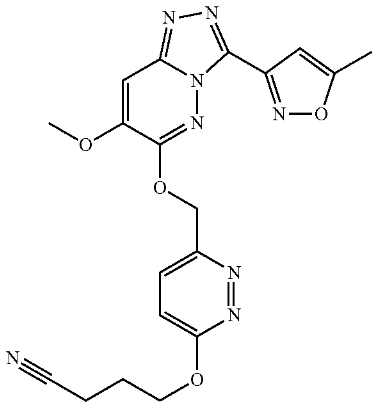 [SMILES: COc1cc2nnc(-c3cc(C)on3)n2nc1OCc1ccc(OCCCC#N)nn1] |
| 28 | 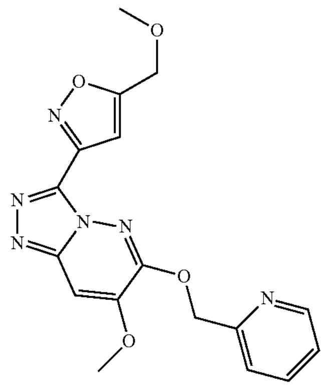 [SMILES: COCc1cc(-c2nnc3cc(OC)c(OCc4ccccn4)nn23)no1] |
| 29 | 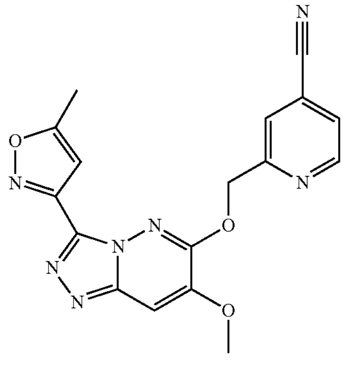 [SMILES: COc1cc2nnc(-c3cc(C)on3)n2nc1OCc1cc(C#N)ccn1] |

-continued
| Embodiment | Structure |
|---|---|
| 30 | 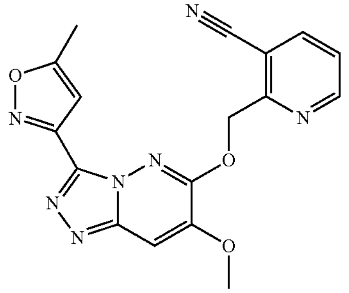 [SMILES: COc1cc2nnc(-c3cc(C)on3)n2nc1OCc1ncccc1C#N] |
| 31 | 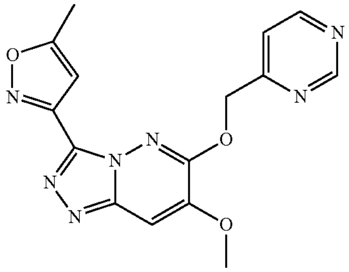 [SMILES: COc1cc2nnc(-c3cc(C)on3)n2nc1OCc1ccncn1] |
| 32 | 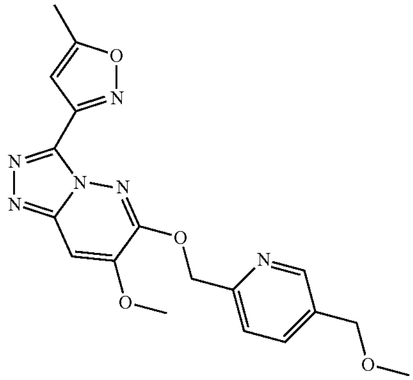 [SMILES: COCc1ccc(COc2nn3c(-c4cc(C)on4)nnc3cc2OC)nc1] |
| 33 | 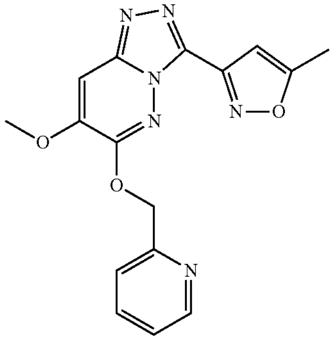 |
| 34 | 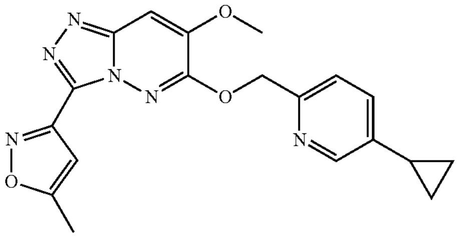 [SMILES: COc1cc2nnc(-c3cc(C)on3)n2nc1OCc1ccc(C2CC2)cn1] |

-continued
| Embodiment | Structure |
| --- | --- |
| 35 | 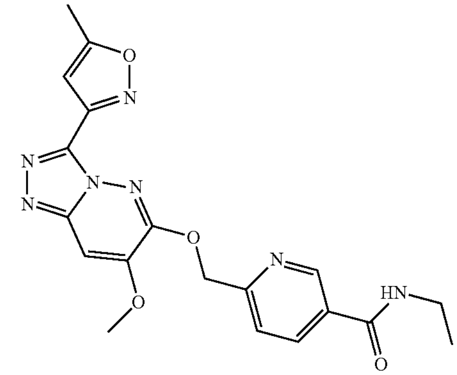 [SMILES: CCNC(=O)c1ccc(COc2nn3c(-c4cc(C)on4)nnc3cc2OC)nc1] |
| 36 | 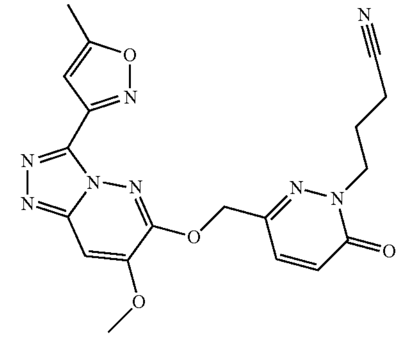 [SMILES: COc1cc2nnc(-c3cc(C)on3)n2nc1OCc1ccc(=O)n(CCCC#N)n1] |
| 37 | 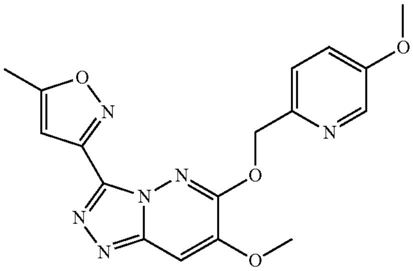 |
| 38 | 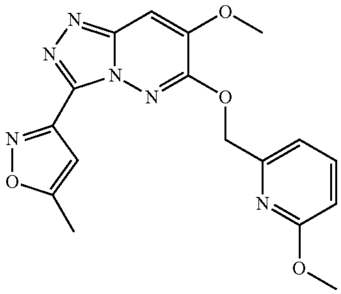 [SMILES: COc1cccc(COc2nn3c(-c4cc(C)on4)nnc3cc2OC)n1] |
| 39 | 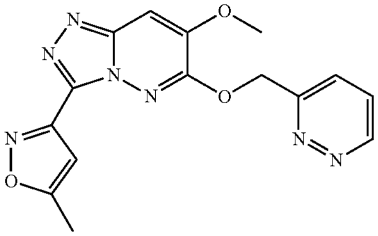 [SMILES: COc1cc2nnc(-c3cc(C)on3)n2nc1OCc1cccnn1] |

-continued
| Embodiment | Structure |
|---|---|
| 40 | 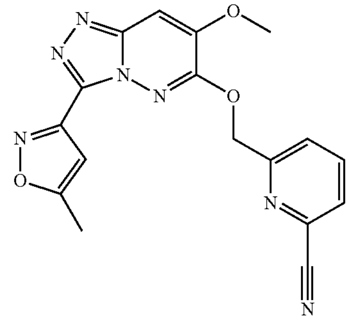 [SMILES: COc1cc2nnc(-c3cc(C)on3)n2nc1OCc1cccc(C#N)n1] |
| 41 | 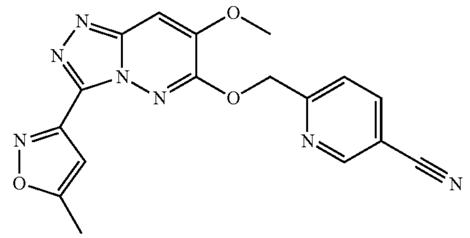 [SMILES: COc1cc2nnc(-c3cc(C)on3)n2nc1OCc1ccc(C#N)cn1] |
| 42 | 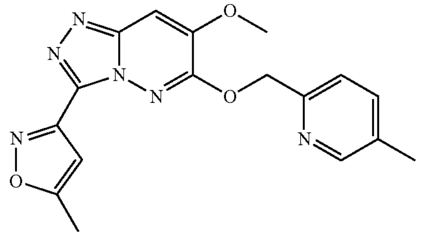 [SMILES: COc1cc2nnc(-c3cc(C)on3)n2nc1OCc1ccc(C)cn1] |
| 43 | 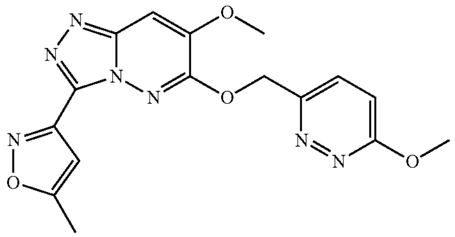 [SMILES: COc1ccc(COc2nn3c(-c4cc(C)on4)nnc3cc2OC)nn1] |
| 44 | 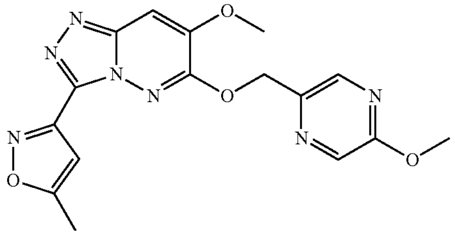 [SMILES: COc1cnc(COc2nn3c(-c4cc(C)on4)nnc3cc2OC)cn1] |
| 45 | 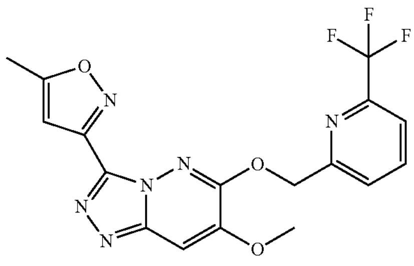 [SMILES: COc1cc2nnc(-c3cc(C)on3)n2nc1OCc1cccc(C(F)(F)F)n1] |

-continued
| Embodiment | Structure |
|---|---|
| 46 | 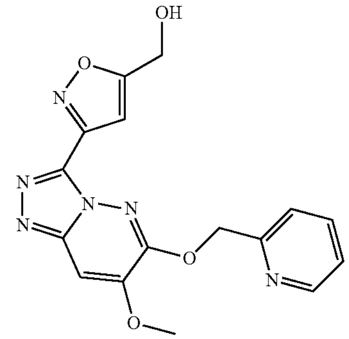 [SMILES: COc1cc2nnc(-c3cc(CO)on3)n2nc1OCc1ccccn1] |
| 47 | 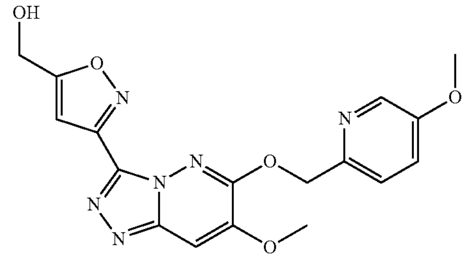 [SMILES: COc1ccc(COc2nn3c(-c4cc(CO)on4)nnc3cc2OC)nc1] |
| 48 | 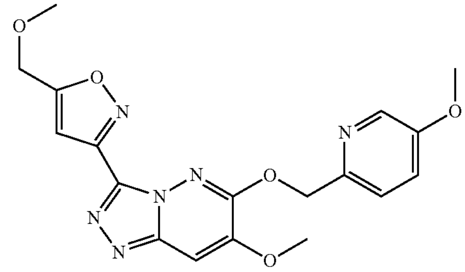 [SMILES: COCc1cc(-c2nnc3cc(OC)c(OCc4ccc(OC)cn4)nn23)no1] |
| 49 | 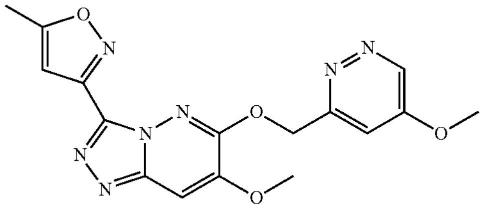 |
| 50 | 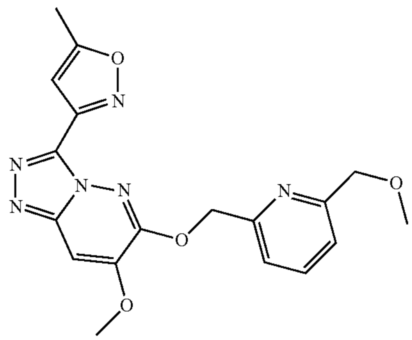 [SMILES: COCc1cccc(COc2nn3c(-c4cc(C)on4)nnc3cc2OC)n1] |

-continued
| Embodiment | Structure |
| --- | --- |
| 51 | 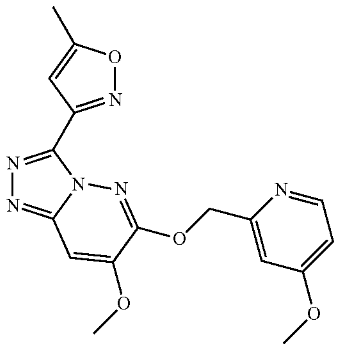 [SMILES: COc1ccnc(COc2nn3c(-c4cc(C)on4)nnc3cc2OC)c1] |
| 52 | 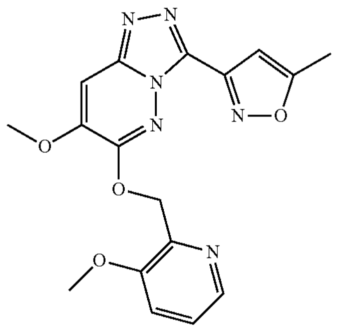 |
| 53 | 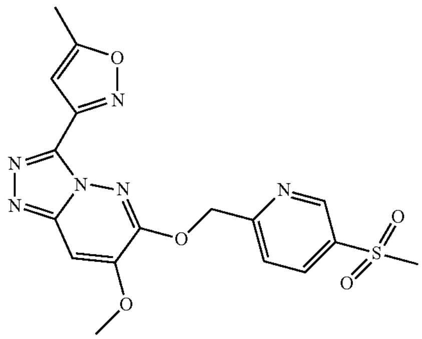 [SMILES: COc1cc2nnc(-c3cc(C)on3)n2nc1OCc1ccc(S(C)(=O)=O)cn1] |
| 54 | 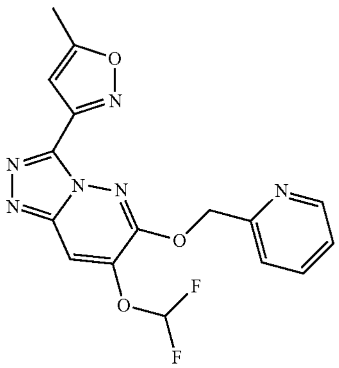 [SMILES: Cc1cc(-c2nnc3cc(OC(F)F)c(OCc4ccccn4)nn23)no1] |

-continued
| Embodiment | Structure |
|---|---|
| 55 | 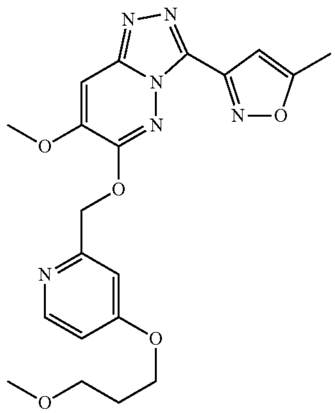 |
| 56 | 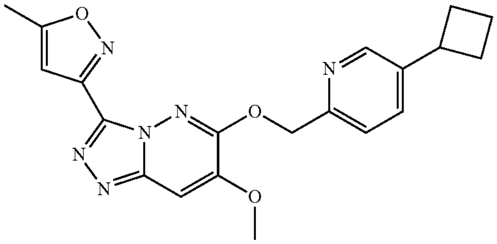 [SMILES: COc1cc2nnc(-c3cc(C)on3)n2nc1OCc1ccc(C2CCC2)cn1] |
| 57 | 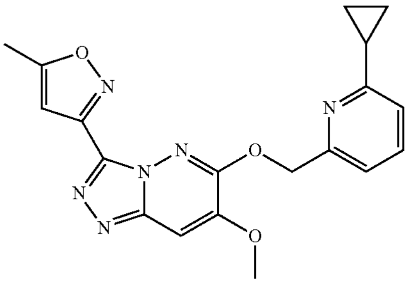 [SMILES: COc1cc2nnc(-c3cc(C)on3)n2nc1OCc1cccc(C2CC2)n1] |
| 58 | 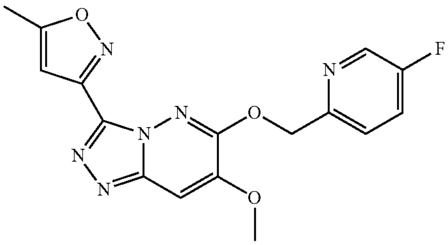 [SMILES: COc1cc2nnc(-c3cc(C)on3)n2nc1OCc1ccc(F)cn1] |
| 59 | 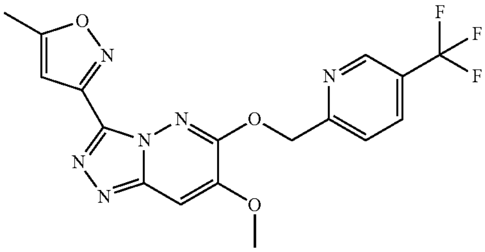 [SMILES: COc1cc2nnc(-c3cc(C)on3)n2nc1OCc1ccc(C(F)(F)F)cn1] |

-continued
| Embodiment | Structure |
|---|---|
| 60 | 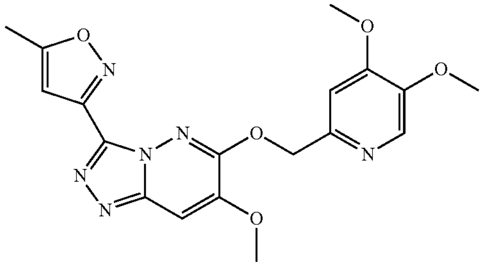 |
| 61 | 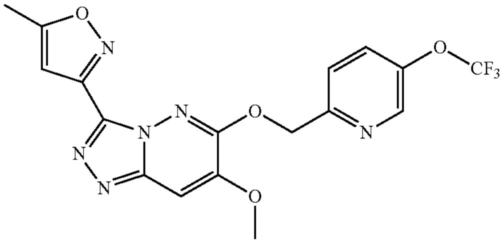 [SMILES: COc1cc2nnc(-c3cc(C)on3)n2nc1OCc1ccc(OC(F)(F)F)cn1] |
| 62 | 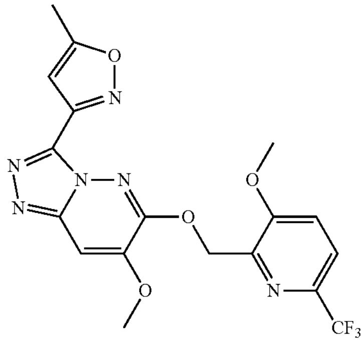 [SMILES: COc1ccc(C(F)(F)F)nc1COc1nn2c(-c3cc(C)on3)nnc2cc1OC] |
| 63 | 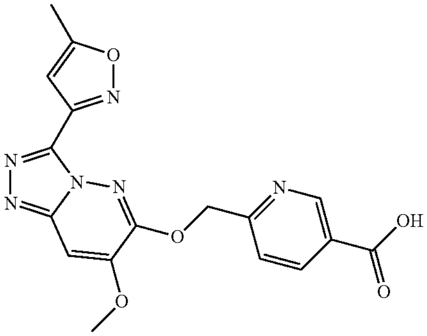 [SMILES: COc1cc2nnc(-c3cc(C)on3)n2nc1OCc1ccc(C(=O)O)cn1] |
| 64 | 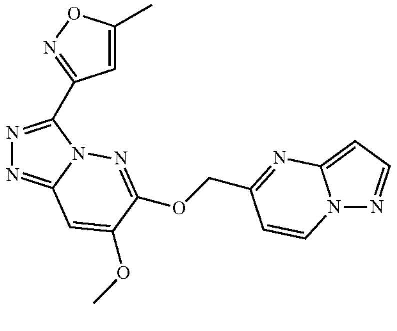 [SMILES: COc1cc2nnc(-c3cc(C)on3)n2nc1OCc1ccn2nccc2n1] |

-continued
| Embodiment | Structure |
| --- | --- |
| 65 | 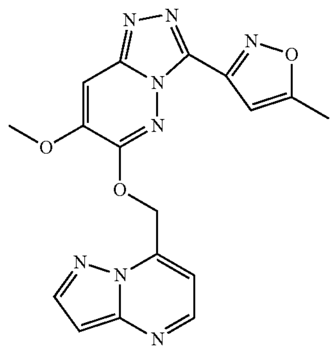 |
| 66 | 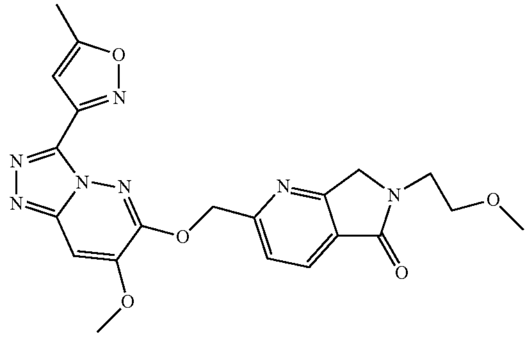 [SMILES: COCCN1Cc2nc(COc3nn4c(-c5cc(C)on5)nnc4cc3OC)ccc2C1=O] |
| 67 | 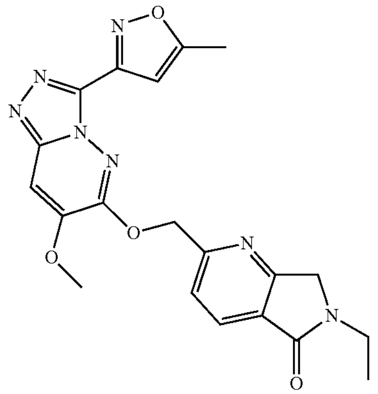 [SMILES: CCN1Cc2nc(COc3nn4c(-c5cc(C)on5)nnc4cc3OC)ccc2C1=O] |
| 68 | 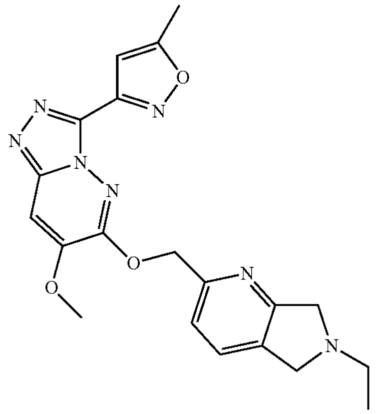 [SMILES: CCN1Cc2ccc(COc3nn4c(-c5cc(C)on5)nnc4cc3OC)nc2C1] |

-continued
| Embodiment | Structure |
|---|---|
| 69 | 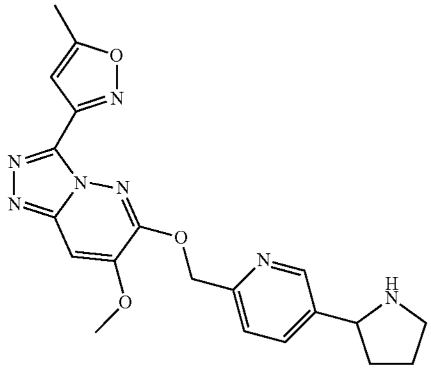 [SMILES: COc1cc2nnc(-c3cc(C)on3)n2nc1OCc1ccc(C2CCCN2)cn1] |
| 70 | 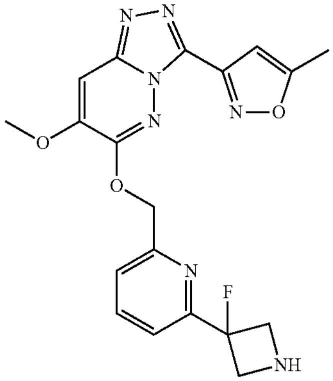 |
| 71 | 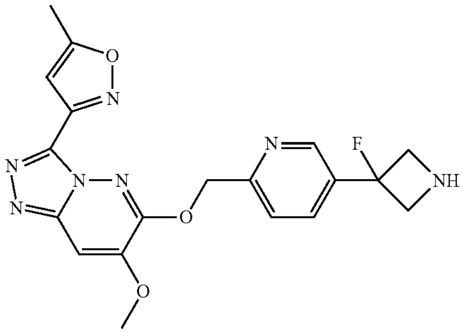 [SMILES: COc1cc2nnc(-c3cc(C)on3)n2nc1OCc1ccc(C2(F)CNC2)cn1] |
| 72 | 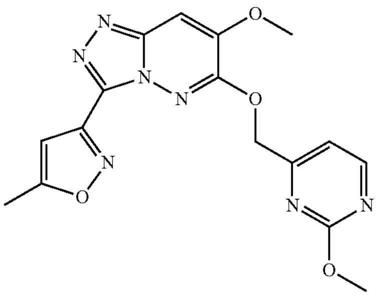 |

-continued
| Embodiment | Structure |
|---|---|
| 73 | 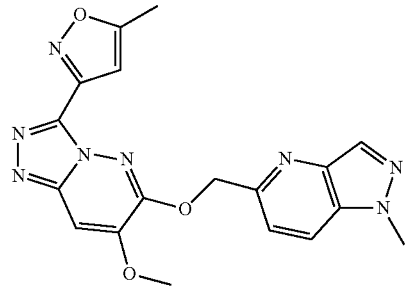 [SMILES: COc1cc2nnc(-c3cc(C)on3)n2nc1OCc1ccc2c(cnn2C)n1] |
| 74 | 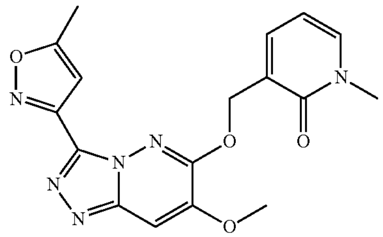 [SMILES: COc1cc2nnc(-c3cc(C)on3)n2nc1OCc1cccn(C)c1=O] |
| 75 | 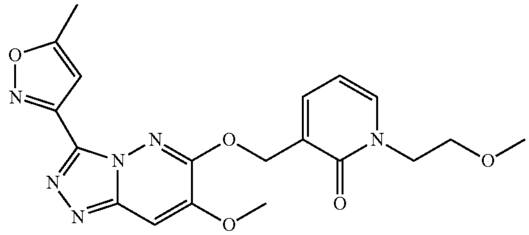 [SMILES: COCCn1cccc(COc2nn3c(-c4cc(C)on4)nnc3cc2OC)c1=O] |
| 76 | 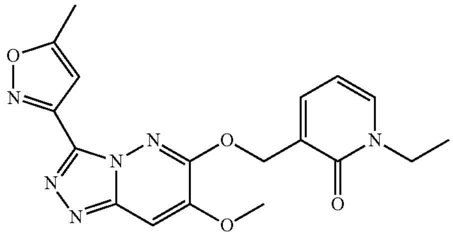 [SMILES: CCn1cccc(COc2nn3c(-c4cc(C)on4)nnc3cc2OC)c1=O] |
| 77 | 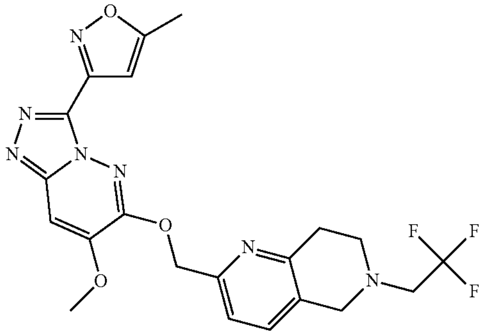 [SMILES: COc1cc2nnc(-c3cc(C)on3)n2nc1OCc1ccc2c(n1)CCN(CC(F)(F)F)C2] |

-continued
| Embodiment | Structure |
| --- | --- |
| 78 | 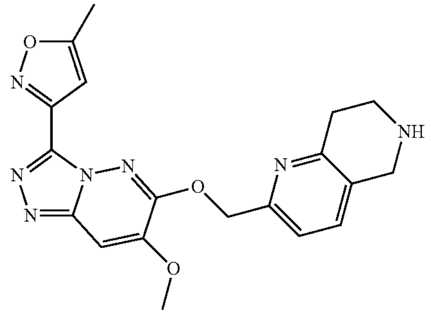 [SMILES: COc1cc2nnc(-c3cc(C)on3)n2nc1OCc1ccc2c(n1)CCNC2] |
| 79 | 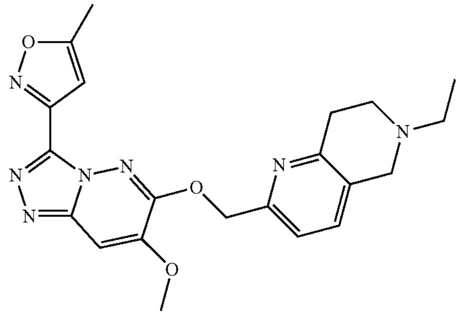 [SMILES: CCN1CCc2nc(COc3nn4c(-c5cc(C)on5)nnc4cc3OC)ccc2C1] |
| 80 | 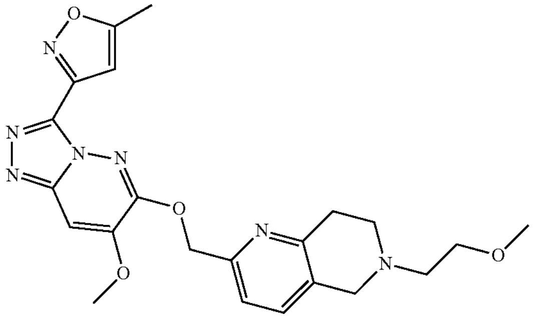 [SMILES: COCCN1CCc2nc(COc3nn4c(-c5cc(C)on5)nnc4cc3OC)ccc2C1] |
| 81 | 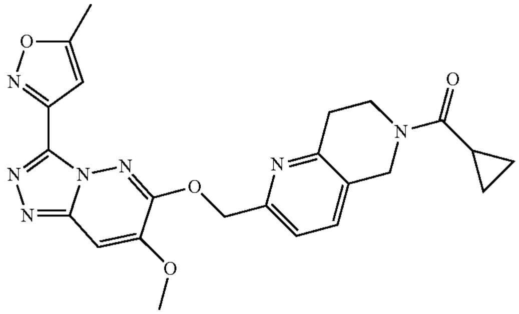 [SMILES: COc1cc2nnc(-c3cc(C)on3)n2nc1OCc1ccc2c(n1)CCN(C(=O)C1CC1)C2] |
| 82 | 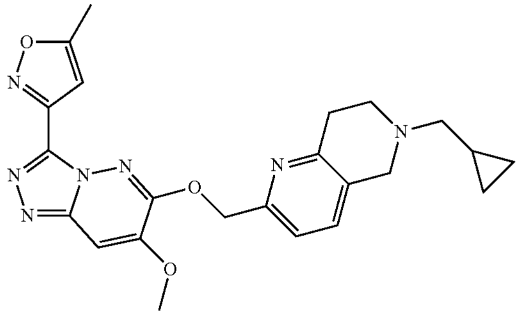 [SMILES: COc1cc2nnc(-c3cc(C)on3)n2nc1OCc1ccc2c(n1)CCN(CC1CC1)C2]

-continued
| Embodiment | Structure |
|---|---|
| 83 | 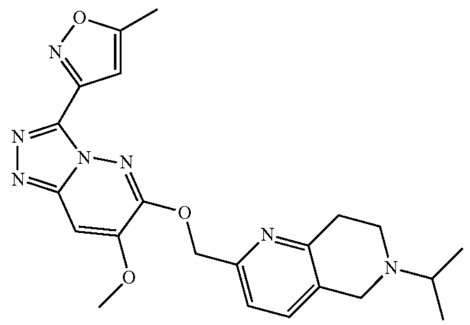 [SMILES: COc1cc2nnc(-c3cc(C)on3)n2nc1OCc1ccc2c(n1)CCN(C(C)C)C2] |
| 84 | 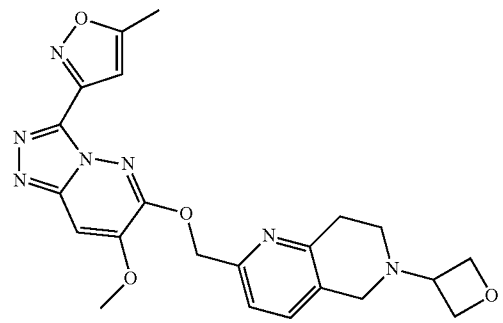 [SMILES: COc1cc2nnc(-c3cc(C)on3)n2nc1OCc1ccc2c(n1)CCN(C1COC1)C2] |
| 85 | 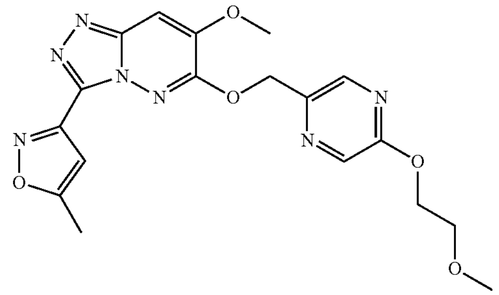 [SMILES: COCCOc1cnc(COc2nn3c(-c4cc(C)on4)nnc3cc2OC)cn1] |
| 86 | 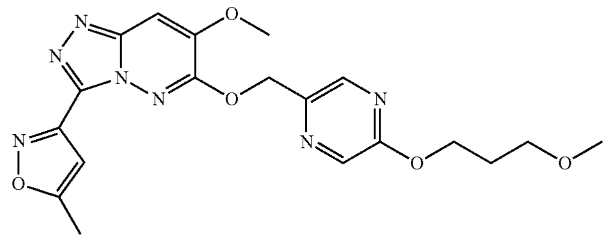 [SMILES: COCCCOc1cnc(COc2nn3c(-c4cc(C)on4)nnc3cc2OC)cn1] |
| 87 | 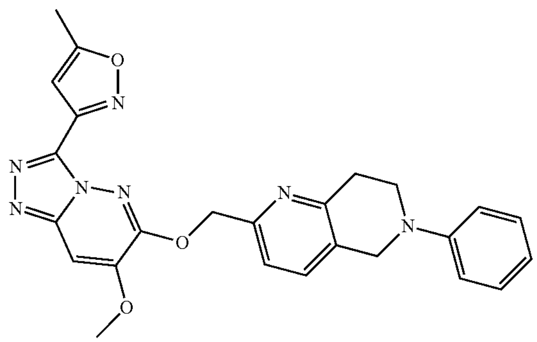 [SMILES: COc1cc2nnc(-c3cc(C)on3)n2nc1OCc1ccc2c(n1)CCN(c1ccccc1)C2] |

-continued
| Embodiment | Structure |
| --- | --- |
| 88 | 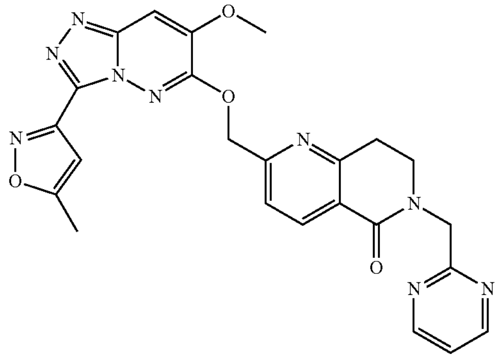 [SMILES: COc1cc2nnc(-c3cc(C)on3)n2nc1OCc1ccc2c(n1)CCN(Cc1ncccn1)C2=O] |
| 89 | 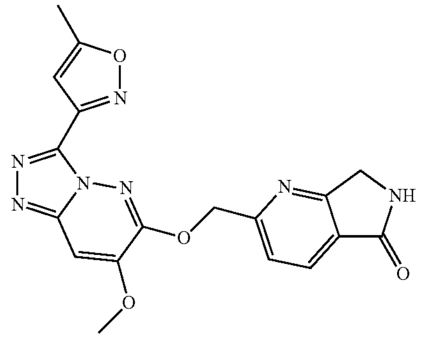 [SMILES: COc1cc2nnc(-c3cc(C)on3)n2nc1OCc1ccc2c(n1)CNC2=O] |
| 90 | 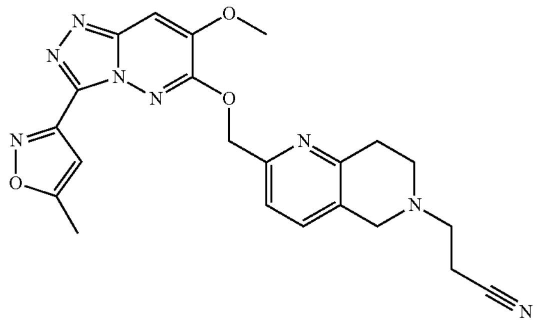 [SMILES: COc1cc2nnc(-c3cc(C)on3)n2nc1OCc1ccc2c(n1)CCN(CCC#N)C2] |
| 91 | 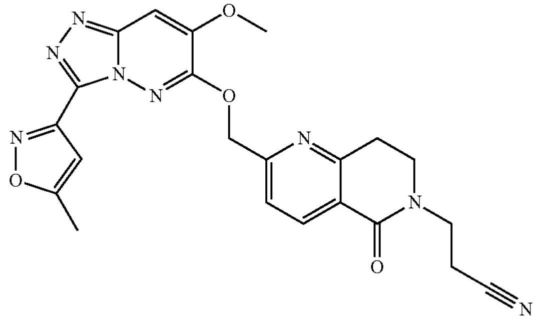 [SMILES: COc1cc2nnc(-c3cc(C)on3)n2nc1OCc1ccc2c(n1)CCN(CCC#N)C2=O] |

-continued
| Embodiment | Structure |
|---|---|
| 92 | 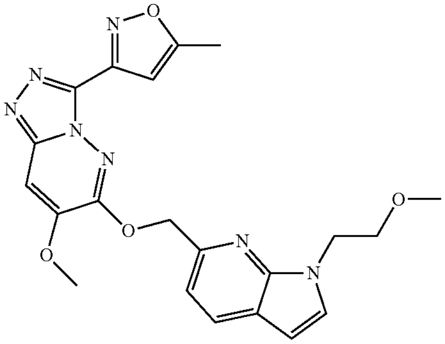 [SMILES: COCCn1ccc2ccc(COc3nn4c(-c5cc(C)on5)nnc4cc3OC)nc21] |
| 93 | 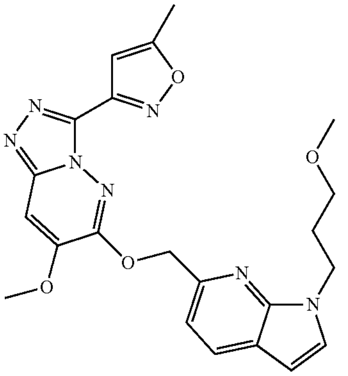 |
| 94 | 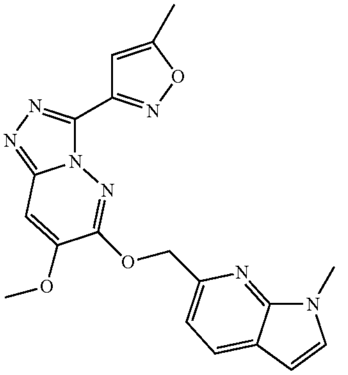 |
| 95 | 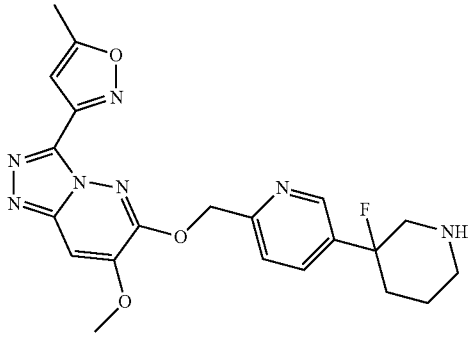 [SMILES: COc1cc2nnc(-c3cc(C)on3)n2nc1OCc1ccc(C2(F)CCCNC2)cn1] |

-continued
| Embodiment | Structure |
| --- | --- |
| 96 | 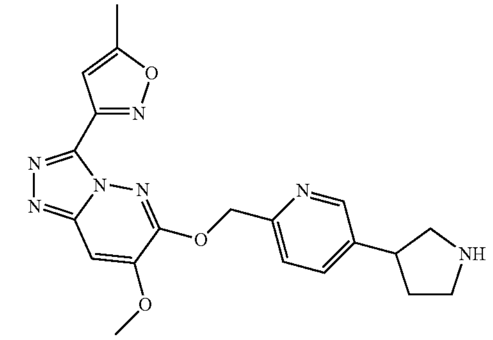 [SMILES: COc1cc2nnc(-c3cc(C)on3)n2nc1OCc1ccc(C2CCNC2)cn1] |
| 97 | 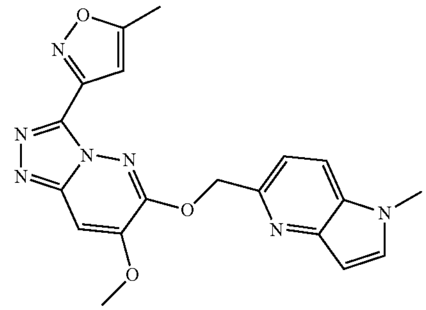 [SMILES: COc1cc2nnc(-c3cc(C)on3)n2nc1OCc1ccc2c(ccn2C)n1] |
| 98 | 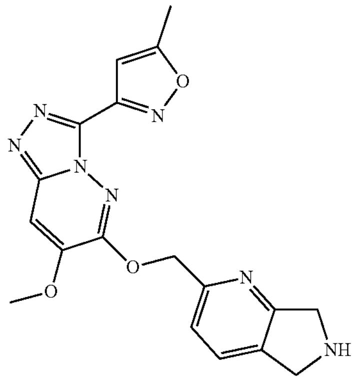 [SMILES: COc1cc2nnc(-c3cc(C)on3)n2nc1OCc1ccc2c(n1)CNC2] |
| 99 | 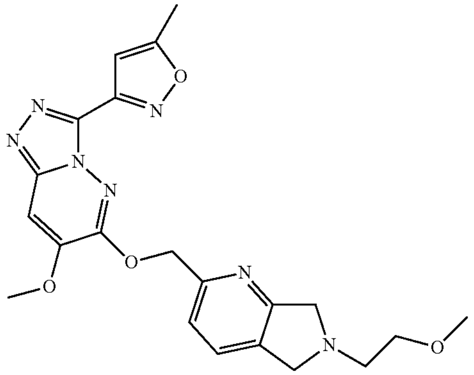 |

-continued
| Embodiment | Structure |
| --- | --- |
| 100 | 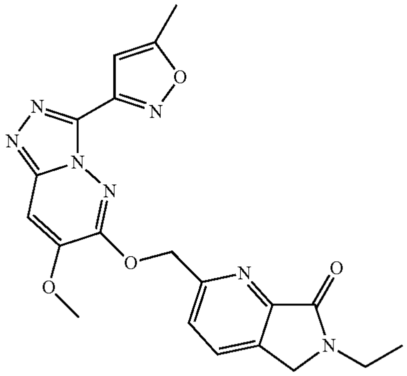 [SMILES: CCN1Cc2ccc(COc3nn4c(-c5cc(C)on5)nnc4cc3OC)nc2C1=O] |
| 101 | 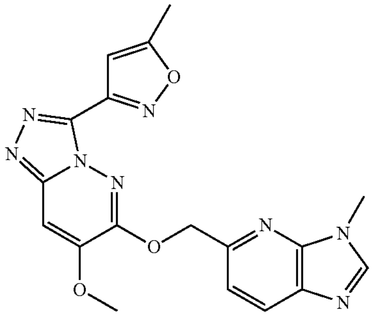 [SMILES: COc1cc2nnc(-c3cc(C)on3)n2nc1OCc1ccc2ncn(C)c2n1] |
| 102 | 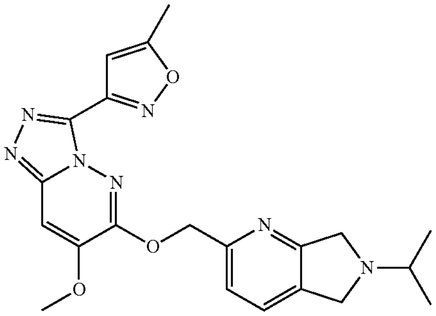 [SMILES: COc1cc2nnc(-c3cc(C)on3)n2nc1OCc1ccc2c(n1)CN(C(C)C)C2] |
| 103 | 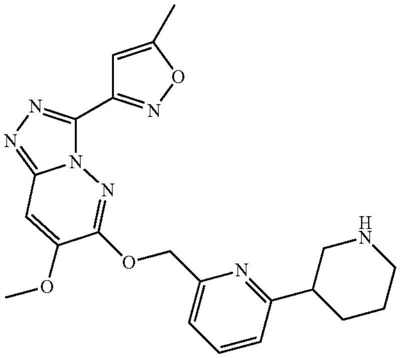 [SMILES: COc1cc2nnc(-c3cc(C)on3)n2nc1OCc1cccc(C2CCCNC2)n1] |

-continued
| Embodiment | Structure |
|---|---|
| 104 | 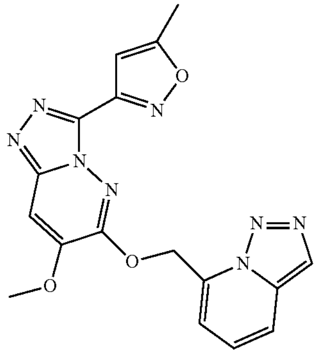 [SMILES: COc1cc2nnc(-c3cc(C)on3)n2nc1OCc1cccc2cnnn12] |
| 105 | 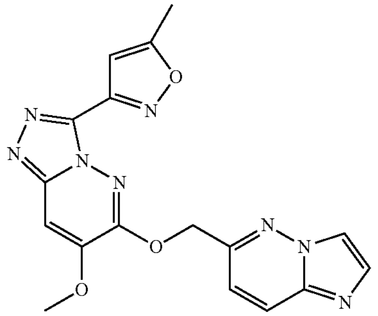 [SMILES: COc1cc2nnc(-c3cc(C)on3)n2nc1OCc1ccc2nccn2n1] |
| 106 | 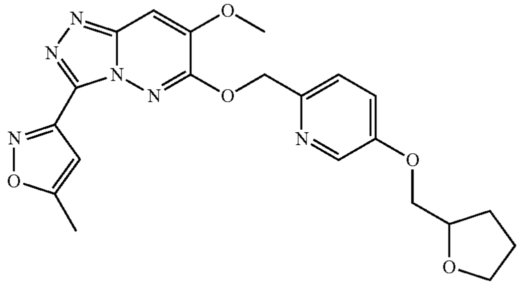 [SMILES: COc1cc2nnc(-c3cc(C)on3)n2nc1OCc1ccc(OCC2CCCO2)cn1] |
| 107 | 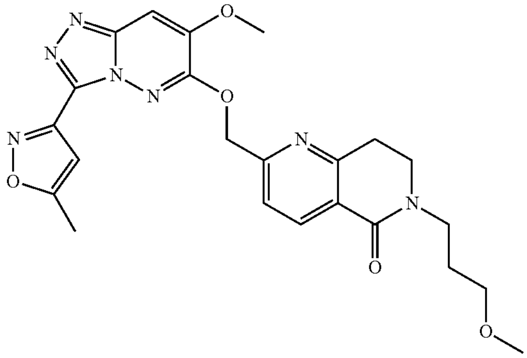 [SMILES: COCCCN1CCc2nc(COc3nn4c(-c5cc(C)on5)nnc4cc3OC)ccc2C1=O] |

-continued
| Embodiment | Structure |
| --- | --- |
| 108 | 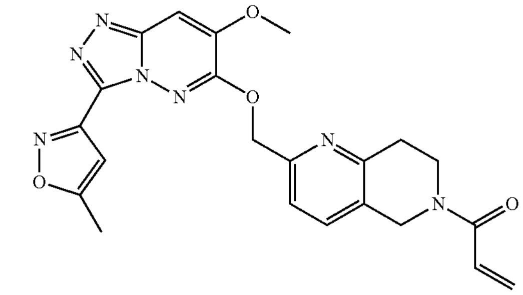 [SMILES: C=CC(=O)N1CCc2nc(COc3nn4c(-c5cc(C)on5)nnc4cc3OC)ccc2C1] |
| 109 | 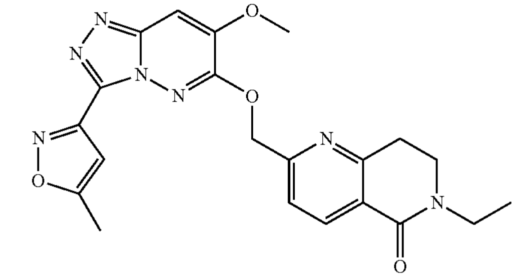 [SMILES: CCN1CCc2nc(COc3nn4c(-c5cc(C)on5)nnc4cc3OC)ccc2C1=O] |
| 110 | 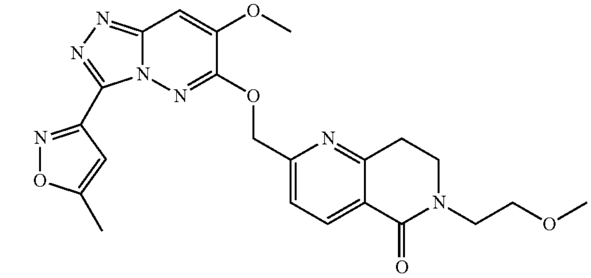 [SMILES: COCCN1CCc2nc(COc3nn4c(-c5cc(C)on5)nnc4cc3OC)ccc2C1=O] |
| 111 | 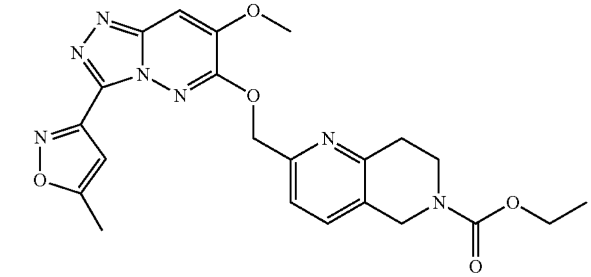 [SMILES: CCOC(=O)N1CCc2nc(COc3nn4c(-c5cc(C)on5)nnc4cc3OC)ccc2C1] |
| 112 | 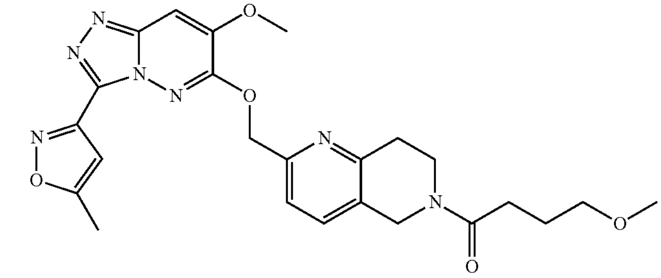 [SMILES: COCCCC(=O)N1CCc2nc(COc3nn4c(-c5cc(C)on5)nnc4cc3OC)ccc2C1] |

-continued
| Embodiment | Structure |
|---|---|
| 113 | 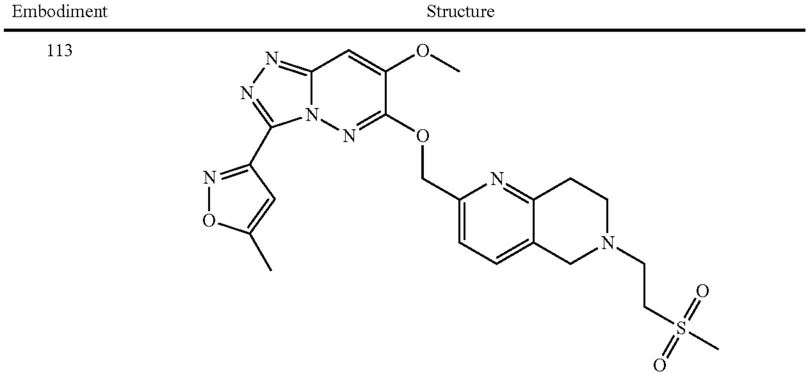 |
| 114 | 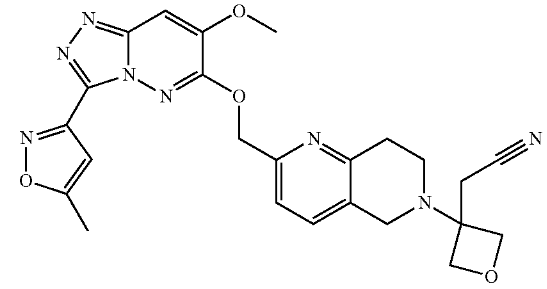 [SMILES: COc1cc2nnc(-c3cc(C)on3)n2nc1OCc1ccc2c(n1)CCN(C1(CC#N)COC1)C2] |
| 115 | 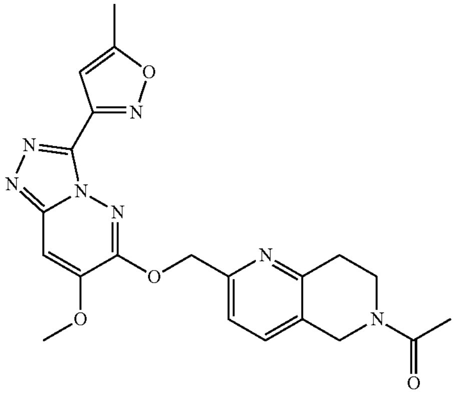 [SMILES: COc1cc2nnc(-c3cc(C)on3)n2nc1OCc1ccc2c(n1)CCN(C(C)=O)C2] |
| 116 | 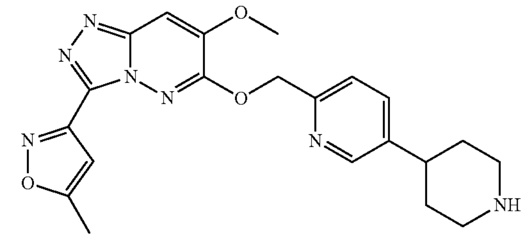 [SMILES: COc1cc2nnc(-c3cc(C)on3)n2nc1OCc1ccc(C2CCNCC2)cn1] |
| 117 | 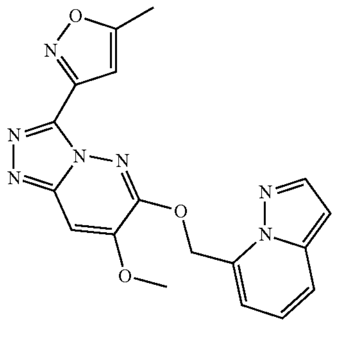 [SMILES: COc1cc2nnc(-c3cc(C)on3)n2nc1OCc1cccc2ccnn12] |

-continued
| Embodiment | Structure |
| --- | --- |
| 118 | 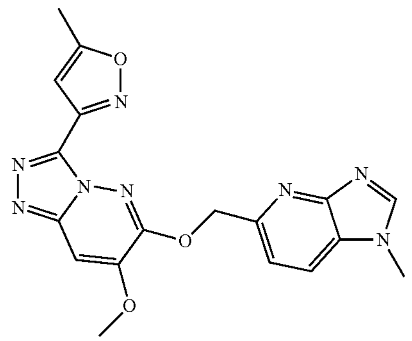 [SMILES: COc1cc2nnc(-c3cc(C)on3)n2nc1OCc1ccc2c(ncn2C)n1] |
| 119 | 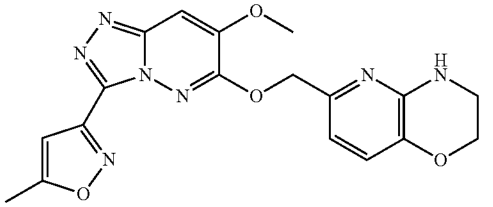 [SMILES: COc1cc2nnc(-c3cc(C)on3)n2nc1OCc1ccc2c(n1)NCCO2] |
| 120 | 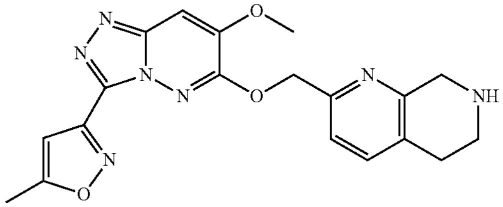 [SMILES: COc1cc2nnc(-c3cc(C)on3)n2nc1OCc1ccc2c(n1)CNCC2] |
| 121 | 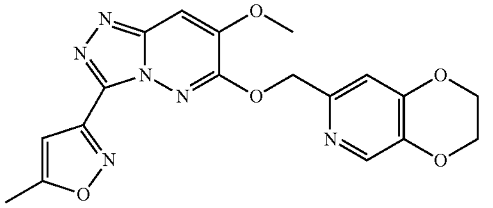 [SMILES: COc1cc2nnc(-c3cc(C)on3)n2nc1OCc1cc2c(cn1)OCCO2] |
| 122 | 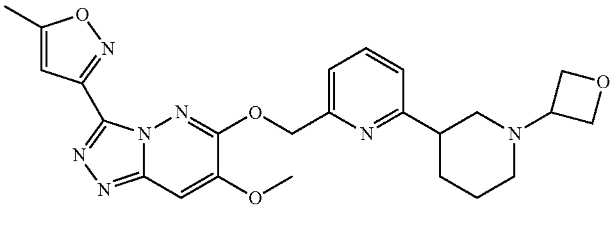 [SMILES: COc1cc2nnc(-c3cc(C)on3)n2nc1OCc1cccc(C2CCCN(C3COC3)C2)n1] |
| 123 | 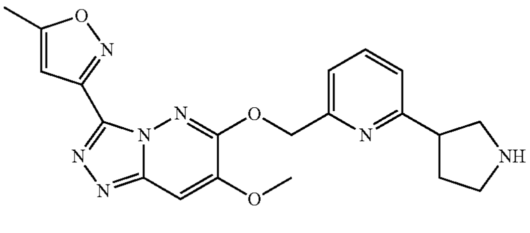 [SMILES: COc1cc2nnc(-c3cc(C)on3)n2nc1OCc1cccc(C2CCNC2)n1] |

-continued
| Embodiment | Structure |
| --- | --- |
| 124 | 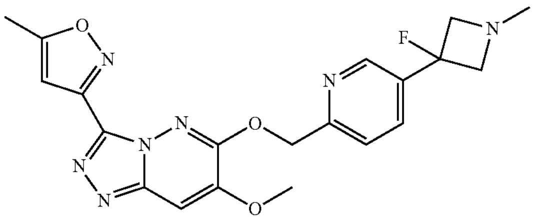 |
| 125 | 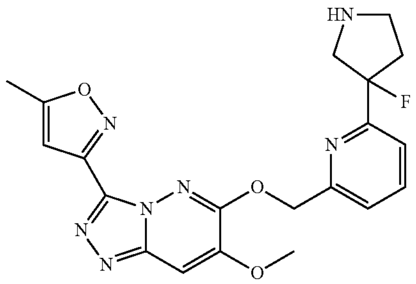 [SMILES: COc1cc2nnc(-c3cc(C)on3)n2nc1OCc1cccc(C2(F)CCNC2)n1] |
| 126 | 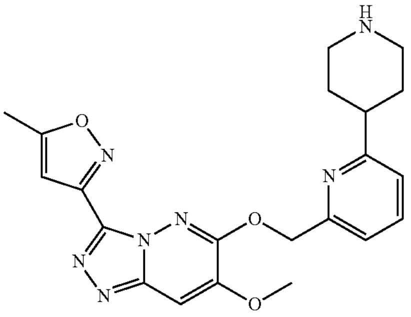 [SMILES: COc1cc2nnc(-c3cc(C)on3)n2nc1OCc1cccc(C2CCNCC2)n1] |
| 127 | 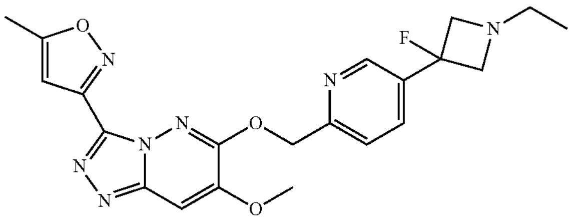 [SMILES: CCN1CC(F)(c2ccc(COc3nn4c(-c5cc(C)on5)nnc4cc3OC)nc2)C1] |
| 128 | 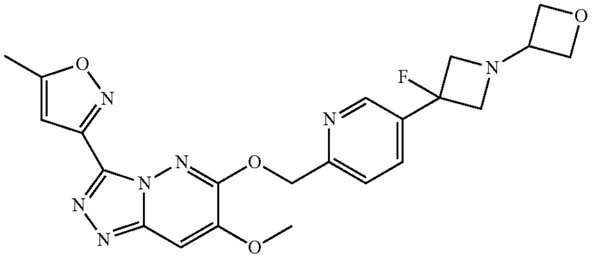 [SMILES: COc1cc2nnc(-c3cc(C)on3)n2nc1OCc1ccc(C2(F)CN(C3COC3)C2)cn1] |

-continued
| Embodiment | Structure |
|---|---|
| 129 | 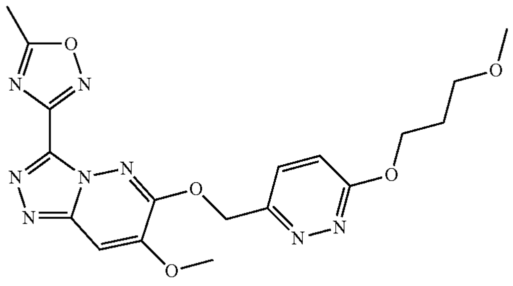 |
| 130 | 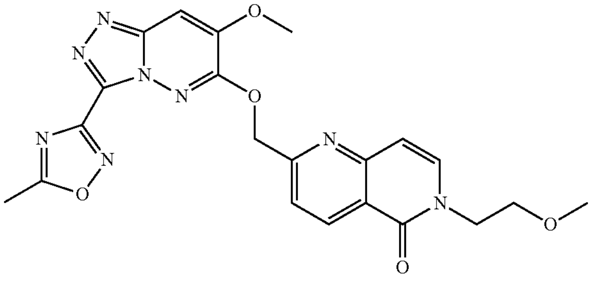 |
| 131 | 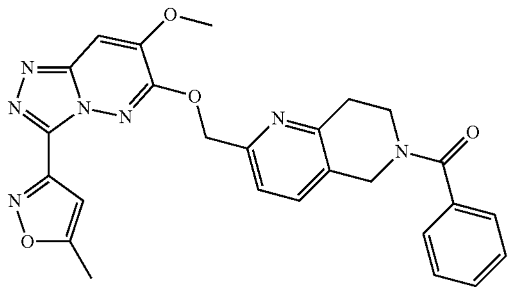 [SMILES: COc1cc2nnc(-c3cc(C)on3)n2nc1OCc1ccc2c(n1)CCN(C(=O)c1ccccc1)C2] |
| 132 | 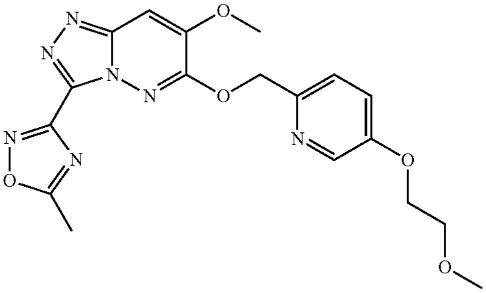 [SMILES: COCCOc1ccc(COc2nn3c(-c4noc(C)n4)nnc3cc2OC)nc1] |
| 133 | 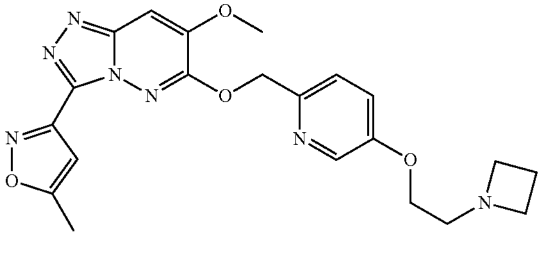 [SMILES: COc1cc2nnc(-c3cc(C)on3)n2nc1OCc1ccc(OCCN2CCC2)cn1] |

-continued
| Embodiment | Structure |
| --- | --- |
| 134 | 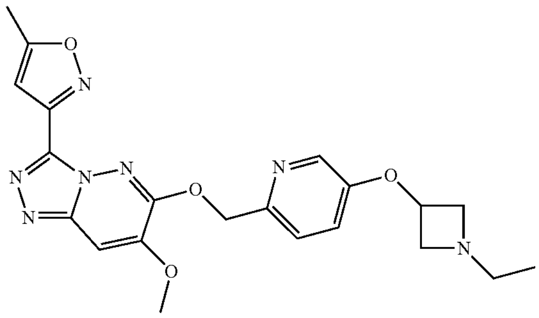 [SMILES: CCN1CC(Oc2ccc(COc3nn4c(-c5cc(C)on5)nnc4cc3OC)nc2)C1] |
| 135 | 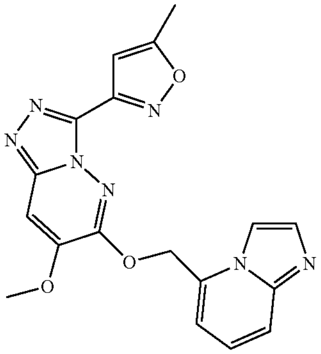 [SMILES: COc1cc2nnc(-c3cc(C)on3)n2nc1OCc1cccc2nccn12] |
| 136 | 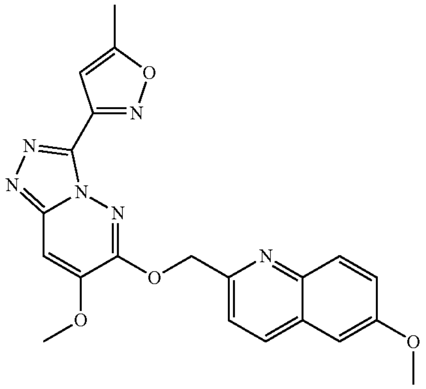 [SMILES: COc1ccc2nc(COc3nn4c(-c5cc(C)on5)nnc4cc3OC)ccc2c1] |
| 137 | 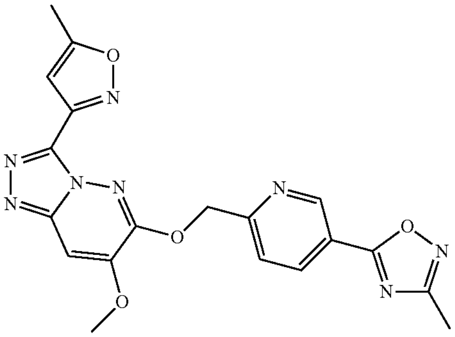 [SMILES: COc1cc2nnc(-c3cc(C)on3)n2nc1OCc1ccc(-c2nc(C)no2)cn1] |

-continued
| Embodiment | Structure |
| --- | --- |
| 138 | 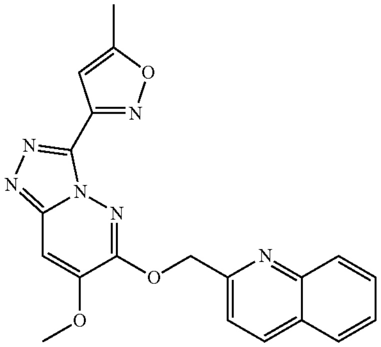 [SMILES: COc1cc2nnc(-c3cc(C)on3)n2nc1OCc1ccc2ccccc2n1] |
| 139 | 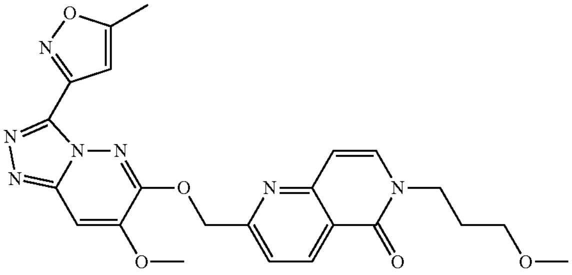 [SMILES: COCCCn1ccc2nc(COc3nn4c(-c5cc(C)on5)nnc4cc3OC)ccc2c1=O] |
| 140 | 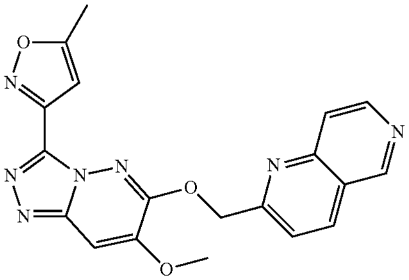 [SMILES: COc1cc2nnc(-c3cc(C)on3)n2nc1OCc1ccc2cnccc2n1] |
| 141 | 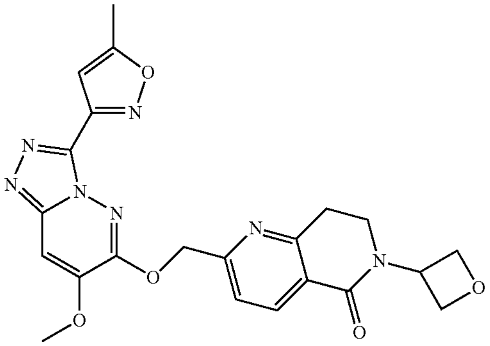 [SMILES: COc1cc2nnc(-c3cc(C)on3)n2nc1OCc1ccc2c(n1)CCN(C1COC1)C2=O] |

-continued
| Embodiment | Structure |
|---|---|
| 142 | 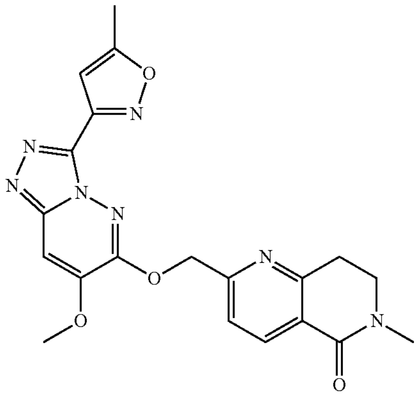 [SMILES: COc1cc2nnc(-c3cc(C)on3)n2nc1OCc1ccc2c(n1)CCN(C)C2=O] |
| 143 | 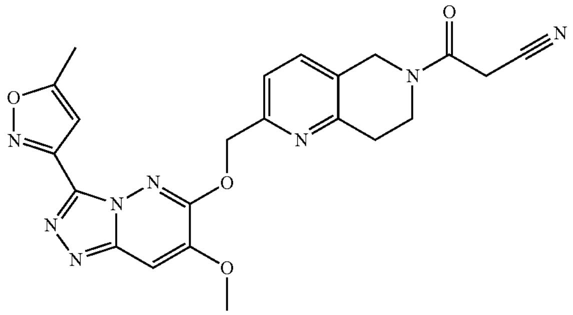 [SMILES: COc1cc2nnc(-c3cc(C)on3)n2nc1OCc1ccc2c(n1)CCN(C(=O)CC#N)C2] |
| 144 | 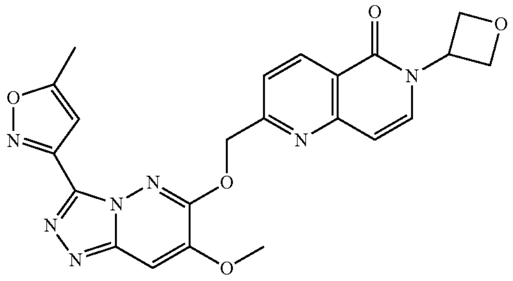 [SMILES: COc1cc2nnc(-c3cc(C)on3)n2nc1OCc1ccc2c(=O)n(C3COC3)ccc2n1] |
| 145 | 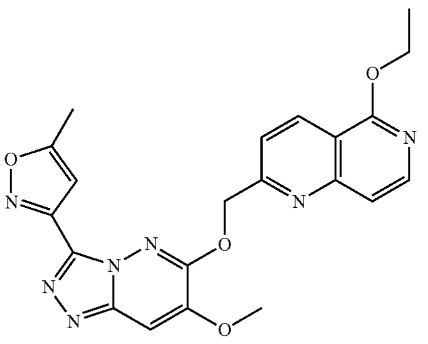 [SMILES: CCOc1nccc2nc(COc3nn4c(-c5cc(C)on5)nnc4cc3OC)ccc12] |

-continued
| Embodiment | Structure |
| --- | --- |
| 146 | 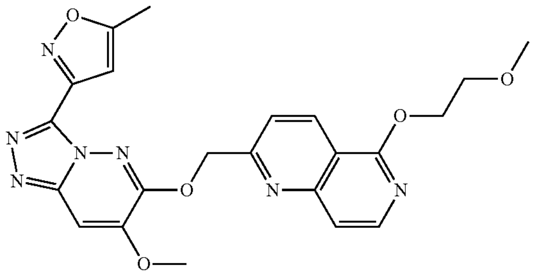 [SMILES: COCCOc1nccc2nc(COc3nn4c(-c5cc(C)on5)nnc4cc3OC)ccc12] |
| 147 | 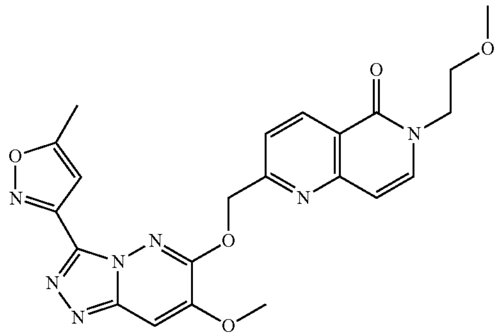 [SMILES: COCCn1ccc2nc(COc3nn4c(-c5cc(C)on5)nnc4cc3OC)ccc2c1=O] |
| 148 | 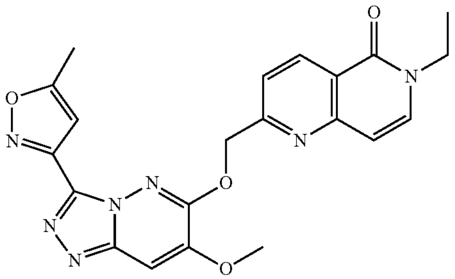 [SMILES: CCn1ccc2nc(COc3nn4c(-c5cc(C)on5)nnc4cc3OC)ccc2c1=O] |
| 149 | 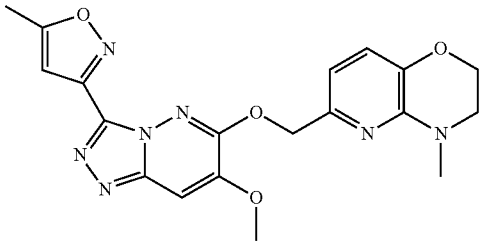 [SMILES: COc1cc2nnc(-c3cc(C)on3)n2nc1OCc1ccc2c(n1)N(C)CCO2] |
| 150 | 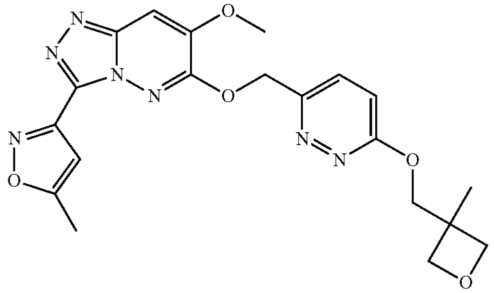 [SMILES: COc1cc2nnc(-c3cc(C)on3)n2nc1OCc1ccc(OCC2(C)COC2)nn1] |

-continued
| Embodiment | Structure |
|---|---|
| 151 | 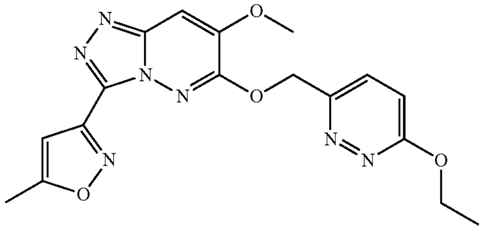 [SMILES: CCOc1ccc(COc2nn3c(-c4cc(C)on4)nnc3cc2OC)nn1] |
| 152 | 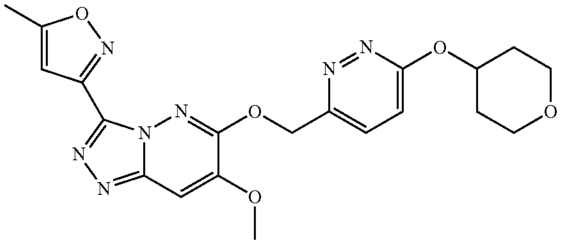 [SMILES: COc1cc2nnc(-c3cc(C)on3)n2nc1OCc1ccc(OC2CCOCC2)nn1] |
| 153 | 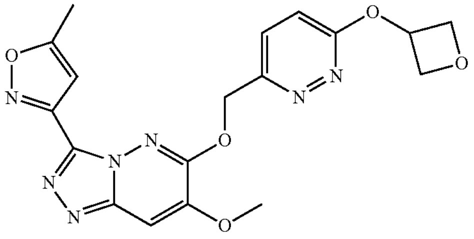 [SMILES: COc1cc2nnc(-c3cc(C)on3)n2nc1OCc1ccc(OC2COC2)nn1] |
| 154 | 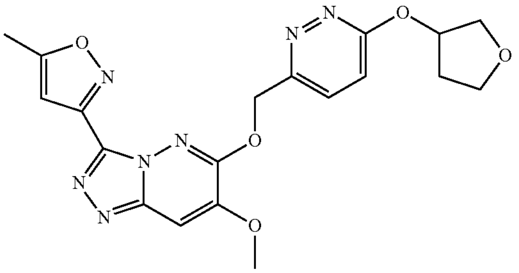 [SMILES: COc1cc2nnc(-c3cc(C)on3)n2nc1OCc1ccc(OC2CCOC2)nn1] |
| 155 | 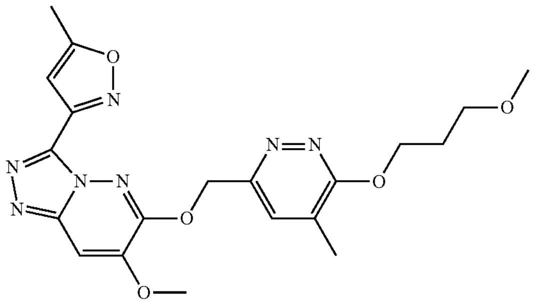 [SMILES: COCCCOc1nnc(COc2nn3c(-c4cc(C)on4)nnc3cc2OC)cc1C] |
| 156 | 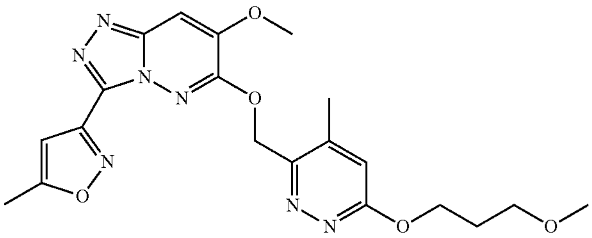 |

-continued
| Embodiment | Structure |
| --- | --- |
| 157 | 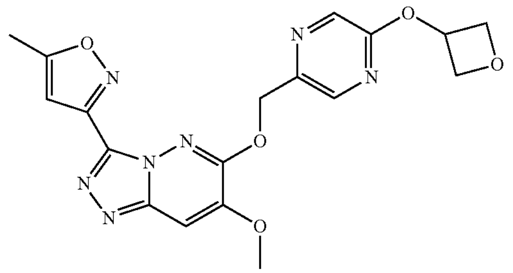 [SMILES: COc1cc2nnc(-c3cc(C)on3)n2nc1OCc1cnc(OC2COC2)cn1] |
| 158 | 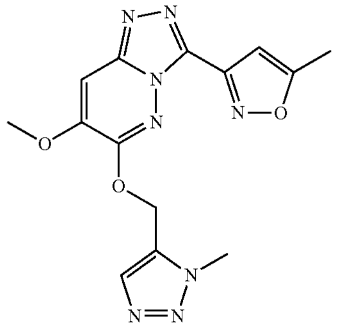 |
| 159 | 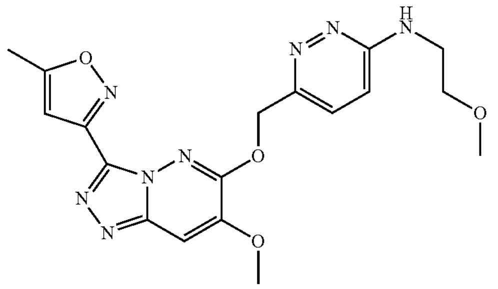 |
| 160 | 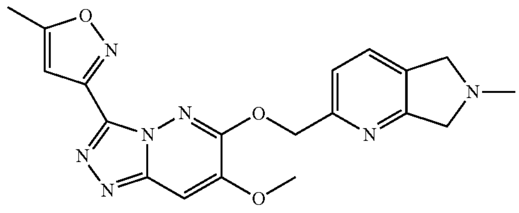 |
| 161 | 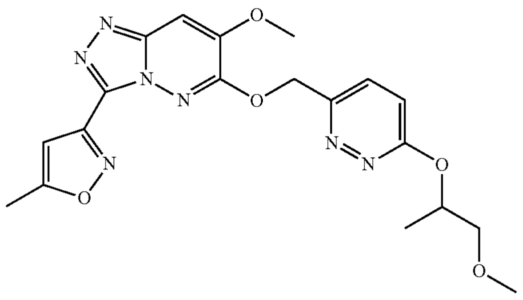 |

-continued
| Embodiment | Structure |
|---|---|
| 162 | 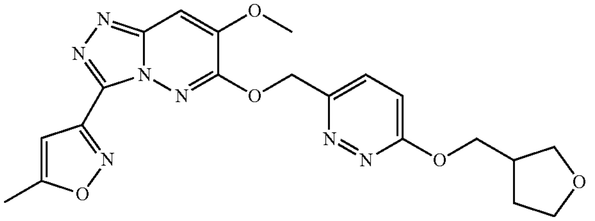 [SMILES: COc1cc2nnc(-c3cc(C)on3)n2nc1OCc1ccc(OCC2CCOC2)nn1] |
| 163 | 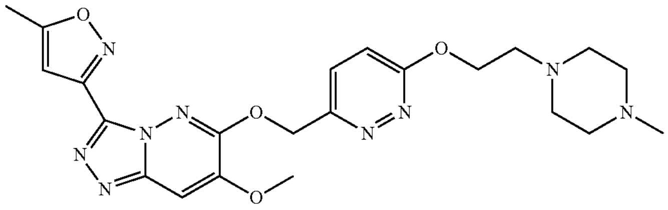 |
| 164 | 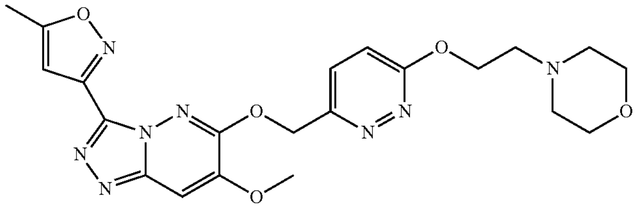 [SMILES: COc1cc2nnc(-c3cc(C)on3)n2nc1OCc1ccc(OCCN2CCOCC2)nn1] |
| 165 | 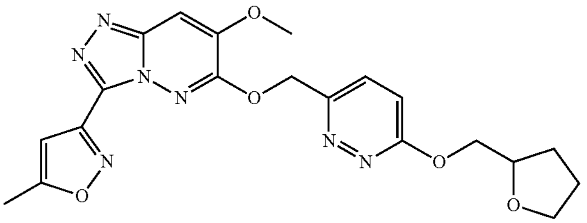 [SMILES: COc1cc2nnc(-c3cc(C)on3)n2nc1OCc1ccc(OCC2CCCO2)nn1] |
| 166 | 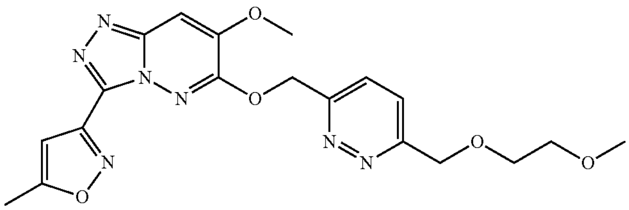 |
| 167 | 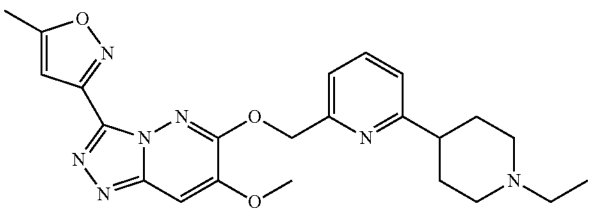 [SMILES: CCN1CCC(c2cccc(COc3nn4c(-c5cc(C)on5)nnc4cc3OC)n2)CC1] |
| 168 | 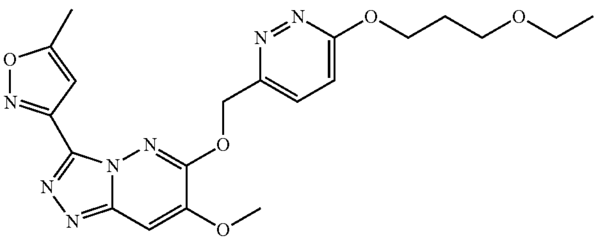 [SMILES: CCOCCCOc1ccc(COc2nn3c(-c4cc(C)on4)nnc3cc2OC)nn1] |

-continued
| Embodiment | Structure |
|---|---|
| 169 | 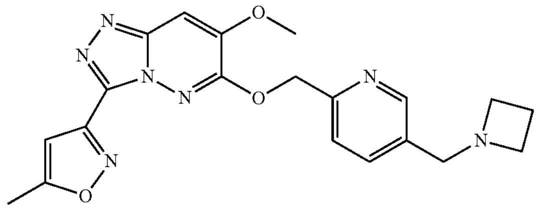 [SMILES: COc1cc2nnc(-c3cc(C)on3)n2nc1OCc1ccc(CN2CCC2)cn1] |
| 170 | 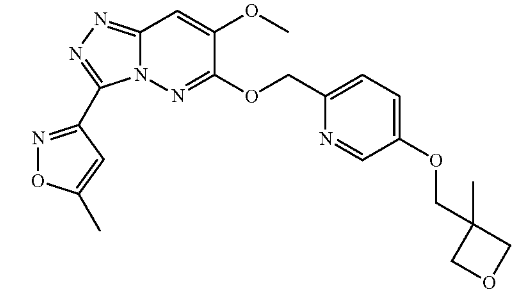 [SMILES: COc1cc2nnc(-c3cc(C)on3)n2nc1OCc1ccc(OCC2(C)COC2)cn1] |
| 171 | 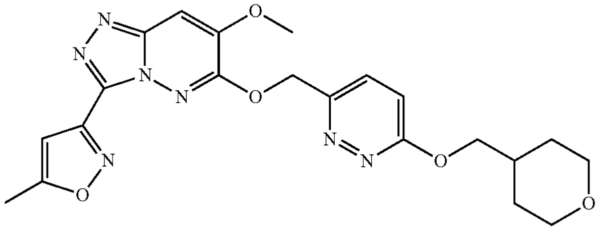 [SMILES: COc1cc2nnc(-c3cc(C)on3)n2nc1OCc1ccc(OCC2CCOCC2)nn1] |
| 172 | 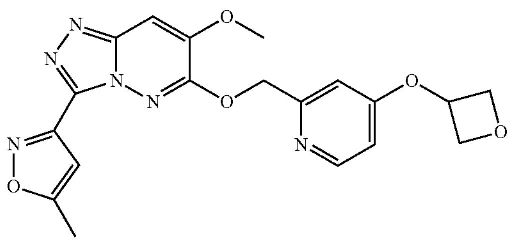 [SMILES: COc1cc2nnc(-c3cc(C)on3)n2nc1OCc1cc(OC2COC2)ccn1] |
| 173 | 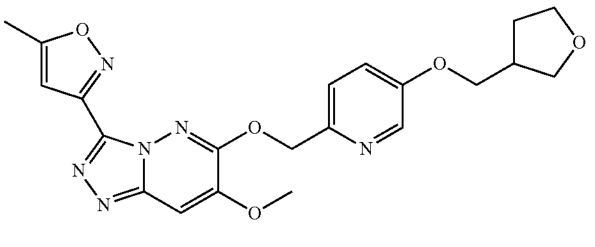 [SMILES: COc1cc2nnc(-c3cc(C)on3)n2nc1OCc1ccc(OCC2CCOC2)cn1] |
| 174 | 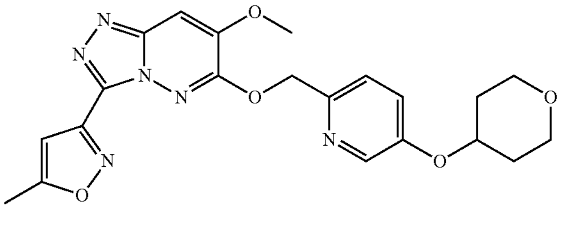 [SMILES: COc1cc2nnc(-c3cc(C)on3)n2nc1OCc1ccc(OC2CCOCC2)cn1] |

-continued
| Embodiment | Structure |
| --- | --- |
| 175 | 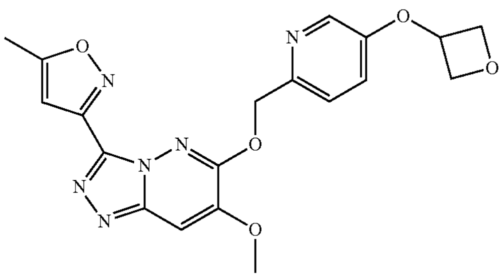 [SMILES: COc1cc2nnc(-c3cc(C)on3)n2nc1OCc1ccc(OC2COC2)cn1] |
| 176 | 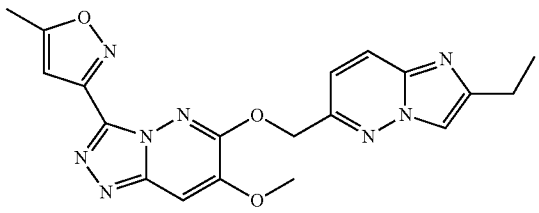 [SMILES: CCc1cn2nc(COc3nn4c(-c5cc(C)on5)nnc4cc3OC)ccc2n1] |
| 177 | 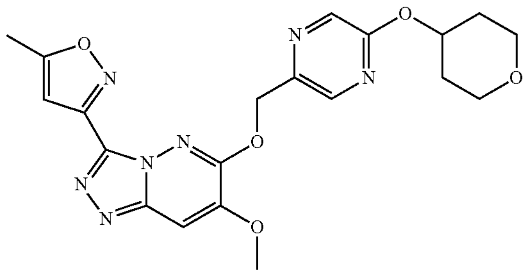 [SMILES: COc1cc2nnc(-c3cc(C)on3)n2nc1OCc1cnc(OC2CCOCC2)cn1] |
| 178 | 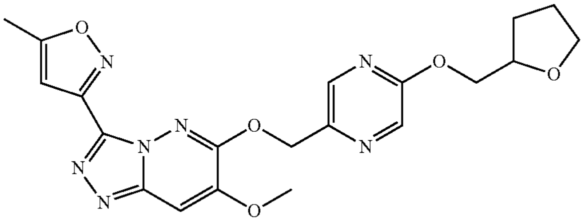 [SMILES: COc1cc2nnc(-c3cc(C)on3)n2nc1OCc1cnc(OCC2CCCO2)cn1] |
| 179 | 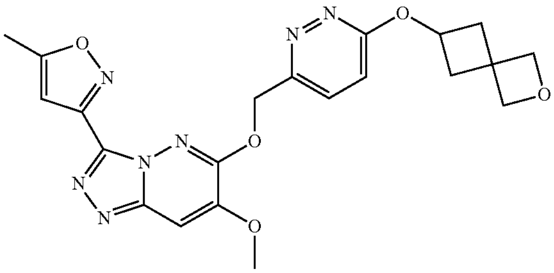 [SMILES: COc1cc2nnc(-c3cc(C)on3)n2nc1OCc1ccc(OC2CC3(COC3)C2)nn1] |
| 180 | 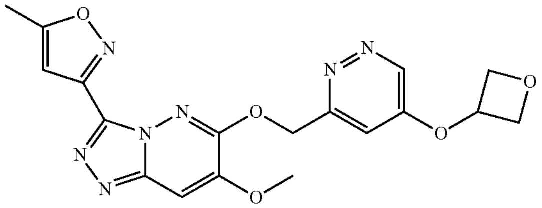 [SMILES: COc1cc2nnc(-c3cc(C)on3)n2nc1OCc1cc(OC2COC2)cnn1] |

-continued
| Embodiment | Structure |
| --- | --- |
| 181 | 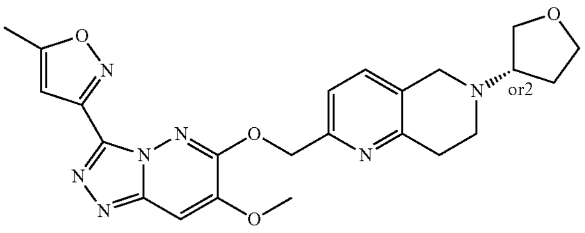 [SMILES: COc1cc2nnc(-c3cc(C)on3)n2nc1OCc1ccc2c(n1)CCN([C@H]1CCOC1)C2] |
| 182 | 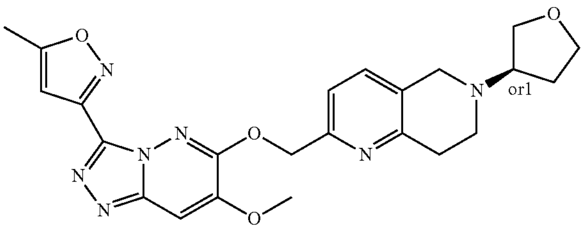 [SMILES: COc1cc2nnc(-c3cc(C)on3)n2nc1OCc1ccc2c(n1)CCN([C@@H]1CCOC1)C2] |
| 183 | 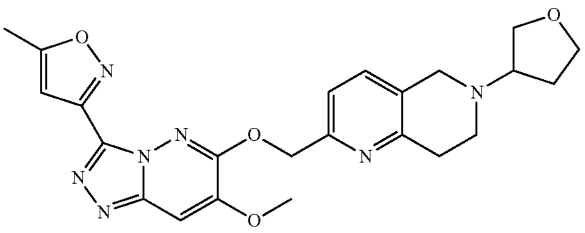 [SMILES: COc1cc2nnc(-c3cc(C)on3)n2nc1OCc1ccc2c(n1)CCN(C1CCOC1)C2] |
| 184 | 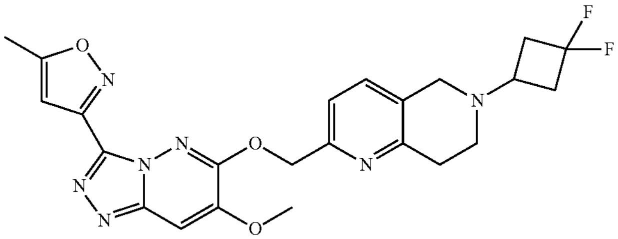 [SMILES: COc1cc2nnc(-c3cc(C)on3)n2nc1OCc1ccc2c(n1)CCN(C1CC(F)(F)C1)C2] |
| 185 | 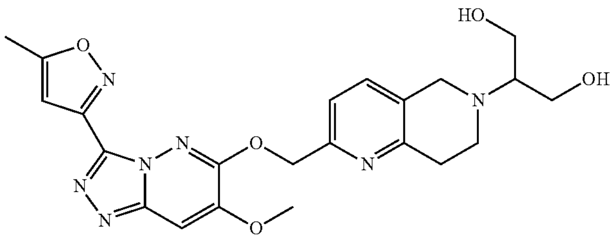 [SMILES: COc1cc2nnc(-c3cc(C)on3)n2nc1OCc1ccc2c(n1)CCN(C(CO)CO)C2] |
| 186 | 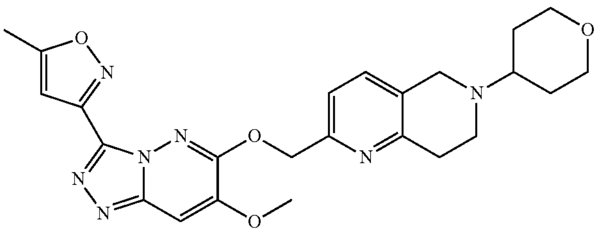 [SMILES: COc1cc2nnc(-c3cc(C)on3)n2nc1OCc1ccc2c(n1)CCN(C1CCOCC1)C2] |

-continued
| Embodiment | Structure |
| --- | --- |
| 187 | 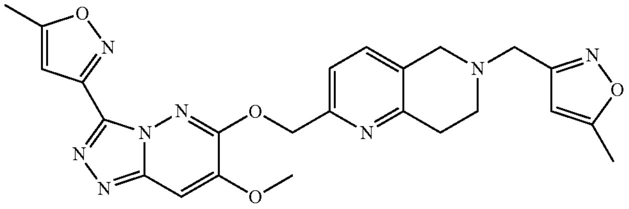 [SMILES: COc1cc2nnc(-c3cc(C)on3)n2nc1OCc1ccc2c(n1)CCN(Cc1cc(C)on1)C2] |
| 188 | 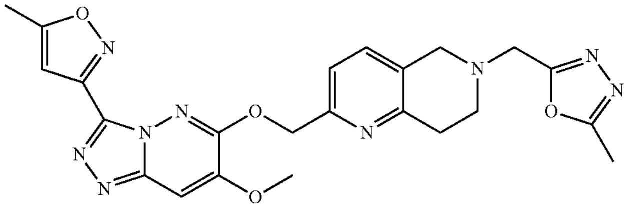 [SMILES: COc1cc2nnc(-c3cc(C)on3)n2nc1OCc1ccc2c(n1)CCN(Cc1nnc(C)o1)C2] |
| 189 | 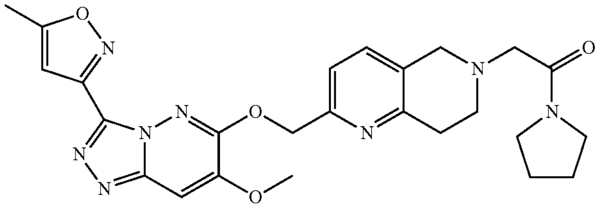 [SMILES: COc1cc2nnc(-c3cc(C)on3)n2nc1OCc1ccc2c(n1)CCN(CC(=O)N1CCCC1)C2] |
| 190 | 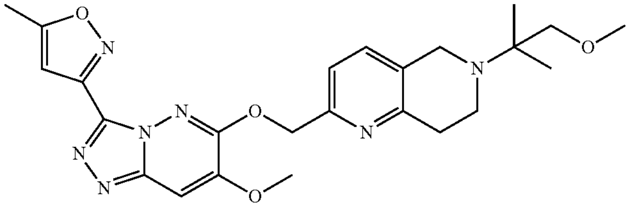 |
| 191 | 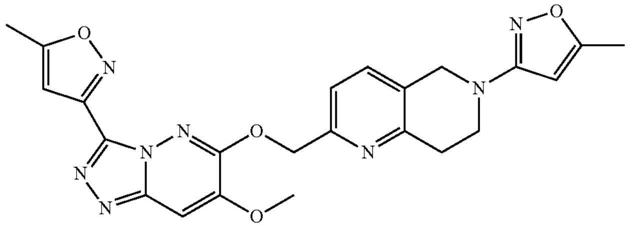 |
| 192 | 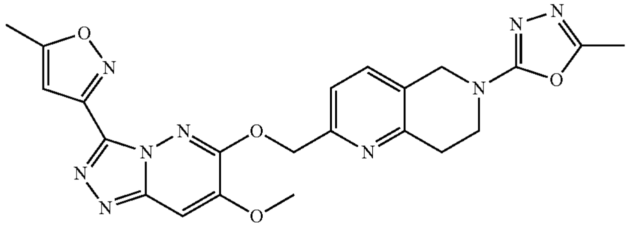 |
| 193 | 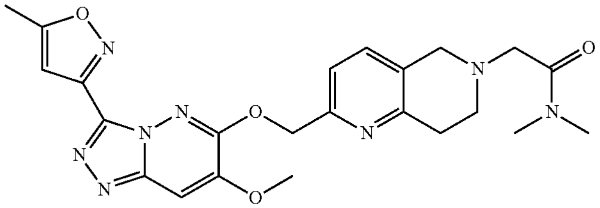 |

-continued
| Embodiment | Structure |
| --- | --- |
| 194 | 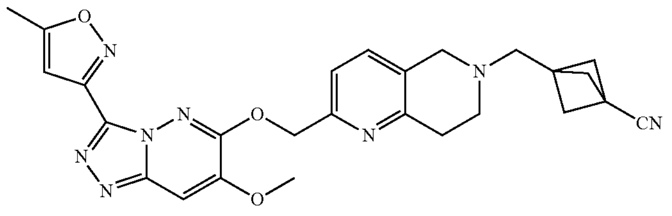 [SMILES: COc1cc2nnc(-c3cc(C)on3)n2nc1OCc1ccc2c(n1)CCN(CC13CC(C#N)(C1)C3)C2] |
| 195 | 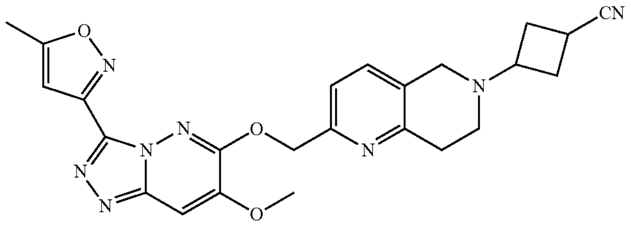 [SMILES: COc1cc2nnc(-c3cc(C)on3)n2nc1OCc1ccc2c(n1)CCN(C1CC(C#N)C1)C2] |
| 196 | 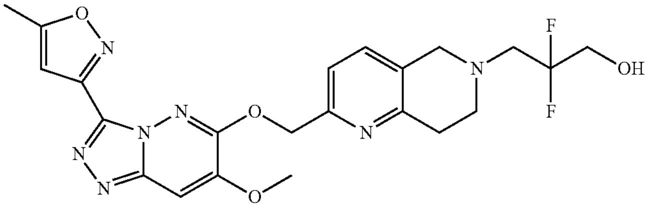 [SMILES: COc1cc2nnc(-c3cc(C)on3)n2nc1OCc1ccc2c(n1)CCN(CC(F)(F)CO)C2] |
| 197 | 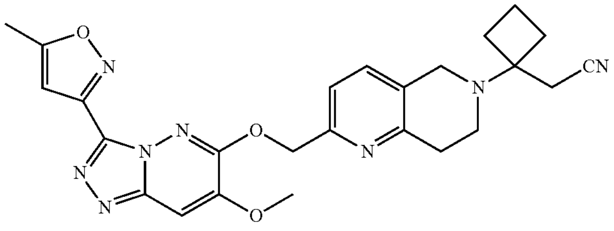 [SMILES: COc1cc2nnc(-c3cc(C)on3)n2nc1OCc1ccc2c(n1)CCN(C1(CC#N)CCC1)C2] |
| 198 | 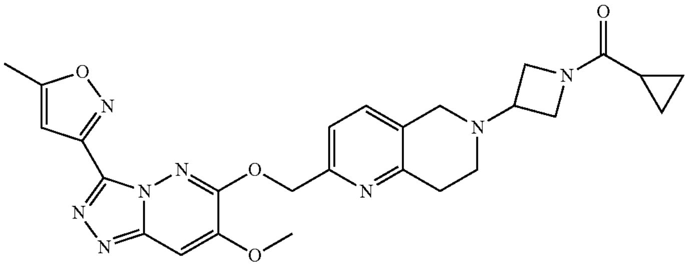 [SMILES: COc1cc2nnc(-c3cc(C)on3)n2nc1OCc1ccc2c(n1)CCN(C1CN(C(=O)C3CC3)C1)C2] |
| 199 | 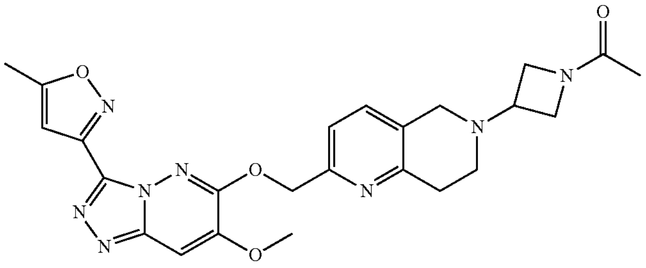 [SMILES: COc1cc2nnc(-c3cc(C)on3)n2nc1OCc1ccc2c(n1)CCN(C1CN(C(C)=O)C1)C2] |

-continued
| Embodiment | Structure |
| --- | --- |
| 200 | 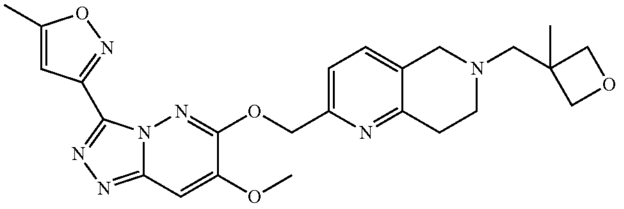 [SMILES: COc1cc2nnc(-c3cc(C)on3)n2nc1OCc1ccc2c(n1)CCN(CC1(C)COC1)C2] |
| 201 | 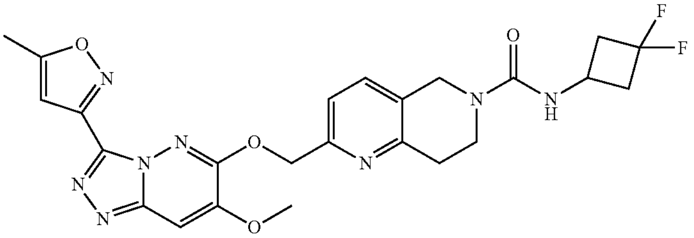 [SMILES: COc1cc2nnc(-c3cc(C)on3)n2nc1OCc1ccc2c(n1)CCN(C(=O)NC1CC(F)(F)C1)C2] |
| 202 | 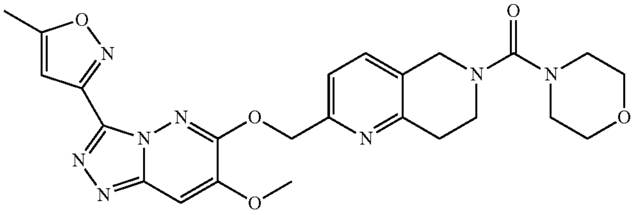 [SMILES: COc1cc2nnc(-c3cc(C)on3)n2nc1OCc1ccc2c(n1)CCN(C(=O)N1CCOCC1)C2] |
| 203 | 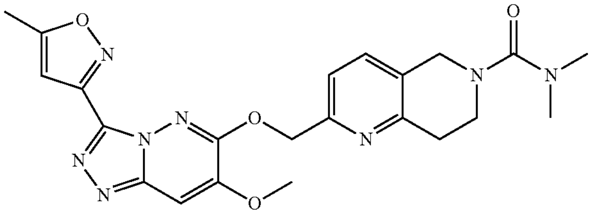 |
| 204 | 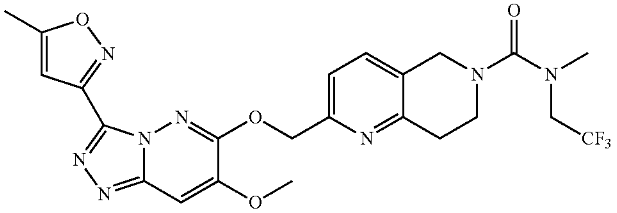 [SMILES: COc1cc2nnc(-c3cc(C)on3)n2nc1OCc1ccc2c(n1)CCN(C(=O)N(C)CC(F)(F)F)C2] |
| 205 | 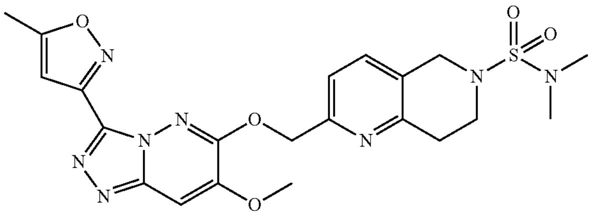 |
| 206 | 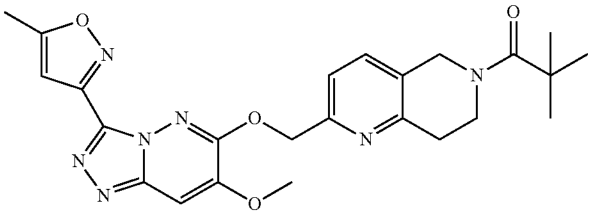 [SMILES: COc1cc2nnc(-c3cc(C)on3)n2nc1OCc1ccc2c(n1)CCN(C(=O)C(C)(C)C)C2] |

-continued
| Embodiment | Structure |
| --- | --- |
| 207 | 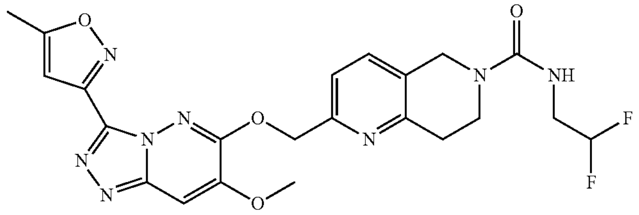 [SMILES: COc1cc2nnc(-c3cc(C)on3)n2nc1OCc1ccc2c(n1)CCN(C(=O)NCC(F)F)C2] |
| 208 | 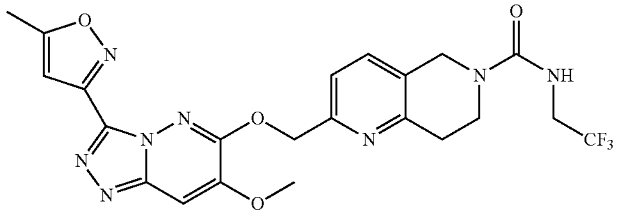 [SMILES: COc1cc2nnc(-c3cc(C)on3)n2nc1OCc1ccc2c(n1)CCN(C(=O)NCC(F)(F)F)C2] |
| 209 | 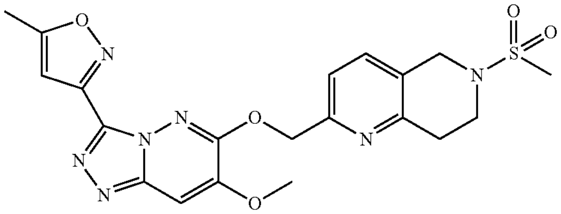 [SMILES: COc1cc2nnc(-c3cc(C)on3)n2nc1OCc1ccc2c(n1)CCN(S(C)(=O)=O)C2] |
| 210 | 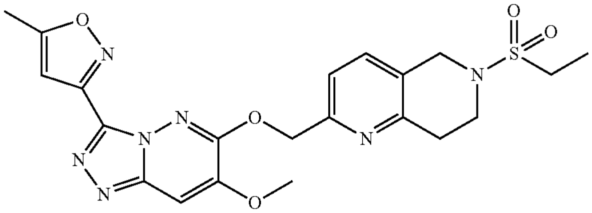 [SMILES: CCS(=O)(=O)N1CCc2nc(COc3nn4c(-c5cc(C)on5)nnc4cc3OC)ccc2C1] |
| 211 | 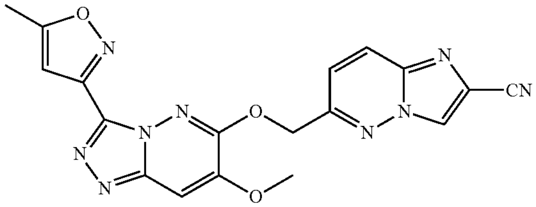 [SMILES: COc1cc2nnc(-c3cc(C)on3)n2nc1OCc1ccc2nc(C#N)cn2n1] |
| 212 | 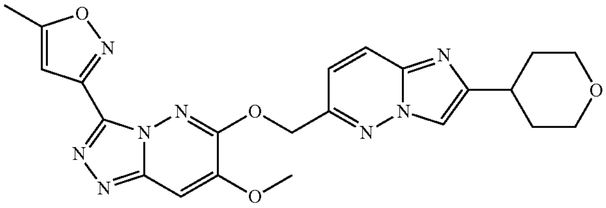 [SMILES: COc1cc2nnc(-c3cc(C)on3)n2nc1OCc1ccc2nc(C3CCOCC3)cn2n1] |
| 213 | 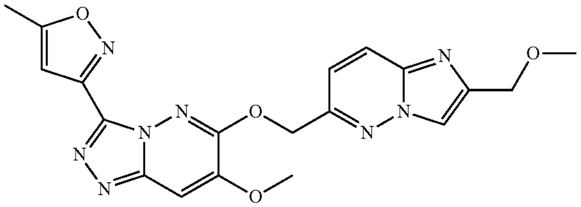 |

-continued
| Embodiment | Structure |
| --- | --- |
| 214 | 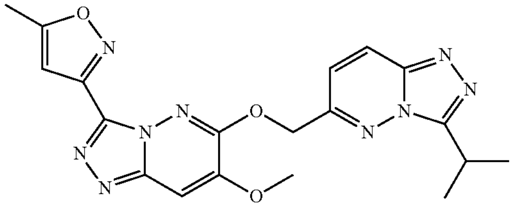 [SMILES: COc1cc2nnc(-c3cc(C)on3)n2nc1OCc1ccc2nnc(C(C)C)n2n1] |
| 215 | 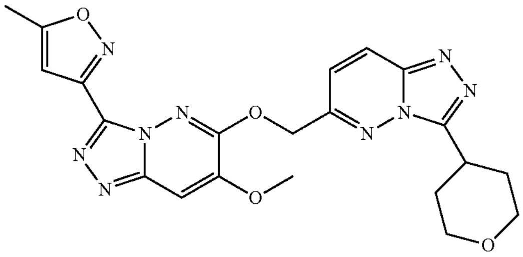 [SMILES: COc1cc2nnc(-c3cc(C)on3)n2nc1OCc1ccc2nnc(C3CCOCC3)n2n1] |
| 216 | 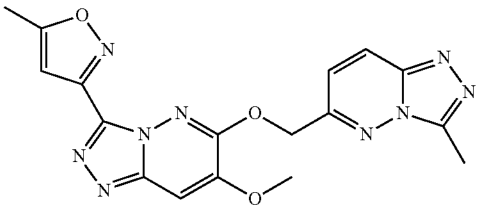 [SMILES: COc1cc2nnc(-c3cc(C)on3)n2nc1OCc1ccc2nnc(C)n2n1] |
| 217 | 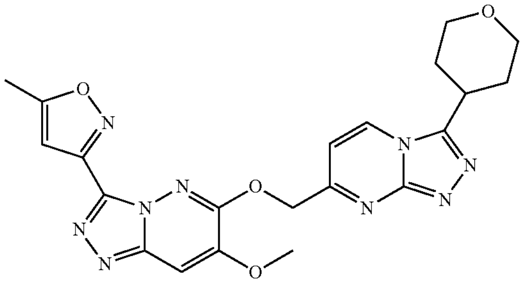 [SMILES: COc1cc2nnc(-c3cc(C)on3)n2nc1OCc1ccn2c(C3CCOCC3)nnc2n1] |
| 218 | 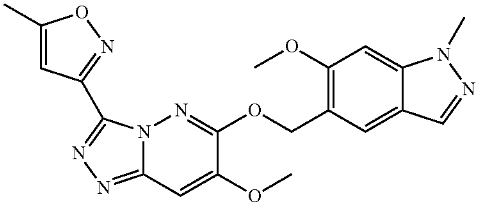 [SMILES: COc1cc2c(cnn2C)cc1COc1nn2c(-c3cc(C)on3)nnc2cc1OC] |
| 219 | 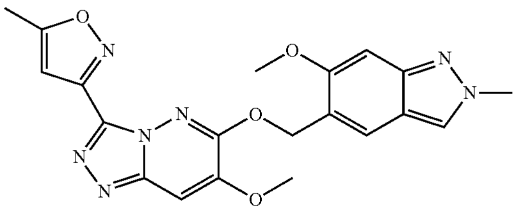 |

-continued
| Embodiment | Structure |
|---|---|
| 220 | 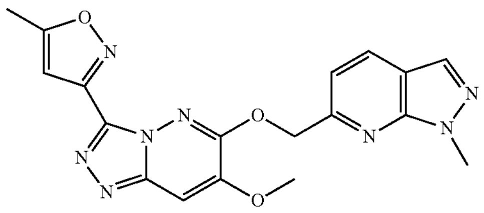 [SMILES: COc1cc2nnc(-c3cc(C)on3)n2nc1OCc1ccc2cnn(C)c2n1] |
| 221 | 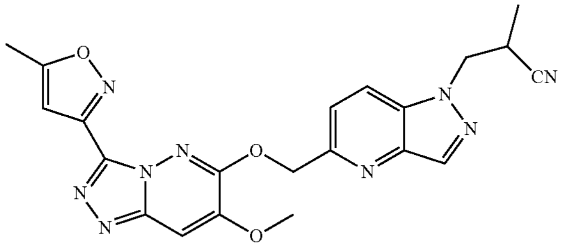 [SMILES: COc1cc2nnc(-c3cc(C)on3)n2nc1OCc1ccc2c(cnn2CC(C)C#N)n1] |
| 222 | 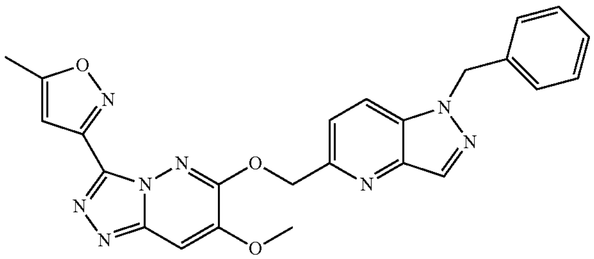 [SMILES: COc1cc2nnc(-c3cc(C)on3)n2nc1OCc1ccc2c(cnn2Cc2ccccc2)n1] |
| 223 | 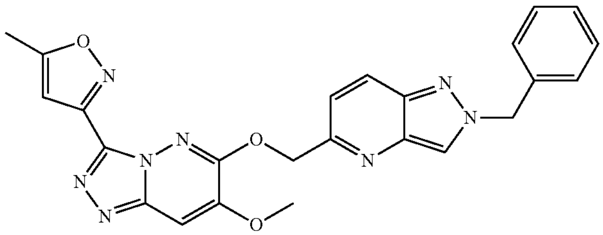 [SMILES: COc1cc2nnc(-c3cc(C)on3)n2nc1OCc1ccc2nn(Cc3ccccc3)cc2n1] |
| 224 | 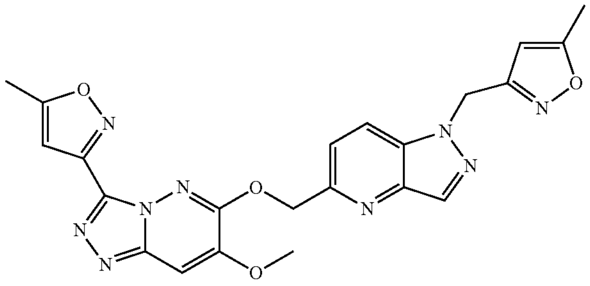 |
| 225 | 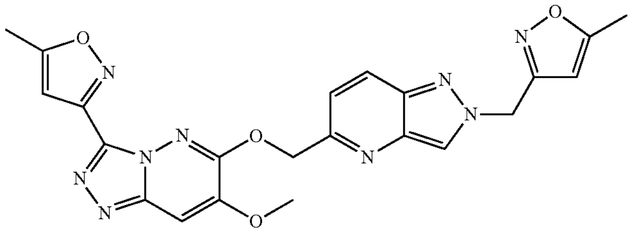 |

-continued
| Embodiment | Structure |
| --- | --- |
| 226 | 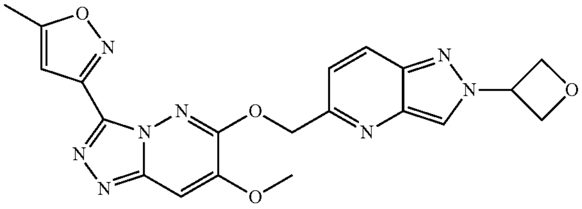 [SMILES: COc1cc2nnc(-c3cc(C)on3)n2nc1OCc1ccc2nn(C3COC3)cc2n1] |
| 227 | 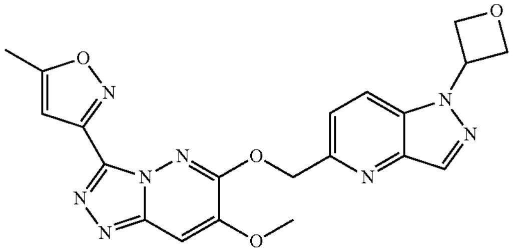 [SMILES: COc1cc2nnc(-c3cc(C)on3)n2nc1OCc1ccc2c(cnn2C2COC2)n1] |
| 228 | 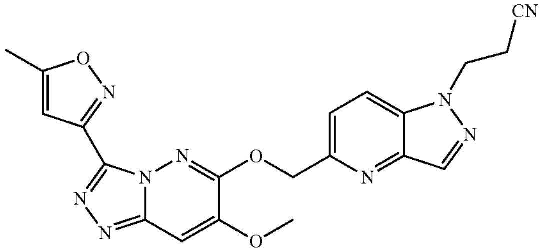 [SMILES: COc1cc2nnc(-c3cc(C)on3)n2nc1OCc1ccc2c(cnn2CCC#N)n1] |
| 229 | 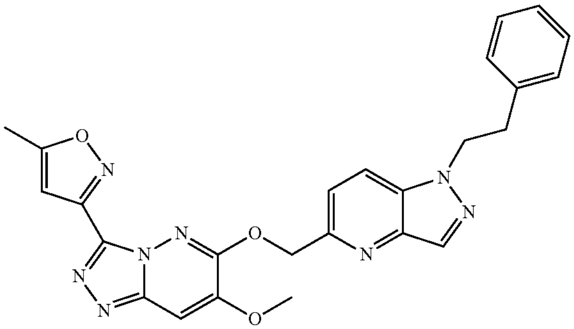 [SMILES: COc1cc2nnc(-c3cc(C)on3)n2nc1OCc1ccc2c(cnn2CCc2ccccc2)n1] |
| 230 | 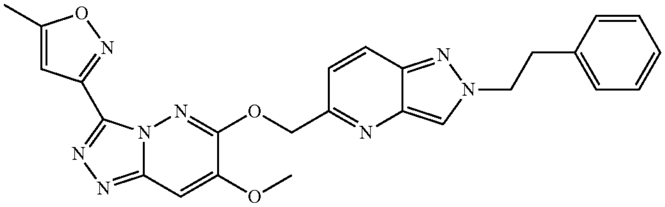 [SMILES: COc1cc2nnc(-c3cc(C)on3)n2nc1OCc1ccc2nn(CCc3ccccc3)cc2n1] |
| 231 | 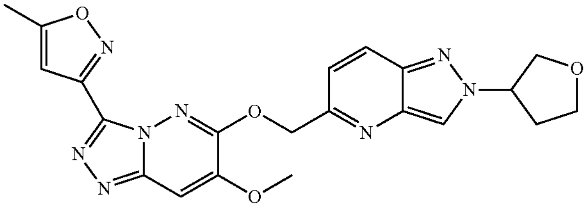 [SMILES: COc1cc2nnc(-c3cc(C)on3)n2nc1OCc1ccc2nn(C3CCOC3)cc2n1] |

-continued
| Embodiment | Structure |
| --- | --- |
| 232 | 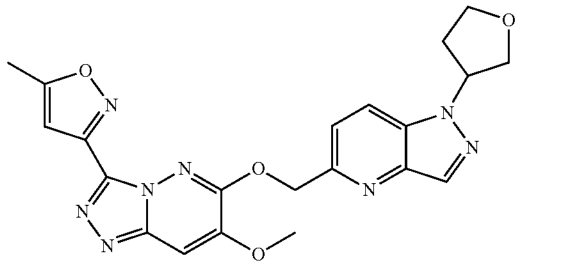 [SMILES: COc1cc2nnc(-c3cc(C)on3)n2nc1OCc1ccc2c(cnn2C2CCOC2)n1] |
| 233 | 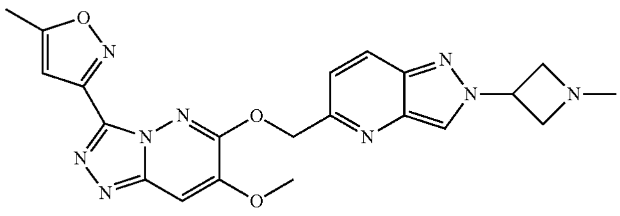 |
| 234 | 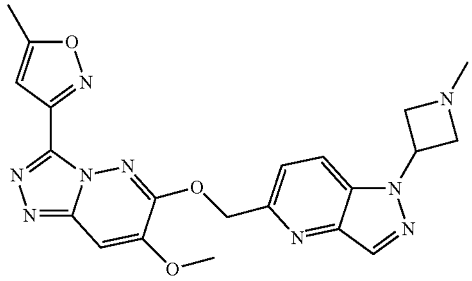 |
| 235 | 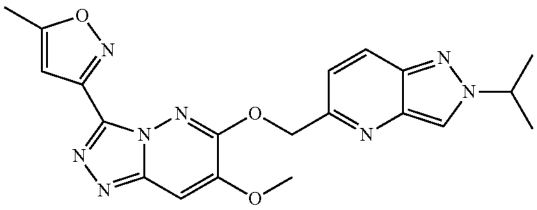 [SMILES: COc1cc2nnc(-c3cc(C)on3)n2nc1OCc1ccc2nn(C(C)C)cc2n1] |
| 236 | 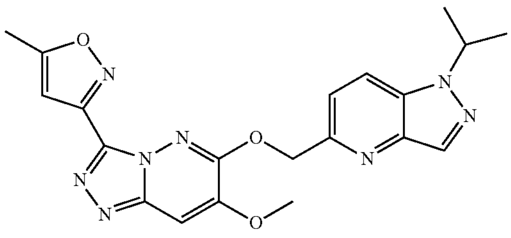 [SMILES: COc1cc2nnc(-c3cc(C)on3)n2nc1OCc1ccc2c(cnn2C(C)C)n1] |
| 237 | 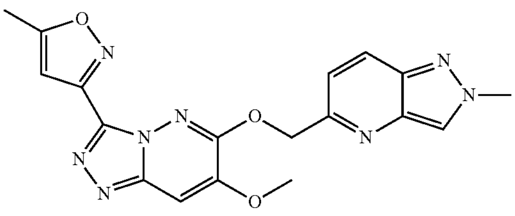 |

-continued
| Embodiment | Structure |
|---|---|
| 238 | 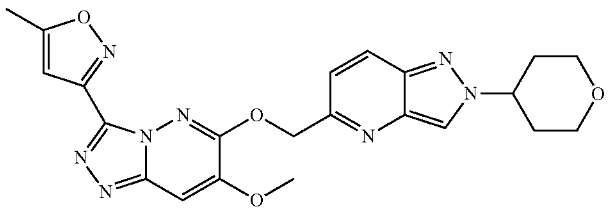 [SMILES: COc1cc2nnc(-c3cc(C)on3)n2nc1OCc1ccc2nn(C3CCOCC3)cc2n1] |
| 239 | 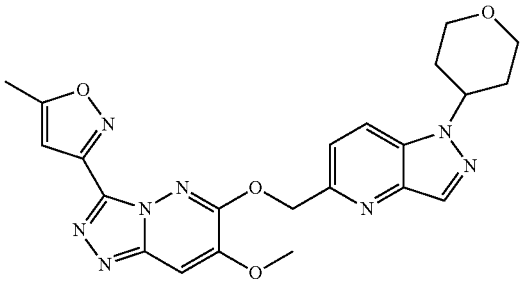 [SMILES: COc1cc2nnc(-c3cc(C)on3)n2nc1OCc1ccc2c(cnn2C2CCOCC2)n1] |
| 240 | 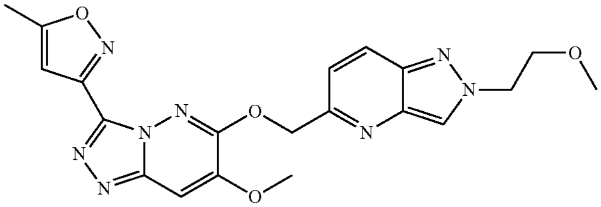 |
| 241 | 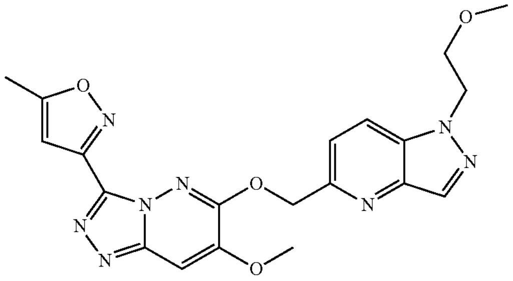 |
| 242 | 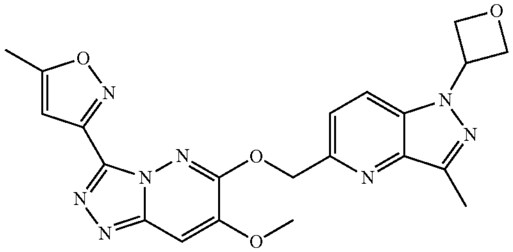 [SMILES: COc1cc2nnc(-c3cc(C)on3)n2nc1OCc1ccc2c(n1)c(C)nn2C1COC1] |
| 243 | 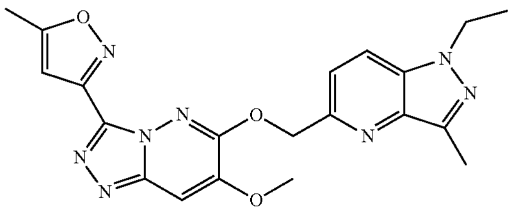 [SMILES: CCn1nc(C)c2nc(COc3nn4c(-c5cc(C)on5)nnc4cc3OC)ccc21] |

-continued
| Embodiment | Structure |
|---|---|
| 244 | 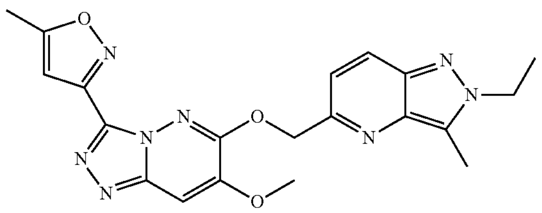 [SMILES: CCn1nc2ccc(COc3nn4c(-c5cc(C)on5)nnc4cc3OC)nc2c1C] |
| 245 | 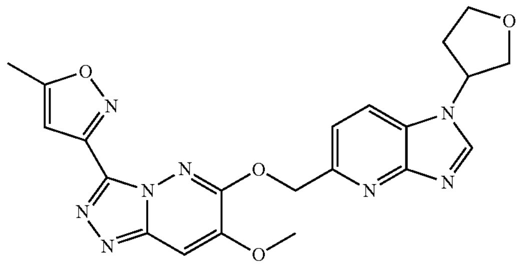 [SMILES: COc1cc2nnc(-c3cc(C)on3)n2nc1OCc1ccc2c(ncn2C2CCOC2)n1] |
| 246 | 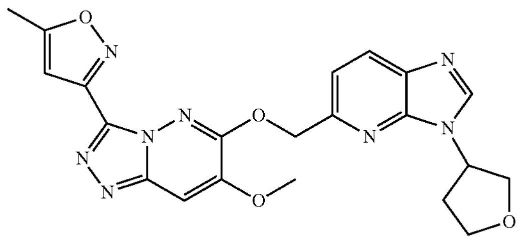 [SMILES: COc1cc2nnc(-c3cc(C)on3)n2nc1OCc1ccc2ncn(C3CCOC3)c2n1] |
| 247 | 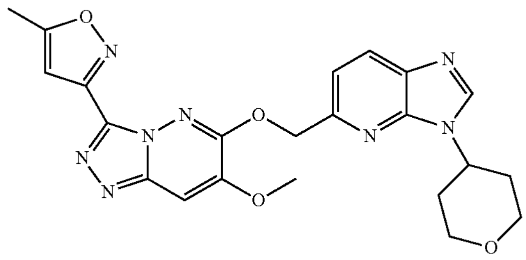 |
| 248 | 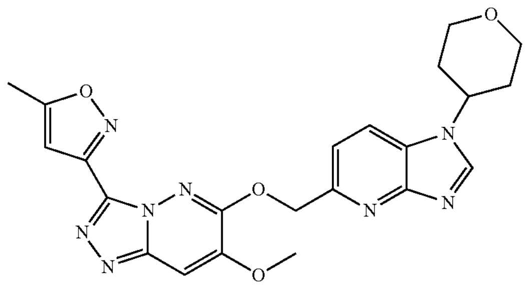 |
| 249 | 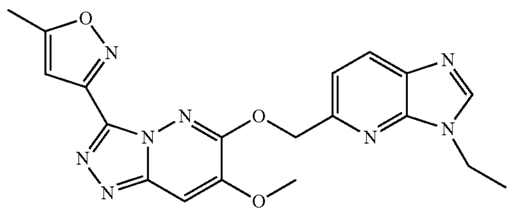 [SMILES: CCn1cnc2ccc(COc3nn4c(-c5cc(C)on5)nnc4cc3OC)nc21] |

-continued
| Embodiment | Structure |
| --- | --- |
| 250 | 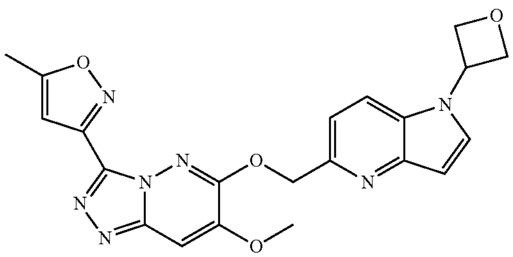 [SMILES: COc1cc2nnc(-c3cc(C)on3)n2nc1OCc1ccc2c(ccn2C2COC2)n1] |
| 251 | 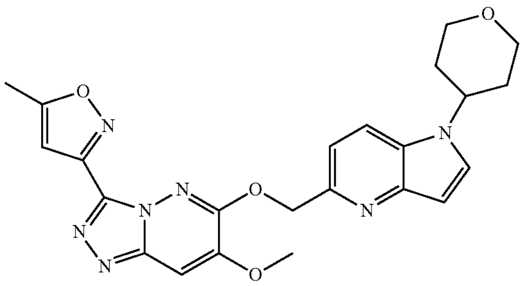 [SMILES: COc1cc2nnc(-c3cc(C)on3)n2nc1OCc1ccc2c(ccn2C2CCOCC2)n1] |
| 252 | 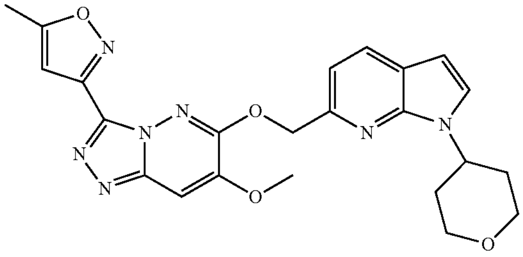 [SMILES: COc1cc2nnc(-c3cc(C)on3)n2nc1OCc1ccc2ccn(C3CCOCC3)c2n1] |
| 253 | 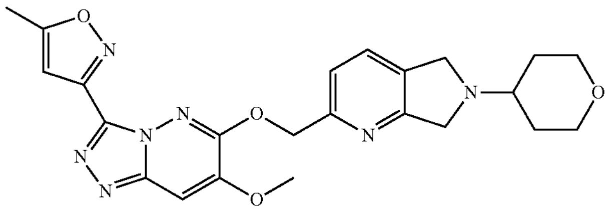 [SMILES: COc1cc2nnc(-c3cc(C)on3)n2nc1OCc1ccc2c(n1)CN(C1CCOCC1)C2] |
| 254 | 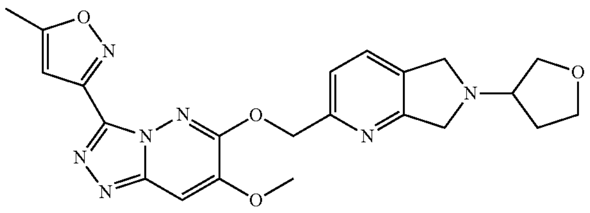 [SMILES: COc1cc2nnc(-c3cc(C)on3)n2nc1OCc1ccc2c(n1)CN(C1CCOC1)C2] |
| 255 | 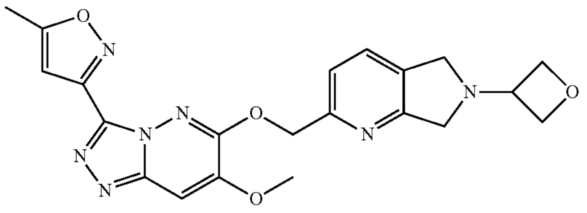 [SMILES: COc1cc2nnc(-c3cc(C)on3)n2nc1OCc1ccc2c(n1)CN(C1COC1)C2] |

-continued
| Embodiment | Structure |
| --- | --- |
| 256 | 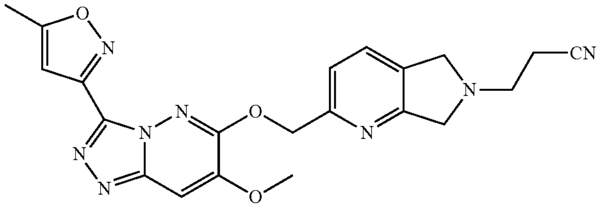 [SMILES: COc1cc2nnc(-c3cc(C)on3)n2nc1OCc1ccc2c(n1)CN(CCC#N)C2] |
| 257 | 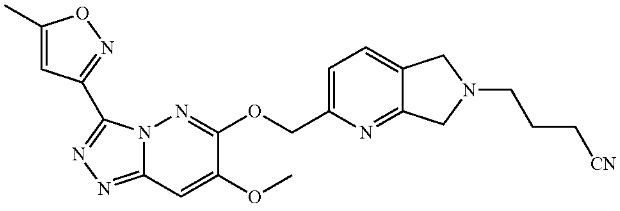 [SMILES: COc1cc2nnc(-c3cc(C)on3)n2nc1OCc1ccc2c(n1)CN(CCCC#N)C2] |
| 258 | 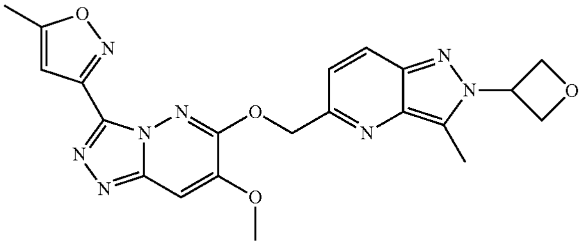 [SMILES: COc1cc2nnc(-c3cc(C)on3)n2nc1OCc1ccc2nn(C3COC3)c(C)c2n1] |
or a pharmaceutically acceptable salt or stereomer thereof.
17. A pharmaceutical composition, comprising the compound as defined in claim 1, or a pharmaceutically acceptable salt or stereomer thereof, and a pharmaceutically acceptable carrier.
* * * * *